(12) United States Patent
Shelton, IV et al.

(10) Patent No.: US 11,559,307 B2
(45) Date of Patent: Jan. 24, 2023

(54) METHOD OF ROBOTIC HUB COMMUNICATION, DETECTION, AND CONTROL

(71) Applicant: Cilag GmbH International, Zug (CH)

(72) Inventors: Frederick E. Shelton, IV, Hillsboro, OH (US); Jerome R. Morgan, Cincinnati, OH (US); Jason L. Harris, Lebanon, OH (US); David C. Yates, Morrow, OH (US)

(73) Assignee: Cilag GmbH International, Zug (CH)

( * ) Notice: Subject to any disclaimer, the term of this patent is extended or adjusted under 35 U.S.C. 154(b) by 39 days.

(21) Appl. No.: 16/209,407

(22) Filed: Dec. 4, 2018

(65) Prior Publication Data

US 2019/0201137 A1    Jul. 4, 2019

Related U.S. Application Data

(60) Provisional application No. 62/773,728, filed on Nov. 30, 2018, provisional application No. 62/773,742, (Continued)

(51) Int. Cl.
*G06F 15/16* (2006.01)
*A61B 17/115* (2006.01)
(Continued)

(52) U.S. Cl.
CPC ...... *A61B 17/1155* (2013.01); *A61B 1/00009* (2013.01); *A61B 1/00045* (2013.01); (Continued)

(58) Field of Classification Search
CPC .......... A61B 17/07207; A61B 17/1114; A61B 17/1155; A61B 17/1285;
(Continued)

(56) References Cited

U.S. PATENT DOCUMENTS 1,853,416 A    4/1932 Hall
2,222,125 A    11/1940 Stehlik
(Continued)

FOREIGN PATENT DOCUMENTS

AU    2015201140 A1    3/2015
CA       2795323 A1    5/2014
(Continued)

OTHER PUBLICATIONS

US 10,504,709 B2, 12/2019, Karancsi et al. (withdrawn)
(Continued)

*Primary Examiner* — Ario Etienne
*Assistant Examiner* — Thorne E Waugh

(57) ABSTRACT

Various surgical systems are disclosed. A surgical system can include a surgical robot and a surgical hub. The surgical robot can include a control unit in signal communication with a control console and a robotic tool. The surgical hub can include a display. The surgical hub can be in signal communication with the control unit. A facility can include a plurality of surgical hubs that communicate data from the surgical robots to a primary server. To alleviate bandwidth competition among the surgical hubs, the surgical hubs can include prioritization protocols for collecting, storing, and/or communicating data to the primary server.

14 Claims, 180 Drawing Sheets

Related U.S. Application Data filed on Nov. 30, 2018, provisional application No. 62/773,741, filed on Nov. 30, 2018, provisional application No. 62/773,778, filed on Nov. 30, 2018, provisional application No. 62/750,529, filed on Oct. 25, 2018, provisional application No. 62/750,539, filed on Oct. 25, 2018, provisional application No. 62/750,555, filed on Oct. 25, 2018, provisional application No. 62/729,191, filed on Sep. 10, 2018, provisional application No. 62/729,195, filed on Sep. 10, 2018, provisional application No. 62/729,183, filed on Sep. 10, 2018, provisional application No. 62/729,176, filed on Sep. 10, 2018, provisional application No. 62/729,182, filed on Sep. 10, 2018, provisional application No. 62/729,184, filed on Sep. 10, 2018, provisional application No. 62/729,186, filed on Sep. 10, 2018, provisional application No. 62/729,185, filed on Sep. 10, 2018, provisional application No. 62/729,177, filed on Sep. 10, 2018, provisional application No. 62/721,996, filed on Aug. 23, 2018, provisional application No. 62/721,998, filed on Aug. 23, 2018, provisional application No. 62/721,999, filed on Aug. 23, 2018, provisional application No. 62/721,994, filed on Aug. 23, 2018, provisional application No. 62/721,995, filed on Aug. 23, 2018, provisional application No. 62/692,748, filed on Jun. 30, 2018, provisional application No. 62/292,747, filed on Jun. 30, 2018, provisional application No. 62/692,768, filed on Jun. 30, 2018, provisional application No. 62/691,257, filed on Jun. 28, 2018, provisional application No. 62/691,219, filed on Jun. 28, 2018, provisional application No. 62/691,251, filed on Jun. 28, 2018, provisional application No. 62/691,228, filed on Jun. 28, 2018, provisional application No. 62/691,227, filed on Jun. 28, 2018, provisional application No. 62/691,262, filed on Jun. 28, 2018, provisional application No. 62/691,230, filed on Jun. 28, 2018, provisional application No. 62/665,134, filed on May 1, 2018, provisional application No. 62/665,139, filed on May 1, 2018, provisional application No. 62/665,177, filed on May 1, 2018, provisional application No. 62/665,192, filed on May 1, 2018, provisional application No. 62/665,128, filed on May 1, 2018, provisional application No. 62/665,129, filed on May 1, 2018, provisional application No. 62/659,900, filed on Apr. 19, 2018, provisional application No. 62/650,882, filed on Mar. 30, 2018, provisional application No. 62/650,887, filed on Mar. 30, 2018, provisional application No. 62/650,877, filed on Mar. 30, 2018, provisional application No. 62/650,898, filed on Mar. 30, 2018, provisional application No. 62/649,302, filed on Mar. 28, 2018, provisional application No. 62/649,310, filed on Mar. 28, 2018, provisional application No. 62/649,294, filed on Mar. 28, 2018, provisional application No. 62/649,300, filed on Mar. 28, 2018, provisional application No. 62/649,323, filed on Mar. 28, 2018, provisional application No. 62/649,315, filed on Mar. 28, 2018, provisional application No. 62/649,291, filed on Mar. 28, 2018, provisional application No. 62/649,333, filed on Mar. 28, 2018, provisional application No. 62/649,320, filed on Mar. 28, 2018, provisional application No. 62/649,309, filed on Mar. 28, 2018, provisional application No. 62/649,313, filed on Mar. 28, 2018, provisional application No. 62/649,307, filed on Mar. 28, 2018, provisional application No. 62/649,296, filed on Mar. 28, 2018, provisional application No. 62/649,327, filed on Mar. 28, 2018, provisional application No. 62/611,341, filed on Dec. 28, 2017, provisional application No. 62/611,339, filed on Dec. 28, 2017, provisional application No. 62/611,340, filed on Dec. 28, 2017.

(51) Int. Cl.

| | |
|---|---|
| *A61M 1/00* | (2006.01) |
| *A61B 34/20* | (2016.01) |
| *A61B 34/32* | (2016.01) |
| *A61B 34/00* | (2016.01) |
| *A61B 90/35* | (2016.01) |
| *A61B 90/00* | (2016.01) |
| *G16H 40/67* | (2018.01) |
| *G16H 10/60* | (2018.01) |
| *G16H 50/20* | (2018.01) |
| *G16H 40/63* | (2018.01) |
| *G16H 70/20* | (2018.01) |
| *A61B 1/00* | (2006.01) |
| *A61B 1/05* | (2006.01) |
| *A61B 1/06* | (2006.01) |
| *A61B 5/00* | (2006.01) |
| *A61B 5/026* | (2006.01) |
| *A61B 6/00* | (2006.01) |
| *A61B 17/068* | (2006.01) |
| *A61B 17/072* | (2006.01) |
| *A61B 17/11* | (2006.01) |
| *A61B 17/128* | (2006.01) |
| *A61B 17/32* | (2006.01) |
| *A61B 18/14* | (2006.01) |
| *B25J 9/16* | (2006.01) |
| *B25J 13/00* | (2006.01) |
| *G06K 7/10* | (2006.01) |
| *G06K 19/077* | (2006.01) |
| *H01Q 1/22* | (2006.01) |
| *H04L 9/40* | (2022.01) |
| *H04L 67/10* | (2022.01) |
| *H04L 67/12* | (2022.01) |
| *H04N 5/272* | (2006.01) |
| *H04N 7/18* | (2006.01) |
| *H05K 1/02* | (2006.01) |
| *H05K 1/18* | (2006.01) |
| *A61B 34/30* | (2016.01) |
| *A61B 90/30* | (2016.01) |
| *A61B 17/00* | (2006.01) |
| *A61B 18/00* | (2006.01) |
| *A61M 13/00* | (2006.01) |

(52) U.S. Cl.
CPC ............ *A61B 1/051* (2013.01); *A61B 1/0661* (2013.01); *A61B 5/0066* (2013.01); *A61B 5/0075* (2013.01); *A61B 5/0261* (2013.01); *A61B 6/5247* (2013.01); *A61B 17/0682* (2013.01); *A61B 17/072* (2013.01); *A61B 17/1114* (2013.01); *A61B 17/1285* (2013.01); *A61B 17/320092* (2013.01); *A61B 18/1442* (2013.01); *A61B 18/1445* (2013.01); *A61B 34/20* (2016.02); *A61B 34/32* (2016.02); *A61B 34/71* (2016.02); *A61B 90/35* (2016.02); *A61B 90/361* (2016.02); *A61M 1/73* (2021.05); *A61M 1/79* (2021.05); *B25J 9/1697* (2013.01); *B25J 13/006* (2013.01); *G06K 7/10316* (2013.01); *G06K 19/07749* (2013.01); *G16H 10/60* (2018.01); *G16H 40/63* (2018.01);

*G16H 40/67* (2018.01); *G16H 50/20* (2018.01); *G16H 70/20* (2018.01); *H01Q 1/22* (2013.01); *H04L 63/1416* (2013.01); *H04L 67/10* (2013.01); *H04L 67/12* (2013.01); *H04N 5/272* (2013.01); *H04N 7/183* (2013.01); *H05K 1/028* (2013.01); *H05K 1/189* (2013.01); A61B 34/30 (2016.02); A61B 2017/0003 (2013.01); A61B 2017/0011 (2013.01); A61B 2017/00022 (2013.01); A61B 2017/00026 (2013.01); A61B 2017/00039 (2013.01); A61B 2017/00044 (2013.01); A61B 2017/00057 (2013.01); A61B 2017/00061 (2013.01); A61B 2017/00075 (2013.01); A61B 2017/00084 (2013.01); A61B 2017/00097 (2013.01); A61B 2017/00106 (2013.01); A61B 2017/00115 (2013.01); A61B 2017/00119 (2013.01); A61B 2017/00199 (2013.01); A61B 2017/00203 (2013.01); A61B 2017/00221 (2013.01); A61B 2017/00398 (2013.01); A61B 2017/00402 (2013.01); A61B 2017/00734 (2013.01); A61B 2017/00809 (2013.01); A61B 2017/00818 (2013.01); A61B 2017/07257 (2013.01); A61B 2017/07271 (2013.01); A61B 2017/07278 (2013.01); A61B 2017/07285 (2013.01); A61B 2017/1132 (2013.01); A61B 2017/32007 (2017.08); A61B 2017/320074 (2017.08); A61B 2017/320084 (2013.01); A61B 2017/320095 (2017.08); A61B 2017/320097 (2017.08); A61B 2018/0063 (2013.01); A61B 2018/00541 (2013.01); A61B 2018/00589 (2013.01); A61B 2018/00595 (2013.01); A61B 2018/00601 (2013.01); A61B 2018/00607 (2013.01); A61B 2018/00642 (2013.01); A61B 2018/00684 (2013.01); A61B 2018/00791 (2013.01); A61B 2018/00827 (2013.01); A61B 2018/00875 (2013.01); A61B 2018/00892 (2013.01); A61B 2018/00988 (2013.01); A61B 2018/00994 (2013.01); A61B 2034/2055 (2016.02); A61B 2034/2057 (2016.02); A61B 2034/301 (2016.02); A61B 2034/305 (2016.02); A61B 2090/309 (2016.02); A61B 2217/005 (2013.01); A61B 2217/007 (2013.01); A61B 2218/002 (2013.01); A61B 2218/007 (2013.01); A61B 2218/008 (2013.01); A61M 1/80 (2021.05); A61M 13/003 (2013.01); A61M 2205/3306 (2013.01); A61M 2205/3327 (2013.01); A61M 2205/3331 (2013.01); A61M 2205/3365 (2013.01); A61M 2205/3368 (2013.01); G05B 2219/40174 (2013.01); G05B 2219/45119 (2013.01)

(58) Field of Classification Search
CPC .... A61B 17/320068; A61B 17/320092; A61B 18/1206; A61B 18/14; A61B 18/1442; A61B 18/1445; A61B 1/00009; A61B 1/00016; A61B 1/00045; A61B 1/00193; A61B 1/051; A61B 1/0661; A61B 2017/00017; A61B 2017/00022; A61B 2017/00026; A61B 2017/0003; A61B 2017/00039; A61B 2017/00044; A61B 2017/00057; A61B 2017/00061; A61B 2017/00075; A61B 2017/00084; A61B 2017/00097; A61B 2017/00106; A61B 2017/0011; A61B 2017/00115; A61B 2017/00203; A61B 2017/00221; A61B 2017/00398; A61B 2017/00402; A61B 2017/00473; A61B 2017/00477; A61B 2017/00725; A61B 2017/00734; A61B 2017/00809; A61B 2017/00818; A61B 2017/07214; A61B 2017/07228; A61B 2017/07257; A61B 2017/07271; A61B 2017/07278; A61B 2017/07285; A61B 2017/1132; A61B 2017/2927; A61B 2017/2929; A61B 2017/32007; A61B 2017/320074; A61B 2017/320084; A61B 2017/320095; A61B 2017/320097; A61B 2018/00541; A61B 2018/00589; A61B 2018/00595; A61B 2018/00601; A61B 2018/00607; A61B 2018/0063; A61B 2018/00642; A61B 2018/00684; A61B 2018/00791; A61B 2018/00827; A61B 2018/00875; A61B 2018/00892; A61B 2018/00988; A61B 2018/00994; A61B 2034/2055; A61B 2034/2057; A61B 2034/301; A61B 2034/302; A61B 2034/305; A61B 2090/061; A61B 2090/064; A61B 2090/065; A61B 2090/066; A61B 2090/0811; A61B 2090/309; A61B 2217/005; A61B 2217/007; A61B 2218/002; A61B 2218/007; A61B 2218/008; A61B 34/20; A61B 34/30; A61B 34/32; A61B 34/37; A61B 34/71; A61B 34/74; A61B 34/76; A61B 5/0066; A61B 5/0075; A61B 5/0261; A61B 6/5247; A61B 90/35; A61B 90/361; A61B 90/37; A61B 90/92; A61B 90/96; A61B 90/98; A61B 17/0218; A61B 17/0682; A61B 17/072; A61B 2017/00199; A61B 2017/00128; A61B 2017/00119; A61M 13/003; A61M 1/0025; A61M 1/0056; A61M 1/0066; A61M 2205/3306; A61M 2205/3327; A61M 2205/3331; A61M 2205/3365; A61M 2205/3368; B25J 13/006; B25J 9/1697; G05B 2219/45119; G06K 19/07749; G06K 7/10316; G16H 10/60; G16H 20/40; G16H 40/63; G16H 40/67; G16H 50/20; G16H 70/20; H01Q 1/22; H04L 63/1416; H04L 67/10; H04L 67/12; H04N 5/272; H04N 7/183; H05K 1/028; H05K 1/189

See application file for complete search history.

(56) References Cited

U.S. PATENT DOCUMENTS

| | | |
|---|---|---|
| 3,082,426 A | 3/1963 | Miles |
| 3,503,396 A | 3/1970 | Pierie et al. |
| 3,584,628 A | 6/1971 | Green |
| 3,626,457 A | 12/1971 | Duerr et al. |
| 3,633,584 A | 1/1972 | Farrell |
| 3,759,017 A | 9/1973 | Young |
| 3,863,118 A | 1/1975 | Lander et al. |
| 3,898,545 A | 8/1975 | Coppa et al. |
| 3,912,121 A | 10/1975 | Steffen |
| 3,915,271 A | 10/1975 | Harper |
| 3,932,812 A | 1/1976 | Milligan |
| 4,041,362 A | 8/1977 | Ichiyanagi |
| 4,052,649 A | 10/1977 | Greenwell et al. |
| 4,087,730 A | 5/1978 | Goles |
| 4,157,859 A | 6/1979 | Terry |
| 4,171,700 A | 10/1979 | Farin |
| 4,202,722 A | 5/1980 | Paquin |

(56) References Cited

U.S. PATENT DOCUMENTS

| | | |
|---|---|---|
| 4,412,539 A | 11/1983 | Jarvik |
| 4,448,193 A | 5/1984 | Ivanov |
| 4,523,695 A | 6/1985 | Braun et al. |
| 4,608,160 A | 8/1986 | Zoch |
| 4,614,366 A | 9/1986 | North et al. |
| 4,633,874 A | 1/1987 | Chow et al. |
| 4,701,193 A | 10/1987 | Robertson et al. |
| 4,735,603 A | 4/1988 | Goodson et al. |
| 4,788,977 A | 12/1988 | Farin et al. |
| 4,849,752 A | 7/1989 | Bryant |
| D303,787 S | 10/1989 | Messenger et al. |
| 4,892,244 A | 1/1990 | Fox et al. |
| 4,976,173 A | 12/1990 | Yang |
| 5,010,341 A | 4/1991 | Huntley et al. |
| 5,026,387 A | 6/1991 | Thomas |
| 5,035,692 A | 7/1991 | Lyon et al. |
| 5,042,460 A | 8/1991 | Sakurai et al. |
| 5,047,043 A | 9/1991 | Kubota et al. |
| 5,084,057 A | 1/1992 | Green et al. |
| 5,100,402 A | 3/1992 | Fan |
| D327,061 S | 6/1992 | Soren et al. |
| 5,129,570 A | 7/1992 | Schulze et al. |
| 5,151,102 A | 9/1992 | Kamiyama et al. |
| 5,156,315 A | 10/1992 | Green et al. |
| 5,158,585 A | 10/1992 | Saho et al. |
| 5,171,247 A | 12/1992 | Hughett et al. |
| 5,189,277 A | 2/1993 | Boisvert et al. |
| 5,197,962 A | 3/1993 | Sansom et al. |
| 5,204,669 A | 4/1993 | Dorfe et al. |
| 5,217,003 A | 6/1993 | Wilk |
| 5,242,474 A | 9/1993 | Herbst et al. |
| 5,253,793 A | 10/1993 | Green et al. |
| 5,271,543 A | 12/1993 | Grant et al. |
| RE34,519 E | 1/1994 | Fox et al. |
| 5,275,323 A | 1/1994 | Schulze et al. |
| 5,318,516 A | 6/1994 | Cosmescu |
| 5,318,563 A | 6/1994 | Malis et al. |
| 5,322,055 A | 6/1994 | Davison et al. |
| 5,342,349 A | 8/1994 | Kaufman |
| 5,364,003 A | 11/1994 | Williamson, IV |
| 5,383,880 A | 1/1995 | Hooven |
| 5,385,544 A | 1/1995 | Edwards et al. |
| 5,396,900 A | 3/1995 | Slater et al. |
| 5,397,046 A | 3/1995 | Savage et al. |
| 5,403,312 A | 4/1995 | Yates et al. |
| 5,403,327 A | 4/1995 | Thornton et al. |
| 5,413,267 A | 5/1995 | Solyntjes et al. |
| 5,415,335 A | 5/1995 | Knodell, Jr. |
| 5,417,699 A | 5/1995 | Klein et al. |
| 5,439,468 A | 8/1995 | Schulze et al. |
| 5,445,304 A | 8/1995 | Plyley et al. |
| 5,462,545 A | 10/1995 | Wang et al. |
| 5,465,895 A | 11/1995 | Knodel et al. |
| 5,467,911 A | 11/1995 | Tsuruta et al. |
| 5,474,566 A | 12/1995 | Alesi et al. |
| 5,485,947 A | 1/1996 | Olson et al. |
| 5,496,315 A | 3/1996 | Weaver et al. |
| 5,496,317 A | 3/1996 | Goble et al. |
| 5,503,320 A | 4/1996 | Webster et al. |
| 5,529,235 A | 6/1996 | Boiarski et al. |
| 5,531,743 A | 7/1996 | Nettekoven et al. |
| 5,545,148 A | 8/1996 | Wurster |
| 5,552,685 A | 9/1996 | Young et al. |
| 5,560,372 A | 10/1996 | Cory |
| 5,584,425 A | 12/1996 | Savage et al. |
| 5,610,379 A | 3/1997 | Muz et al. |
| 5,610,811 A | 3/1997 | Honda |
| 5,613,966 A | 3/1997 | Makower et al. |
| 5,624,452 A | 4/1997 | Yates |
| D379,346 S | 5/1997 | Mieki |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,042 A | 12/1997 | Boiarski et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,724,468 A | 3/1998 | Leone et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,458 A | 6/1998 | Wang et al. |
| 5,766,186 A | 6/1998 | Faraz et al. |
| 5,769,791 A | 6/1998 | Benaron et al. |
| 5,775,331 A | 7/1998 | Raymond et al. |
| 5,797,537 A | 8/1998 | Oberlin et al. |
| 5,800,350 A | 9/1998 | Coppleson et al. |
| D399,561 S | 10/1998 | Ellingson |
| 5,817,093 A | 10/1998 | Williamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,869 A | 11/1998 | Kudo et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,987,346 A | 11/1999 | Benaron et al. |
| 5,997,528 A | 12/1999 | Bisch et al. |
| 6,004,269 A | 12/1999 | Crowley et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,102,907 A | 8/2000 | Smethers et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,131,789 A | 10/2000 | Schulze et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,269,411 B1 | 7/2001 | Reasoner |
| 6,273,887 B1 | 8/2001 | Yamauchi et al. |
| 6,283,960 B1 | 9/2001 | Ashley |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,331,181 B1 | 12/2001 | Tierney et al. |
| 6,341,164 B1 | 1/2002 | Dilkie et al. |
| 6,391,102 B1 | 5/2002 | Bodden et al. |
| 6,423,057 B1 | 7/2002 | He et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |

(56) References Cited

U.S. PATENT DOCUMENTS

| | | |
|---|---|---|
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,584,358 B2 | 6/2003 | Carter et al. |
| 6,585,791 B1 | 7/2003 | Garito et al. |
| 6,611,793 B1 | 8/2003 | Burnside et al. |
| 6,618,626 B2 | 9/2003 | West, Jr. et al. |
| 6,633,234 B2 | 10/2003 | Wiener et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,699,187 B2 | 3/2004 | Webb et al. |
| 6,731,514 B2 | 5/2004 | Evans |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,652 B1 | 9/2004 | Whitman et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,913,471 B2 | 7/2005 | Smith |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,009,511 B2 | 3/2006 | Mazar et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,044,949 B2 | 5/2006 | Orszulak et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 * | 9/2006 | Strong ............. H04L 12/40163 710/60 |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,207,472 B2 | 4/2007 | Wukusick et al. |
| 7,208,005 B2 | 4/2007 | Frecker et al. |
| 7,217,269 B2 | 5/2007 | El-Galley et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,252,664 B2 | 8/2007 | Nasab et al. |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,344,532 B2 | 3/2008 | Goble et al. |
| 7,353,068 B2 | 4/2008 | Tanaka et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,408,439 B2 | 8/2008 | Wang et al. |
| 7,422,136 B1 | 9/2008 | Marczyk |
| 7,422,139 B2 | 9/2008 | Shelton, IV et al. |
| 7,423,972 B2 | 9/2008 | Shaham et al. |
| D579,876 S | 11/2008 | Novotney et al. |
| 7,457,804 B2 | 11/2008 | Uber, III et al. |
| D583,328 S | 12/2008 | Chiang |
| 7,464,847 B2 | 12/2008 | Viola et al. |
| 7,464,849 B2 | 12/2008 | Shelton, IV et al. |
| 7,496,418 B2 | 2/2009 | Kim et al. |
| D589,447 S | 3/2009 | Sasada et al. |
| 7,515,961 B2 | 4/2009 | Germanson et al. |
| 7,518,502 B2 | 4/2009 | Austin et al. |
| 7,554,343 B2 | 6/2009 | Bromfield |
| 7,563,259 B2 | 7/2009 | Takahashi |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomla et al. |
| 7,631,793 B2 | 12/2009 | Rethy et al. |
| 7,637,410 B2 | 12/2009 | Marczyk |
| 7,637,907 B2 | 12/2009 | Blaha |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,757,028 B2 | 7/2010 | Druke et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |

(56) References Cited

U.S. PATENT DOCUMENTS

| | | | |
|---|---|---|---|
| 7,836,085 | B2 | 11/2010 | Petakov et al. |
| 7,837,079 | B2 | 11/2010 | Holsten et al. |
| 7,837,680 | B2 | 11/2010 | Isaacson et al. |
| 7,841,980 | B2 | 11/2010 | Minosawa et al. |
| 7,845,537 | B2 | 12/2010 | Shelton, IV et al. |
| 7,857,185 | B2 | 12/2010 | Swayze et al. |
| D631,252 | S | 1/2011 | Leslie |
| 7,862,560 | B2 | 1/2011 | Marion |
| 7,862,579 | B2 | 1/2011 | Ortiz et al. |
| 7,865,236 | B2 | 1/2011 | Cory et al. |
| 7,884,735 | B2 | 2/2011 | Newkirk |
| 7,887,530 | B2 | 2/2011 | Zemlok et al. |
| 7,892,337 | B2 | 2/2011 | Palmerton et al. |
| 7,907,166 | B2 | 3/2011 | Lamprecht et al. |
| 7,913,891 | B2 | 3/2011 | Doll et al. |
| 7,918,230 | B2 | 4/2011 | Whitman et al. |
| 7,918,377 | B2 | 4/2011 | Measamer et al. |
| 7,920,706 | B2 | 4/2011 | Asokan et al. |
| 7,927,014 | B2 | 4/2011 | Dehler |
| 7,932,826 | B2 | 4/2011 | Fritchie et al. |
| 7,942,300 | B2 | 5/2011 | Rethy et al. |
| 7,945,065 | B2 | 5/2011 | Menzl et al. |
| 7,945,342 | B2 | 5/2011 | Tsai et al. |
| 7,951,148 | B2 | 5/2011 | McClurken |
| 7,954,682 | B2 | 6/2011 | Giordano et al. |
| 7,955,322 | B2 | 6/2011 | Devengenzo et al. |
| 7,956,620 | B2 | 6/2011 | Gilbert |
| 7,963,433 | B2 | 6/2011 | Whitman et al. |
| 7,966,269 | B2 | 6/2011 | Bauer et al. |
| 7,967,180 | B2 | 6/2011 | Scirica |
| 7,976,553 | B2 | 7/2011 | Shelton, IV et al. |
| 7,979,157 | B2 | 7/2011 | Anvari |
| 7,980,443 | B2 | 7/2011 | Scheib et al. |
| 7,982,776 | B2 | 7/2011 | Dunki-Jacobs et al. |
| 7,988,028 | B2 | 8/2011 | Farascioni et al. |
| 7,993,140 | B2 | 8/2011 | Sakezles |
| 7,995,045 | B2 | 8/2011 | Dunki-Jacobs |
| 8,005,947 | B2 | 8/2011 | Morris et al. |
| 8,007,494 | B1 | 8/2011 | Taylor et al. |
| 8,007,513 | B2 | 8/2011 | Nalagatla et al. |
| 8,010,180 | B2 | 8/2011 | Quaid et al. |
| 8,012,170 | B2 | 9/2011 | Whitman et al. |
| 8,015,976 | B2 | 9/2011 | Shah |
| 8,016,855 | B2 | 9/2011 | Whitman et al. |
| 8,019,094 | B2 | 9/2011 | Hsieh et al. |
| 8,025,199 | B2 | 9/2011 | Whitman et al. |
| 8,027,710 | B1 | 9/2011 | Dannan |
| 8,035,685 | B2 | 10/2011 | Jensen |
| 8,038,686 | B2 | 10/2011 | Huitema et al. |
| 8,038,693 | B2 | 10/2011 | Allen |
| 8,043,560 | B2 | 10/2011 | Okumoto et al. |
| 8,054,184 | B2 | 11/2011 | Cline et al. |
| 8,054,752 | B2 | 11/2011 | Druke et al. |
| 8,062,306 | B2 | 11/2011 | Nobis et al. |
| 8,062,330 | B2 | 11/2011 | Prommersberger et al. |
| 8,066,721 | B2 | 11/2011 | Kortenbach et al. |
| 8,074,861 | B2 | 12/2011 | Ehrenfels et al. |
| 8,075,571 | B2 | 12/2011 | Vitali et al. |
| 8,096,459 | B2 | 1/2012 | Ortiz et al. |
| 8,118,206 | B2 | 2/2012 | Zand et al. |
| 8,120,301 | B2 | 2/2012 | Goldberg et al. |
| 8,123,764 | B2 | 2/2012 | Meade et al. |
| D655,678 | S | 3/2012 | Kobayashi et al. |
| 8,128,625 | B2 | 3/2012 | Odom |
| 8,131,565 | B2 | 3/2012 | Dicks et al. |
| 8,136,712 | B2 | 3/2012 | Zingman |
| D657,368 | S | 4/2012 | Magee et al. |
| 8,147,486 | B2 | 4/2012 | Honour et al. |
| 8,155,479 | B2 | 4/2012 | Hoffman et al. |
| 8,157,145 | B2 | 4/2012 | Shelton, IV et al. |
| 8,157,150 | B2 | 4/2012 | Viola et al. |
| 8,157,151 | B2 | 4/2012 | Ingmanson et al. |
| 8,160,098 | B1 | 4/2012 | Yan et al. |
| 8,160,690 | B2 | 4/2012 | Wilfley et al. |
| 8,161,977 | B2 | 4/2012 | Shelton, IV et al. |
| 8,170,396 | B2 | 5/2012 | Kuspa et al. |
| 8,172,836 | B2 | 5/2012 | Ward |
| 8,181,839 | B2 | 5/2012 | Beetel |
| 8,185,409 | B2 | 5/2012 | Putnam et al. |
| 8,206,345 | B2 | 6/2012 | Abboud et al. |
| 8,208,707 | B2 | 6/2012 | Mendonca et al. |
| 8,210,411 | B2 | 7/2012 | Yates et al. |
| 8,214,007 | B2 | 7/2012 | Baker et al. |
| 8,216,849 | B2 | 7/2012 | Petty |
| 8,220,688 | B2 | 7/2012 | Laurent et al. |
| 8,225,643 | B2 | 7/2012 | Abboud et al. |
| 8,225,979 | B2 | 7/2012 | Farascioni et al. |
| 8,229,549 | B2 | 7/2012 | Whitman et al. |
| 8,231,042 | B2 | 7/2012 | Hessler et al. |
| 8,239,066 | B2 | 8/2012 | Jennings et al. |
| 8,241,322 | B2 | 8/2012 | Whitman et al. |
| 8,255,045 | B2 | 8/2012 | Gharib et al. |
| D667,838 | S | 9/2012 | Magee et al. |
| 8,257,387 | B2 | 9/2012 | Cunningham |
| 8,260,016 | B2 | 9/2012 | Maeda et al. |
| 8,262,560 | B2 | 9/2012 | Whitman |
| 8,292,639 | B2 | 10/2012 | Achammer et al. |
| 8,292,888 | B2 | 10/2012 | Whitman |
| 8,295,902 | B2 | 10/2012 | Salahieh et al. |
| 8,308,040 | B2 | 11/2012 | Huang et al. |
| 8,321,581 | B2 | 11/2012 | Katis et al. |
| 8,322,590 | B2 | 12/2012 | Patel et al. |
| 8,328,065 | B2 | 12/2012 | Shah |
| 8,335,590 | B2 | 12/2012 | Costa et al. |
| D675,164 | S | 1/2013 | Kobayashi et al. |
| 8,343,065 | B2 | 1/2013 | Bartol et al. |
| 8,346,392 | B2 | 1/2013 | Walser et al. |
| 8,360,299 | B2 | 1/2013 | Zemlok et al. |
| 8,364,222 | B2 | 1/2013 | Cook et al. |
| D676,392 | S | 2/2013 | Gassauer |
| 8,365,975 | B1 | 2/2013 | Manoux et al. |
| D678,196 | S | 3/2013 | Miyauchi et al. |
| D678,304 | S | 3/2013 | Yakoub et al. |
| 8,388,652 | B2 | 3/2013 | Viola |
| 8,393,514 | B2 | 3/2013 | Shelton, IV et al. |
| 8,397,972 | B2 | 3/2013 | Kostrzewski |
| 8,398,541 | B2 | 3/2013 | DiMaio et al. |
| 8,403,944 | B2 | 3/2013 | Pain et al. |
| 8,403,945 | B2 | 3/2013 | Whitfield et al. |
| 8,403,946 | B2 | 3/2013 | Whitfield et al. |
| 8,406,859 | B2 | 3/2013 | Zuzak et al. |
| 8,411,034 | B2 | 4/2013 | Boillot et al. |
| 8,413,871 | B2 | 4/2013 | Racenet et al. |
| 8,422,035 | B2 | 4/2013 | Hinderling et al. |
| 8,423,182 | B2 | 4/2013 | Robinson et al. |
| 8,428,722 | B2 | 4/2013 | Verhoef et al. |
| 8,429,153 | B2 | 4/2013 | Birdwell et al. |
| 8,439,910 | B2 | 5/2013 | Greep et al. |
| 8,444,663 | B2 | 5/2013 | Houser et al. |
| 8,452,615 | B2 | 5/2013 | Abri |
| 8,454,506 | B2 | 6/2013 | Rothman et al. |
| 8,461,744 | B2 | 6/2013 | Wiener et al. |
| 8,468,030 | B2 | 6/2013 | Stroup et al. |
| 8,469,973 | B2 | 6/2013 | Meade et al. |
| 8,472,630 | B2 | 6/2013 | Konrad et al. |
| D687,146 | S | 7/2013 | Juzkiw et al. |
| 8,476,227 | B2 | 7/2013 | Kaplan et al. |
| 8,478,418 | B2 | 7/2013 | Fahey |
| 8,489,235 | B2 | 7/2013 | Moll et al. |
| 8,499,992 | B2 | 8/2013 | Whitman et al. |
| 8,500,728 | B2 | 8/2013 | Newton et al. |
| 8,500,756 | B2 | 8/2013 | Papa et al. |
| 8,503,759 | B2 | 8/2013 | Greer et al. |
| 8,505,801 | B2 | 8/2013 | Ehrenfels et al. |
| 8,506,478 | B2 | 8/2013 | Mizuyoshi |
| 8,512,325 | B2 | 8/2013 | Mathonnet |
| 8,512,365 | B2 | 8/2013 | Wener et al. |
| 8,515,520 | B2 | 8/2013 | Brunnett et al. |
| 8,517,239 | B2 | 8/2013 | Scheib et al. |
| 8,521,331 | B2 | 8/2013 | Itkowitz |
| 8,523,043 | B2 | 9/2013 | Ullrich et al. |
| 8,540,709 | B2 | 9/2013 | Allen |
| 8,546,996 | B2 | 10/2013 | Messerly et al. |
| 8,554,697 | B2 | 10/2013 | Claus et al. |

(56) References Cited

U.S. PATENT DOCUMENTS

| | | |
|---|---|---|
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,567,393 B2 | 10/2013 | Hickle et al. |
| 8,571,598 B2 | 10/2013 | Valavi |
| 8,573,459 B2 | 11/2013 | Smith et al. |
| 8,573,465 B2 | 11/2013 | Shelton, IV |
| 8,574,229 B2 | 11/2013 | Eder et al. |
| 8,585,631 B2 | 11/2013 | Dacquay |
| 8,585,694 B2 | 11/2013 | Amoah et al. |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,617,155 B2 | 12/2013 | Johnson et al. |
| 8,620,055 B2 | 12/2013 | Barratt et al. |
| 8,620,473 B2 | 12/2013 | Diolaiti et al. |
| 8,622,275 B2 | 1/2014 | Baxter, III et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wener et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| D704,839 S | 5/2014 | Juzkiw et al. |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,795,001 B1 | 8/2014 | Lam et al. |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,819,581 B2 | 8/2014 | Nakamura et al. |
| 8,820,603 B2 | 9/2014 | Shelton, IV et al. |
| 8,820,608 B2 | 9/2014 | Miyamoto |
| 8,827,134 B2 | 9/2014 | Viola et al. |
| 8,840,003 B2 | 9/2014 | Morgan et al. |
| D716,333 S | 10/2014 | Chotin et al. |
| 8,851,354 B2 | 10/2014 | Swensgard et al. |
| 8,852,174 B2 | 10/2014 | Burbank |
| 8,875,973 B2 | 11/2014 | Whitman |
| 8,876,857 B2 | 11/2014 | Burbank |
| 8,882,662 B2 | 11/2014 | Charles |
| 8,886,790 B2 | 11/2014 | Harrang et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,917,513 B1 | 12/2014 | Hazzard |
| 8,918,207 B2 | 12/2014 | Prisco |
| 8,920,186 B2 | 12/2014 | Shishikura |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,936,614 B2 | 1/2015 | Allen, IV |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,296 B2 | 3/2015 | McPherson |
| 8,968,309 B2 | 3/2015 | Roy et al. |
| 8,968,312 B2 | 3/2015 | Marczyk et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,288 B2 | 3/2015 | Konishi |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,608 B2 | 4/2015 | Casasanta, Jr. et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| D729,267 S | 5/2015 | Yoo et al. |
| 9,023,032 B2 | 5/2015 | Robinson |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,055,870 B2 | 6/2015 | Meador et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |

(56) References Cited

U.S. PATENT DOCUMENTS

| | | |
|---|---|---|
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,155,503 B2 | 10/2015 | Cadwell |
| 9,160,853 B1 | 10/2015 | Daddi et al. |
| 9,161,803 B2 | 10/2015 | Yates et al. |
| 9,168,054 B2 | 10/2015 | Turner et al. |
| 9,168,091 B2 | 10/2015 | Janssen et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,198,711 B2 | 12/2015 | Joseph |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,211,120 B2 | 12/2015 | Scheib et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,226,791 B2 | 1/2016 | McCarthy et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,265,429 B2 | 2/2016 | St. Pierre et al. |
| 9,265,585 B2 | 2/2016 | Wingardner et al. |
| 9,272,406 B2 | 3/2016 | Aronhalt et al. |
| 9,277,956 B2 | 3/2016 | Zhang |
| 9,277,961 B2 | 3/2016 | Panescu et al. |
| 9,277,969 B2 | 3/2016 | Brannan et al. |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,326,770 B2 | 5/2016 | Shelton, IV et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,900 B2 | 5/2016 | Wu et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Durie |
| 9,364,230 B2 | 6/2016 | Shelton, IV et al. |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,463,646 B2 | 10/2016 | Payne et al. |
| 9,468,438 B2 | 10/2016 | Baber et al. |
| 9,474,565 B2 | 10/2016 | Shikhman et al. |
| D772,252 S | 11/2016 | Myers et al. |
| 9,480,492 B2 | 11/2016 | Aranyi et al. |
| 9,485,475 B2 | 11/2016 | Speier et al. |
| 9,486,271 B2 | 11/2016 | Dunning |
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,231 B2 | 11/2016 | Haider et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |

(56) References Cited

U.S. PATENT DOCUMENTS

| | | |
|---|---|---|
| 9,526,587 B2 | 12/2016 | Zhao et al. |
| 9,532,827 B2 | 1/2017 | Morgan et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,561,082 B2 | 2/2017 | Yen et al. |
| 9,561,982 B2 | 2/2017 | Enicks et al. |
| 9,566,708 B2 | 2/2017 | Kurnianto |
| 9,572,592 B2 | 2/2017 | Price et al. |
| 9,579,099 B2 | 2/2017 | Penna et al. |
| 9,579,503 B2 | 2/2017 | McKinney et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,600,031 B2 | 3/2017 | Kaneko et al. |
| 9,600,138 B2 | 3/2017 | Thomas et al. |
| 9,603,024 B2 | 3/2017 | Wang et al. |
| 9,603,277 B2 | 3/2017 | Morgan et al. |
| D783,675 S | 4/2017 | Yagisawa et al. |
| D784,270 S | 4/2017 | Bhattacharya |
| 9,610,114 B2 | 4/2017 | Baxter, III et al. |
| 9,610,412 B2 | 4/2017 | Zemlok et al. |
| 9,615,877 B2 | 4/2017 | Tyrrell et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,112 B2 | 5/2017 | Penna et al. |
| 9,636,188 B2 | 5/2017 | Gattani et al. |
| 9,636,239 B2 | 5/2017 | Durand et al. |
| 9,636,825 B2 * | 5/2017 | Penn .................. B25J 13/08 |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 * | 6/2017 | Acquista .............. A61B 5/6823 |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,700,320 B2 | 7/2017 | Dinardo et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,713,503 B2 | 7/2017 | Goldschmidt |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,100 B2 | 8/2017 | Scheib et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,750,563 B2 | 9/2017 | Shikhman et al. |
| 9,753,135 B2 | 9/2017 | Bosch |
| 9,753,568 B2 | 9/2017 | McMillen |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,775,611 B2 | 10/2017 | Kostrzewski |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,835 B2 | 10/2017 | Morgan et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,833,254 B1 | 12/2017 | Barral et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,467 B2 | 12/2017 | Harper et al. |
| 9,839,470 B2 | 12/2017 | Gilbert et al. |
| 9,839,487 B2 | 12/2017 | Dachs, II |
| 9,844,321 B1 | 12/2017 | Ekvall et al. |
| 9,844,368 B2 | 12/2017 | Boudreaux et al. |

(56) References Cited

U.S. PATENT DOCUMENTS

| | | |
|---|---|---|
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,864,839 B2 | 1/2018 | Baym et al. |
| 9,867,612 B2 | 1/2018 | Parihar et al. |
| 9,867,651 B2 | 1/2018 | Wham |
| 9,867,670 B2 | 1/2018 | Brannan et al. |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondoni et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,196 B2 | 2/2018 | Susini et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,326 B2 | 3/2018 | Gilson et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,949,785 B2 | 4/2018 | Price et al. |
| 9,962,157 B2 | 5/2018 | Sapre |
| 9,968,355 B2 | 5/2018 | Shelton, IV et al. |
| 9,974,595 B2 | 5/2018 | Anderson et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,987,068 B2 | 6/2018 | Anderson et al. |
| 9,987,072 B2 | 6/2018 | McPherson |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,402 B1 | 7/2018 | Walker |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |
| 10,039,565 B2 | 8/2018 | Vezzu |
| 10,039,589 B2 | 8/2018 | Virshek et al. |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,092,355 B1 | 10/2018 | Hannaford et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,102,926 B1 | 10/2018 | Leonardi |
| 10,105,140 B2 | 10/2018 | Malinouskas et al. |
| 10,105,142 B2 | 10/2018 | Baxter, III et al. |
| 10,105,470 B2 | 10/2018 | Reasoner et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,111,703 B2 | 10/2018 | Cosman, Jr. et al. |
| D834,541 S | 11/2018 | You et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,136,954 B2 | 11/2018 | Johnson et al. |
| 10,137,245 B2 | 11/2018 | Melker et al. |
| 10,143,526 B2 | 12/2018 | Walker et al. |

(56) References Cited

U.S. PATENT DOCUMENTS

| | | |
|---|---|---|
| 10,143,948 B2 | 12/2018 | Bonifas et al. |
| 10,147,148 B2 | 12/2018 | Wu et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,166,061 B2 | 1/2019 | Berry et al. |
| 10,169,862 B2 | 1/2019 | Andre et al. |
| 10,172,618 B2 | 1/2019 | Shelton, IV et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,891 B2 | 2/2019 | Jeong et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,254 B2 | 3/2019 | Cabrera et al. |
| 10,226,302 B2 * | 3/2019 | Lacal .................. A61B 34/30 |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,245,040 B2 | 4/2019 | Milliman |
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,004 B2 | 4/2019 | Yamaguchi et al. |
| 10,265,035 B2 | 4/2019 | Fehre et al. |
| 10,265,066 B2 | 4/2019 | Measamer et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,769 B1 | 5/2019 | Yu |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,870 B2 | 5/2019 | Connolly et al. |
| 10,305,926 B2 | 5/2019 | Mihan et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,327,779 B2 | 6/2019 | Richard et al. |
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,339,496 B2 | 7/2019 | Matson et al. |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,939 B2 | 7/2019 | Shelton, IV et al. |
| 10,349,941 B2 | 7/2019 | Marczyk et al. |
| 10,350,016 B2 | 7/2019 | Burbank et al. |
| 10,357,184 B2 | 7/2019 | Crawford et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,386,990 B2 | 8/2019 | Shikhman et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |

(56) References Cited

U.S. PATENT DOCUMENTS

| | | |
|---|---|---|
| 10,404,521 B2 | 9/2019 | McChord et al. |
| 10,404,801 B2 | 9/2019 | Martch |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,847 B2 | 12/2019 | Latimer et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,512,413 B2 | 12/2019 | Schepis et al. |
| 10,512,461 B2 | 12/2019 | Gupta et al. |
| 10,512,499 B2 | 12/2019 | McHenry et al. |
| 10,512,514 B2 * | 12/2019 | Nowlin ............... A61B 34/30 |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,579 B2 | 1/2020 | Hsiao et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| D876,466 S | 2/2020 | Kobayashi et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,422 B2 | 2/2020 | Schellin et al. |
| 10,561,471 B2 | 2/2020 | Nichogi |
| 10,561,753 B2 | 2/2020 | Thompson et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savaii et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,964 B2 | 3/2020 | Weinberg et al. |
| 10,586,074 B2 | 3/2020 | Rose et al. |
| 10,588,623 B2 | 3/2020 | Schmid et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,007 B2 | 3/2020 | Takano |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,667 B2 | 4/2020 | Faller et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |

(56) References Cited

U.S. PATENT DOCUMENTS

| | | |
|---|---|---|
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,035 B2 | 6/2020 | Zingman |
| 10,675,100 B2 | 6/2020 | Frushour |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,055 B2 | 6/2020 | Shelton, IV et al. |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,702,271 B2 | 7/2020 | Aranyi et al. |
| 10,709,446 B2 | 7/2020 | Harris et al. |
| 10,716,489 B2 | 7/2020 | Kalvoy et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,233 B2 | 7/2020 | Wellman |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,733,267 B2 | 8/2020 | Pedersen |
| 10,736,219 B2 | 8/2020 | Seow et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,052 B2 | 8/2020 | Stokes et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| D896,379 S | 9/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,630 B2 | 9/2020 | Wixey |
| 10,772,651 B2 | 9/2020 | Shelton, IV et al. |
| 10,772,673 B2 | 9/2020 | Allen, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,317 B2 | 9/2020 | Zhou et al. |
| 10,786,327 B2 | 9/2020 | Anderson et al. |
| 10,792,038 B2 | 10/2020 | Becerra et al. |
| 10,792,118 B2 | 10/2020 | Prpa et al. |
| 10,792,422 B2 | 10/2020 | Douglas et al. |
| 10,799,304 B2 | 10/2020 | Kapadia et al. |
| 10,803,977 B2 | 10/2020 | Sanmugalingham |
| 10,806,445 B2 | 10/2020 | Penna et al. |
| 10,806,453 B2 | 10/2020 | Chen et al. |
| 10,806,454 B2 | 10/2020 | Kopp |
| 10,806,499 B2 | 10/2020 | Castaneda et al. |
| 10,806,506 B2 | 10/2020 | Gaspredes et al. |
| 10,806,532 B2 | 10/2020 | Grubbs et al. |
| 10,813,638 B2 | 10/2020 | Shelton, IV et al. |
| 10,813,703 B2 | 10/2020 | Swayze et al. |
| 10,818,383 B2 | 10/2020 | Sharifi Sedeh et al. |
| 10,828,028 B2 | 11/2020 | Harris et al. |
| 10,828,030 B2 | 11/2020 | Weir et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,842,473 B2 | 11/2020 | Scheib et al. |
| 10,842,490 B2 | 11/2020 | DiNardo et al. |
| 10,842,492 B2 | 11/2020 | Shelton, IV et al. |
| 10,842,522 B2 | 11/2020 | Messerly et al. |
| 10,842,523 B2 | 11/2020 | Shelton, IV et al. |
| 10,842,575 B2 | 11/2020 | Panescu et al. |
| 10,842,897 B2 | 11/2020 | Schwartz et al. |
| D904,612 S | 12/2020 | Wynn et al. |
| 10,849,697 B2 | 12/2020 | Yates et al. |
| 10,849,700 B2 | 12/2020 | Kopp et al. |
| 10,856,768 B2 | 12/2020 | Osadchy et al. |
| 10,856,867 B2 | 12/2020 | Shelton, IV et al. |
| 10,856,868 B2 | 12/2020 | Shelton, IV et al. |
| 10,856,870 B2 | 12/2020 | Harris et al. |
| 10,863,984 B2 | 12/2020 | Shelton, IV et al. |
| 10,864,037 B2 | 12/2020 | Mun et al. |
| 10,864,050 B2 | 12/2020 | Tabandeh et al. |
| 10,872,684 B2 | 12/2020 | McNutt et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,881,464 B2 | 1/2021 | Odermatt et al. |
| 10,888,321 B2 | 1/2021 | Shelton, IV et al. |
| 10,888,322 B2 | 1/2021 | Morgan et al. |
| 10,892,899 B2 | 1/2021 | Shelton, IV et al. |
| 10,892,995 B2 | 1/2021 | Shelton, IV et al. |
| 10,893,863 B2 | 1/2021 | Shelton, IV et al. |
| 10,893,864 B2 | 1/2021 | Harris et al. |
| 10,893,884 B2 | 1/2021 | Stoddard et al. |
| 10,898,183 B2 | 1/2021 | Shelton, IV et al. |
| 10,898,186 B2 | 1/2021 | Bakos et al. |
| 10,898,189 B2 | 1/2021 | McDonald, II |
| 10,898,256 B2 | 1/2021 | Yates et al. |
| 10,898,280 B2 | 1/2021 | Kopp |
| 10,898,622 B2 | 1/2021 | Shelton, IV et al. |
| 10,902,944 B1 | 1/2021 | Casey et al. |
| 10,903,685 B2 | 1/2021 | Yates et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,912,567 B2 | 2/2021 | Shelton, IV et al. |
| 10,916,415 B2 | 2/2021 | Karancsi et al. |
| D914,878 S | 3/2021 | Shelton, IV et al. |
| 10,932,784 B2 | 3/2021 | Mozdzierz et al. |
| 10,950,982 B2 | 3/2021 | Regnier et al. |
| 11,000,276 B2 | 5/2021 | Shelton, IV et al. |
| 11,051,817 B2 | 7/2021 | Shelton, IV et al. |
| 11,058,501 B2 | 7/2021 | Tokarchuk et al. |
| 11,071,595 B2 | 7/2021 | Johnson et al. |
| 11,141,213 B2 | 10/2021 | Yates et al. |
| 11,185,325 B2 | 11/2021 | Shelton, IV et al. |
| D950,728 S | 5/2022 | Bakos et al. |
| D952,144 S | 5/2022 | Boudreaux |
| 2001/0056237 A1 | 12/2001 | Cane et al. |
| 2002/0049551 A1 | 4/2002 | Friedman et al. |
| 2002/0052616 A1 | 5/2002 | Wiener et al. |
| 2002/0072746 A1 | 6/2002 | Lingenfelder et al. |
| 2002/0138642 A1 | 9/2002 | Miyazawa et al. |
| 2002/0169584 A1 | 11/2002 | Fu et al. |
| 2003/0009111 A1 | 1/2003 | Cory et al. |
| 2003/0018329 A1 | 1/2003 | Hooven |
| 2003/0046109 A1 | 3/2003 | Uchikubo |
| 2003/0069573 A1 | 4/2003 | Kadhiresan et al. |
| 2003/0093503 A1 | 5/2003 | Yamaki et al. |
| 2003/0114851 A1 | 6/2003 | Truckai et al. |
| 2003/0130711 A1 | 7/2003 | Pearson et al. |
| 2003/0210812 A1 | 11/2003 | Khamene et al. |

(56) References Cited

U.S. PATENT DOCUMENTS

| | | |
|---|---|---|
| 2003/0223877 A1 | 12/2003 | Anstine et al. |
| 2004/0015053 A1 | 1/2004 | Bieger et al. |
| 2004/0078236 A1 | 4/2004 | Stoodley et al. |
| 2004/0108825 A1 | 6/2004 | Lee et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0243147 A1 | 12/2004 | Lipow |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0020918 A1 | 1/2005 | Wilk et al. |
| 2005/0021027 A1 | 1/2005 | Shields et al. |
| 2005/0023324 A1 | 2/2005 | Doll et al. |
| 2005/0063575 A1 | 3/2005 | Ma et al. |
| 2005/0065438 A1 | 3/2005 | Miller |
| 2005/0100867 A1 | 5/2005 | Hilscher et al. |
| 2005/0131390 A1 | 6/2005 | Heinrich et al. |
| 2005/0143759 A1 | 6/2005 | Kelly |
| 2005/0149001 A1 | 7/2005 | Uchikubo et al. |
| 2005/0149356 A1 | 7/2005 | Cyr et al. |
| 2005/0165390 A1 | 7/2005 | Mauti et al. |
| 2005/0182655 A1 | 8/2005 | Merzlak et al. |
| 2005/0192633 A1 | 9/2005 | Montpetit |
| 2005/0203380 A1 | 9/2005 | Sauer et al. |
| 2005/0203384 A1 | 9/2005 | Sati et al. |
| 2005/0203504 A1 | 9/2005 | Wham et al. |
| 2005/0222631 A1 | 10/2005 | Dalal et al. |
| 2005/0228425 A1 | 10/2005 | Boukhny et al. |
| 2005/0236474 A1 | 10/2005 | Onuma et al. |
| 2005/0251233 A1 | 11/2005 | Kanzius |
| 2005/0277913 A1 | 12/2005 | McCary |
| 2006/0020272 A1 | 1/2006 | Gildenberg |
| 2006/0025816 A1 | 2/2006 | Shelton |
| 2006/0059018 A1 | 3/2006 | Shiobara et al. |
| 2006/0069388 A1 | 3/2006 | Truckai et al. |
| 2006/0079872 A1 | 4/2006 | Eggleston |
| 2006/0079874 A1 | 4/2006 | Faller et al. |
| 2006/0116908 A1 | 6/2006 | Dew et al. |
| 2006/0136622 A1 | 6/2006 | Rouvelin et al. |
| 2006/0184160 A1 | 8/2006 | Ozaki et al. |
| 2006/0241399 A1 | 10/2006 | Fabian |
| 2007/0010838 A1 | 1/2007 | Shelton et al. |
| 2007/0016235 A1 | 1/2007 | Tanaka et al. |
| 2007/0016979 A1 | 1/2007 | Damaj et al. |
| 2007/0027459 A1 | 2/2007 | Horvath et al. |
| 2007/0038080 A1 | 2/2007 | Salisbury et al. |
| 2007/0049947 A1 | 3/2007 | Menn et al. |
| 2007/0066970 A1 | 3/2007 | Ineson |
| 2007/0078678 A1 | 4/2007 | DiSilvestro et al. |
| 2007/0084896 A1 | 4/2007 | Doll et al. |
| 2007/0156019 A1 | 7/2007 | Larkin et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175955 A1 | 8/2007 | Shelton et al. |
| 2007/0179482 A1 | 8/2007 | Anderson |
| 2007/0179508 A1 | 8/2007 | Arndt |
| 2007/0191713 A1 | 8/2007 | Eichmann et al. |
| 2007/0203744 A1 | 8/2007 | Scholl |
| 2007/0225556 A1 | 9/2007 | Ortiz et al. |
| 2007/0225690 A1 | 9/2007 | Sekiguchi et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282195 A1 | 12/2007 | Masini et al. |
| 2007/0282321 A1 | 12/2007 | Shah et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0033404 A1 | 2/2008 | Romoda et al. |
| 2008/0040151 A1 | 2/2008 | Moore |
| 2008/0059658 A1 | 3/2008 | Williams |
| 2008/0077158 A1 | 3/2008 | Haider et al. |
| 2008/0083414 A1 | 4/2008 | Messerges |
| 2008/0091071 A1 | 4/2008 | Kumar et al. |
| 2008/0114212 A1 | 5/2008 | Messerges |
| 2008/0114350 A1 | 5/2008 | Park et al. |
| 2008/0129465 A1 | 6/2008 | Rao |
| 2008/0140090 A1 | 6/2008 | Aranyi et al. |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0234708 A1 | 9/2008 | Houser et al. |
| 2008/0255413 A1 | 10/2008 | Zemlok et al. |
| 2008/0262654 A1 | 10/2008 | Omori et al. |
| 2008/0272172 A1 | 11/2008 | Zemlok et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0017910 A1 | 1/2009 | Rofougaran et al. |
| 2009/0030437 A1 | 1/2009 | Houser et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0048611 A1 | 2/2009 | Funda et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0114699 A1 | 5/2009 | Viola |
| 2009/0128084 A1 | 5/2009 | Johnson et al. |
| 2009/0182577 A1 | 7/2009 | Squilla et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0299214 A1 | 12/2009 | Wu et al. |
| 2009/0306581 A1 | 12/2009 | Claus |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0036374 A1 | 2/2010 | Ward |
| 2010/0036405 A1 | 2/2010 | Giordano et al. |
| 2010/0038403 A1 | 2/2010 | D'Arcangelo |
| 2010/0057106 A1 | 3/2010 | Sorrentino et al. |
| 2010/0065604 A1 | 3/2010 | Weng |
| 2010/0069939 A1 | 3/2010 | Konishi |
| 2010/0069942 A1 | 3/2010 | Shelton, IV |
| 2010/0070417 A1 | 3/2010 | Flynn et al. |
| 2010/0120266 A1 | 5/2010 | Rimborg |
| 2010/0132334 A1 | 6/2010 | Duclos et al. |
| 2010/0137845 A1 | 6/2010 | Ramstein et al. |
| 2010/0137886 A1 | 6/2010 | Zergiebel et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0198200 A1 | 8/2010 | Horvath |
| 2010/0198248 A1 | 8/2010 | Vakharia |
| 2010/0204717 A1 | 8/2010 | Knodel |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0250571 A1 | 9/2010 | Pierce et al. |
| 2010/0258327 A1 | 10/2010 | Esenwein et al. |
| 2010/0292535 A1 | 11/2010 | Paskar |
| 2010/0292684 A1 | 11/2010 | Cybulski et al. |
| 2010/0301095 A1 | 12/2010 | Shelton, IV et al. |
| 2011/0022032 A1 | 1/2011 | Zemlok et al. |
| 2011/0036890 A1 | 2/2011 | Ma |
| 2011/0071530 A1 | 3/2011 | Carson |
| 2011/0077512 A1 | 3/2011 | Boswell |
| 2011/0087238 A1 | 4/2011 | Wang et al. |
| 2011/0105895 A1 | 5/2011 | Kornblau et al. |
| 2011/0112569 A1 | 5/2011 | Friedman et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |

(56) References Cited

U.S. PATENT DOCUMENTS

| | | |
|---|---|---|
| 2011/0152712 A1 | 6/2011 | Cao et al. |
| 2011/0163147 A1 | 7/2011 | Laurent et al. |
| 2011/0166883 A1 | 7/2011 | Palmer et al. |
| 2011/0196398 A1 | 8/2011 | Robertson et al. |
| 2011/0237883 A1 | 9/2011 | Chun |
| 2011/0251612 A1 | 10/2011 | Faller et al. |
| 2011/0264000 A1 | 10/2011 | Paul et al. |
| 2011/0264078 A1 | 10/2011 | Lipow et al. |
| 2011/0273465 A1 | 11/2011 | Konishi et al. |
| 2011/0278343 A1 | 11/2011 | Knodel et al. |
| 2011/0290024 A1 | 12/2011 | Lefler |
| 2011/0295270 A1 | 12/2011 | Giordano et al. |
| 2011/0306840 A1 | 12/2011 | Allen et al. |
| 2012/0021684 A1 | 1/2012 | Schultz et al. |
| 2012/0022519 A1 | 1/2012 | Huang et al. |
| 2012/0029354 A1 | 2/2012 | Mark et al. |
| 2012/0046662 A1 | 2/2012 | Gilbert |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0083786 A1 | 4/2012 | Artale et al. |
| 2012/0100517 A1 | 4/2012 | Bowditch et al. |
| 2012/0101488 A1 | 4/2012 | Aldridge et al. |
| 2012/0116265 A1 | 5/2012 | Houser et al. |
| 2012/0116381 A1 | 5/2012 | Houser et al. |
| 2012/0116394 A1 | 5/2012 | Timm et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0190981 A1 | 7/2012 | Harris et al. |
| 2012/0191091 A1 | 7/2012 | Allen |
| 2012/0191162 A1 | 7/2012 | Villa |
| 2012/0197619 A1 | 8/2012 | Namer Yelin et al. |
| 2012/0203785 A1 | 8/2012 | Awada |
| 2012/0211542 A1 | 8/2012 | Racenet |
| 2012/0226150 A1 | 9/2012 | Balicki et al. |
| 2012/0245958 A1 | 9/2012 | Lawrence et al. |
| 2012/0253329 A1 | 10/2012 | Zemlok et al. |
| 2012/0253847 A1 | 10/2012 | Dell'Anno et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0001121 A1 | 1/2013 | Metzger |
| 2013/0006241 A1 | 1/2013 | Takashino |
| 2013/0008677 A1 | 1/2013 | Huifu |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0046295 A1 | 2/2013 | Kerr et al. |
| 2013/0066647 A1 | 3/2013 | Andrie et al. |
| 2013/0090526 A1 | 4/2013 | Suzuki et al. |
| 2013/0093829 A1 | 4/2013 | Rosenblatt et al. |
| 2013/0096597 A1 | 4/2013 | Anand et al. |
| 2013/0116218 A1 | 5/2013 | Kaplan et al. |
| 2013/0144284 A1 | 6/2013 | Behnke, II et al. |
| 2013/0165776 A1 | 6/2013 | Blomqvist |
| 2013/0178853 A1 | 7/2013 | Hyink et al. |
| 2013/0191647 A1 | 7/2013 | Ferrara, Jr. et al. |
| 2013/0193188 A1 | 8/2013 | Shelton, IV et al. |
| 2013/0197531 A1 | 8/2013 | Boukhny et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0268283 A1 | 10/2013 | Vann et al. |
| 2013/0277410 A1 | 10/2013 | Fernandez et al. |
| 2013/0304256 A1* | 11/2013 | Moll ............... A61B 34/30 700/247 |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0006943 A1 | 1/2014 | Robbins et al. |
| 2014/0009894 A1 | 1/2014 | Yu |
| 2014/0013565 A1 | 1/2014 | MacDonald et al. |
| 2014/0018788 A1 | 1/2014 | Engelman et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0066700 A1 | 3/2014 | Wilson et al. |
| 2014/0073893 A1 | 3/2014 | Bencini |
| 2014/0074076 A1 | 3/2014 | Gertner |
| 2014/0081255 A1 | 3/2014 | Johnson et al. |
| 2014/0081659 A1* | 3/2014 | Nawana ............ A61B 5/4833 705/3 |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | Wiliam et al. |
| 2014/0121669 A1 | 5/2014 | Claus |
| 2014/0148729 A1 | 5/2014 | Schmitz et al. |
| 2014/0148803 A1 | 5/2014 | Taylor |
| 2014/0163359 A1 | 6/2014 | Sholev et al. |
| 2014/0166724 A1 | 6/2014 | Schellin et al. |
| 2014/0171778 A1 | 6/2014 | Tsusaka et al. |
| 2014/0187856 A1 | 7/2014 | Holoien et al. |
| 2014/0188131 A1* | 7/2014 | Toth ............... G16H 40/40 901/41 |
| 2014/0188440 A1 | 7/2014 | Donhowe et al. |
| 2014/0194864 A1 | 7/2014 | Martin et al. |
| 2014/0195052 A1 | 7/2014 | Tsusaka et al. |
| 2014/0204190 A1 | 7/2014 | Rosenblatt, III et al. |
| 2014/0226572 A1 | 8/2014 | Thota et al. |
| 2014/0243799 A1 | 8/2014 | Parihar |
| 2014/0243809 A1 | 8/2014 | Gelfand et al. |
| 2014/0243811 A1 | 8/2014 | Reschke et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0275760 A1 | 9/2014 | Lee et al. |
| 2014/0276749 A1 | 9/2014 | Johnson |
| 2014/0287393 A1 | 9/2014 | Kumar et al. |
| 2014/0303660 A1 | 10/2014 | Boyden et al. |
| 2014/0303990 A1 | 10/2014 | Schoenefeld et al. |
| 2014/0337052 A1 | 11/2014 | Pellini et al. |
| 2014/0364691 A1 | 12/2014 | Krivopisk et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051598 A1 | 2/2015 | Orszulak et al. |
| 2015/0051617 A1 | 2/2015 | Takemura et al. |
| 2015/0053737 A1 | 2/2015 | Leimbach et al. |
| 2015/0053743 A1 | 2/2015 | Yates et al. |
| 2015/0057675 A1 | 2/2015 | Akeel et al. |
| 2015/0066000 A1 | 3/2015 | An et al. |
| 2015/0070187 A1 | 3/2015 | Wesner et al. |
| 2015/0073400 A1 | 3/2015 | Sverdlik et al. |
| 2015/0077528 A1 | 3/2015 | Awdeh |
| 2015/0108198 A1 | 4/2015 | Estrella |
| 2015/0133945 A1 | 5/2015 | Dushyant et al. |
| 2015/0136833 A1 | 5/2015 | Shelton, IV et al. |
| 2015/0140982 A1* | 5/2015 | Postrel ............. H04L 67/18 455/418 |
| 2015/0145682 A1 | 5/2015 | Harris |
| 2015/0148830 A1 | 5/2015 | Stulen et al. |
| 2015/0157354 A1 | 6/2015 | Bales, Jr. et al. |
| 2015/0173673 A1 | 6/2015 | Toth et al. |
| 2015/0173756 A1 | 6/2015 | Baxter, III et al. |
| 2015/0182220 A1 | 7/2015 | Yates et al. |
| 2015/0196295 A1 | 7/2015 | Shelton, IV et al. |
| 2015/0199109 A1 | 7/2015 | Lee |
| 2015/0202014 A1 | 7/2015 | Kim et al. |
| 2015/0208934 A1 | 7/2015 | Sztrubel et al. |

(56) References Cited

U.S. PATENT DOCUMENTS

| | | |
|---|---|---|
| 2015/0223725 A1 | 8/2015 | Engel et al. |
| 2015/0223868 A1 | 8/2015 | Brandt et al. |
| 2015/0237502 A1 | 8/2015 | Schmidt et al. |
| 2015/0238355 A1 | 8/2015 | Vezzu et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272694 A1 | 10/2015 | Charles |
| 2015/0282821 A1 | 10/2015 | Look et al. |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0320423 A1 | 11/2015 | Aranyi |
| 2015/0324114 A1 | 11/2015 | Hurley et al. |
| 2015/0328474 A1 | 11/2015 | Flyash et al. |
| 2015/0332003 A1 | 11/2015 | Stamm et al. |
| 2015/0332196 A1 | 11/2015 | Stiller et al. |
| 2015/0335344 A1 | 11/2015 | Aljuri et al. |
| 2015/0374259 A1 | 12/2015 | Garbey et al. |
| 2015/0375398 A1* | 12/2015 | Penn .................. B25J 5/005 700/218 |
| 2016/0000437 A1 | 1/2016 | Giordano et al. |
| 2016/0001411 A1 | 1/2016 | Alberti |
| 2016/0015471 A1 | 1/2016 | Piron et al. |
| 2016/0022374 A1 | 1/2016 | Haider et al. |
| 2016/0034648 A1 | 2/2016 | Mohlenbrock et al. |
| 2016/0038253 A1 | 2/2016 | Piron et al. |
| 2016/0048780 A1 | 2/2016 | Sethumadhavan et al. |
| 2016/0058439 A1 | 3/2016 | Shelton, IV et al. |
| 2016/0066913 A1 | 3/2016 | Swayze et al. |
| 2016/0078190 A1 | 3/2016 | Greene et al. |
| 2016/0106516 A1 | 4/2016 | Mesallum |
| 2016/0106934 A1 | 4/2016 | Hiraga et al. |
| 2016/0121143 A1 | 5/2016 | Mumaw et al. |
| 2016/0157717 A1 | 6/2016 | Gaster |
| 2016/0158468 A1 | 6/2016 | Tang et al. |
| 2016/0174998 A1 | 6/2016 | Lal et al. |
| 2016/0175025 A1 | 6/2016 | Strobl |
| 2016/0180045 A1 | 6/2016 | Syed |
| 2016/0184054 A1 | 6/2016 | Lowe |
| 2016/0192960 A1 | 7/2016 | Bueno et al. |
| 2016/0206202 A1 | 7/2016 | Frangioni |
| 2016/0206362 A1 | 7/2016 | Mehta et al. |
| 2016/0224760 A1 | 8/2016 | Petak et al. |
| 2016/0225551 A1 | 8/2016 | Shedletsky |
| 2016/0228061 A1 | 8/2016 | Kallback et al. |
| 2016/0228204 A1 | 8/2016 | Quaid et al. |
| 2016/0235303 A1 | 8/2016 | Fleming et al. |
| 2016/0242836 A1 | 8/2016 | Eggers et al. |
| 2016/0249910 A1 | 9/2016 | Shelton, IV et al. |
| 2016/0249920 A1 | 9/2016 | Gupta et al. |
| 2016/0278841 A1 | 9/2016 | Panescu et al. |
| 2016/0287312 A1 | 10/2016 | Tegg et al. |
| 2016/0287316 A1 | 10/2016 | Worrell et al. |
| 2016/0287912 A1 | 10/2016 | Warnking |
| 2016/0292456 A1 | 10/2016 | Dubey et al. |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0310204 A1 | 10/2016 | McHenry et al. |
| 2016/0314716 A1 | 10/2016 | Grubbs |
| 2016/0314717 A1 | 10/2016 | Grubbs |
| 2016/0321400 A1 | 11/2016 | Durrant et al. |
| 2016/0323283 A1 | 11/2016 | Kang et al. |
| 2016/0324537 A1 | 11/2016 | Green et al. |
| 2016/0331460 A1 | 11/2016 | Cheatham, III et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0345976 A1 | 12/2016 | Gonzalez et al. |
| 2016/0350490 A1 | 12/2016 | Martinez et al. |
| 2016/0354162 A1 | 12/2016 | Yen et al. |
| 2016/0361070 A1 | 12/2016 | Ardel et al. |
| 2016/0367305 A1 | 12/2016 | Hareland |
| 2016/0367401 A1 | 12/2016 | Claus |
| 2016/0374723 A1 | 12/2016 | Frankhouser et al. |
| 2016/0374762 A1 | 12/2016 | Case et al. |
| 2016/0379504 A1 | 12/2016 | Bailey et al. |
| 2017/0000516 A1 | 1/2017 | Stolen et al. |
| 2017/0000553 A1 | 1/2017 | Wiener et al. |
| 2017/0027603 A1 | 2/2017 | Pandey |
| 2017/0042604 A1 | 2/2017 | McFarland et al. |
| 2017/0068792 A1 | 3/2017 | Reiner |
| 2017/0079530 A1 | 3/2017 | DiMaio et al. |
| 2017/0079730 A1 | 3/2017 | Azizian et al. |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0116873 A1 | 4/2017 | Lendvay et al. |
| 2017/0127499 A1 | 5/2017 | Unoson et al. |
| 2017/0132374 A1 | 5/2017 | Lee et al. |
| 2017/0132385 A1 | 5/2017 | Hunter et al. |
| 2017/0132785 A1 | 5/2017 | Wshah et al. |
| 2017/0143284 A1 | 5/2017 | Sehnert et al. |
| 2017/0143442 A1 | 5/2017 | Tesar et al. |
| 2017/0156076 A1 | 6/2017 | Eom et al. |
| 2017/0164997 A1 | 6/2017 | Johnson et al. |
| 2017/0165008 A1 | 6/2017 | Finley |
| 2017/0165012 A1 | 6/2017 | Chaplin et al. |
| 2017/0172550 A1 | 6/2017 | Mukherjee et al. |
| 2017/0172565 A1 | 6/2017 | Heneveld |
| 2017/0172614 A1 | 6/2017 | Scheib et al. |
| 2017/0173262 A1 | 6/2017 | Veltz |
| 2017/0177807 A1 | 6/2017 | Fabian |
| 2017/0196583 A1 | 7/2017 | Sugiyama |
| 2017/0196637 A1 | 7/2017 | Shelton, IV et al. |
| 2017/0202591 A1 | 7/2017 | Shelton, IV et al. |
| 2017/0202595 A1 | 7/2017 | Shelton, IV |
| 2017/0202607 A1 | 7/2017 | Shelton, IV et al. |
| 2017/0202608 A1 | 7/2017 | Shelton, IV et al. |
| 2017/0215944 A1 | 8/2017 | Keffeler |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231627 A1 | 8/2017 | Shelton, IV et al. |
| 2017/0231628 A1 | 8/2017 | Shelton, IV et al. |
| 2017/0245809 A1 | 8/2017 | Ma et al. |
| 2017/0249431 A1 | 8/2017 | Shelton, IV et al. |
| 2017/0249432 A1 | 8/2017 | Grantcharov |
| 2017/0262604 A1 | 9/2017 | Francois |
| 2017/0265864 A1 | 9/2017 | Hessler et al. |
| 2017/0265943 A1 | 9/2017 | Sela et al. |
| 2017/0273715 A1 | 9/2017 | Piron et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowskl |
| 2017/0304007 A1 | 10/2017 | Piron et al. |
| 2017/0304020 A1 | 10/2017 | Ng et al. |
| 2017/0311777 A1 | 11/2017 | Hirayama et al. |
| 2017/0312456 A1 | 11/2017 | Phillips |
| 2017/0325876 A1 | 11/2017 | Nakadate et al. |
| 2017/0325878 A1 | 11/2017 | Messerly et al. |
| 2017/0337043 A1 | 11/2017 | Brincat et al. |
| 2017/0360358 A1 | 12/2017 | Amiot et al. |
| 2017/0360499 A1 | 12/2017 | Greep et al. |
| 2017/0367583 A1 | 12/2017 | Black et al. |
| 2017/0367695 A1 | 12/2017 | Shelton, IV et al. |
| 2017/0367754 A1 | 12/2017 | Narisawa |
| 2017/0367771 A1 | 12/2017 | Tako et al. |
| 2017/0367772 A1 | 12/2017 | Gunn et al. |

(56) References Cited

U.S. PATENT DOCUMENTS

| | | |
|---|---|---|
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0021058 A1 | 1/2018 | Meglan |
| 2018/0042659 A1 | 2/2018 | Rupp et al. |
| 2018/0050196 A1 | 2/2018 | Pawsey et al. |
| 2018/0052971 A1 | 2/2018 | Hanina et al. |
| 2018/0055529 A1 | 3/2018 | Messerly et al. |
| 2018/0065248 A1 | 3/2018 | Barral et al. |
| 2018/0078170 A1 | 3/2018 | Panescu et al. |
| 2018/0098816 A1 | 4/2018 | Govari et al. |
| 2018/0108438 A1 | 4/2018 | Ryan et al. |
| 2018/0110523 A1 | 4/2018 | Shelton, IV |
| 2018/0116662 A1 | 5/2018 | Shelton, IV et al. |
| 2018/0116735 A1* | 5/2018 | Tierney .................. G16H 40/63 |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0144243 A1 | 5/2018 | Hsieh et al. |
| 2018/0153574 A1 | 6/2018 | Faller et al. |
| 2018/0153628 A1 | 6/2018 | Grover et al. |
| 2018/0153632 A1 | 6/2018 | Tokarchuk et al. |
| 2018/0154297 A1 | 6/2018 | Maletich et al. |
| 2018/0161062 A1 | 6/2018 | Kaga et al. |
| 2018/0161716 A1 | 6/2018 | Li et al. |
| 2018/0165780 A1 | 6/2018 | Romeo |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168586 A1 | 6/2018 | Shelton, IV et al. |
| 2018/0168590 A1 | 6/2018 | Overmyer et al. |
| 2018/0168592 A1 | 6/2018 | Overmyer et al. |
| 2018/0168593 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168627 A1 | 6/2018 | Weaner et al. |
| 2018/0168628 A1 | 6/2018 | Hunter et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0177383 A1 | 6/2018 | Noonan et al. |
| 2018/0182475 A1 | 6/2018 | Cossler et al. |
| 2018/0193579 A1 | 7/2018 | Hanrahan et al. |
| 2018/0206884 A1 | 7/2018 | Beaupre |
| 2018/0206905 A1 | 7/2018 | Batchelor et al. |
| 2018/0211726 A1 | 7/2018 | Courtemanche et al. |
| 2018/0214025 A1 | 8/2018 | Homyk et al. |
| 2018/0221005 A1 | 8/2018 | Hamel et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0235719 A1 | 8/2018 | Jarc |
| 2018/0235722 A1 | 8/2018 | Baghdadi et al. |
| 2018/0242967 A1 | 8/2018 | Meade |
| 2018/0247128 A1 | 8/2018 | Alvi et al. |
| 2018/0247711 A1 | 8/2018 | Terry |
| 2018/0250086 A1 | 9/2018 | Grubbs |
| 2018/0263699 A1 | 9/2018 | Murphy et al. |
| 2018/0263710 A1 | 9/2018 | Sakaguchi et al. |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0289427 A1 | 10/2018 | Griffiths et al. |
| 2018/0294060 A1 | 10/2018 | Kassab |
| 2018/0296286 A1 | 10/2018 | Peine et al. |
| 2018/0303552 A1 | 10/2018 | Ryan et al. |
| 2018/0304471 A1 | 10/2018 | Tokuchi |
| 2018/0310935 A1 | 11/2018 | Wixey |
| 2018/0310986 A1 | 11/2018 | Batchelor et al. |
| 2018/0315492 A1 | 11/2018 | Bishop et al. |
| 2018/0317826 A1 | 11/2018 | Muhsin et al. |
| 2018/0333188 A1 | 11/2018 | Nott et al. |
| 2018/0333207 A1 | 11/2018 | Moctezuma De la Barrera |
| 2018/0333209 A1 | 11/2018 | Frushour et al. |
| 2018/0351987 A1 | 12/2018 | Patel et al. |
| 2018/0353186 A1 | 12/2018 | Mozdzierz et al. |
| 2018/0357383 A1 | 12/2018 | Allen et al. |
| 2018/0360454 A1 | 12/2018 | Shelton, IV et al. |
| 2018/0360456 A1 | 12/2018 | Shelton, IV et al. |
| 2018/0366213 A1 | 12/2018 | Fidone et al. |
| 2018/0368930 A1 | 12/2018 | Esterberg et al. |
| 2018/0369511 A1 | 12/2018 | Zergiebel et al. |
| 2019/0000446 A1 | 1/2019 | Shelton, IV et al. |
| 2019/0000478 A1 | 1/2019 | Messerly et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreasen et al. |
| 2019/0036688 A1 | 1/2019 | Wasily et al. |
| 2019/0038335 A1* | 2/2019 | Mohr .................. A61B 18/1206 |
| 2019/0038364 A1 | 2/2019 | Enoki |
| 2019/0046198 A1 | 2/2019 | Stokes et al. |
| 2019/0053801 A1 | 2/2019 | Wixey et al. |
| 2019/0053866 A1 | 2/2019 | Seow et al. |
| 2019/0059986 A1 | 2/2019 | Shelton, IV et al. |
| 2019/0069949 A1 | 3/2019 | Vrba et al. |
| 2019/0069964 A1 | 3/2019 | Hagn |
| 2019/0069966 A1 | 3/2019 | Petersen et al. |
| 2019/0070550 A1 | 3/2019 | Lalomia et al. |
| 2019/0070731 A1 | 3/2019 | Bowling et al. |
| 2019/0083190 A1 | 3/2019 | Graves et al. |
| 2019/0087544 A1 | 3/2019 | Peterson |
| 2019/0090969 A1 | 3/2019 | Jarc et al. |
| 2019/0099221 A1 | 4/2019 | Schmidt et al. |
| 2019/0104919 A1 | 4/2019 | Shelton, IV et al. |
| 2019/0110828 A1 | 4/2019 | Despatie |
| 2019/0110855 A1 | 4/2019 | Barral et al. |
| 2019/0115108 A1 | 4/2019 | Hegedus et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125337 A1 | 5/2019 | Shelton, IV et al. |
| 2019/0125338 A1 | 5/2019 | Shelton, IV et al. |
| 2019/0125339 A1 | 5/2019 | Shelton, IV et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125383 A1 | 5/2019 | Scheib et al. |
| 2019/0125384 A1 | 5/2019 | Scheib et al. |
| 2019/0125385 A1 | 5/2019 | Scheib et al. |
| 2019/0125386 A1 | 5/2019 | Shelton, IV et al. |
| 2019/0125387 A1 | 5/2019 | Parihar et al. |

(56) References Cited

U.S. PATENT DOCUMENTS

| | | |
|---|---|---|
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142449 A1 | 5/2019 | Shelton, IV et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159777 A1 | 5/2019 | Ehrenfels et al. |
| 2019/0159778 A1 | 5/2019 | Shelton, IV et al. |
| 2019/0162179 A1 | 5/2019 | O'Shea et al. |
| 2019/0163875 A1 | 5/2019 | Allen et al. |
| 2019/0167296 A1 | 6/2019 | Tsubuku et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201119 A1 | 7/2019 | Harris et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201144 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206216 A1 | 7/2019 | Shelton, IV et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0207911 A1 | 7/2019 | Wiener et al. |
| 2019/0208641 A1 | 7/2019 | Yates et al. |
| 2019/0224434 A1 | 7/2019 | Silver et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cutl et al. |
| 2019/0274716 A1 | 9/2019 | Nott et al. |
| 2019/0274717 A1 | 9/2019 | Nott et al. |

(56) References Cited

U.S. PATENT DOCUMENTS

| | | |
|---|---|---|
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0278262 A1 | 9/2019 | Taylor et al. |
| 2019/0282311 A1 | 9/2019 | Nowlin et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298351 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0298481 A1 | 10/2019 | Rosenberg et al. |
| 2019/0307520 A1 | 10/2019 | Peine et al. |
| 2019/0311802 A1 | 10/2019 | Kokubo et al. |
| 2019/0314015 A1 | 10/2019 | Shelton, IV et al. |
| 2019/0314016 A1 | 10/2019 | Huitema et al. |
| 2019/0314081 A1 | 10/2019 | Brogna |
| 2019/0320929 A1 | 10/2019 | Spencer et al. |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0374140 A1 | 12/2019 | Tucker et al. |
| 2019/0374292 A1 | 12/2019 | Barral et al. |
| 2019/0378610 A1 | 12/2019 | Barral et al. |
| 2020/0000470 A1 | 1/2020 | Du et al. |
| 2020/0000509 A1 | 1/2020 | Hayashida et al. |
| 2020/0038120 A1 | 2/2020 | Ziraknejad et al. |
| 2020/0046353 A1 | 2/2020 | Deck et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054326 A1 | 2/2020 | Harris et al. |
| 2020/0054327 A1 | 2/2020 | Harris et al. |
| 2020/0054328 A1 | 2/2020 | Harris et al. |
| 2020/0054330 A1 | 2/2020 | Harris et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078096 A1 | 3/2020 | Barbagli et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |
| 2020/0178760 A1 | 6/2020 | Kashima et al. |
| 2020/0178971 A1 | 6/2020 | Harris et al. |
| 2020/0193600 A1 | 6/2020 | Shameli et al. |
| 2020/0197027 A1 | 6/2020 | Hershberger et al. |
| 2020/0203004 A1 | 6/2020 | Shanbhag et al. |
| 2020/0214699 A1 | 7/2020 | Shelton, IV et al. |
| 2020/0226751 A1 | 7/2020 | Jin et al. |
| 2020/0237372 A1 | 7/2020 | Park |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0305924 A1 | 10/2020 | Carroll |
| 2020/0305945 A1 | 10/2020 | Morgan et al. |
| 2020/0314569 A1 | 10/2020 | Morgan et al. |
| 2020/0348662 A1 | 11/2020 | Cella et al. |
| 2020/0405304 A1 | 12/2020 | Mozdzierz et al. |
| 2020/0405375 A1 | 12/2020 | Shelton, IV et al. |
| 2021/0000555 A1 | 1/2021 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |
| 2021/0068834 A1 | 3/2021 | Shelton, IV et al. |
| 2021/0076966 A1* | 3/2021 | Grantcharov .......... G06N 20/00 |
| 2021/0128149 A1 | 5/2021 | Whitfield et al. |
| 2021/0153889 A1 | 5/2021 | Nott et al. |
| 2021/0169516 A1 | 6/2021 | Houser et al. |
| 2021/0176179 A1 | 6/2021 | Shelton, IV |
| 2021/0177452 A1 | 6/2021 | Nott et al. |
| 2021/0177489 A1 | 6/2021 | Yates et al. |
| 2021/0186454 A1 | 6/2021 | Behzadi et al. |
| 2021/0192914 A1 | 6/2021 | Shelton, IV et al. |
| 2021/0201646 A1 | 7/2021 | Shelton, IV et al. |
| 2021/0205020 A1 | 7/2021 | Shelton, IV et al. |
| 2021/0205021 A1 | 7/2021 | Shelton, IV et al. |
| 2021/0205028 A1 | 7/2021 | Shelton, IV et al. |
| 2021/0205029 A1 | 7/2021 | Wiener et al. |
| 2021/0205030 A1 | 7/2021 | Shelton, IV et al. |
| 2021/0205031 A1 | 7/2021 | Shelton, IV et al. |
| 2021/0212602 A1 | 7/2021 | Shelton, IV et al. |
| 2021/0212694 A1 | 7/2021 | Shelton, IV et al. |
| 2021/0212717 A1 | 7/2021 | Yates et al. |
| 2021/0212719 A1 | 7/2021 | Houser et al. |
| 2021/0212770 A1 | 7/2021 | Messerly et al. |
| 2021/0212771 A1 | 7/2021 | Shelton, IV et al. |
| 2021/0212774 A1 | 7/2021 | Shelton, IV et al. |
| 2021/0212775 A1 | 7/2021 | Shelton, IV et al. |
| 2021/0212782 A1 | 7/2021 | Shelton, IV et al. |
| 2021/0219976 A1 | 7/2021 | DiNardo et al. |
| 2021/0220058 A1 | 7/2021 | Messerly et al. |
| 2021/0240852 A1 | 8/2021 | Shelton, IV et al. |
| 2021/0241898 A1 | 8/2021 | Shelton, IV et al. |
| 2021/0249125 A1 | 8/2021 | Morgan et al. |
| 2021/0251487 A1 | 8/2021 | Shelton, IV et al. |
| 2021/0259687 A1 | 8/2021 | Gonzalez et al. |
| 2021/0259697 A1 | 8/2021 | Shelton, IV et al. |
| 2021/0259698 A1 | 8/2021 | Shelton, IV et al. |
| 2021/0282780 A1 | 9/2021 | Shelton, IV et al. |

(56) References Cited

U.S. PATENT DOCUMENTS

| | | |
|---|---|---|
| 2021/0282781 A1 | 9/2021 | Shelton, IV et al. |
| 2021/0306176 A1 | 9/2021 | Park et al. |
| 2021/0315579 A1 | 10/2021 | Shelton, IV et al. |
| 2021/0315580 A1 | 10/2021 | Shelton, IV et al. |
| 2021/0315581 A1 | 10/2021 | Shelton, IV et al. |
| 2021/0315582 A1 | 10/2021 | Shelton, IV et al. |
| 2021/0322014 A1 | 10/2021 | Shelton, IV et al. |
| 2021/0322015 A1 | 10/2021 | Shelton, IV et al. |
| 2021/0322017 A1 | 10/2021 | Shelton, IV et al. |
| 2021/0322018 A1 | 10/2021 | Shelton, IV et al. |
| 2021/0322019 A1 | 10/2021 | Shelton, IV et al. |
| 2021/0322020 A1 | 10/2021 | Shelton, IV et al. |
| 2021/0336939 A1 | 10/2021 | Wiener et al. |
| 2021/0353287 A1 | 11/2021 | Shelton, IV et al. |
| 2021/0353288 A1 | 11/2021 | Shelton, IV et al. |
| 2021/0358599 A1 | 11/2021 | Alvi et al. |
| 2021/0361284 A1 | 11/2021 | Shelton, IV et al. |
| 2022/0000484 A1 | 1/2022 | Shelton, IV et al. |
| 2022/0054158 A1 | 2/2022 | Shelton, IV et al. |
| 2022/0079591 A1 | 3/2022 | Bakos et al. |
| 2022/0160438 A1 | 5/2022 | Shelton, IV et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| CN | 108652695 A | 10/2018 |
| DE | 2037167 A1 | 7/1980 |
| DE | 3016131 A1 | 10/1981 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 0408160 A1 | 1/1991 |
| EP | 0473987 A1 | 3/1992 |
| EP | 0929263 B1 | 7/1999 |
| EP | 1214913 A2 | 6/2002 |
| EP | 2730209 A1 | 5/2014 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| FR | 2838234 A1 | 10/2003 |
| GB | 2509523 A | 7/2014 |
| JP | S5373315 A | 6/1978 |
| JP | 2001029353 A | 2/2001 |
| JP | 2007123394 A | 5/2007 |
| JP | 2010057642 A | 3/2010 |
| JP | 2017513561 A | 6/2017 |
| KR | 20140104587 A | 8/2014 |
| KR | 101587721 B1 | 1/2016 |
| WO | WO-9734533 A1 | 9/1997 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-03079909 A2 | 10/2003 |
| WO | WO-2007137304 A2 | 11/2007 |
| WO | WO-2008053485 A1 | 5/2008 |
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014031800 A1 | 2/2014 |
| WO | WO-2014071184 A1 | 5/2014 |
| WO | WO-2014134196 A1 | 9/2014 |
| WO | WO-2015129395 A1 | 9/2015 |
| WO | WO-2016100719 A1 | 6/2016 |
| WO | WO-2016118752 A1 | 7/2016 |
| WO | WO-2016206015 A1 | 12/2016 |
| WO | WO-2017011382 A1 | 1/2017 |
| WO | WO-2017011646 A1 | 1/2017 |
| WO | WO-2017058617 | 4/2017 |
| WO | WO-2017058695 A1 | 4/2017 |
| WO | WO-2017151996 A1 | 9/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018116247 A1 | 6/2018 |
| WO | WO-2018152141 A1 | 8/2018 |
| WO | WO-2018176414 A1 | 10/2018 |

OTHER PUBLICATIONS

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

Khazaei et al., "Health Informatics for Neonatal Intensive Care Units: An Analytical Modeling Perspective, IEEE Journal of Translational Engineering in Health and Medicine," vol. 3, pp. 1-9, Oct. 21, 2015.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.

Miksch et al., "Utilizing temporal data abstraction for data validation and therapy planning for artificially ventilated newborn infants," Artificial Intelligence in Medicine, vol. 8, No. 6, pp. 543-576 (1996).

Horn et al., "Effective data validation of high-frequency data: Time-point-time-interval-, and trend-based methods," Computers in Biology and Medic, New York, NY, vol. 27, No. 5, pp. 389-409 (1997).

Stacey et al., "Temporal abstraction in intelligent clinical data analysis: A survey," Artificial Intelligence in Medicine, vol. 39, No. 1, pp. 1-24 (2006).

Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Takahashi et al., "Automatic smoke evacuation in laparoscopic surgery: a simplified method for objective evaluation," Surgical Endoscopy, vol. 27, No. 8, pp. 2980-2987, Feb. 23, 2013.

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Slocinski et al., "Distance measure for impedance spectra for quantified evaluations," Lecture Notes on Impedance Spectroscopy, vol. 3, Taylor and Francis Group (Jul. 2012)—Book Not Attached.

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].

(56) References Cited

OTHER PUBLICATIONS

Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.
Phumzile Malindi, "5. QoS in Telemedicine," "Telemedicine," Jun. 20, 2011, IntechOpen, pp. 119-138.
Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.
Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.
Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.
Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.
Altenberg et al., "Genes of Glycolysis are Ubiquitously Overexpressed in 24 Cancer Classes," Genomics, vol. 84, pp. 1014-1020 (2004).
Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).
Marshall Brain, How Microcontrollers Work, 2006, retrieved from the internet <https://web.archive.org/web/20060221235221/http://electronics.howstuffworks.com/microcontroller.htm/printable> (Year: 2006).
CRC Press, "The Measurement, Instrumentation and Sensors Handbook," 1999, Section VII, Chapter 41, Peter O'Shea, "Phase Measurement," pp. 1303-1321, ISBN 0-8493-2145-X.
Jiang, "'Sound of Silence' : a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.
Dottorato, "Analysis and Design of the Rectangular Microstrip Patch Antennas for TM0n0 operating mode,"Article, Oct. 8, 2010, pp. 1-9, Microwave Journal.
Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.
Hsiao-Wei Tang, "ARCM", Video, Sep. 2012, YouTube, 5 screenshots, Retrieved from internet: <https://www.youtube.com/watch?v=UldQaxb3fRw&feature=youtu.be>.
Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.
Vander Heiden, et al., "Understanding the Warburg effect: the metabolic requirements of cell proliferation," Article, May 22, 2009, pp. 1-12, vol. 324, Issue 5930, Science.
Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.
Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.
Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.
"ATM-MPLS Network Interworking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.
IEEE Std No. 177, "Standard Definitions and Methods of Measurement for Piezoelectric Vibrators," published May 1966, The Institute of Electrical and Electronics Engineers, Inc., New York, N.Y.
Shi et al., An Intuitive control console for robotic syrgery system, 2014, IEEE, p. 404-407 (Year: 2014).
Choi et al., A haptic augmented reality surgeon console for a laparoscopic surgery robot system, 2013, IEEE, p. 355-357 (Year: 2013).
Xie et al., Development of stereo vision and master-slave controller for a compact surgical robot system, 2015, IEEE, p. 403-407 (Year: 2015).
Sun et al., Innovative effector design for simulation training in robotic surgery, 2010, IEEE, p. 1735-1759 (Year: 2010).
Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.
Draijer, Matthijs et al., "Review of laser pseckle contrast techniques for visualizing tissue perfusion," Lasers in Medical Science, Springer-Verlag, LO, vol. 24, No. 4, Dec. 3, 2008, pp. 639-651.
Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.
"Surgical instrumentation: the true cost of instrument trays and a potential strategy for optimization"; Mhlaba et al.; Sep. 23, 2015 (Year: 2015).
Nabil Simaan et al, "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.
Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.
Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].
Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.
Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).
Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

\* cited by examiner

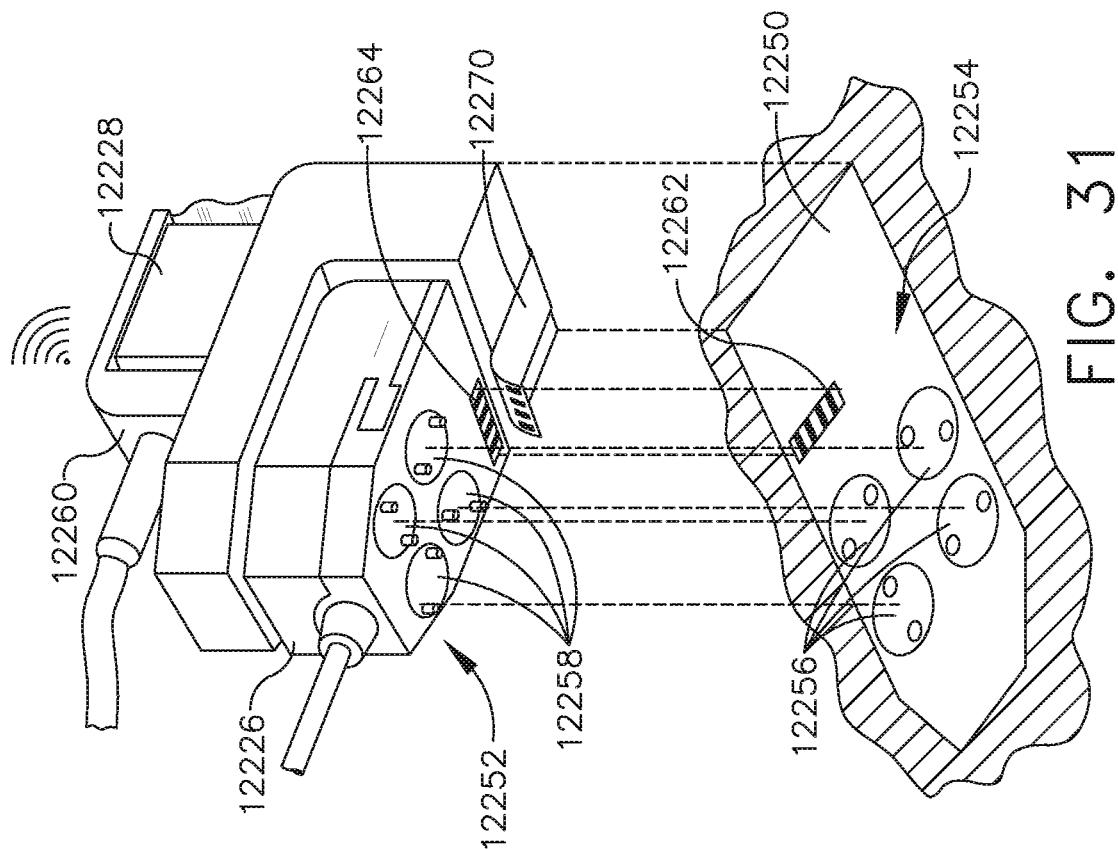
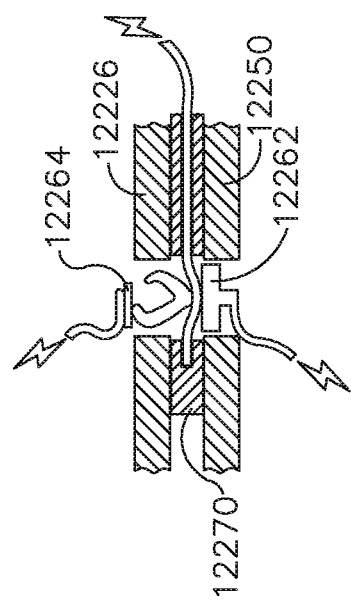

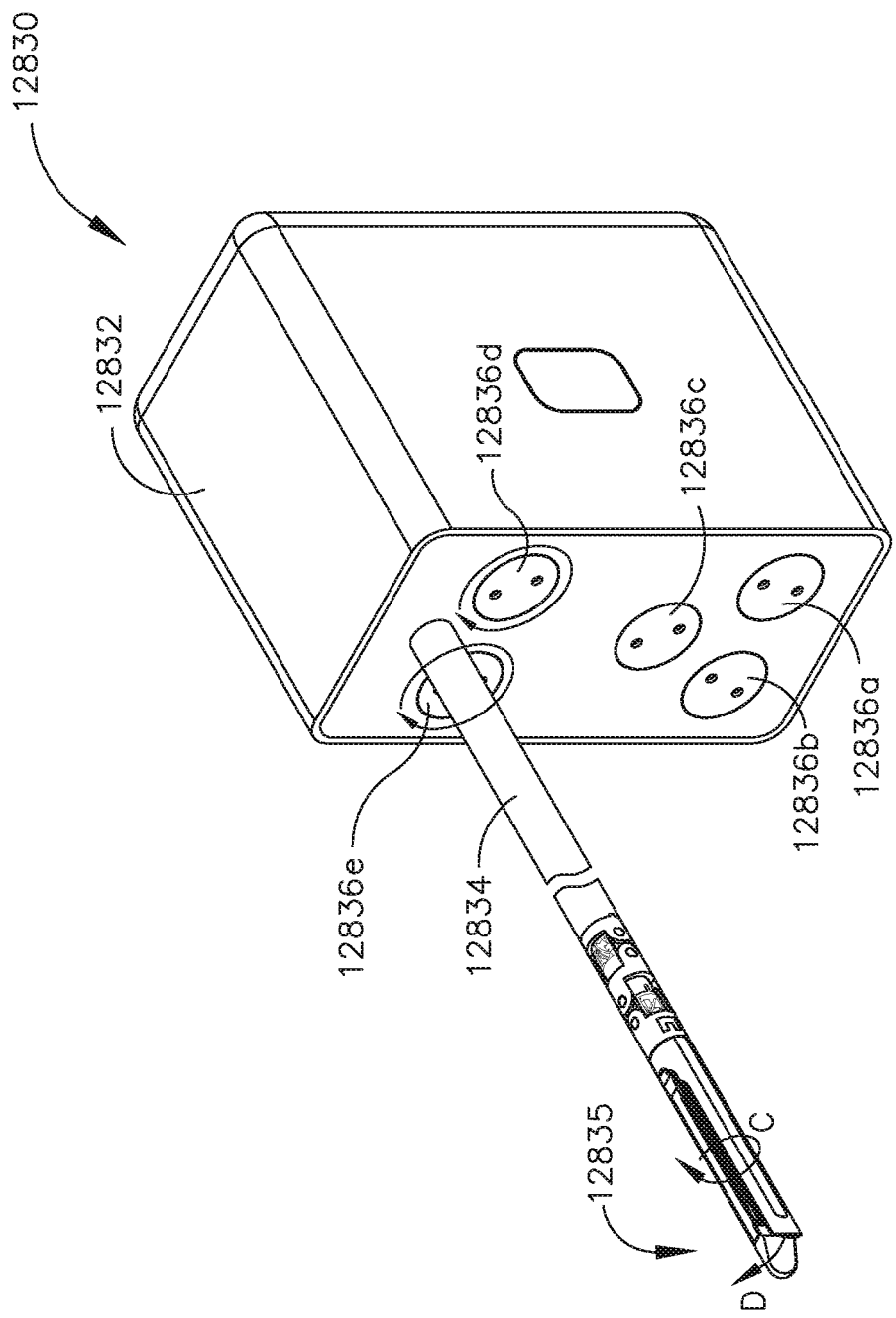

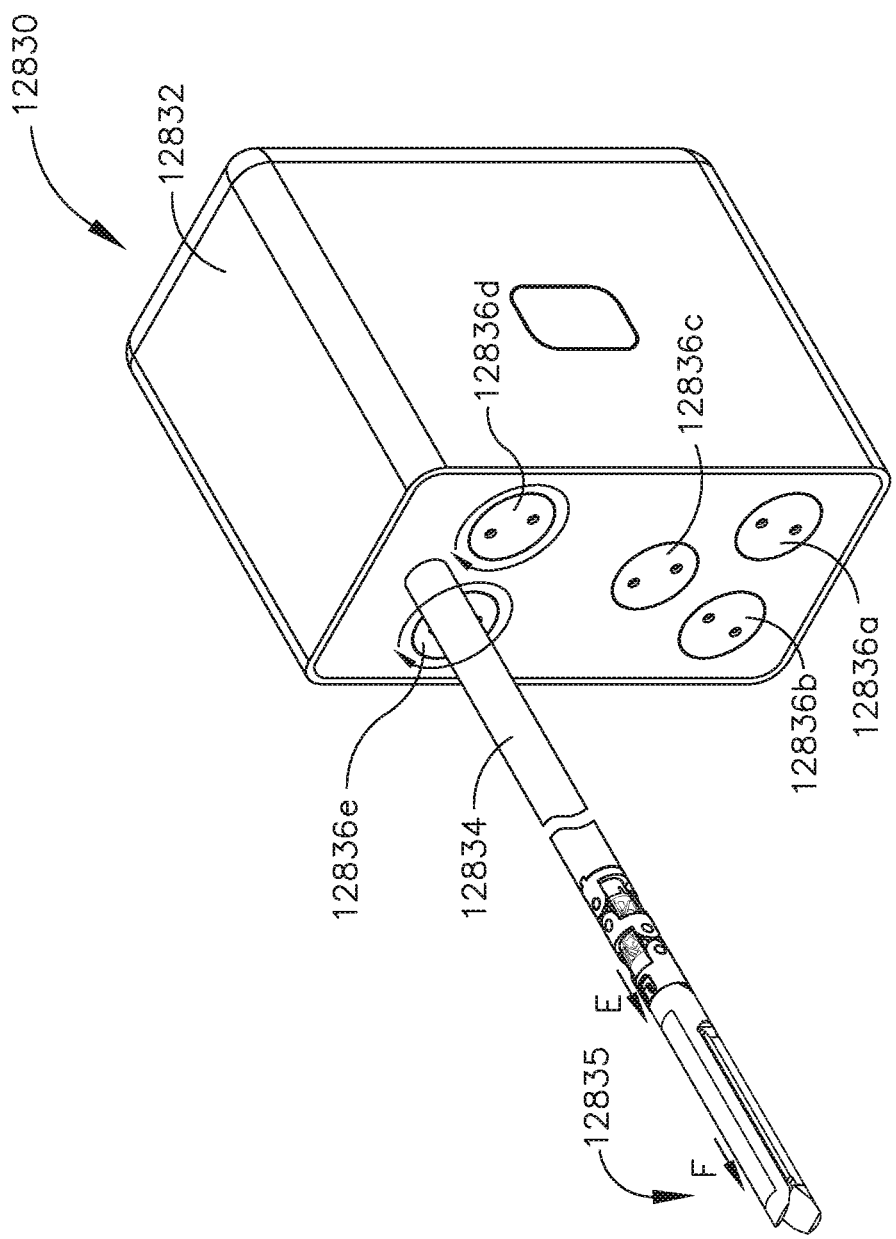

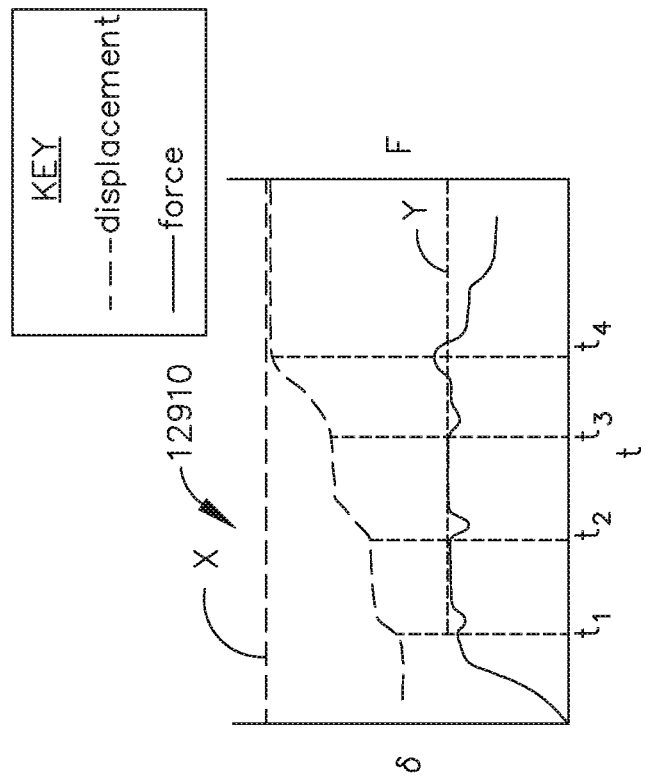
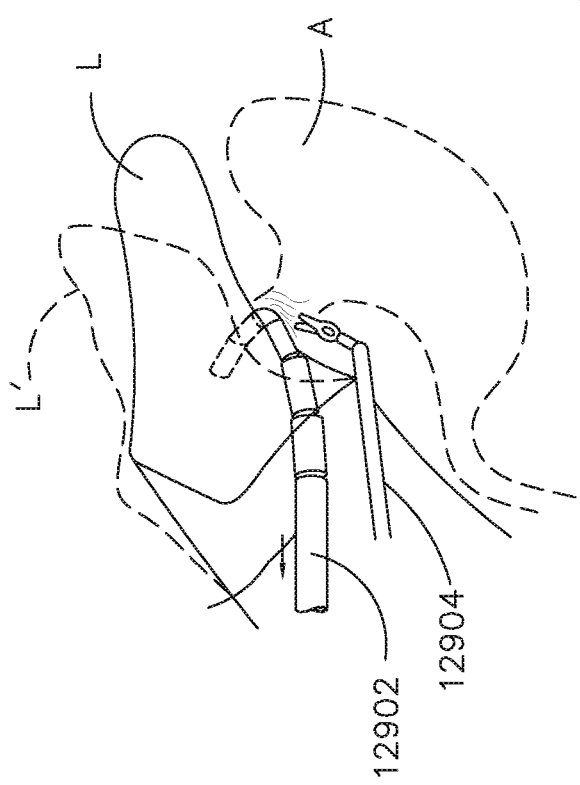
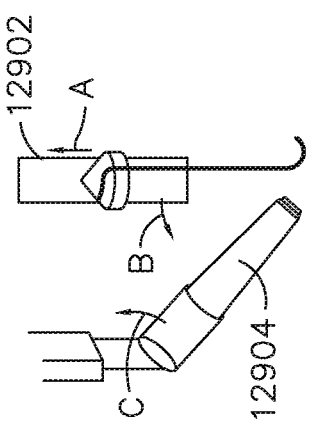

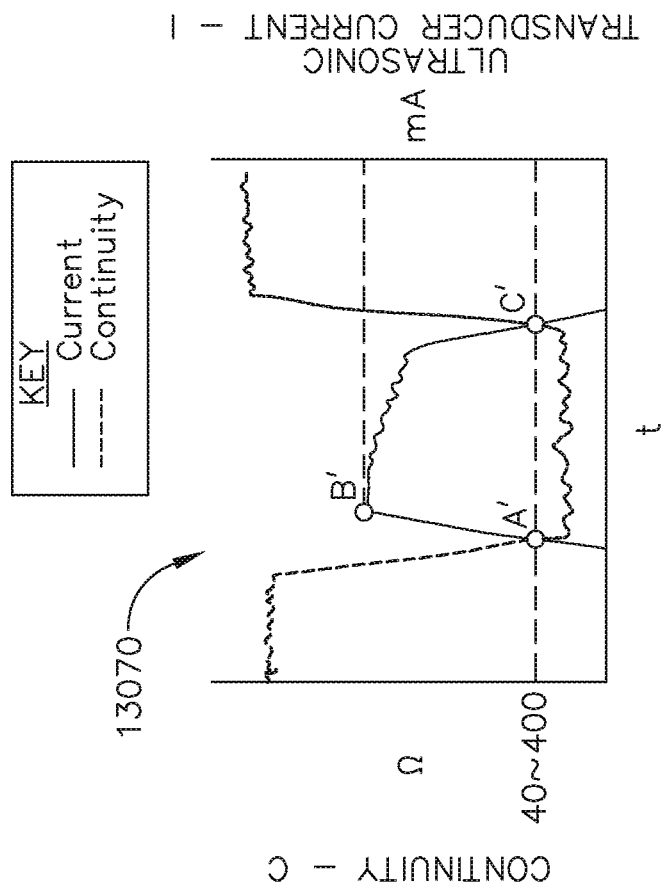
FIG. 61
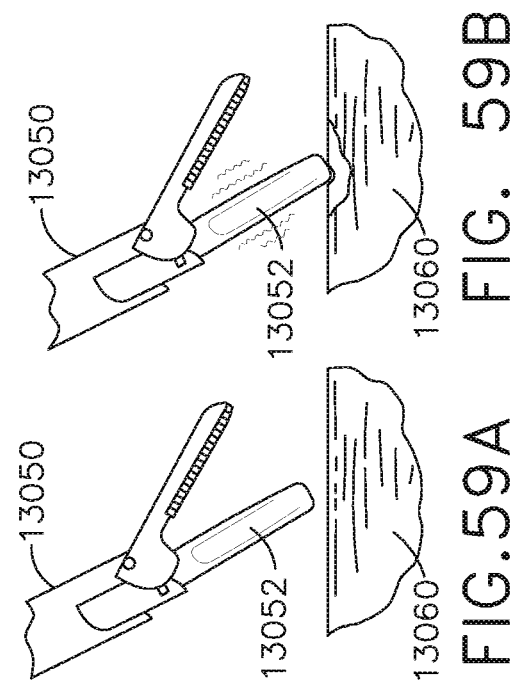
FIG. 59B
FIG. 59A

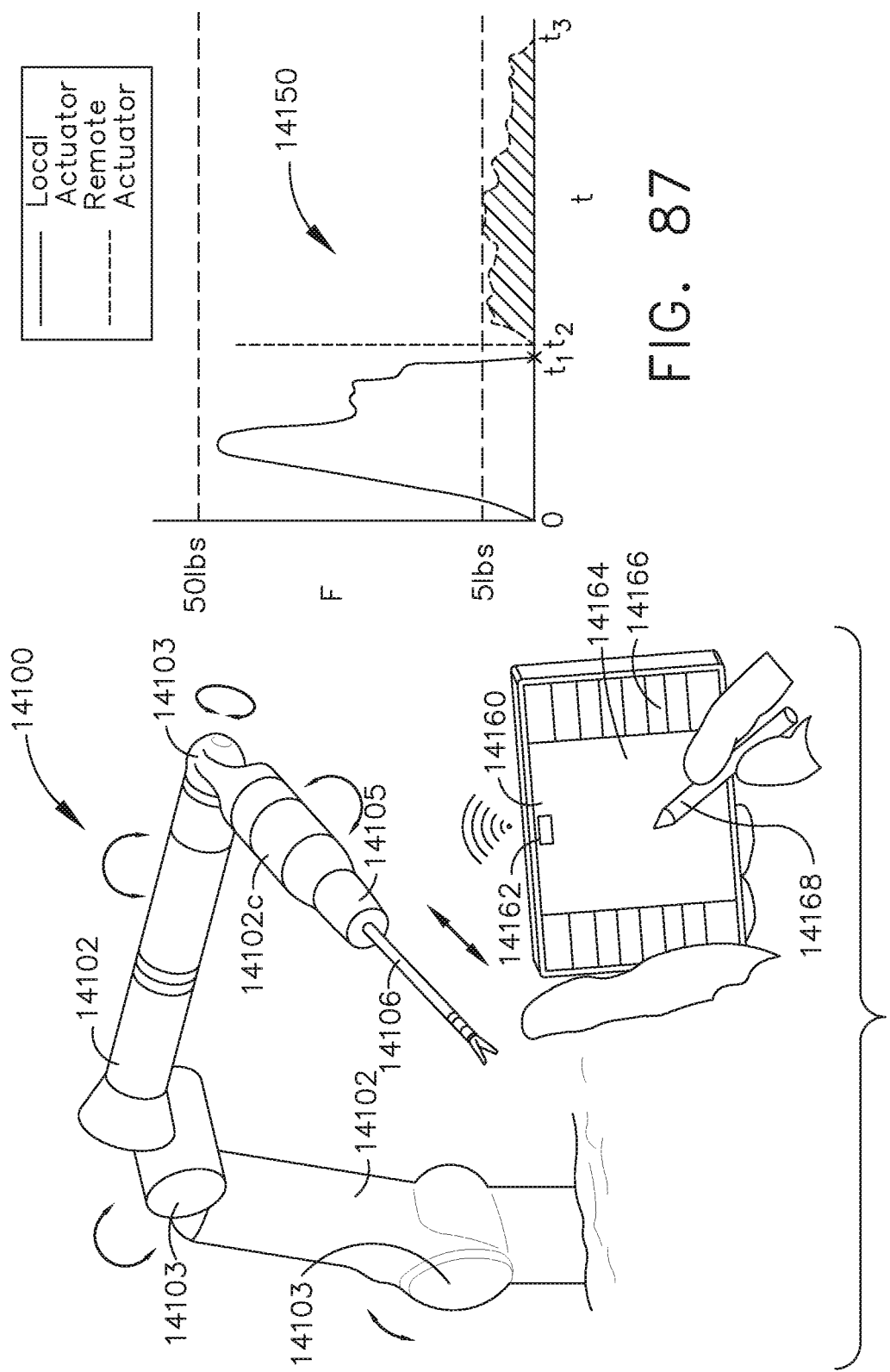

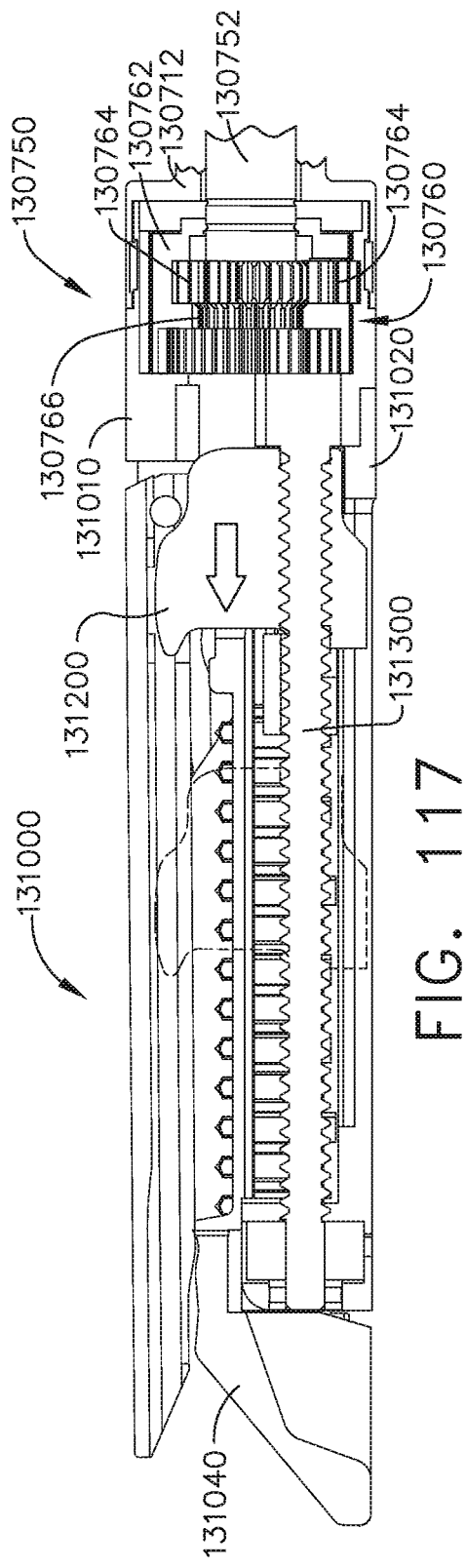
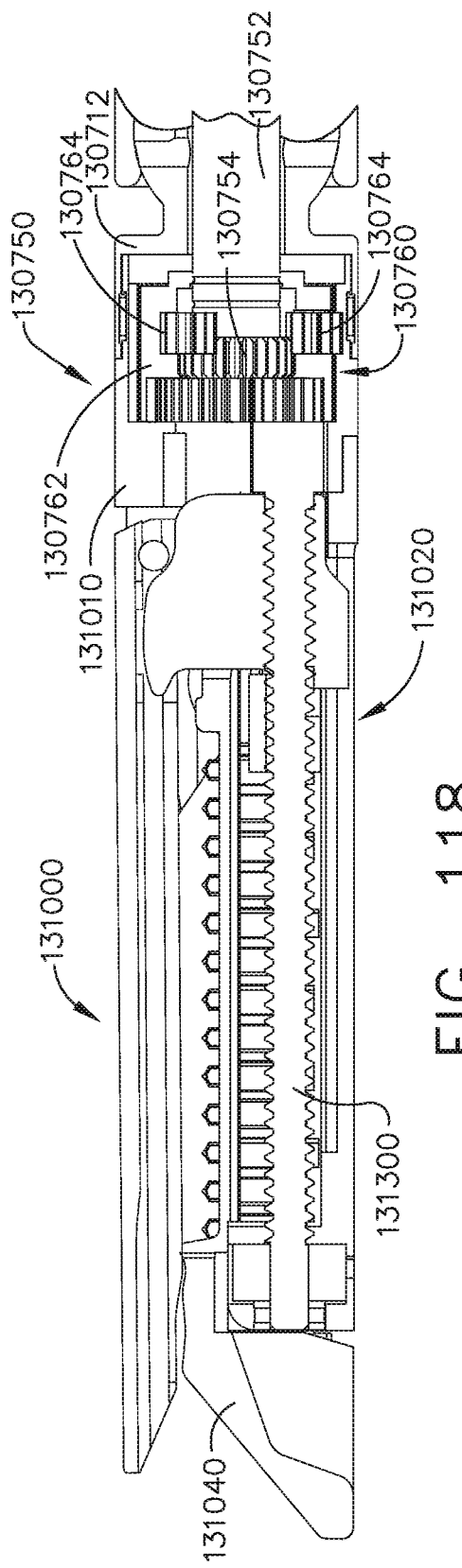

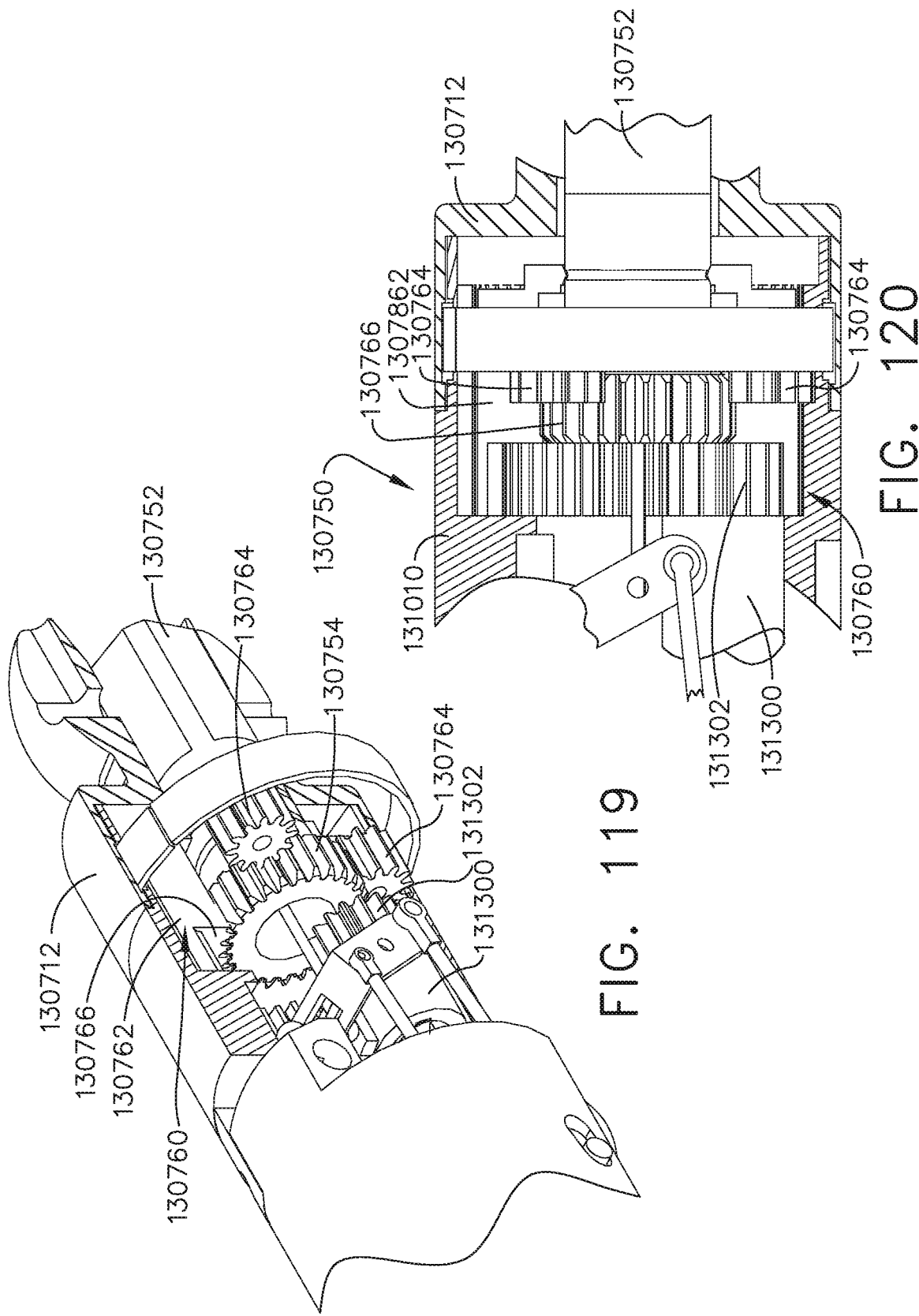

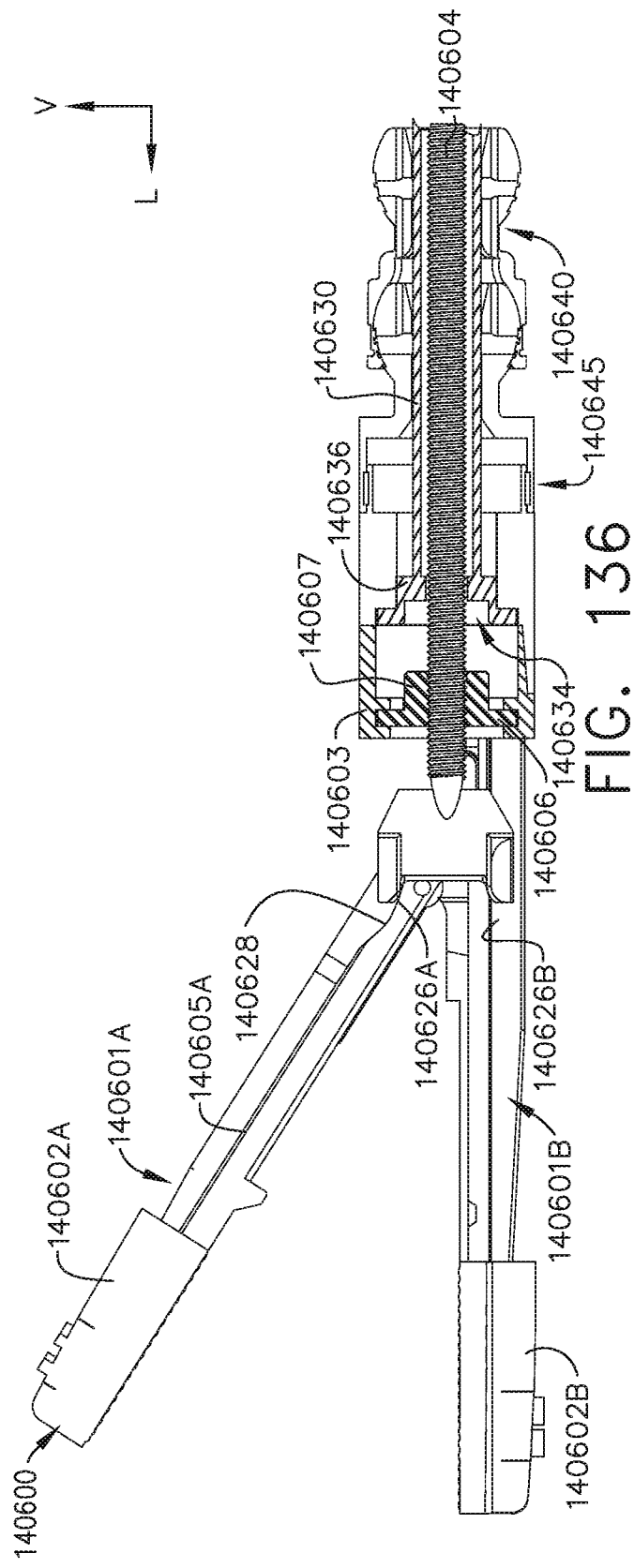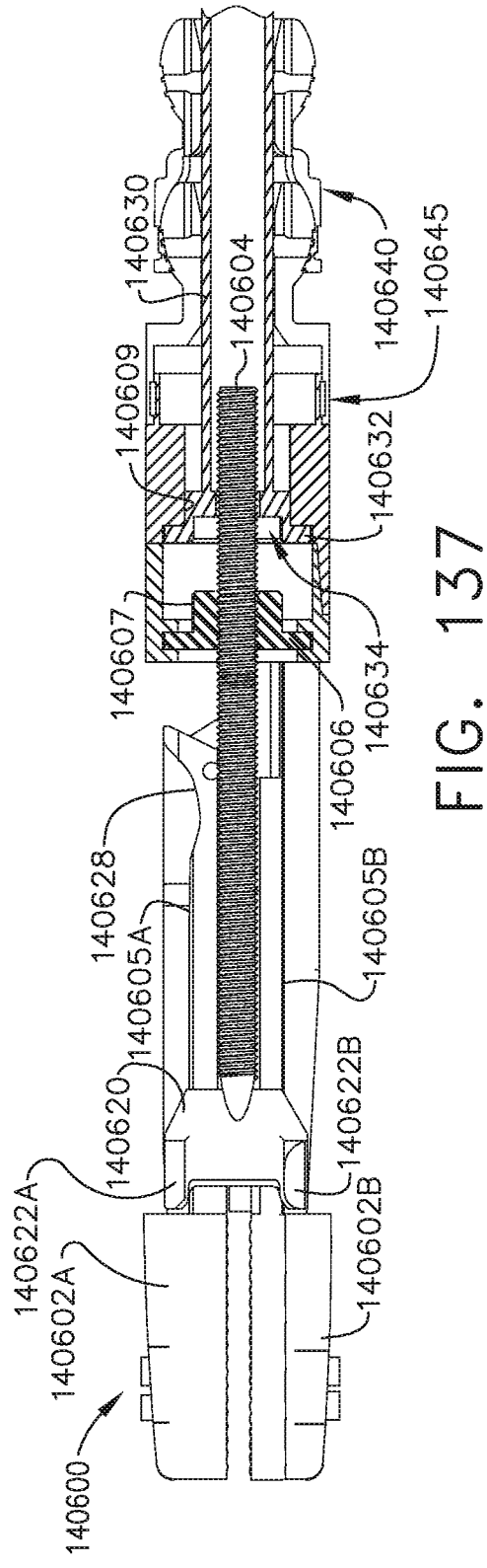

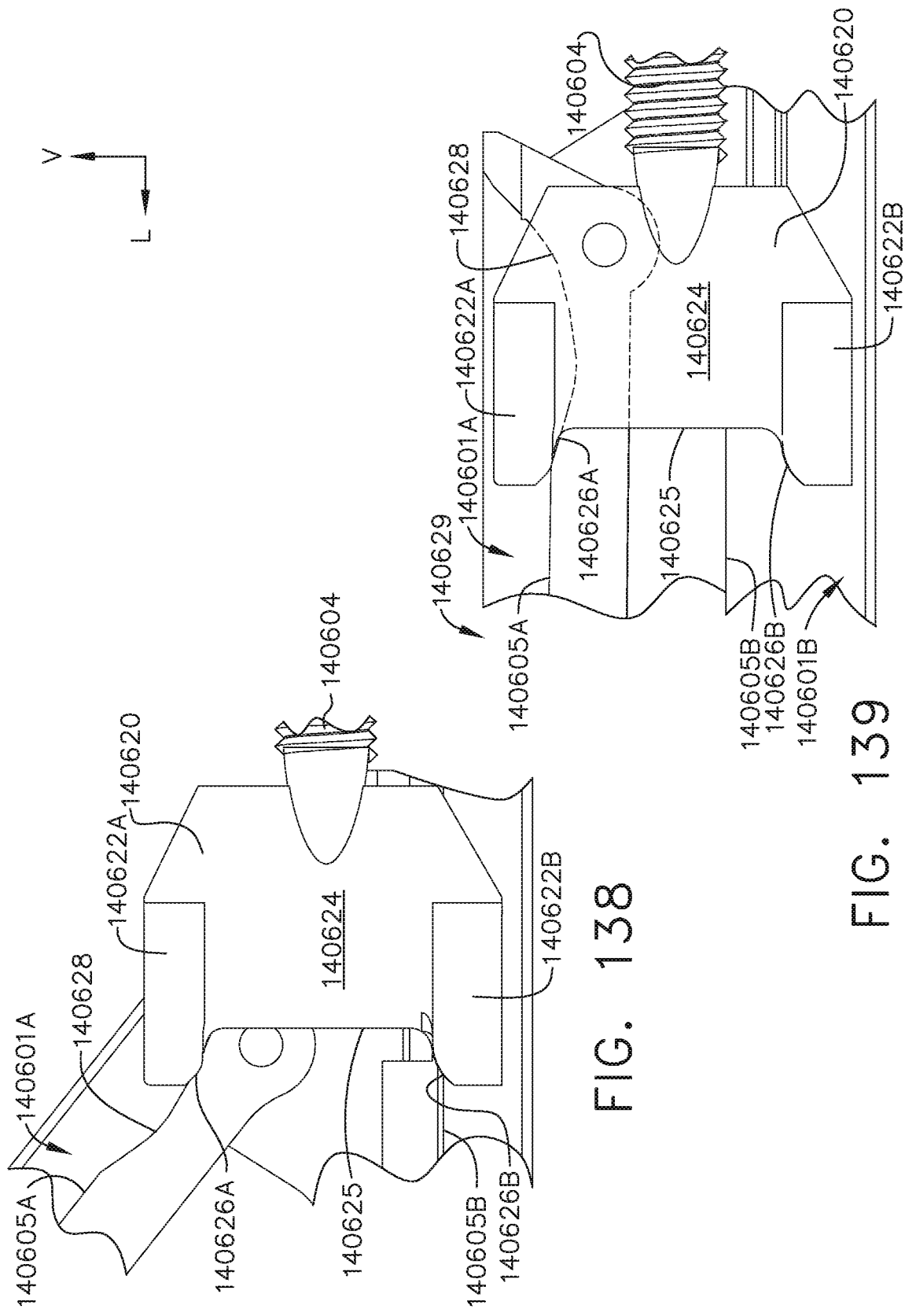

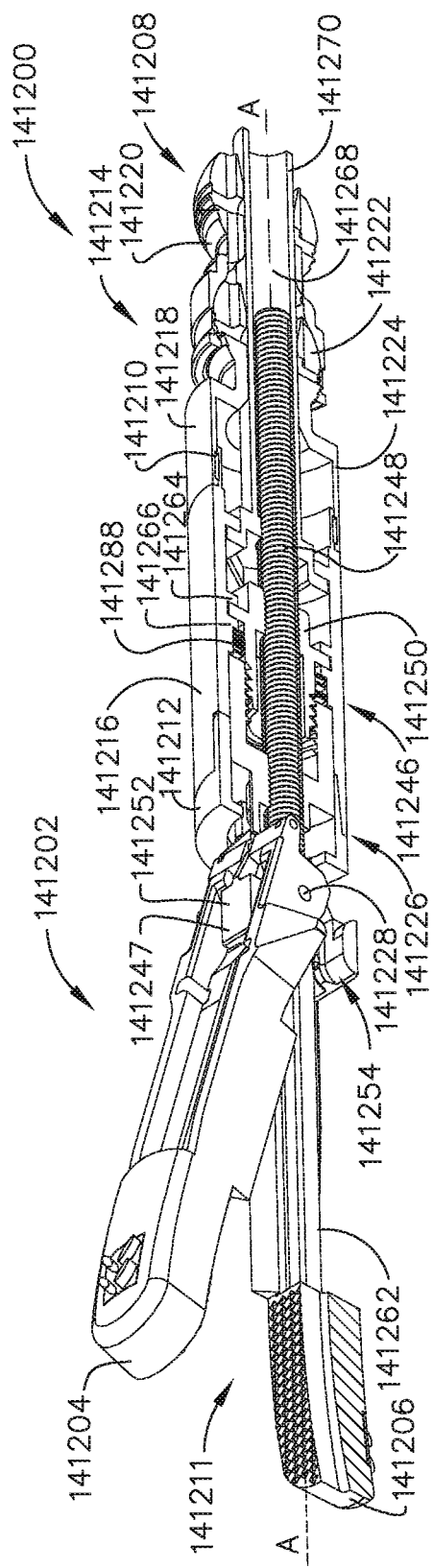
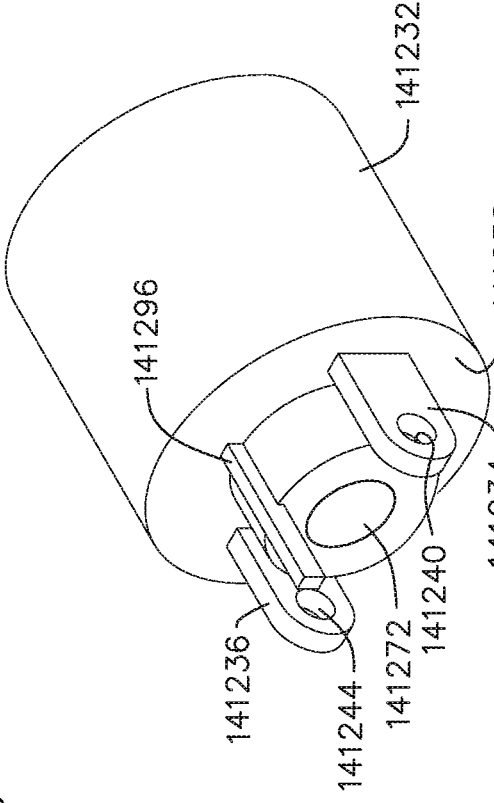
FIG. 140
FIG. 141

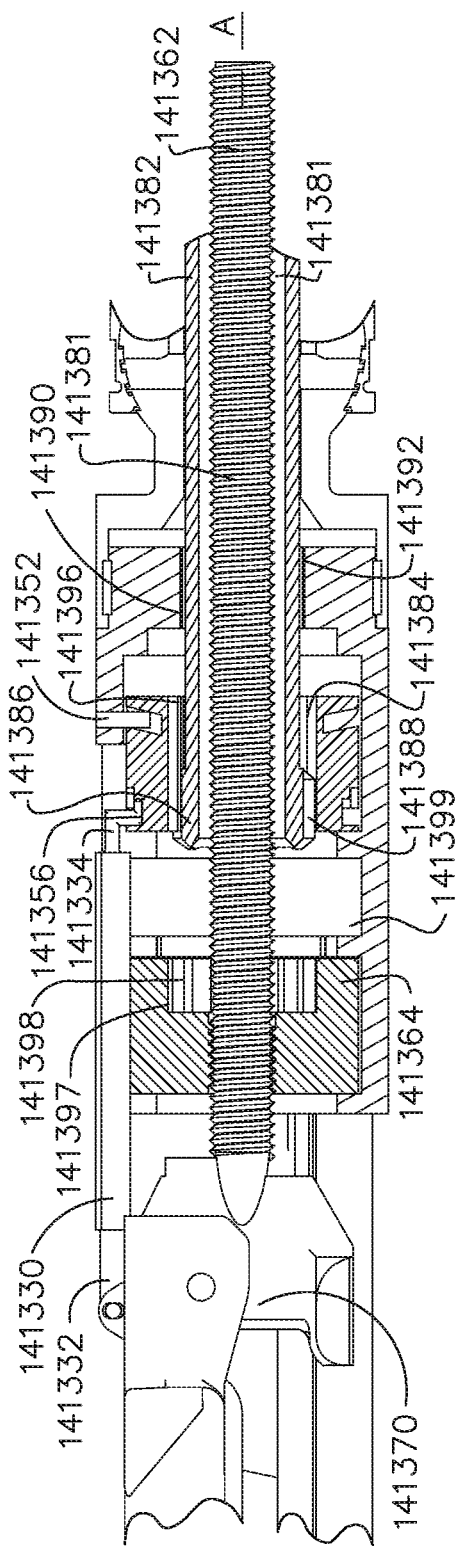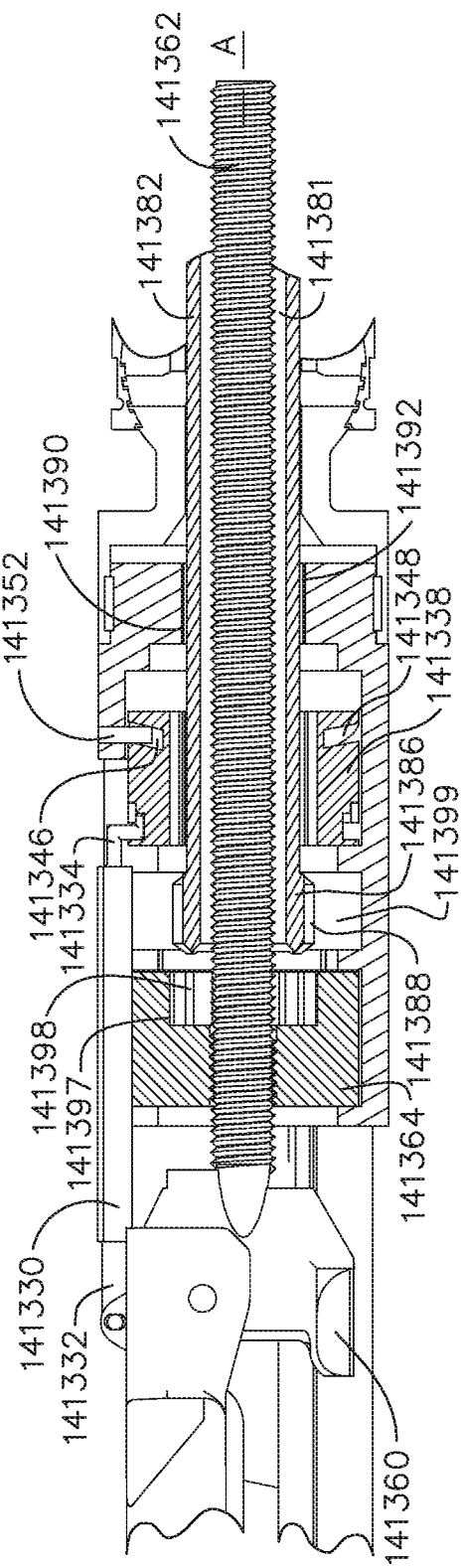

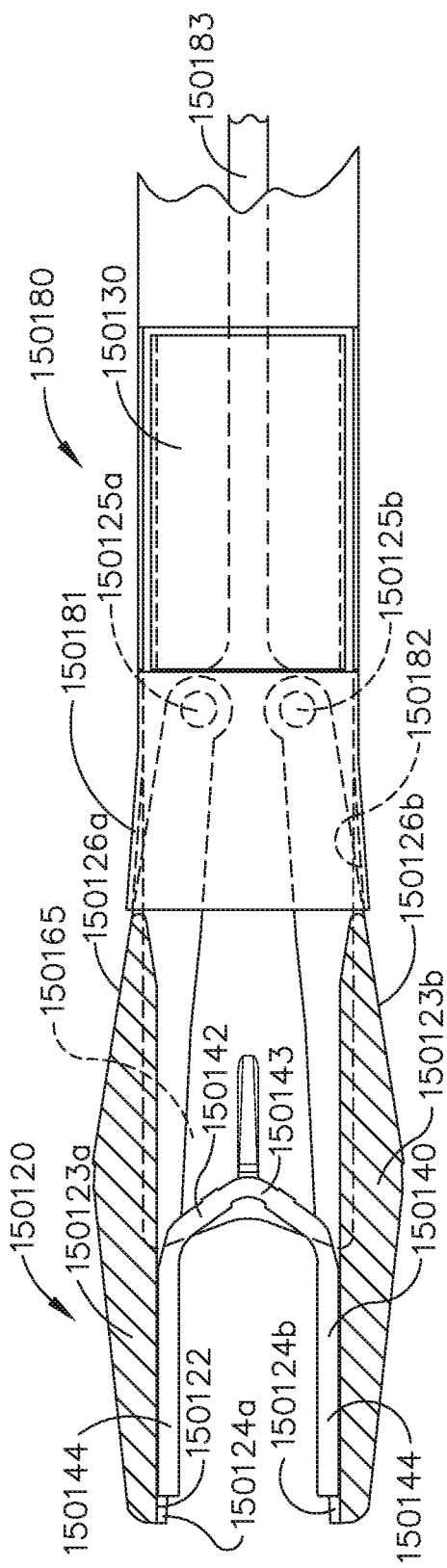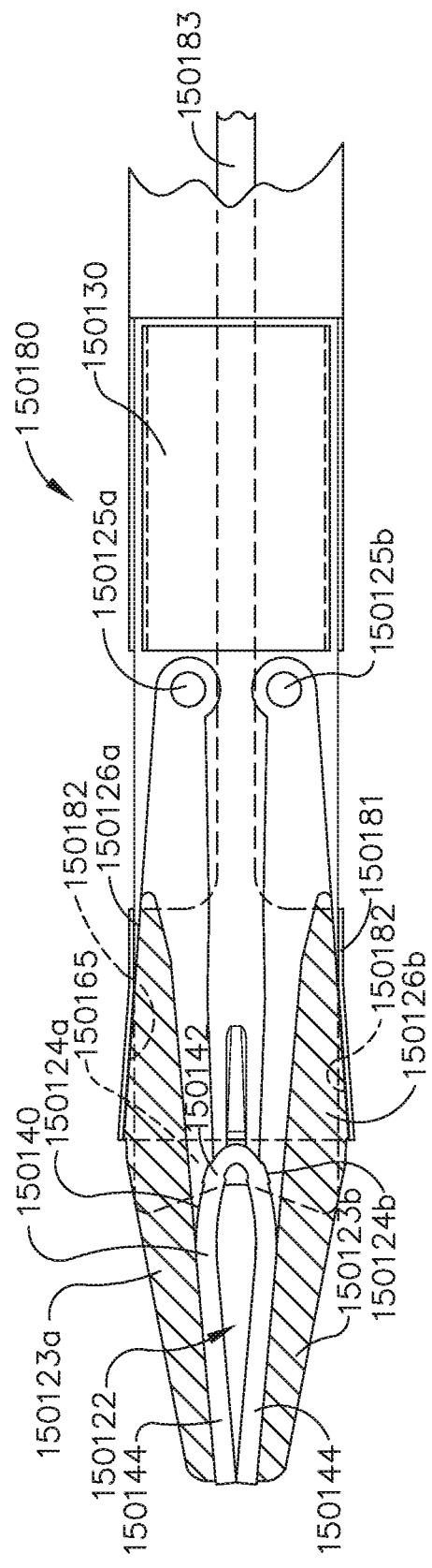

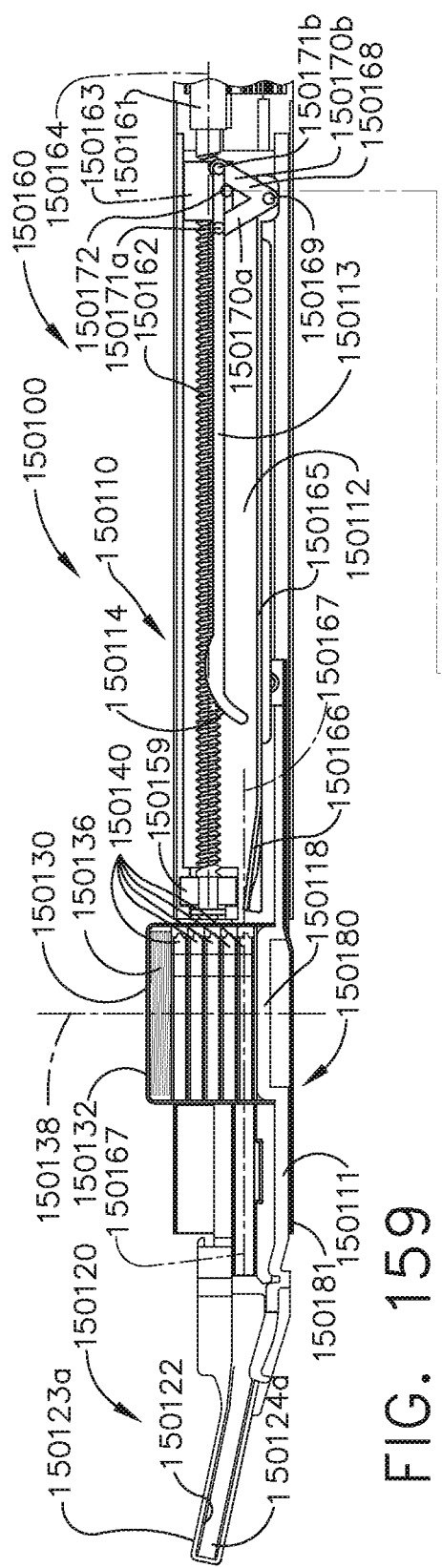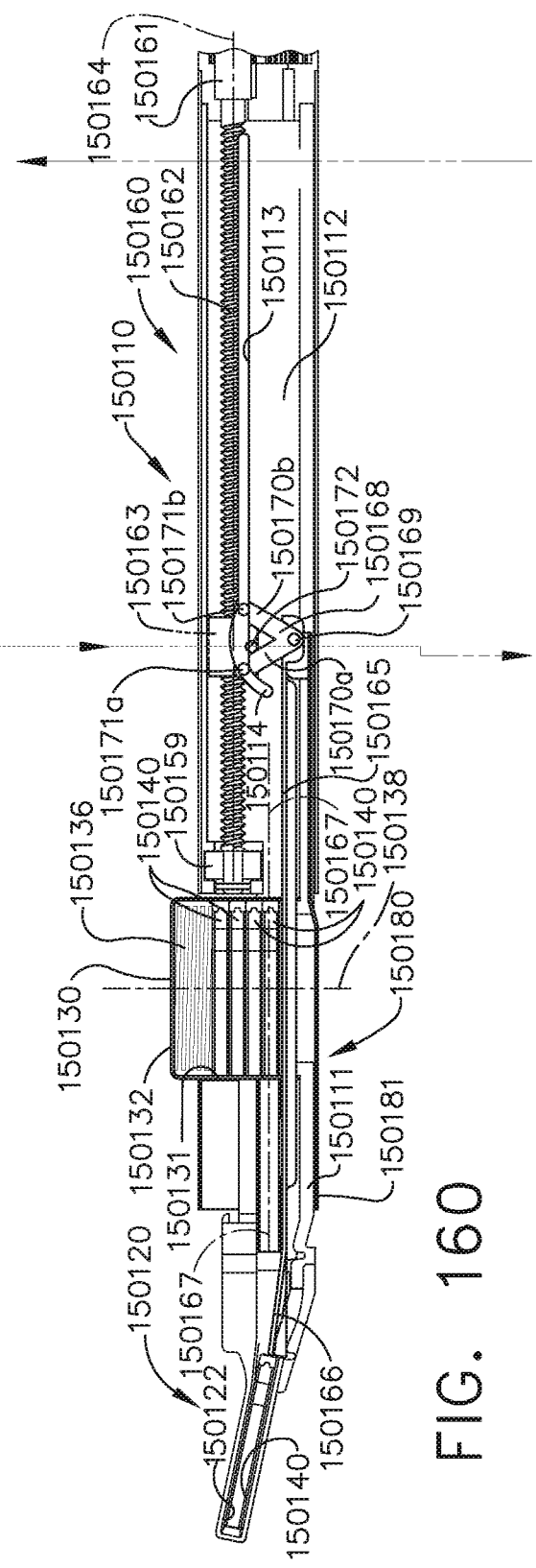
FIG. 159
FIG. 160

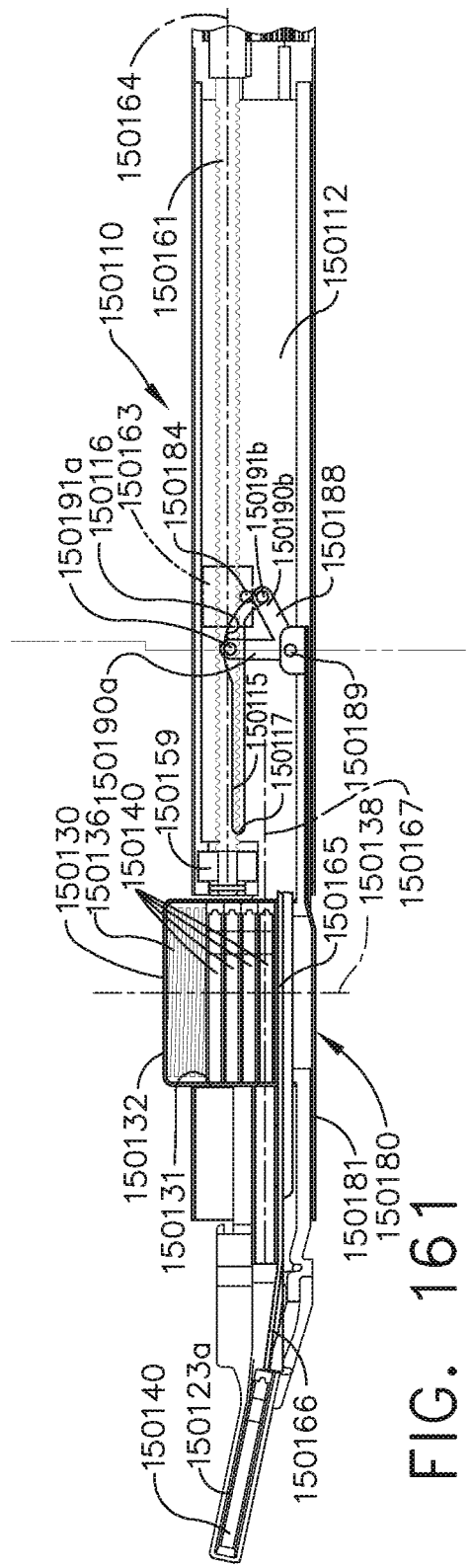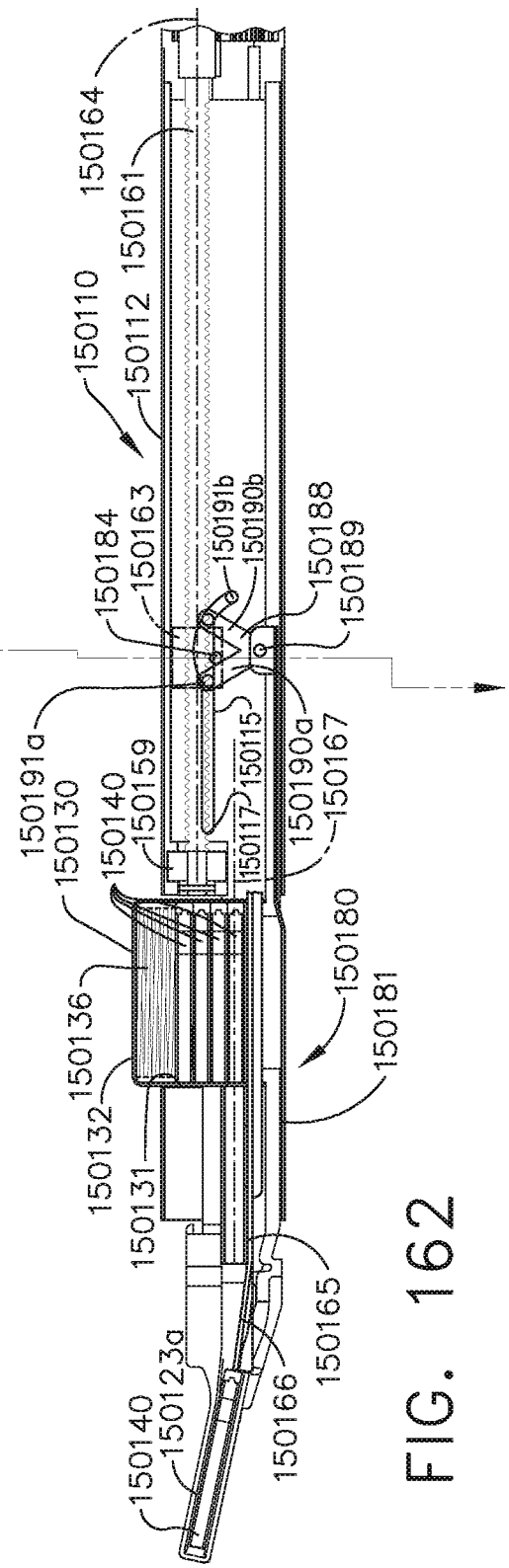

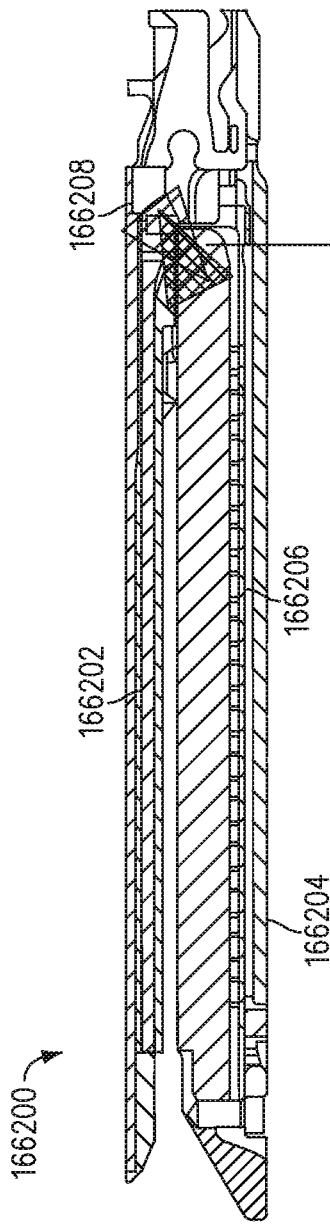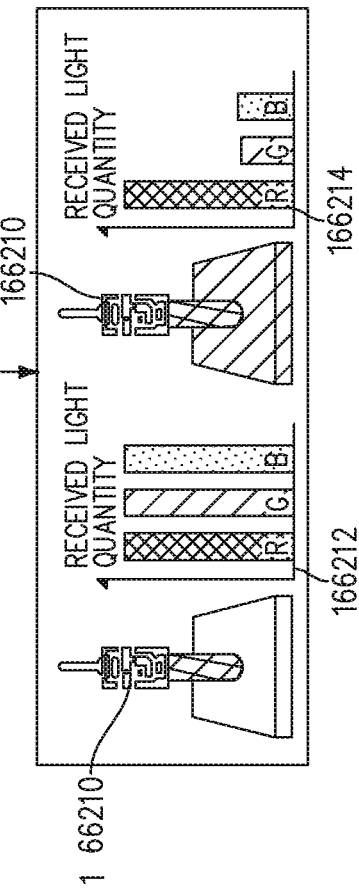
FIG. 184
FIG. 185

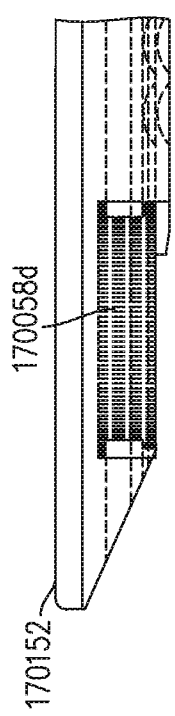
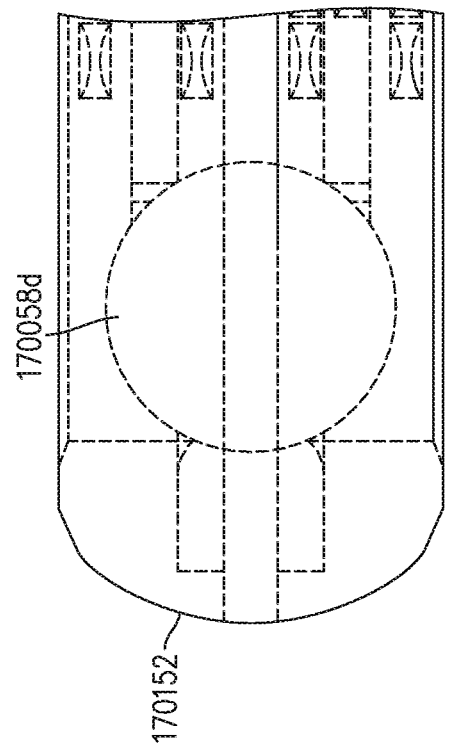
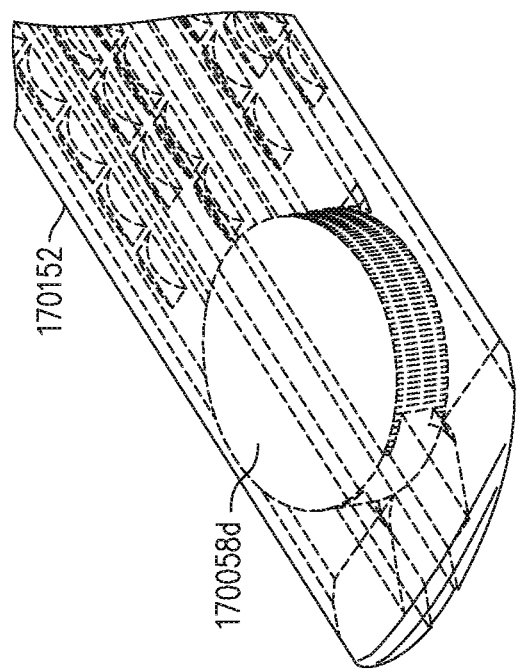
FIG. 195
FIG. 196
FIG. 194

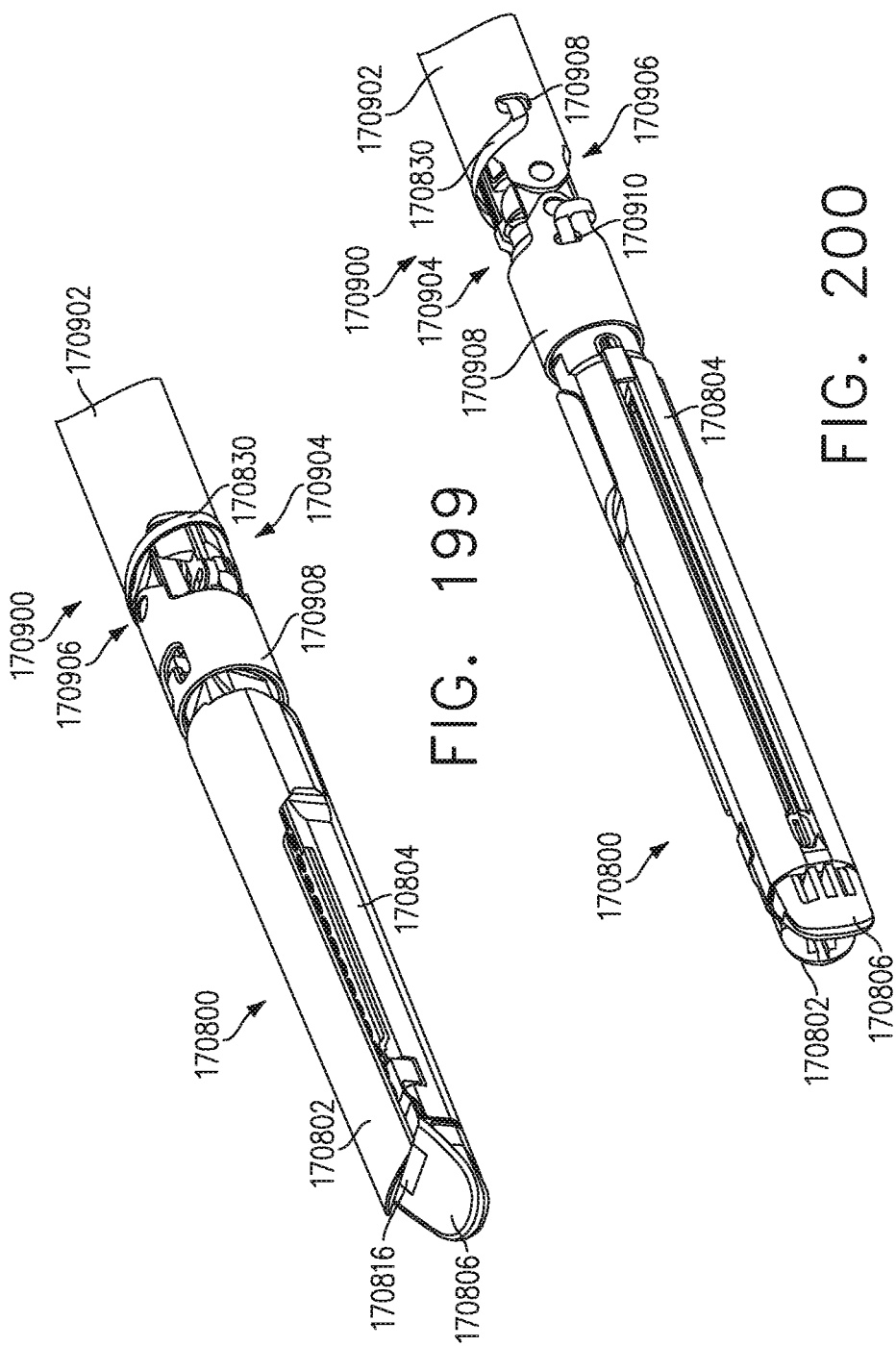

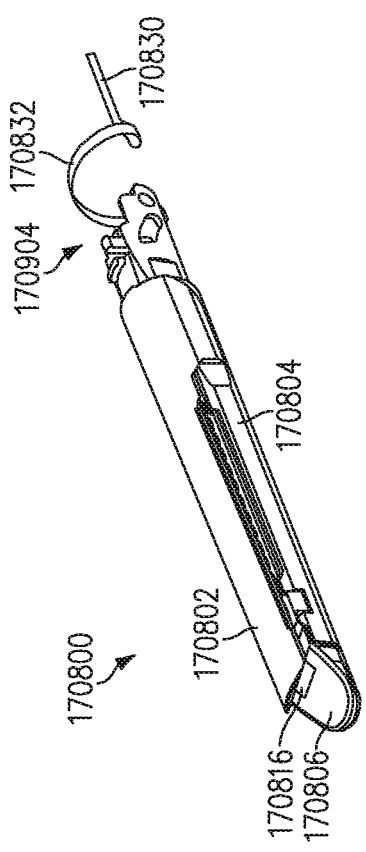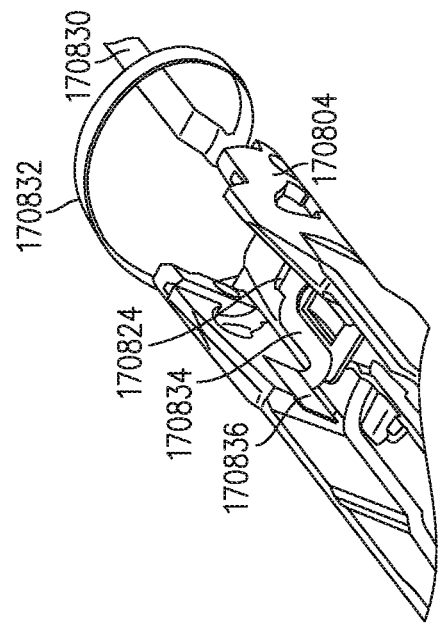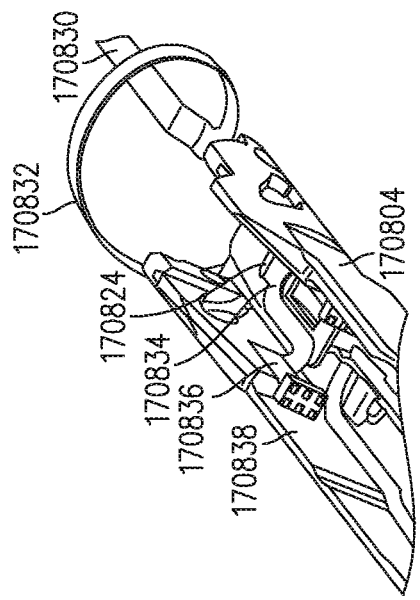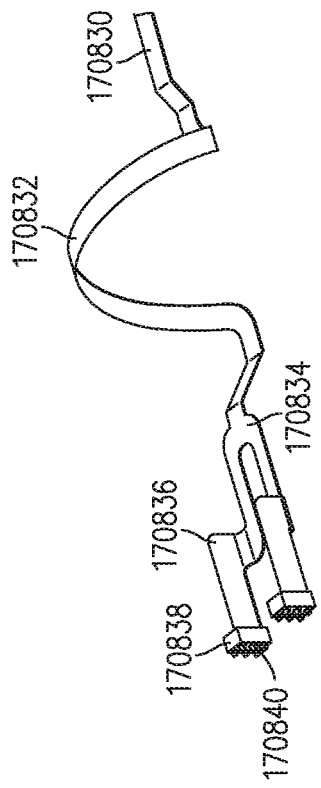

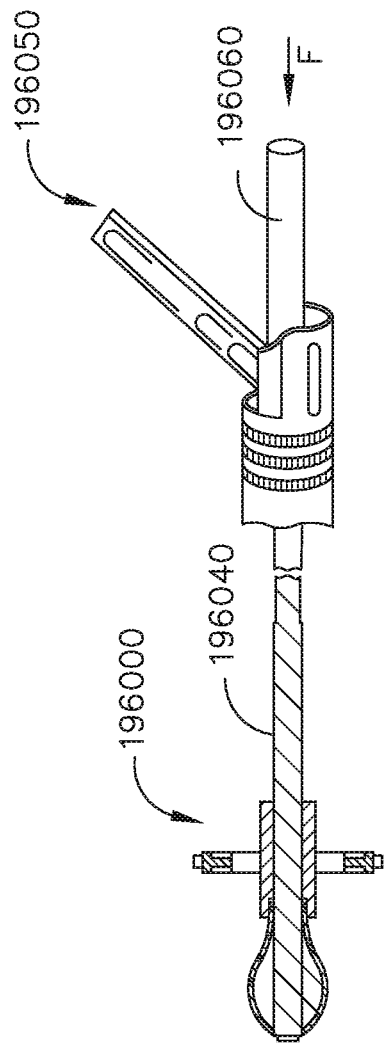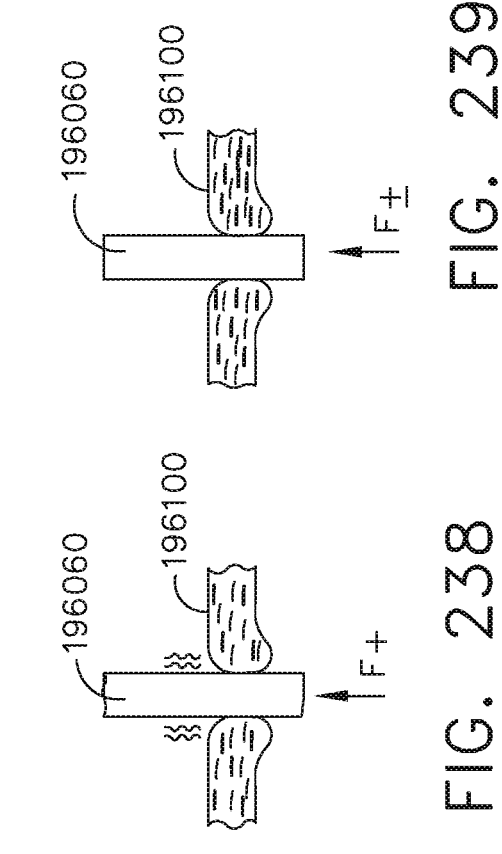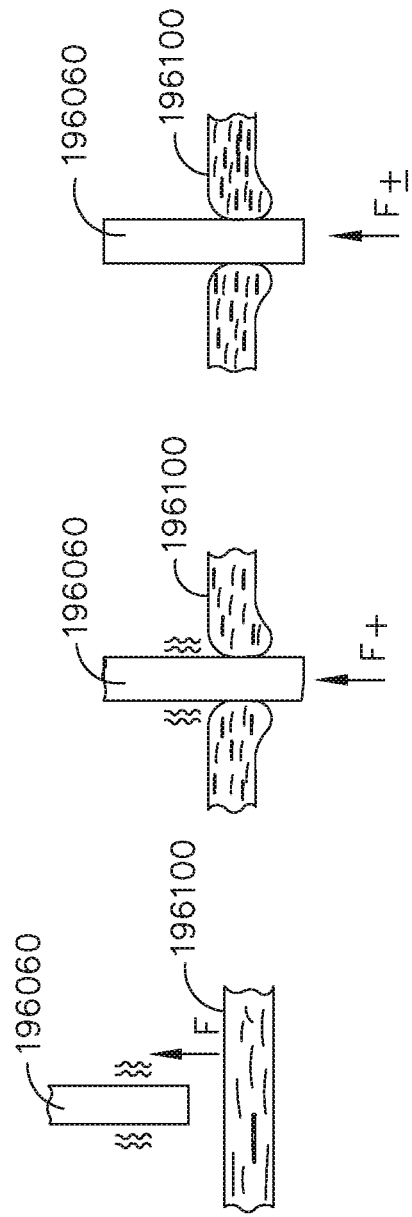
FIG. 236
FIG. 239
FIG. 238
FIG. 237

METHOD OF ROBOTIC HUB COMMUNICATION, DETECTION, AND CONTROL

CROSS-REFERENCE TO RELATED APPLICATIONS

The present application claims priority under 35 U.S.C. § 119(e) to U.S. Provisional Patent Application No. 62/773,778, titled METHOD FOR ADAPTIVE CONTROL SCHEMES FOR SURGICAL NETWORK CONTROL AND INTERACTION, filed Nov. 30, 2018, to U.S. Provisional Patent Application No. 62/773,728, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Nov. 30, 2018, to U.S. Provisional Patent Application No. 62/773,741, titled METHOD FOR FACILITY DATA COLLECTION AND INTERPRETATION, filed Nov. 30, 2018, and to U.S. Provisional Patent Application No. 62/773,742, titled METHOD FOR CIRCULAR STAPLER CONTROL ALGORITHM ADJUSTMENT BASED ON SITUATIONAL AWARENESS, filed Nov. 30, 2018, the disclosure of each of which is herein incorporated by reference in its entirety.

The present application claims priority under 35 U.S.C. § 119(e) to U.S. Provisional Patent Application No. 62/750,529, titled METHOD FOR OPERATING A POWERED ARTICULATING MULTI-CLIP APPLIER, filed Oct. 25, 2018, to U.S. Provisional Patent Application No. 62/750,539, titled SURGICAL CLIP APPLIER, filed Oct. 25, 2018, and to U.S. Provisional Patent Application No. 62/750,555, titled SURGICAL CLIP APPLIER, filed Oct. 25, 2018, the disclosure of each of which is herein incorporated by reference in its entirety.

The present application also claims priority under 35 U.S.C. § 119(e) to U.S. Provisional Patent Application No. 62/729,183, titled CONTROL FOR A SURGICAL NETWORK OR SURGICAL NETWORK CONNECTED DEVICE THAT ADJUSTS ITS FUNCTION BASED ON A SENSED SITUATION OR USAGE, filed Sep. 10, 2018, to U.S. Provisional Patent Application No. 62/729,177, titled AUTOMATED DATA SCALING, ALIGNMENT, AND ORGANIZING BASED ON PREDEFINED PARAMETERS WITHIN A SURGICAL NETWORK BEFORE TRANSMISSION, filed Sep. 10, 2018, to U.S. Provisional Patent Application No. 62/729,176, titled INDIRECT COMMAND AND CONTROL OF A FIRST OPERATING ROOM SYSTEM THROUGH THE USE OF A SECOND OPERATING ROOM SYSTEM WITHIN A STERILE FIELD WHERE THE SECOND OPERATING ROOM SYSTEM HAS PRIMARY AND SECONDARY OPERATING MODES, filed Sep. 10, 2018, to U.S. Provisional Patent Application No. 62/729,185, titled POWERED STAPLING DEVICE THAT IS CAPABLE OF ADJUSTING FORCE, ADVANCEMENT SPEED, AND OVERALL STROKE OF CUTTING MEMBER OF THE DEVICE BASED ON SENSED PARAMETER OF FIRING OR CLAMPING, filed Sep. 10, 2018, to U.S. Provisional Patent Application No. 62/729,184, titled POWERED SURGICAL TOOL WITH A PREDEFINED ADJUSTABLE CONTROL ALGORITHM FOR CONTROLLING AT LEAST ONE END EFFECTOR PARAMETER AND A MEANS FOR LIMITING THE ADJUSTMENT, filed Sep. 10, 2018, to U.S. Provisional Patent Application No. 62/729,182, titled SENSING THE PATIENT POSITION AND CONTACT UTILIZING THE MONO-POLAR RETURN PAD ELECTRODE TO PROVIDE SITUATIONAL AWARENESS TO THE HUB, filed Sep. 10, 2018, to U.S. Provisional Patent Application No. 62/729,191, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION, filed Sep. 10, 2018, to U.S. Provisional Patent Application No. 62/729,195, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, filed Sep. 10, 2018, and to U.S. Provisional Patent Application No. 62/729,186, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES, filed Sep. 10, 2018, the disclosure of each of which is herein incorporated by reference in its entirety.

The present application also claims priority under 35 U.S.C. § 119(e) to U.S. Provisional Patent Application No. 62/721,995, titled CONTROLLING AN ULTRASONIC SURGICAL INSTRUMENT ACCORDING TO TISSUE LOCATION, filed Aug. 23, 2018, to U.S. Provisional Patent Application No. 62/721,998, titled SITUATIONAL AWARENESS OF ELECTROSURGICAL SYSTEMS, filed Aug. 23, 2018, to U.S. Provisional Patent Application No. 62/721,999, titled INTERRUPTION OF ENERGY DUE TO INADVERTENT CAPACITIVE COUPLING, filed Aug. 23, 2018, to U.S. Provisional Patent Application No. 62/721,994, titled BIPOLAR COMBINATION DEVICE THAT AUTOMATICALLY ADJUSTS PRESSURE BASED ON ENERGY MODALITY, filed Aug. 23, 2018, and to U.S. Provisional Patent Application No. 62/721,996, titled RADIO FREQUENCY ENERGY DEVICE FOR DELIVERING COMBINED ELECTRICAL SIGNALS, filed Aug. 23, 2018, the disclosure of each of which is herein incorporated by reference in its entirety.

The present application also claims priority under 35 U.S.C. § 119(e) to U.S. Provisional Patent Application No. 62/692,747, titled SMART ACTIVATION OF AN ENERGY DEVICE BY ANOTHER DEVICE, filed on Jun. 30, 2018, to U.S. Provisional Patent Application No. 62/692,748, titled SMART ENERGY ARCHITECTURE, filed on Jun. 30, 2018, and to U.S. Provisional Patent Application No. 62/692,768, titled SMART ENERGY DEVICES, filed on Jun. 30, 2018, the disclosure of each of which is herein incorporated by reference in its entirety.

The present application also claims priority under 35 U.S.C. § 119(e) to U.S. Provisional Patent Application No. 62/691,228, titled METHOD OF USING REINFORCED FLEX CIRCUITS WITH MULTIPLE SENSORS WITH ELECTROSURGICAL DEVICES, filed Jun. 28, 2018, to U.S. Provisional Patent Application No. 62/691,227, titled CONTROLLING A SURGICAL INSTRUMENT ACCORDING TO SENSED CLOSURE PARAMETERS, filed Jun. 28, 2018, to U.S. Provisional Patent Application No. 62/691,230, titled SURGICAL INSTRUMENT HAVING A FLEXIBLE ELECTRODE, filed Jun. 28, 2018, to U.S. Provisional Patent Application No. 62/691,219, titled SURGICAL EVACUATION SENSING AND MOTOR CONTROL, filed Jun. 28, 2018, to U.S. Provisional Patent Application No. 62/691,257, titled COMMUNICATION OF SMOKE EVACUATION SYSTEM PARAMETERS TO HUB OR CLOUD IN SMOKE EVACUATION MODULE FOR INTERACTIVE SURGICAL PLATFORM, filed Jun.

28, 2018, to U.S. Provisional Patent Application No. 62/691,262, titled SURGICAL EVACUATION SYSTEM WITH A COMMUNICATION CIRCUIT FOR COMMUNICATION BETWEEN A FILTER AND A SMOKE EVACUATION DEVICE, filed Jun. 28, 2018, and to U.S. Provisional Patent Application No. 62/691,251, titled DUAL IN-SERIES LARGE AND SMALL DROPLET FILTERS, filed Jun. 28, 2018, the disclosure of each of which is herein incorporated by reference in its entirety.

The present application claims priority under 35 U.S.C. § 119(e) to U.S. Provisional Patent Application No. 62/665,129, titled SURGICAL SUTURING SYSTEMS, filed May 1, 2018, to U.S. Provisional Patent Application No. 62/665,139, titled SURGICAL INSTRUMENTS COMPRISING CONTROL SYSTEMS, filed May 1, 2018, to U.S. Provisional Patent Application No. 62/665,177, titled SURGICAL INSTRUMENTS COMPRISING HANDLE ARRANGEMENTS, filed May 1, 2018, to U.S. Provisional Patent Application No. 62/665,128, titled MODULAR SURGICAL INSTRUMENTS, filed May 1, 2018, to U.S. Provisional Patent Application No. 62/665,192, titled SURGICAL DISSECTORS, filed May 1, 2018, and to U.S. Provisional Patent Application No. 62/665,134, titled SURGICAL CLIP APPLIER, filed May 1, 2018, the disclosure of each of which is herein incorporated by reference in its entirety.

The present application also claims priority under 35 U.S.C. § 119(e) to U.S. Provisional Patent Application No. 62/659,900, titled METHOD OF HUB COMMUNICATION, filed on Apr. 19, 2018, the disclosure of which is herein incorporated by reference in its entirety.

The present application also claims priority under 35 U.S.C. § 119(e) to U.S. Provisional Patent Application No. 62/650,898, filed on Mar. 30, 2018, titled CAPACITIVE COUPLED RETURN PATH PAD WITH SEPARABLE ARRAY ELEMENTS, to U.S. Provisional Patent Application No. 62/650,887, titled SURGICAL SYSTEMS WITH OPTIMIZED SENSING CAPABILITIES, filed Mar. 30, 2018, to U.S. Provisional Patent Application No. 62/650,882, titled SMOKE EVACUATION MODULE FOR INTERACTIVE SURGICAL PLATFORM, filed Mar. 30, 2018, and to U.S. Provisional Patent Application No. 62/650,877, titled SURGICAL SMOKE EVACUATION SENSING AND CONTROLS, filed Mar. 30, 2018, the disclosure of each of which is herein incorporated by reference in its entirety.

This application also claims the benefit of priority under 35 U.S.C. § 119(e) to U.S. Provisional Patent Application No. 62/649,302, titled INTERACTIVE SURGICAL SYSTEMS WITH ENCRYPTED COMMUNICATION CAPABILITIES, filed Mar. 28, 2018, to U.S. Provisional Patent Application No. 62/649,294, titled DATA STRIPPING METHOD TO INTERROGATE PATIENT RECORDS AND CREATE ANONYMIZED RECORD, filed Mar. 28, 2018, to U.S. Provisional Patent Application No. 62/649,300, titled SURGICAL HUB SITUATIONAL AWARENESS, filed Mar. 28, 2018, to U.S. Provisional Patent Application No. 62/649,309, titled SURGICAL HUB SPATIAL AWARENESS TO DETERMINE DEVICES IN OPERATING THEATER, filed Mar. 28, 2018, to U.S. Provisional Patent Application No. 62/649,310, titled COMPUTER IMPLEMENTED INTERACTIVE SURGICAL SYSTEMS, filed Mar. 28, 2018, to U.S. Provisional Patent Application No. 62/649,291, titled USE OF LASER LIGHT AND RED-GREEN-BLUE COLORATION TO DETERMINE PROPERTIES OF BACK SCATTERED LIGHT, filed Mar. 28, 2018, to U.S. Provisional Patent Application No. 62/649,296, titled ADAPTIVE CONTROL PROGRAM UPDATES FOR SURGICAL DEVICES, filed Mar. 28, 2018, to U.S. Provisional Patent Application No. 62/649,333, titled CLOUD-BASED MEDICAL ANALYTICS FOR CUSTOMIZATION AND RECOMMENDATIONS TO A USER, filed Mar. 28, 2018, to U.S. Provisional Patent Application No. 62/649,327, titled CLOUD-BASED MEDICAL ANALYTICS FOR SECURITY AND AUTHENTICATION TRENDS AND REACTIVE MEASURES, filed Mar. 28, 2018, to U.S. Provisional Patent Application No. 62/649,315, titled DATA HANDLING AND PRIORITIZATION IN A CLOUD ANALYTICS NETWORK, filed Mar. 28, 2018, to U.S. Provisional Patent Application No. 62/649,313, titled CLOUD INTERFACE FOR COUPLED SURGICAL DEVICES, filed Mar. 28, 2018, to U.S. Provisional Patent Application No. 62/649,320, titled DRIVE ARRANGEMENTS FOR ROBOT-ASSISTED SURGICAL PLATFORMS, filed Mar. 28, 2018, to U.S. Provisional Patent Application No. 62/649,307, titled AUTOMATIC TOOL ADJUSTMENTS FOR ROBOT-ASSISTED SURGICAL PLATFORMS, filed Mar. 28, 2018, and to U.S. Provisional Patent Application No. 62/649,323, titled SENSING ARRANGEMENTS FOR ROBOT-ASSISTED SURGICAL PLATFORMS, filed Mar. 28, 2018, the disclosure of each of which is herein incorporated by reference in its entirety.

This application also claims the benefit of priority under 35 U.S.C. § 119(e) to U.S. Provisional Patent Application No. 62/611,341, titled INTERACTIVE SURGICAL PLATFORM, filed Dec. 28, 2017, to U.S. Provisional Patent Application No. 62/611,340, titled CLOUD-BASED MEDICAL ANALYTICS, filed Dec. 28, 2017, and to U.S. Provisional Patent Application No. 62/611,339, titled ROBOT ASSISTED SURGICAL PLATFORM, filed Dec. 28, 2017, the disclosure of each of which is herein incorporated by reference in its entirety.

BACKGROUND

The present disclosure relates to robotic surgical systems. Robotic surgical systems can include a central control unit, a surgeon's command console, and a robot having one or more robotic arms. Robotic surgical tools can be releasably mounted to the robotic arm(s). The number and type of robotic surgical tools can depend on the type of surgical procedure. Robotic surgical systems can be used in connection with one or more displays and/or one or more handheld surgical instruments during a surgical procedure.

SUMMARY

A method comprising collecting a first set of data by a first robotic hub, storing the first set of data in a first memory of the first robotic hub, wirelessly communicating the first set of data to a primary server at a first time, collecting a second set of data by a second robotic hub, storing the second set of data in a second memory of the second robotic hub, wirelessly communicating the second set of data to the primary server at a second time, and prioritizing the first set of data and the second set of data within a queue in the primary server, wherein the queue is configured to prioritize analysis of the first set of data and the second set of data based on a prioritization protocol.

A method comprising collecting a first set of data by a first surgical hub, storing the first set of data temporarily in a first memory of the first surgical hub, communicating the first set of data to a primary server, collecting a second set of data by a second surgical hub, storing the second set of data temporarily in a second memory of the second surgical hub, communicating the second set of data to the primary server, and prioritizing the first set of data and the second set of data within a queue in the primary server, wherein the queue is configured to prioritize analysis of the first set of data and the second set of data based on a prioritization protocol.

A method comprising collecting a first set of data by a first robotic hub during a first surgical procedure, storing the first set of data in a first memory of the first robotic hub, communicating the first set of data to a primary server, collecting a second set of data by a second robotic hub during a second surgical procedure, storing the second set of data in a second memory of the second robotic hub, communicating the second set of data to a primary server, prioritizing the first set of data and the second set of data within a data export queue in the primary server based on a prioritization protocol, and exporting the first set of data and the second set of data to an external server based on the prioritization protocol.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIG. 31 is a perspective, exploded view of an interface between a robotic tool and a tool mounting portion of the robotic surgical system of FIG. 30.

FIG. 32 is a detail view of the interface of FIG. 31, in accordance with one aspect of the present disclosure.

Figure 40:
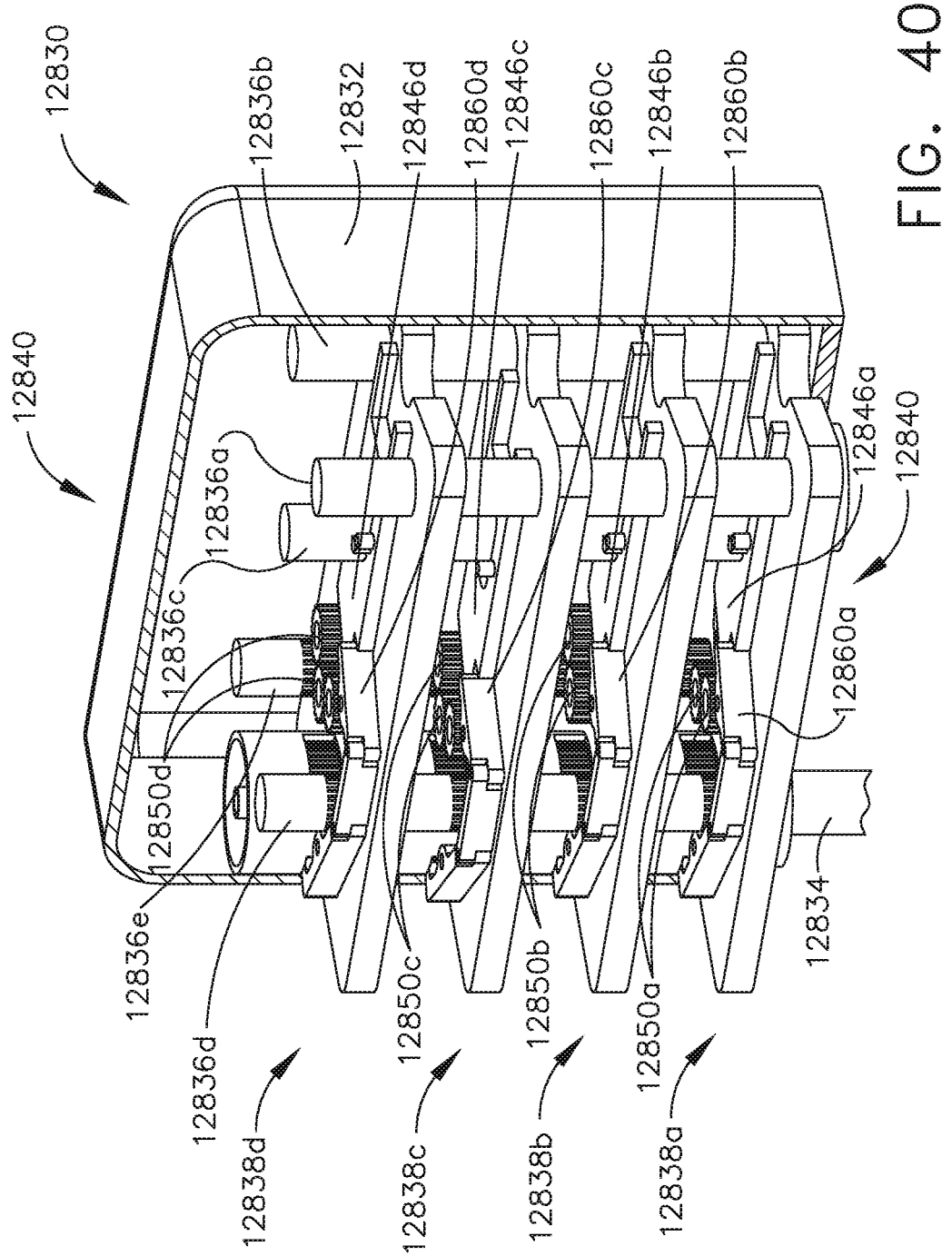
FIG. 40 is a perspective, partial cross-section view of a proximal housing of the robotic surgical tool of FIG. 38, depicting a transmission arrangement within the proximal housing, in accordance with at least one aspect of the present disclosure.
Figure 42:
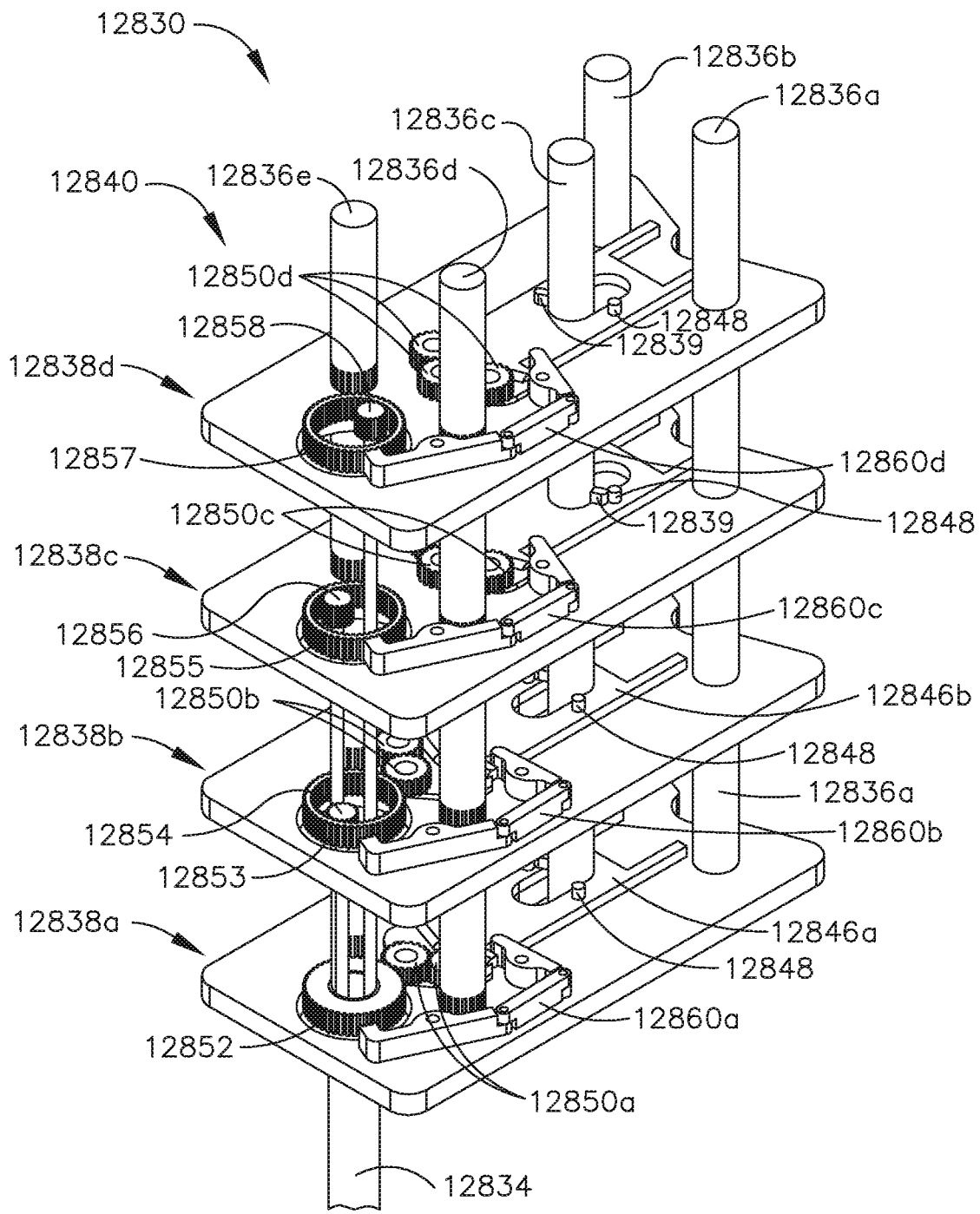

FIG. 42 is an exploded perspective view of the transmission arrangement of FIG. 40 with various parts removed for clarity, depicting the transmission arrangement in a first configuration in which a first cooperative drive is drivingly coupled to a first output shaft and a second cooperative drive is drivingly coupled to a second output shaft, in accordance with one aspect of the present disclosure.

Figure 43:
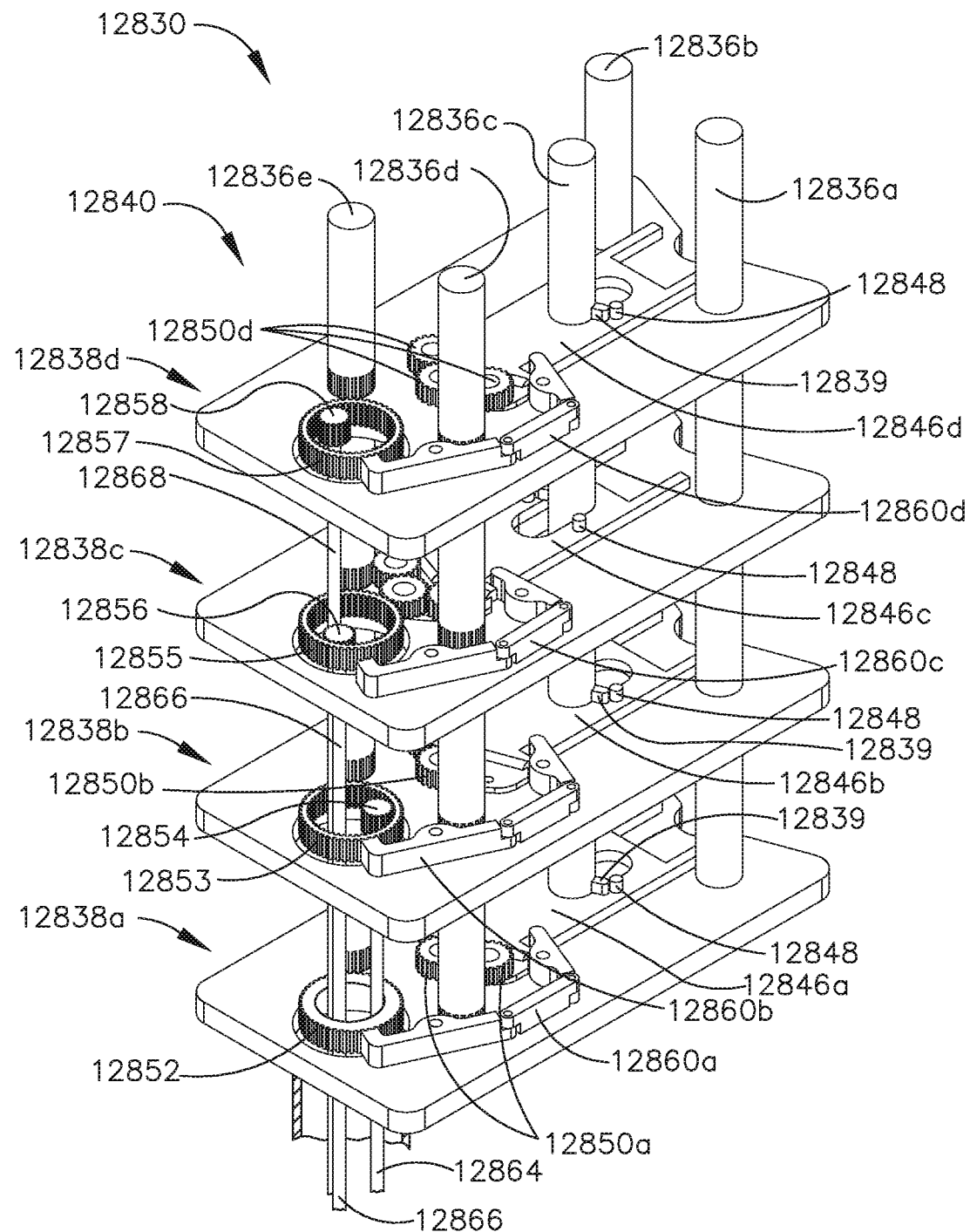

FIG. 43 is an exploded perspective view of the transmission arrangement of FIG. 40 with various parts removed for clarity, depicting the transmission arrangement in a second configuration in which the first cooperative drive and the second cooperative drive are drivingly coupled to a third output shaft, in accordance with one aspect of the present disclosure.

Figure 44:
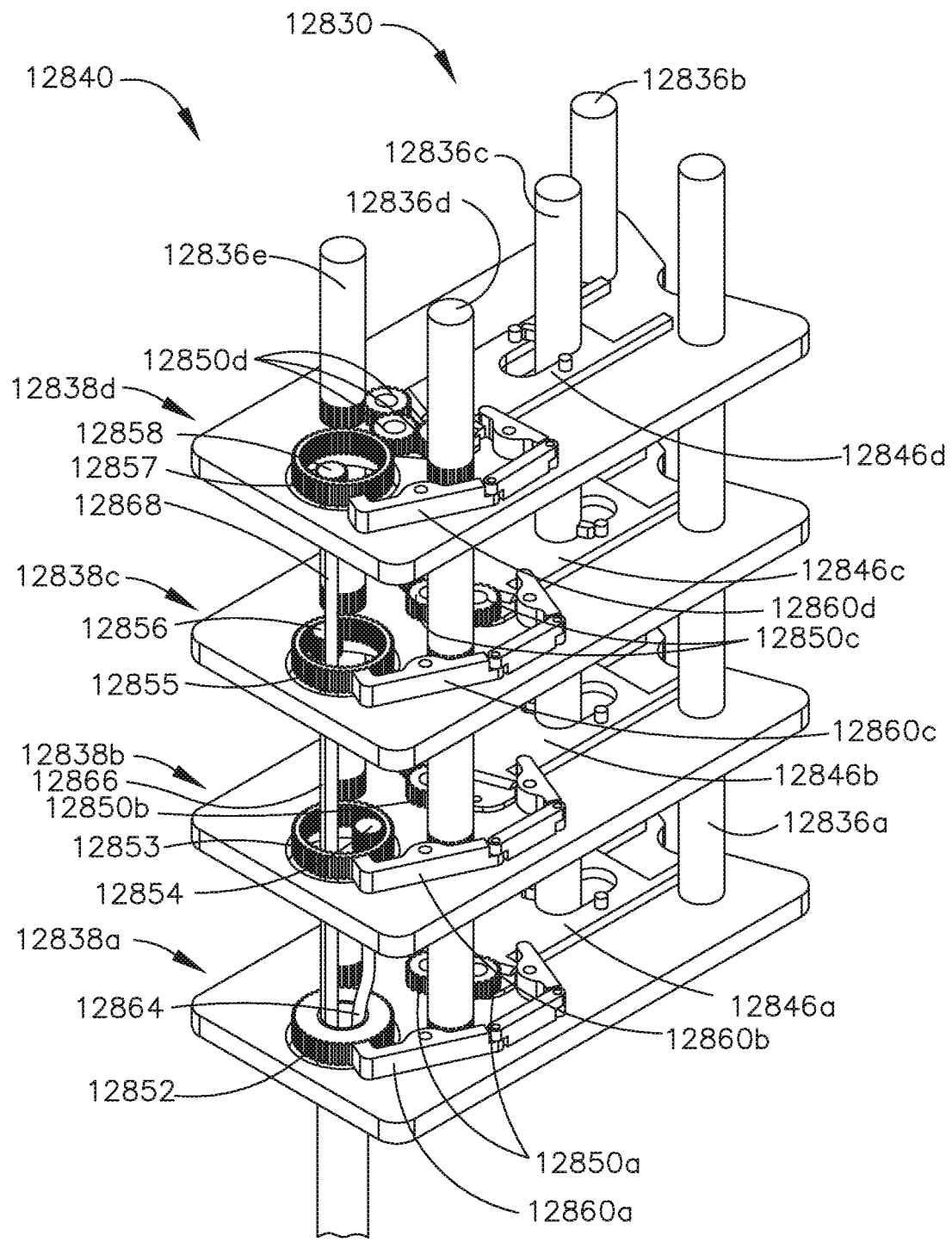

FIG. 44 is an exploded perspective view of the transmission arrangement of FIG. 40 with various parts removed for clarity, depicting the transmission arrangement in a third configuration in which the first cooperative drive and the second cooperative drive are drivingly coupled to a fourth output shaft, in accordance with one aspect of the present disclosure.

Figure 45:
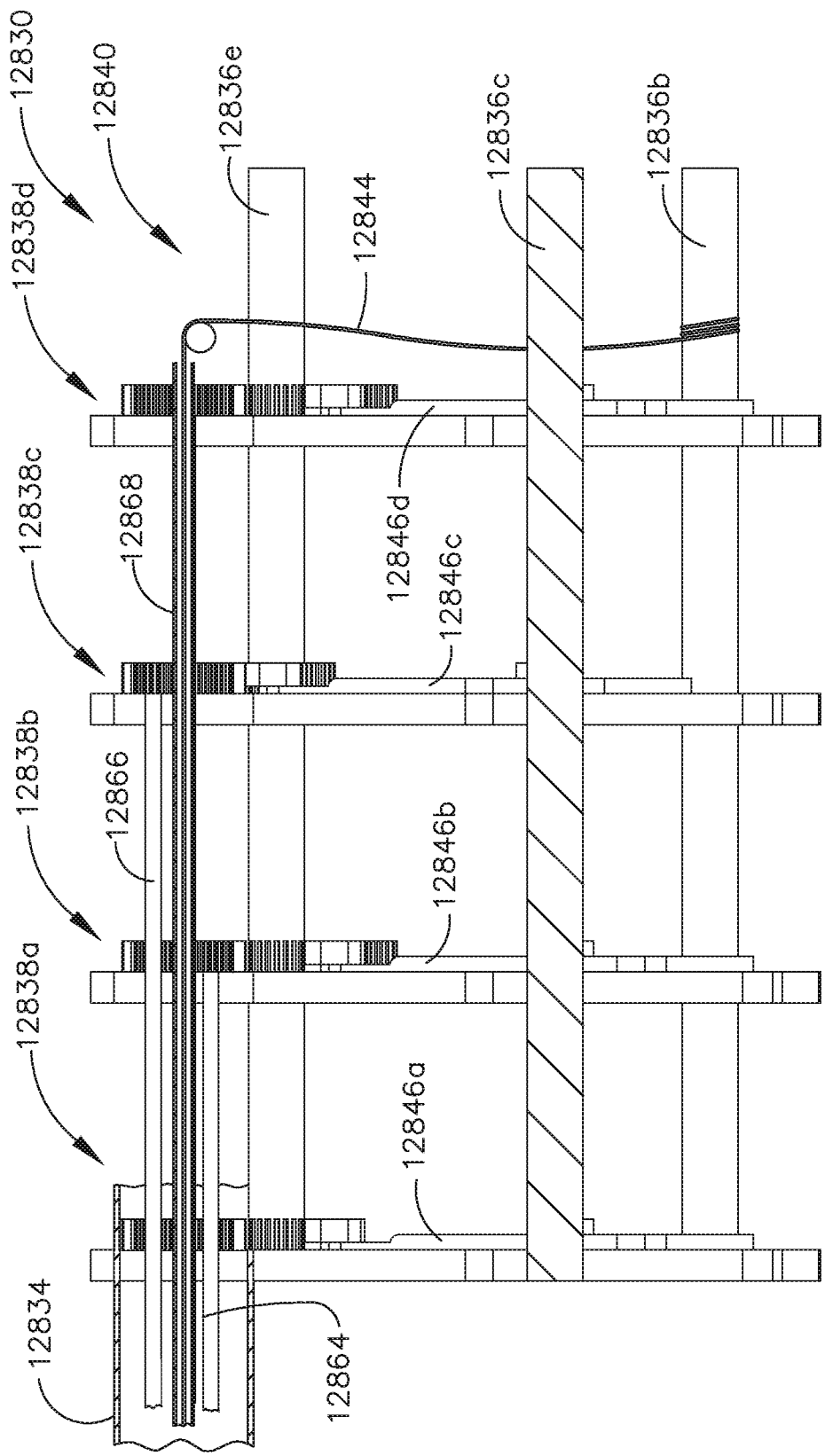

FIG. 45 is an exploded, cross-section elevation view of the transmission arrangement of FIG. 40, in accordance with at least one aspect of the present disclosure.

Figure 38:
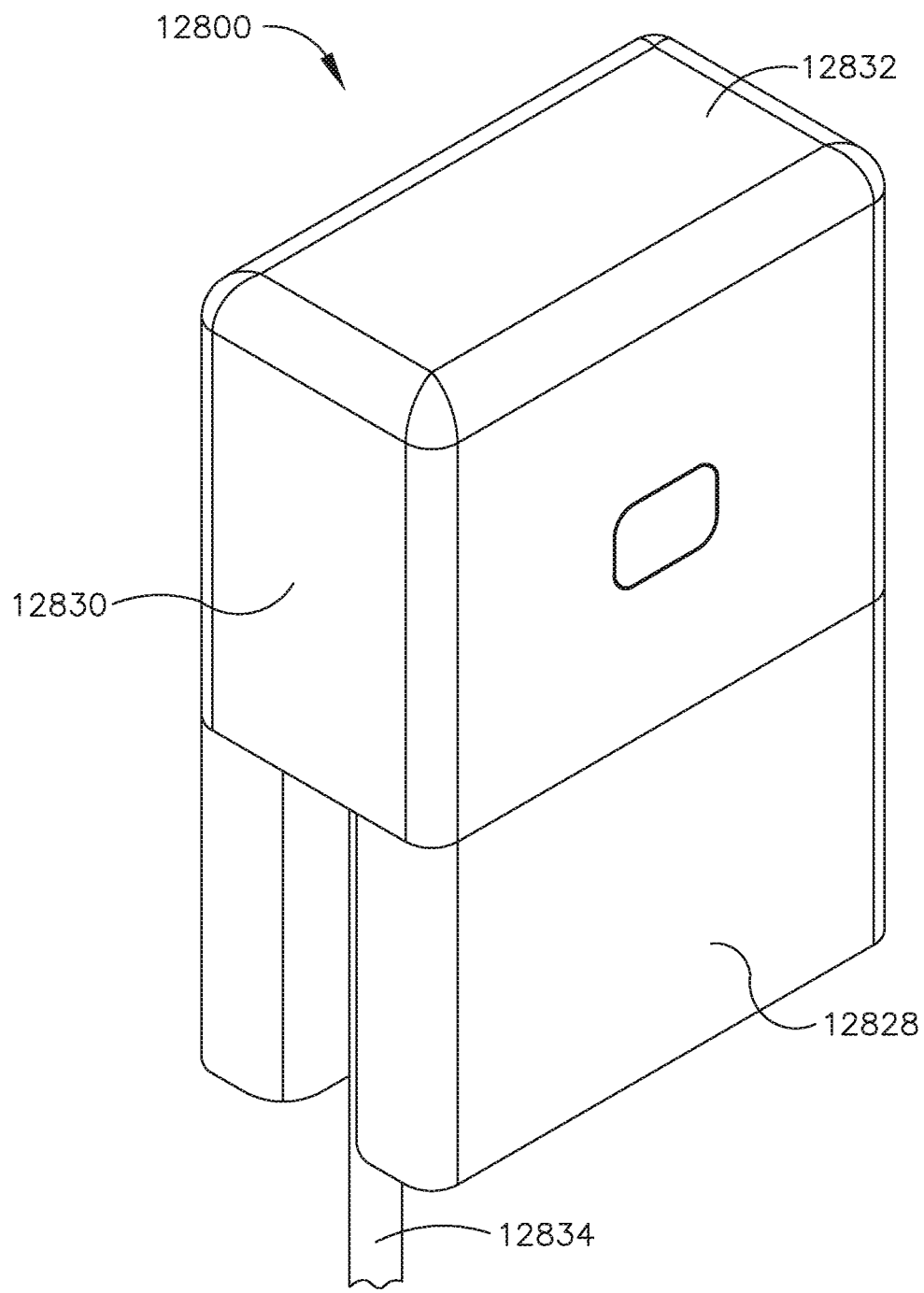
FIG. 38 is a perspective view of a drive system for a robotic surgical tool, in accordance with one aspect of the present disclosure.
Figure 46:
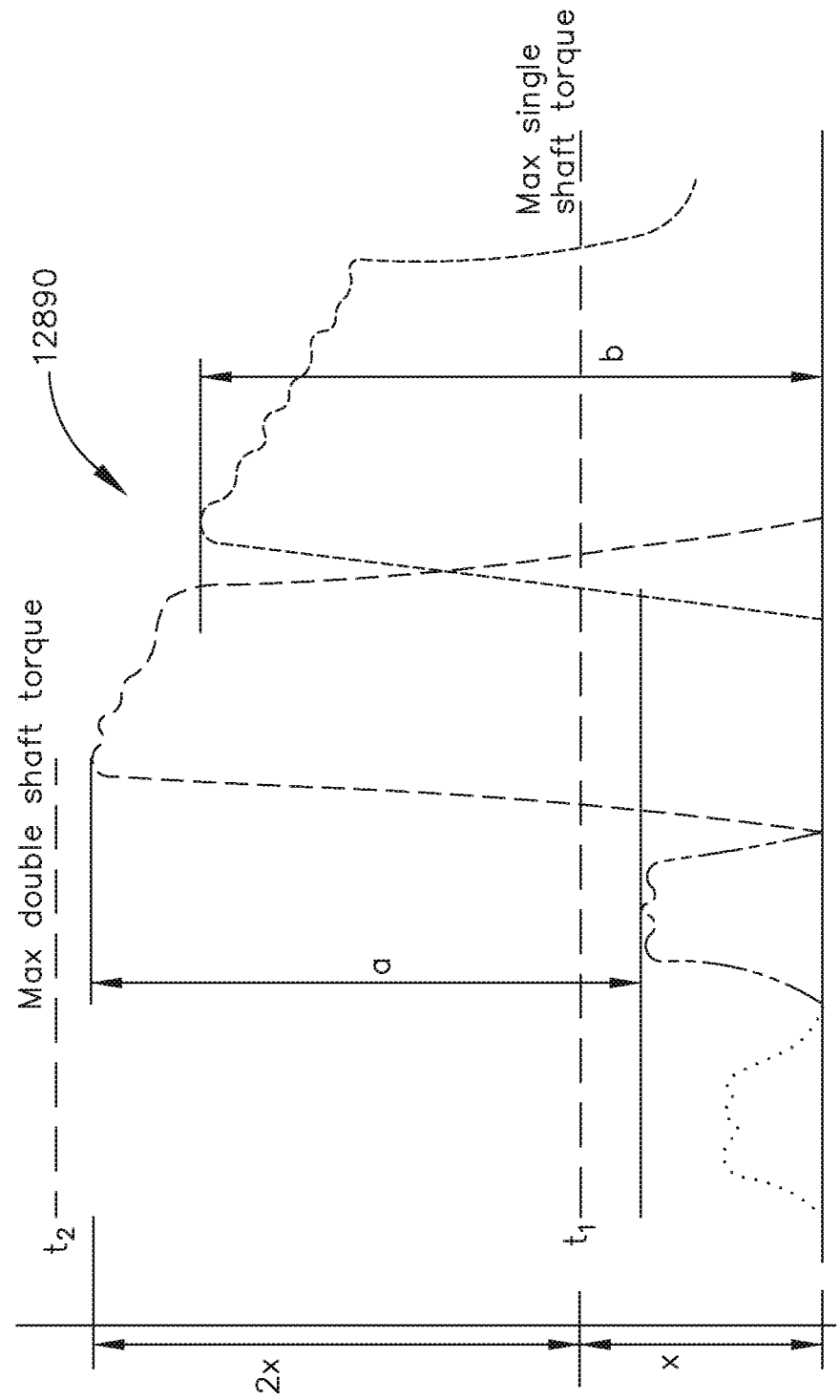

FIG. 46 is a graphical display of output torque for different surgical functions of the robotic surgical tool of FIG. 38, in accordance with at least one aspect of the present disclosure.

Figure 47:
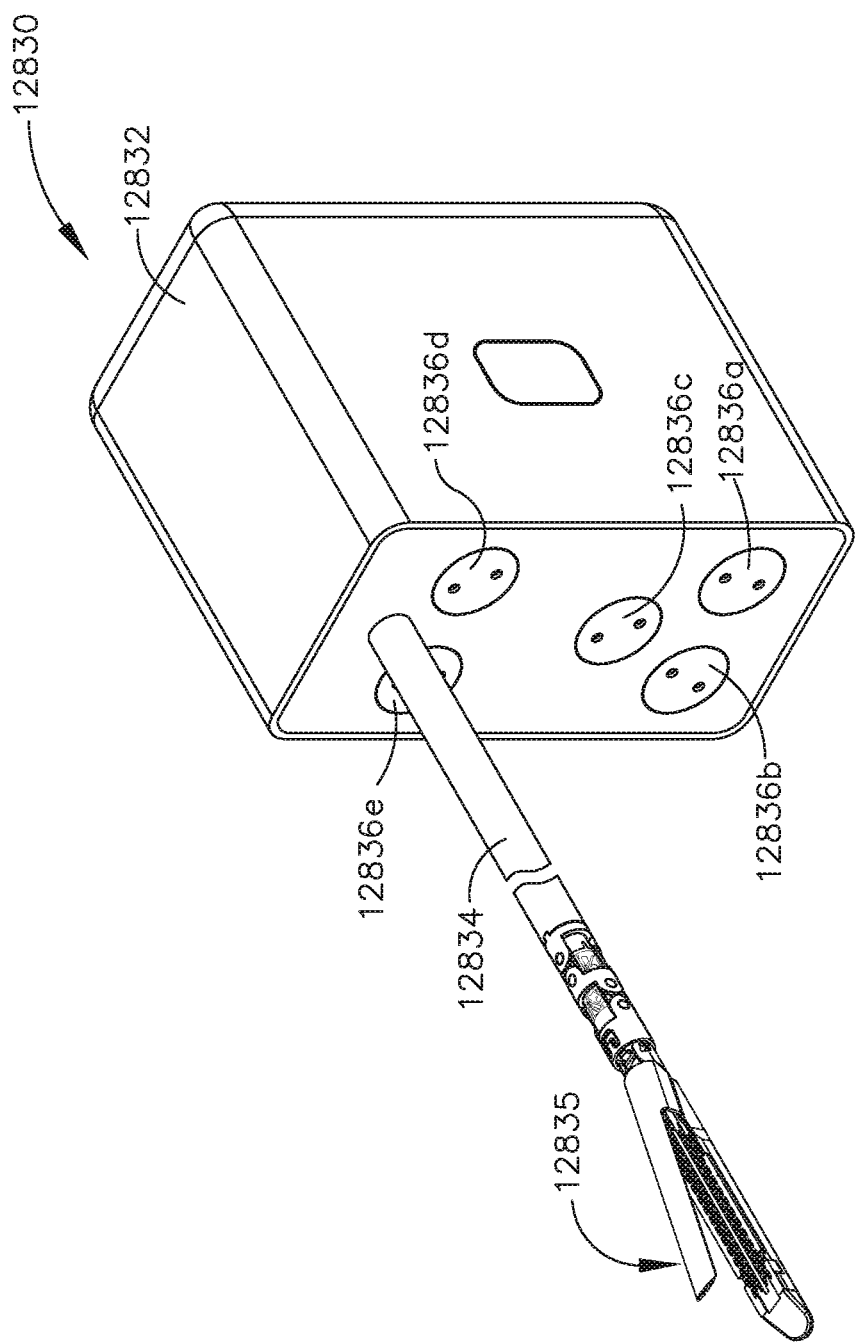

FIG. 47 is a perspective view of the robotic surgical tool of FIG. 38 in an unactuated configuration, in accordance with one aspect of the present disclosure.

Figure 48:
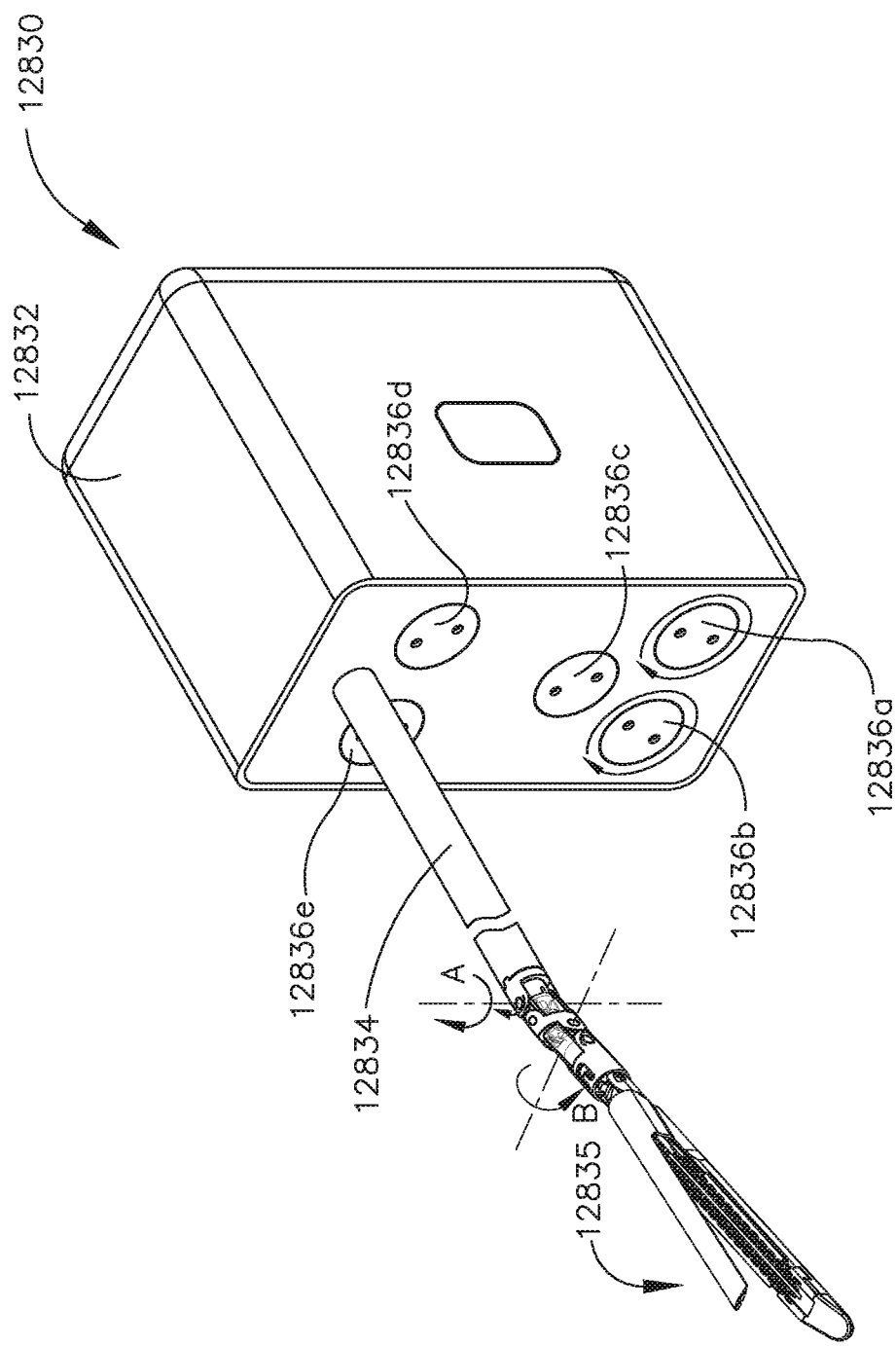

FIG. 48 is a perspective view of the robotic surgical tool of FIG. 38 in an articulated configuration, in accordance with one aspect of the present disclosure.

FIG. 49 is a perspective view of the robotic surgical tool of FIG. 38 in a rotated configuration, in accordance with one aspect of the present disclosure.

FIG. 50 is a perspective view of the robotic surgical tool of FIG. 38 in a clamped and fired configuration, in accordance with one aspect of the present disclosure.

FIG. 51 is a view of robotically-controlled end effectors at a surgical site, in accordance with one aspect of the present disclosure.

FIG. 52 is a view of the robotically-controlled end effectors of FIG. 51, in accordance with one aspect of the present disclosure.

FIG. 53 is a graphical display of force and displacement over time for one of the robotically-controlled end effectors of FIG. 51, in accordance with one aspect of the present disclosure.

Figure 54:
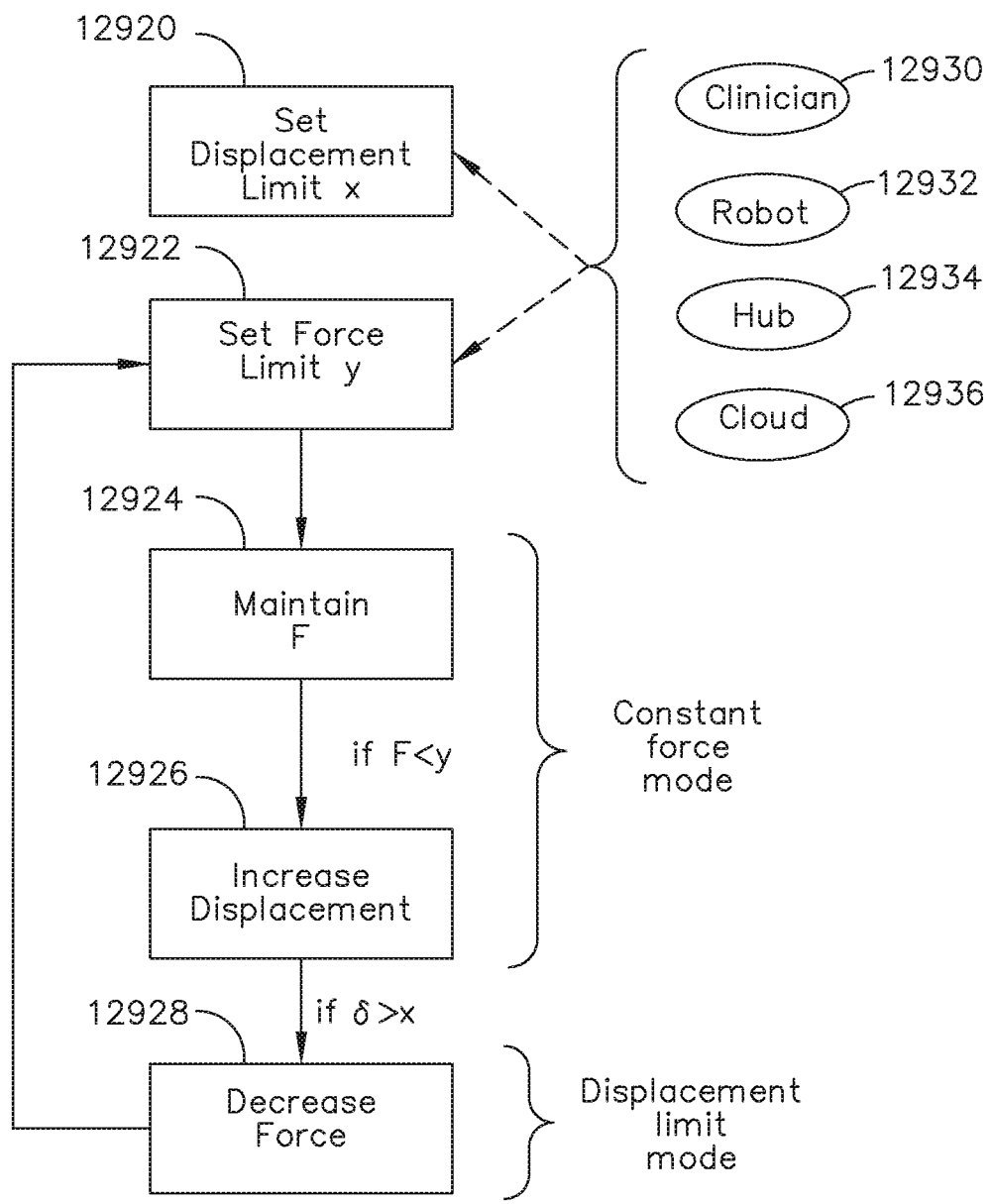

FIG. 54 is a flow chart of a control algorithm for one a surgical tool for use with a robotic surgical system, in accordance with one aspect of the present disclosure.

Figure 55:
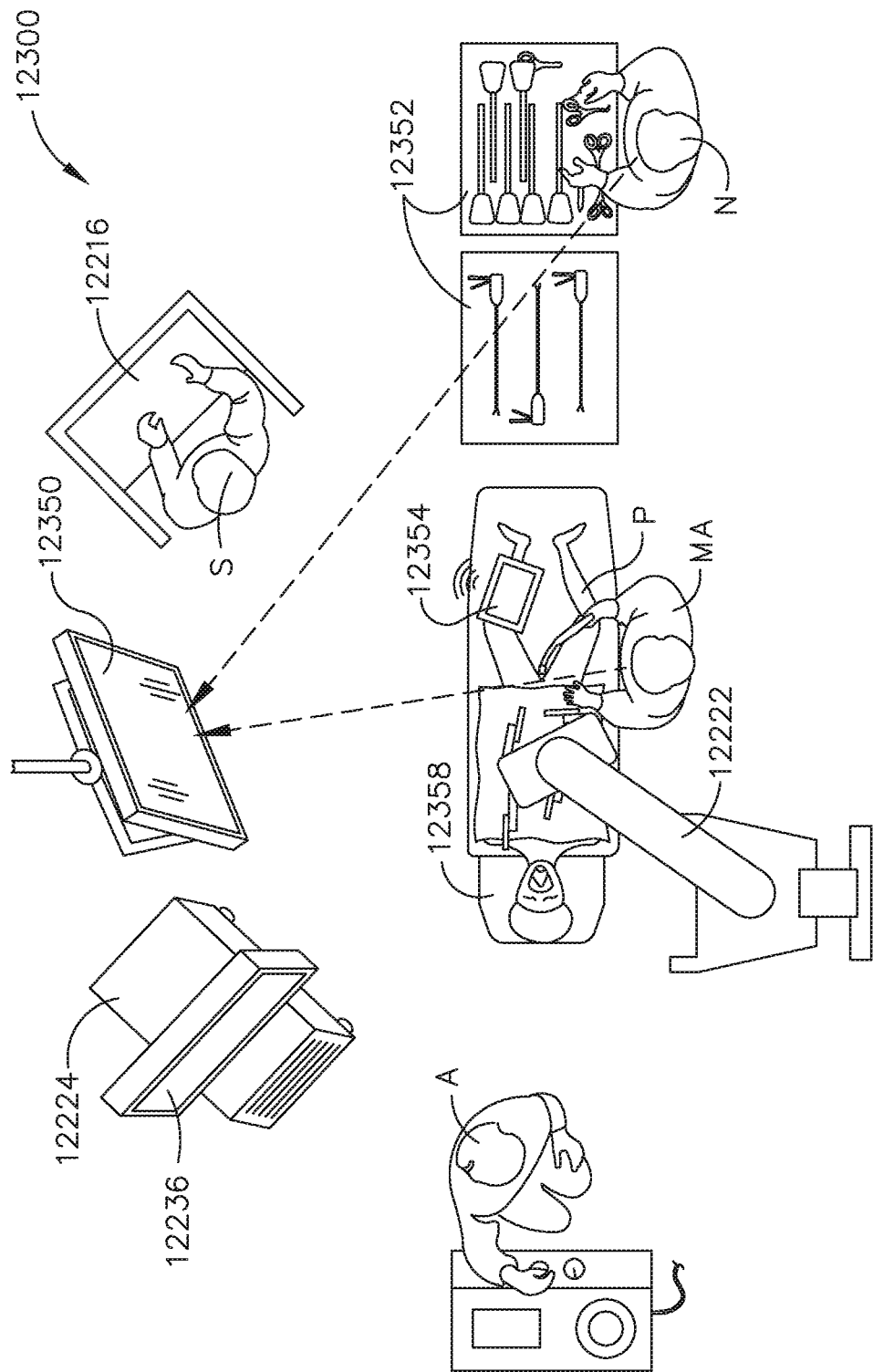

FIG. 55 is an elevation view of a surgical procedure involving a robotic surgical system and a handheld surgical instrument and depicting multiple displays in the surgical theater, in accordance with one aspect of the present disclosure.

Figure 56:
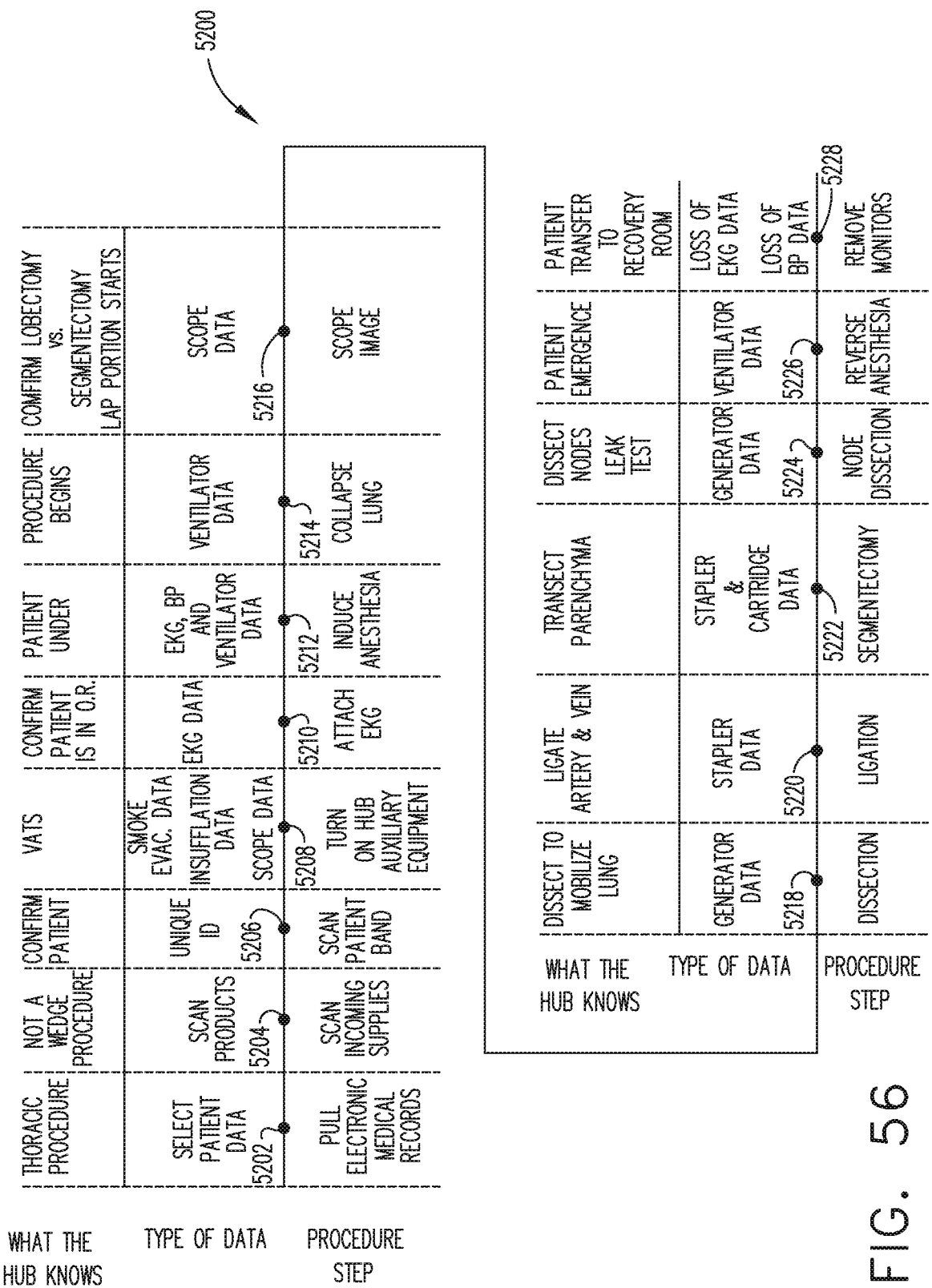

FIG. 56 is a timeline depicting situational awareness of a surgical hub, in accordance with one aspect of the present disclosure.

Figure 57:
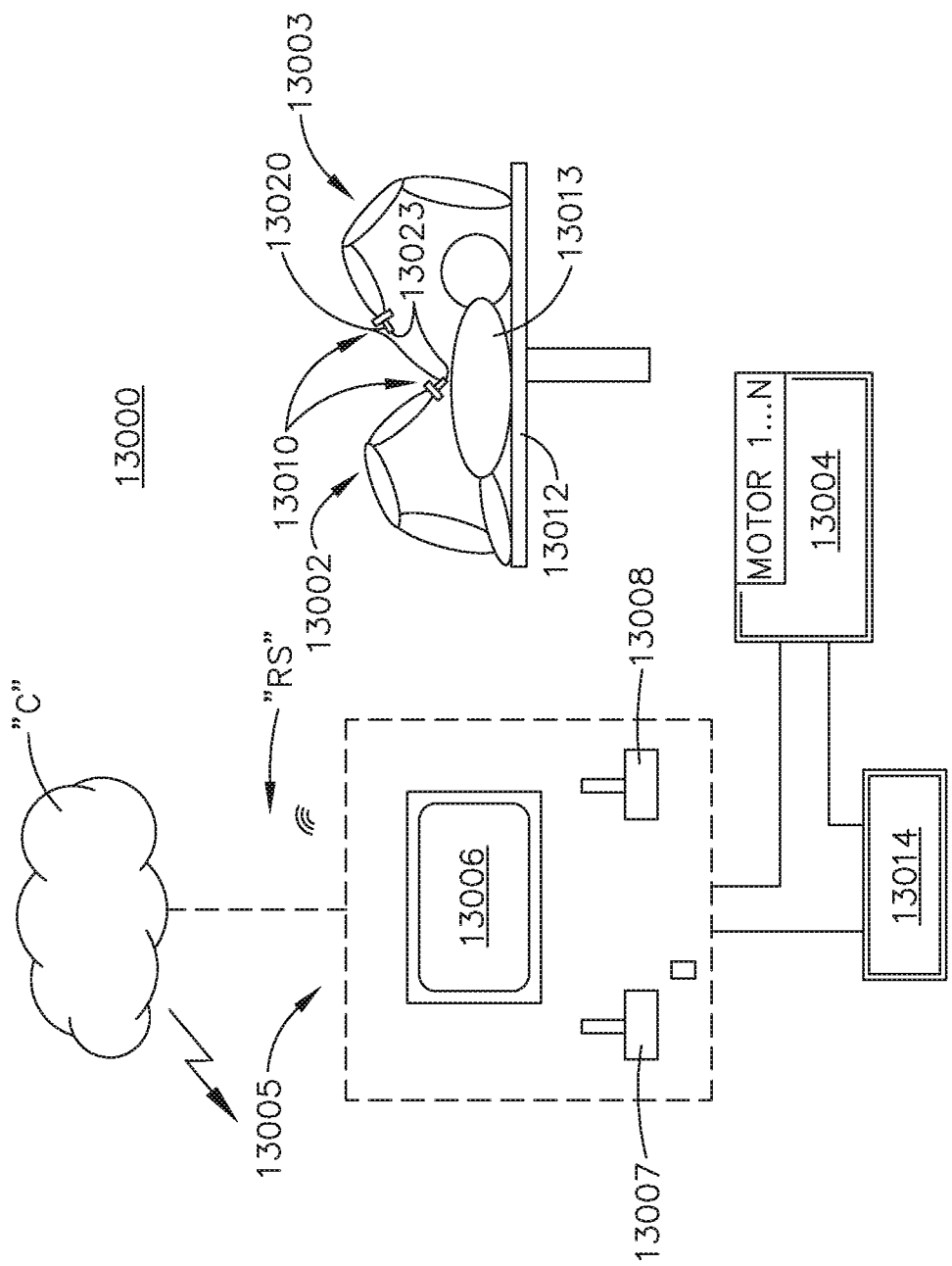

FIG. 57 is a schematic of a robotic surgical system, in accordance with at least one aspect of the present disclosure.

Figure 58:
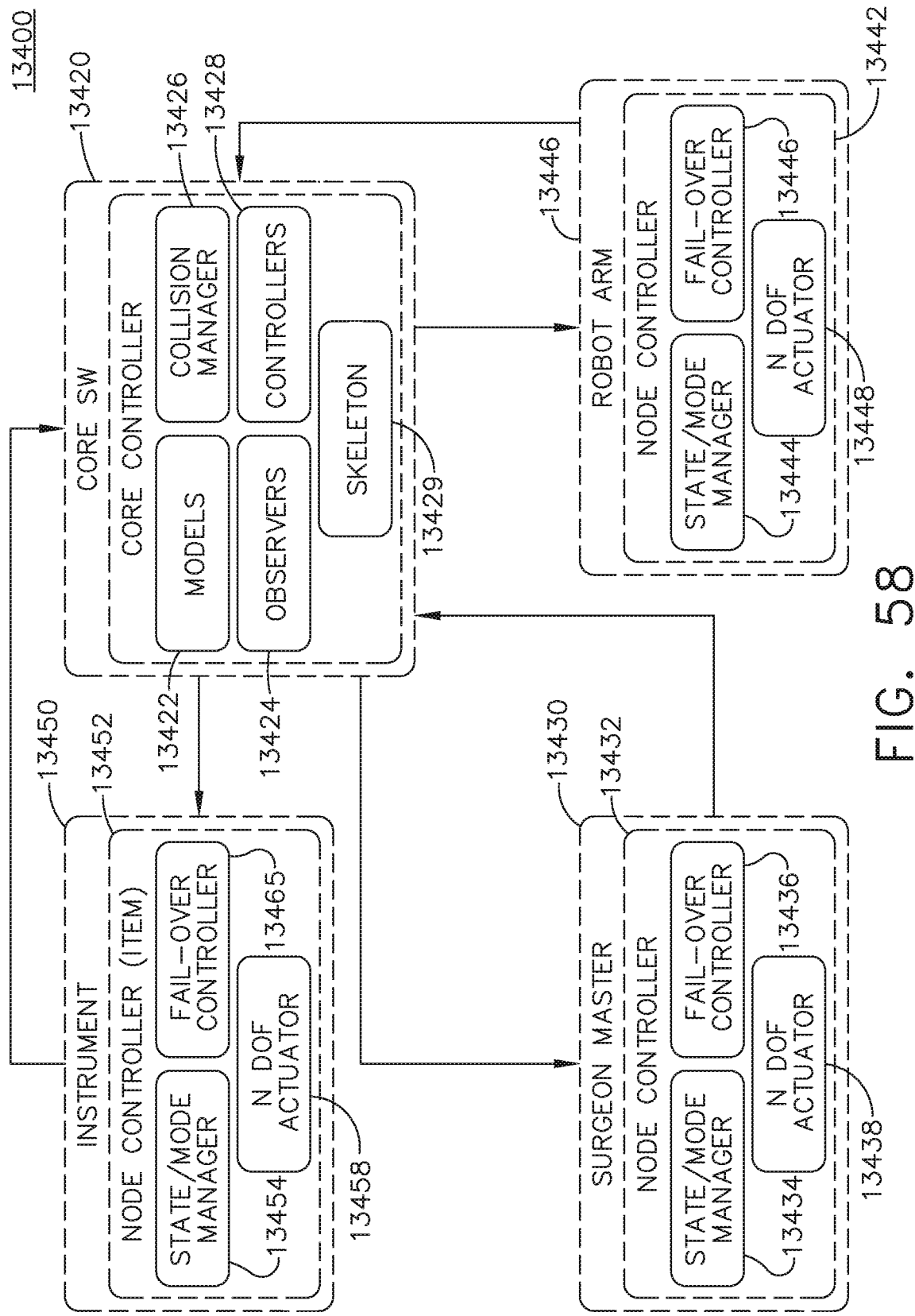

FIG. 58 is a block diagram of control components for the robotic surgical system of FIG. 57, in accordance with at least one aspect of the present disclosure.

FIG. 59A is an elevation view of an ultrasonic surgical tool positioned out of contact with tissue, in accordance with at least one aspect of the present disclosure.

FIG. 59B is an elevation view of the ultrasonic surgical tool of FIG. 59A positioned in abutting contact with tissue, in accordance with at least one aspect of the present disclosure.

Figure 60B:
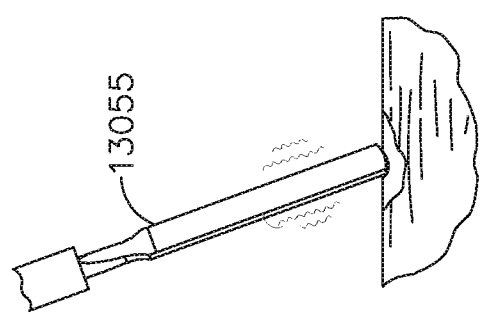
Figure 60A:
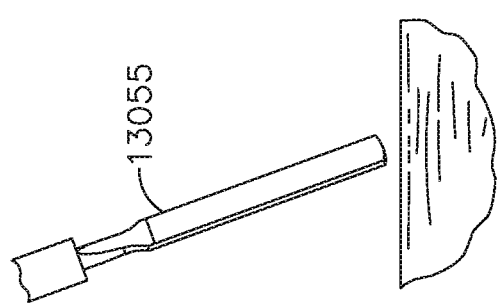

FIG. 60A is an elevation view of a monopolar cautery pencil positioned out of contact with tissue, in accordance with at least one aspect of the present disclosure.

FIG. 60B is an elevation view of the monopolar cautery pencil of FIG. 60A positioned in abutting contact with tissue, in accordance with at least one aspect of the present disclosure.

FIG. 61 is a graphical display of continuity and current over time for the ultrasonic surgical tool of FIGS. 59A and 59B, in accordance with at least one aspect of the present disclosure.

Figure 62:
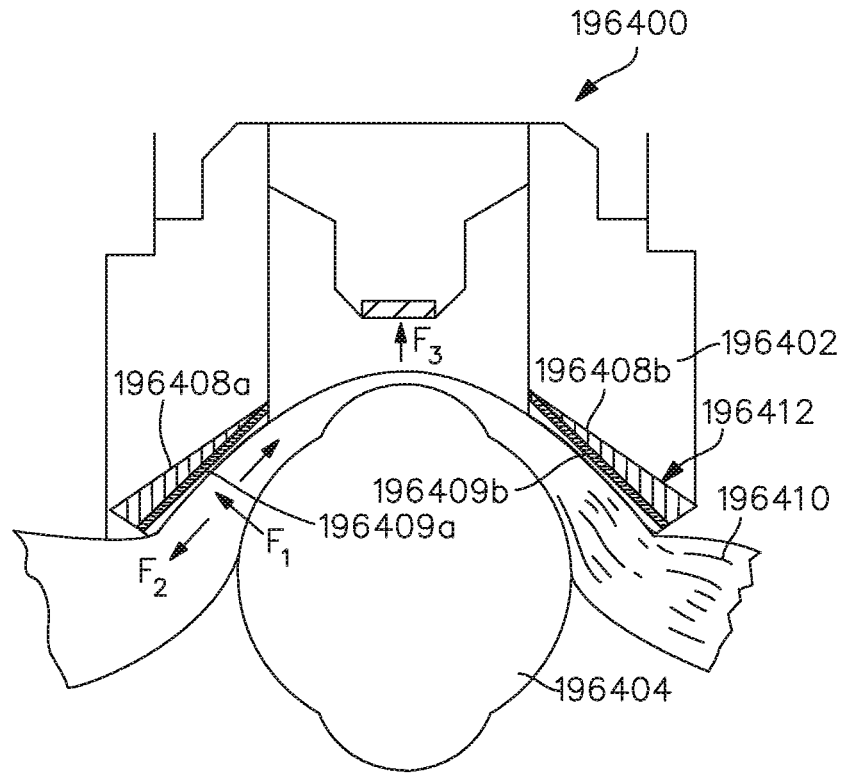

FIG. 62 illustrates an end effector comprising radio frequency (RF) data sensors located on a jaw member, in accordance with at least one aspect of the present disclosure.

Figure 63:
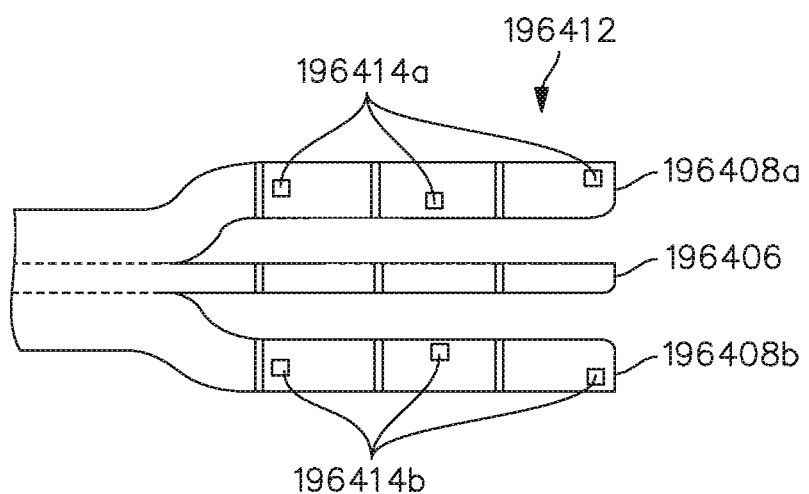

FIG. 63 illustrates the sensors shown in FIG. 62 mounted to or formed integrally with a flexible circuit, in accordance with at least one aspect of the present disclosure.

Figure 64:
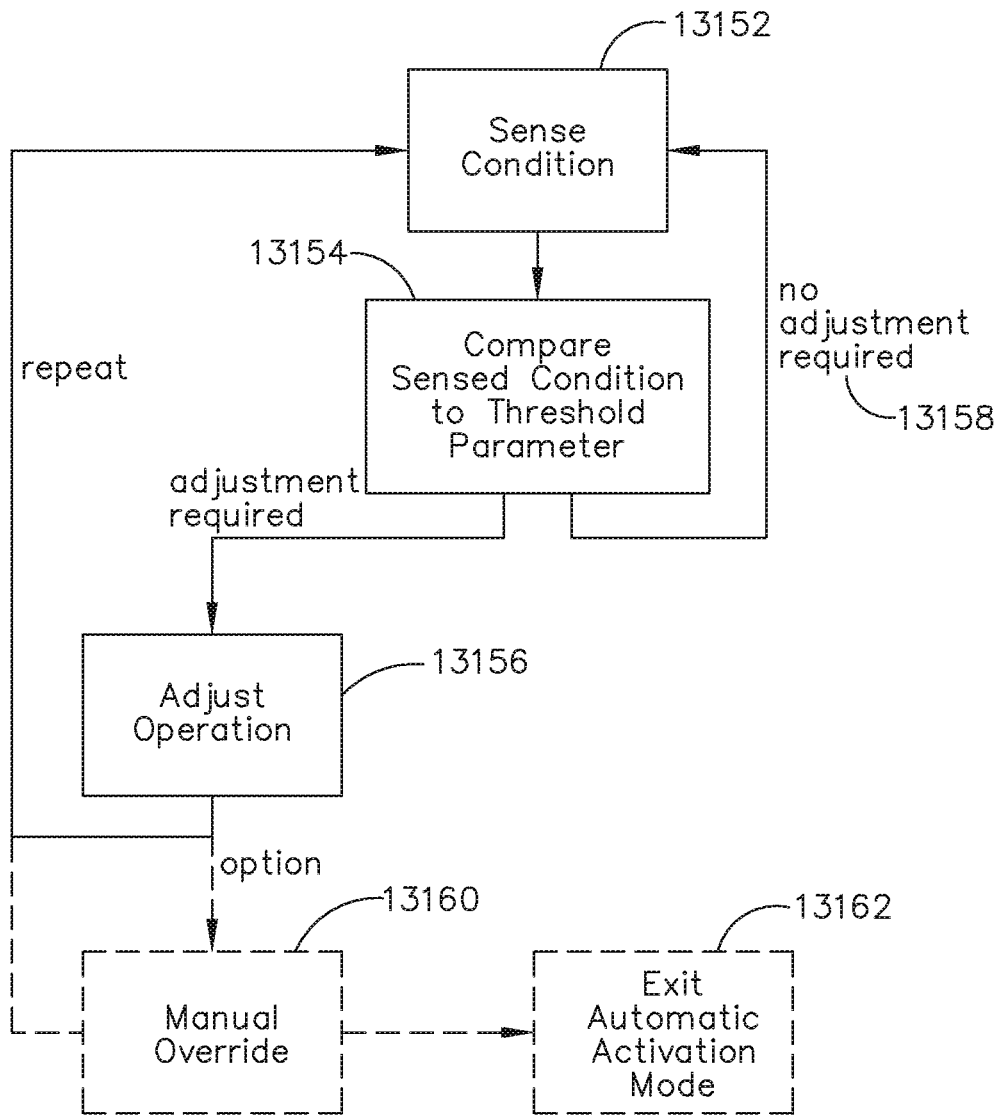

FIG. 64 is a flow chart depicting an automatic activation mode of a surgical instrument, in accordance with at least one aspect of the present disclosure.

Figure 65:
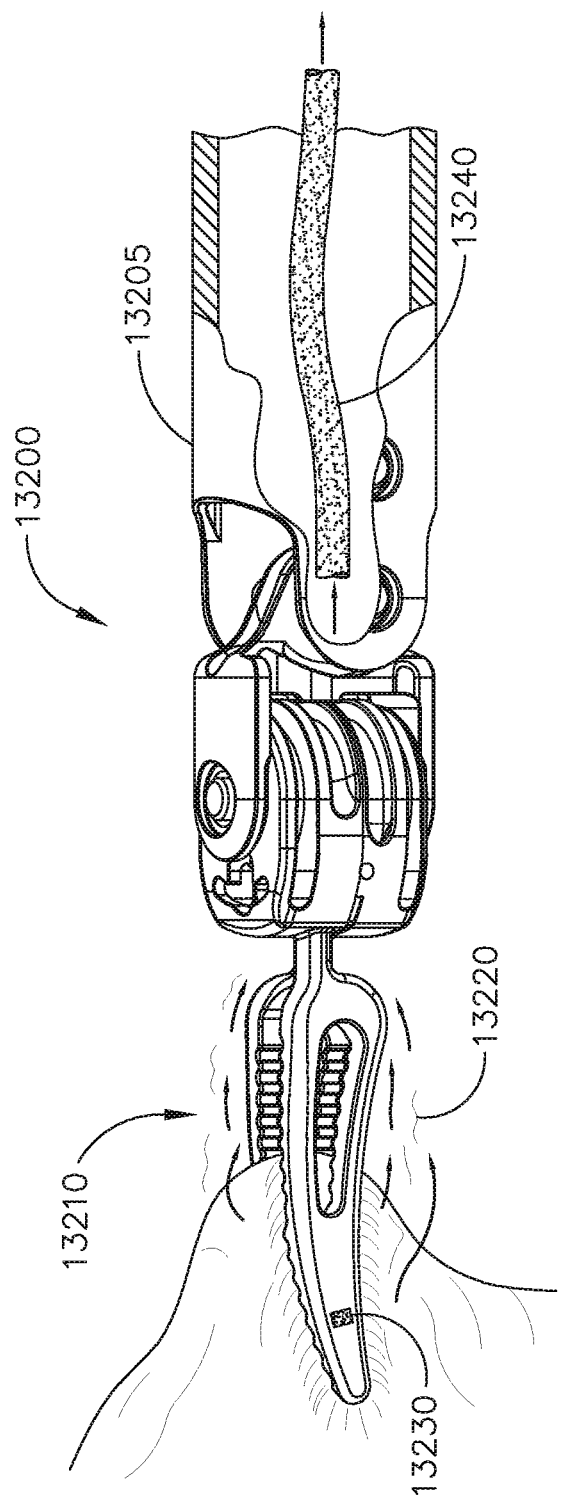

FIG. 65 is a perspective view of an end effector of a bipolar radio frequency (RF) surgical tool having a smoke evacuation pump for use with a robotic surgical system, depicting the surgical tool clamping and treating tissue, in accordance with at least one aspect of the present disclosure.

Figure 66:
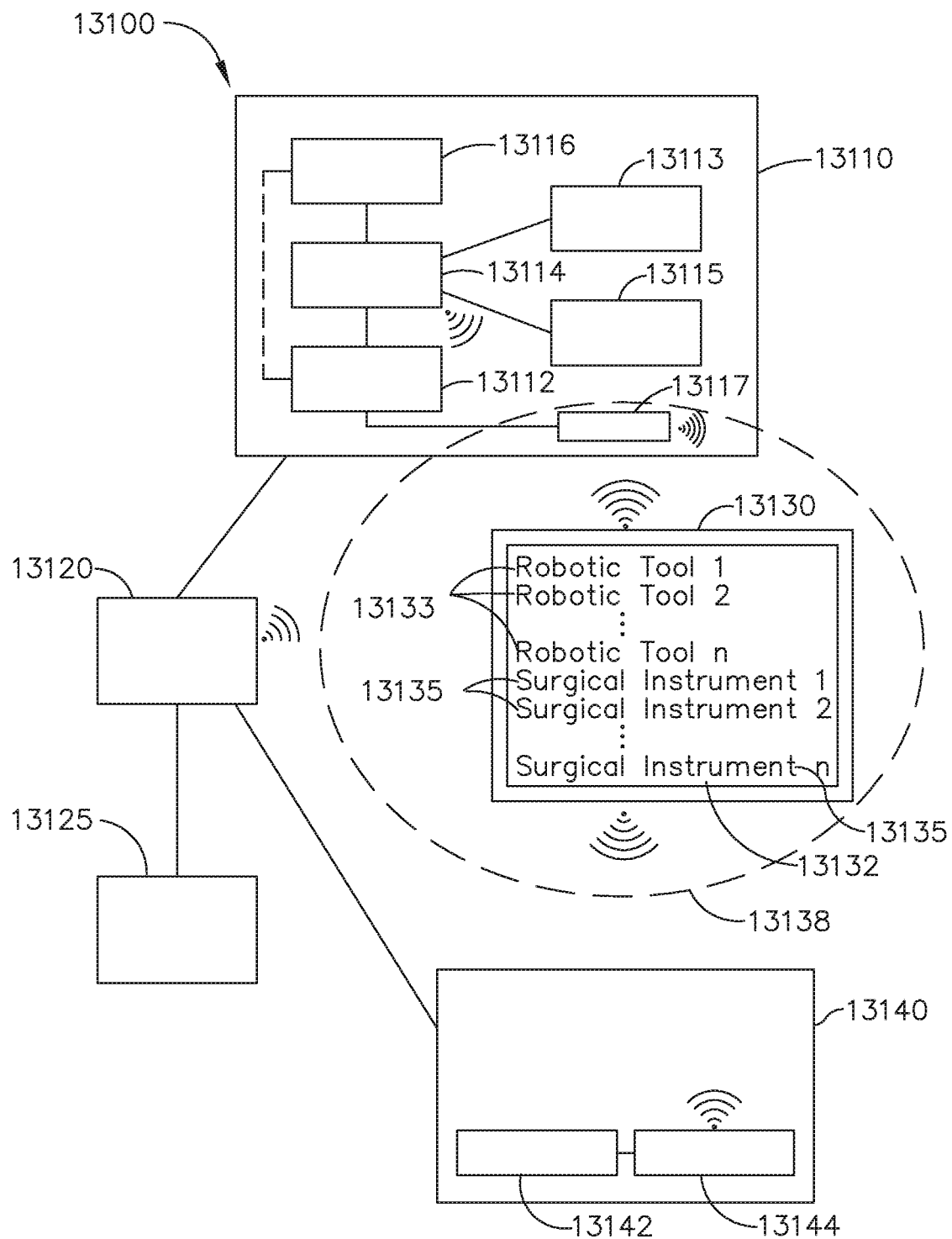

FIG. 66 is a block diagram of a surgical system comprising a robotic surgical system, a handheld surgical instrument, and a surgical hub, in accordance with at least one aspect of the present disclosure.

Figure 67:
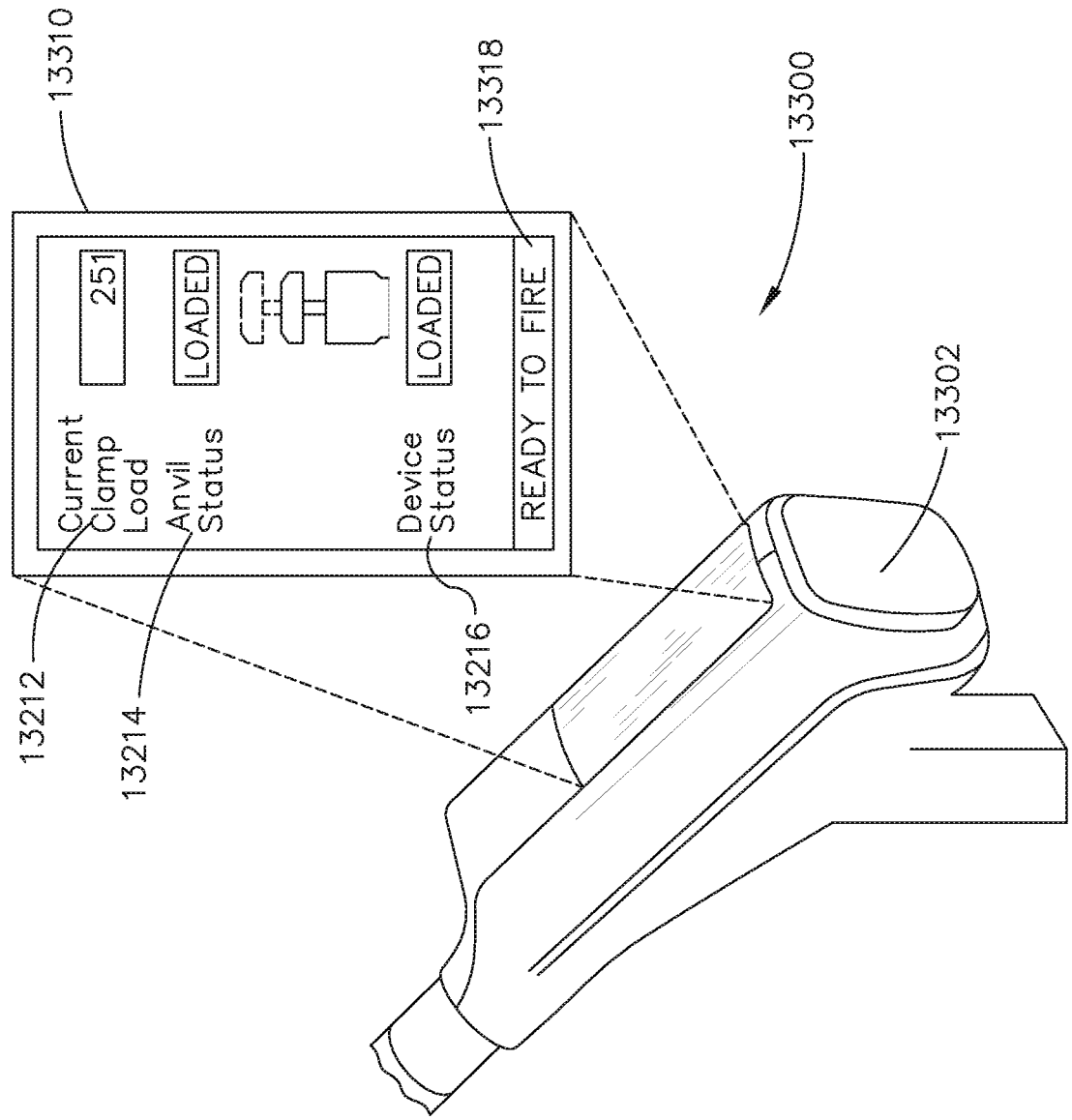

FIG. 67 is a perspective view of a handle portion of a handheld surgical instrument including a display and further depicting a detail view of the display depicting information from the instrument itself, in accordance with at least one aspect of the present disclosure.

Figure 68:
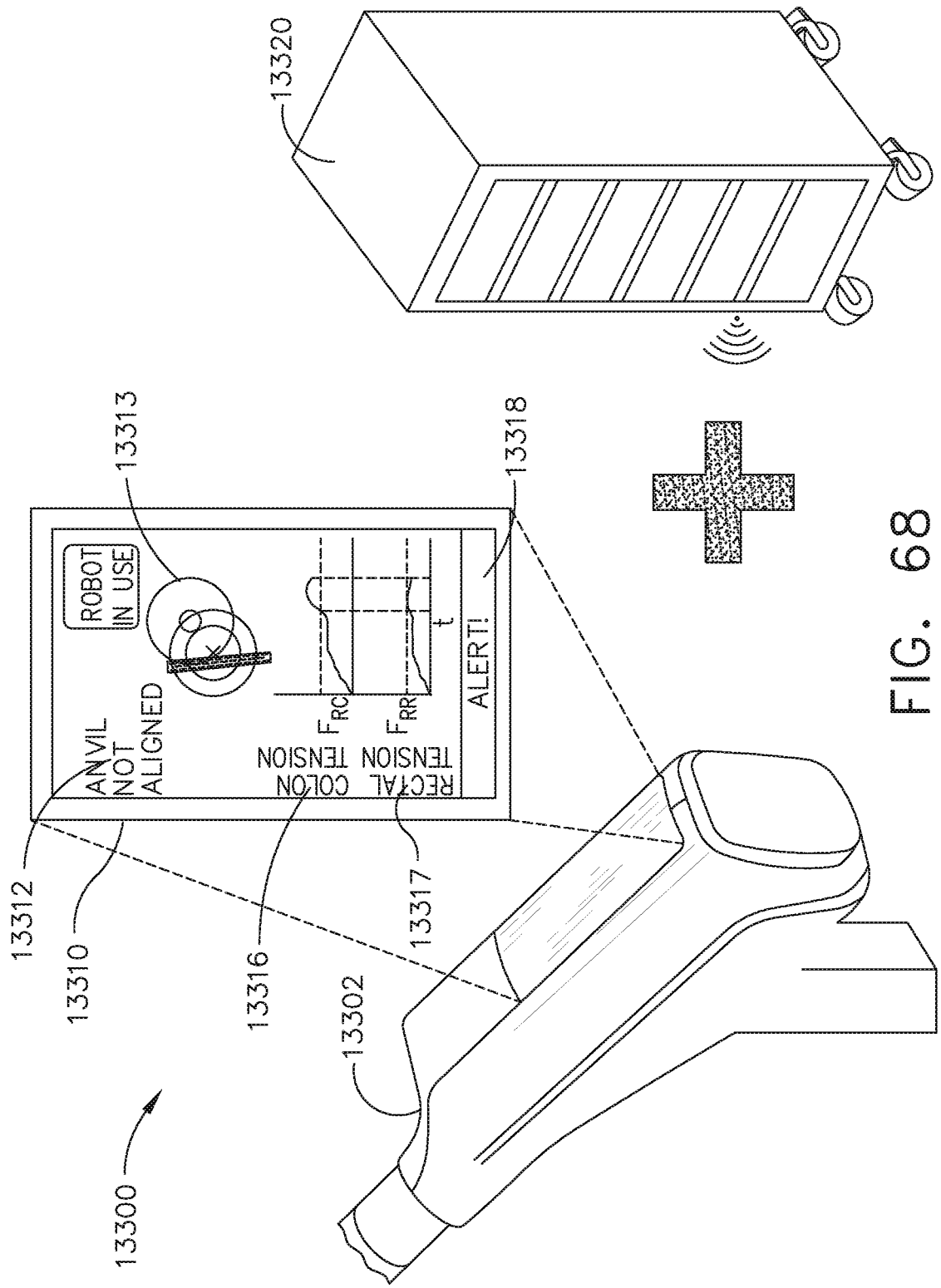

FIG. 68 is a perspective view of the handle portion of the handheld surgical instrument of FIG. 67 depicting the instrument paired with a surgical hub and further including a detail view of the display depicting information from the surgical hub, in accordance with at least one aspect of the present disclosure.

Figure 69:
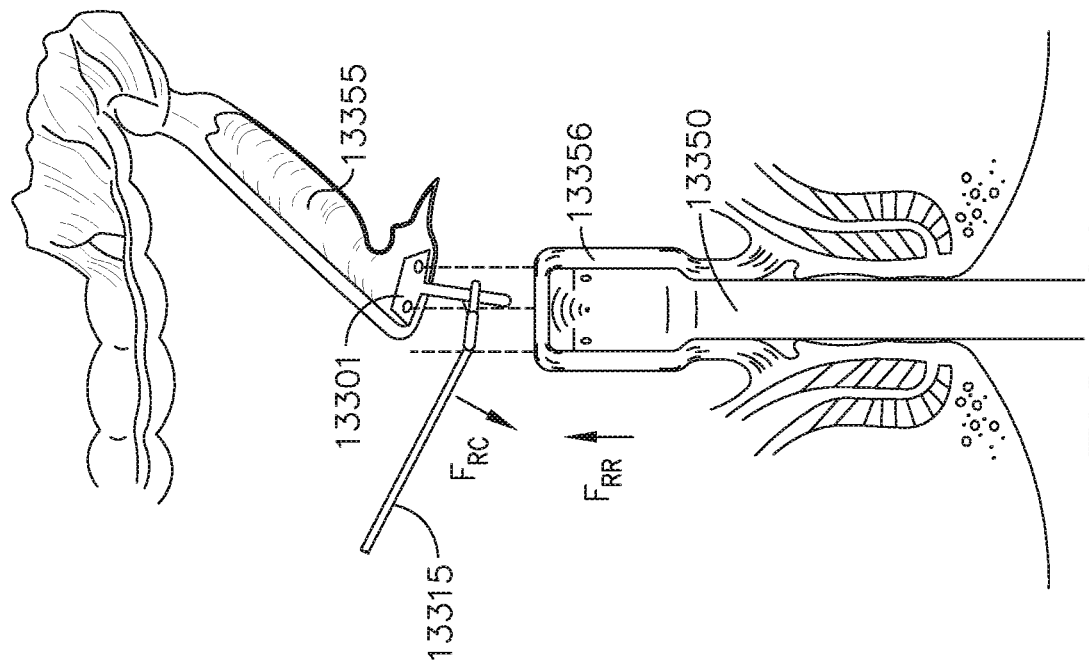

FIG. 69 is a schematic of a colon resection procedure, in accordance with at least one aspect of the present disclosure.

Figure 70:
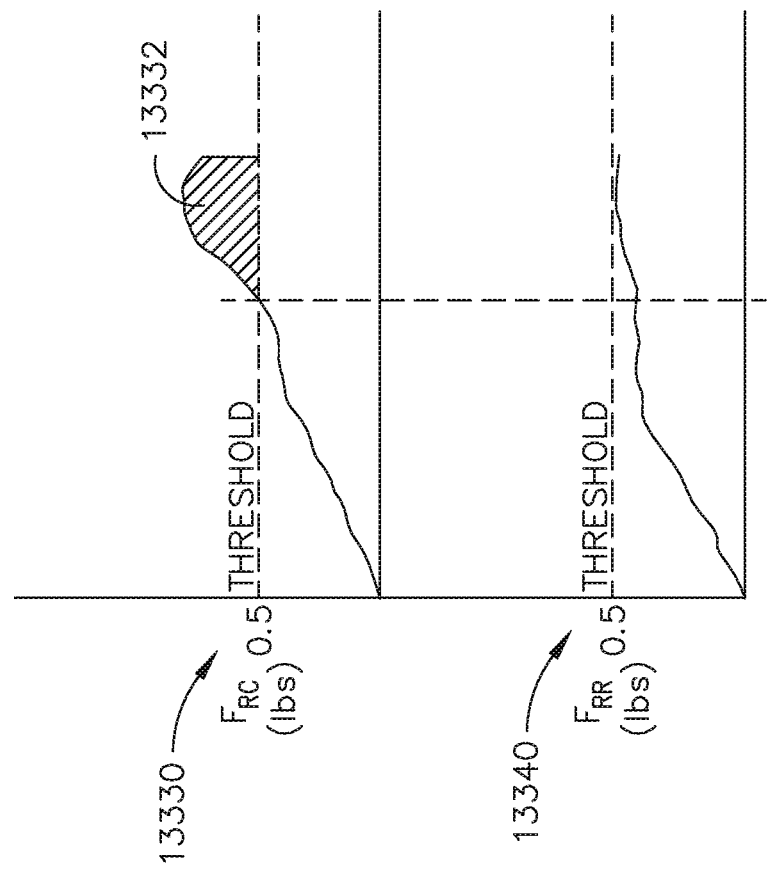

FIG. 70 is a graphical display of force over time for the colon resection procedure displayed on the instrument display in FIG. 69, in accordance with at least one aspect of the present disclosure.

Figure 71:
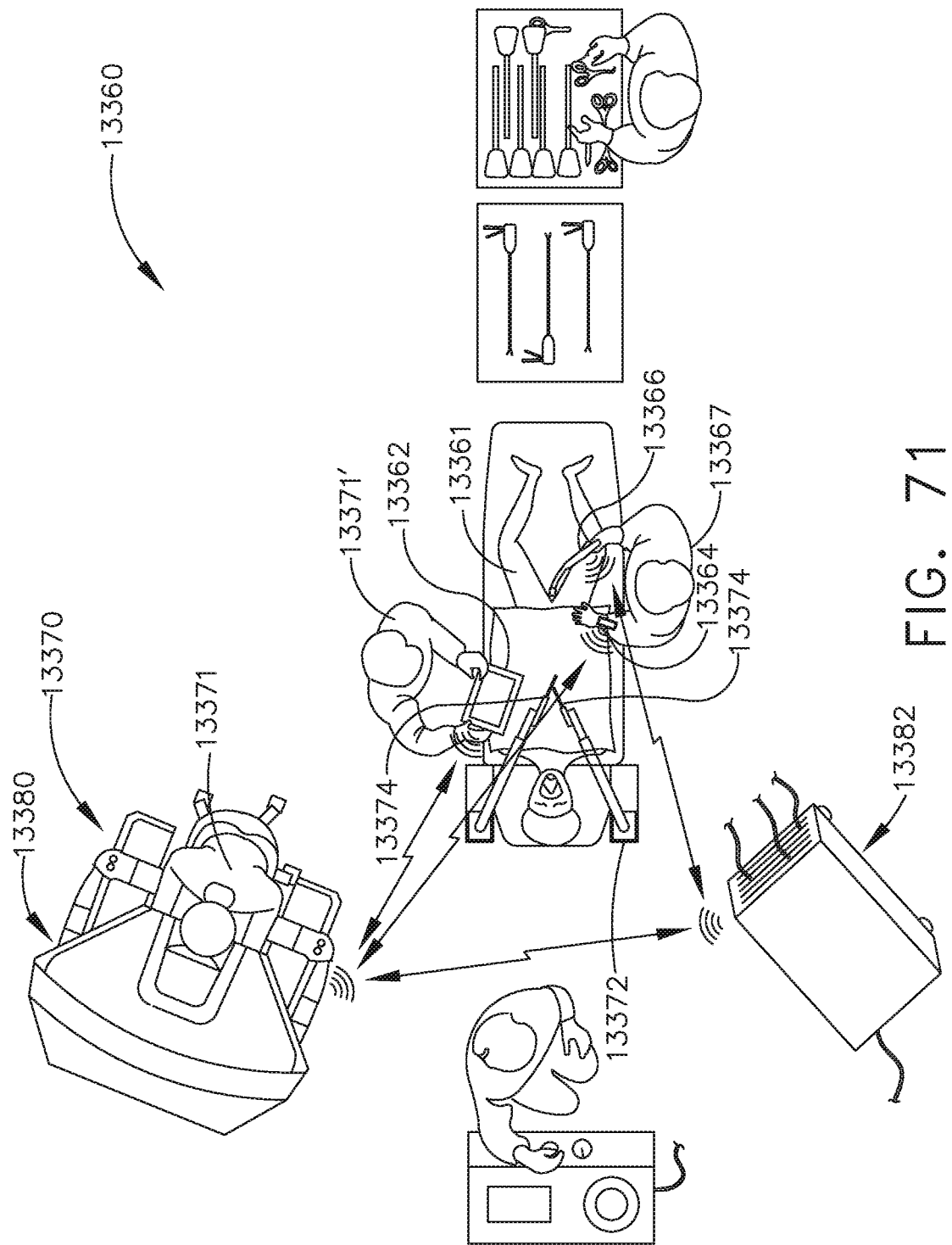

FIG. 71 is a schematic of a robotic surgical system during a surgical procedure including a plurality of hubs and interactive secondary displays, in accordance with at least one aspect of the present disclosure.

Figure 72:
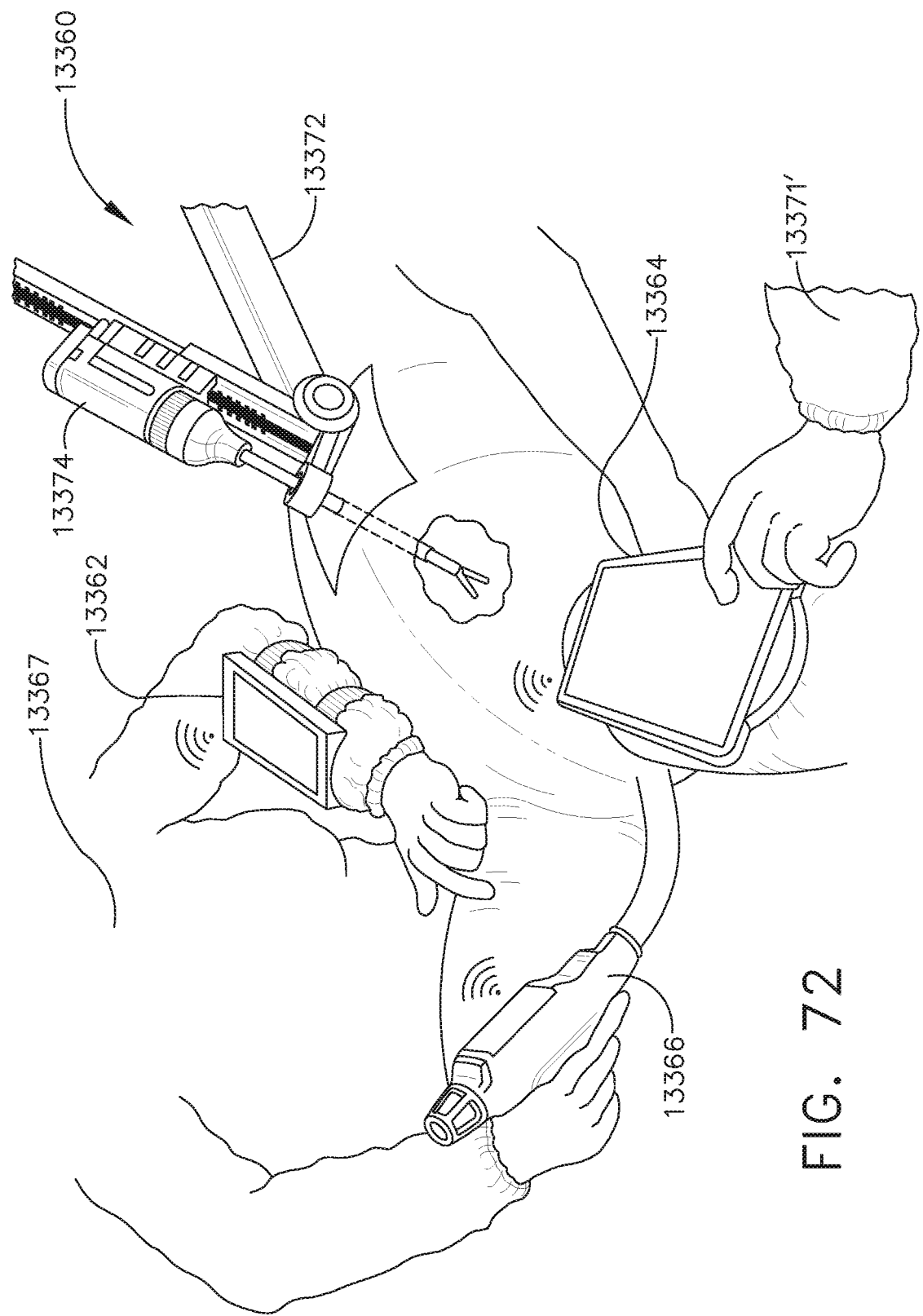

FIG. 72 is a detail view of the interactive secondary displays of FIG. 71, in accordance with at least one aspect of the present disclosure.

Figure 73:
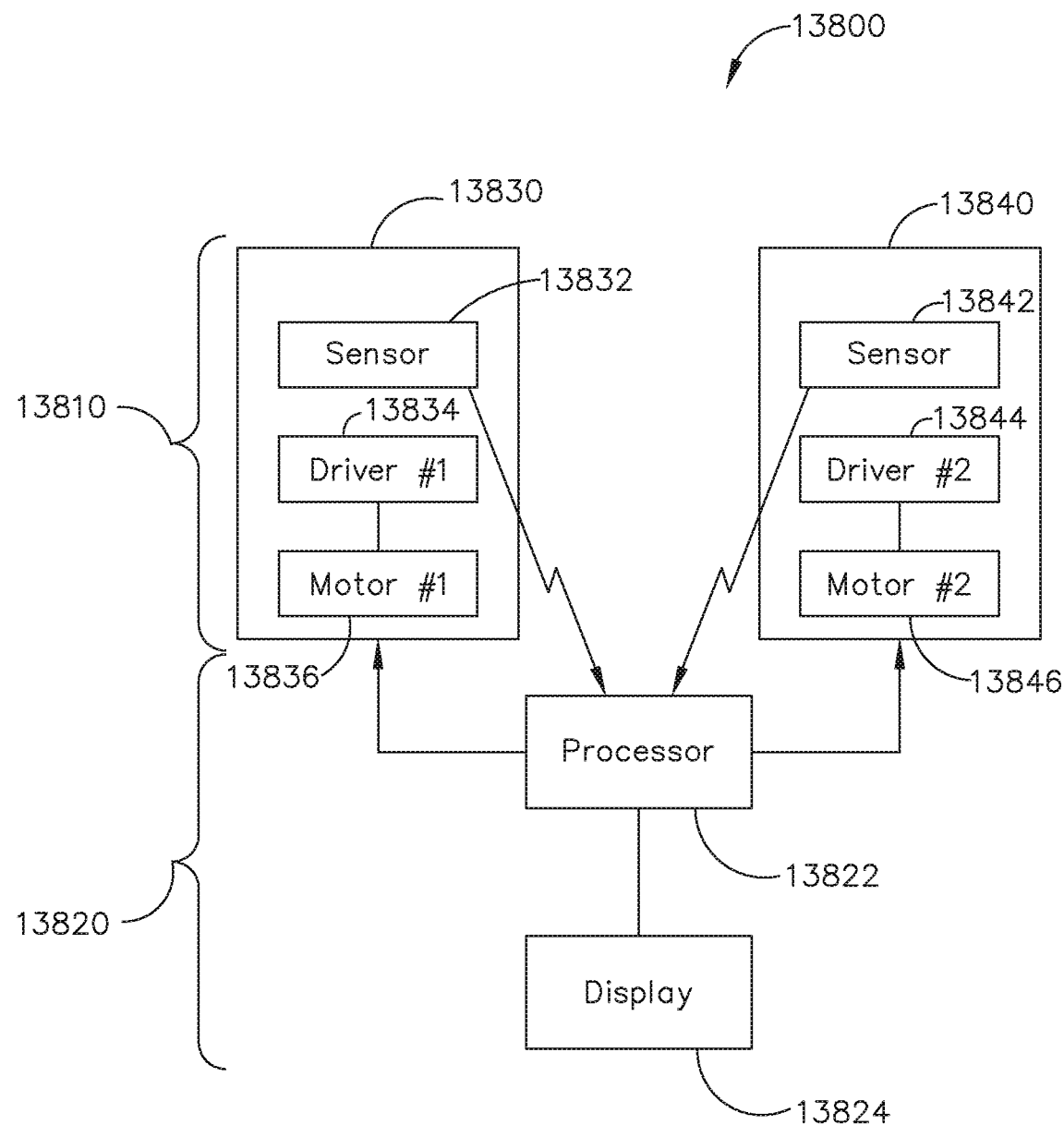

FIG. 73 is a block diagram of a robotic surgical system comprising more than one robotic arm, in accordance with at least one aspect of the present disclosure.

Figure 74:
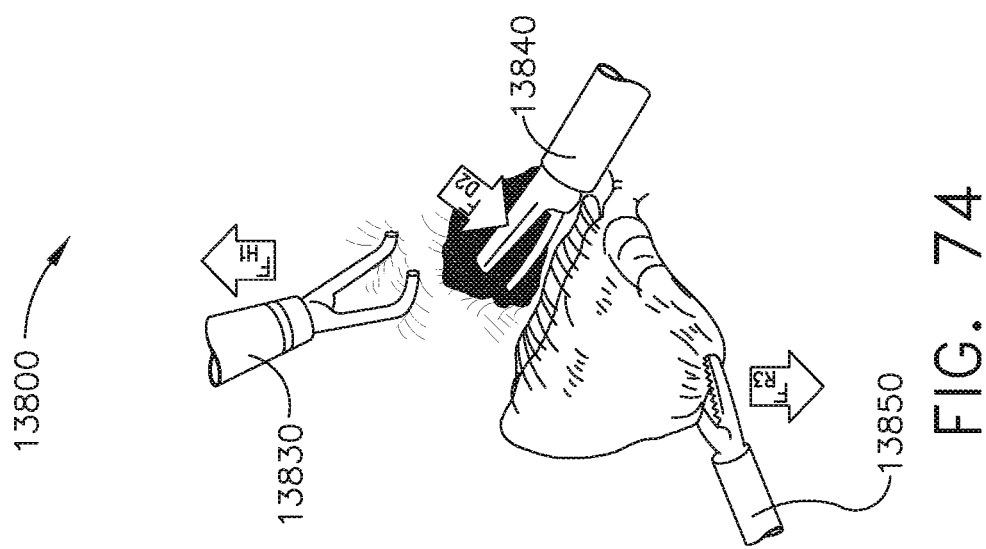

FIG. 74 is a schematic of a surgical procedure utilizing the robotic surgical system of FIG. 73, in accordance with at least one aspect of the present disclosure.

Figure 75:
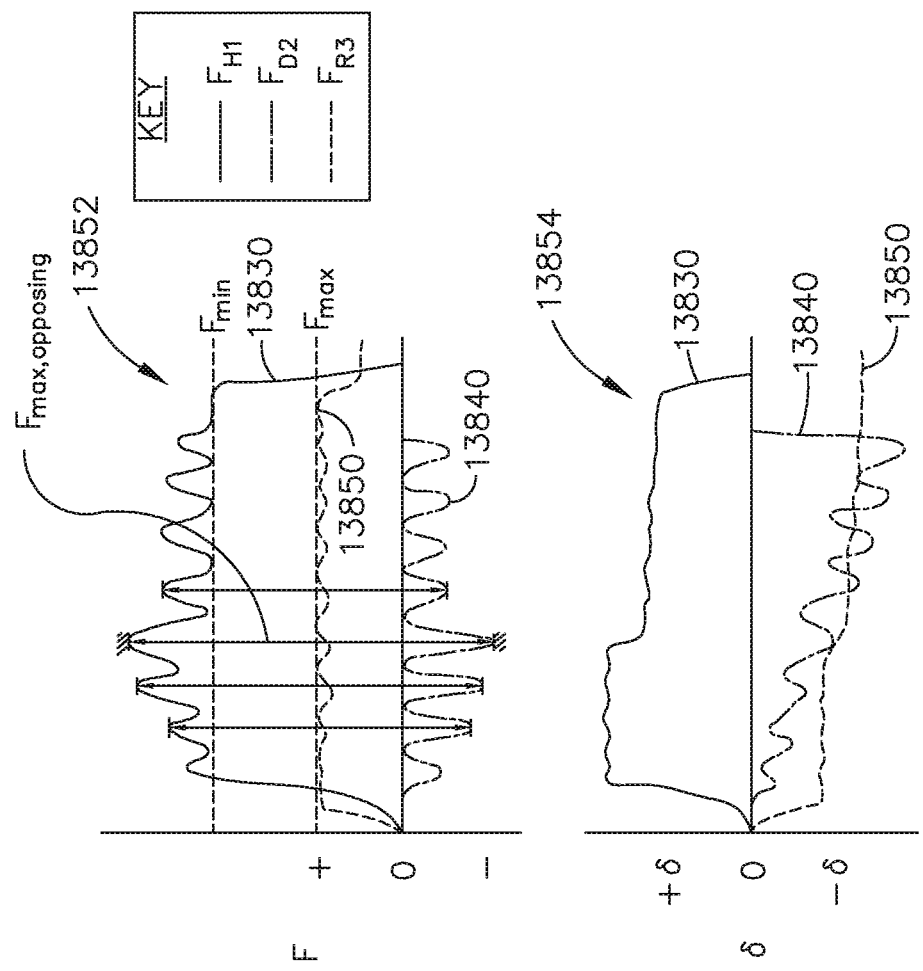

FIG. 75 shows graphical representations of forces and positional displacements experienced by the robotic arms of FIG. 73, in accordance with at least one aspect of the present disclosure.

Figure 76:
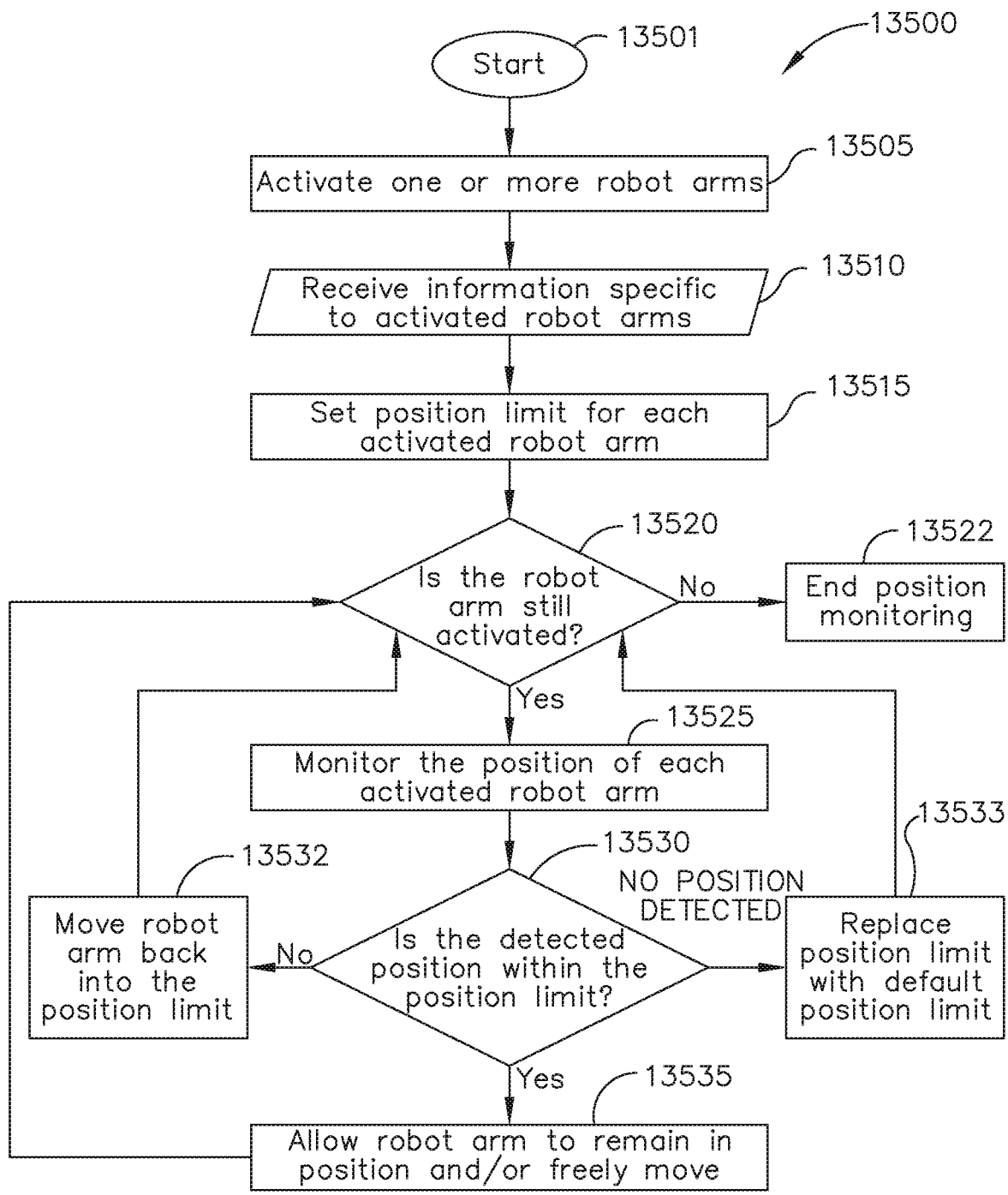

FIG. 76 is a flow chart depicting an algorithm for controlling the position of the robotic arms of a robotic surgical system, in accordance with at least one aspect of the present disclosure.

Figure 77:
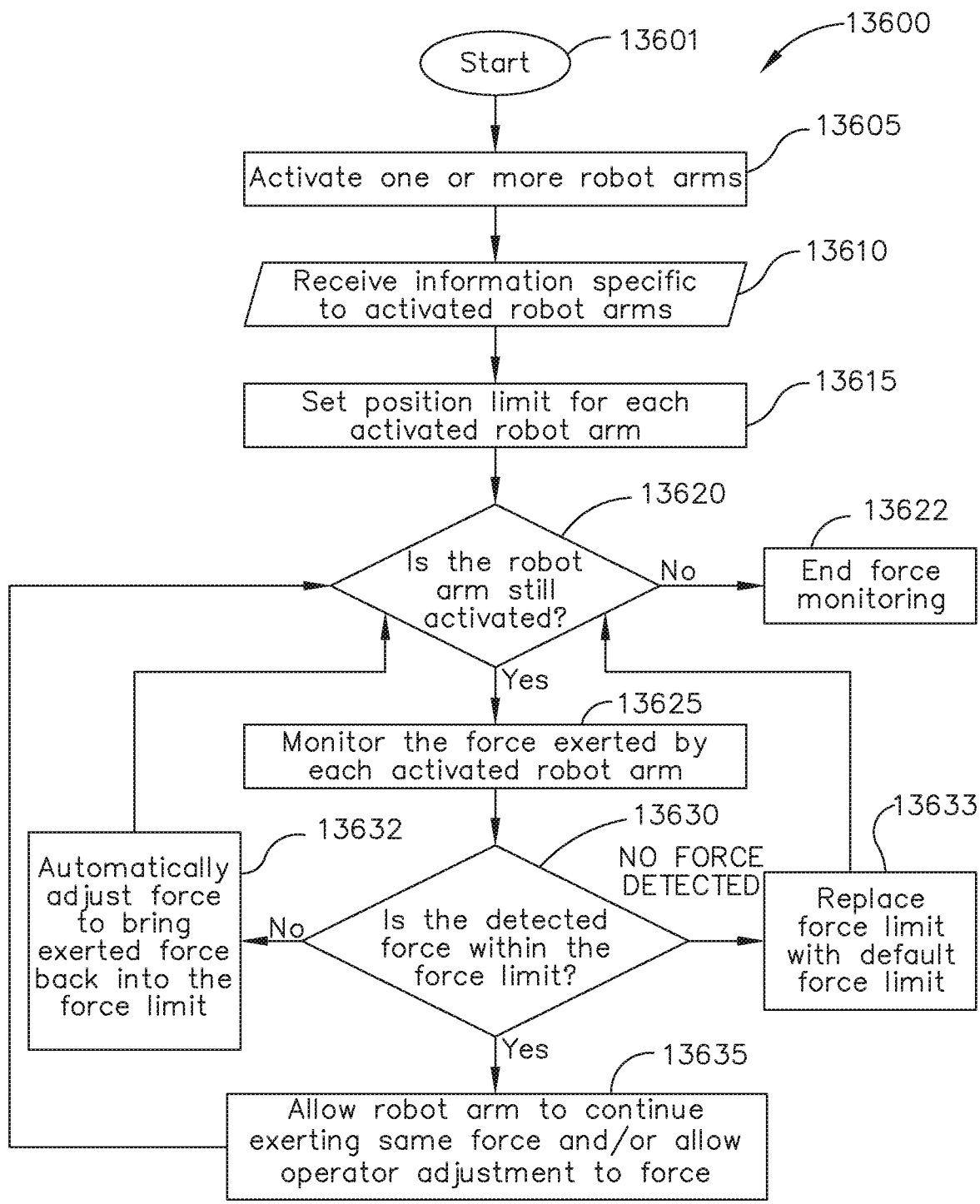

FIG. 77 is a flow chart depicting an algorithm for controlling the forces exerted by robotic arms of a robotic surgical system, in accordance with at least one aspect of the present disclosure.

Figure 78:
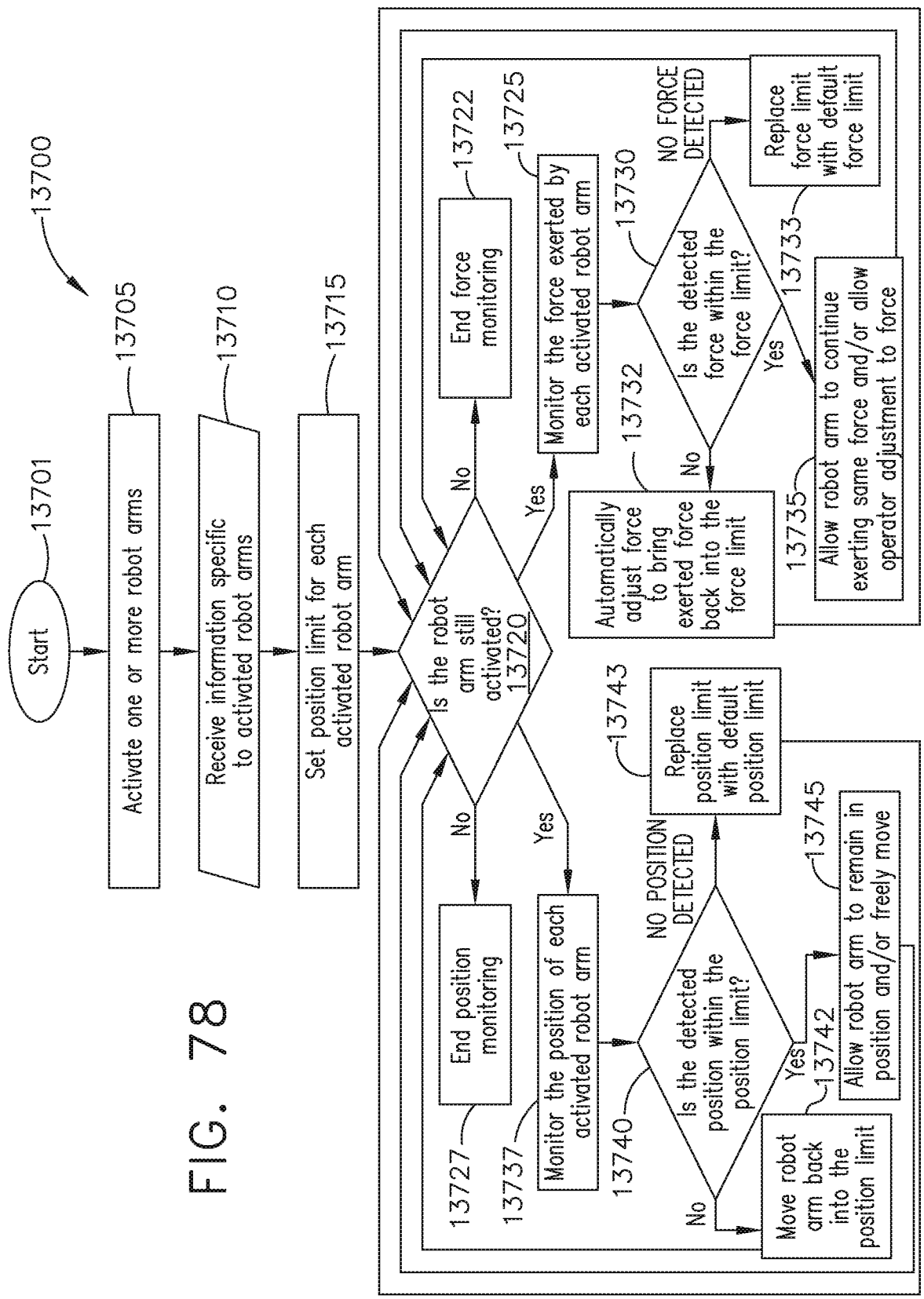

FIG. 78 is a flow chart depicting an algorithm for monitoring the position and forces exerted by robotic arms of a robotic surgical system, in accordance with at least one aspect of the present disclosure.

Figure 79:
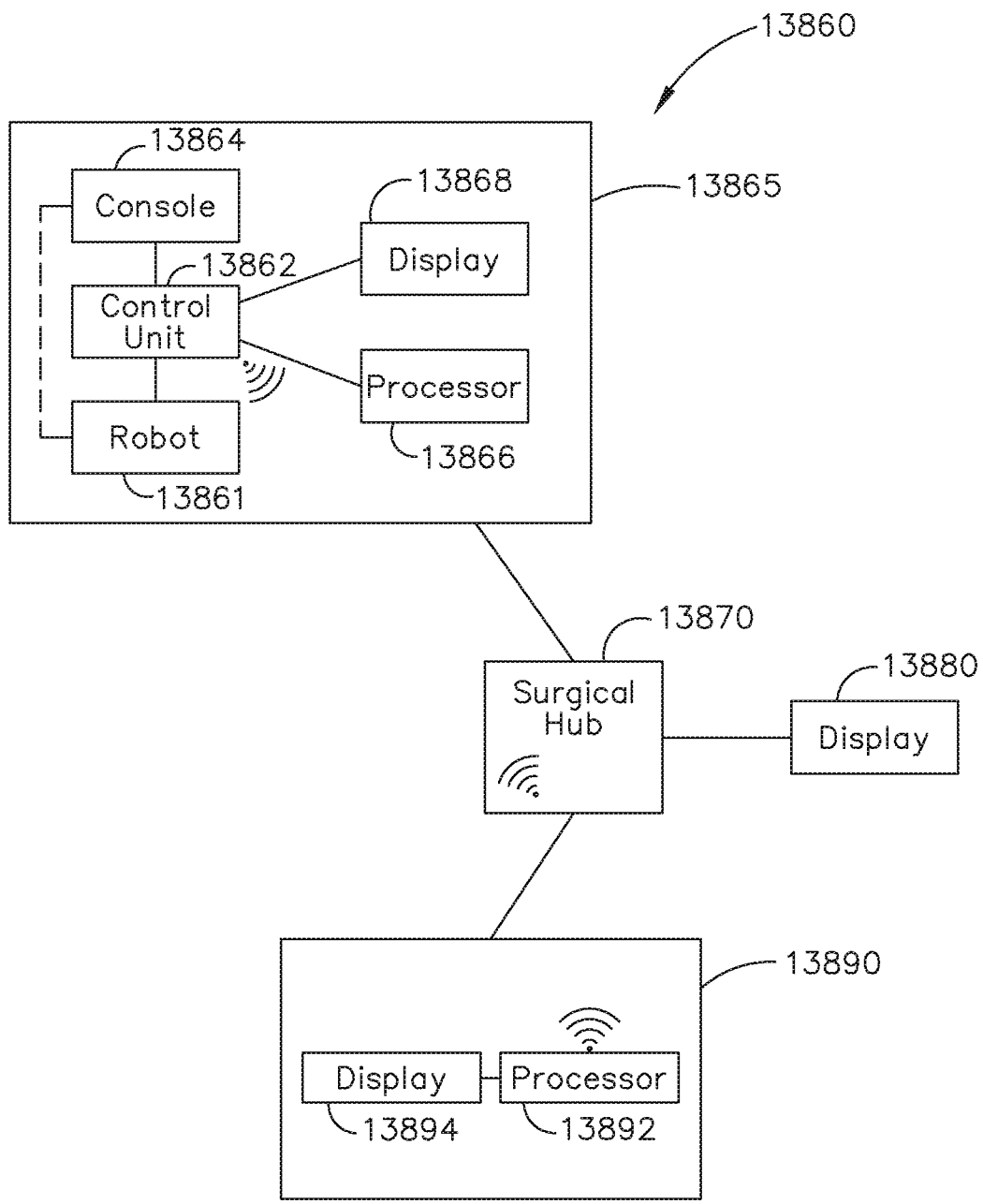

FIG. 79 is a block diagram of a surgical system comprising a robotic surgical system, a powered handheld surgical instrument, and a surgical hub, in accordance with at least one aspect of the present disclosure.

Figure 80:
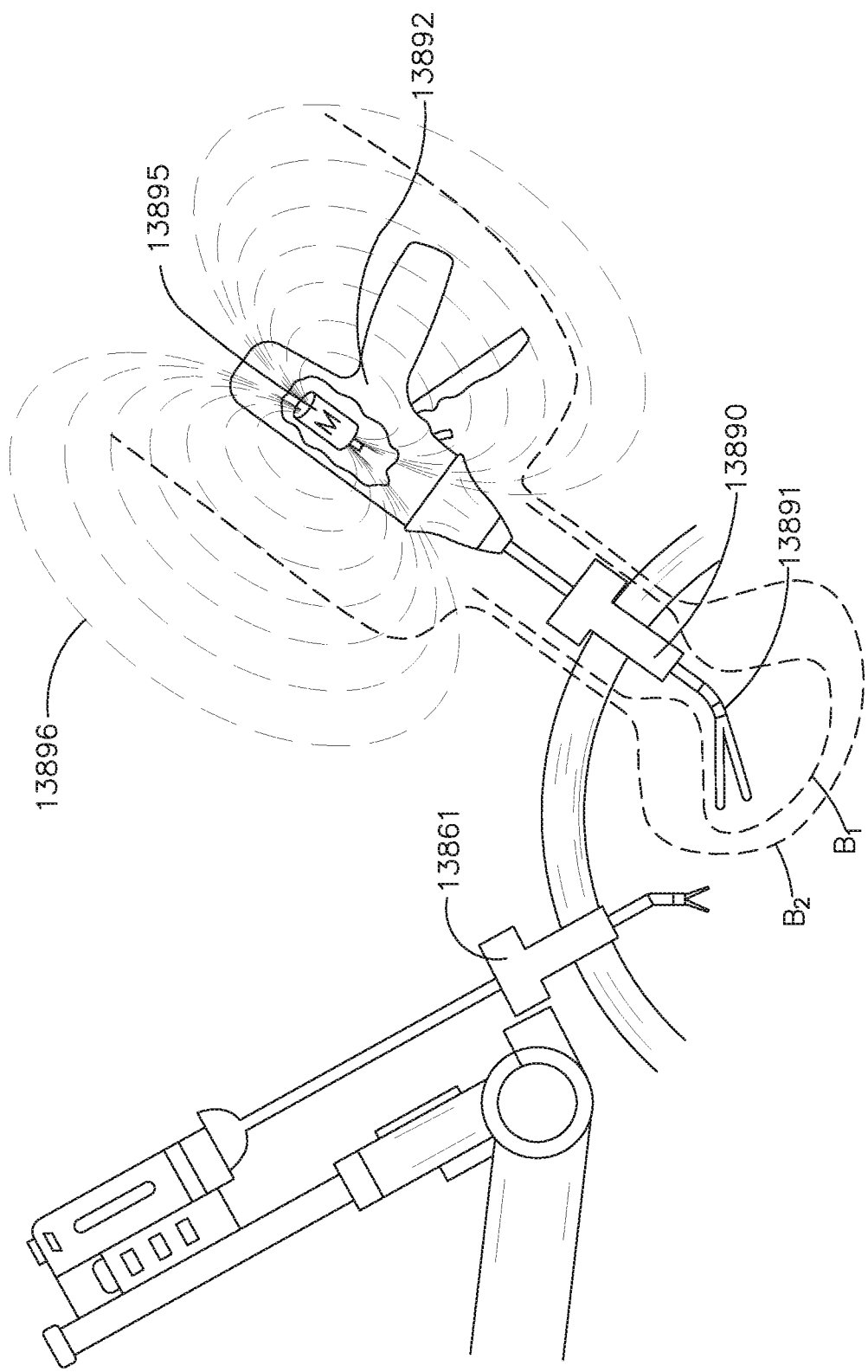

FIG. 80 is a perspective view of a robotic tool and a handheld surgical instrument during a surgical procedure, in accordance with at least one aspect of the present disclosure.

Figure 81:
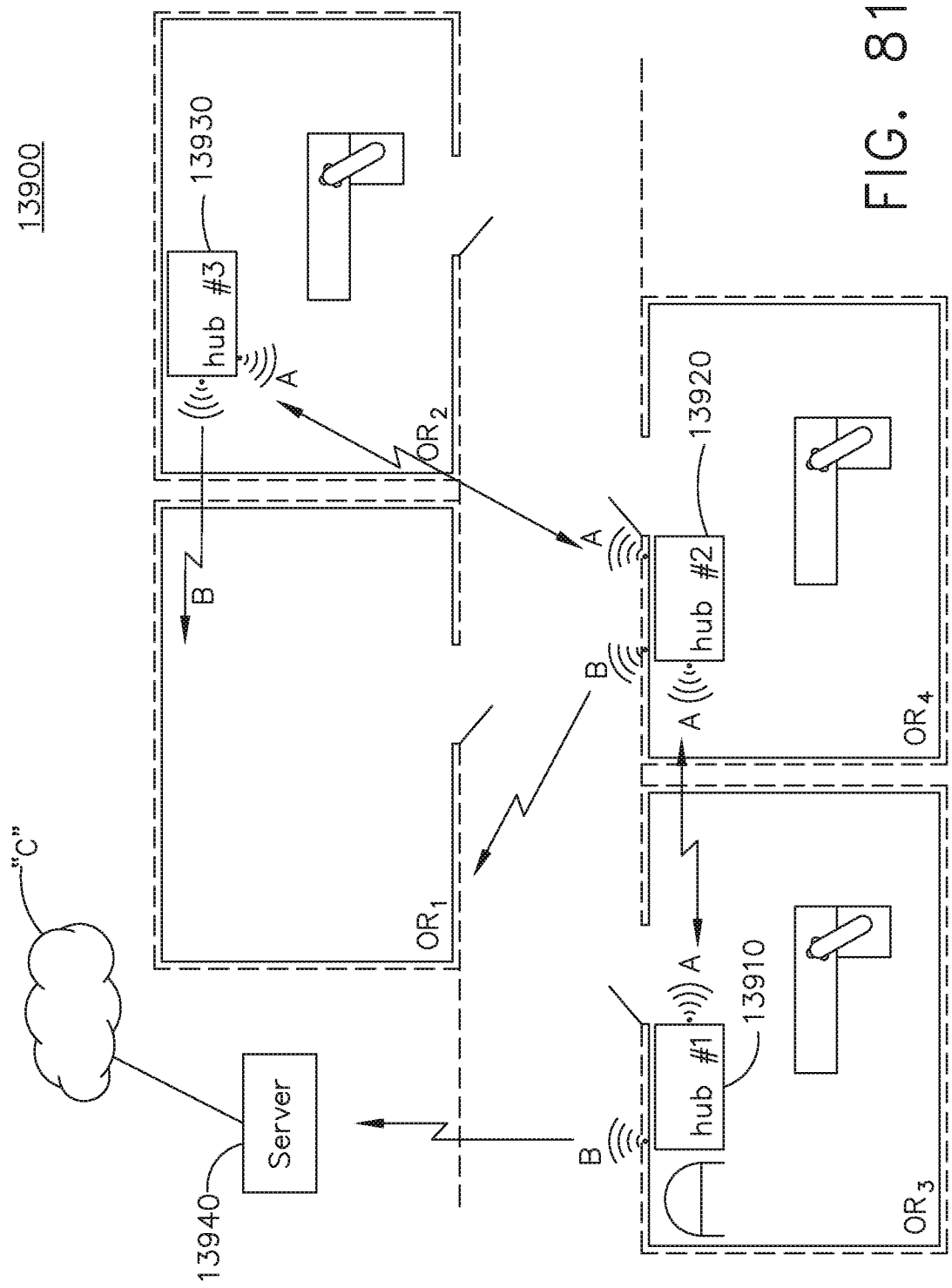

FIG. 81 is a schematic depicting communication links between surgical hubs and a primary server, in accordance with at least one aspect of the present disclosure.

Figure 82:
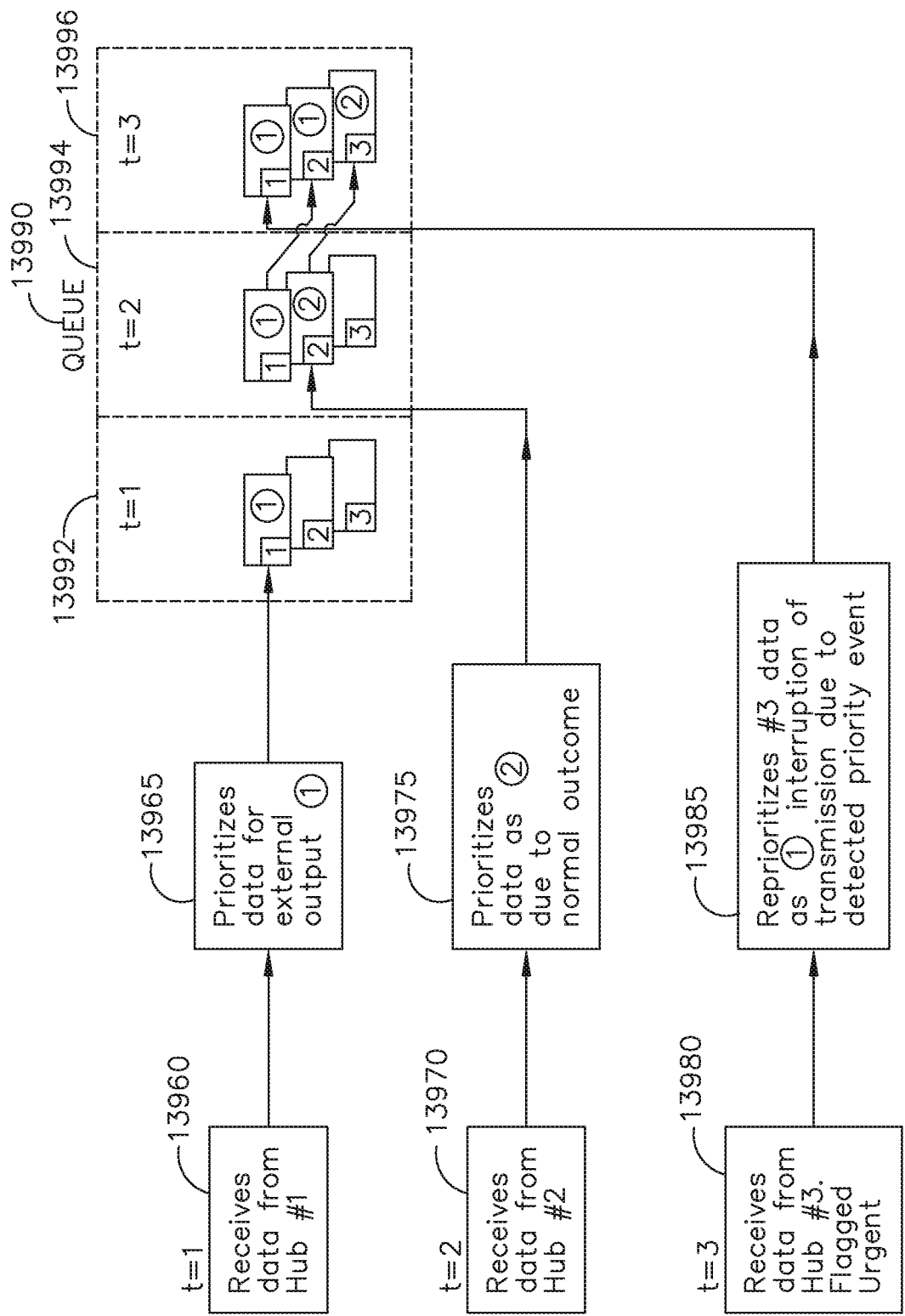

FIG. 82 is a flow chart depicting a queue for external output of data received from the various surgical hubs of FIG. 81, in accordance with at least one aspect of the present disclosure.

Figure 83:
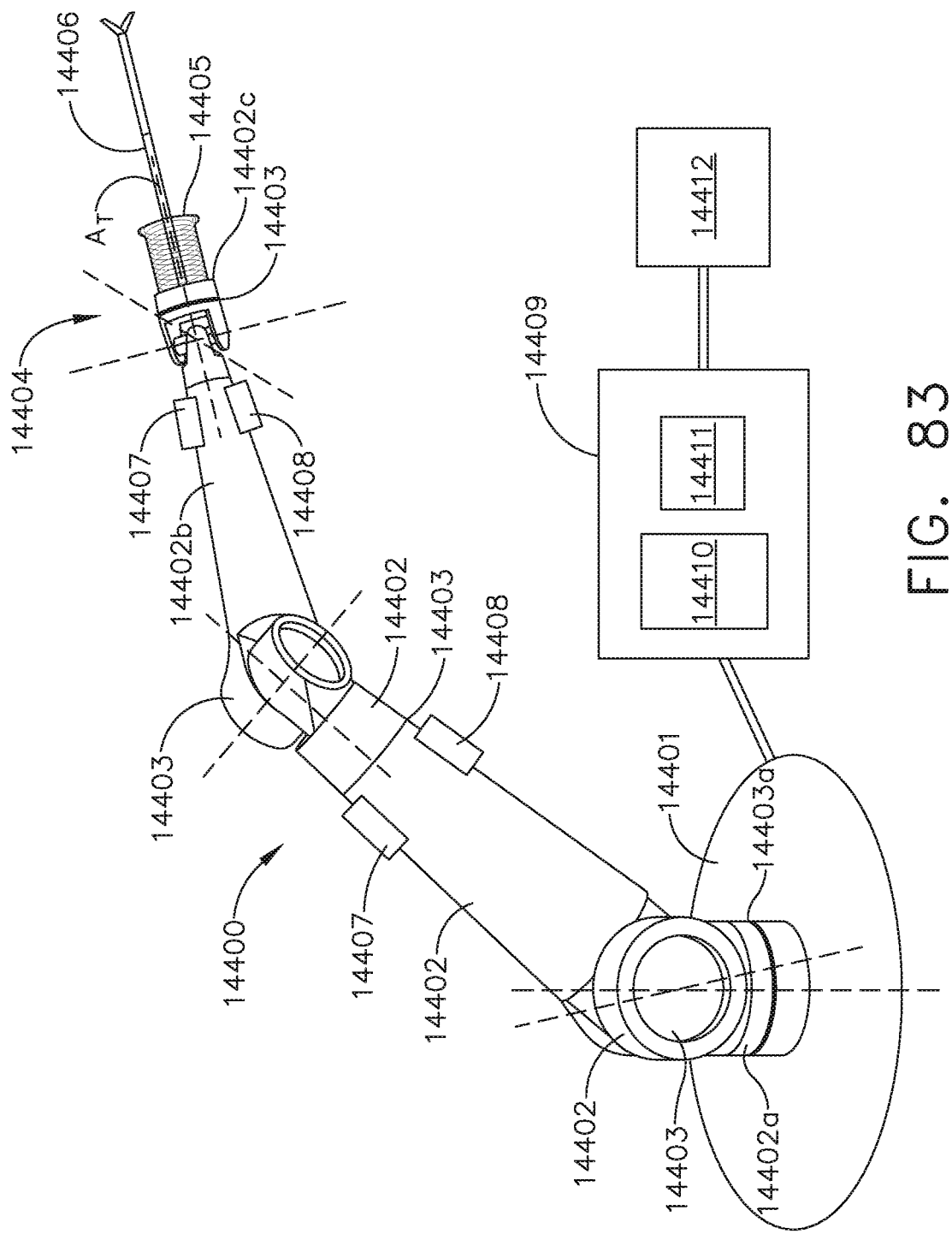

FIG. 83 is a perspective view of a robot arm of a robotic surgical system and schematically depicts additional components of the robotic surgical system, in accordance with one aspect of the present disclosure.

Figure 84:
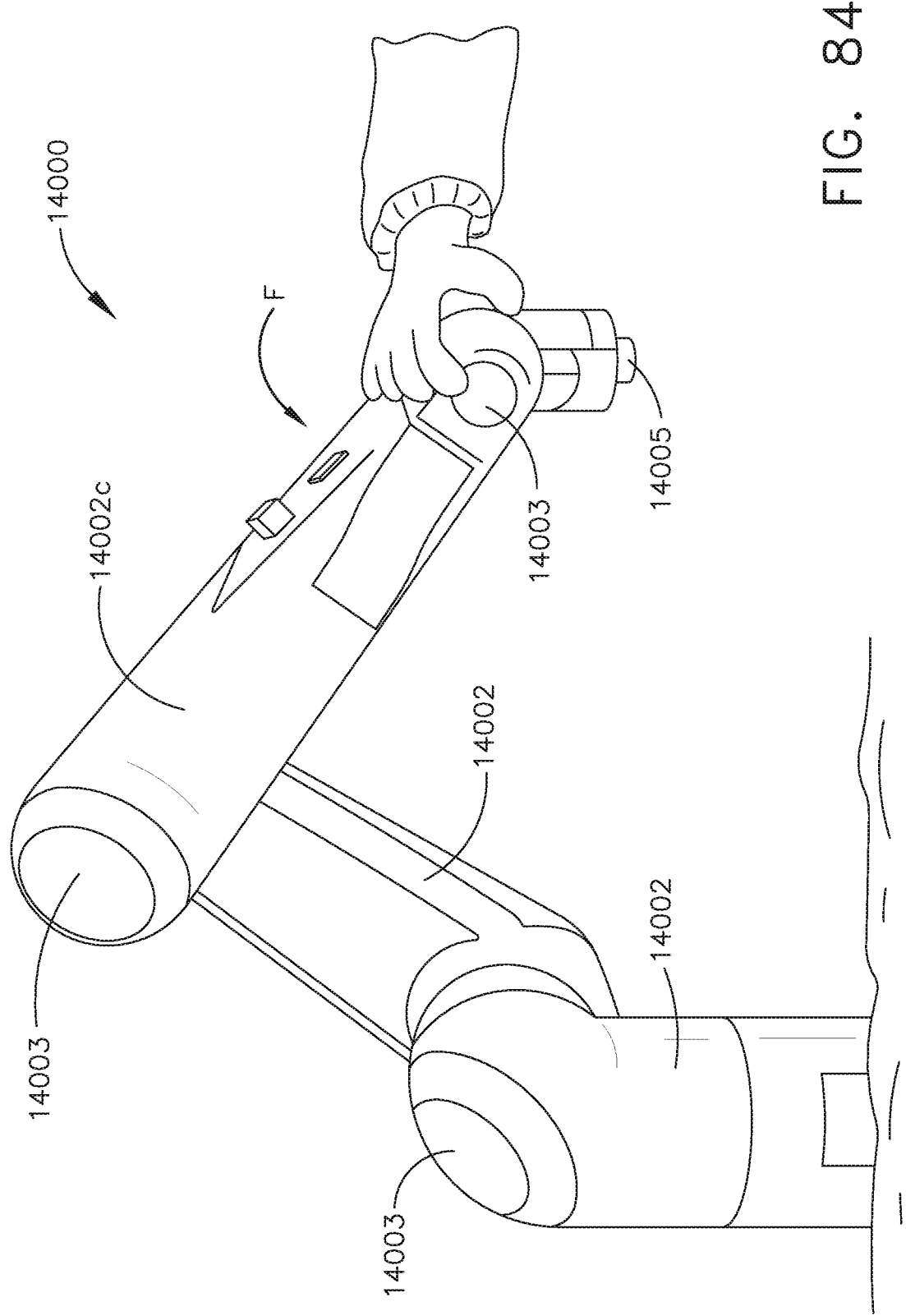

FIG. 84 is a perspective view of a robotic arm of a robotic surgical system, and further depicts an operator manually adjusting the position of the robotic arm, in accordance with one aspect of the present disclosure.

Figure 85:
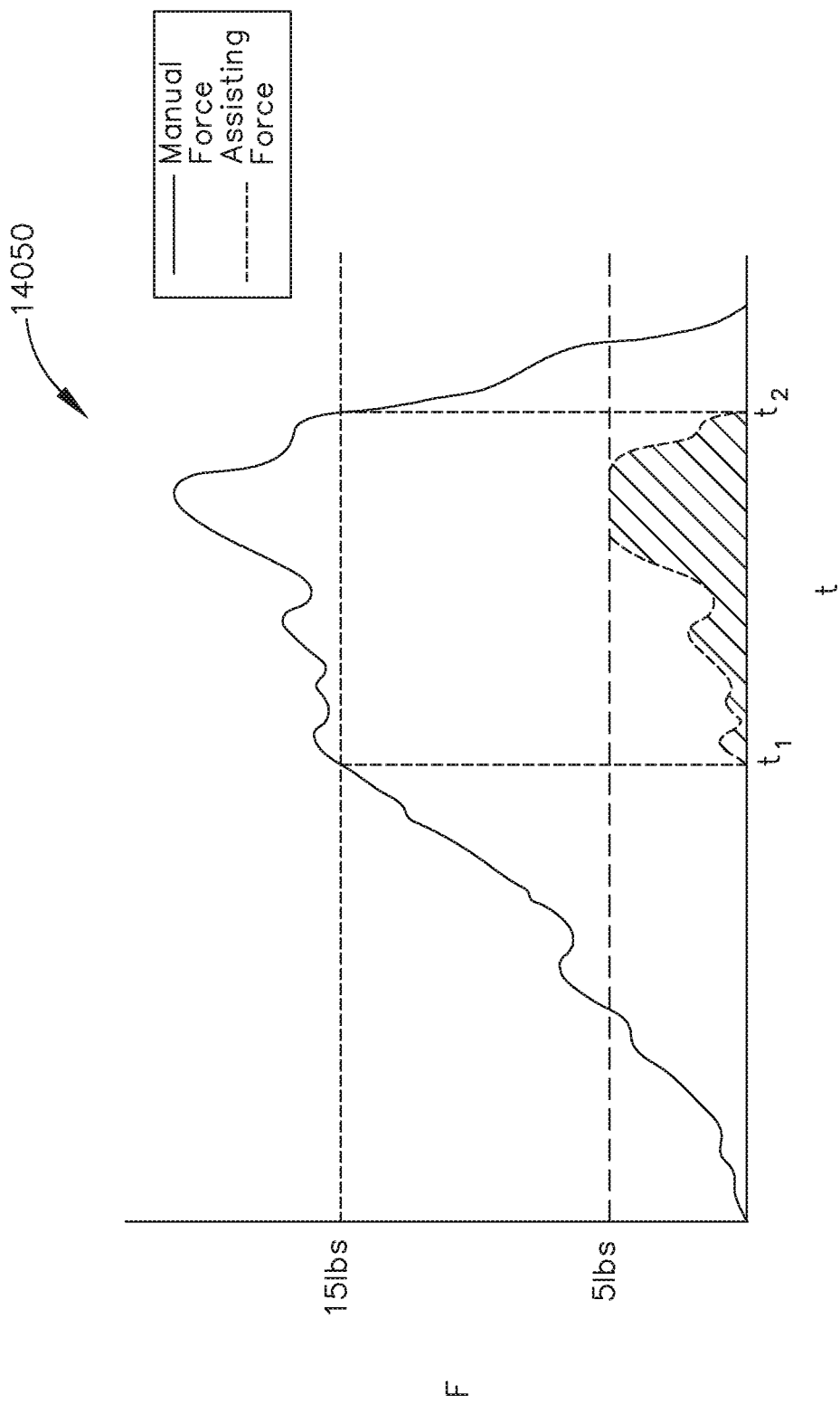

FIG. 85 is a graphical display of force over time of the robotic arm of FIG. 84 in a passive power assist mode, in accordance with one aspect of the present disclosure.

FIG. 86 is a perspective view of a robotic arm and a secondary interactive display within a sterile field, in accordance with at least one aspect of the present disclosure.

FIG. 87 is a graphical display of force over time of the robotic arm of FIG. 86, in accordance with one aspect of the present disclosure.

Figure 88:
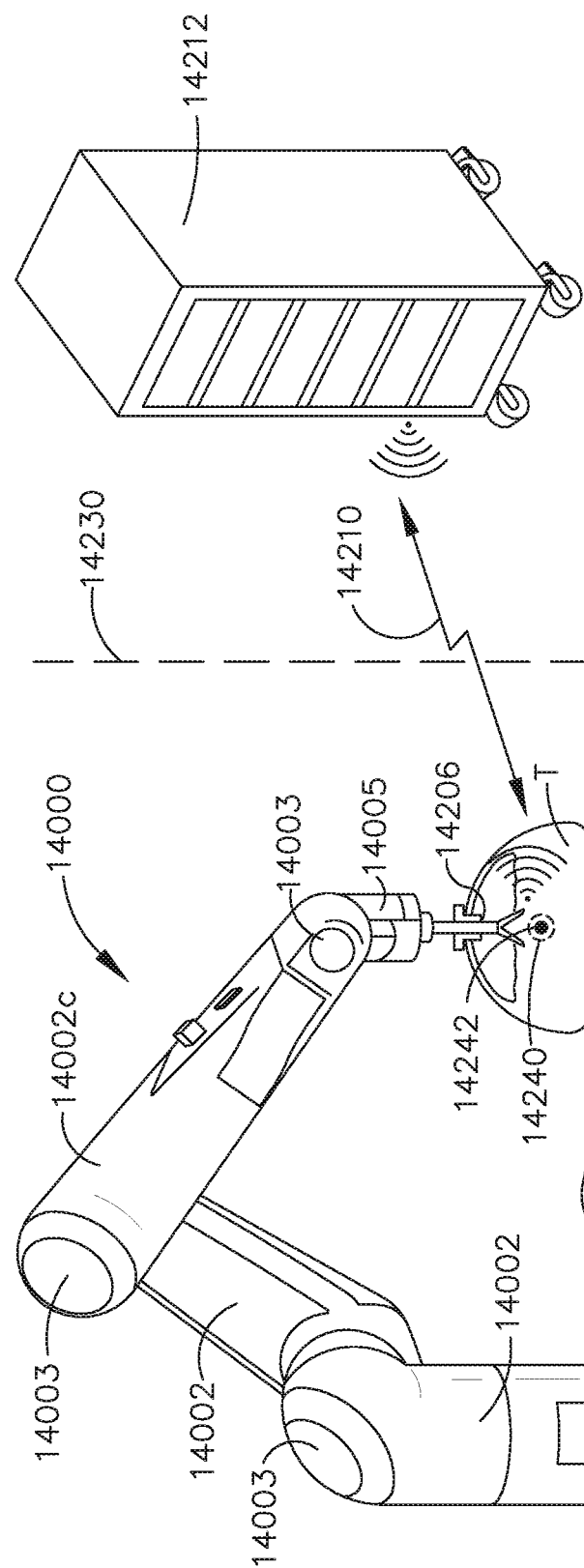

FIG. 88 is a perspective view of a robotic arm and a robotic hub of a robotic surgical system, in accordance with at least one aspect of the present disclosure.

Figure 89:
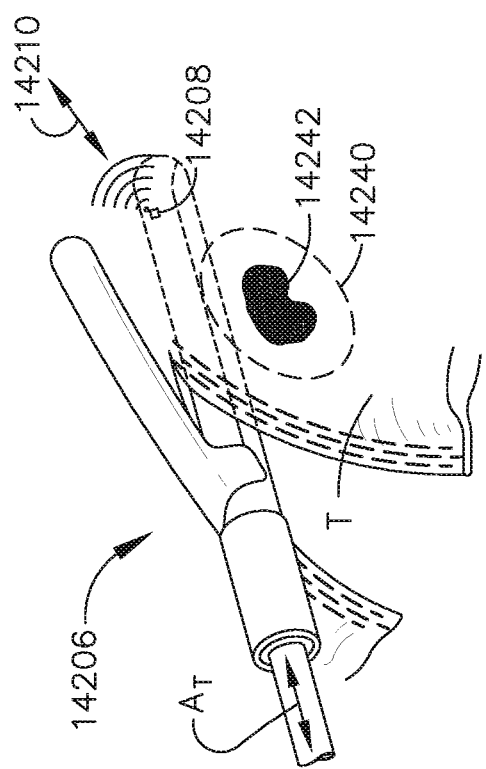

FIG. 89 is a detail view of an end effector of a linear stapler attached to the robotic arm of FIG. 88, depicting the end effector positioned relative to a targeted tissue region during a surgical procedure, in accordance with at least one aspect of the present disclosure.

Figure 90:
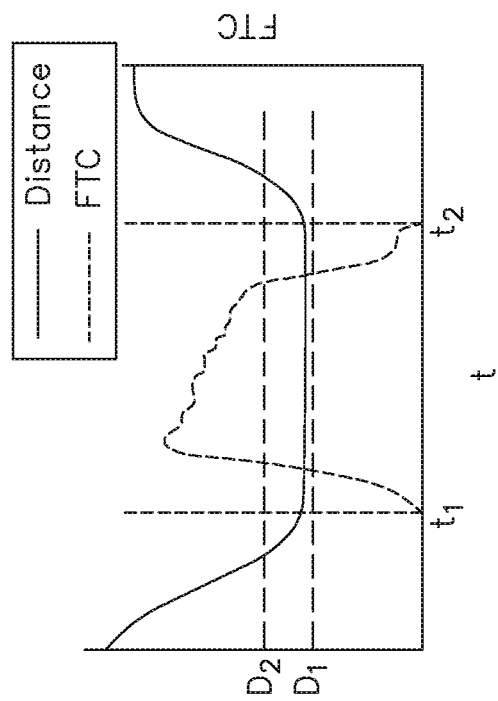

FIG. 90 is a graphical display of distance and force-to-close over time for the linear stapler of FIG. 89, in accordance with one aspect of the present disclosure.

Figure 91:
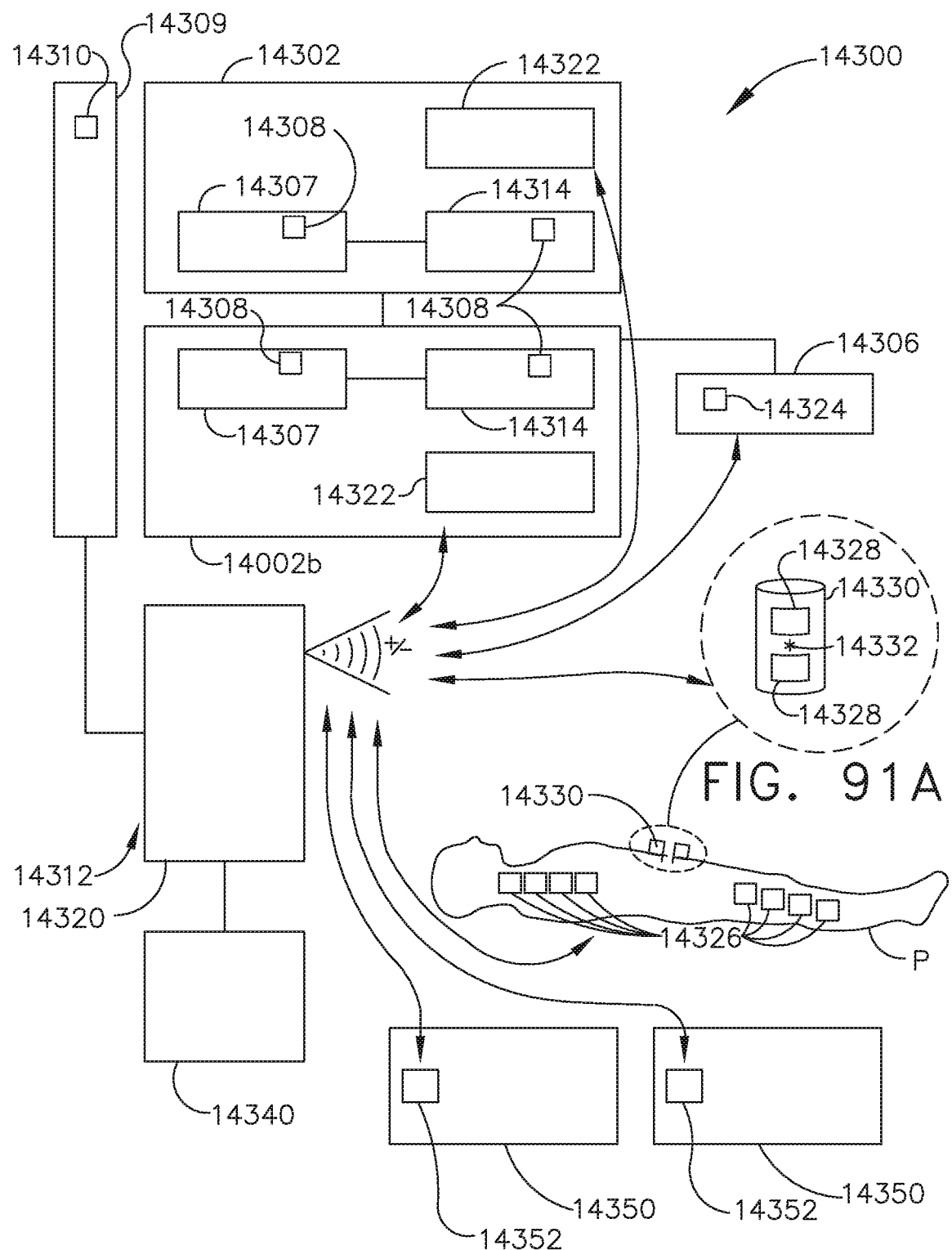

FIG. 91 is a schematic depicting a robotic surgical system having a plurality of sensing systems, in accordance with one aspect of the present disclosure.

FIG. 91A is a detail view of a trocar of FIG. 91, in accordance with at least one aspect of the present disclosure.

Figure 92:
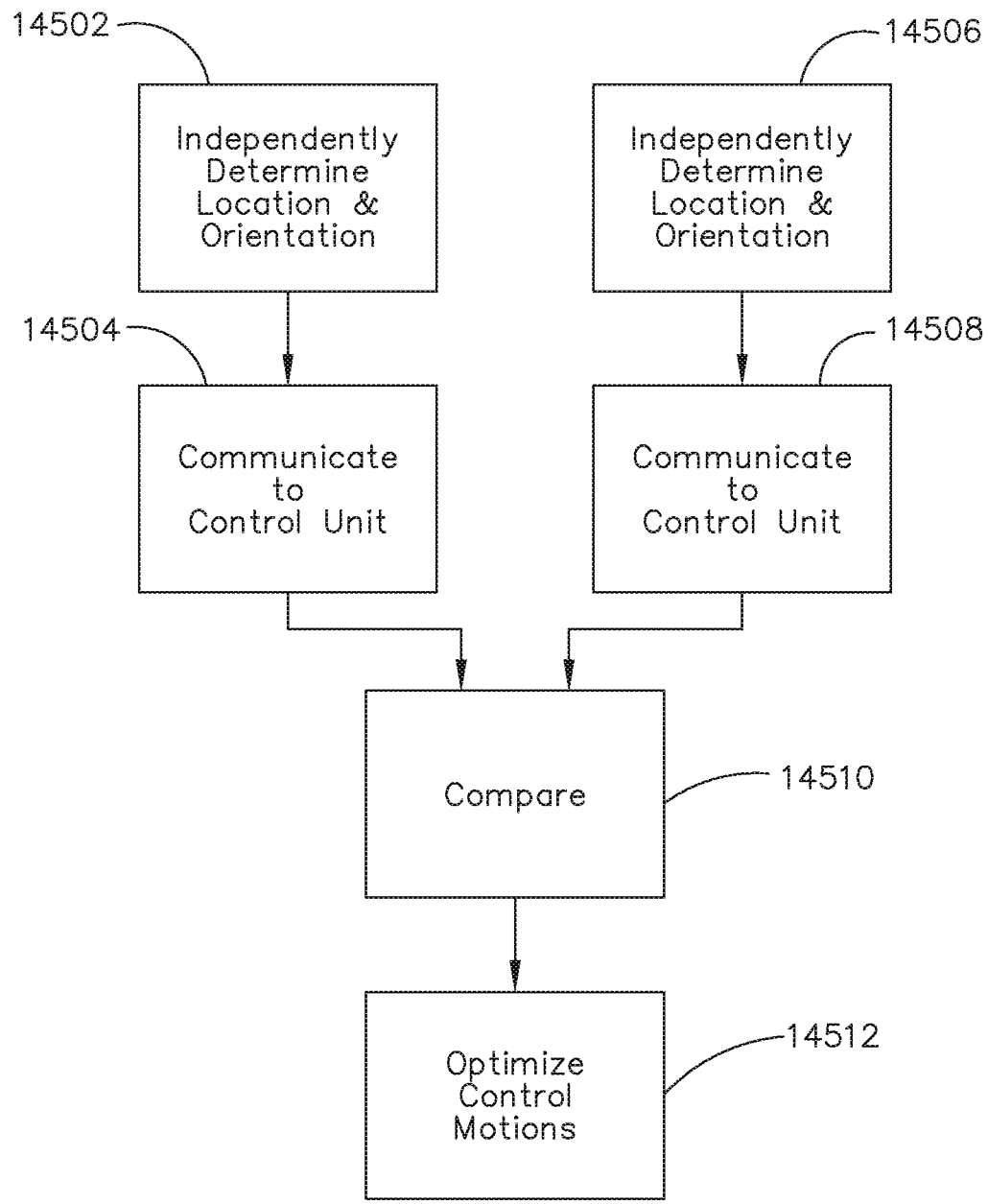

FIG. 92 is a flowchart depicting a robotic surgical system utilizing a plurality of independent sensing systems, in accordance with one aspect of the present disclosure.

Figure 93:
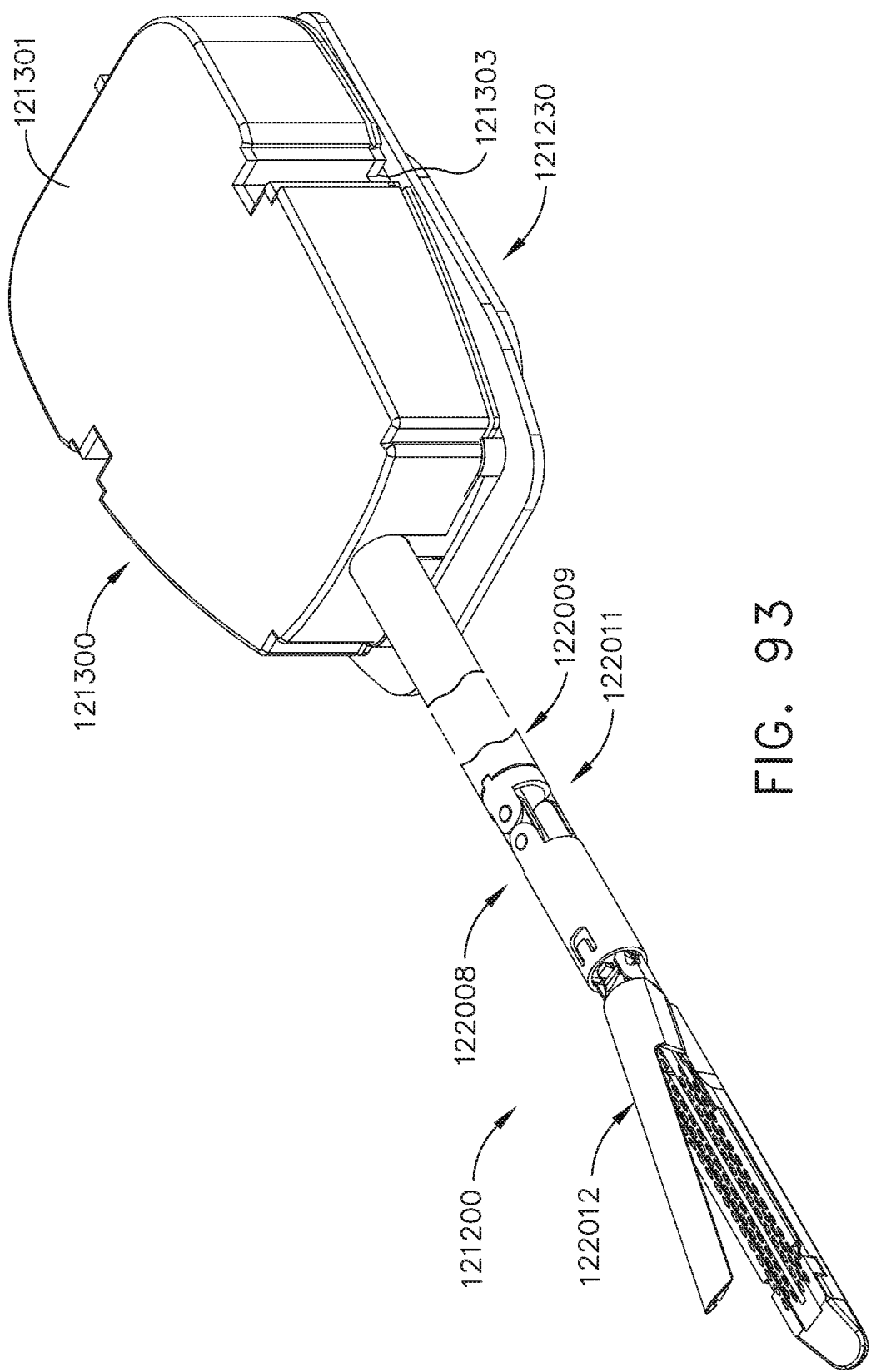

FIG. 93 is a perspective view of a surgical tool, according to one aspect of the present disclosure.

Figure 94:
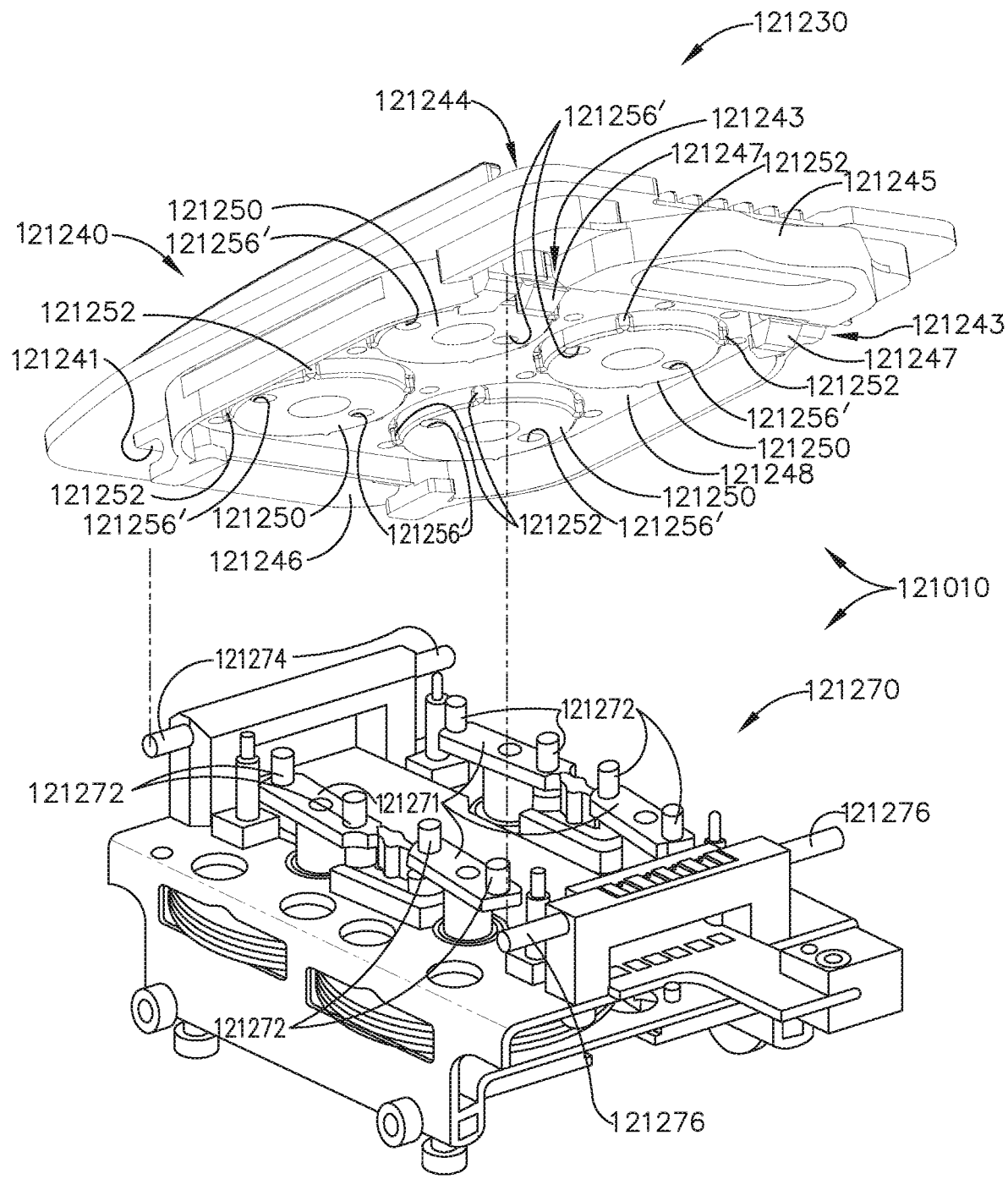

FIG. 94 is an exploded assembly view of an adapter and tool holder arrangement for attaching various surgical tools to a robotic system, according to one aspect of the present disclosure.

Figure 95:
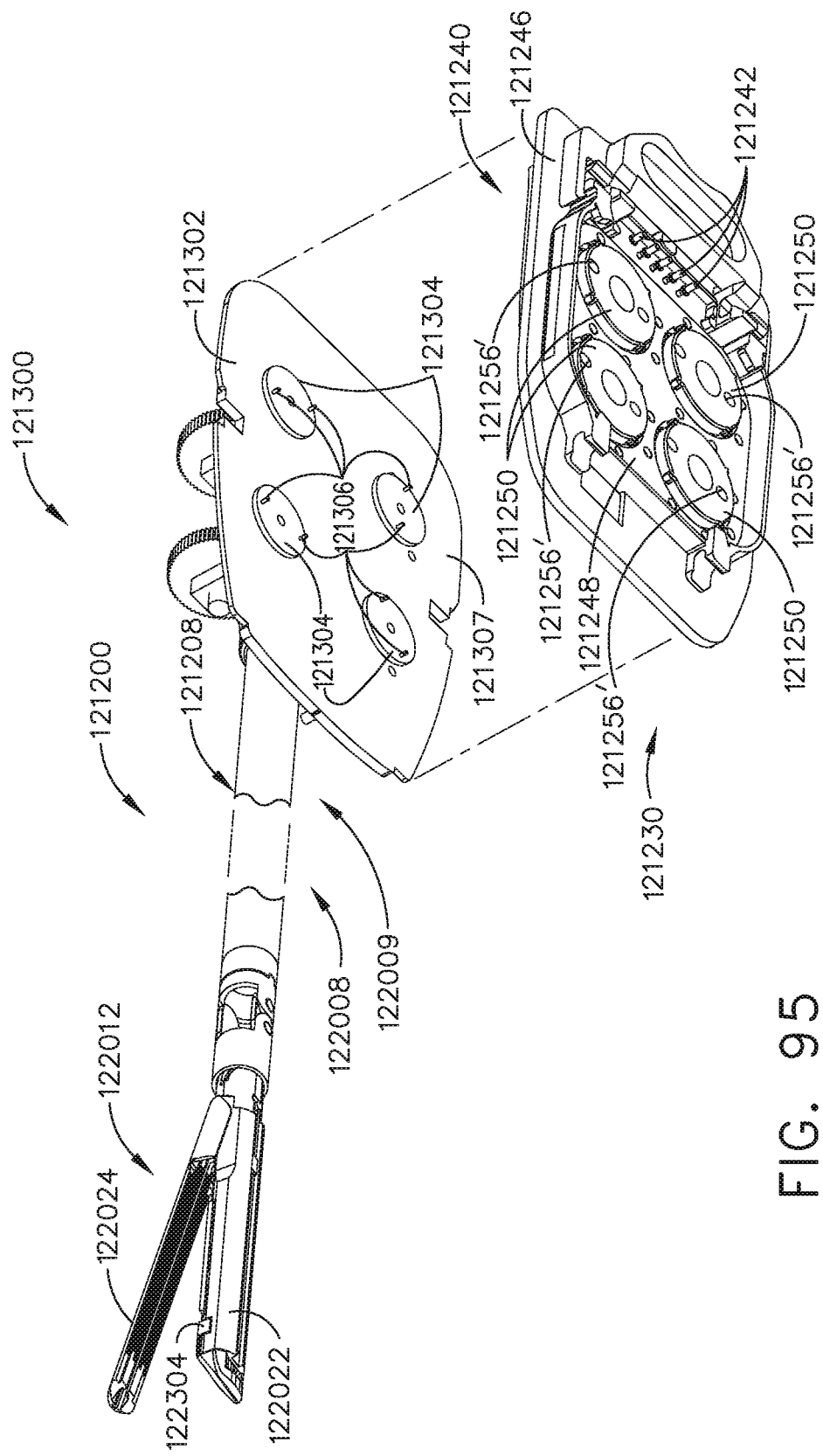

FIG. 95 is a partial bottom perspective view of the surgical tool of FIG. 93, according to one aspect of the present disclosure.

Figure 96:
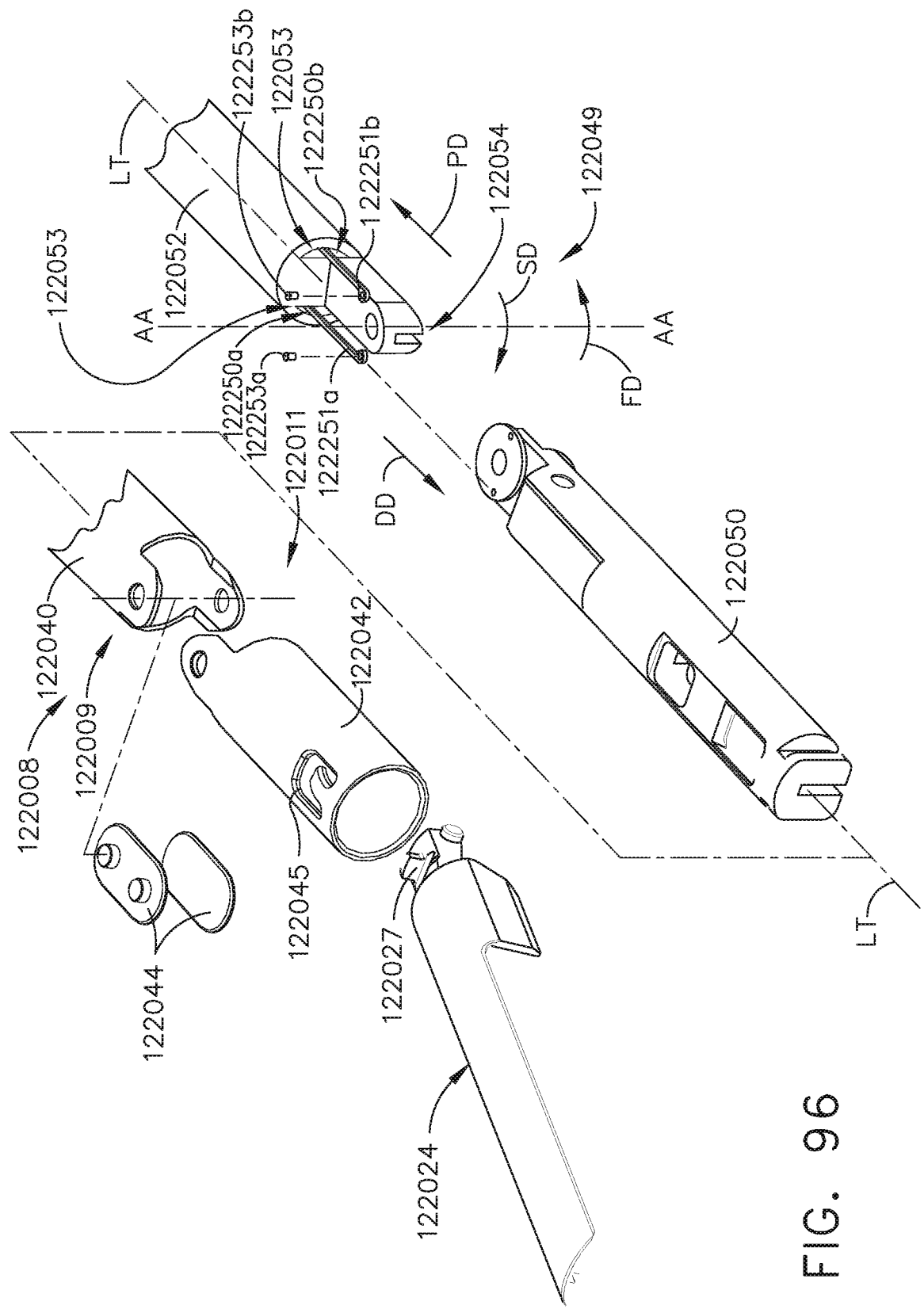

FIG. 96 is a partial exploded view of a portion of an articulatable surgical end effector, according to one aspect of the present disclosure.

Figure 97:
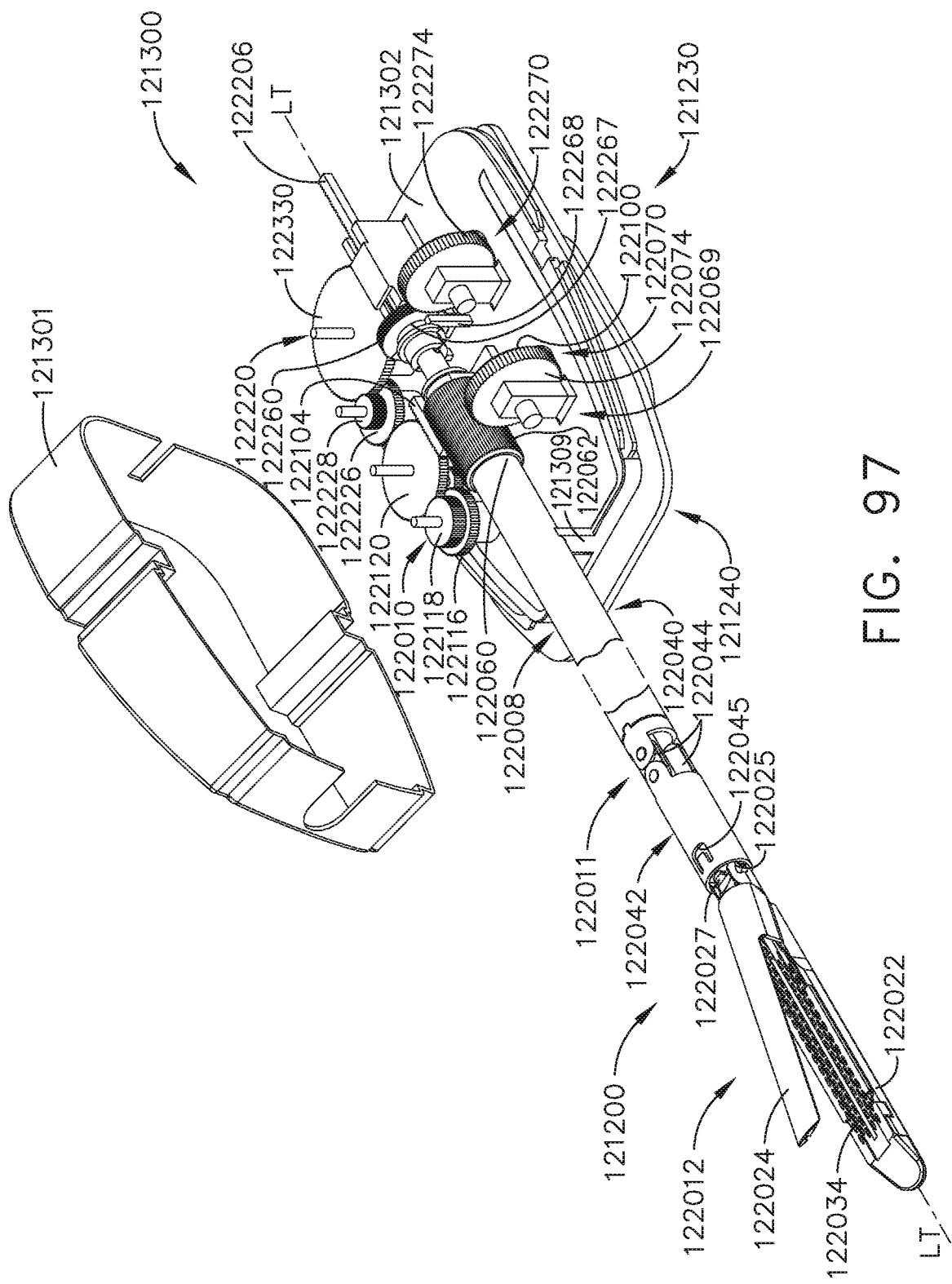

FIG. 97 is a perspective view of the surgical tool of FIG. 95 with the tool mounting housing removed, according to one aspect of the present disclosure.

Figure 98:
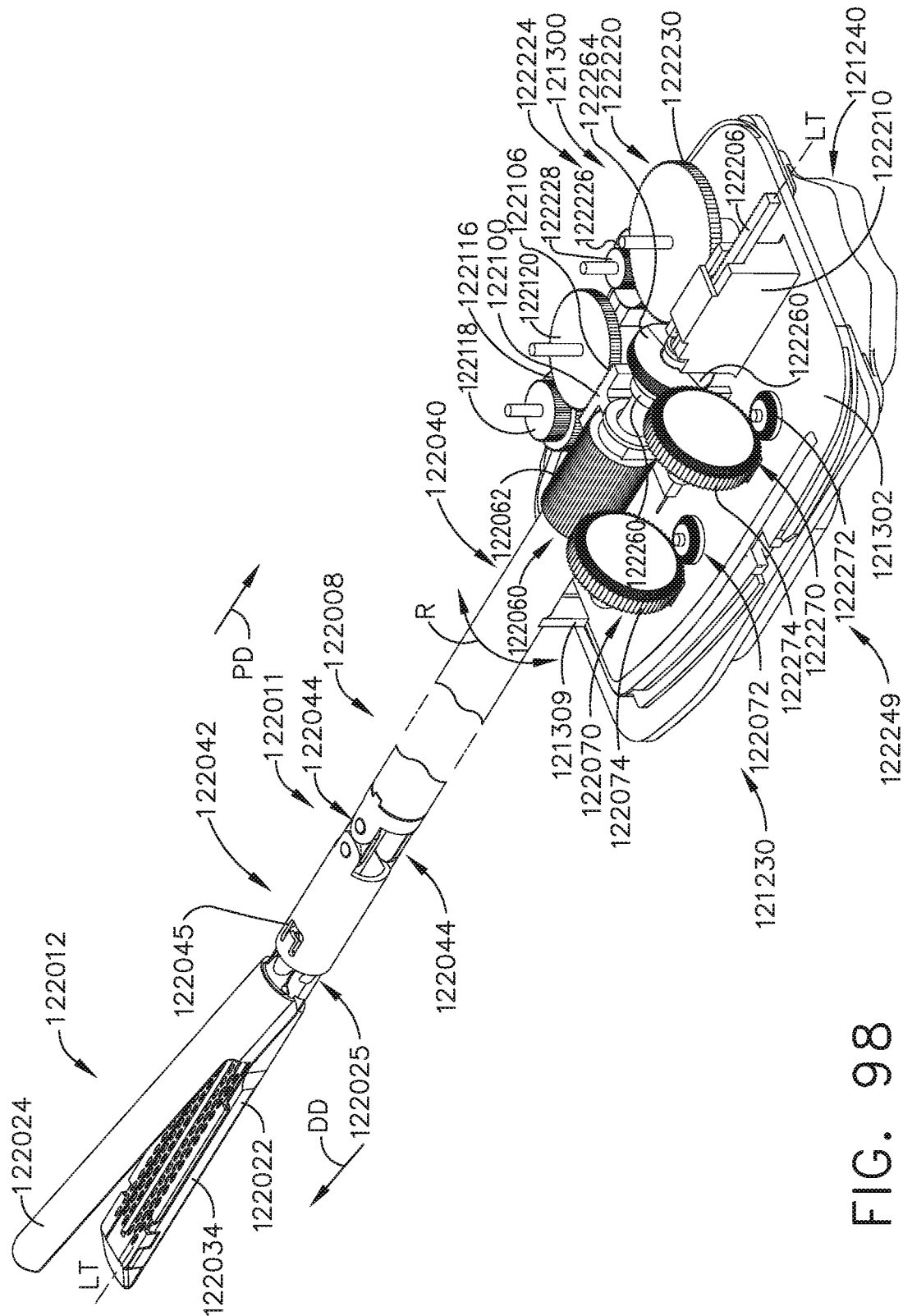

FIG. 98 is a rear perspective view of the surgical tool of FIG. 95 with the tool mounting housing removed, according to one aspect of the present disclosure.

Figure 99:
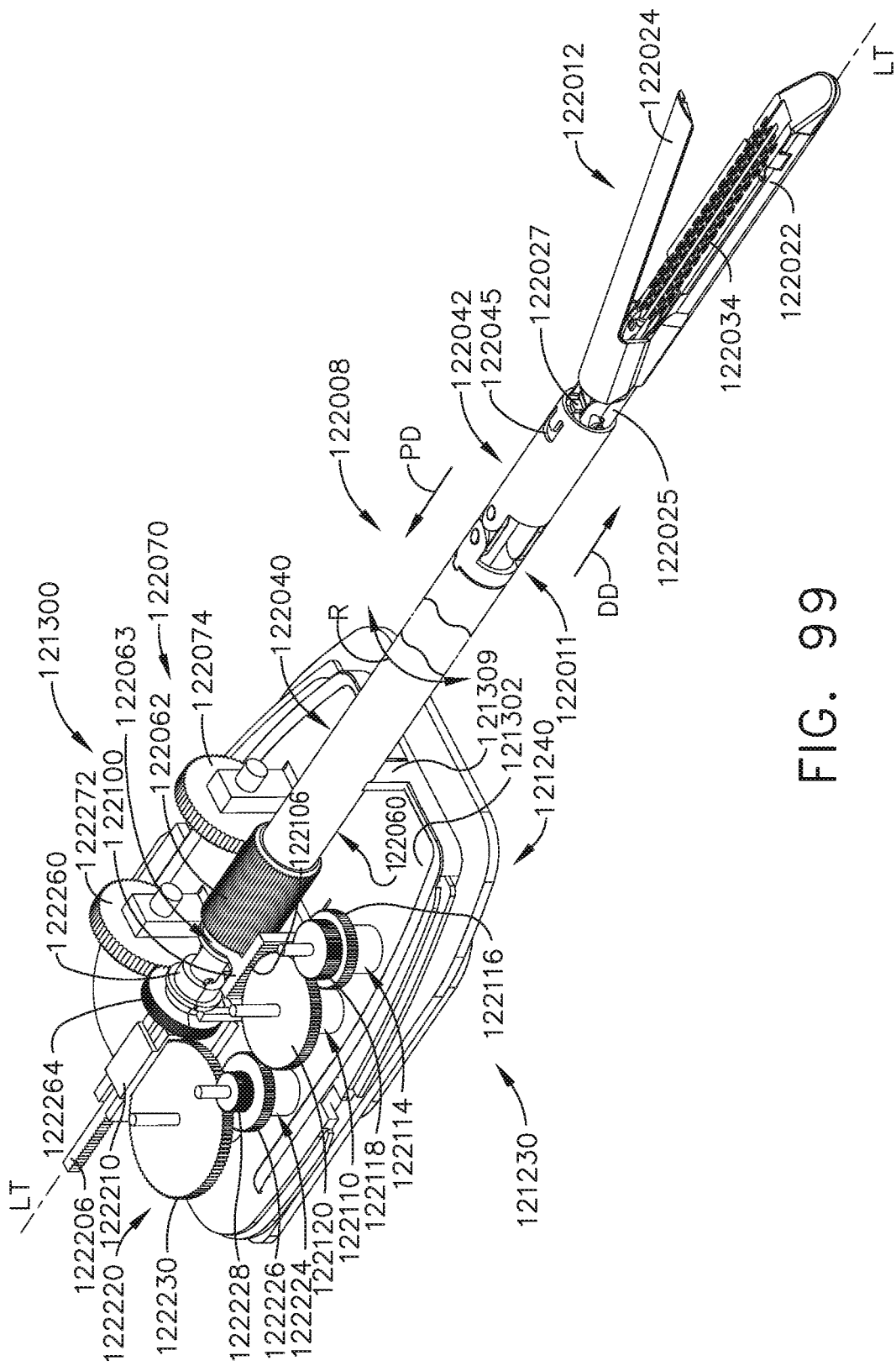

FIG. 99 is a front perspective view of the surgical tool of FIG. 95 with the tool mounting housing removed, according to one aspect of the present disclosure.

Figure 100:
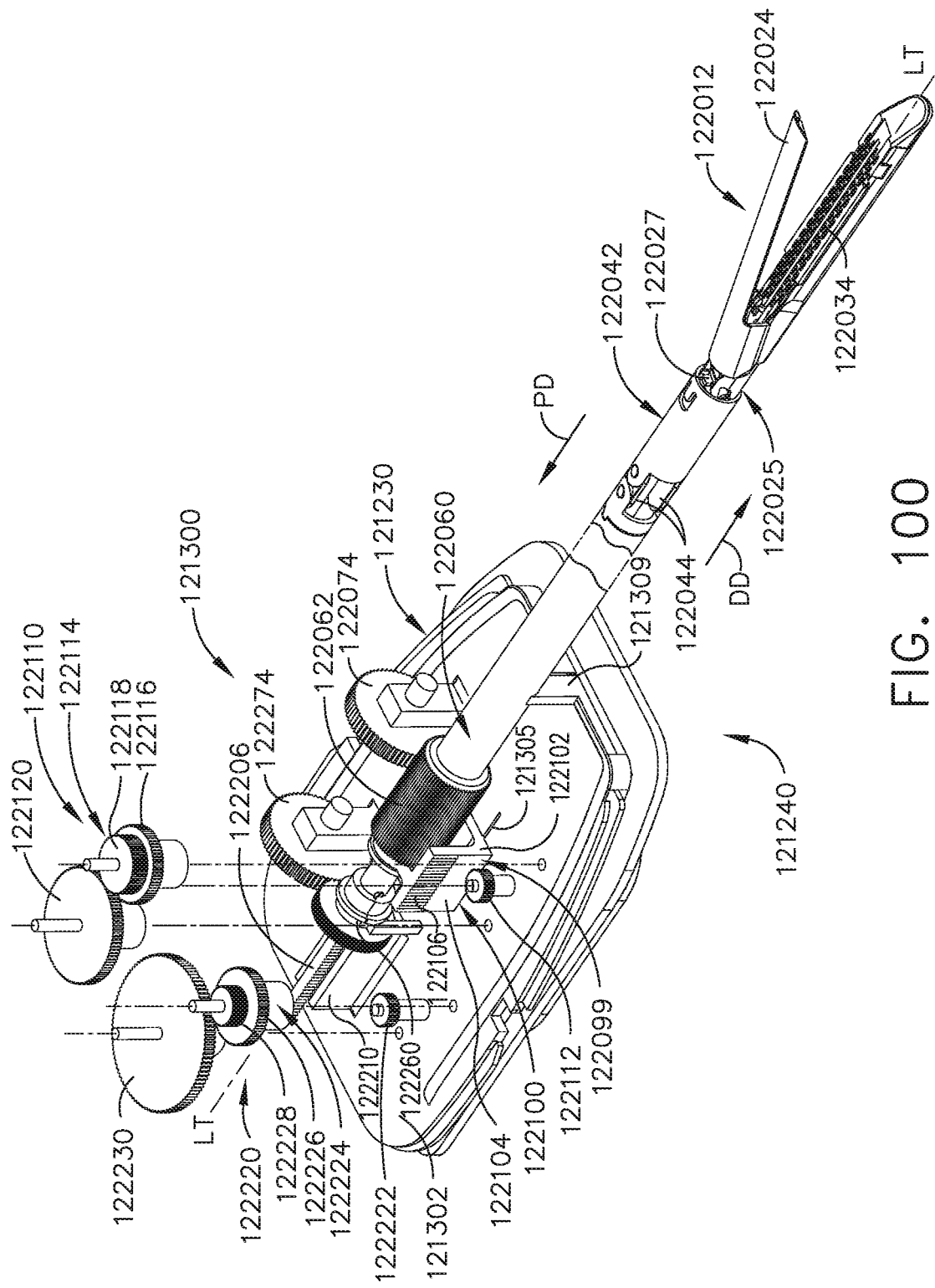

FIG. 100 is a partial exploded perspective view of the surgical tool of FIG. 99, according to one aspect of the present disclosure.

Figure 101:
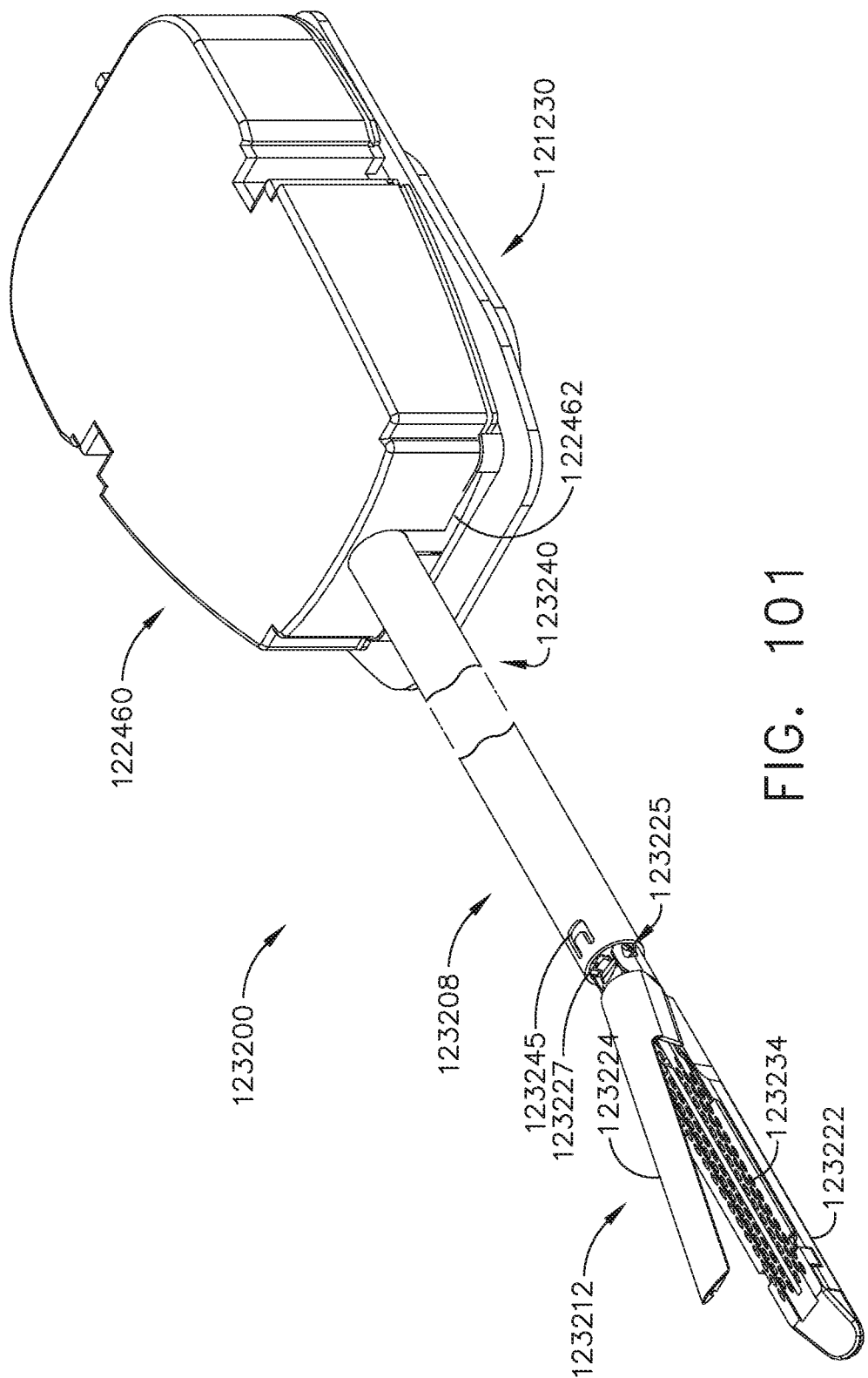

FIG. 101 is a perspective view of another surgical tool, according to one aspect of the present disclosure.

Figure 102:
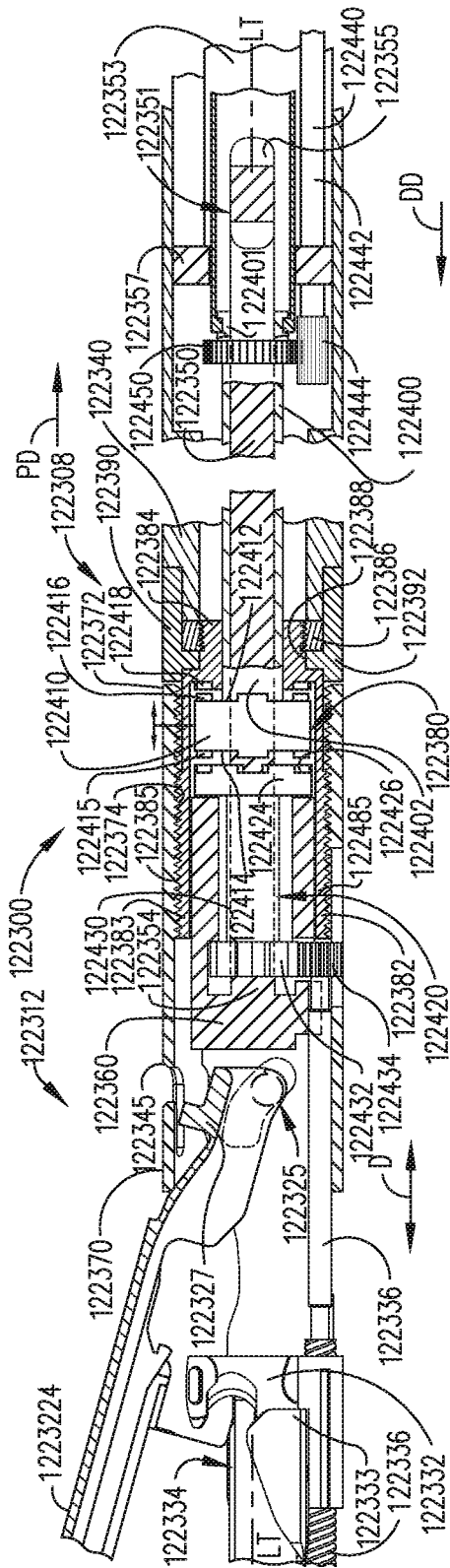

FIG. 102 is a cross-sectional side view of a portion of the surgical end effector and elongated shaft assembly of the surgical tool of FIG. 101 with the anvil in the open position and the closure clutch assembly in a neutral position, according to one aspect of the present disclosure.

Figure 103:
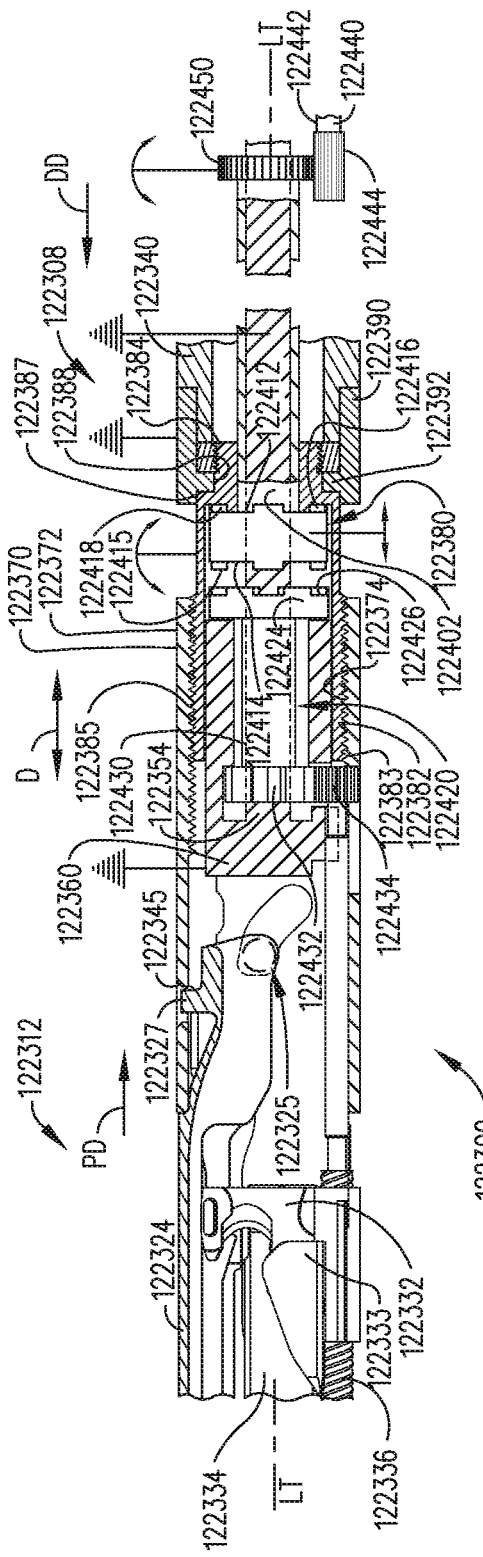

FIG. 103 is another cross-sectional side view of the surgical end effector and elongated shaft assembly shown in FIG. 102 with the clutch assembly engaged in a closure position, according to one aspect of the present disclosure.

Figure 104:
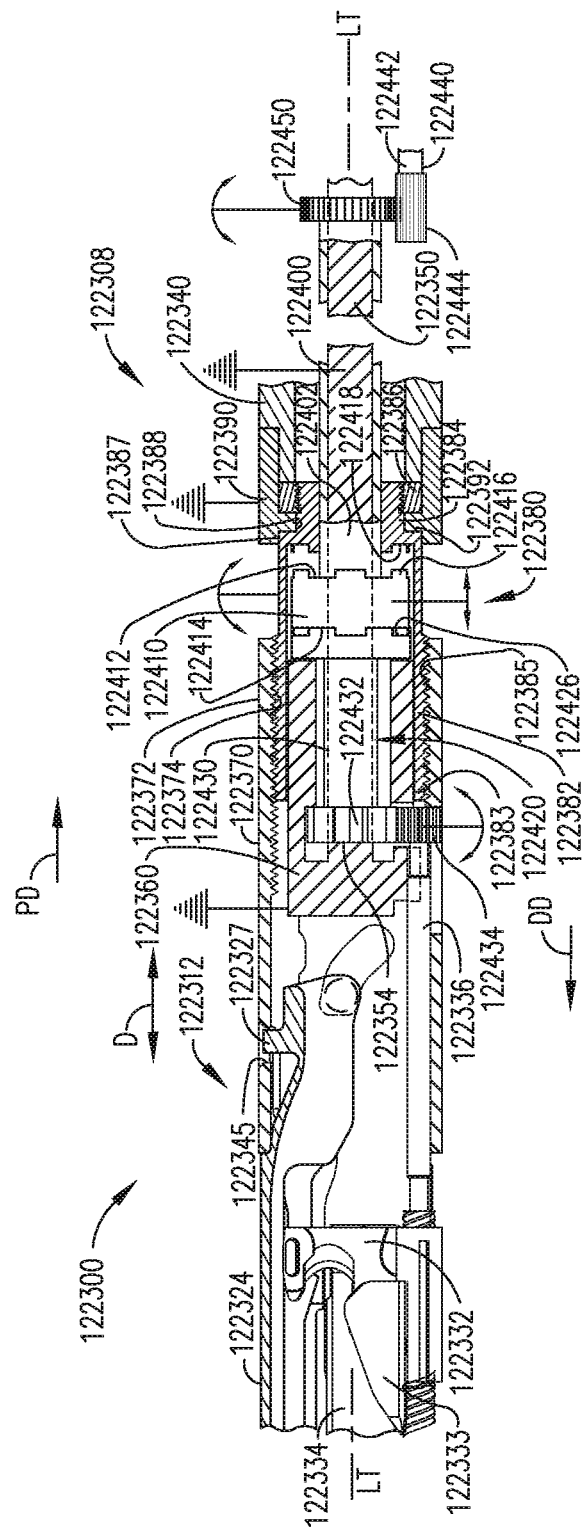

FIG. 104 is another cross-sectional side view of the surgical end effector and elongated shaft assembly shown in FIG. 102 with the clutch assembly engaged in a firing position, according to one aspect of the present disclosure.

Figure 105:
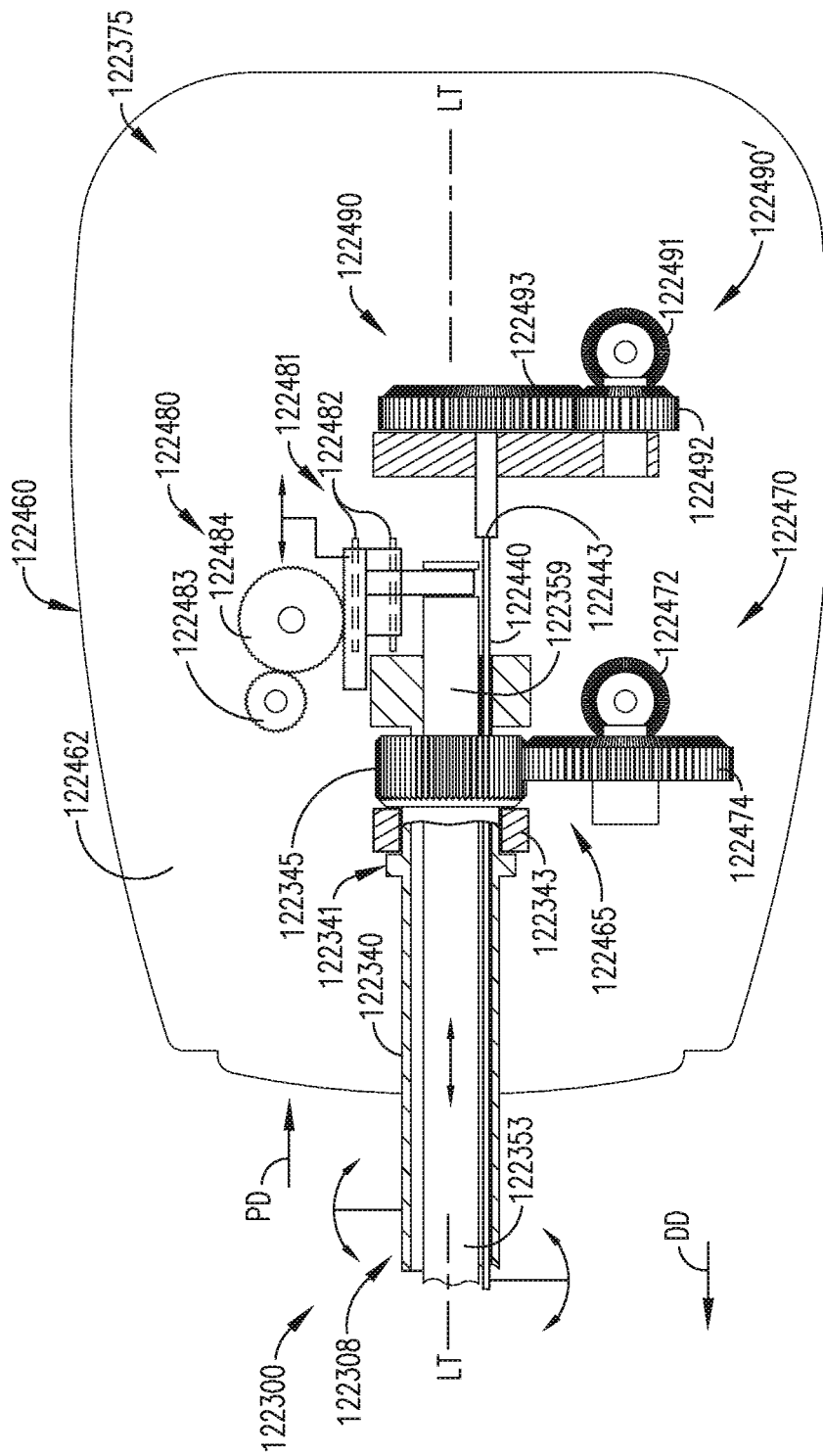

FIG. 105 is a top view of a portion of a tool mounting portion, according to one aspect of the present disclosure.

Figure 106:
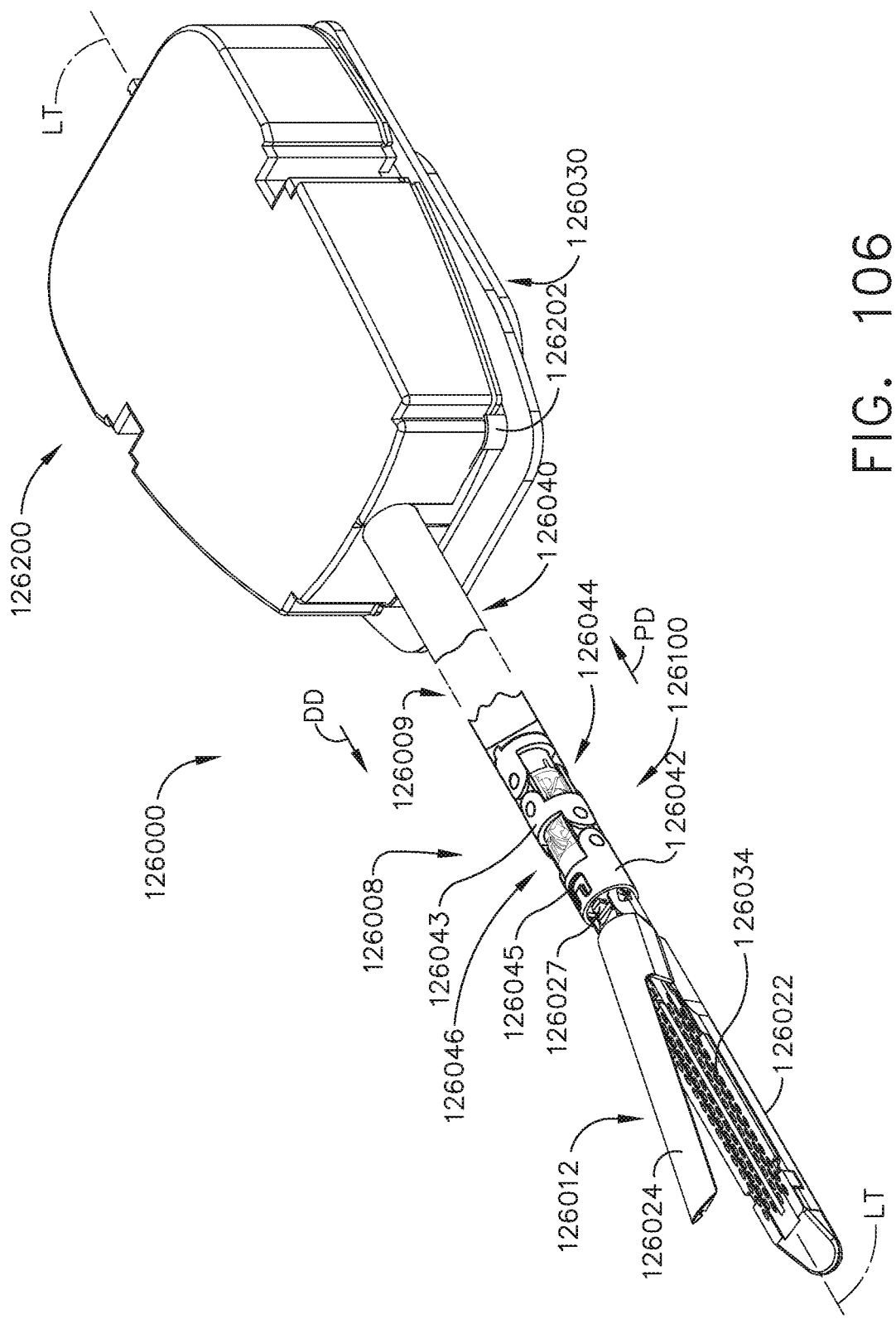

FIG. 106 is a perspective view of another surgical tool according to one aspect of the present disclosure.

Figure 107:
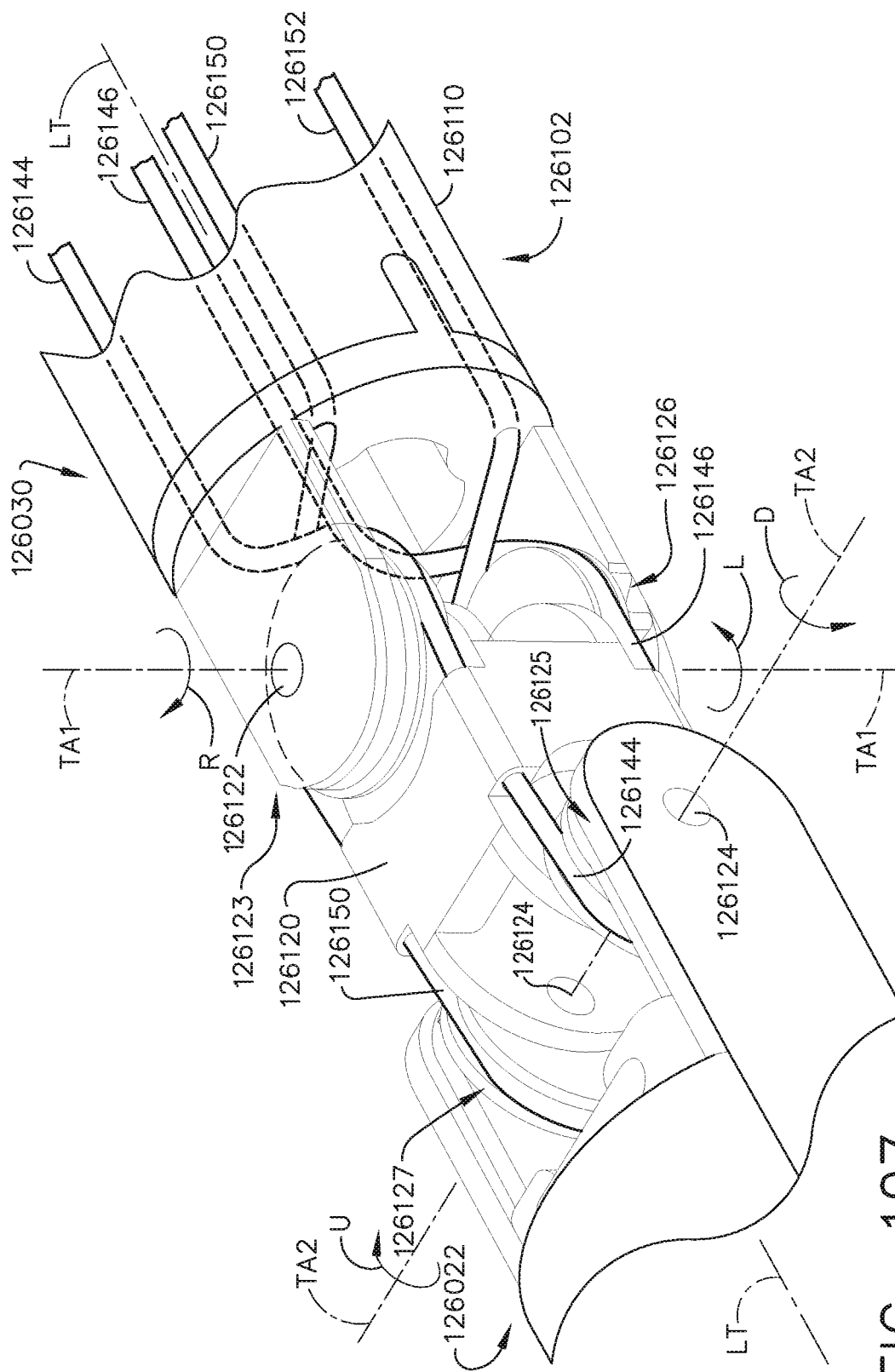

FIG. 107 is a partial perspective view of an articulation joint, according to one aspect of the present disclosure.

Figure 108:
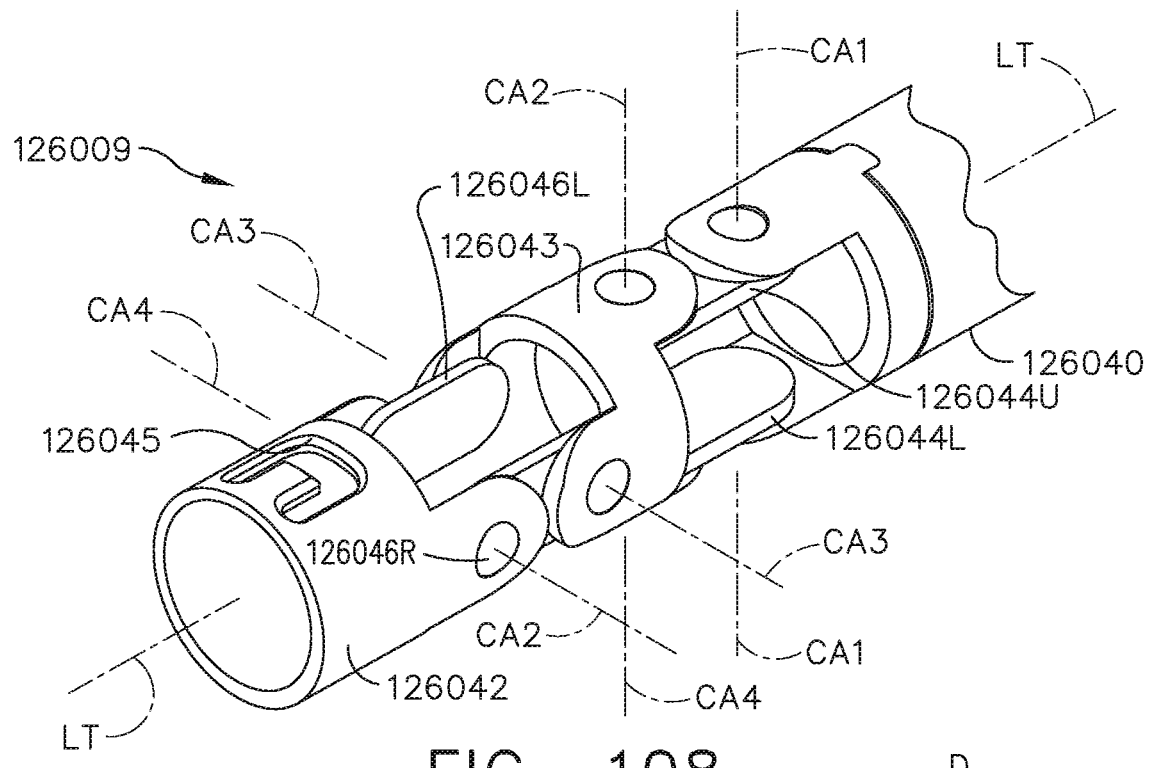

FIG. 108 is a perspective view of a closure tube of a surgical tool, according to one aspect of the present disclosure.

Figure 109:
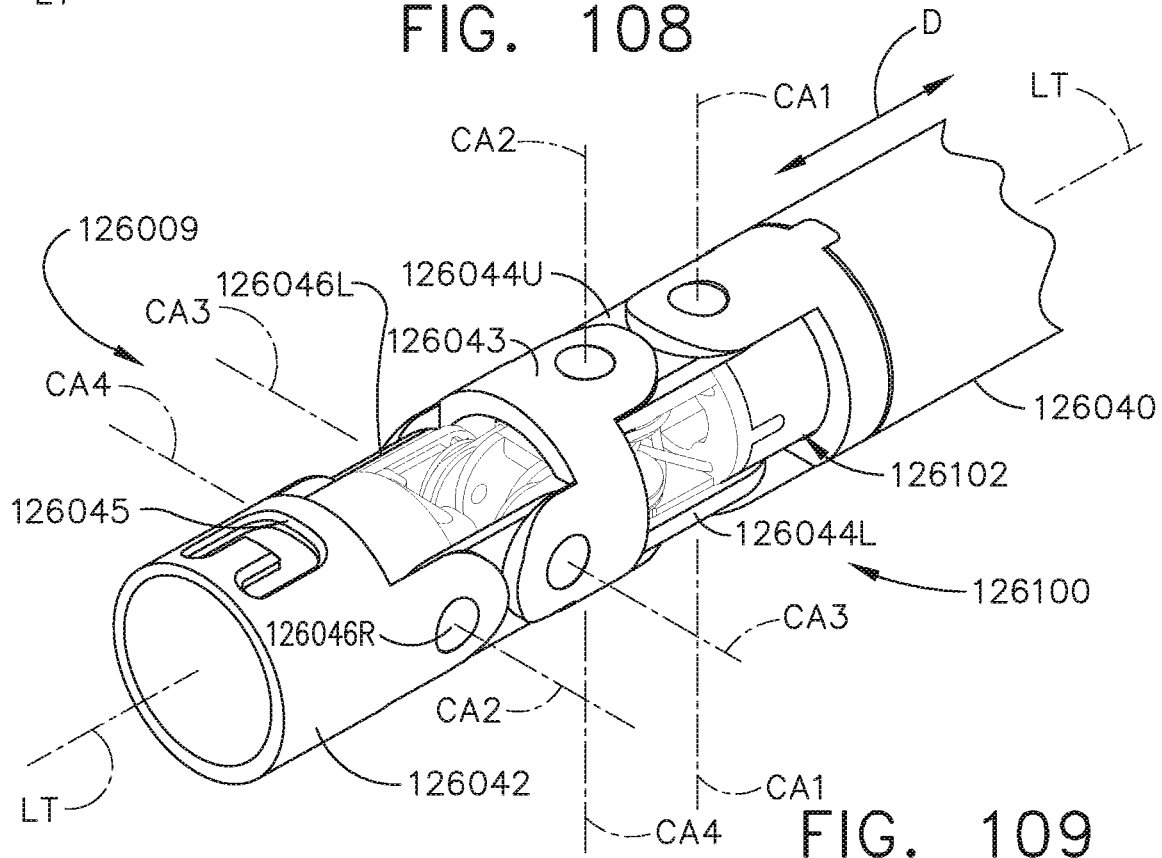

FIG. 109 is a perspective view of the closure tube of FIG. 108 assembled on the articulation joint of FIG. 107, according to one aspect of the present disclosure.

Figure 110:
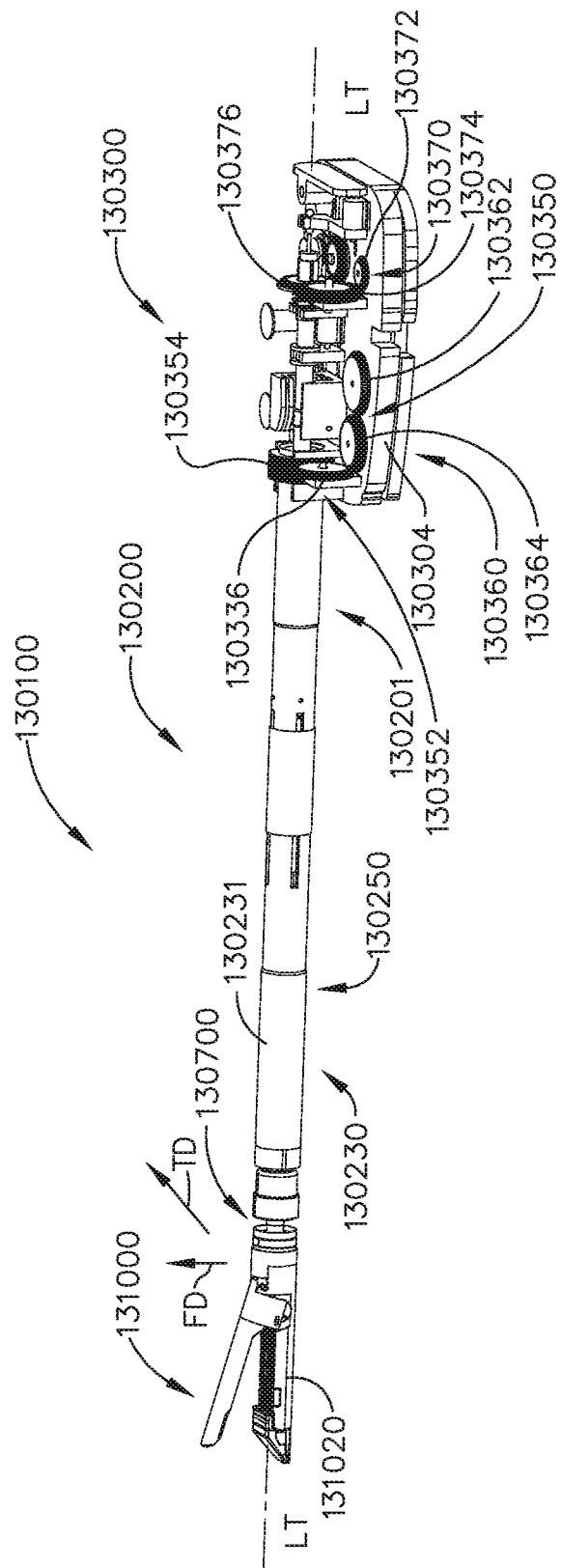

FIG. 110 is a perspective view of a surgical tool and a surgical end effector, according to one aspect of the present disclosure.

Figure 111:
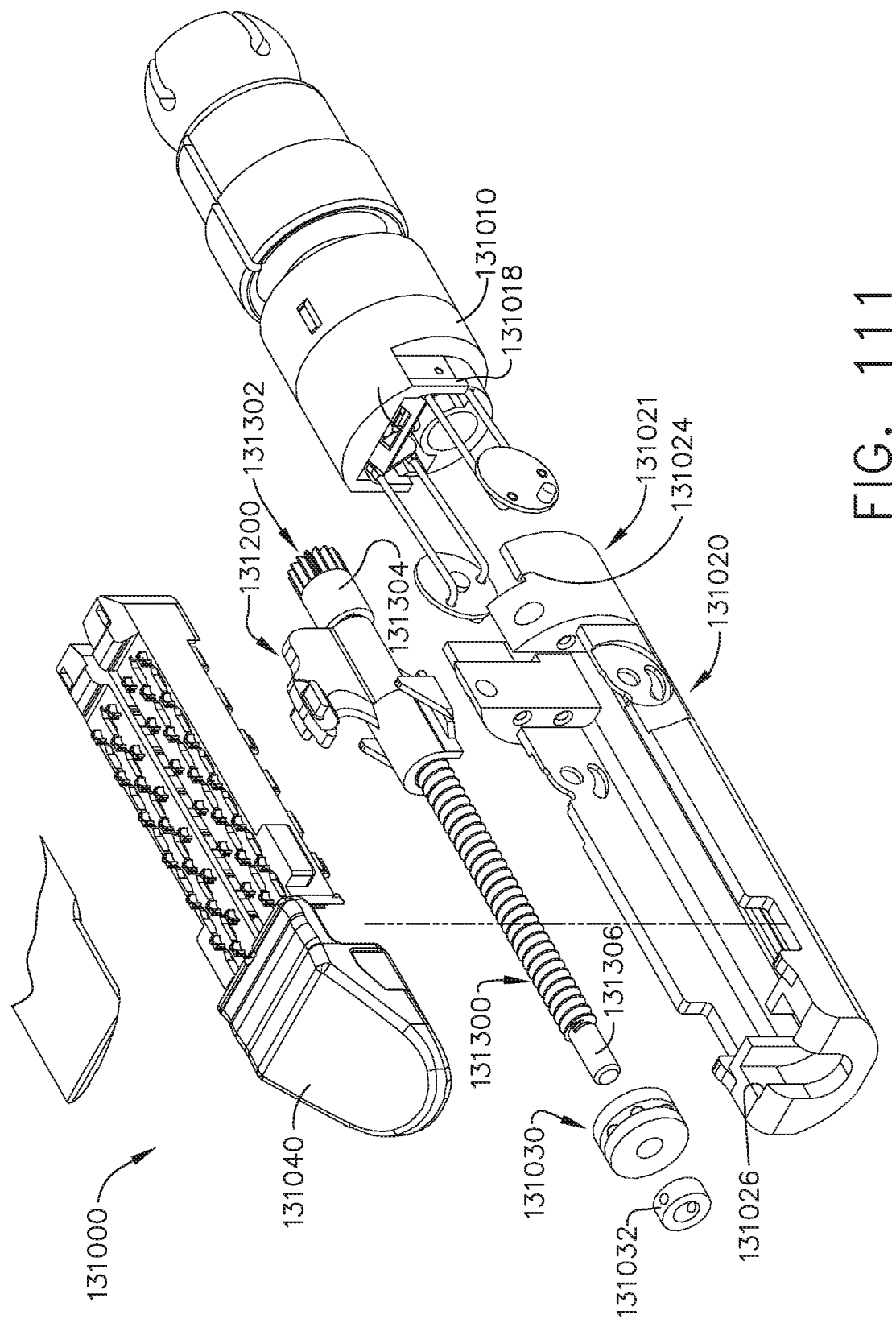

FIG. 111 is an exploded assembly view of another end effector, according to one aspect of the present disclosure.

Figure 112:
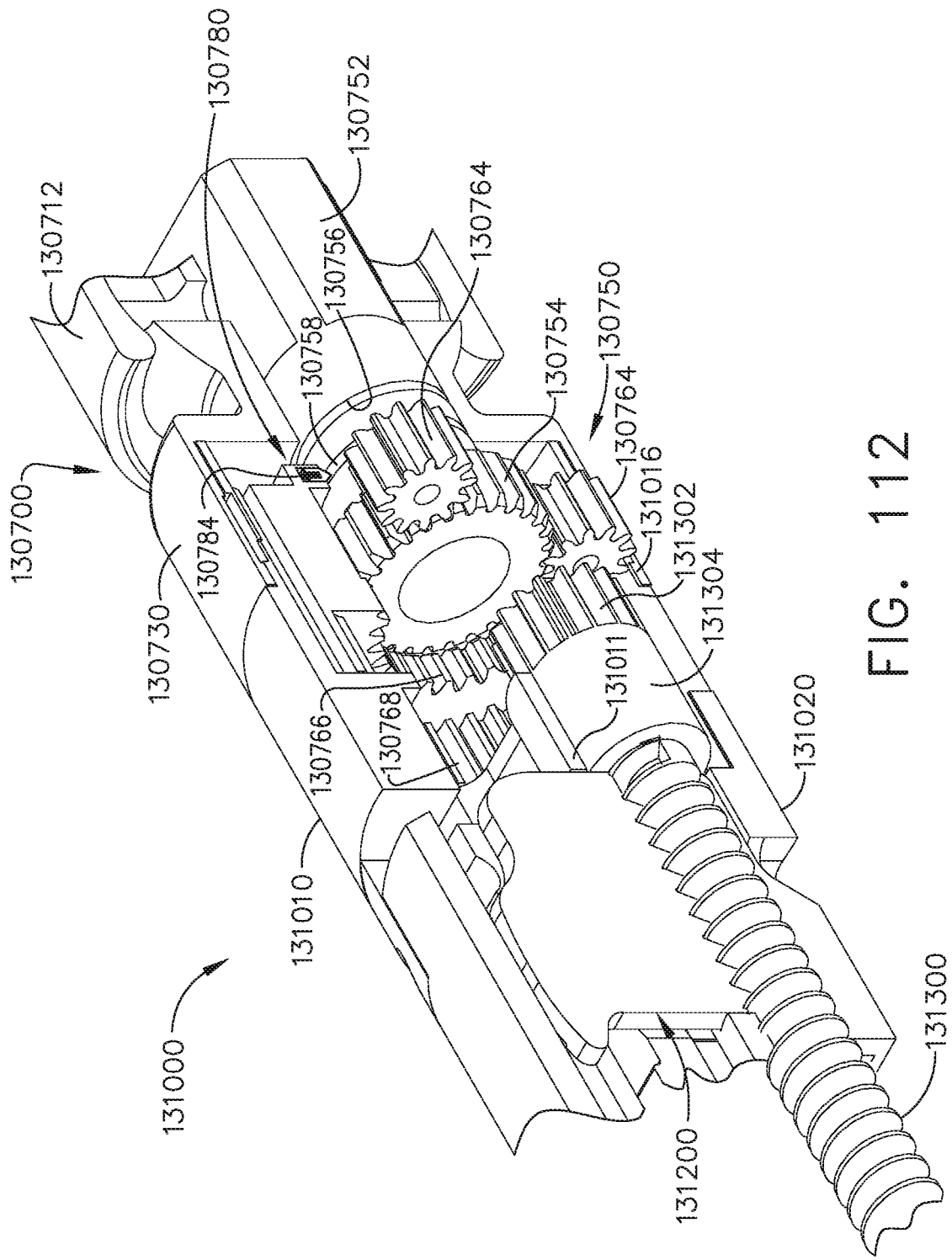

FIG. 112 is a partial perspective view of a drive system, according to one aspect of the present disclosure.

Figure 113:
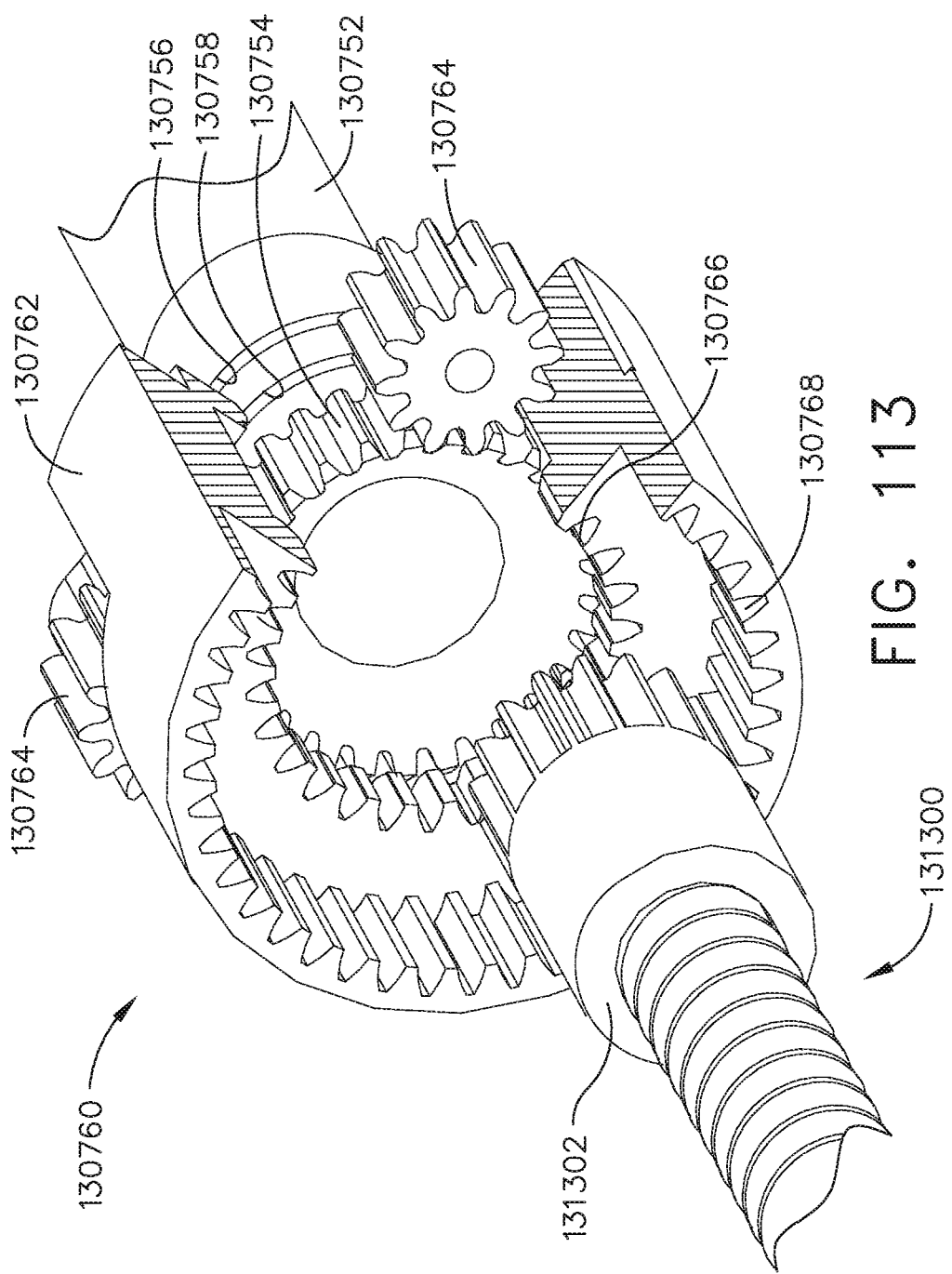

FIG. 113 is a partial front perspective view of a portion of the drive system of FIG. 112.

Figure 114:
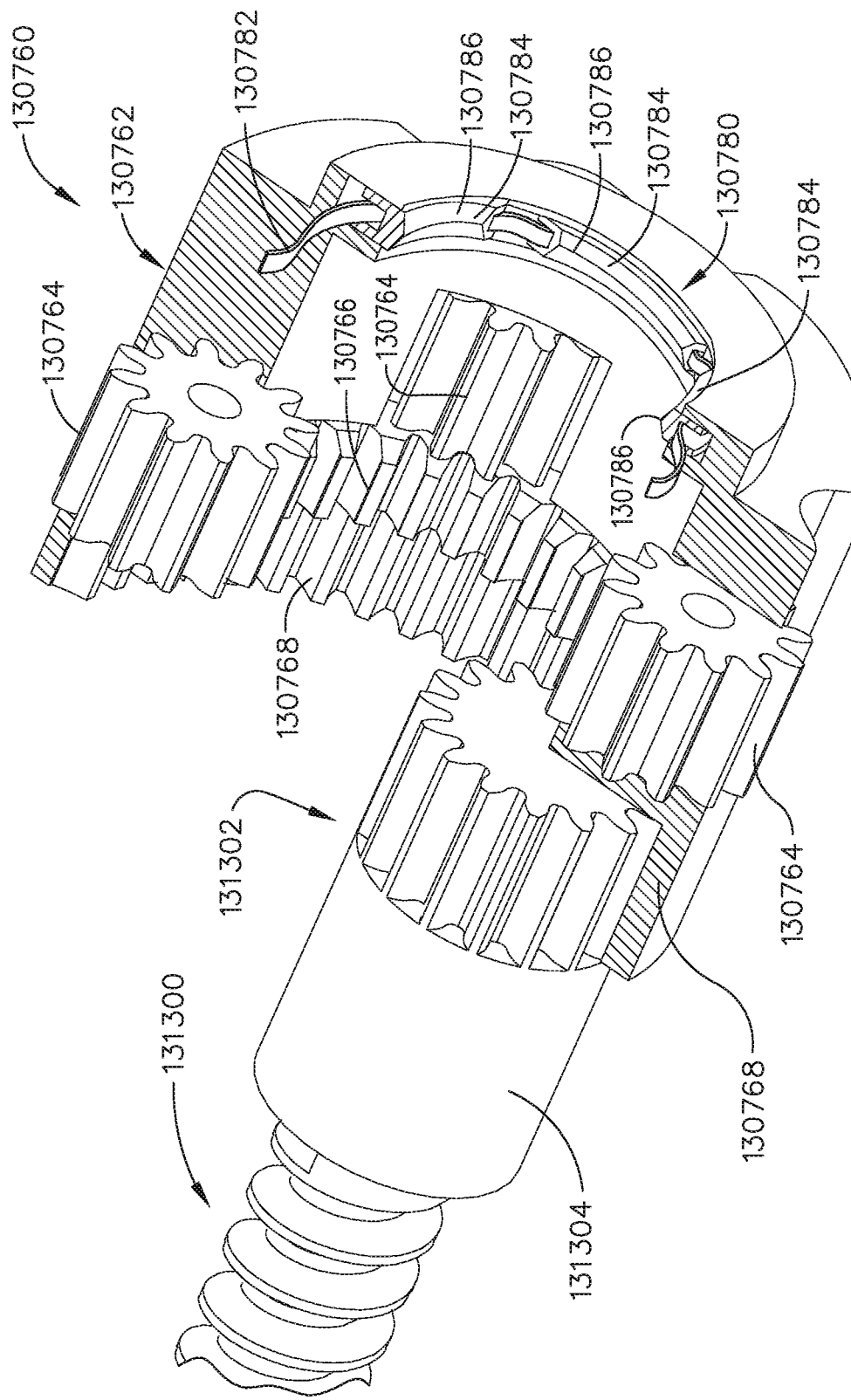

FIG. 114 is a partial rear perspective view of a portion of the drive system of FIGS. 112 and 113, according to one aspect of the present disclosure.

Figure 115:
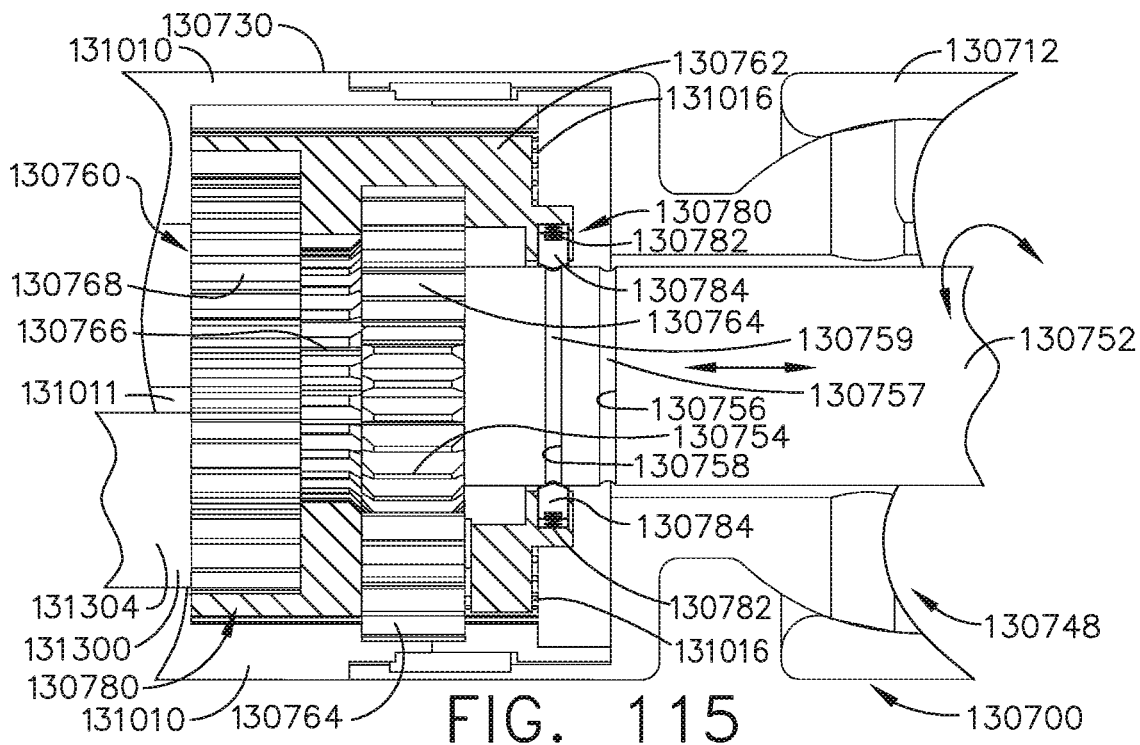

FIG. 115 is a partial cross-sectional side view of the drive system of FIGS. 112-114 in a first axial drive position, according to one aspect of the present disclosure.

Figure 116:
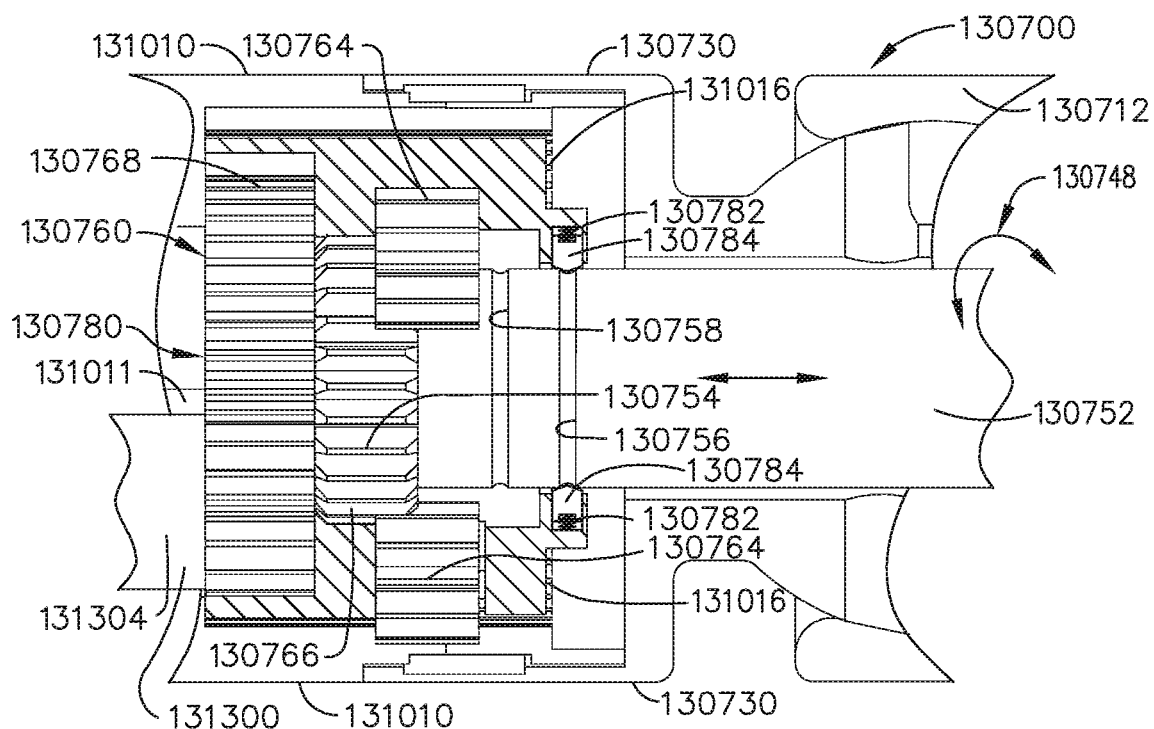

FIG. 116 is another partial cross-sectional side view of the drive system of FIGS. 112-115 in a second axial drive position, according to one aspect of the present disclosure.

FIG. 117 is a cross-sectional view of an end effector and drive system wherein the drive system is configured to fire the firing member, according to one aspect of the present disclosure.

FIG. 118 is another cross-sectional view of the end effector and drive system wherein the drive system is configured to rotate the entire end effector, according to one aspect of the present disclosure.

FIG. 119 is a cross-sectional perspective view of a portion of an end effector and articulation joint, according to one aspect of the present disclosure.

FIG. 120 is a cross-sectional side view of the end effector and articulation joint depicted in FIG. 119, according to one aspect of the present disclosure.

Figure 121:
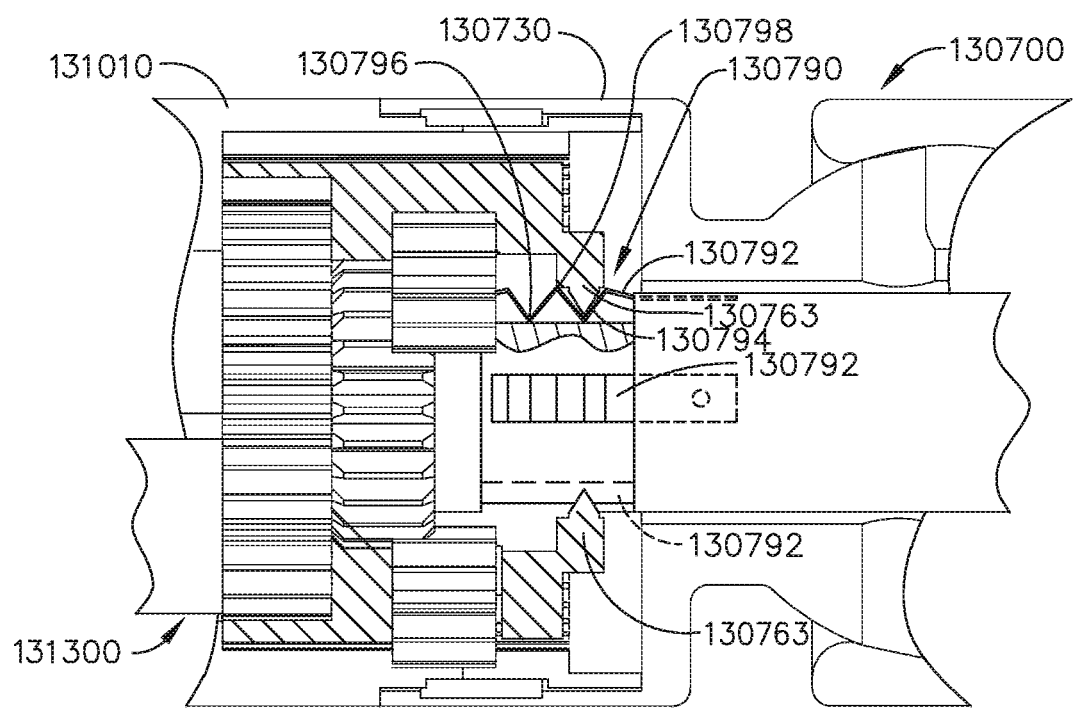

FIG. 121 is a cross-sectional view of another end effector and drive system wherein the drive system is configured to rotate the entire end effector, according to one aspect of the present disclosure.

Figure 122:
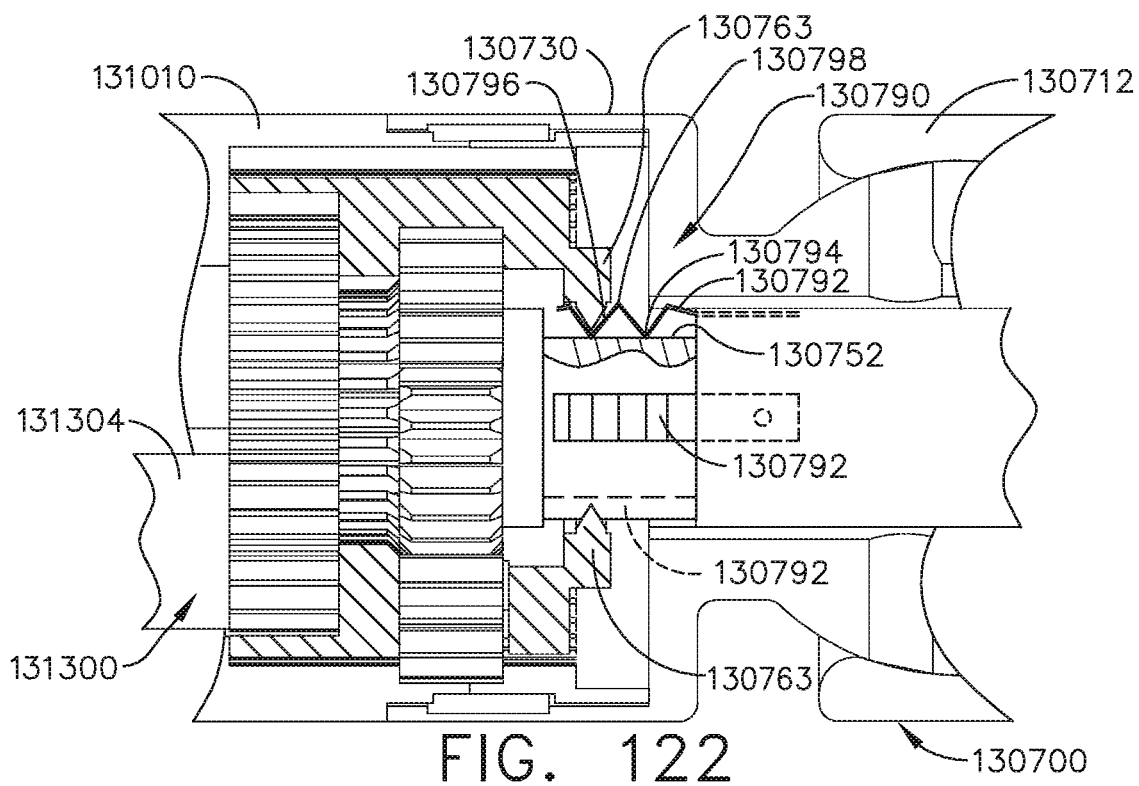

FIG. 122 is another cross-sectional view of the end effector and drive system of FIG. 121 wherein the drive system is configured to fire the firing member of the end effector, according to one aspect of the present disclosure.

Figure 123:
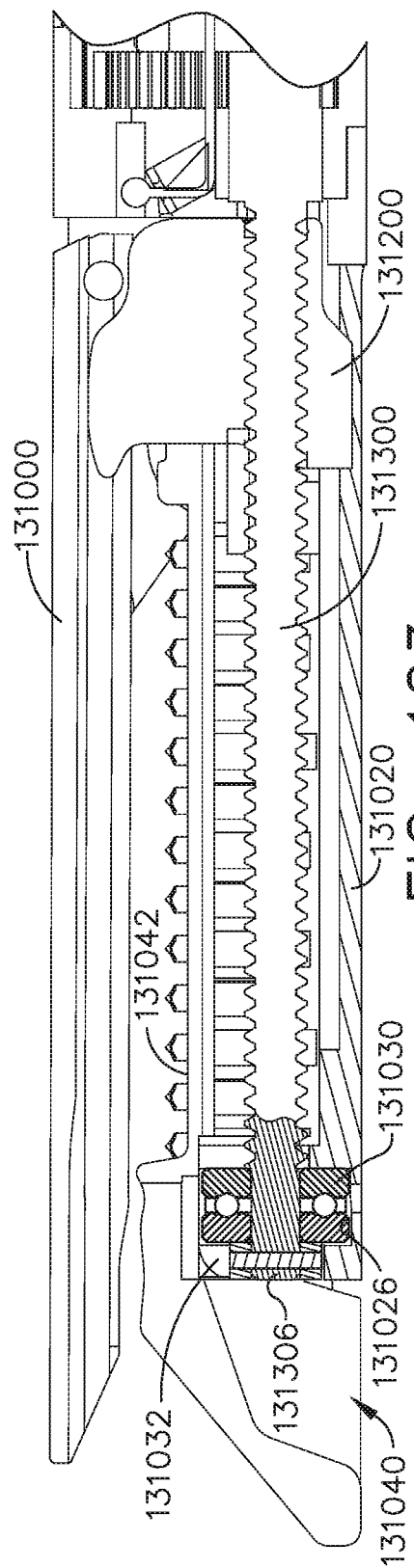

FIG. 123 is a cross-sectional side view of an end effector, according to one aspect of the present disclosure.

Figure 124:
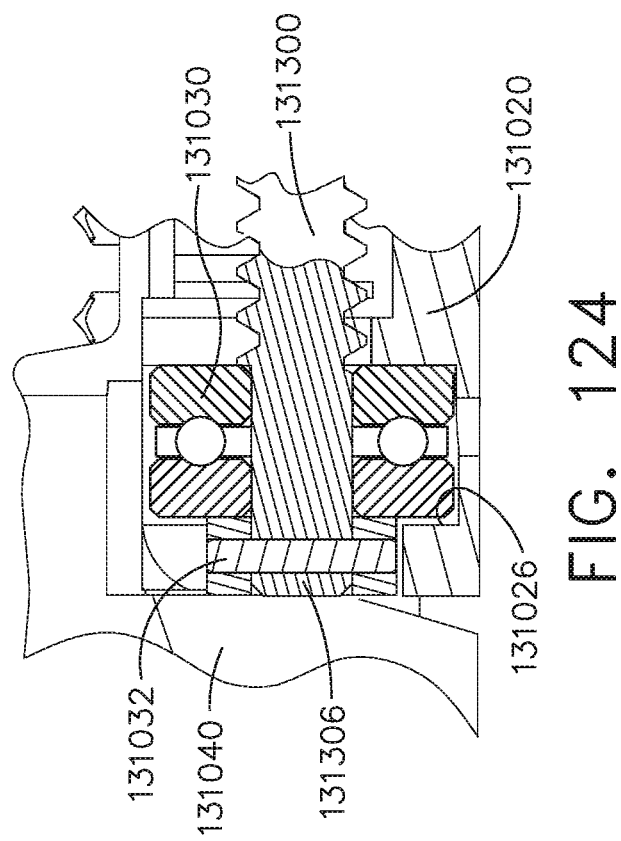

FIG. 124 is an enlarged cross-sectional view of a portion of the end effector of FIG. 123, according to one aspect of the present disclosure.

Figure 125:
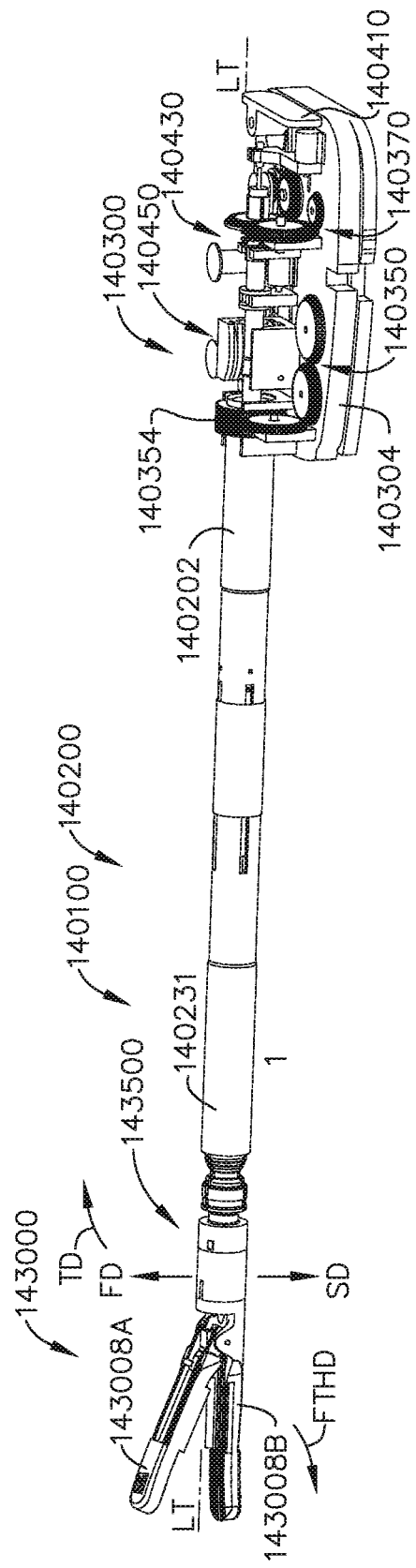

FIG. 125 is a perspective view of a surgical tool and a surgical end effector, according to one aspect of the present disclosure.

Figure 126:
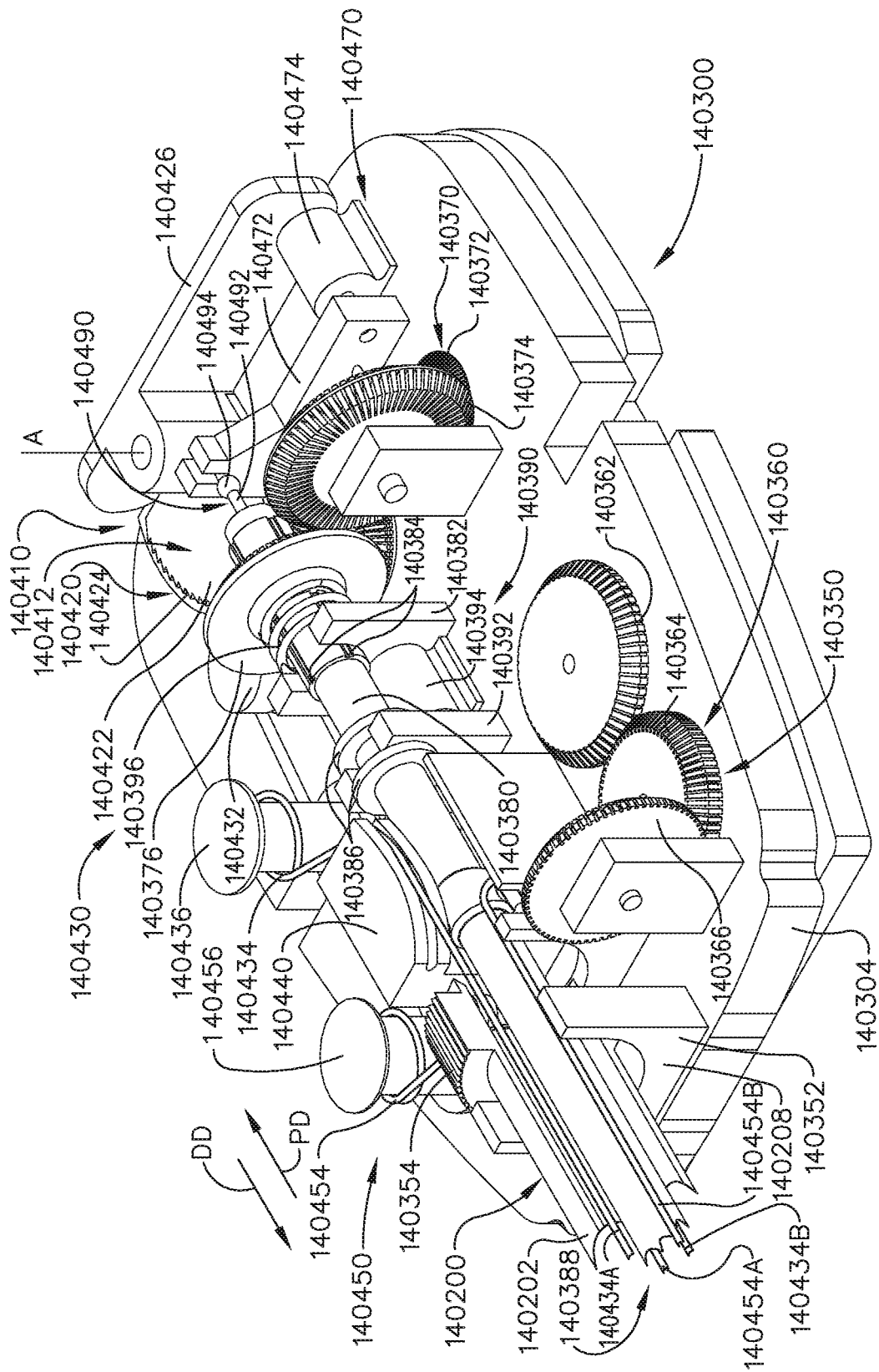

FIG. 126 is a front perspective view of one exemplification of a portion of a surgical tool with some elements thereof omitted for clarity, according to one aspect of the present disclosure.

Figure 127:
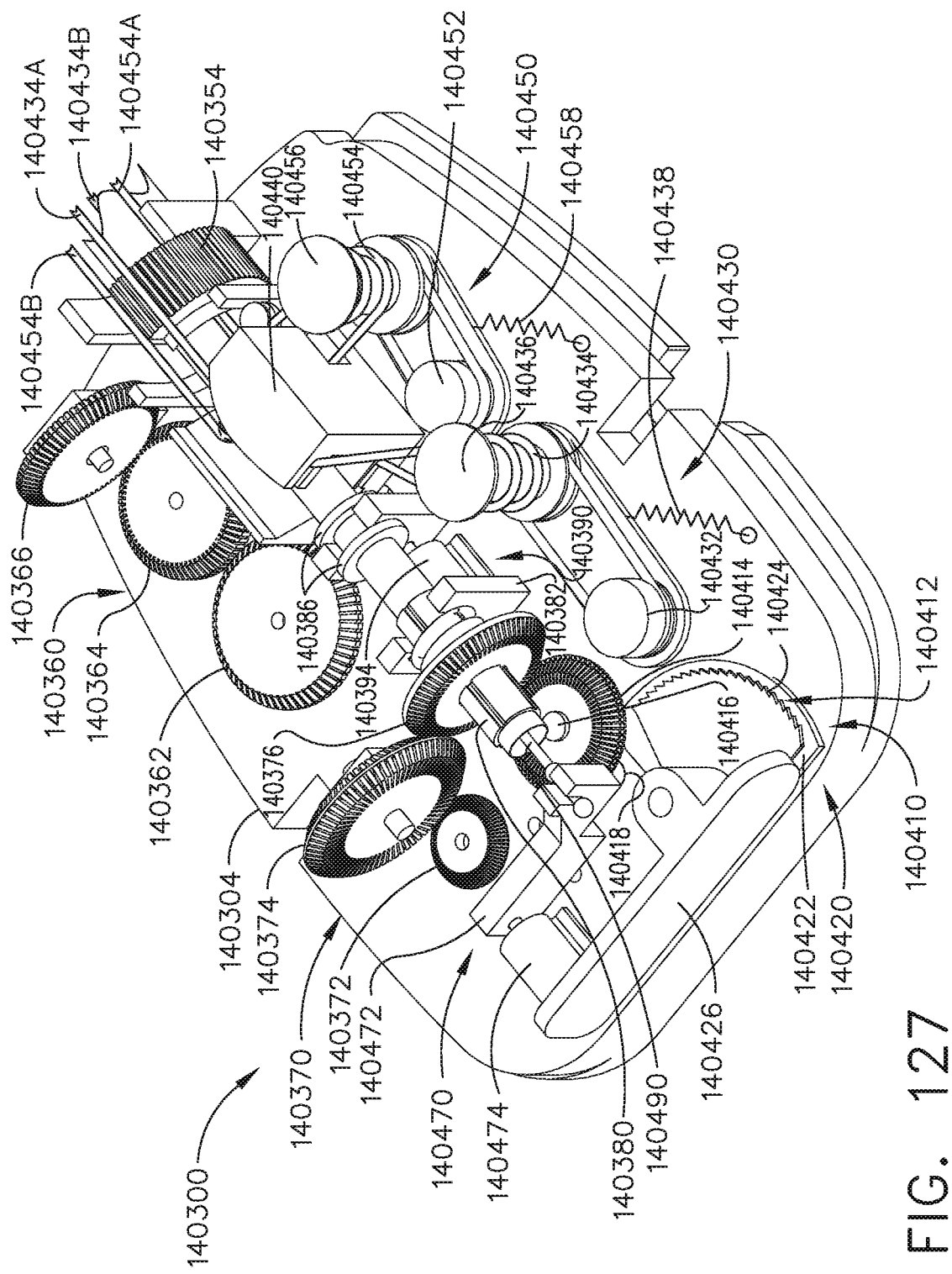

FIG. 127 is a rear perspective view of one exemplification of the surgical tool of FIG. 126.

Figure 128:
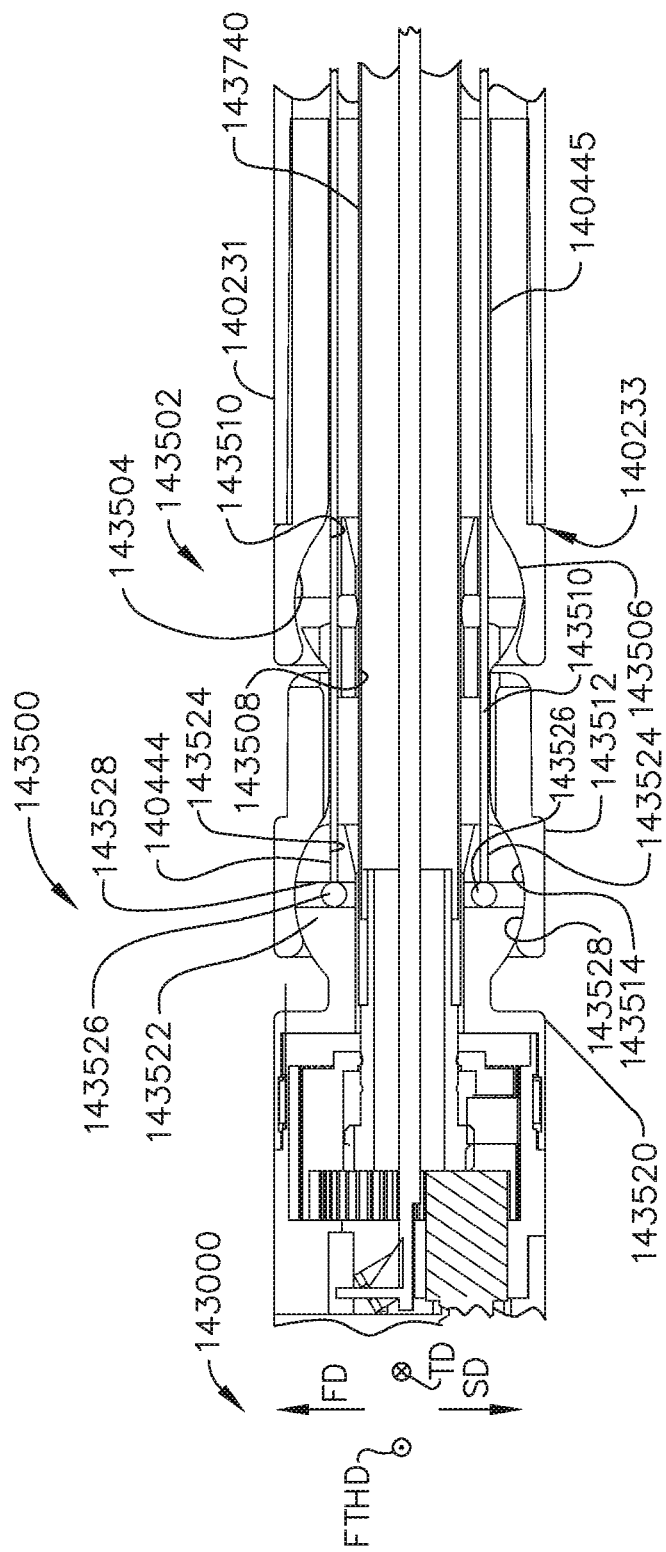

FIG. 128 is a cross-sectional view of one exemplification of a portion of an articulation joint and end effector, according to one aspect of the present disclosure.

Figure 129:
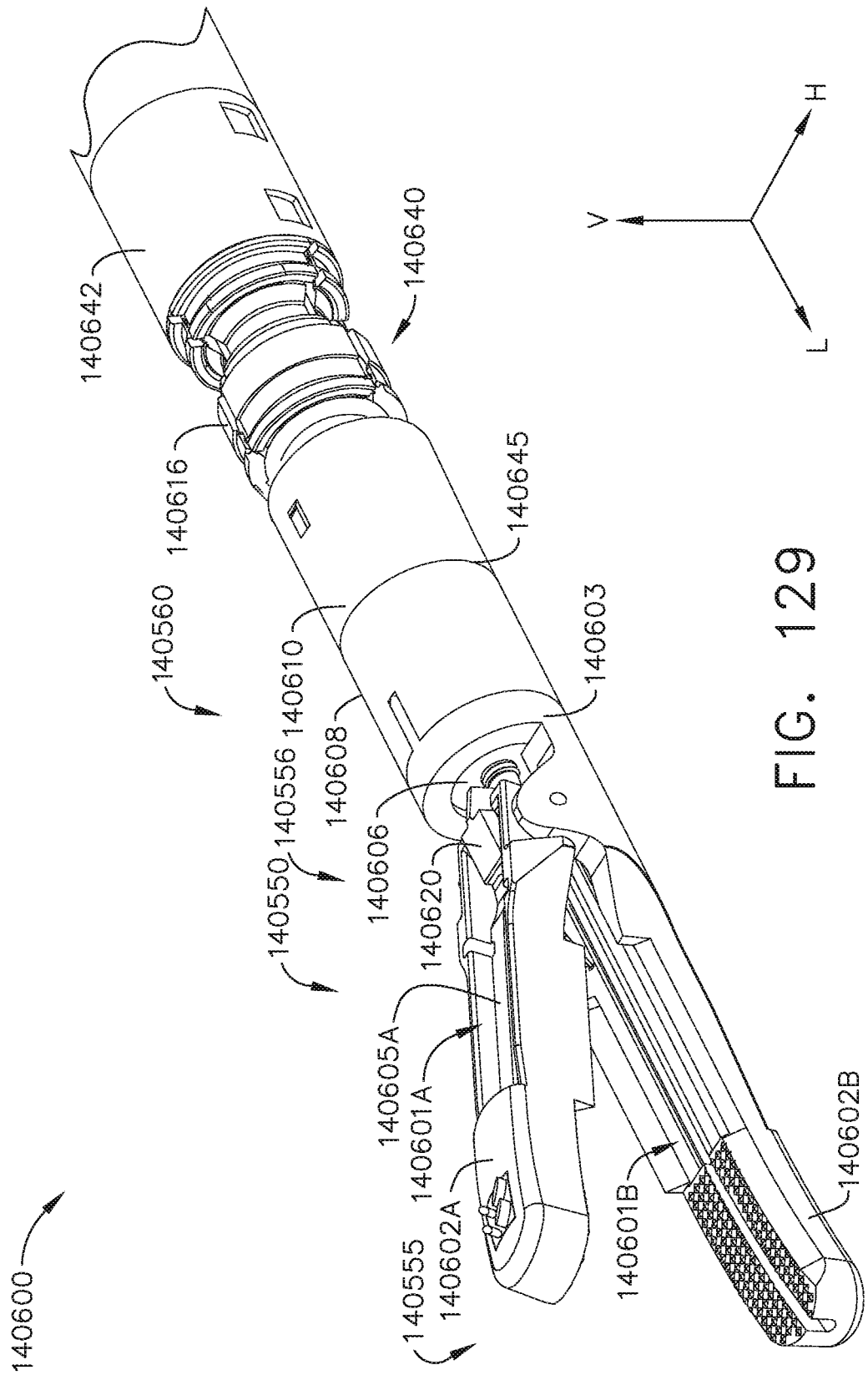

FIG. 129 is a perspective view of an exemplification of a multi-axis articulating and rotating surgical tool, according to one aspect of the present disclosure.

Figure 130:
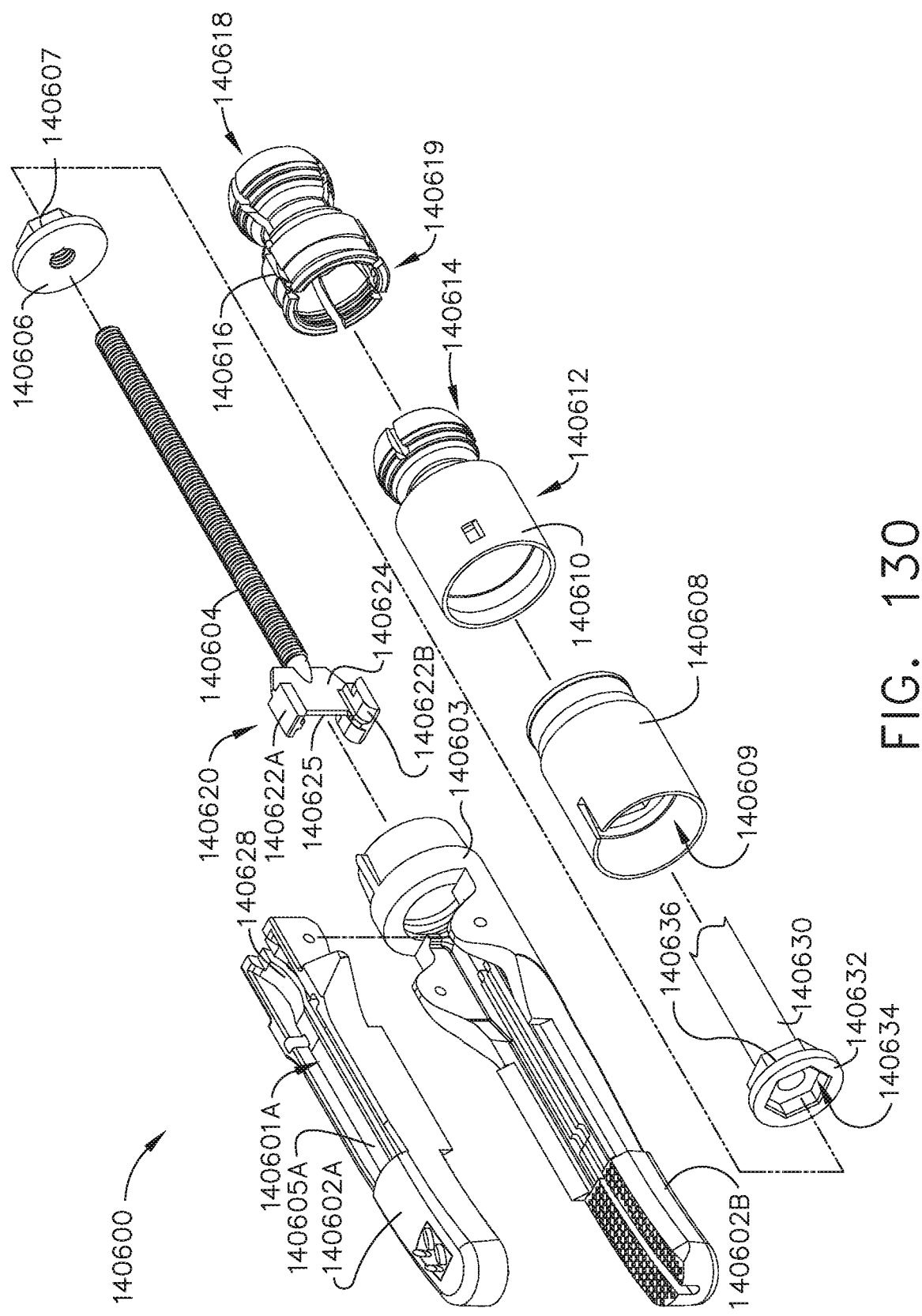

FIG. 130 is an exploded perspective view of various components of one exemplification of the surgical tool shown in FIG. 129, according to one aspect of the present disclosure.

Figure 131:
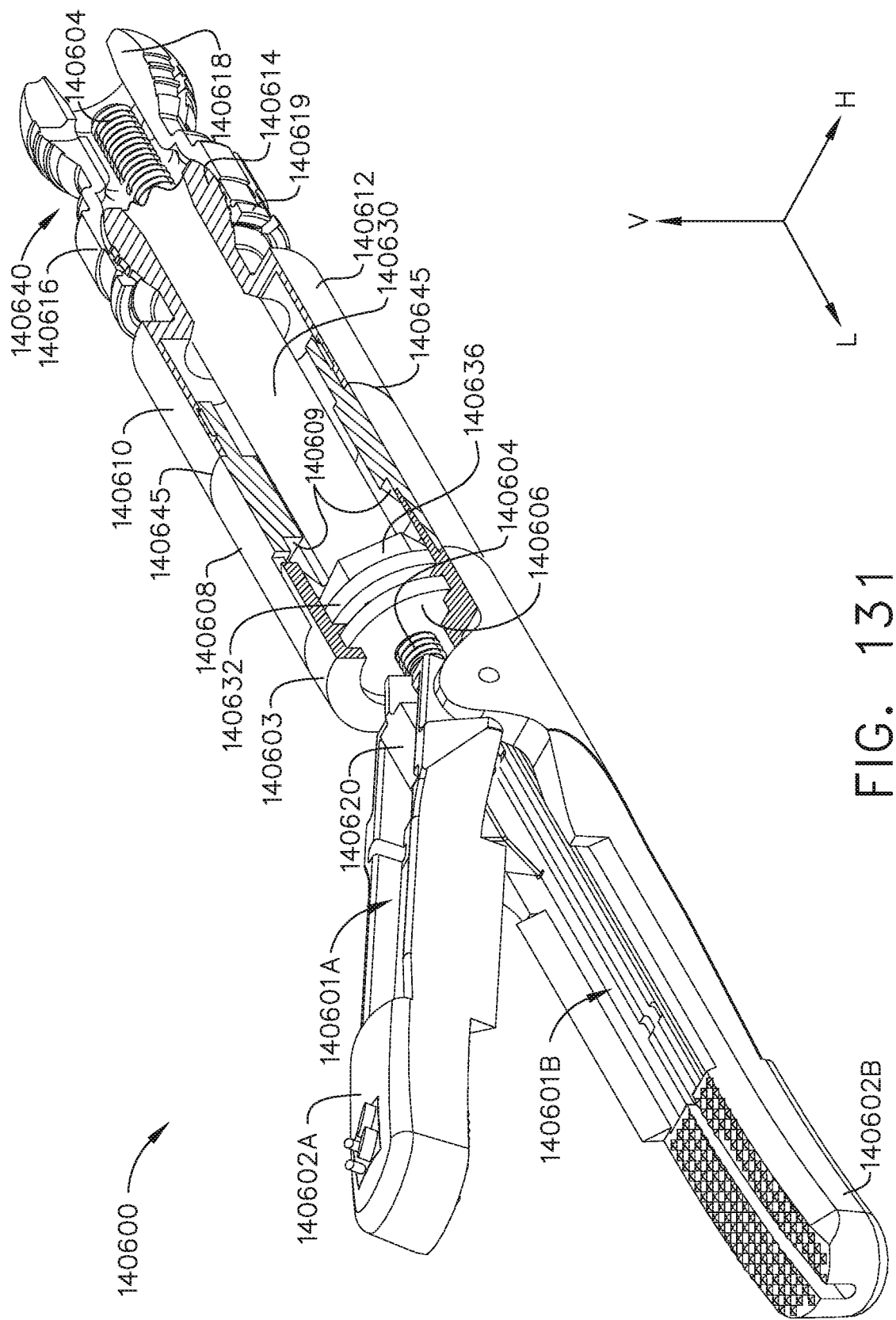

FIG. 131 is a partial cross-sectional perspective view of one exemplification of the surgical tool shown in FIG. 129, illustrating a rotary drive shaft engaging a rotary drive nut for actuating translation of an I-beam member and closure of a jaw assembly of an end effector, according to one aspect of the present disclosure.

Figure 132:
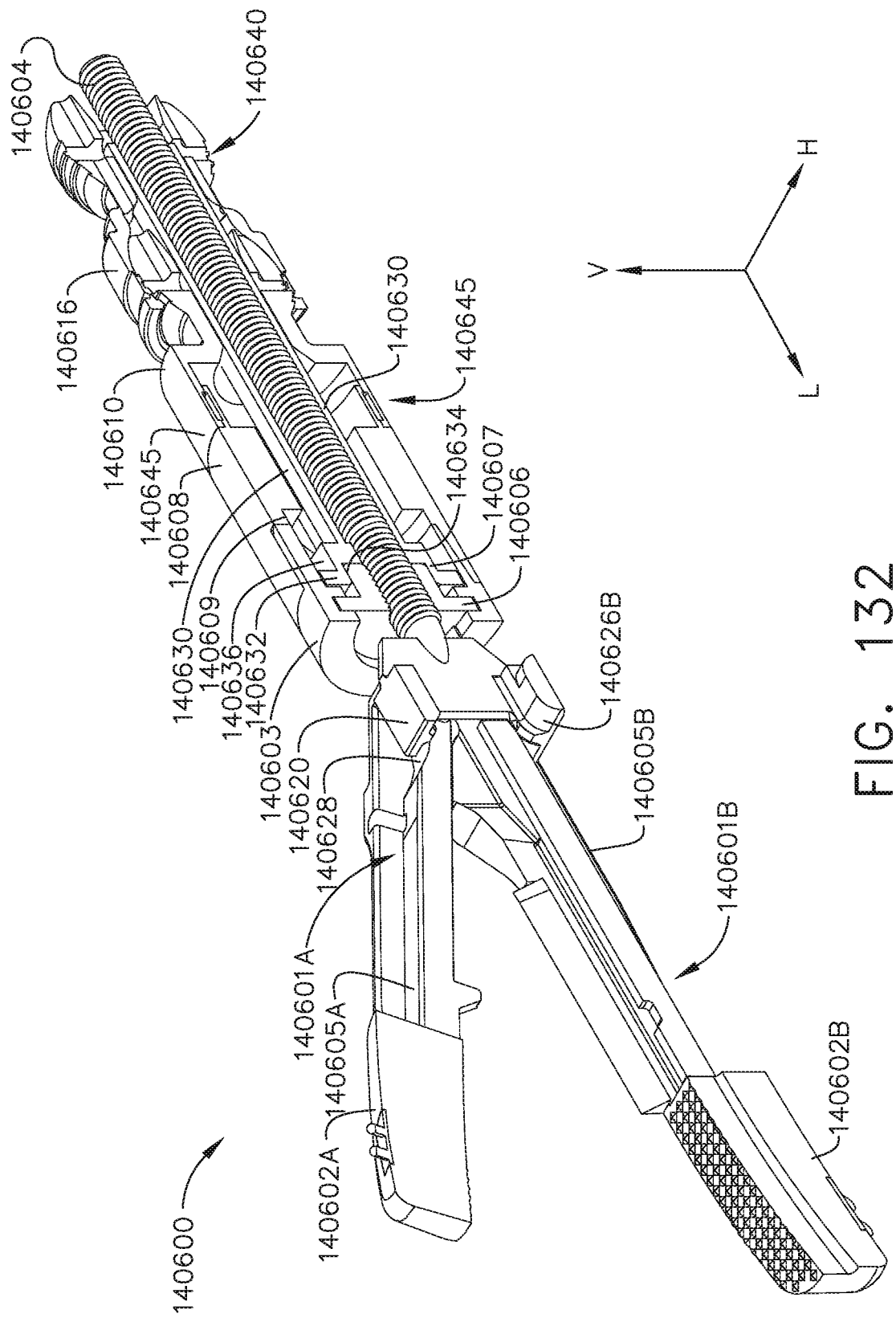

FIG. 132 is a cross-sectional perspective view of one exemplification of the surgical tool shown in FIG. 129, illustrating a rotary drive shaft engaging a rotary drive nut for actuating translation of an I-beam member and closure of a jaw assembly of an end effector.

Figure 133:
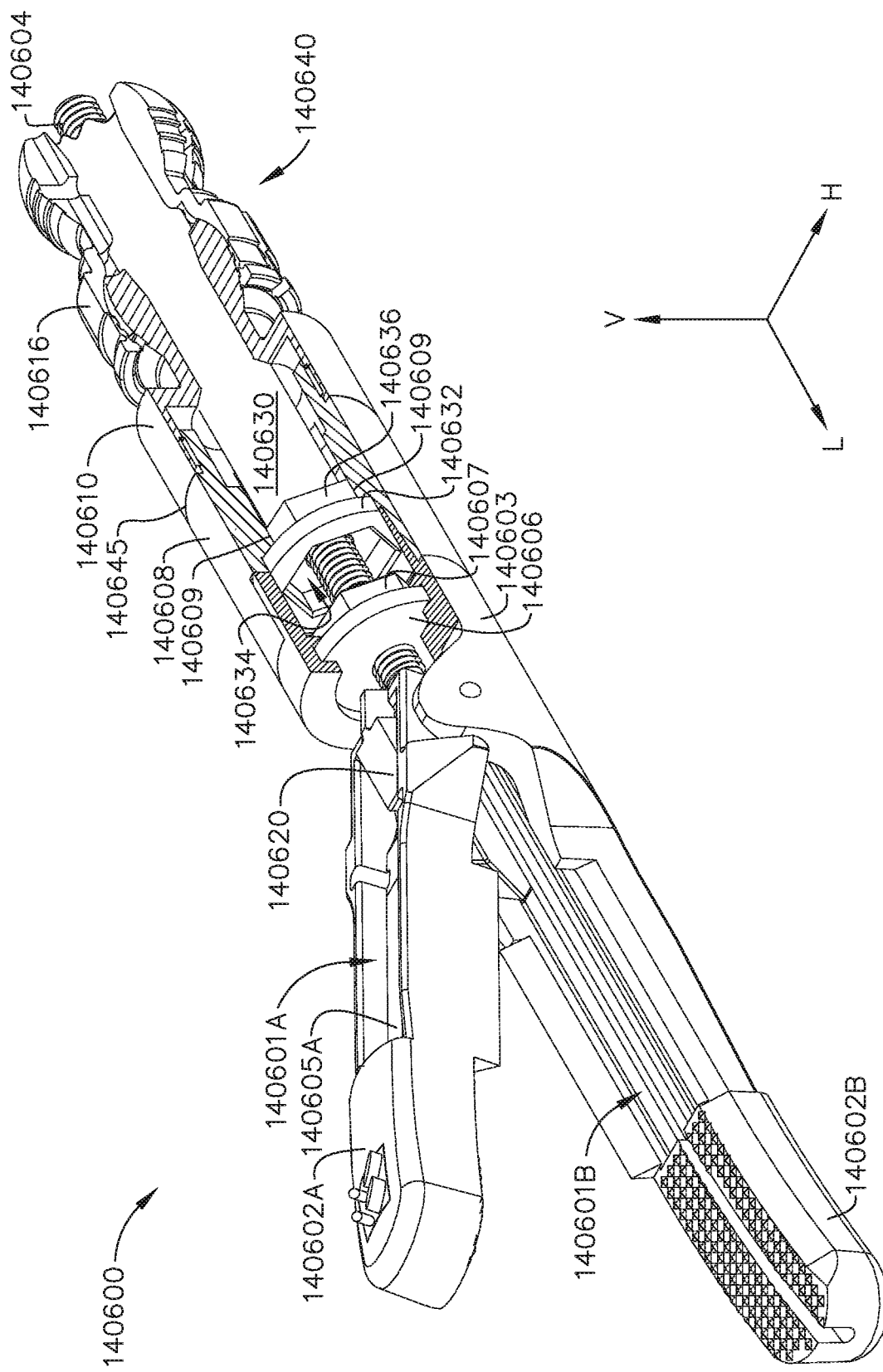

FIG. 133 is a partial cross-sectional perspective view of one exemplification of the surgical tool shown in FIG. 129, illustrating a rotary drive shaft engaging a shaft coupling for actuating rotation of an end effector, according to one aspect of the present disclosure.

Figure 134:
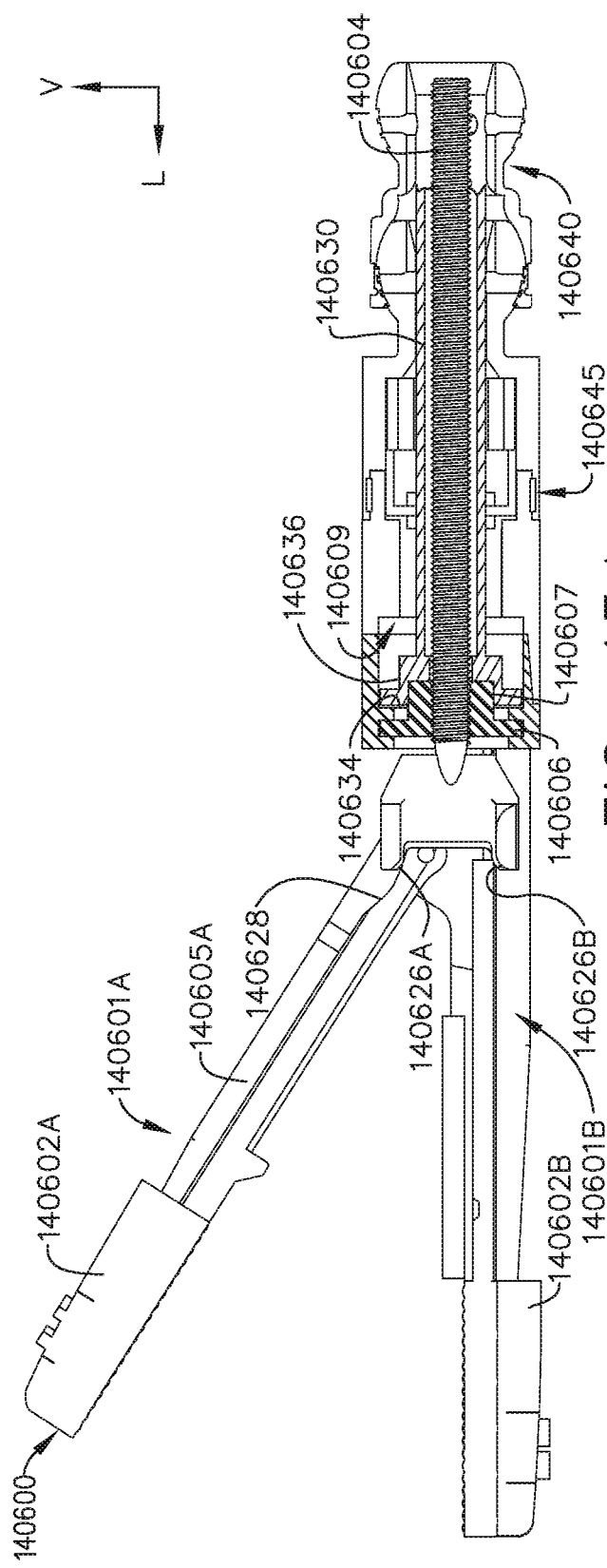

FIG. 134 is a side cross-sectional view of one exemplification of the surgical tool shown in FIG. 129, illustrating the jaw assembly of an end effector in an open position, an I-beam member in a proximally retracted position, and a rotary drive shaft engaging a rotary drive nut for actuating translation of the I-beam member and closure of the jaw assembly of the end effector, according to one aspect of the present disclosure.

Figure 135:
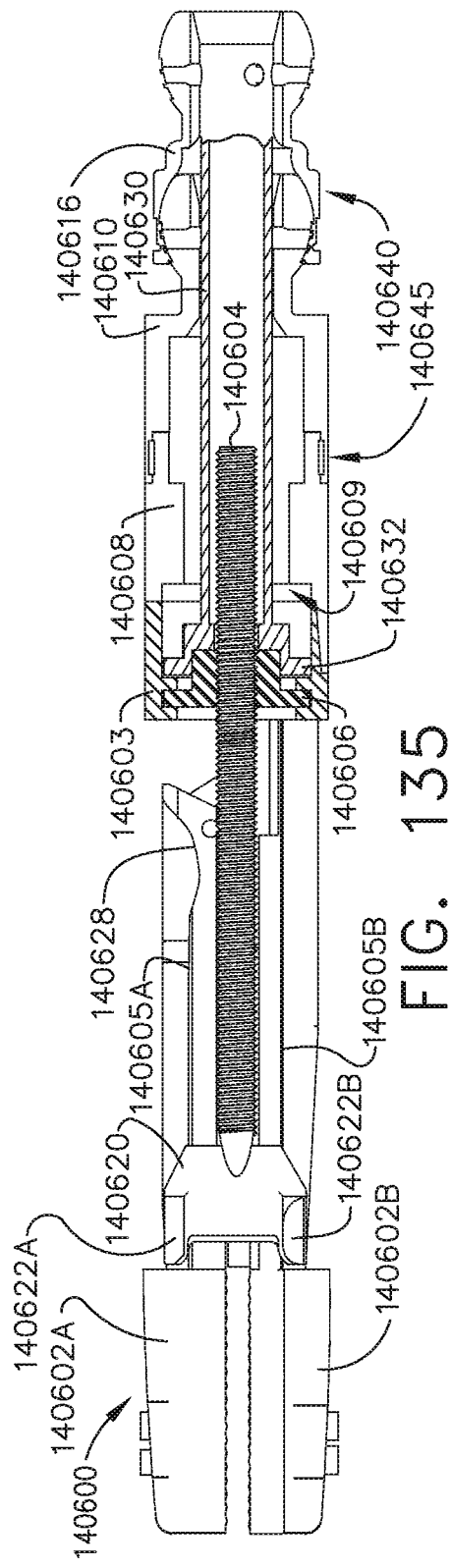

FIG. 135 is a side cross-sectional view of one exemplification of the surgical tool shown in FIG. 129, illustrating the jaw assembly of an end effector in a closed position, an I-beam member in a distally advanced position, and a rotary drive shaft engaging a rotary drive nut for actuating translation of the I-beam member and opening of the jaw assembly of the end effector, according to one aspect of the present disclosure.

FIG. 136 is a side cross-sectional view of one exemplification of the surgical tool shown in FIG. 129, illustrating the jaw assembly of an end effector in an open position, an I-beam member in a proximally retracted position, and a rotary drive shaft engaging a shaft coupling for actuating rotation of the end effector, according to one aspect of the present disclosure.

FIG. 137 is a side cross-sectional view of one exemplification of the surgical tool shown in FIG. 129, illustrating the jaw assembly of an end effector in a closed position, an I-beam member in a distally advanced position, and a rotary drive shaft engaging a shaft coupling for actuating rotation of the end effector, according to one aspect of the present disclosure.

FIGS. 138 and 139 are side cross-sectional detail views of one exemplification of the surgical tool shown in FIG. 129, illustrating the engagement of cam surfaces of an I-beam member with anvil surfaces of a first jaw member to move the first jaw member relative to a second jaw member between an open position and a closed position, according to one aspect of the present disclosure.

FIG. 140 is a cross sectional perspective view of a surgical tool having first and second jaw members, according to one aspect of the present disclosure.

FIG. 141 is prospective view of a closure nut of one example of the surgical tool of FIG. 140, according to one aspect of the present disclosure.

Figure 142:
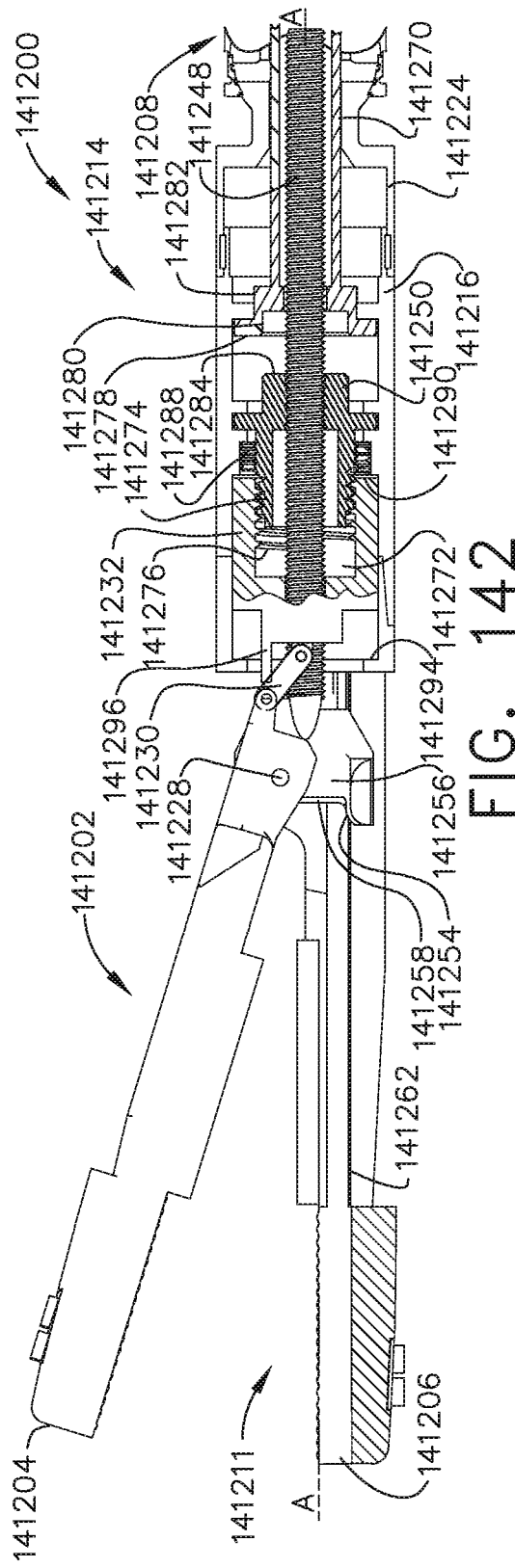

FIG. 142 is a cross sectional elevation view of one exemplification of the surgical tool of FIG. 140 wherein the first jaw member and the second jaw member are in an at least partially open position, and wherein the rotary drive shaft is operably disengaged with the rotary drive nut, according to one aspect of the present disclosure.

Figure 143:
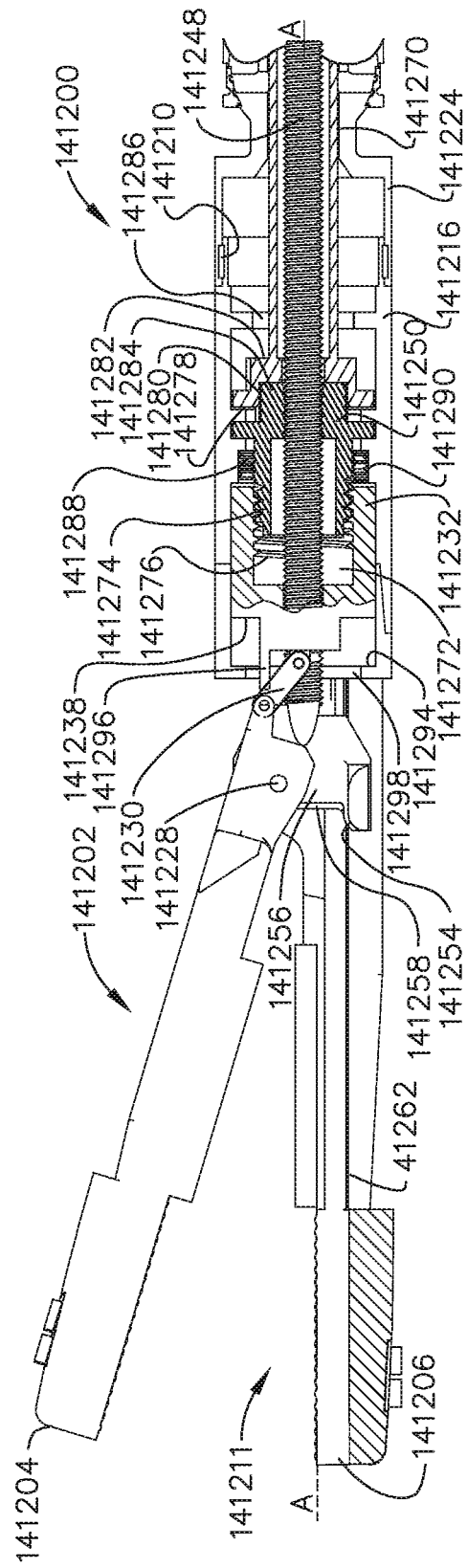

FIG. 143 is a cross sectional elevation view of one exemplification of the surgical tool of FIG. 140 wherein the first jaw member and the second jaw member are in an at least partially open position, and wherein the rotary drive shaft is operably engaged with the rotary drive nut, according to one aspect of the present disclosure.

Figure 144:
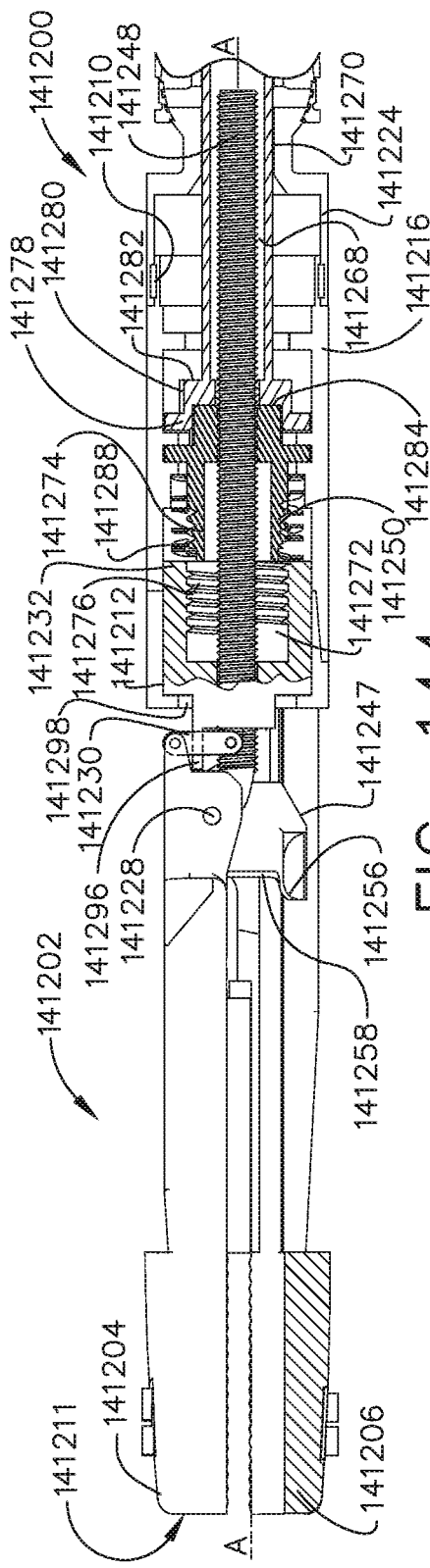

FIG. 144 is a cross sectional elevation view of one exemplification of the surgical tool of FIG. 140 wherein the first jaw member and the second jaw member are in an at least partially closed position, wherein the rotary drive shaft is operably engaged with the rotary drive nut, and wherein the closure nut is operably disengaged from the rotary drive nut, according to one aspect of the present disclosure.

Figure 145:
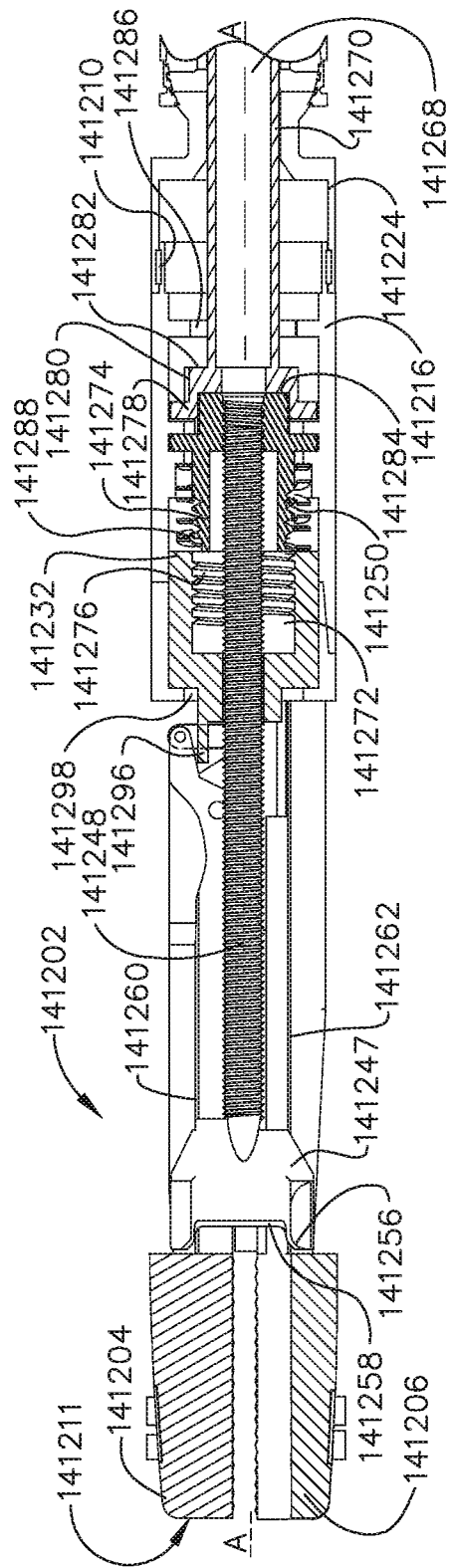

FIG. 145 is a cross sectional elevation view of one exemplification of the surgical tool of FIG. 140 wherein the first jaw member and the second jaw member are in an at least partially closed position, wherein the rotary drive shaft is operably engaged with the rotary drive nut, and wherein the I-beam member is at least partially extended, according to one aspect of the present disclosure.

Figure 146:
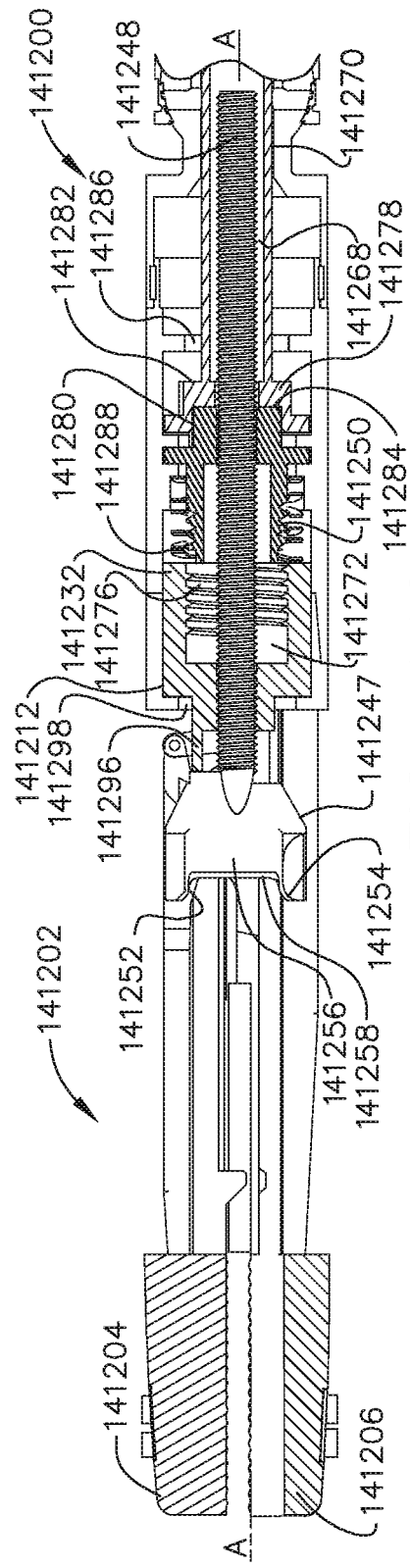

FIG. 146 is a cross sectional elevation view of one exemplification of the surgical tool of FIG. 140 wherein the first jaw member and the second jaw member are in an at least partially closed position, wherein the rotary drive shaft is operably engaged with the rotary drive nut, and wherein the I-beam member is at least partially retracted, according to one aspect of the present disclosure.

Figure 147:
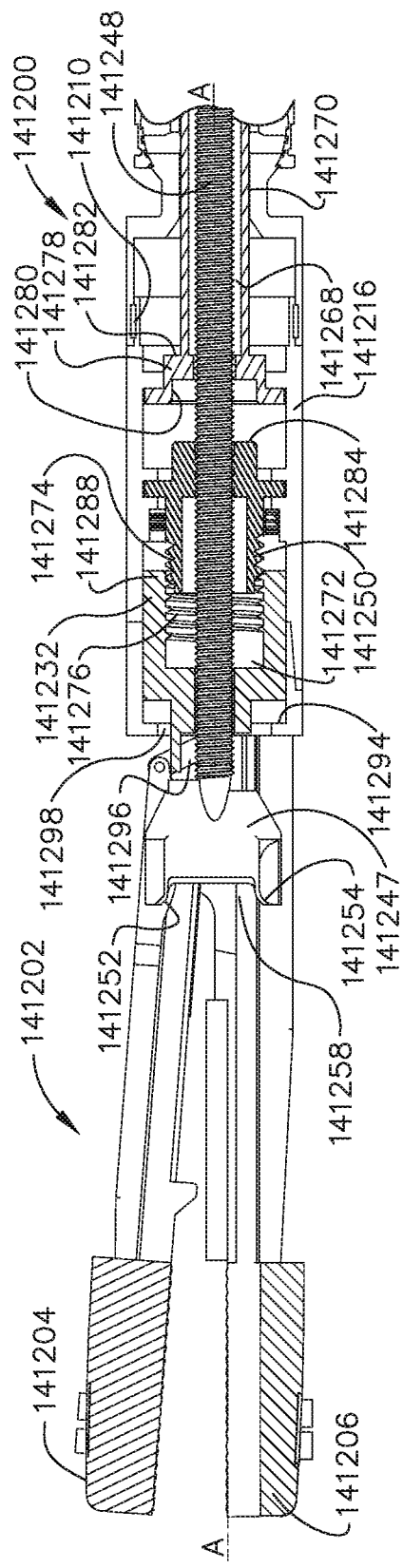

FIG. 147 is a cross sectional elevation view of one exemplification of the surgical tool of FIG. 140 wherein the first jaw member and the second jaw member are in an at least partially closed position, wherein the rotary drive shaft is operably engaged with the rotary drive nut, and wherein the I-beam member is at least partially retracted, according to one aspect of the present disclosure.

Figure 148:
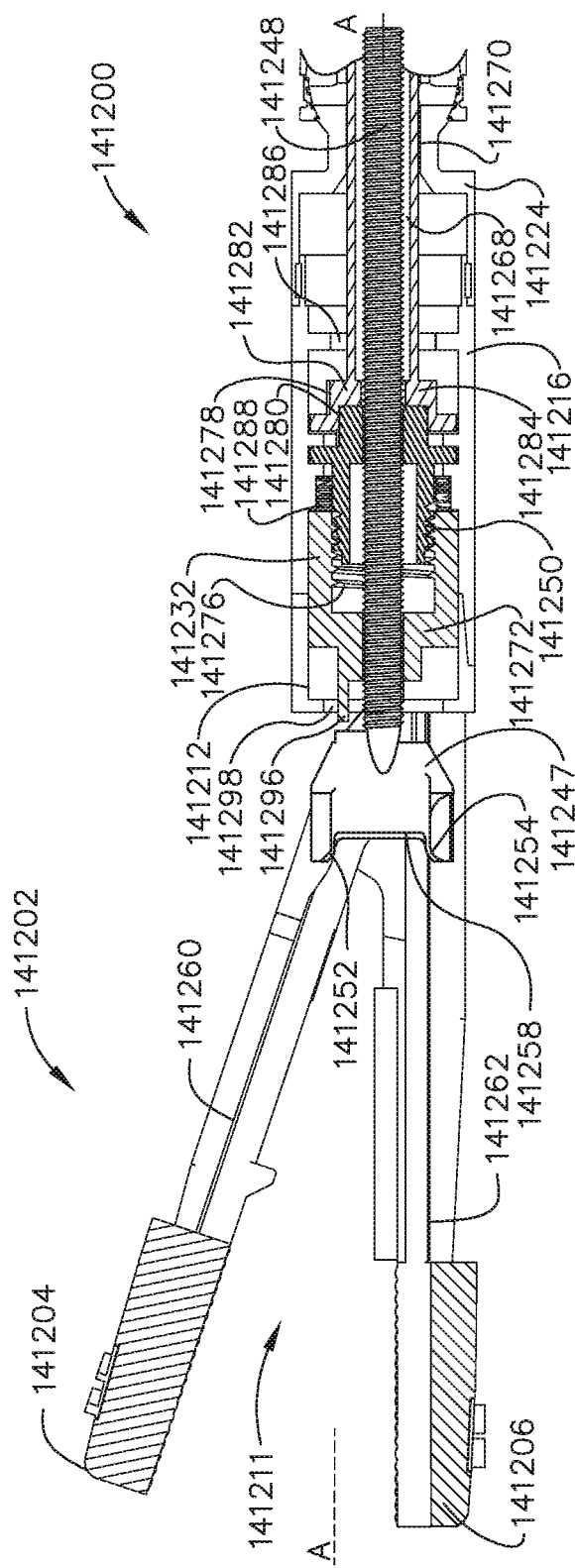

FIG. 148 is a cross sectional elevation view of one exemplification of the surgical tool of FIG. 140 wherein the first jaw member and the second jaw member are in an at least partially open position, wherein the rotary drive shaft is operably engaged with the rotary drive nut, and wherein the closure nut is operably engaged from the rotary drive nut, according to one aspect of the present disclosure.

Figure 149:
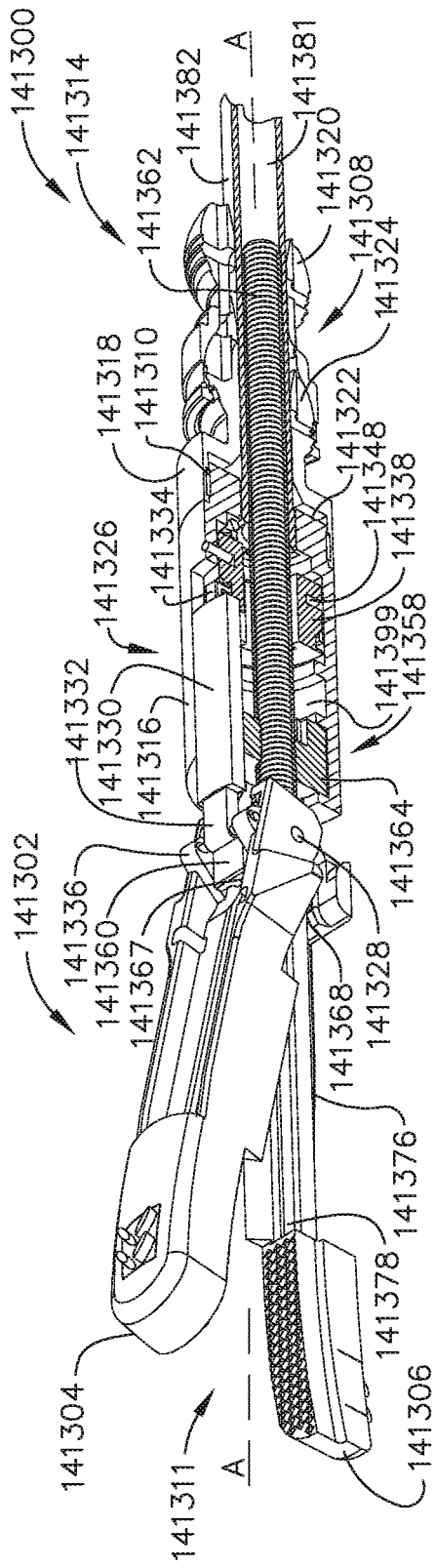

FIG. 149 is a cross sectional perspective view of a surgical tool having first and second jaw members, according to one aspect of the present disclosure.

Figure 150:
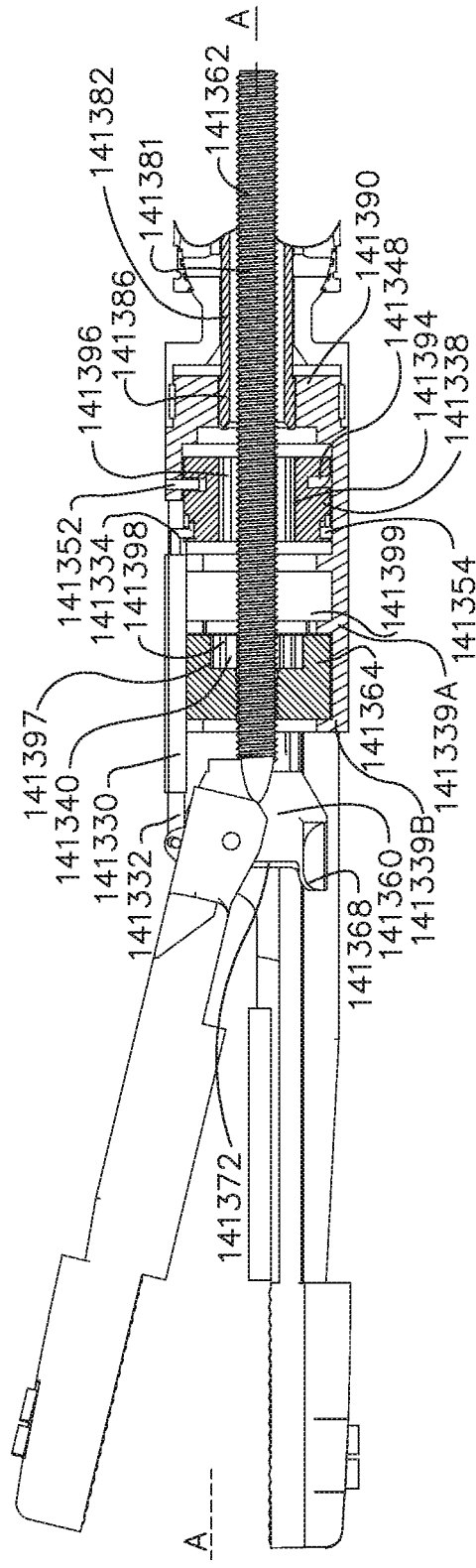

FIG. 150 is a cross sectional elevation view of one exemplification of the surgical tool of FIG. 149 wherein the first jaw member and the second jaw member are in an at least partially open position, and wherein the rotary drive shaft is operably engaged with spline coupling portion of the end effector drive housing, according to one aspect of the present disclosure.

FIG. 151 is a cross sectional elevation view of one exemplification of the surgical tool of FIG. 149 wherein the first jaw member and the second jaw member are in an at least partially closed position, and wherein the rotary drive shaft is operably engaged with spline coupling portion of the barrel cam, according to one aspect of the present disclosure.

FIG. 152 is a cross sectional elevation view of one exemplification of the surgical tool of FIG. 149 wherein the first jaw member and the second jaw member are in an at least partially closed position, and wherein the rotary drive shaft is not operably engaged with any of the spline coupling portions, according to one aspect of the present disclosure.

Figure 153:
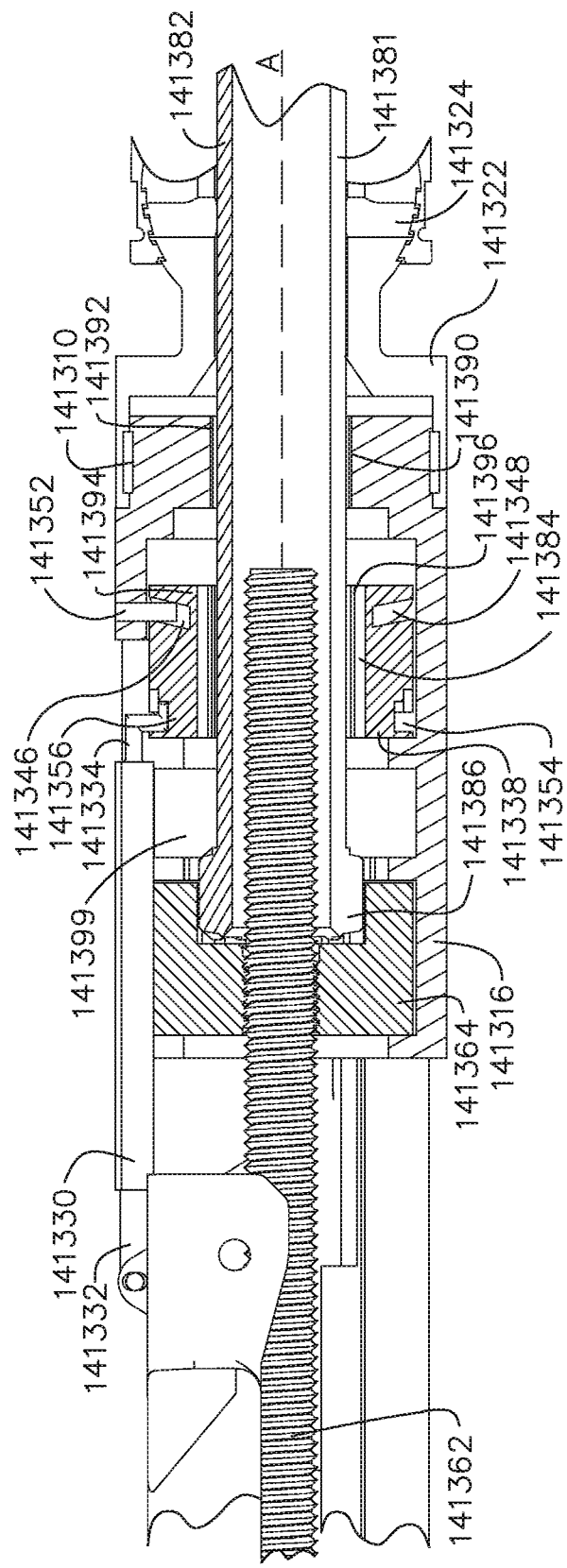

FIG. 153 is a cross sectional elevation view of one exemplification of the surgical tool of FIG. 149 wherein the first jaw member and the second jaw member are in an at least partially closed position, and wherein the rotary drive shaft is operably engaged with spline coupling portion of the rotary drive nut, according to one aspect of the present disclosure.

Figure 154:
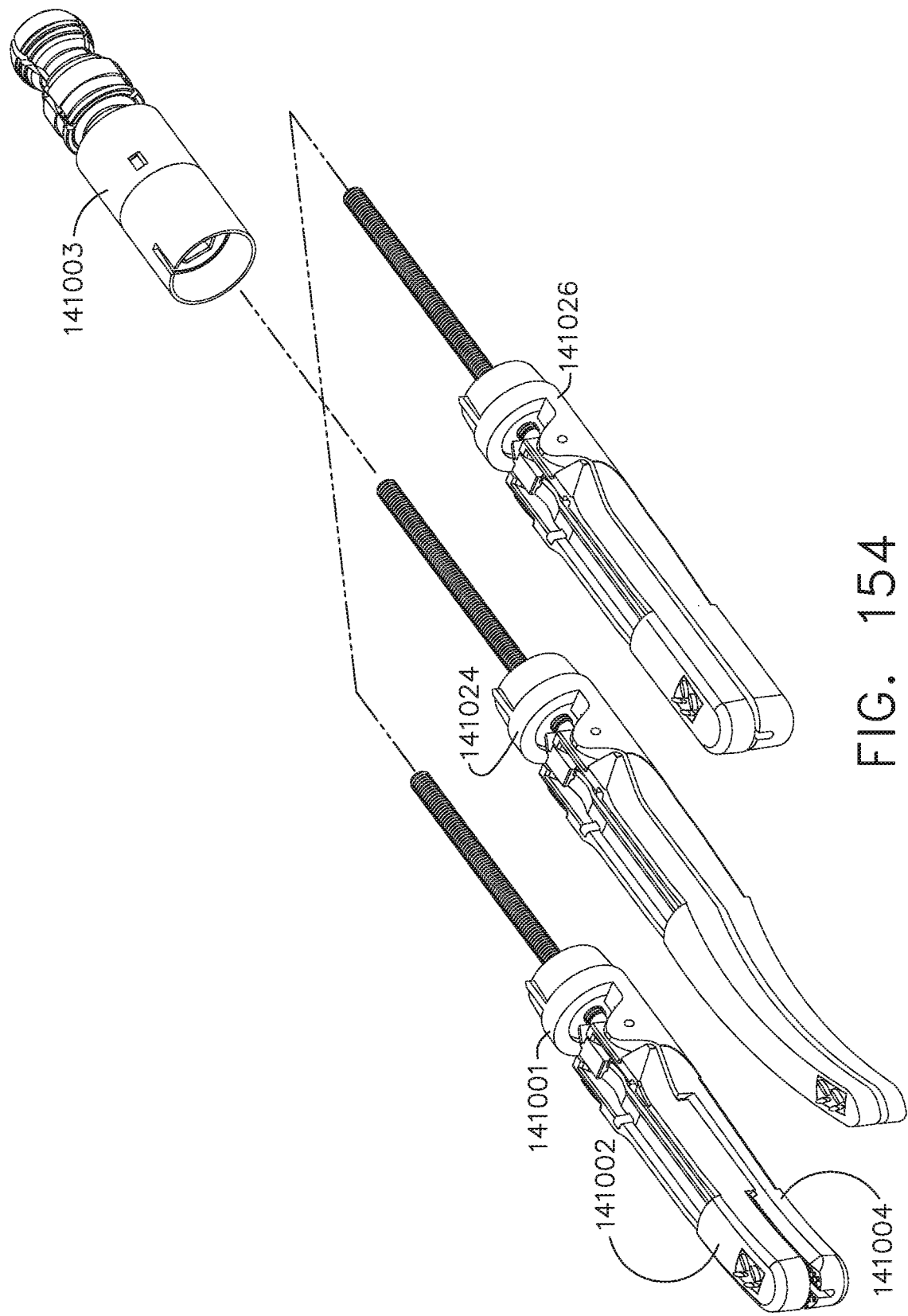

FIG. 154 is a perspective view of multiple interchangeable surgical end effectors, according to one aspect of the present disclosure.

Figure 155:
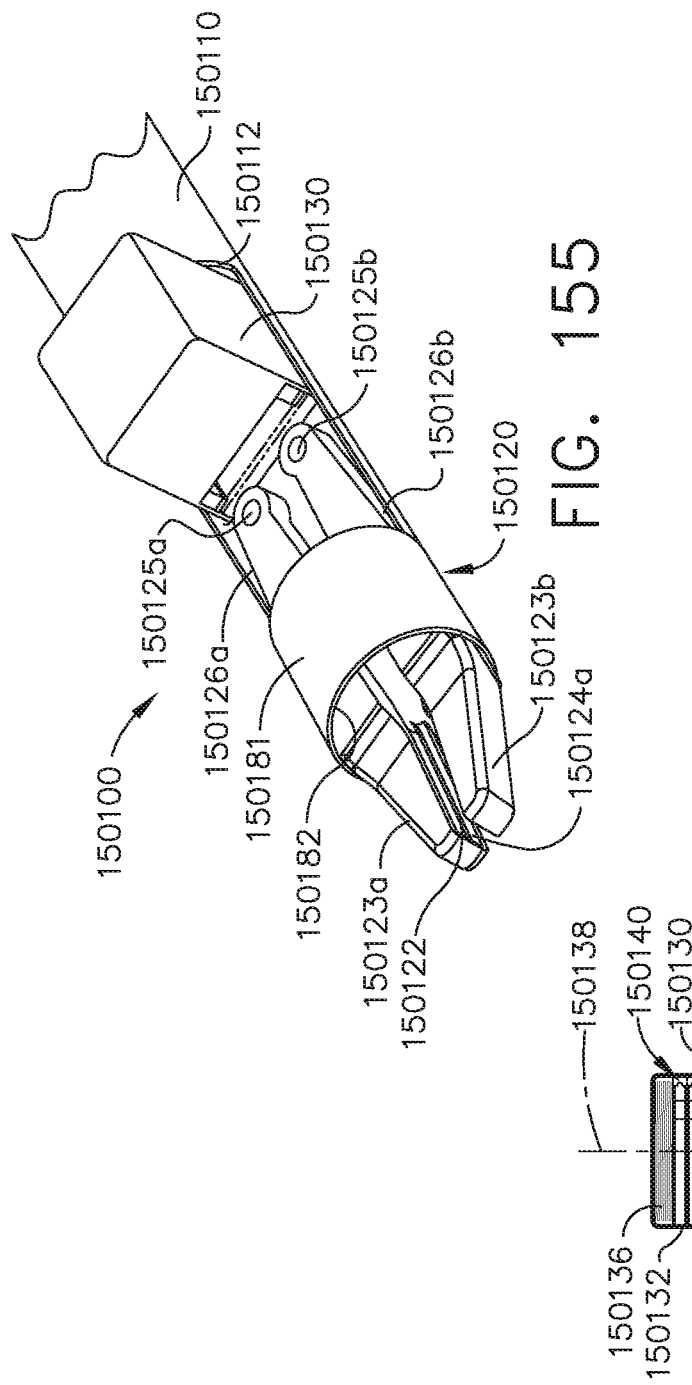

FIG. 155 is a partial perspective view of a clip applier, according to one aspect of the present disclosure.

Figure 156:
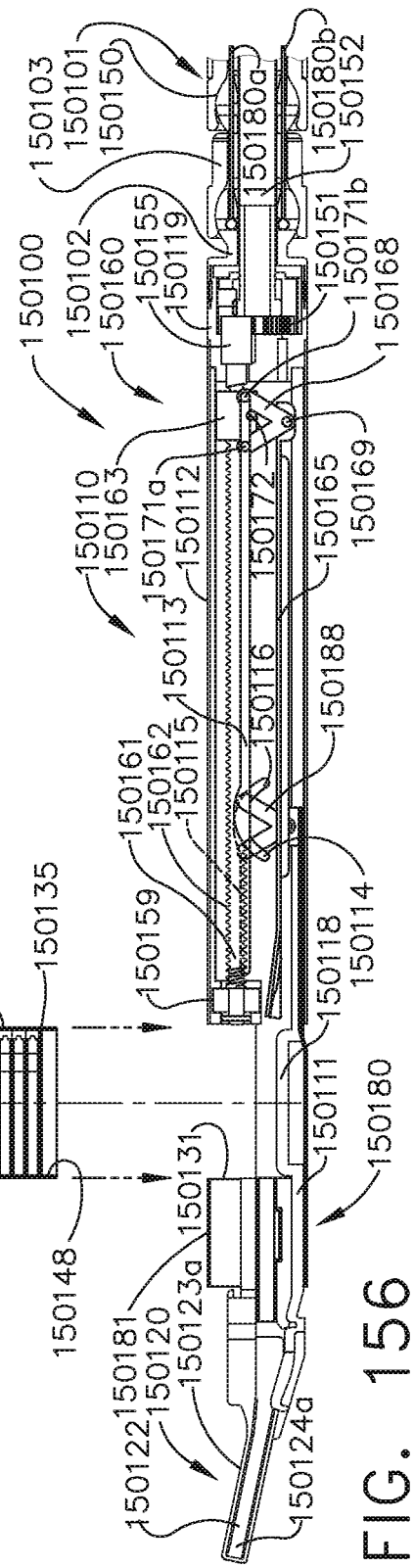

FIG. 156 is a cross-sectional view of an end effector of the clip applier of FIG. 155 comprising a removable clip cartridge, a reciprocating firing drive for sequentially advancing the clips, a receiver for receiving the clips, and a crimping drive for deforming the clips, according to one aspect of the present disclosure.

FIG. 157 is a partial cross-sectional view of the clip applier of FIG. 155 in an open configuration, according to one aspect of the present disclosure.

FIG. 158 is a partial cross-sectional view of the clip applier of FIG. 155 in a closed configuration, according to one aspect of the present disclosure.

FIG. 159 is a cross-sectional view of the end effector of FIG. 156 in an unfired condition, according to one aspect of the present disclosure.

FIG. 160 is a cross-sectional view of the end effector of FIG. 156 illustrating the firing drive in a partially fired condition in which a firing member of the firing drive has advanced a clip into the receiver.

FIG. 161 is a cross-sectional view of the end effector of FIG. 156 illustrating the firing drive coming into engagement with the crimping drive, according to one aspect of the present disclosure.

FIG. 162 is a cross-sectional view of the end effector of FIG. 156 illustrating the crimping drive in an at least partially fired condition, according to one aspect of the present disclosure.

Figure 163:
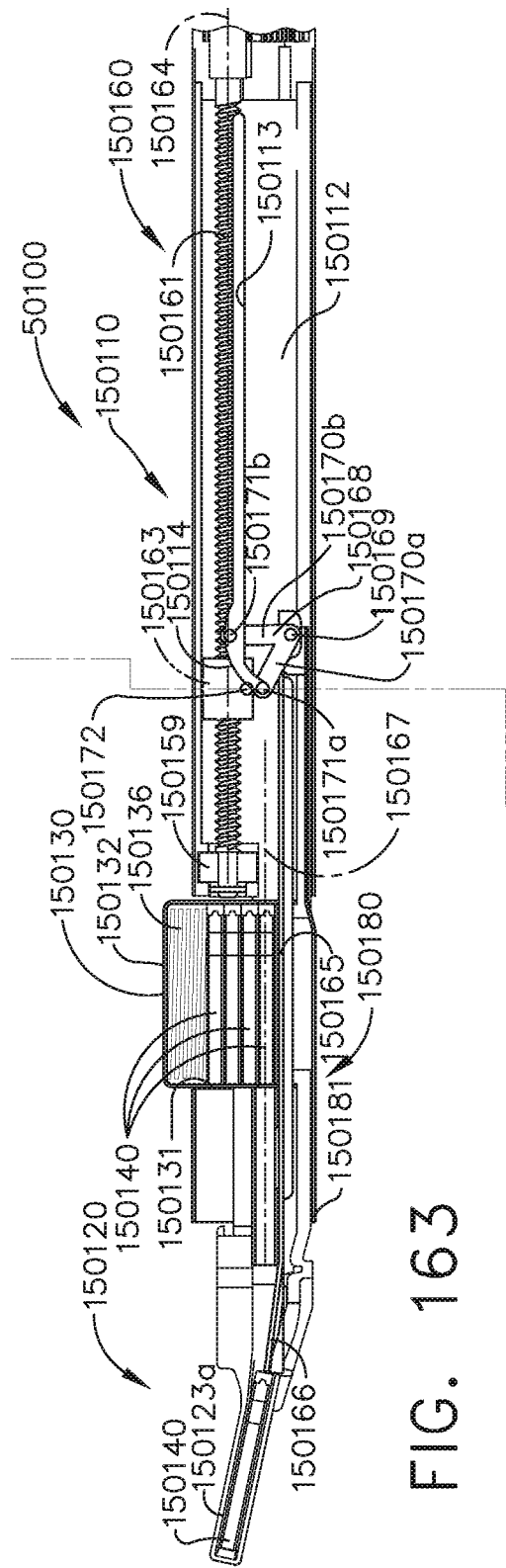

FIG. 163 is a cross-sectional view of the end effector of FIG. 156 illustrating the firing drive becoming disengaged from the firing member, according to one aspect of the present disclosure.

Figure 164:
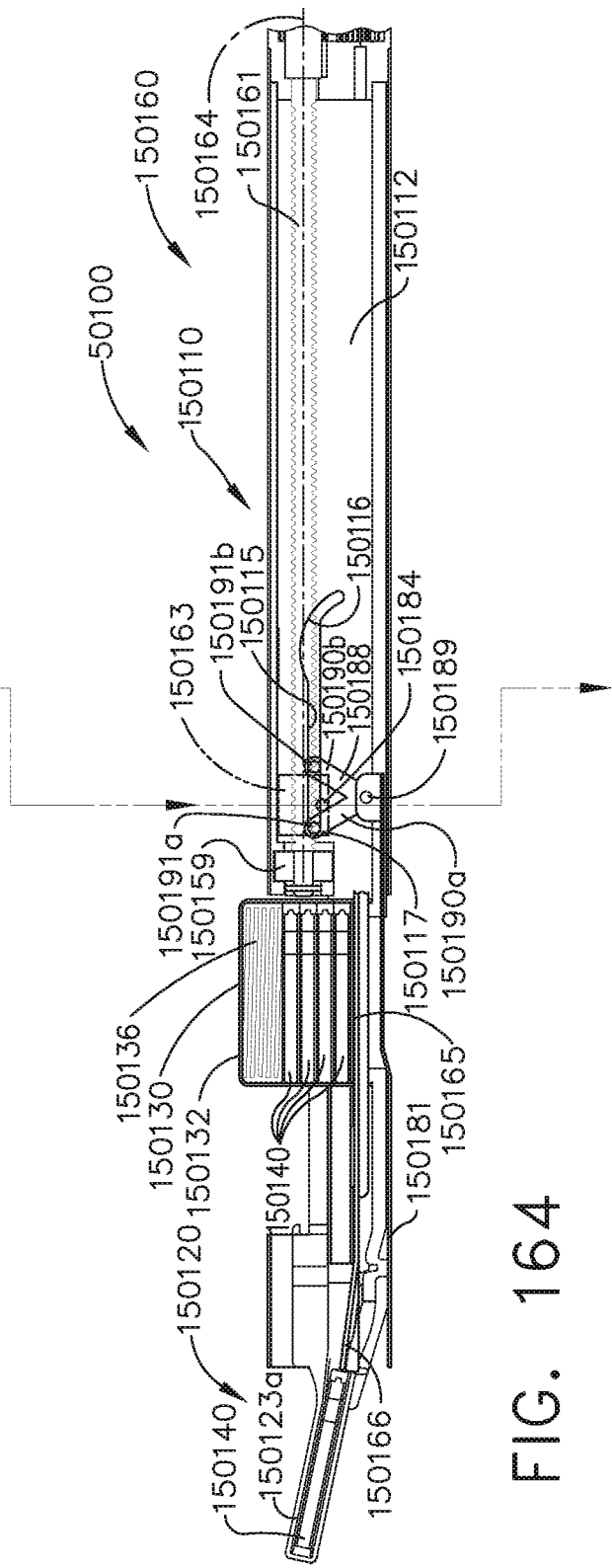

FIG. 164 is a cross-sectional view of the end effector of FIG. 156 illustrating the crimping drive in its fully fired condition, according to one aspect of the present disclosure.

Figure 165:
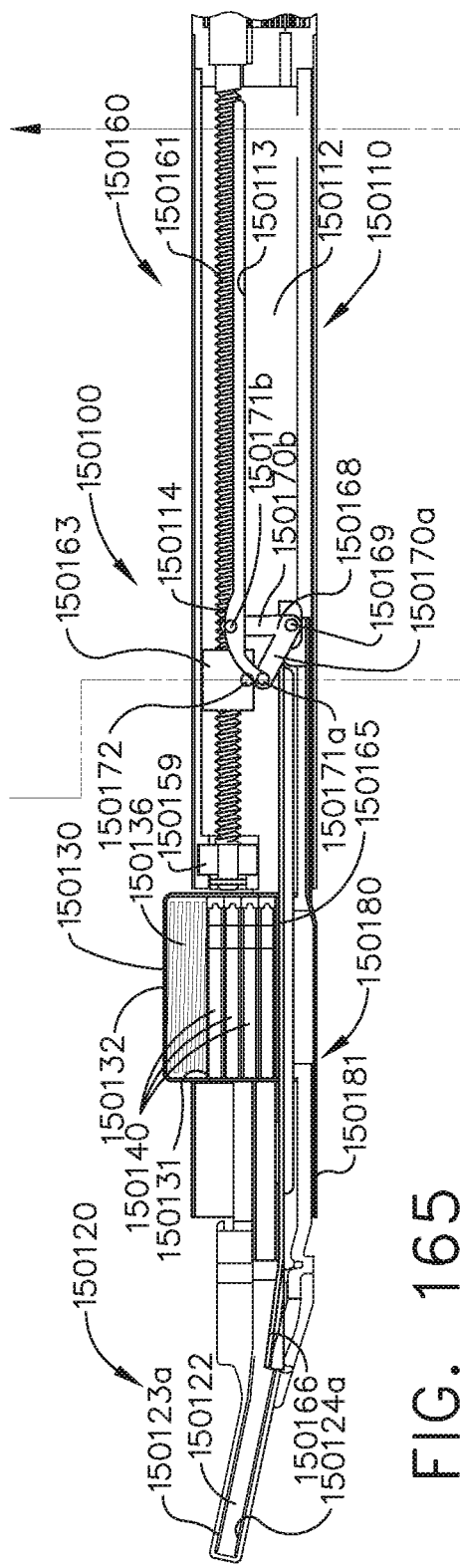

FIG. 165 is a cross-sectional view of the firing drive of the end effector of FIG. 156 in a partially retracted position in which the firing drive is being re-engaged with the firing member, according to one aspect of the present disclosure.

Figure 166:
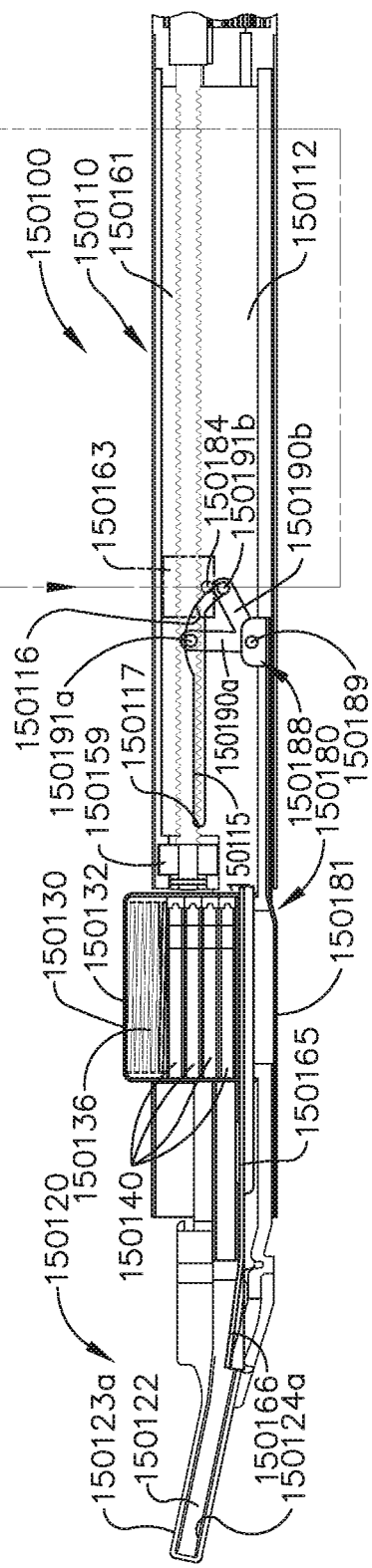

FIG. 166 is a cross-sectional view of the firing drive of the end effector of FIG. 156 being disengaged from the crimping drive, according to one aspect of the present disclosure.

Figure 167:
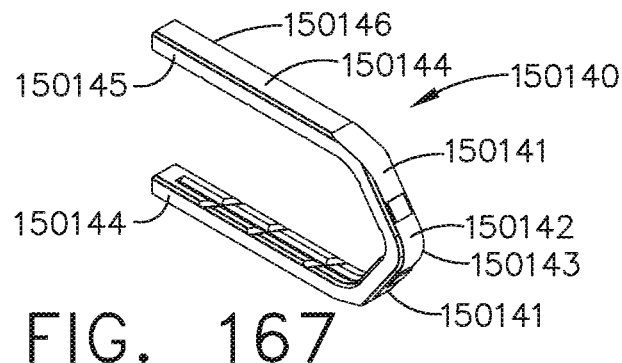

FIG. 167 is a perspective view of a clip illustrated in FIGS. 156-166, according to one aspect of the present disclosure.

Figures 168, 169:
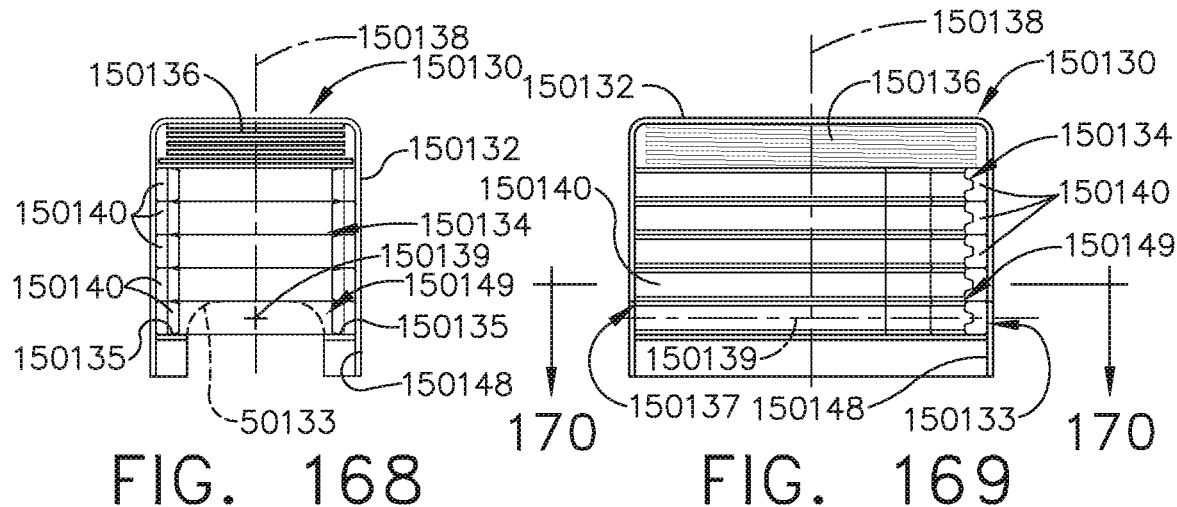

FIG. 168 is a front view of a cartridge illustrated in FIGS. 155-166 comprising a plurality of clips with portions of the cartridge removed to illustrate the clips stored in the cartridge, according to one aspect of the present disclosure.

FIG. 169 is a side view of the cartridge of FIG. 168 illustrated with portions removed to illustrate the clips stored in the cartridge, according to one aspect of the present disclosure.

Figure 170:
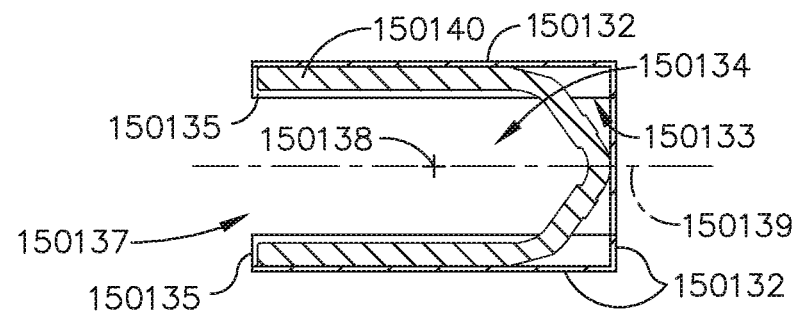

FIG. 170 is a cross-sectional plan view of the cartridge of FIG. 168 taken along line 170-170 in FIG. 169, according to one aspect of the present disclosure.

Figure 171:
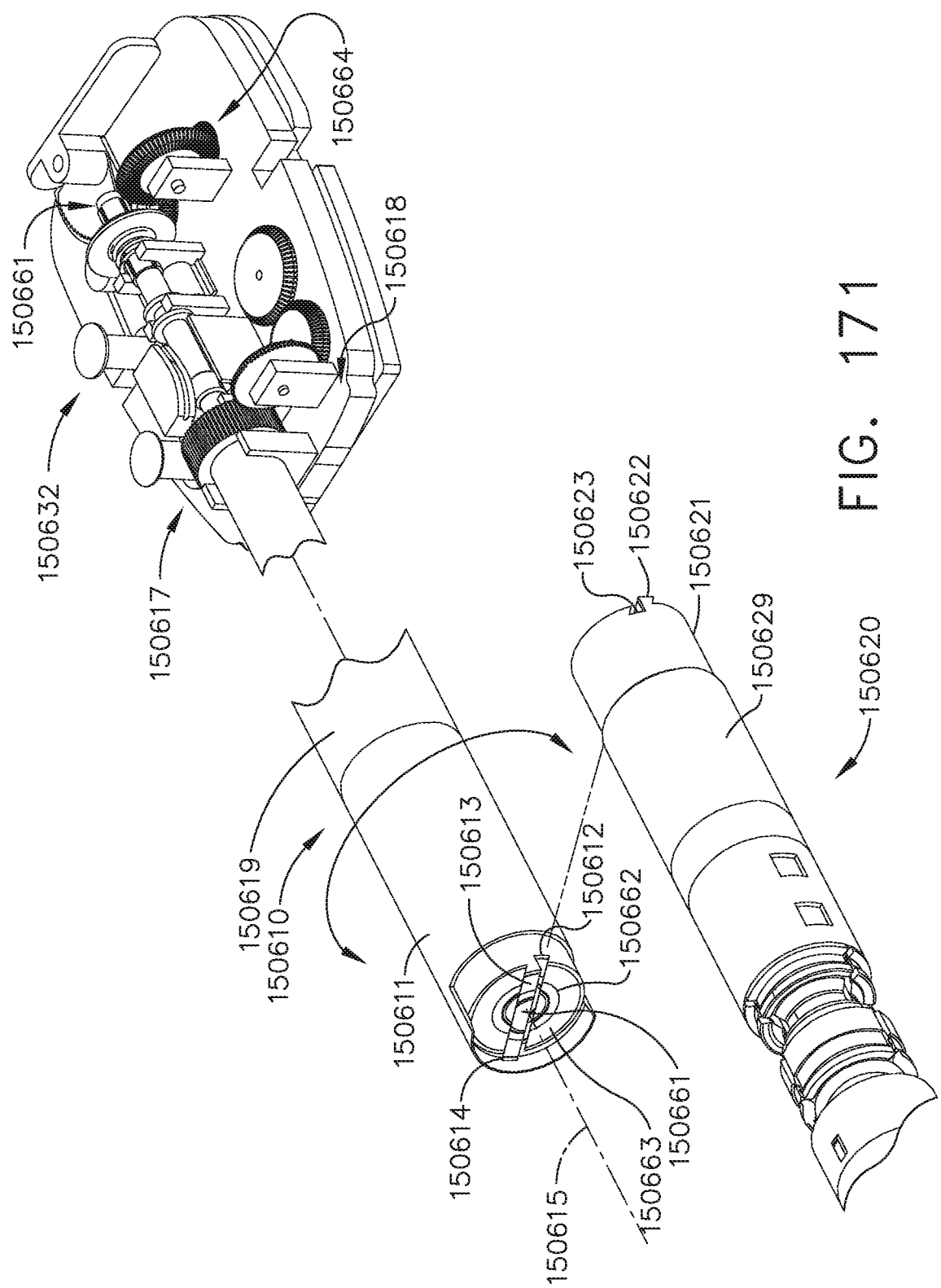

FIG. 171 is a perspective view of a surgical tool including an actuator module, a shaft extending from the actuator module, and a replaceable end effector, according to one aspect of the present disclosure.

Figure 172:
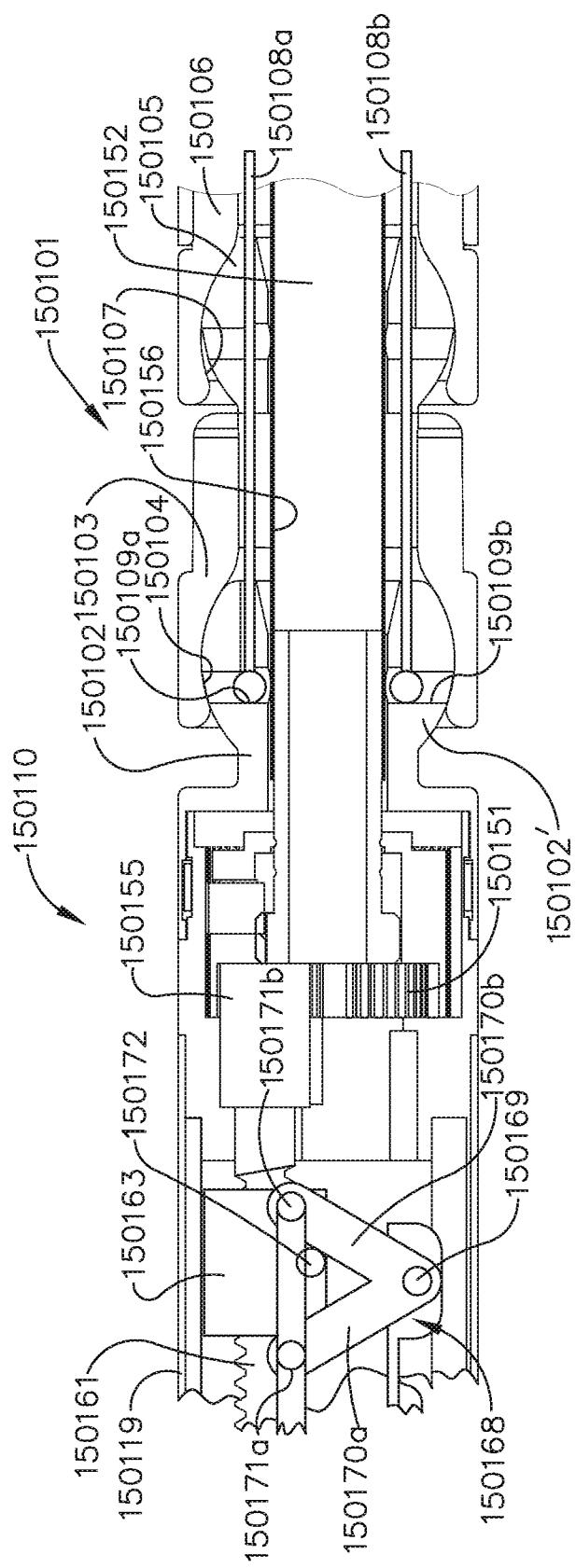

FIG. 172 is a cross-sectional view of the articulation joint illustrated in FIG. 156, according to one aspect of the present disclosure.

Figure 173:
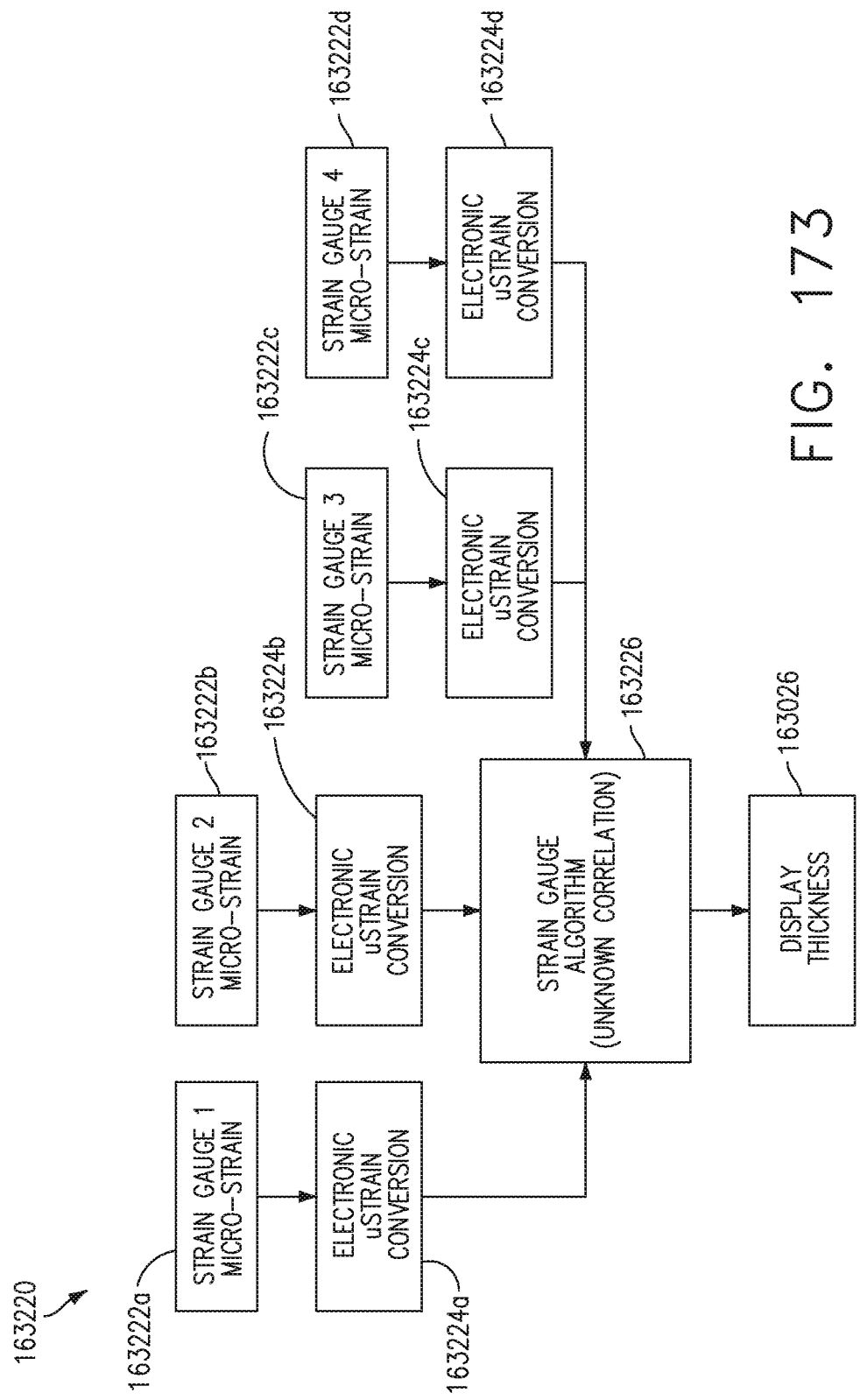

FIG. 173 is a logic diagram illustrating one exemplification of a process for determining one or more tissue properties based on a plurality of sensors, according to one aspect of the present disclosure.

Figure 174:
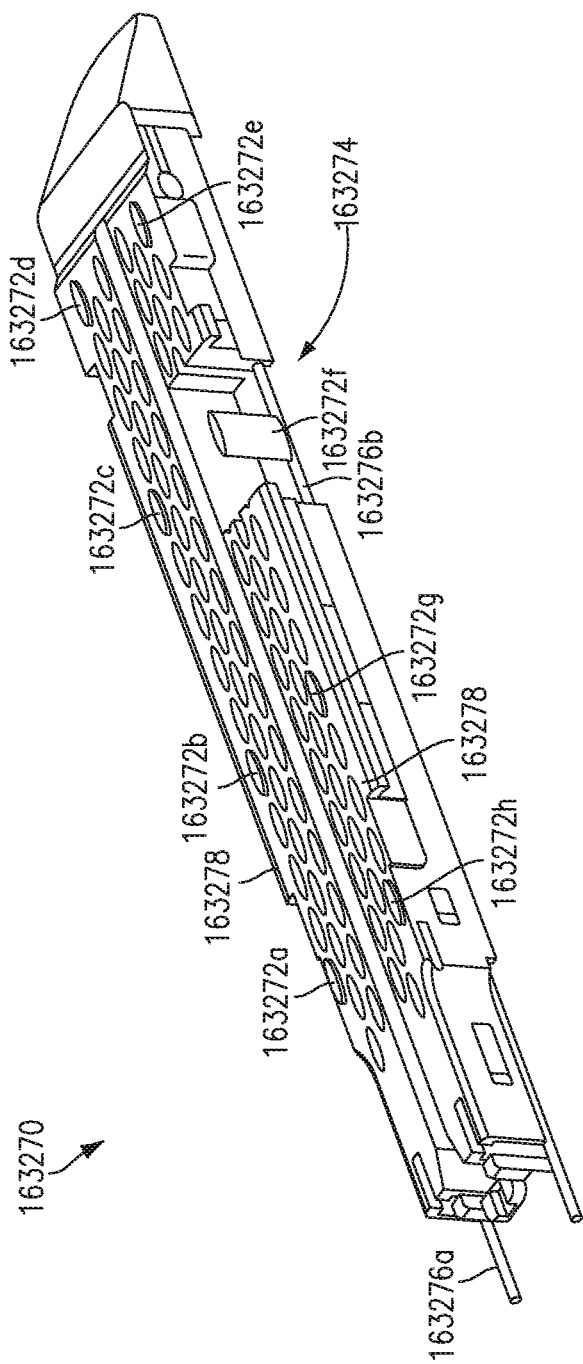

FIG. 174 illustrates one exemplification of a staple cartridge comprising a plurality of sensors formed integrally therein, according to one aspect of the present disclosure.

Figure 175:
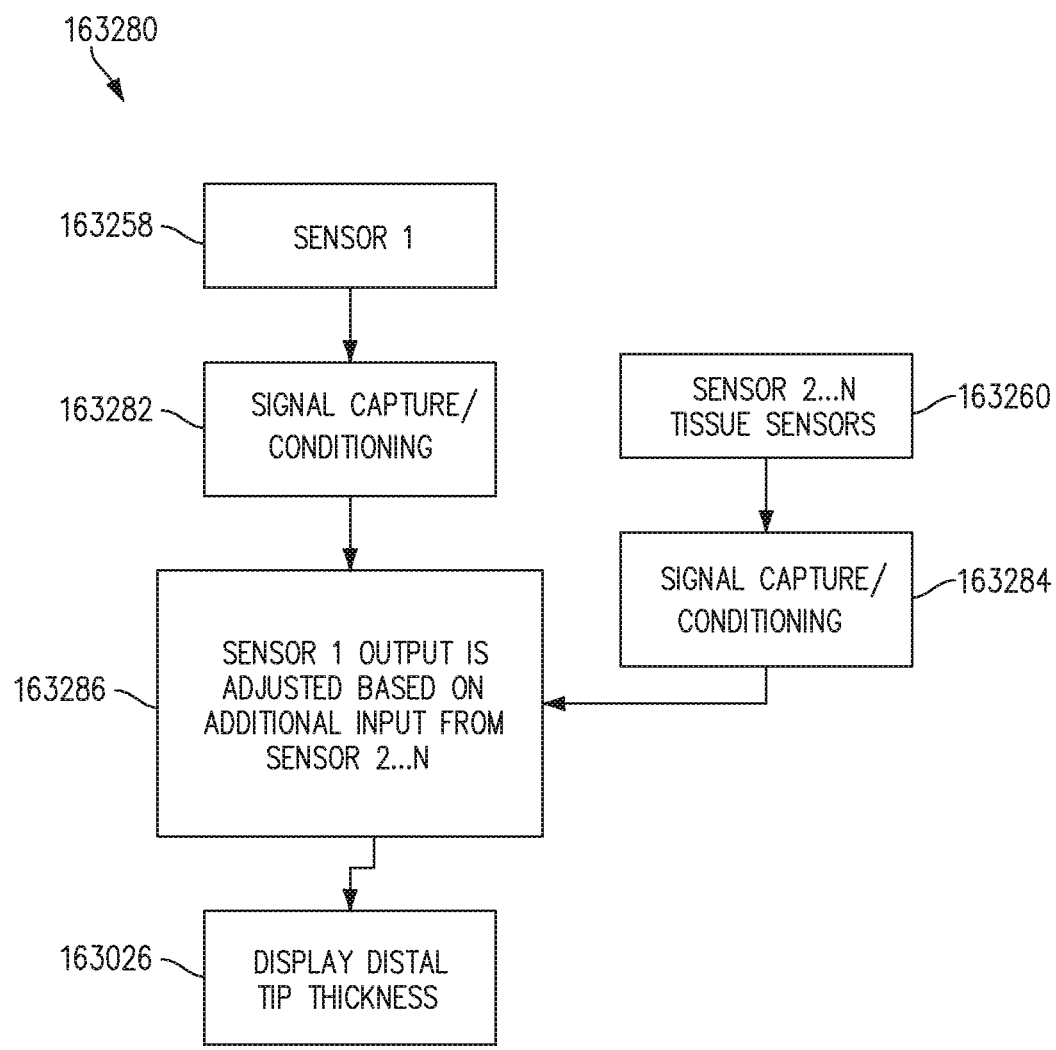

FIG. 175 is a logic diagram illustrating one exemplification of a process for determining one or more parameters of a tissue section clamped within an end effector, according to one aspect of the present disclosure.

Figure 176:
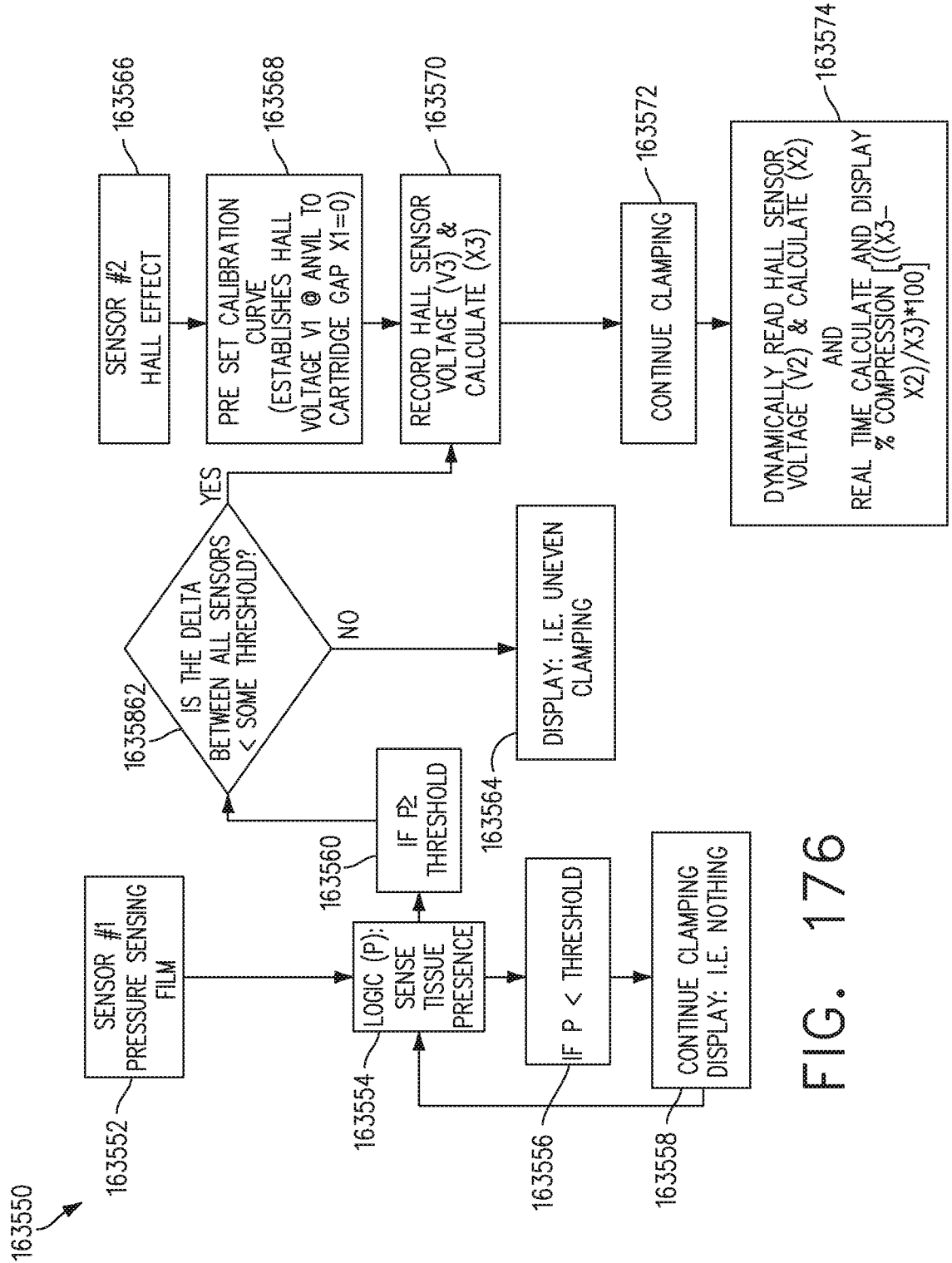

FIG. 176 is a flow chart illustrating one exemplification of a process for determining uneven tissue loading in an end effector, according to one aspect of the present disclosure.

Figure 177:
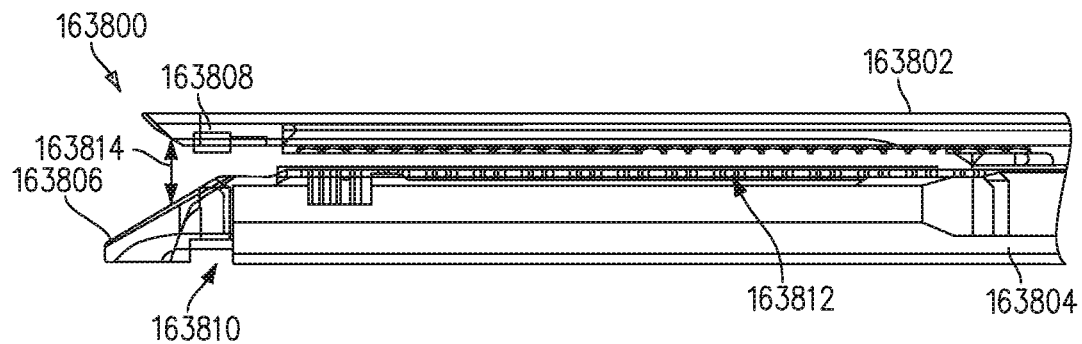
Figure 178:
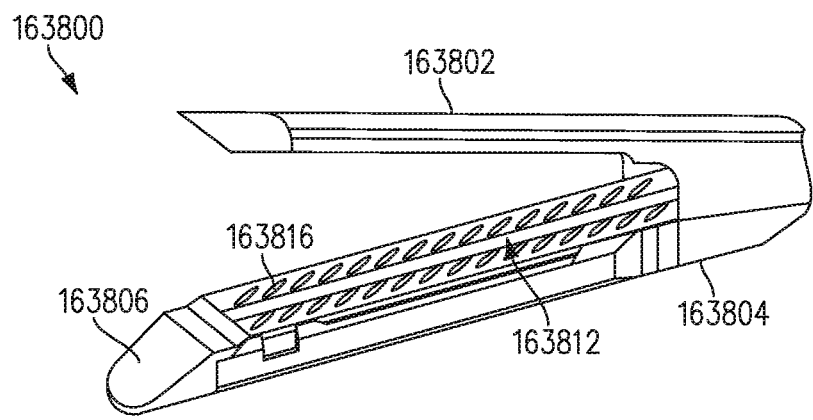

FIGS. 177 and 178 illustrate one exemplification of an end effector comprising a pressure sensor, according to one aspect of the present disclosure.

Figure 179:
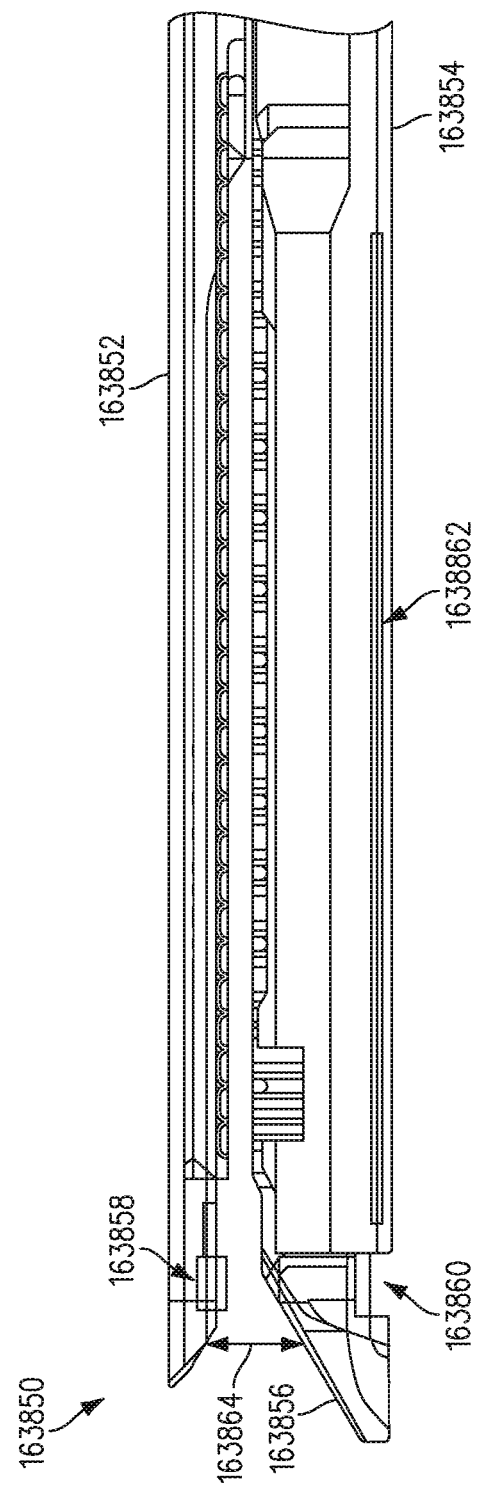

FIG. 179 illustrates one exemplification of an end effector comprising a second sensor located between a staple cartridge and a second jaw member, according to one aspect of the present disclosure.

Figure 180:
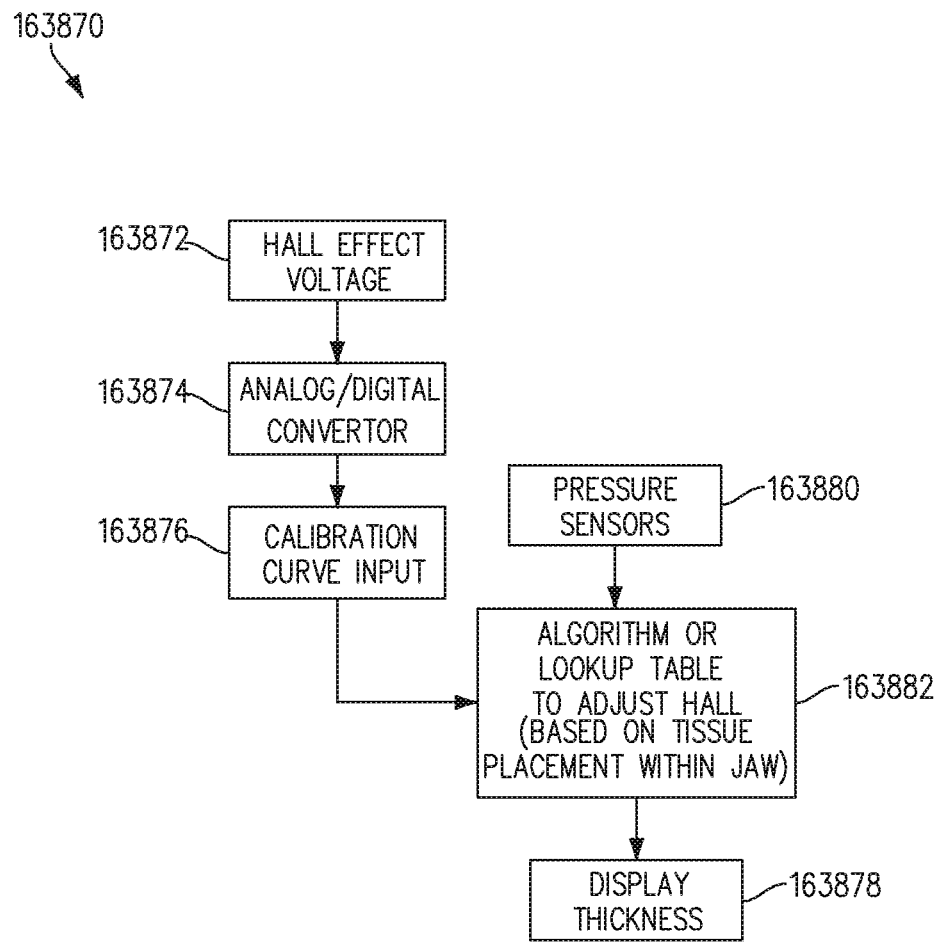

FIG. 180 is a logic diagram illustrating one exemplification of a process for determining and displaying the thickness of a tissue section clamped in an end effector, according to FIGS. 177-178 or FIG. 179, according to one aspect of the present disclosure.

Figure 181:
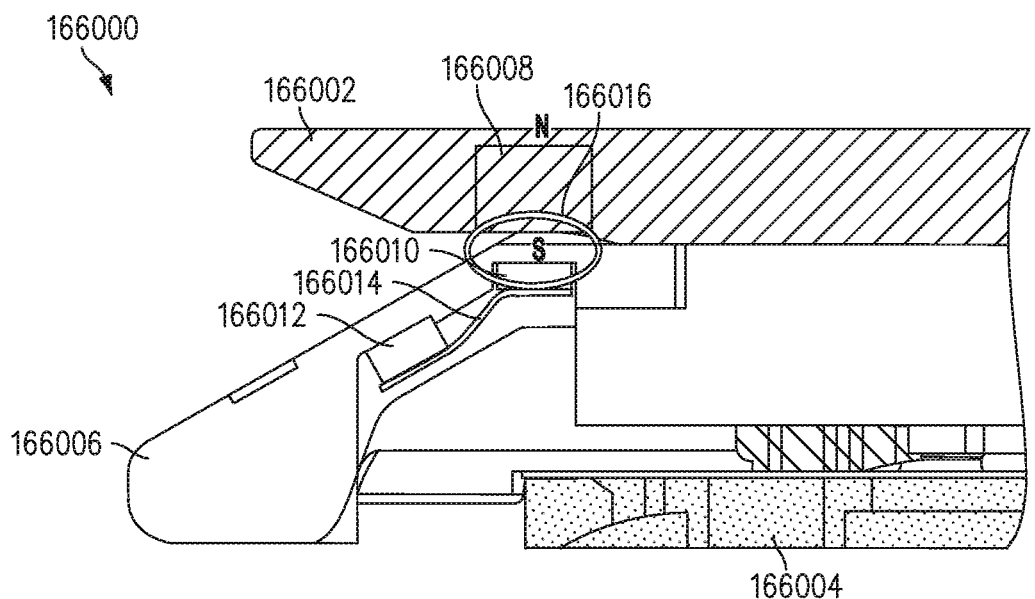

FIG. 181 illustrates one exemplification of an end effector comprising a magnet and a Hall effect sensor wherein the detected magnetic field can be used to identify a staple cartridge, according to one aspect of the present disclosure.

Figure 182:
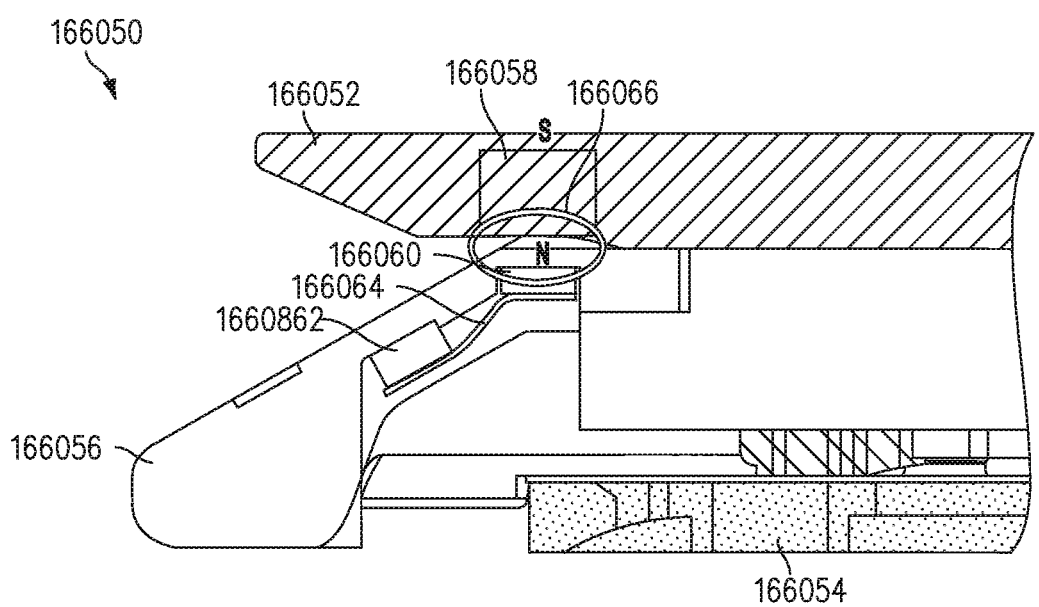

FIG. 182 illustrates one exemplification of an end effector comprising a magnet and a Hall effect sensor wherein the detected magnetic field can be used to identify a staple cartridge, according to one aspect of the present disclosure.

Figure 183:
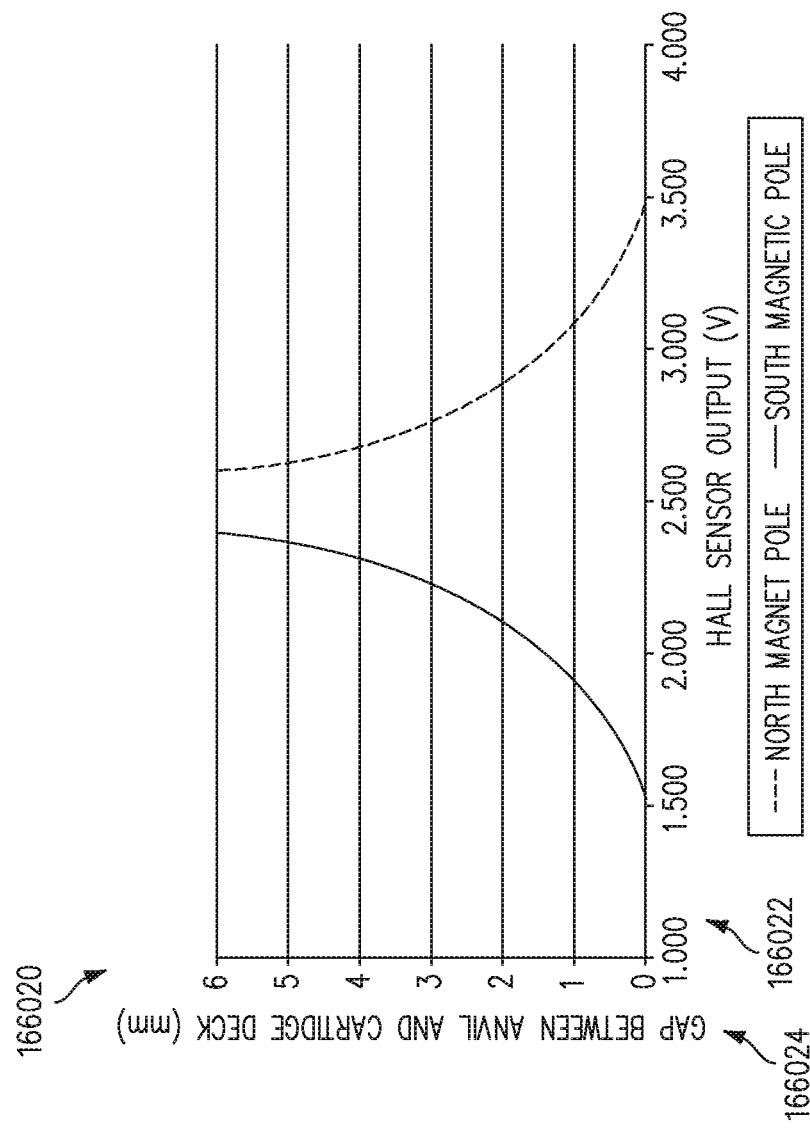

FIG. 183 illustrates a graph of the voltage detected by a Hall effect sensor located in the distal tip of a staple cartridge, such as is illustrated in FIGS. 181 and 182, in response to the distance or gap between a magnet located in the anvil and the Hall effect sensor in the staple cartridge, such as illustrated in FIGS. 181 and 182, according to one aspect of the present disclosure.

FIGS. 184 and 185 illustrate one exemplification of an end effector comprising a sensor for identifying staple cartridges of different types, according to one aspect of the present disclosure.

Figure 186:
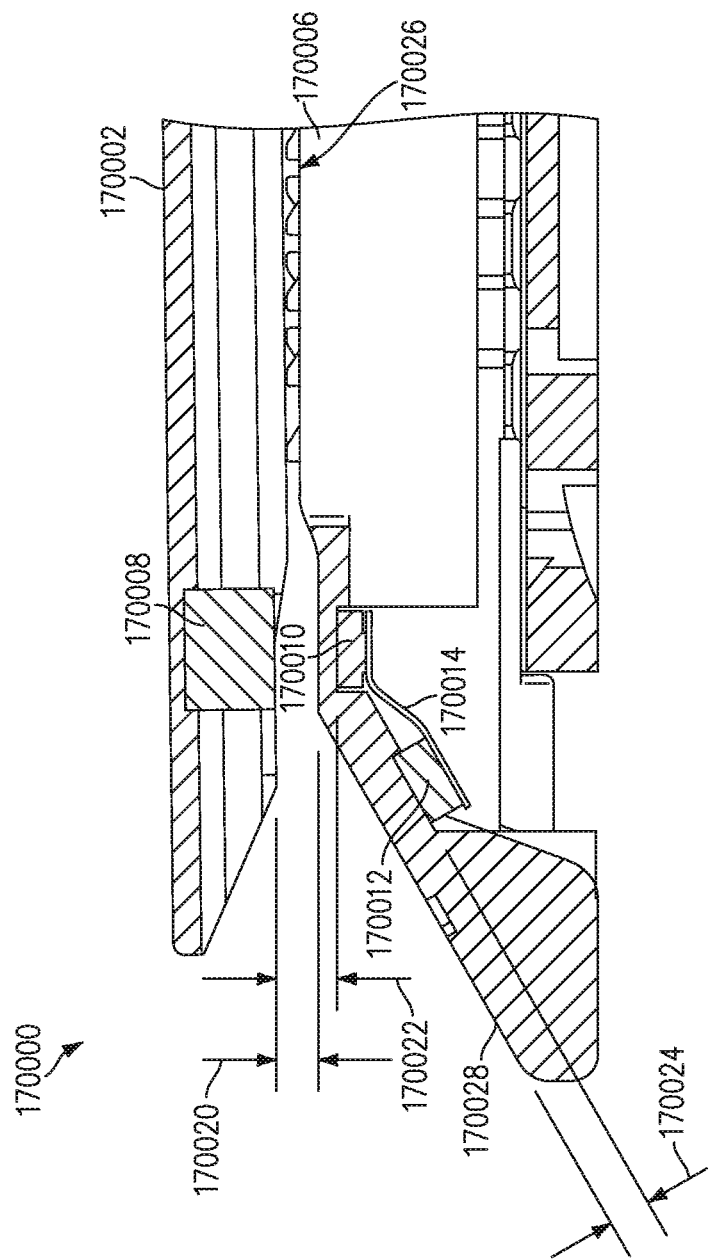

FIG. 186 illustrates one exemplification of the operable dimensions that relate to the operation of the Hall effect sensor, according to one aspect of the present disclosure.

Figure 188:
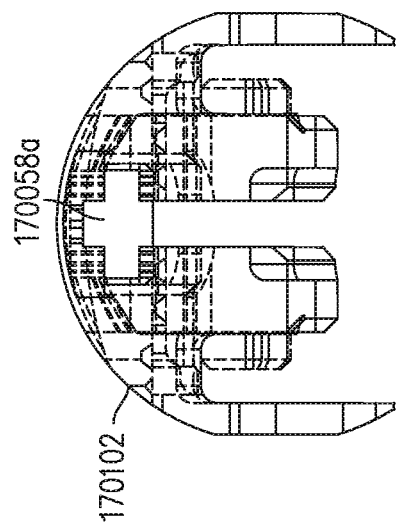
Figure 187:
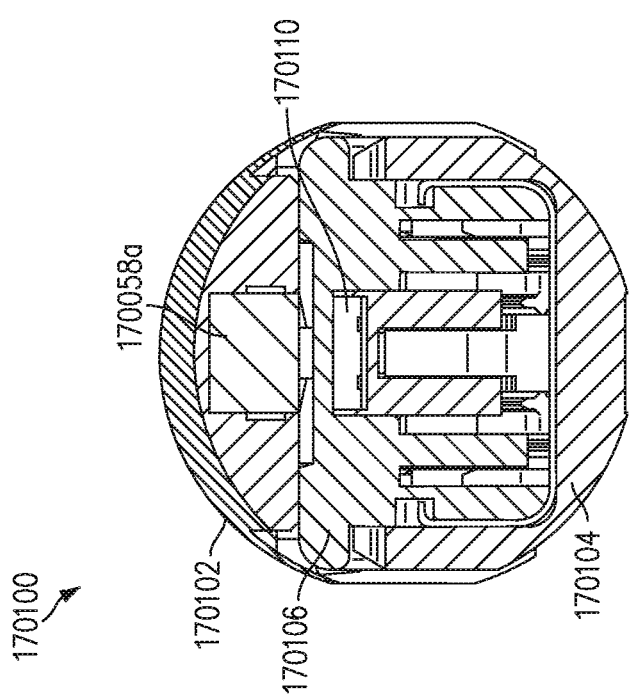
Figure 190:
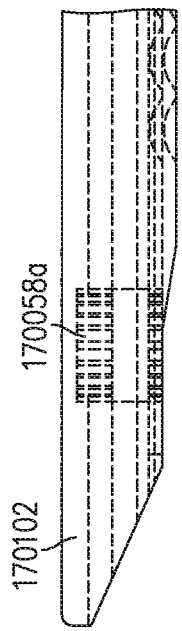
Figure 191:
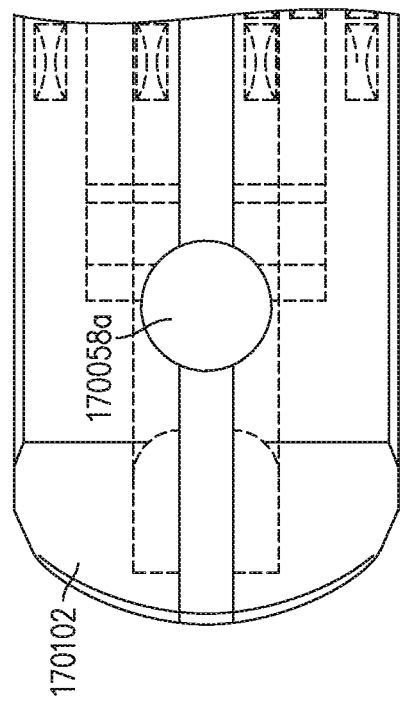
Figure 189:
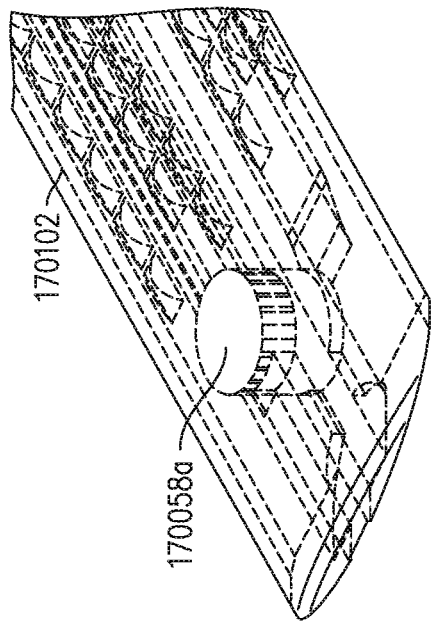

FIGS. 187-191 illustrate one exemplification of an end effector that comprises a magnet where FIG. 187 illustrates a front-end cross-sectional view of the end effector, FIG. 188 illustrates a front-end cutaway view of the anvil and the magnet in situ, FIG. 189 illustrates a perspective cutaway view of the anvil and the magnet, FIG. 190 illustrates a side cutaway view of the anvil and the magnet, and FIG. 191 illustrates a top cutaway view of the anvil and the magnet, according to one aspect of the present disclosure.

Figure 193:
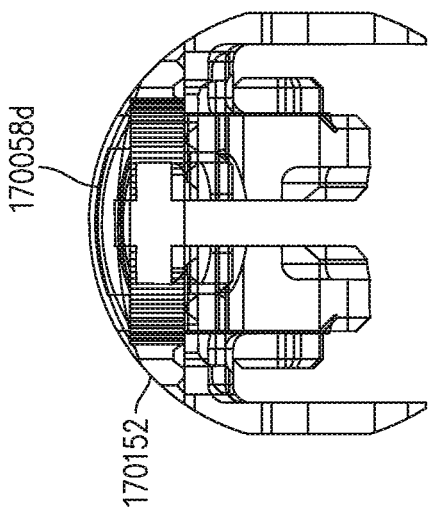
Figure 192:
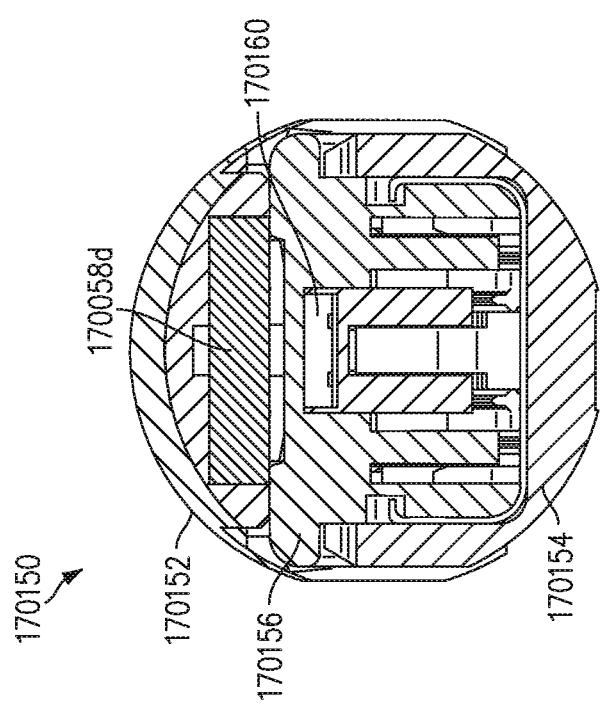

FIGS. 192-196 illustrate another exemplification of an end effector that comprises a magnet where FIG. 192 illustrates a front-end cross-sectional view of the end effector, FIG. 193 illustrates a front-end cutaway view of the anvil and the magnet, in situ, FIG. 194 illustrates a perspective cutaway view of the anvil and the magnet, FIG. 195 illustrates a side cutaway view of the anvil and the magnet, and FIG. 196 illustrates a top cutaway view of the anvil and magnet, according to one aspect of the present disclosure.

Figure 197:
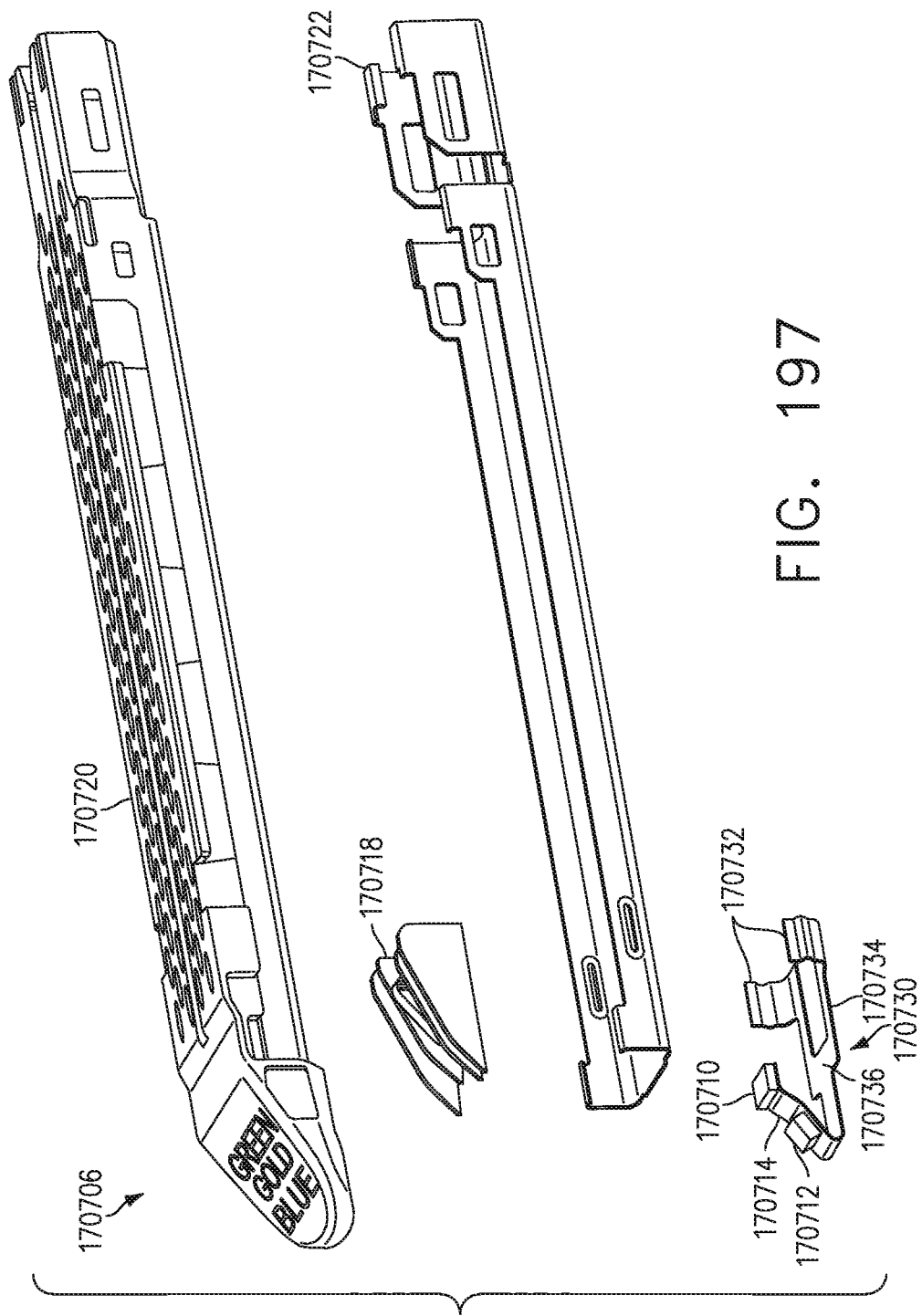
Figure 198:
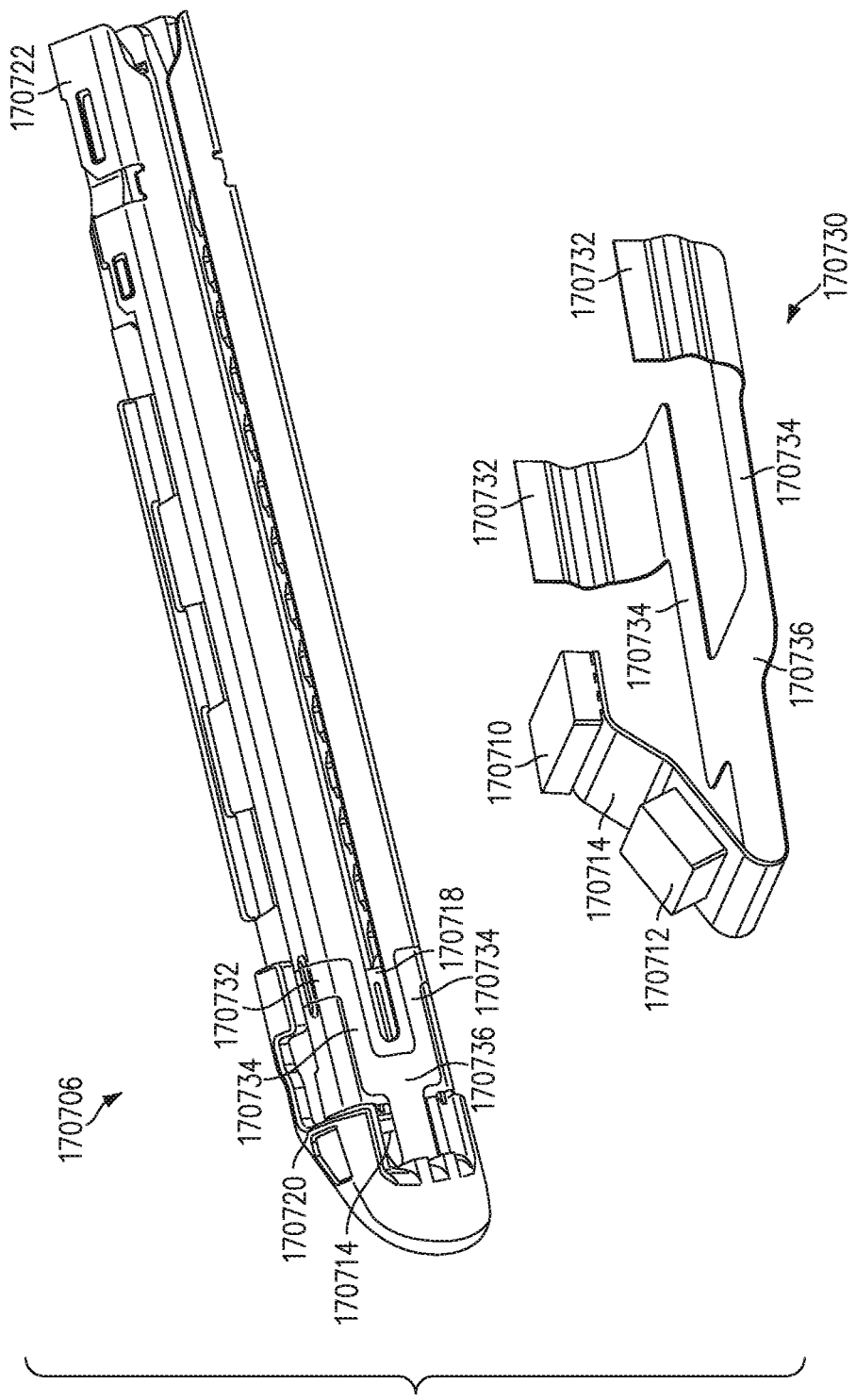

FIGS. 197 and 198 illustrates one exemplification of a staple cartridge that comprises a flex cable, a Hall effect sensor, and a processor where FIG. 197 is an exploded view of the staple cartridge and FIG. 198 illustrates the assembly of the staple cartridge and the flex cable in greater detail, according to one aspect of the present disclosure.

FIG. 199 illustrates a perspective view of an end effector coupled to a shaft assembly, according to one aspect of the present disclosure.

FIG. 200 illustrates a perspective view of an underside of the end effector and shaft assembly shown in FIG. 199, according to one aspect of the present disclosure.

FIG. 201 illustrates the end effector shown in FIGS. 199 and 200 with a flex cable and without the shaft assembly, according to one aspect of the present disclosure.

FIGS. 202 and 203 illustrate an elongated channel portion of the end effector shown in FIGS. 199 and 200 without the anvil or the staple cartridge, to illustrate how the flex cable shown in FIG. 201 can be seated within the elongated channel, according to one aspect of the present disclosure.

FIG. 204 illustrates the flex cable, shown in FIGS. 201-203, alone.

Figure 205:
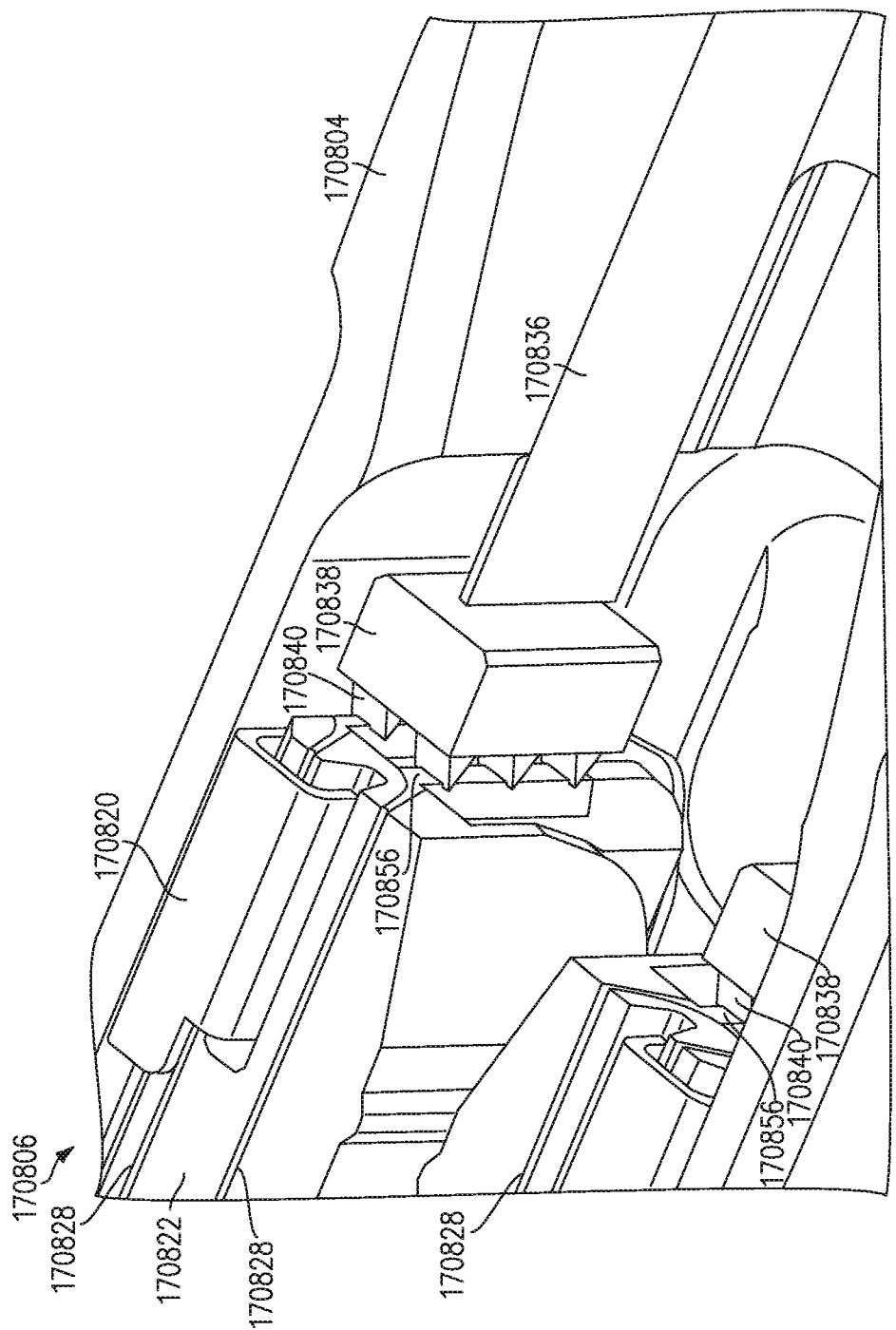

FIG. 205 illustrates a close up view of the elongated channel shown in FIGS. 202 and 203 with a staple cartridge coupled thereto, according to one aspect of the present disclosure.

Figure 208:
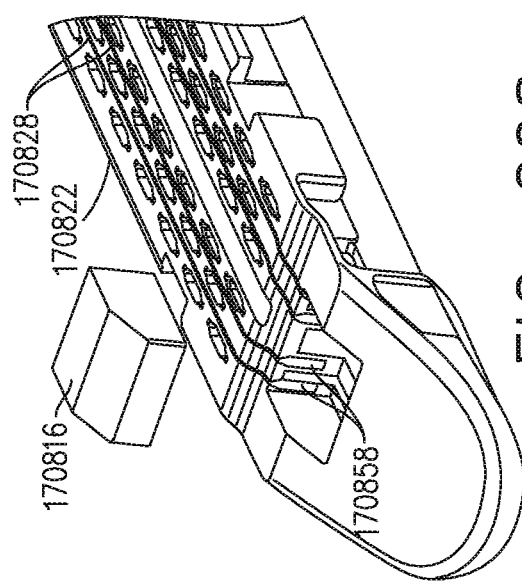
Figure 209:
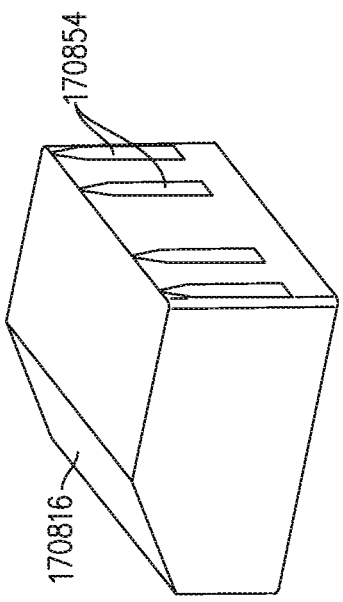
Figure 206:
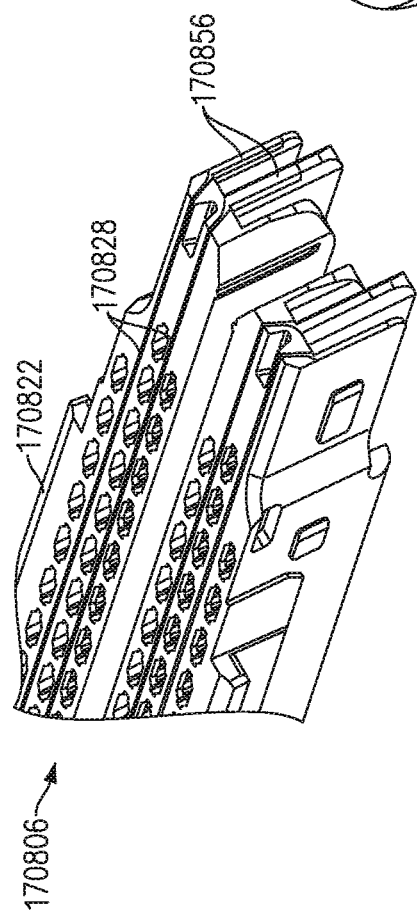
Figure 207:
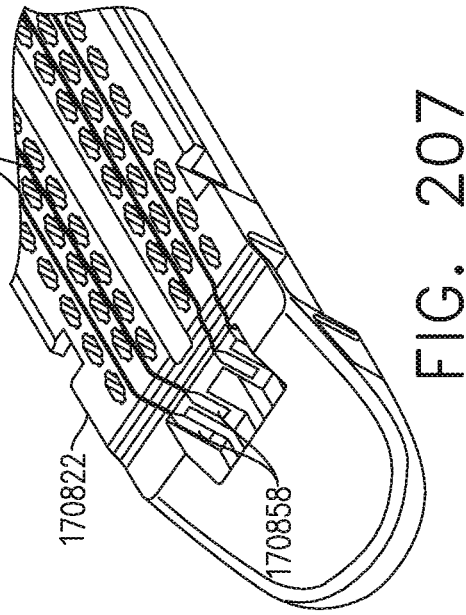

FIGS. 206-209 further illustrate one exemplification of a staple cartridge operative with the present exemplification of an end effector where FIG. 206 illustrates a close up view of the proximal end of the staple cartridge, FIG. 207 illustrates a close-up view of the distal end of the staple cartridge, with a space for a distal sensor plug, FIG. 208 further illustrates the distal sensor plug, and FIG. 209 illustrates the proximal-facing side of the distal sensor plug, according to one aspect of the present disclosure.

Figure 210:
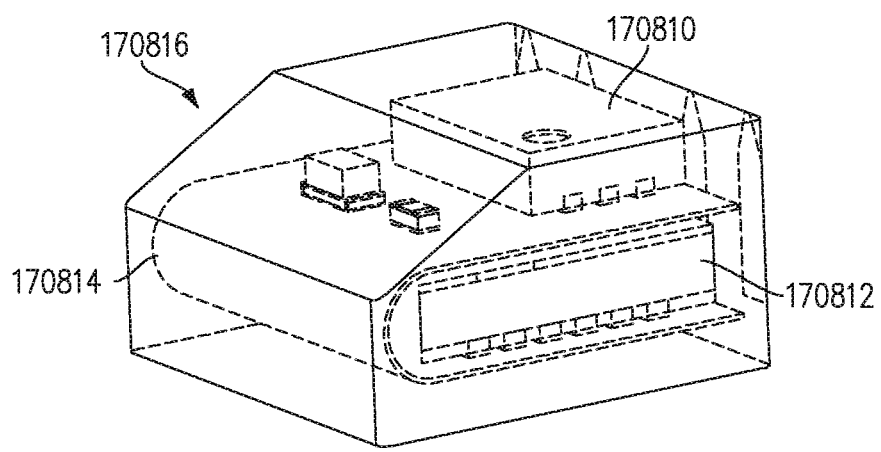
Figure 211:
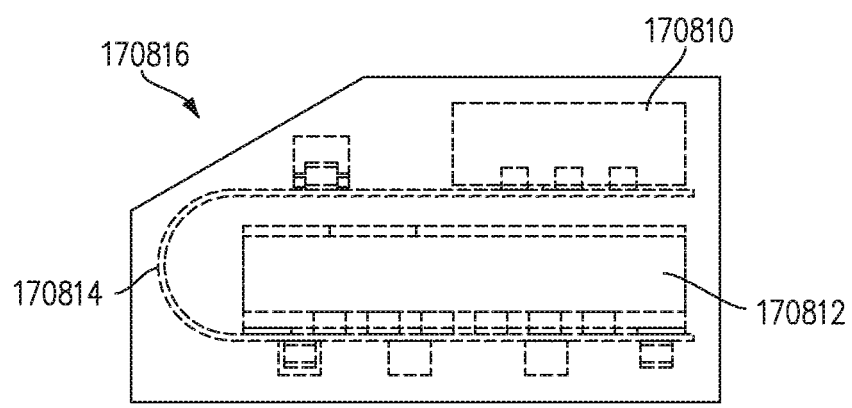

FIGS. 210 and 211 illustrate one exemplification of a distal sensor plug where FIG. 210 illustrates a cutaway view of the distal sensor plug and FIG. 211 further illustrates the Hall effect sensor and the processor operatively coupled to the flex board such that they are capable of communicating, according to one aspect of the present disclosure.

Figure 212:
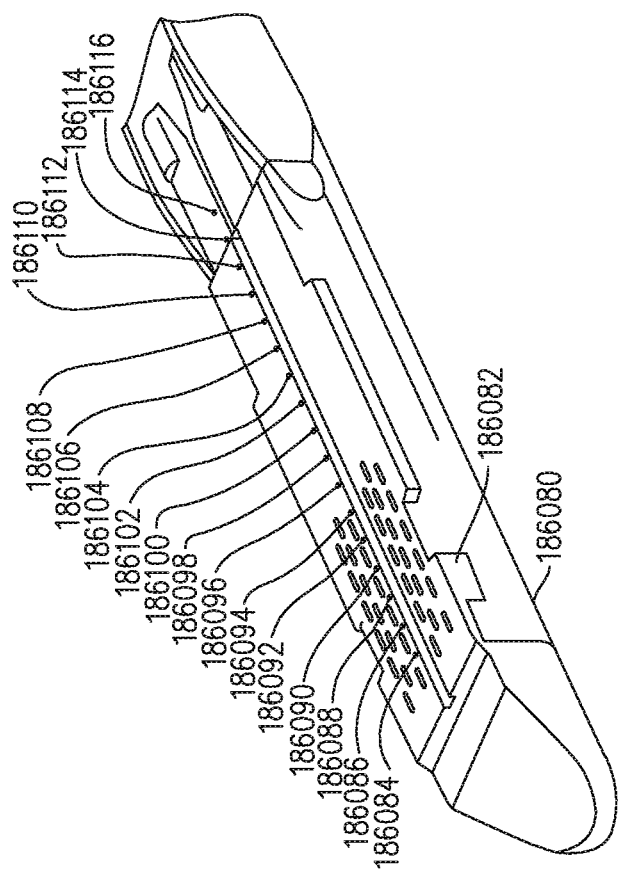

FIG. 212 also depicts an example end-effector channel frame, according to one aspect of the present disclosure.

Figure 213:
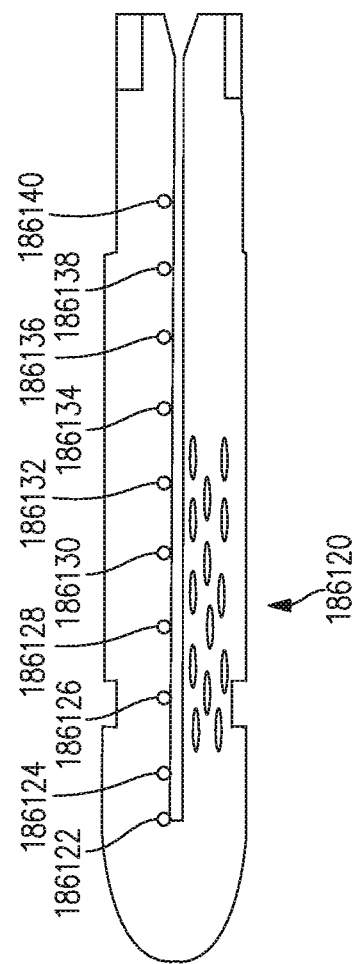

FIG. 213 also depicts an example end-effector channel frame, according to one aspect of the present disclosure.

Figure 214:
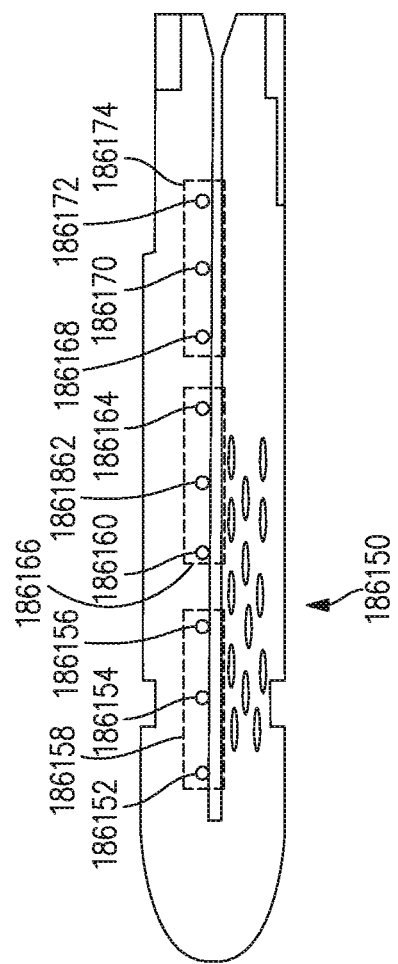

FIG. 214 also depicts an example end-effector channel frame, according to one aspect of the present disclosure.

Figure 215:
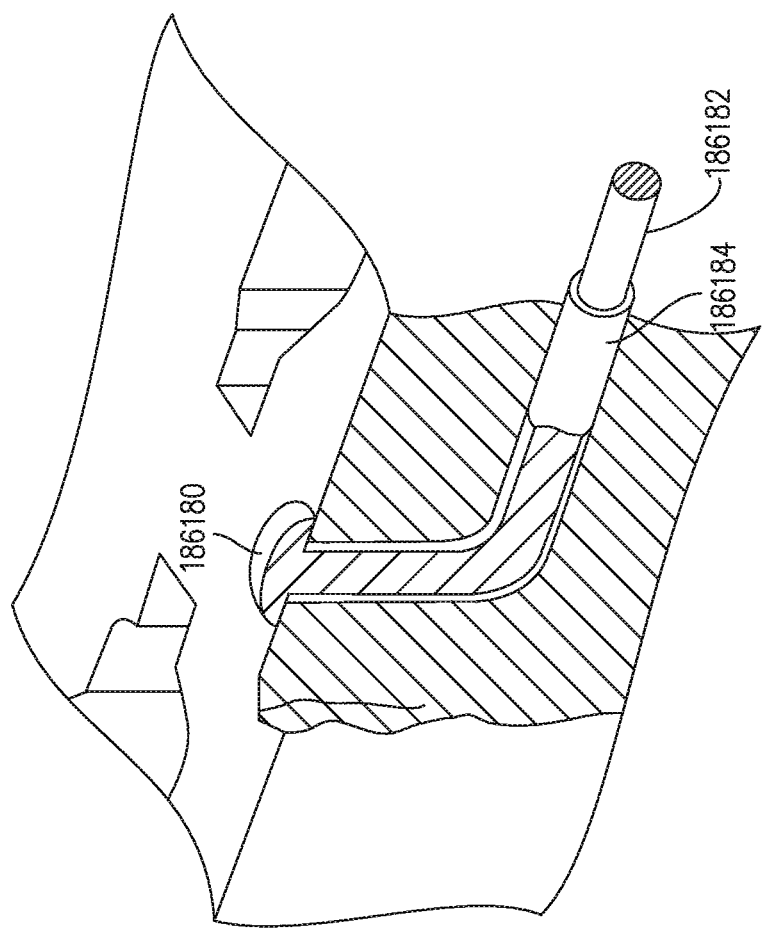

FIG. 215 depicts an example electrode, according to one aspect of the present disclosure.

Figure 216:
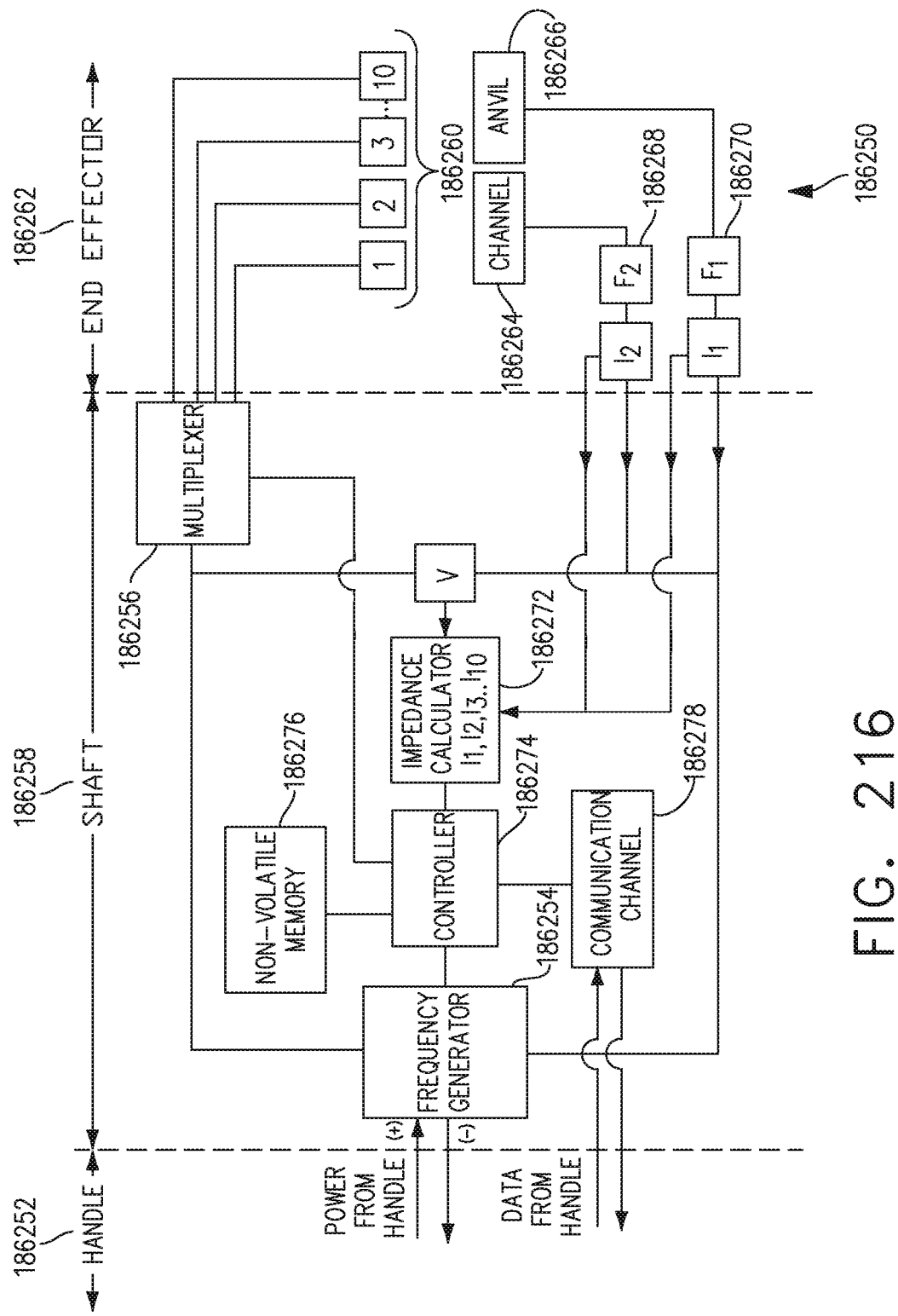

FIG. 216 is also an example circuit diagram, according to one aspect of the present disclosure.

Figure 217:
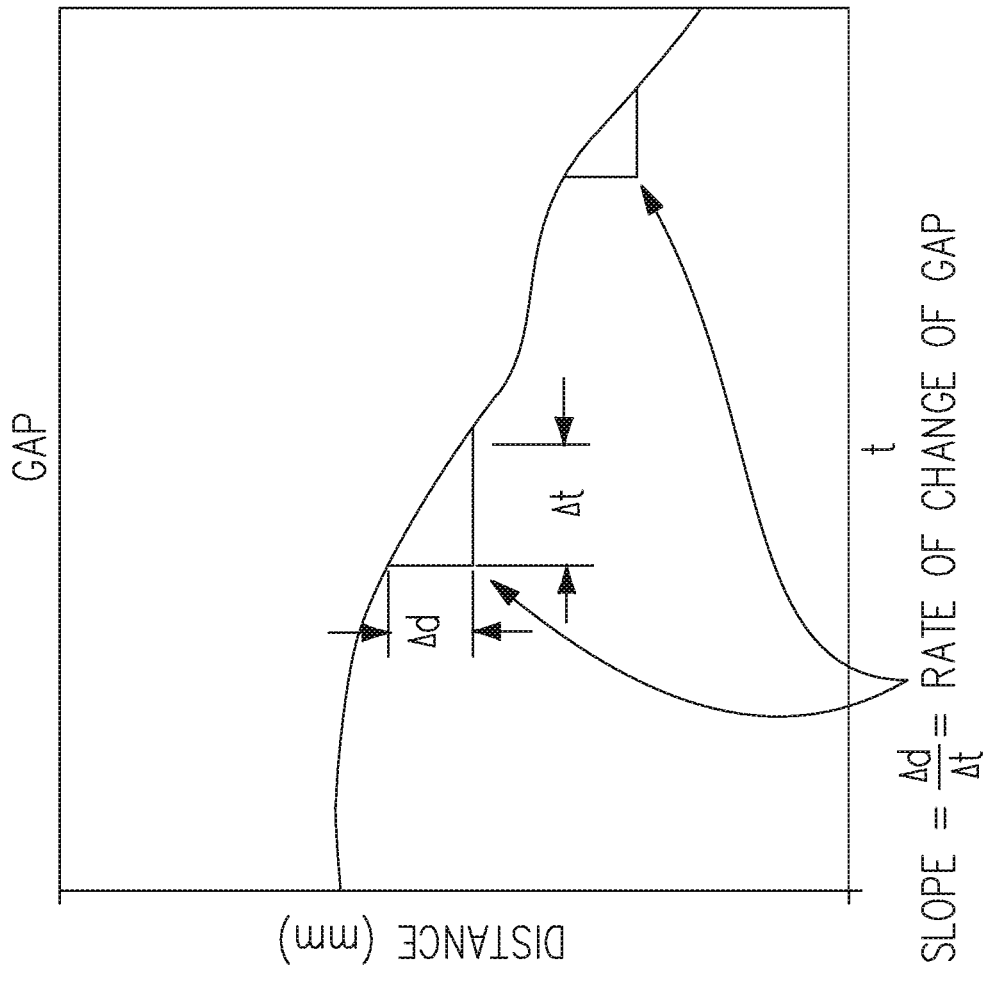
Figure 218:
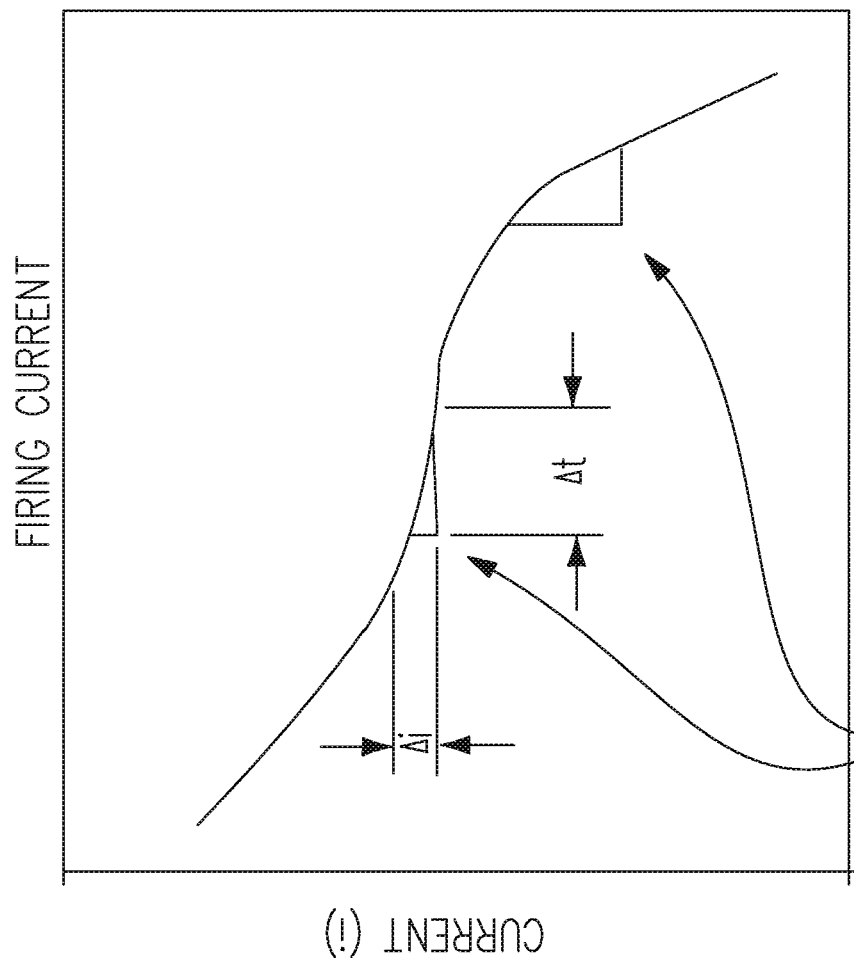
Figure 219:
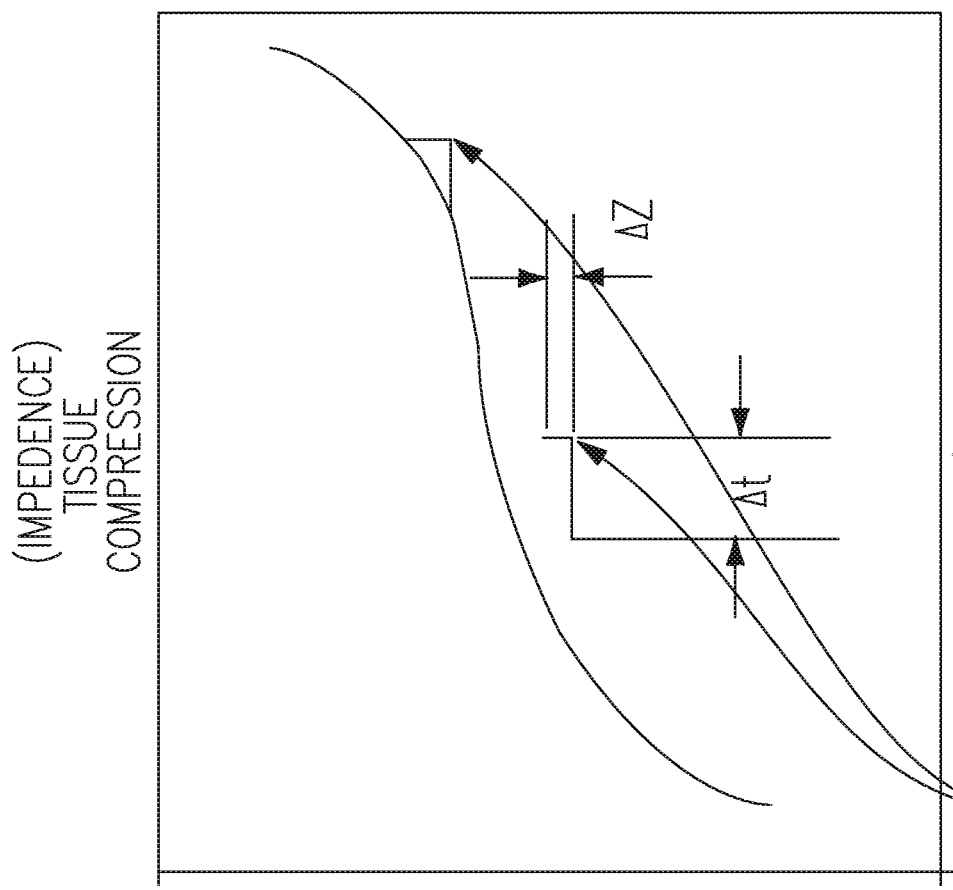

FIGS. 217-219 are graphs plotting gap size over time (FIG. 217), firing current over time (FIG. 218), and tissue compression over time (FIG. 219), according to one aspect of the present disclosure.

Figure 220:
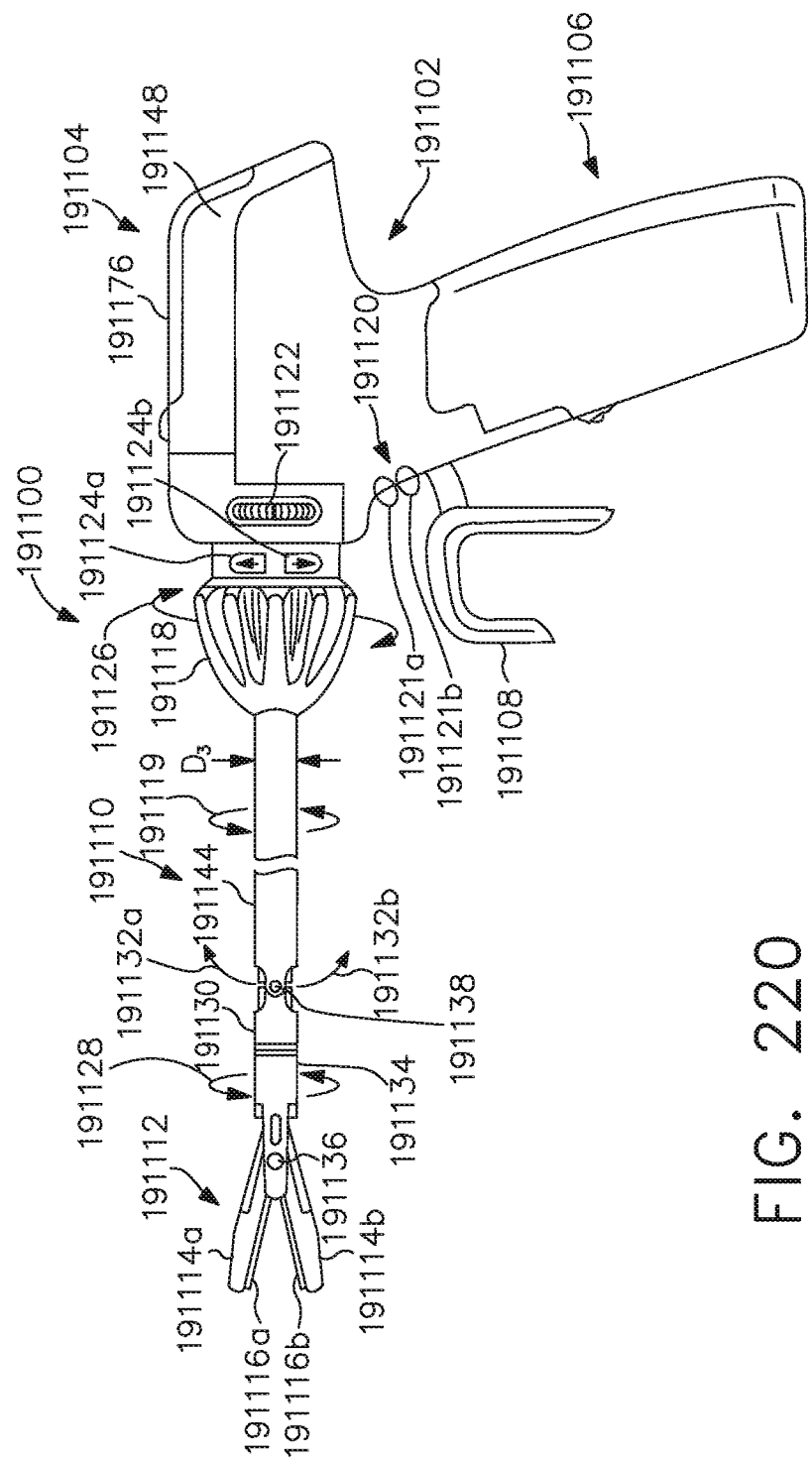

FIG. 220 illustrates a modular battery powered handheld electrosurgical instrument with distal articulation, according to one aspect of the present disclosure.

Figure 221:
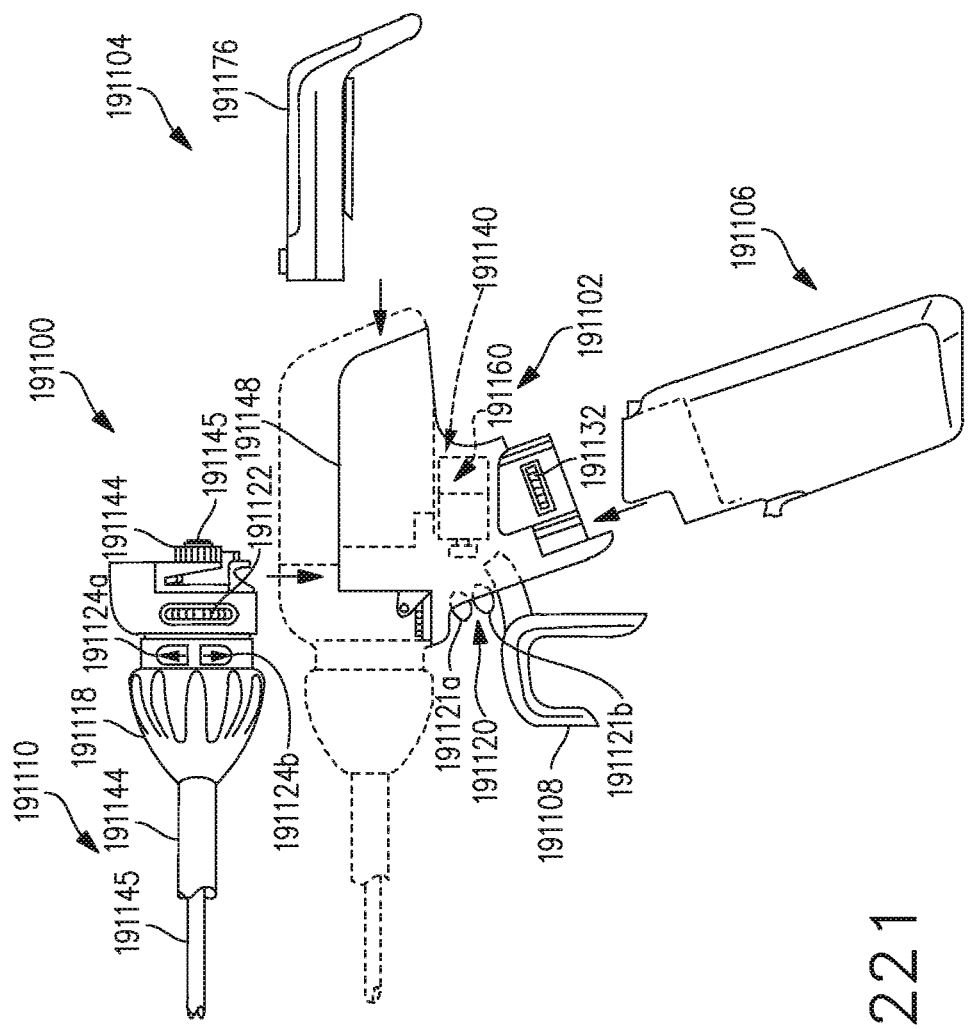

FIG. 221 is an exploded view of the surgical instrument shown in FIG. 220, according to one aspect of the present disclosure.

Figure 222:
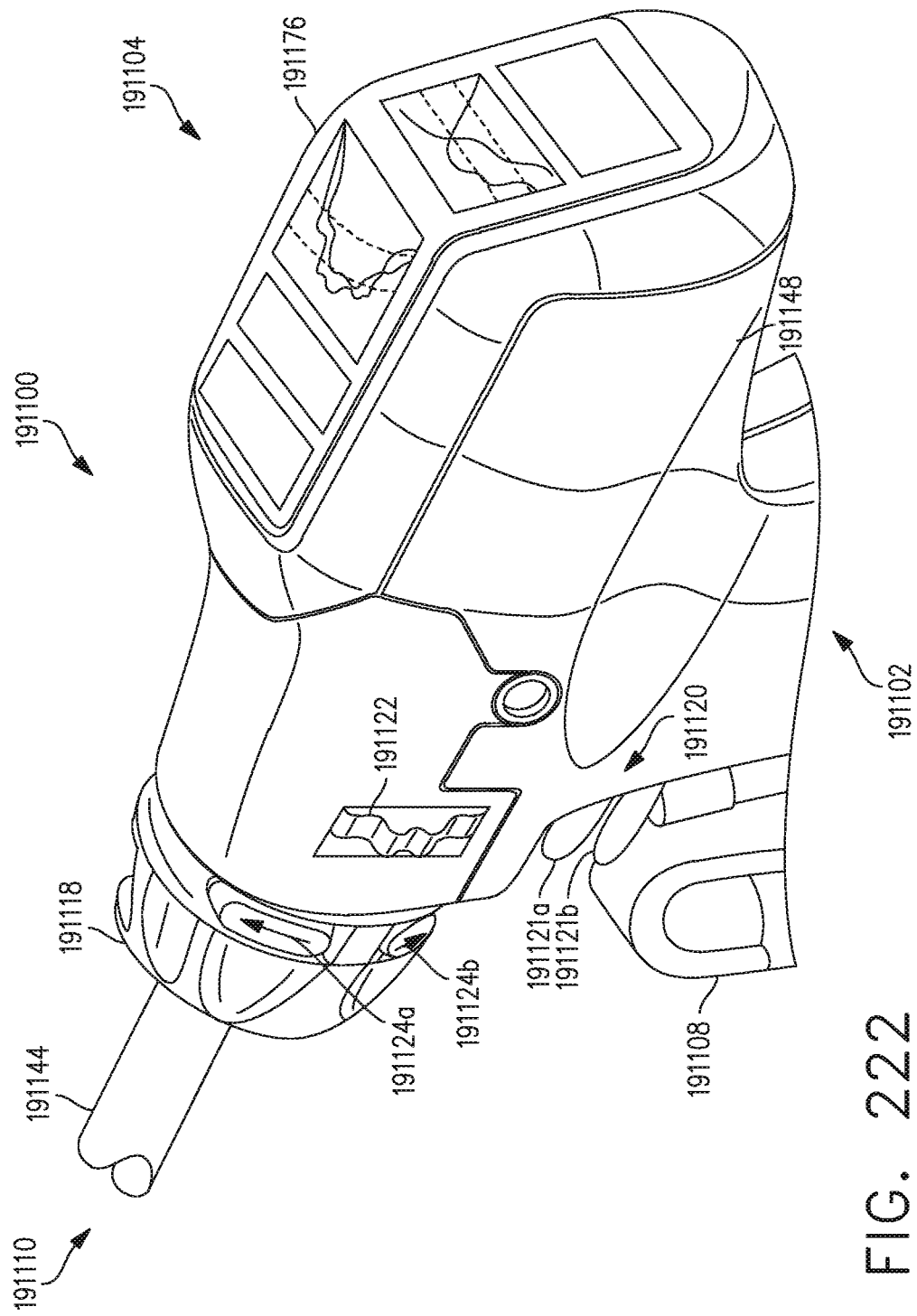

FIG. 222 is a perspective view of the surgical instrument shown in FIGS. 220 and 221 with a display located on the handle assembly, according to one aspect of the present disclosure.

Figure 223:
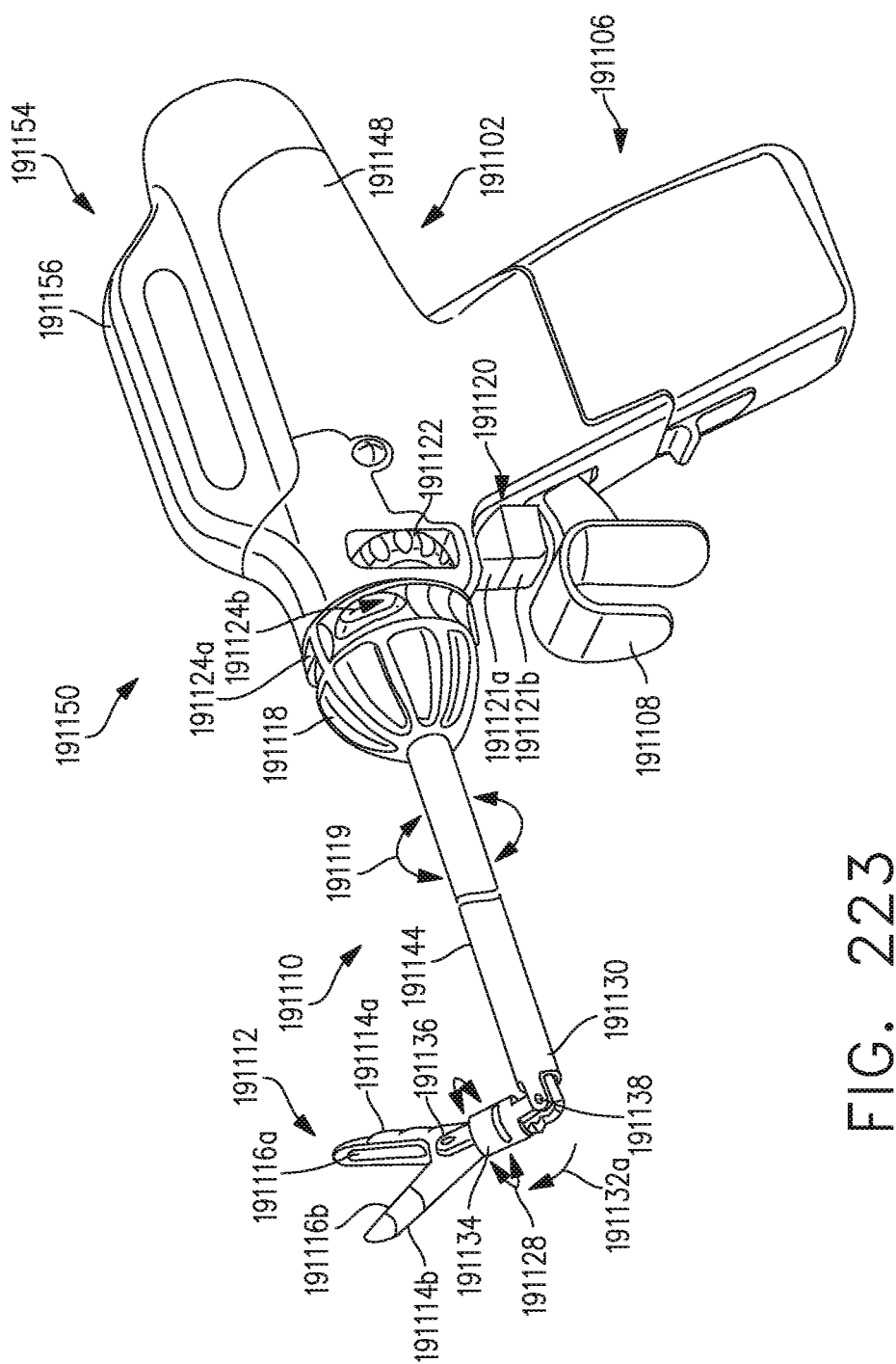

FIG. 223 is a perspective view of the instrument shown in FIGS. 220 and 221 without a display located on the handle assembly, according to one aspect of the present disclosure.

Figure 224:
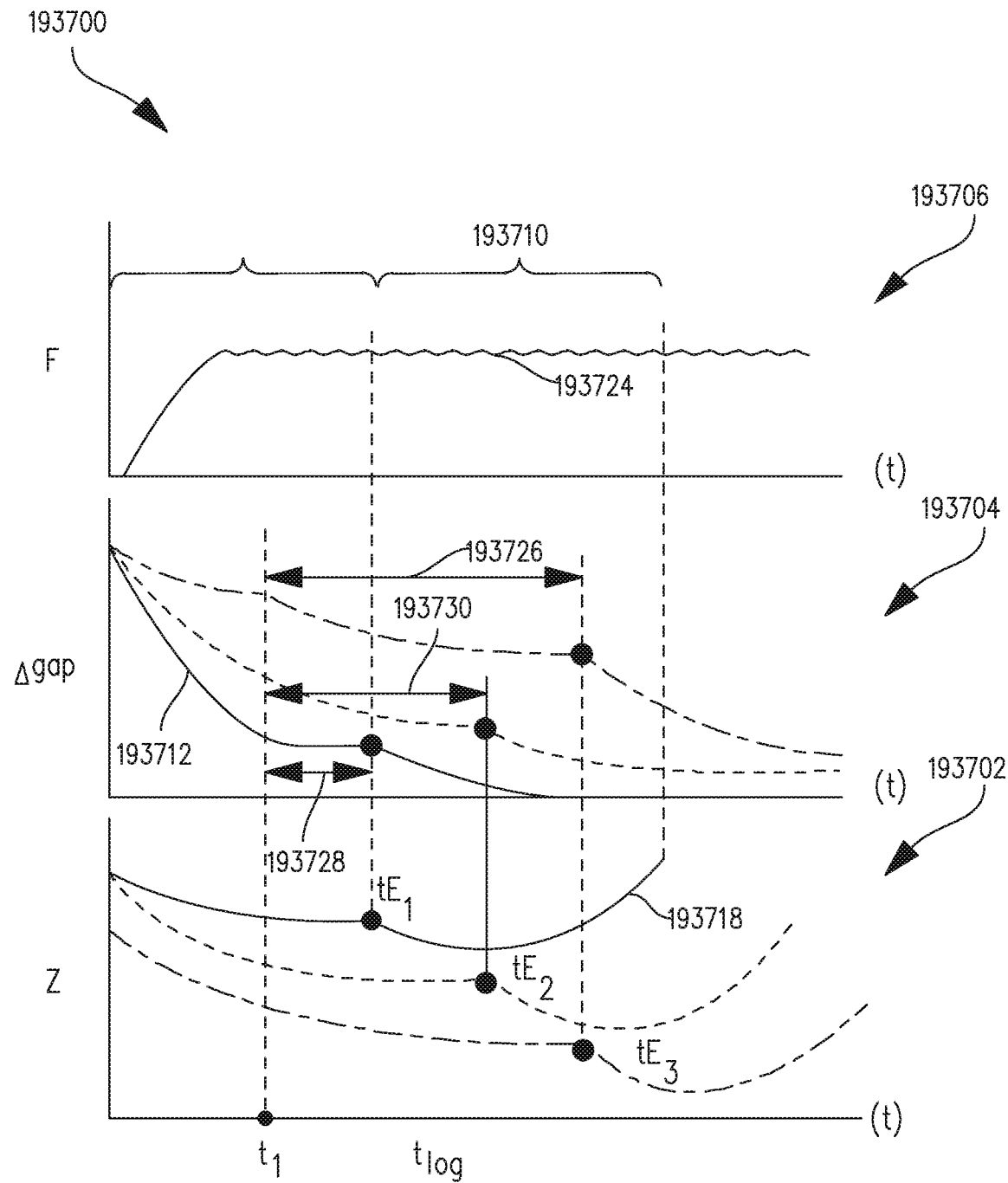

FIG. 224 is a graphical representation of determining wait time based on tissue thickness, according to aspects of the present disclosure.

Figure 225:
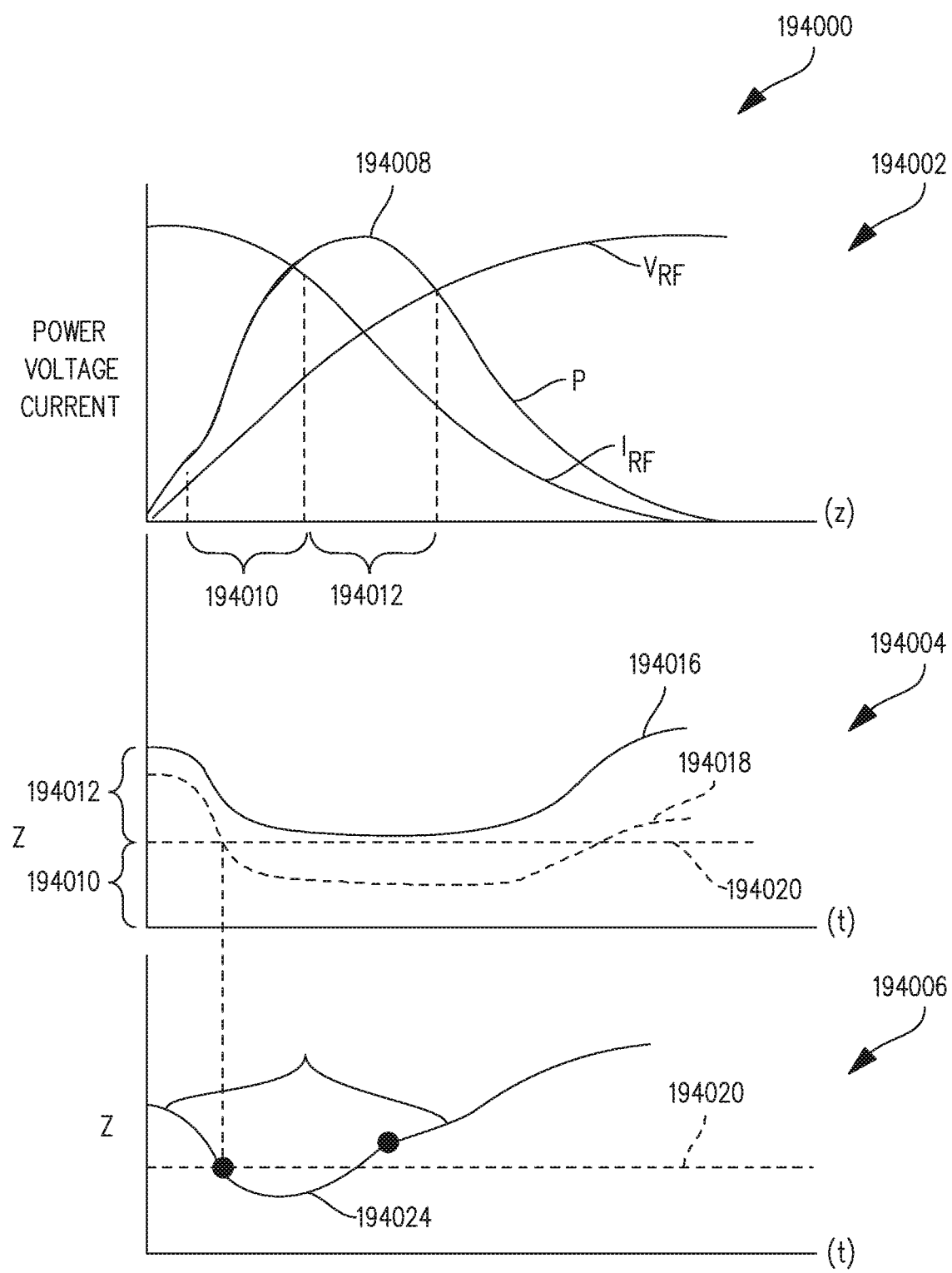

FIG. 225 is a graphical depiction of impedance bath tub, according to aspects of the present disclosure.

Figure 226:
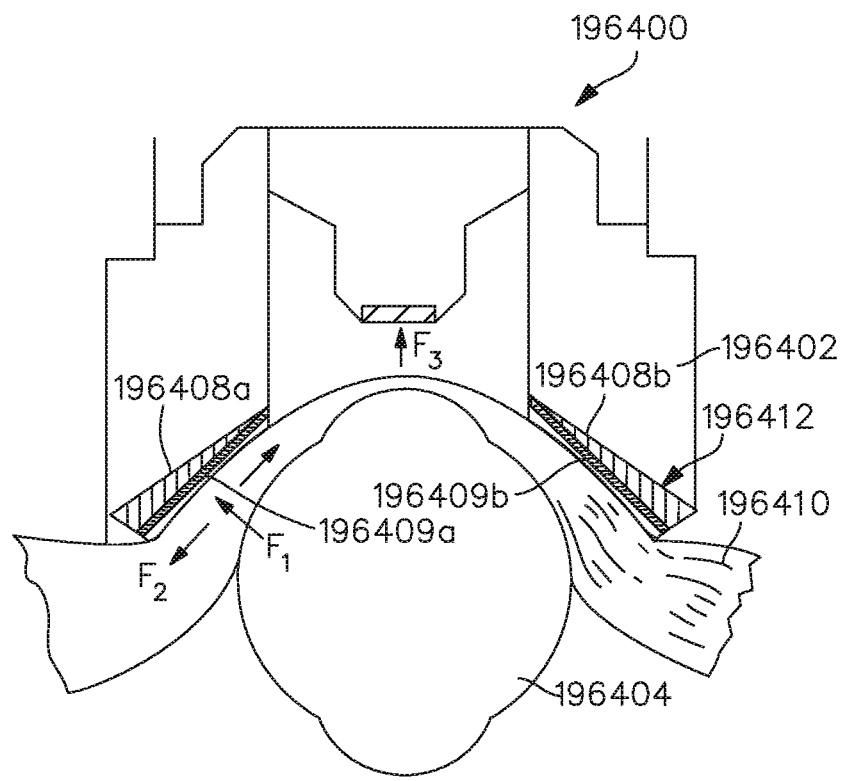

FIG. 226 illustrates one aspect of an end effector comprising RF data sensors located on the jaw member, according to one aspect of the present disclosure.

Figure 227:
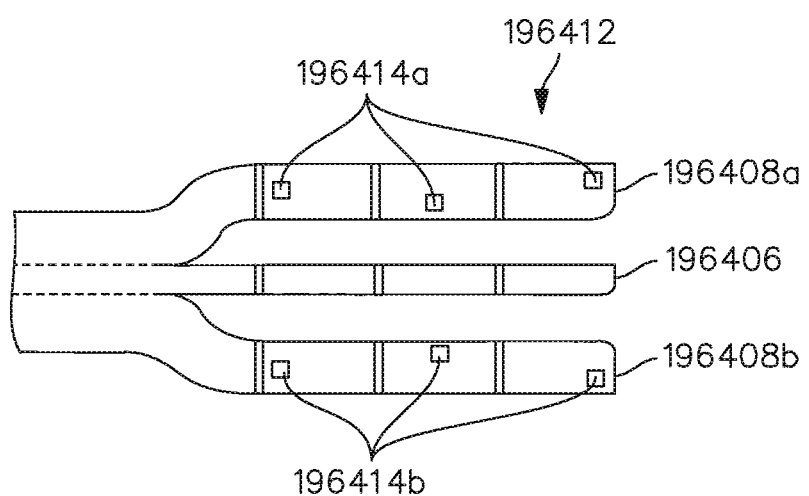

FIG. 227 illustrates one aspect of the flexible circuit shown in FIG. 226 in which the sensors may be mounted to or formed integrally therewith, according to one aspect of the present disclosure.

Figure 228:
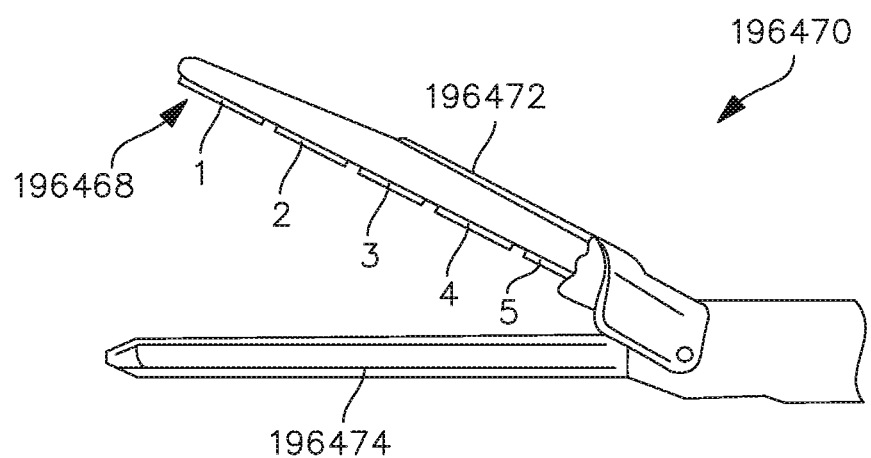

FIG. 228 illustrates one aspect of an end effector comprising segmented flexible circuit, according to one aspect of the present disclosure.

Figure 229:
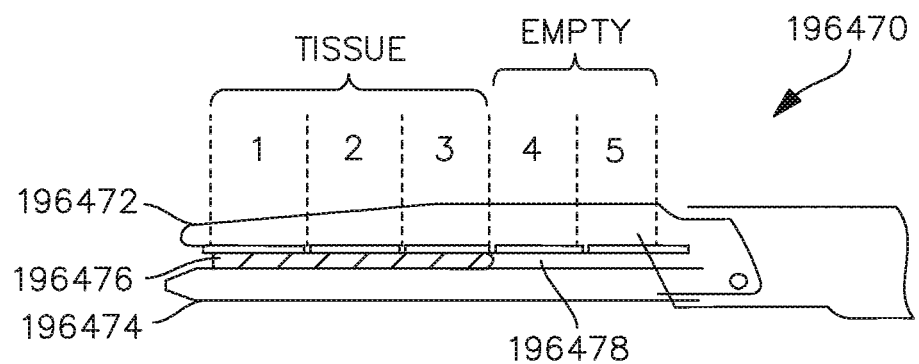

FIG. 229 illustrates the end effector shown in FIG. 228 with the jaw member clamping tissue between the jaw member and the ultrasonic blade, according to one aspect of the present disclosure.

Figure 230:
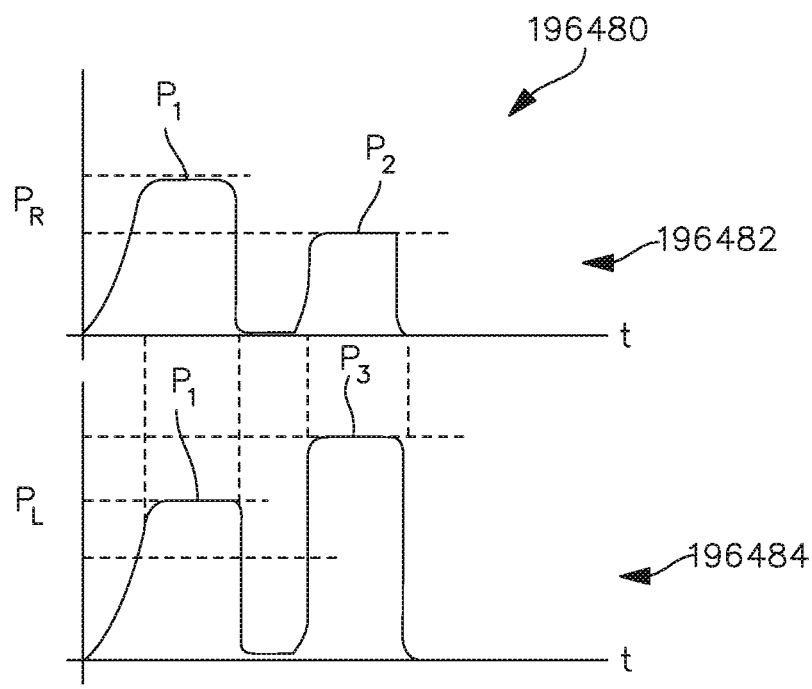

FIG. 230 illustrates graphs of energy applied by the right and left side of an end effector based on locally sensed tissue parameters, according to one aspect of the present disclosure.

Figure 231:
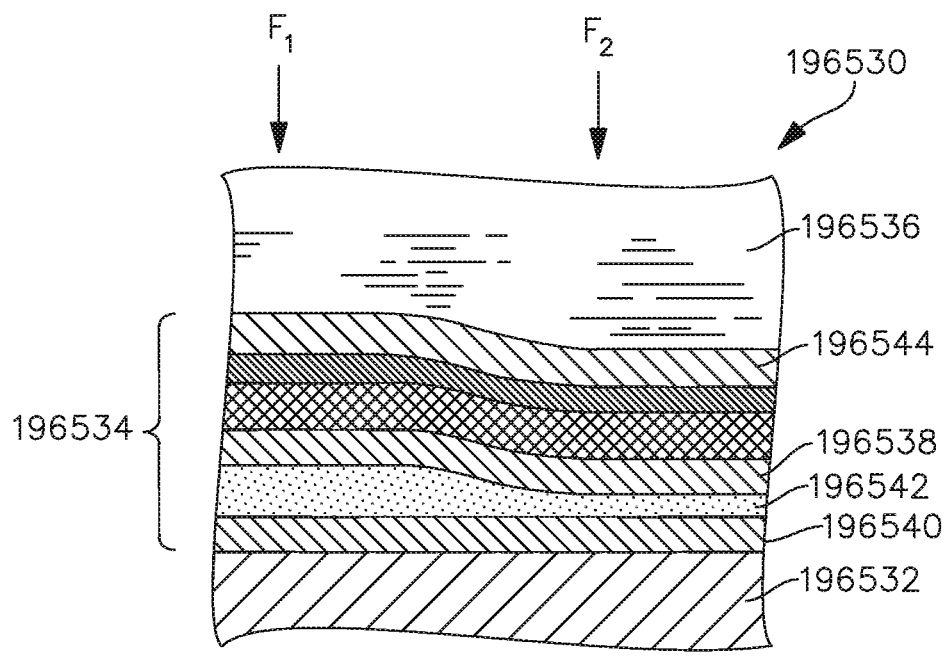

FIG. 231 is a cross-sectional view of one aspect of an end effector configured to sense force or pressure applied to tissue located between a jaw member and an ultrasonic blade, according to one aspect of the present disclosure.

Figure 232:
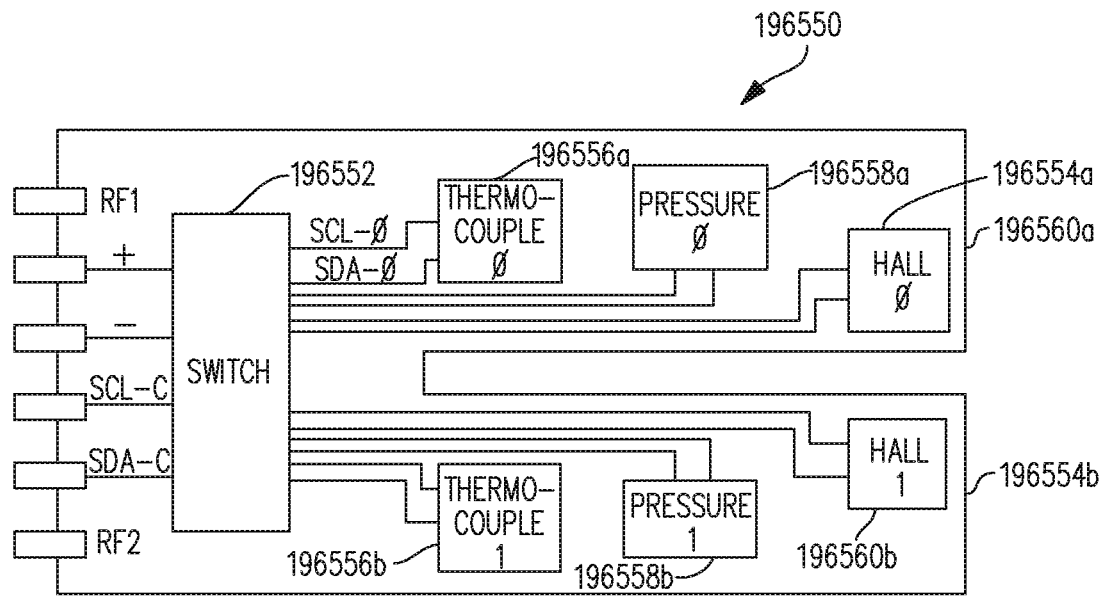

FIG. 232 is a schematic diagram of one aspect of a signal layer of a flexible circuit, according to one aspect of the present disclosure.

Figure 233:
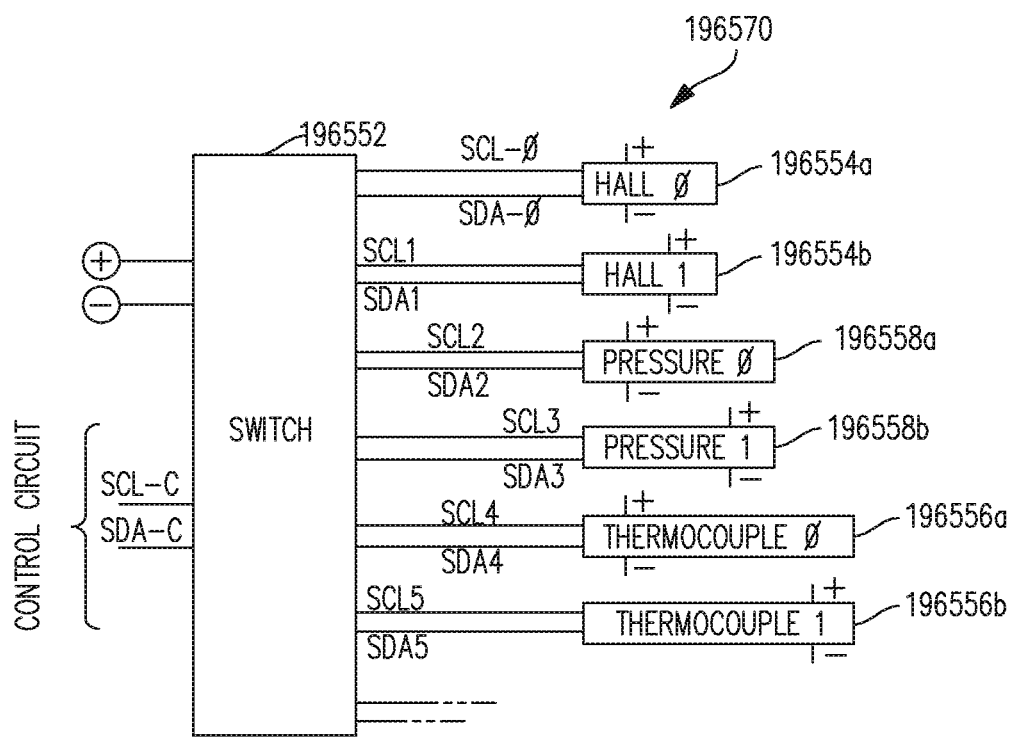

FIG. 233 is a schematic diagram of sensor wiring for the flexible circuit shown in FIG. 232, according to one aspect of the present disclosure.

Figure 234:
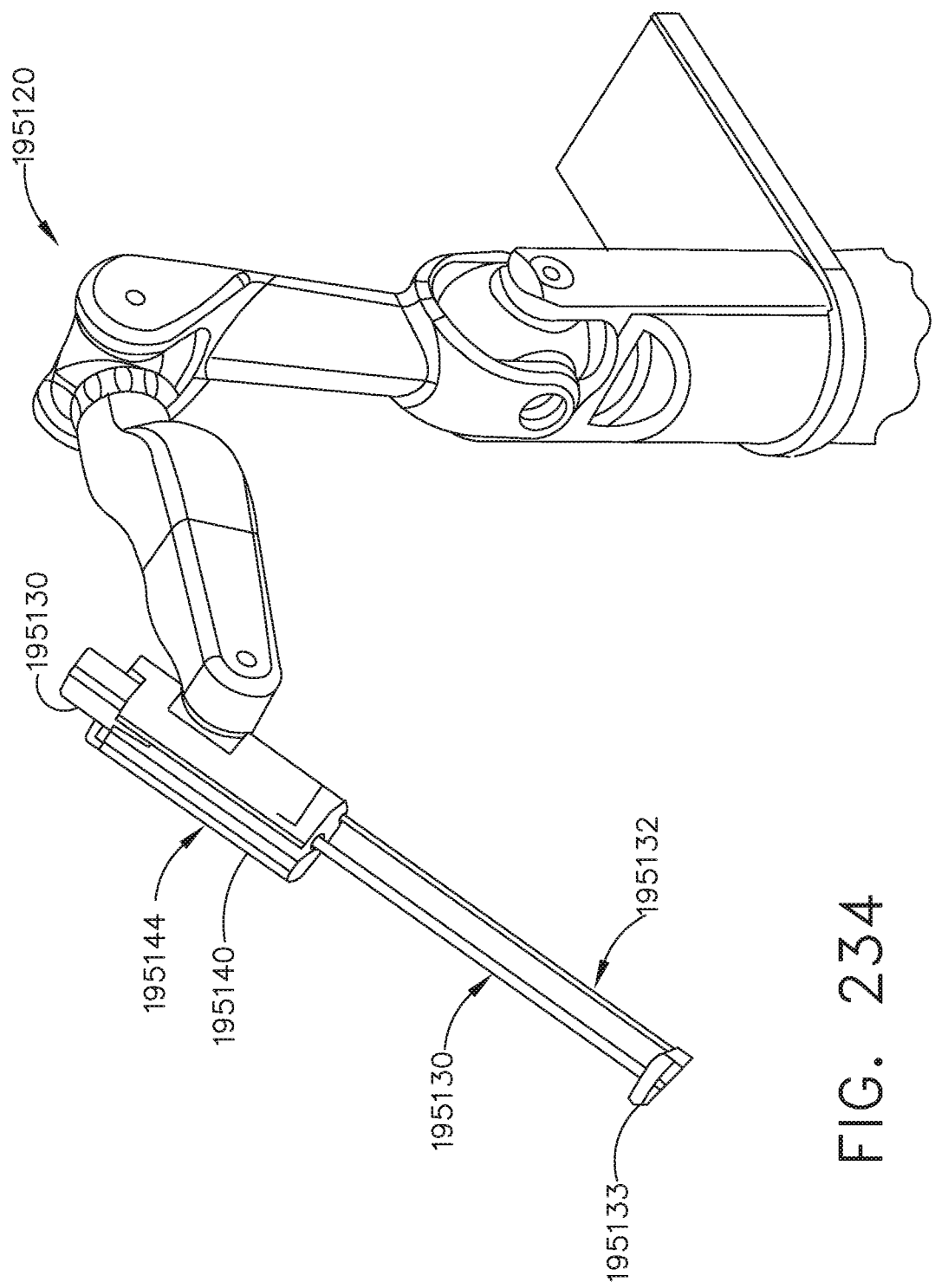

FIG. 234 illustrates another exemplification of a robotic arm and another exemplification of a tool assembly releasably coupled to the robotic arm, according to one aspect of the present disclosure.

Figure 235:
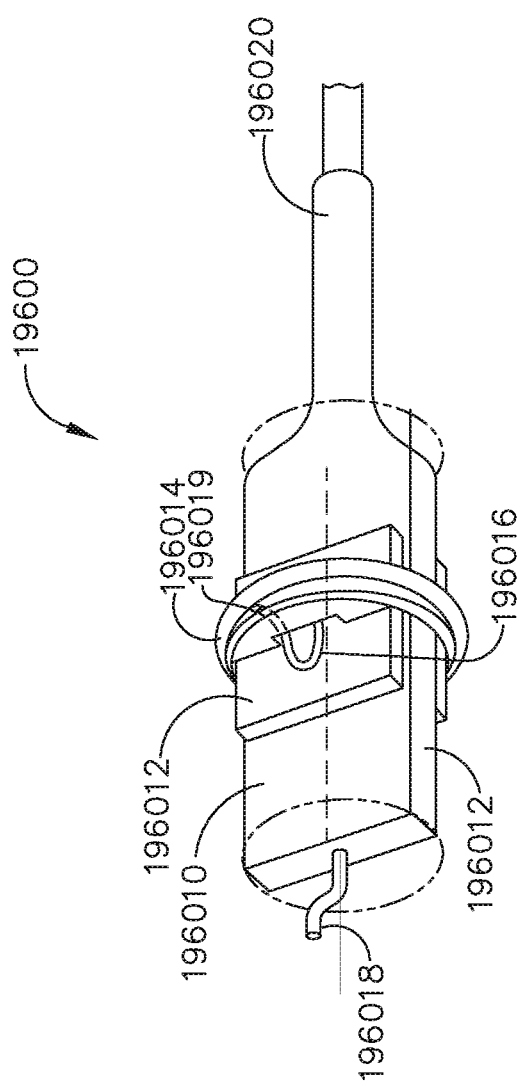

FIG. 235 illustrates an exemplification of a sensor assembly that is configured to sense an applied force along a part of the end effector of a tool assembly, such as the tool assemblies shown in FIG. 234, according to one aspect of the present disclosure.

FIG. 236 illustrates the sensor assembly of FIG. 235 coupled to a shaft of the tool assembly and showing an end effector having a cutting tool, according to one aspect of the present disclosure.

FIG. 237 illustrates the distal end of the cutting tool of FIG. 236 positioned a distance from a tissue of a patient, according to one aspect of the present disclosure.

FIG. 238 illustrates the distal end of the cutting tool of FIG. 237 boring through the tissue, according to one aspect of the present disclosure.

FIG. 239 illustrates the distal end of the cutting tool of FIG. 238 extending through the tissue, according to one aspect of the present disclosure.

Figure 240:
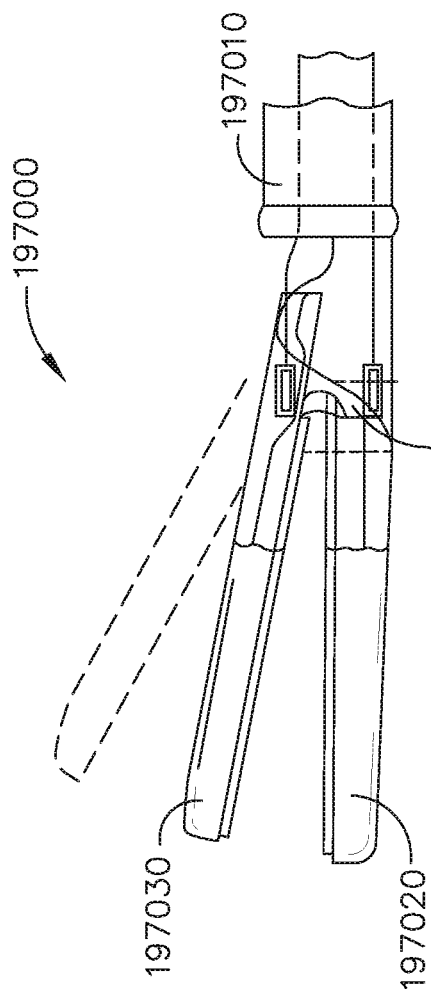

FIG. 240 illustrates another exemplification of end effector positioned at a distal end of a shaft of a tool assembly that is coupled to a robotic arm with the end effector including first and second jaws that are configured to releasably capture tissue therebetween, according to one aspect of the present disclosure.

Figure 241:
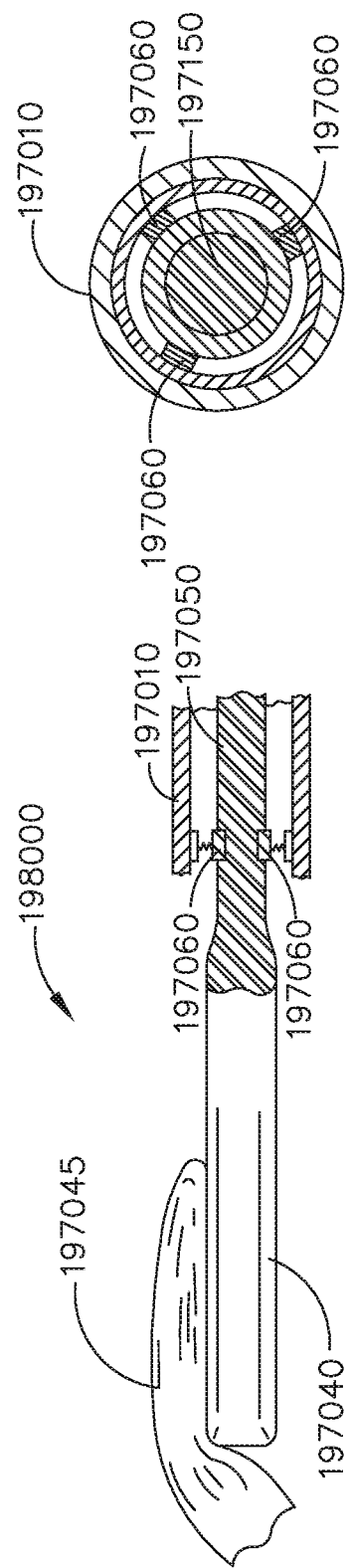

FIG. 241 illustrates a section of tissue applying a force against a distal end of a blade that is positioned along a first jaw of the end effector with a proximal end of the blade being coupled to a strain gauge for measuring tension in the tissue, according to one aspect of the present disclosure.

Figure 242:

FIG. 242 illustrates a cross sectional view of the shaft of FIG. 241 showing at least one strain gauge positioned adjacent the blade, according to one aspect of the present disclosure.

Figure 243:
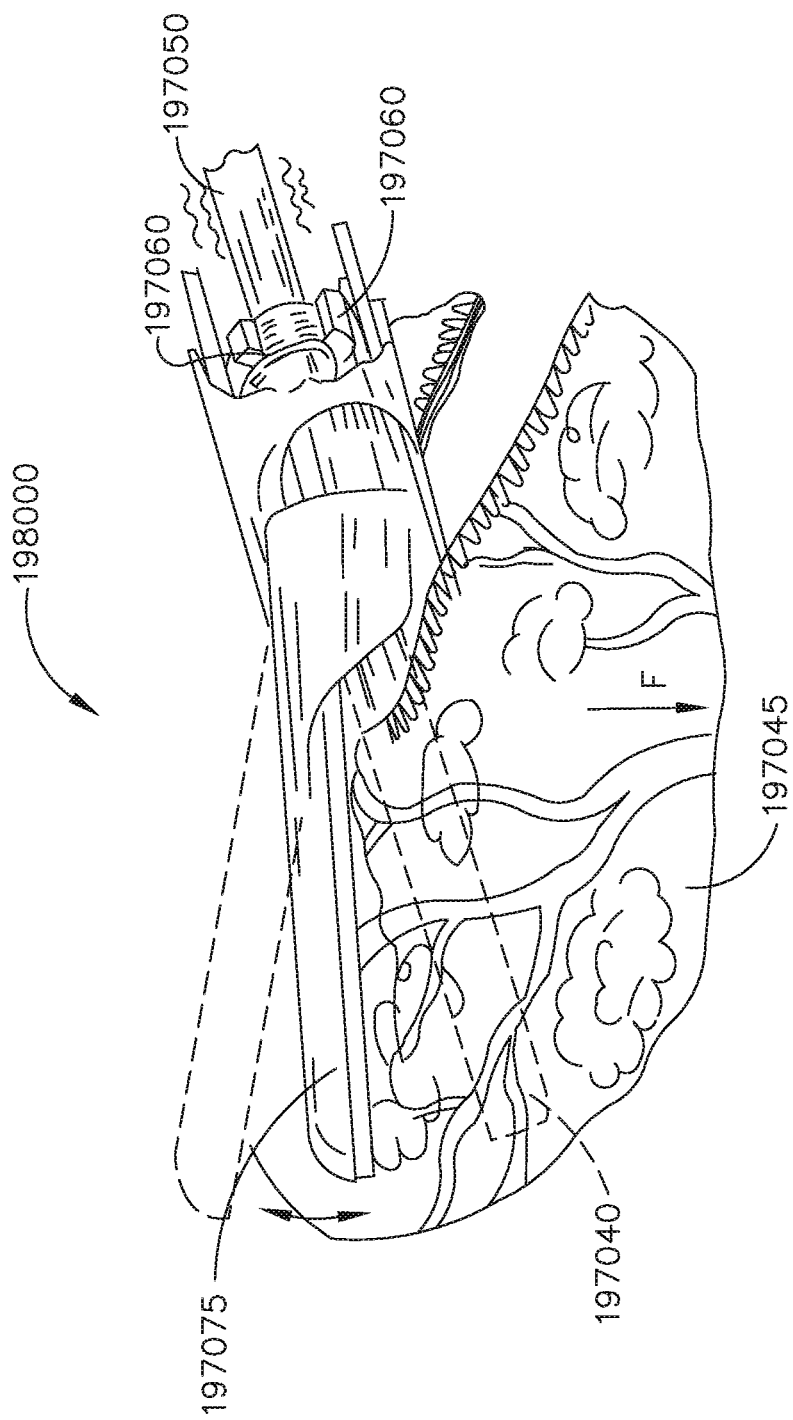

FIG. 243 illustrates the end effector of FIG. 240 being angled relative to the tissue in order to create a desired tension in the tissue, according to one aspect of the present disclosure.

Figure 244:
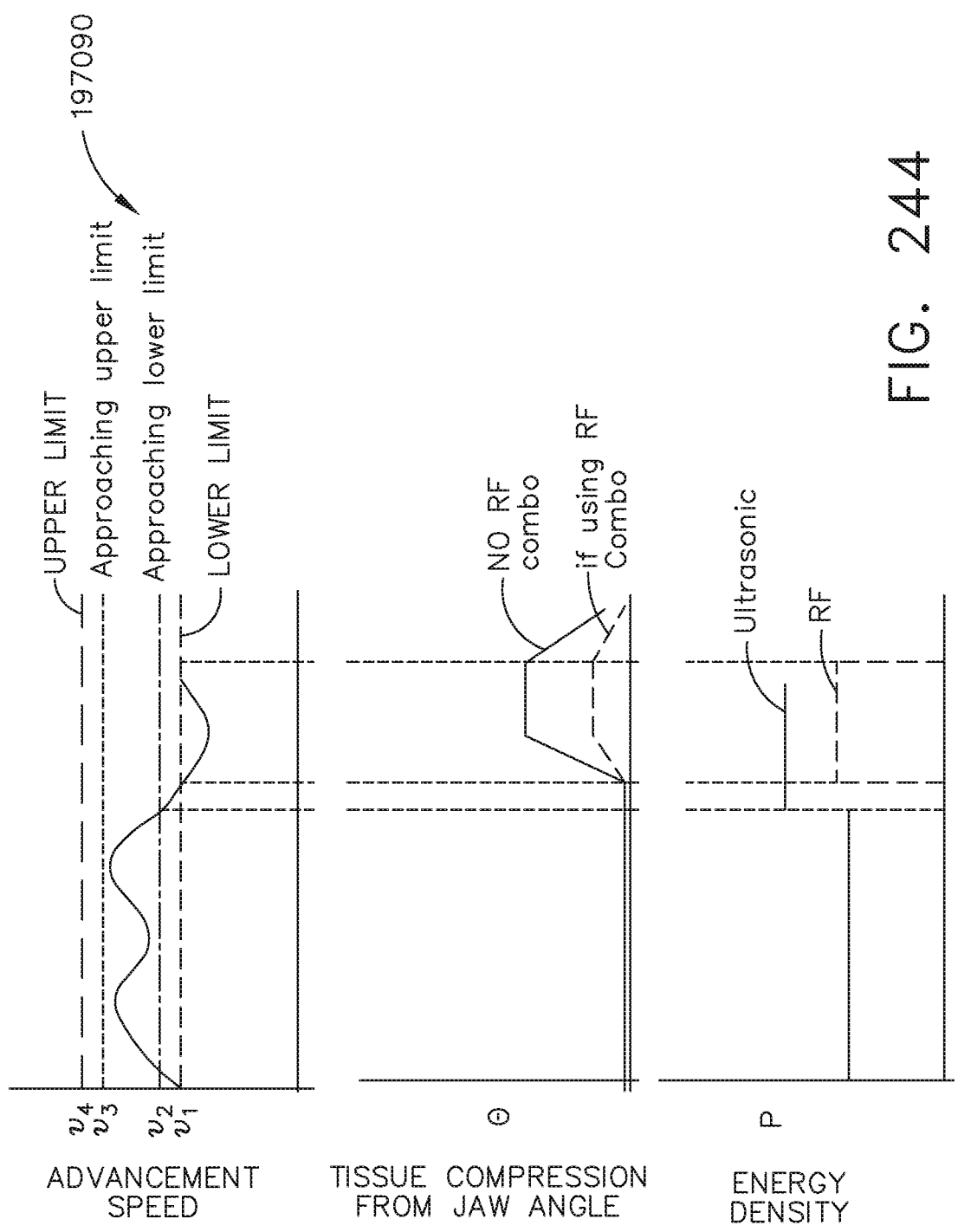

FIG. 244 illustrates a first graph showing examples of relationships between the advancement speed of the robotic arm or end effector compared to the angle of the end effector relative to the tissue thereby effecting tissue tension) and energy density in the blade, according to one aspect of the present disclosure.

Figure 245:
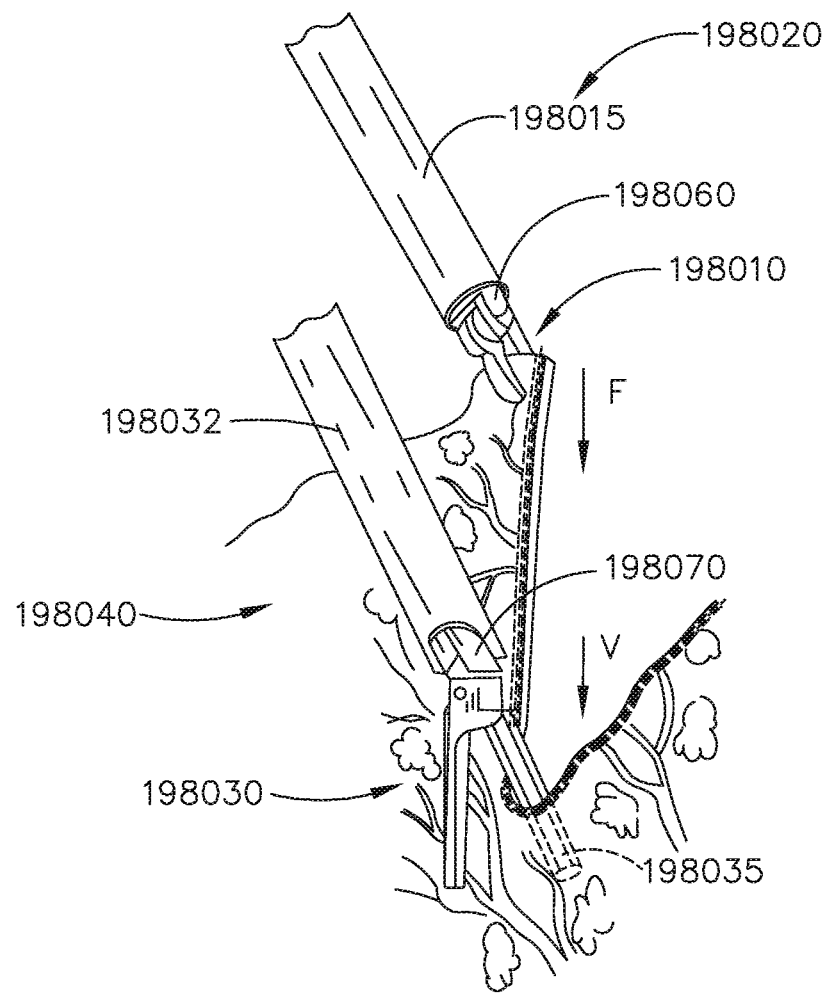

FIG. 245 illustrates an exemplification of a first end effector whose position is controlled by a first robotic arm and includes first and second jaws that are configured to releasably capture tissue therebetween, as well as a second end effector whose position is controlled by a second robotic arm and includes a cutting tool that advances based on a sensed tension detected by a sensor coupled to the first end effector, according to one aspect of the present disclosure.

DESCRIPTION

Applicant of the present application owns the following U.S. Patent Applications, filed on Dec. 4, 2018, the disclosure of each of which is herein incorporated by reference in its entirety:

U.S. patent application Ser. No. 16/209,385, titled METHOD OF HUB COMMUNICATION, PROCESSING, STORAGE AND DISPLAY, now U.S. Patent Application Publication No. 2019/0200844;

U.S. patent application Ser. No. 16/209,395, titled METHOD OF HUB COMMUNICATION, now U.S. Patent Application Publication No. 2019/0201136;

U.S. patent application Ser. No. 16/209,403, titled METHOD OF CLOUD BASED DATA ANALYTICS FOR USE WITH THE HUB, now U.S. Patent Application Publication No. 2019/0206569;

U.S. patent application Ser. No. 16/209,416, titled METHOD OF HUB COMMUNICATION, PROCESSING, DISPLAY, AND CLOUD ANALYTICS, now U.S. Patent Application Publication No. 2019/0206562;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Patent Application Publication No. 2019/0208641;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Patent Application Publication No. 2019/0201594;

U.S. patent application Ser.No. 16/209,447, titled METHOD FOR SMOKE EVACUATION FOR SURGICAL HUB;, now U.S. Patent Application Publication No. 2019/0201045;

U.S. patent application Ser. No. 16/209,453, tided METHOD FOR CONTROLLING SMART ENERGY DEVICES, now U.S. Patent Application Publication No. 2019/0201046;

U.S. patent application Ser. No. 16/209,458, titled METHOD FOR SMART ENERGY DEVICE INFRASTRUCTURE, now U.S. Patent Application Publication No. 2019/0201047;

U.S. patent application Ser. No. 16/209,465, tided METHOD FOR ADAPTIVE CONTROL SCHEMES FOR SURGICAL NETWORK CONTROL AND INTERACTION, now U.S. Pat. No. 11,304,699;

U.S. patent application Ser. No. 16/209,478, tided METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, now U.S. Patent Application Publication No. 2019/0104919;

U.S. patent application Ser. No. 16/209,490, tided METHOD FOR FACILITY DATA COLLECTION AND INTERPRETATION, now U.S. Patent Application Publication No. 2019/0206564; and U.S. patent application Ser. No. 16/209,491, titled METHOD FOR CIRCULAR STAPLER CONTROL ALGORITHM ADJUSTMENT BASED ON SITUATIONAL AWARENESS, now U.S. Pat. No. 11,109,866.

Applicant of the present application owns the following U.S. Patent Applications, filed on Nov. 6, 2018, the disclosure of each of which is herein incorporated by reference in its entirety:

U.S. patent application Ser. No. 16/182,224, titled SURGICAL NETWORK, INSTRUMENT, AND CLOUD RESPONSES BASED ON VALIDATION OF RECEIVED DATASET AND AUTHENTICATION OF ITS SOURCE AND INTEGRITY;

U.S. patent application Ser. No. 16/182,230, titled SURGICAL SYSTEM FOR PRESENTING INFORMATION INTERPRETED FROM EXTERNAL DATA;

U.S. patent application Ser. No. 16/182,233, titled SURGICAL SYSTEMS WITH AUTONOMOUSLY ADJUSTABLE CONTROL PROGRAMS;

U.S. patent application Ser. No. 16/182,239, titled ADJUSTMENT OF DEVICE CONTROL PROGRAMS BASED ON STRATIFIED CONTEXTUAL DATA IN ADDITION TO THE DATA;

U.S. patent application Ser. No. 16/182,243, titled SURGICAL HUB AND MODULAR DEVICE RESPONSE ADJUSTMENT BASED ON SITUATIONAL AWARENESS;

U.S. patent application Ser. No. 16/182,248, titled DETECTION AND ESCALATION OF SECURITY RESPONSES OF SURGICAL INSTRUMENTS TO INCREASING SEVERITY THREATS;

U.S. patent application Ser. No. 16/182,251, titled INTERACTIVE SURGICAL SYSTEM;

U.S. patent application Ser. No. 16/182,260, titled AUTOMATED DATA SCALING, ALIGNMENT, AND ORGANIZING BASED ON PREDEFINED PARAMETERS WITHIN SURGICAL NETWORKS;

U.S. patent application Ser. No. 16/182,267, titled SENSING THE PATIENT POSITION AND CONTACT UTILIZING THE MONO-POLAR RETURN PAD ELECTRODE TO PROVIDE SITUATIONAL AWARENESS TO THE HUB;

U.S. patent application Ser. No. 16/182,249, titled POWERED SURGICAL TOOL WITH PREDEFINED ADJUSTABLE CONTROL ALGORITHM FOR CONTROLLING END EFFECTOR PARAMETER;

U.S. patent application Ser. No. 16/182,246, titled ADJUSTMENTS BASED ON AIRBORNE PARTICLE PROPERTIES;

U.S. patent application Ser. No. 16/182,256, titled ADJUSTMENT OF A SURGICAL DEVICE FUNCTION BASED ON SITUATIONAL AWARENESS;

U.S. patent application Ser. No. 16/182,242, titled REAL-TIME ANALYSIS OF COMPREHENSIVE COST OF ALL INSTRUMENTATION USED IN SURGERY UTILIZING DATA FLUIDITY TO TRACK INSTRUMENTS THROUGH STOCKING AND IN-HOUSE PROCESSES;

U.S. patent application Ser. No. 16/182,255, titled USAGE AND TECHNIQUE ANALYSIS OF SURGEON/STAFF PERFORMANCE AGAINST A BASELINE TO OPTIMIZE DEVICE UTILIZATION AND PERFORMANCE FOR BOTH CURRENT AND FUTURE PROCEDURES;

U.S. patent application Ser. No. 16/182,269, titled IMAGE CAPTURING OF THE AREAS OUTSIDE THE ABDOMEN TO IMPROVE PLACEMENT AND CONTROL OF A SURGICAL DEVICE IN USE;

U.S. patent application Ser. No. 16/182,278, titled COMMUNICATION OF DATA WHERE A SURGICAL NETWORK IS USING CONTEXT OF THE DATA AND REQUIREMENTS OF A RECEIVING SYSTEM/USER TO INFLUENCE INCLUSION OR LINKAGE OF DATA AND METADATA TO ESTABLISH CONTINUITY;

U.S. patent application Ser. No. 16/182,290, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION;

U.S. patent application Ser. No. 16/182,232, titled CONTROL OF A SURGICAL SYSTEM THROUGH A SURGICAL BARRIER;

U.S. patent application Ser. No. 16/182,227, titled SURGICAL NETWORK DETERMINATION OF PRIORITIZATION OF COMMUNICATION, INTERACTION, OR PROCESSING BASED ON SYSTEM OR DEVICE NEEDS;

U.S. patent application Ser. No. 16/182,231, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES;

U.S. patent application Ser. No. 16/182,229, titled ADJUSTMENT OF STAPLE HEIGHT OF AT LEAST ONE ROW OF STAPLES BASED ON THE SENSED TISSUE THICKNESS OR FORCE IN CLOSING;

U.S. patent application Ser. No. 16/182,234, titled STAPLING DEVICE WITH BOTH COMPULSORY AND DISCRETIONARY LOCKOUTS BASED ON SENSED PARAMETERS;

U.S. patent application Ser. No. 16/182,240, titled POWERED STAPLING DEVICE CONFIGURED TO ADJUST FORCE, ADVANCEMENT SPEED, AND OVERALL STROKE OF CUTTING MEMBER BASED ON SENSED PARAMETER OF FIRING OR CLAMPING;

U.S. patent application Ser. No. 16/182,235, titled VARIATION OF RADIO FREQUENCY AND ULTRASONIC POWER LEVEL IN COOPERATION WITH VARYING CLAMP ARM PRESSURE TO ACHIEVE PREDEFINED HEAT FLUX OR POWER APPLIED TO TISSUE; and U.S. patent application Ser. No. 16/182,238, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION.

Applicant of the present application owns the following U.S. Patent Applications that were filed on Oct. 26, 2018, the disclosure of each of which is herein incorporated by reference in its entirety:

U.S. patent application Ser. No. 16/172,303, titled METHOD FOR OPERATING A POWERED ARTICULATING MULTI-CLIP APPLIER;

U.S. patent application Ser. No. 16/172,130, titled CLIP APPLIER COMPRISING INTERCHANGEABLE CLIP RELOADS;

U.S. patent application Ser. No. 16/172,066, titled CLIP APPLIER COMPRISING A MOVABLE CLIP MAGAZINE;

U.S. patent application Ser. No. 16/172,078, titled CLIP APPLIER COMPRISING A ROTATABLE CLIP MAGAZINE;

U.S. patent application Ser. No. 16/172,087, titled CLIP APPLIER COMPRISING CLIP ADVANCING SYSTEMS;

U.S. patent application Ser. No. 16/172,094, titled CLIP APPLIER COMPRISING A CLIP CRIMPING SYSTEM;

U.S. patent application Ser. No. 16/172,128, titled CLIP APPLIER COMPRISING A RECIPROCATING CLIP ADVANCING MEMBER;

U.S. patent application Ser. No. 16/172,168, titled CLIP APPLIER COMPRISING A MOTOR CONTROLLER;

U.S. patent application Ser. No. 16/172,164, titled SURGICAL SYSTEM COMPRISING A SURGICAL TOOL AND A SURGICAL HUB;

U.S. patent application Ser. No. 16/172,328, titled METHOD OF HUB COMMUNICATION WITH SURGICAL INSTRUMENT SYSTEMS;

U.S. patent application Ser. No. 16/172,280, titled METHOD FOR PRODUCING A SURGICAL INSTRUMENT COMPRISING A SMART ELECTRICAL SYSTEM;

U.S. patent application Ser. No. 16/172,219, titled METHOD OF HUB COMMUNICATION WITH SURGICAL INSTRUMENT SYSTEMS;

U.S. patent application Ser. No. 16/172,248, titled METHOD OF HUB COMMUNICATION WITH SURGICAL INSTRUMENT SYSTEMS;

U.S. patent application Ser. No. 16/172,198, titled METHOD OF HUB COMMUNICATION WITH SURGICAL INSTRUMENT SYSTEMS; and U.S. patent application Ser. No. 16/172,155, titled METHOD OF HUB COMMUNICATION WITH SURGICAL INSTRUMENT SYSTEMS.

Applicant of the present application owns the following U.S. Patent Applications, filed on Aug. 28, 2018, the disclosure of each of which is herein incorporated by reference in its entirety:

U.S. patent application Ser. No. 16/115,214, titled ESTIMATING STATE OF ULTRASONIC END EFFECTOR AND CONTROL SYSTEM THEREFOR;

U.S. patent application Ser. No. 16/115,205, titled TEMPERATURE CONTROL OF ULTRASONIC END EFFECTOR AND CONTROL SYSTEM THEREFOR;

U.S. patent application Ser. No. 16/115,233, titled RADIO FREQUENCY ENERGY DEVICE FOR DELIVERING COMBINED ELECTRICAL SIGNALS;

U.S. patent application Ser. No. 16/115,208, titled CONTROLLING AN ULTRASONIC SURGICAL INSTRUMENT ACCORDING TO TISSUE LOCATION;

U.S. patent application Ser. No. 16/115,220, titled CONTROLLING ACTIVATION OF AN ULTRASONIC SURGICAL INSTRUMENT ACCORDING TO THE PRESENCE OF TISSUE;

U.S. patent application Ser. No. 16/115,232, titled DETERMINING TISSUE COMPOSITION VIA AN ULTRASONIC SYSTEM;

U.S. patent application Ser. No. 16/115,239, titled DETERMINING THE STATE OF AN ULTRASONIC ELECTROMECHANICAL SYSTEM ACCORDING TO FREQUENCY SHIFT;

U.S. patent application Ser. No. 16/115,247, titled DETERMINING THE STATE OF AN ULTRASONIC END EFFECTOR;

U.S. patent application Ser. No. 16/115,211, titled SITUATIONAL AWARENESS OF ELECTROSURGICAL SYSTEMS;

U.S. patent application Ser. No. 16/115,226, titled MECHANISMS FOR CONTROLLING DIFFERENT ELECTROMECHANICAL SYSTEMS OF AN ELECTROSURGICAL INSTRUMENT;

U.S. patent application Ser. No. 16/115,240, titled DETECTION OF END EFFECTOR EMERSION IN LIQUID;

U.S. patent application Ser. No. 16/115,249, titled INTERRUPTION OF ENERGY DUE TO INADVERTENT CAPACITIVE COUPLING;

U.S. patent application Ser. No. 16/115,256, titled INCREASING RADIO FREQUENCY TO CREATE PAD-LESS MONOPOLAR LOOP;

U.S. patent application Ser. No. 16/115,223, titled BIPOLAR COMBINATION DEVICE THAT AUTOMATI- CALLY ADJUSTS PRESSURE BASED ON ENERGY MODALITY; and U.S. patent application Ser. No. 16/115,238, titled ACTIVATION OF ENERGY DEVICES.

Applicant of the present application owns the following U.S. Patent Applications, filed on Aug. 24, 2018, the disclosure of each of which is herein incorporated by reference in its entirety:

U.S. patent application Ser. No. 16/112,129, titled SURGICAL SUTURING INSTRUMENT CONFIGURED TO MANIPULATE TISSUE USING MECHANICAL AND ELECTRICAL POWER;

U.S. patent application Ser. No. 16/112,155, titled SURGICAL SUTURING INSTRUMENT COMPRISING A CAPTURE WIDTH WHICH IS LARGER THAN TROCAR DIAMETER;

U.S. patent application Ser. No. 16/112,168, titled SURGICAL SUTURING INSTRUMENT COMPRISING A NON-CIRCULAR NEEDLE;

U.S. patent application Ser. No. 16/112,180, titled ELECTRICAL POWER OUTPUT CONTROL BASED ON MECHANICAL FORCES;

U.S. patent application Ser. No. 16/112,193, titled REACTIVE ALGORITHM FOR SURGICAL SYSTEM;

U.S. patent application Ser. No. 16/112,099, titled SURGICAL INSTRUMENT COMPRISING AN ADAPTIVE ELECTRICAL SYSTEM;

U.S. patent application Ser. No. 16/112,112, titled CONTROL SYSTEM ARRANGEMENTS FOR A MODULAR SURGICAL INSTRUMENT;

U.S. patent application Ser. No. 16/112,119, titled ADAPTIVE CONTROL PROGRAMS FOR A SURGICAL SYSTEM COMPRISING MORE THAN ONE TYPE OF CARTRIDGE;

U.S. patent application Ser. No. 16/112,097, titled SURGICAL INSTRUMENT SYSTEMS COMPRISING BATTERY ARRANGEMENTS;

U.S. patent application Ser. No. 16/112,109, titled SURGICAL INSTRUMENT SYSTEMS COMPRISING HANDLE ARRANGEMENTS;

U.S. patent application Ser. No. 16/112,114, titled SURGICAL INSTRUMENT SYSTEMS COMPRISING FEEDBACK MECHANISMS;

U.S. patent application Ser. No. 16/112,117, titled SURGICAL INSTRUMENT SYSTEMS COMPRISING LOCKOUT MECHANISMS;

U.S. patent application Ser. No. 16/112,095, titled SURGICAL INSTRUMENTS COMPRISING A LOCKABLE END EFFECTOR SOCKET;

U.S. patent application Ser. No. 16/112,121, titled SURGICAL INSTRUMENTS COMPRISING A SHIFTING MECHANISM;

U.S. patent application Ser. No. 16/112,151, titled SURGICAL INSTRUMENTS COMPRISING A SYSTEM FOR ARTICULATION AND ROTATION COMPENSATION;

U.S. patent application Ser. No. 16/112,154, titled SURGICAL INSTRUMENTS COMPRISING A BIASED SHIFTING MECHANISM;

U.S. patent application Ser. No. 16/112,226, titled SURGICAL INSTRUMENTS COMPRISING AN ARTICULATION DRIVE THAT PROVIDES FOR HIGH ARTICULATION ANGLES;

U.S. patent application Ser. No. 16/112,062, titled SURGICAL DISSECTORS AND MANUFACTURING TECHNIQUES;

U.S. patent application Ser. No. 16/112,098, titled SURGICAL DISSECTORS CONFIGURED TO APPLY MECHANICAL AND ELECTRICAL ENERGY;

U.S. patent application Ser. No. 16/112,237, titled SURGICAL CLIP APPLIER CONFIGURED TO STORE CLIPS IN A STORED STATE;

U.S. patent application Ser. No. 16/112,245, titled SURGICAL CLIP APPLIER COMPRISING AN EMPTY CLIP CARTRIDGE LOCKOUT;

U.S. patent application Ser. No. 16/112,249, titled SURGICAL CLIP APPLIER COMPRISING AN AUTOMATIC CLIP FEEDING SYSTEM;

U.S. patent application Ser. No. 16/112,253, titled SURGICAL CLIP APPLIER COMPRISING ADAPTIVE FIRING CONTROL; and U.S. patent application Ser. No. 16/112,257, titled SURGICAL CLIP APPLIER COMPRISING ADAPTIVE CONTROL IN RESPONSE TO A STRAIN GAUGE CIRCUIT.

Applicant of the present application owns the following U.S. Patent Applications, filed on Jun. 29, 2018, the disclosure of each of which is herein incorporated by reference in its entirety:

U.S. patent application Ser. No. 16/024,090, titled CAPACITIVE COUPLED RETURN PATH PAD WITH SEPARABLE ARRAY ELEMENTS;

U.S. patent application Ser. No. 16/024,057, titled CONTROLLING A SURGICAL INSTRUMENT ACCORDING TO SENSED CLOSURE PARAMETERS;

U.S. patent application Ser. No. 16/024,067, titled SYSTEMS FOR ADJUSTING END EFFECTOR PARAMETERS BASED ON PERIOPERATIVE INFORMATION;

U.S. patent application Ser. No. 16/024,075, titled SAFETY SYSTEMS FOR SMART POWERED SURGICAL STAPLING;

U.S. patent application Ser. No. 16/024,083, titled SAFETY SYSTEMS FOR SMART POWERED SURGICAL STAPLING;

U.S. patent application Ser. No. 16/024,094, titled SURGICAL SYSTEMS FOR DETECTING END EFFECTOR TISSUE DISTRIBUTION IRREGULARITIES;

U.S. patent application Ser. No. 16/024,138, titled SYSTEMS FOR DETECTING PROXIMITY OF SURGICAL END EFFECTOR TO CANCEROUS TISSUE;

U.S. patent application Ser. No. 16/024,150, titled SURGICAL INSTRUMENT CARTRIDGE SENSOR ASSEMBLIES;

U.S. patent application Ser. No. 16/024,160, titled VARIABLE OUTPUT CARTRIDGE SENSOR ASSEMBLY;

U.S. patent application Ser. No. 16/024,124, titled SURGICAL INSTRUMENT HAVING A FLEXIBLE ELECTRODE;

U.S. patent application Ser. No. 16/024,132, titled SURGICAL INSTRUMENT HAVING A FLEXIBLE CIRCUIT;

U.S. patent application Ser. No. 16/024,141, titled SURGICAL INSTRUMENT WITH A TISSUE MARKING ASSEMBLY;

U.S. patent application Ser. No. 16/024,162, titled SURGICAL SYSTEMS WITH PRIORITIZED DATA TRANSMISSION CAPABILITIES;

U.S. patent application Ser. No. 16/024,066, titled SURGICAL EVACUATION SENSING AND MOTOR CONTROL;

U.S. patent application Ser. No. 16/024,096, titled SURGICAL EVACUATION SENSOR ARRANGEMENTS;

U.S. patent application Ser. No. 16/024,116, titled SURGICAL EVACUATION FLOW PATHS;

U.S. patent application Ser. No. 16/024,149, titled SURGICAL EVACUATION SENSING AND GENERATOR CONTROL;

U.S. patent application Ser. No. 16/024,180, titled SURGICAL EVACUATION SENSING AND DISPLAY;

U.S. patent application Ser. No. 16/024,245, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;

U.S. patent application Ser. No. 16/024,258, titled SMOKE EVACUATION SYSTEM INCLUDING A SEGMENTED CONTROL CIRCUIT FOR INTERACTIVE SURGICAL PLATFORM;

U.S. patent application Ser. No. 16/024,265, titled SURGICAL EVACUATION SYSTEM WITH A COMMUNICATION CIRCUIT FOR COMMUNICATION BETWEEN A FILTER AND A SMOKE EVACUATION DEVICE; and U.S. patent application Ser. No. 16/024,273, titled DUAL IN-SERIES LARGE AND SMALL DROPLET FILTERS.

Applicant of the present application owns the following U.S. Patent Applications, filed on Mar. 29, 2018, the disclosure of each of which is herein incorporated by reference in its entirety:

U.S. patent application Ser. No. 15/940,641, titled INTERACTIVE SURGICAL SYSTEMS WITH ENCRYPTED COMMUNICATION CAPABILITIES;

U.S. patent application Ser. No. 15/940,648, titled INTERACTIVE SURGICAL SYSTEMS WITH CONDITION HANDLING OF DEVICES AND DATA CAPABILITIES;

U.S. patent application Ser. No. 15/940,656, titled SURGICAL HUB COORDINATION OF CONTROL AND COMMUNICATION OF OPERATING ROOM DEVICES;

U.S. patent application Ser. No. 15/940,666, titled SPATIAL AWARENESS OF SURGICAL HUBS IN OPERATING ROOMS;

U.S. patent application Ser. No. 15/940,670, titled COOPERATIVE UTILIZATION OF DATA DERIVED FROM SECONDARY SOURCES BY INTELLIGENT SURGICAL HUBS;

U.S. patent application Ser. No. 15/940,677, titled SURGICAL HUB CONTROL ARRANGEMENTS;

U.S. patent application Ser. No. 15/940,632, titled DATA STRIPPING METHOD TO INTERROGATE PATIENT RECORDS AND CREATE ANONYMIZED RECORD;

U.S. patent application Ser. No. 15/940,640, titled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, titled SELF DESCRIBING DATA PACKETS GENERATED AT AN ISSUING INSTRUMENT;

U.S. patent application Ser. No. 15/940,649, titled DATA PAIRING TO INTERCONNECT A DEVICE MEASURED PARAMETER WITH AN OUTCOME;

U.S. patent application Ser. No. 15/940,654, titled SURGICAL HUB SITUATIONAL AWARENESS;

U.S. patent application Ser. No. 15/940,663, titled SURGICAL SYSTEM DISTRIBUTED PROCESSING;

U.S. patent application Ser. No. 15/940,668, titled AGGREGATION AND REPORTING OF SURGICAL HUB DATA;

U.S. patent application Ser. No. 15/940,671, titled SURGICAL HUB SPATIAL AWARENESS TO DETERMINE DEVICES IN OPERATING THEATER;

U.S. patent application Ser. No. 15/940,686, titled DISPLAY OF ALIGNMENT OF STAPLE CARTRIDGE TO PRIOR LINEAR STAPLE LINE;

U.S. patent application Ser. No. 15/940,700, titled STERILE FIELD INTERACTIVE CONTROL DISPLAYS;

U.S. patent application Ser. No. 15/940,629, titled COMPUTER IMPLEMENTED INTERACTIVE SURGICAL SYSTEMS;

U.S. patent application Ser. No. 15/940,704, titled USE OF LASER LIGHT AND RED-GREEN-BLUE COLORATION TO DETERMINE PROPERTIES OF BACK SCATTERED LIGHT;

U.S. patent application Ser. No. 15/940,722, titled CHARACTERIZATION OF TISSUE IRREGULARITIES THROUGH THE USE OF MONO-CHROMATIC LIGHT REFRACTIVITY;

U.S. patent application Ser. No. 15/940,742, titled DUAL CMOS ARRAY IMAGING;

U.S. patent application Ser. No. 15/940,636, titled ADAPTIVE CONTROL PROGRAM UPDATES FOR SURGICAL DEVICES;

U.S. patent application Ser. No. 15/940,653, titled ADAPTIVE CONTROL PROGRAM UPDATES FOR SURGICAL HUBS;

U.S. patent application Ser. No. 15/940,660, titled CLOUD-BASED MEDICAL ANALYTICS FOR CUSTOMIZATION AND RECOMMENDATIONS TO A USER;

U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, titled CLOUD-BASED MEDICAL ANALYTICS FOR SECURITY AND AUTHENTICATION TRENDS AND REACTIVE MEASURES;

U.S. patent application Ser. No. 15/940,706, titled DATA HANDLING AND PRIORITIZATION IN A CLOUD ANALYTICS NETWORK;

U.S. patent application Ser. No. 15/940,675, titled CLOUD INTERFACE FOR COUPLED SURGICAL DEVICES;

U.S. patent application Ser. No. 15/940,627, titled DRIVE ARRANGEMENTS FOR ROBOT-ASSISTED SURGICAL PLATFORMS;

U.S. patent application Ser. No. 15/940,637, titled COMMUNICATION ARRANGEMENTS FOR ROBOT-ASSISTED SURGICAL PLATFORMS;

U.S. patent application Ser. No. 15/940,642, titled CONTROLS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS;

U.S. patent application Ser. No. 15/940,680, titled CONTROLLERS FOR ROBOT-ASSISTED SURGICAL PLATFORMS;

U.S. patent application Ser. No. 15/940,683, titled COOPERATIVE SURGICAL ACTIONS FOR ROBOT-ASSISTED SURGICAL PLATFORMS;

U.S. patent application Ser. No. 15/940,690, titled DISPLAY ARRANGEMENTS FOR ROBOT-ASSISTED SURGICAL PLATFORMS; and U.S. patent application Ser. No. 15/940,711, titled SENSING ARRANGEMENTS FOR ROBOT-ASSISTED SURGICAL PLATFORMS.

Applicant of the present application owns the following U.S. Provisional Patent Applications, filed on Mar. 8, 2018, the disclosure of each of which is herein incorporated by reference in its entirety:

U.S. Provisional Patent Application No. 62/640,417, titled TEMPERATURE CONTROL IN ULTRASONIC DEVICE AND CONTROL SYSTEM THEREFOR; and U.S. Provisional Patent Application No. 62/640,415, titled ESTIMATING STATE OF ULTRASONIC END EFFECTOR AND CONTROL SYSTEM THEREFOR.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Figure 1:
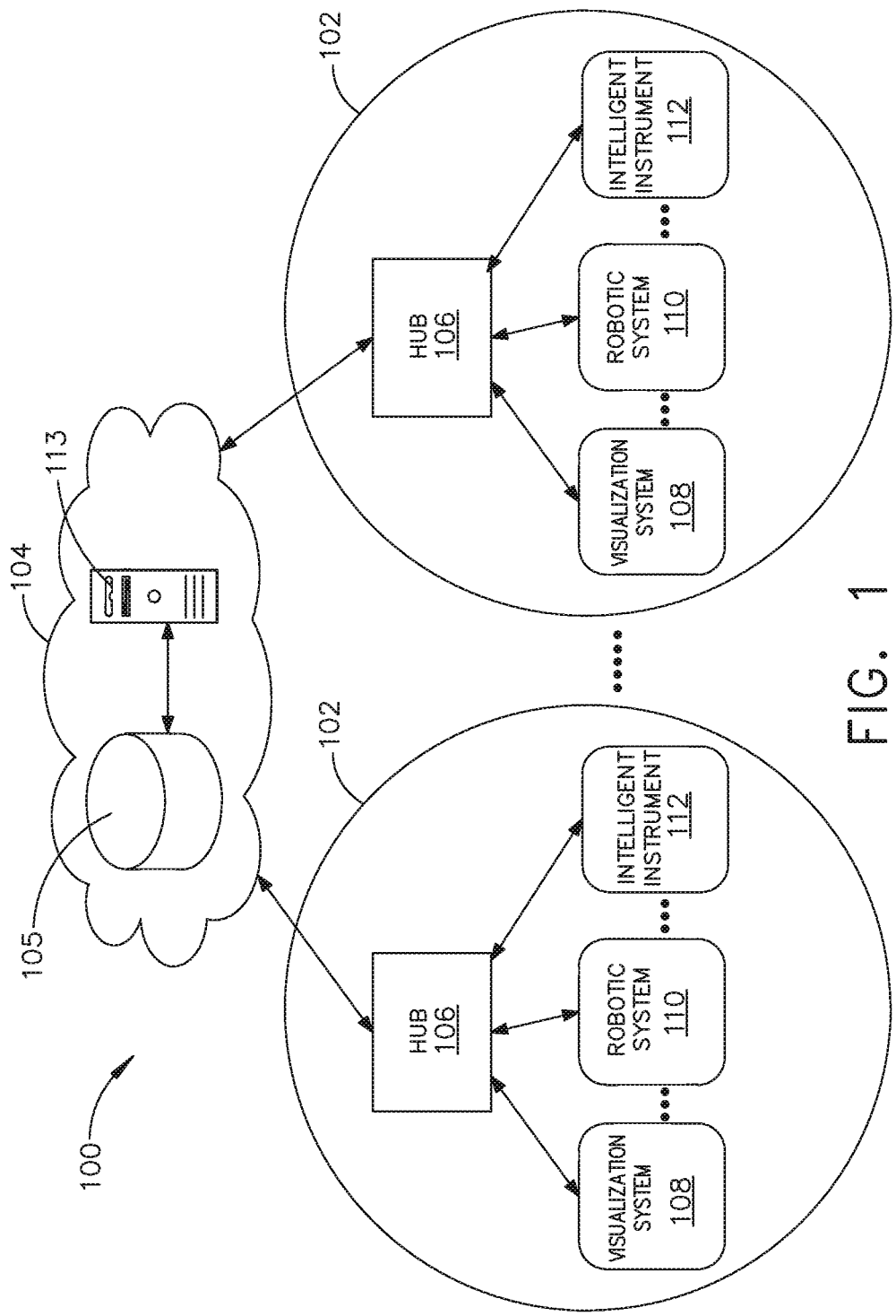
FIG. 1 is a block diagram of a computer-implemented interactive surgical system, in accordance with at least one aspect of the present disclosure.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 3:
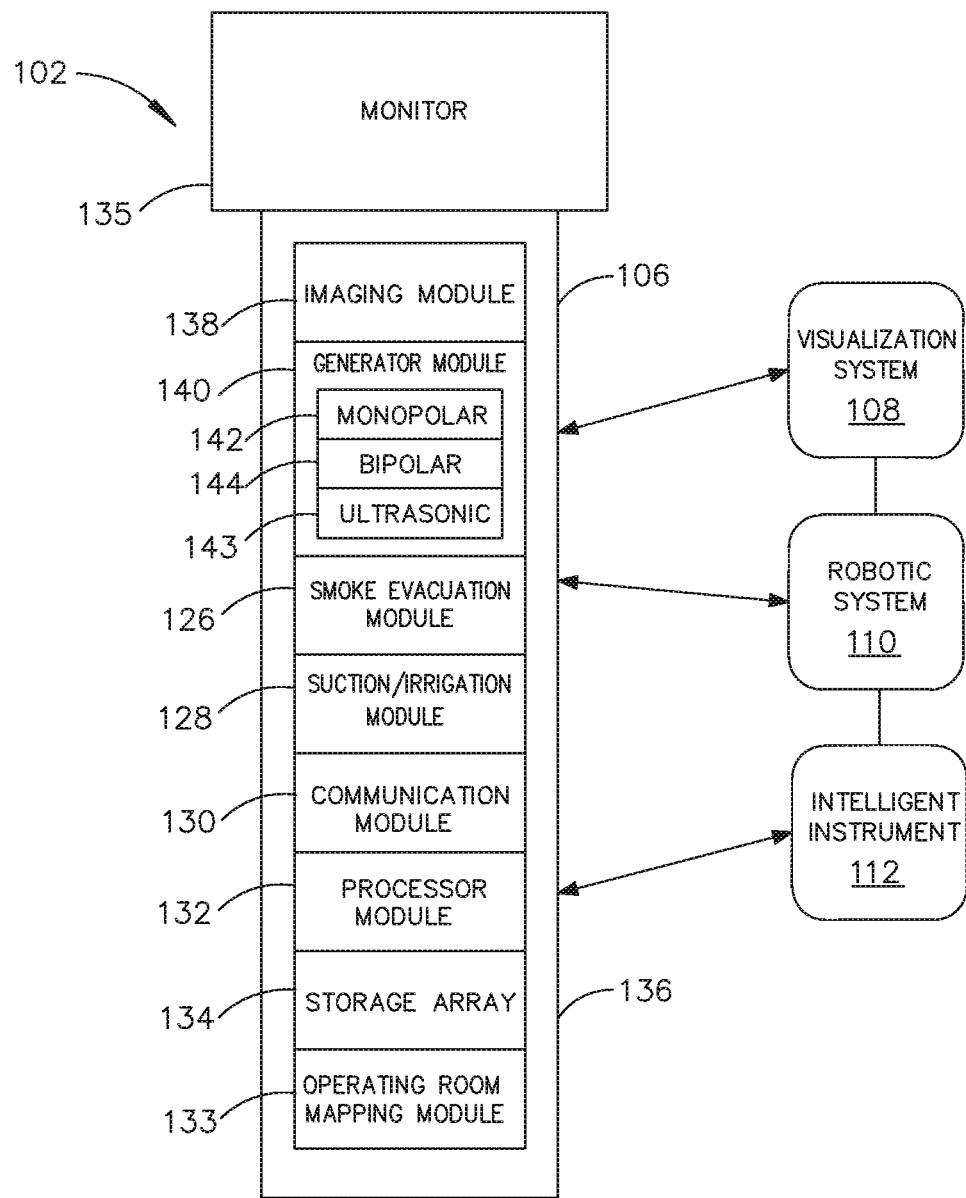
FIG. 3 is a surgical hub paired with a visualization system, a robotic system, and an intelligent instrument, in accordance with at least one aspect of the present disclosure.

FIG. 3 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 2:
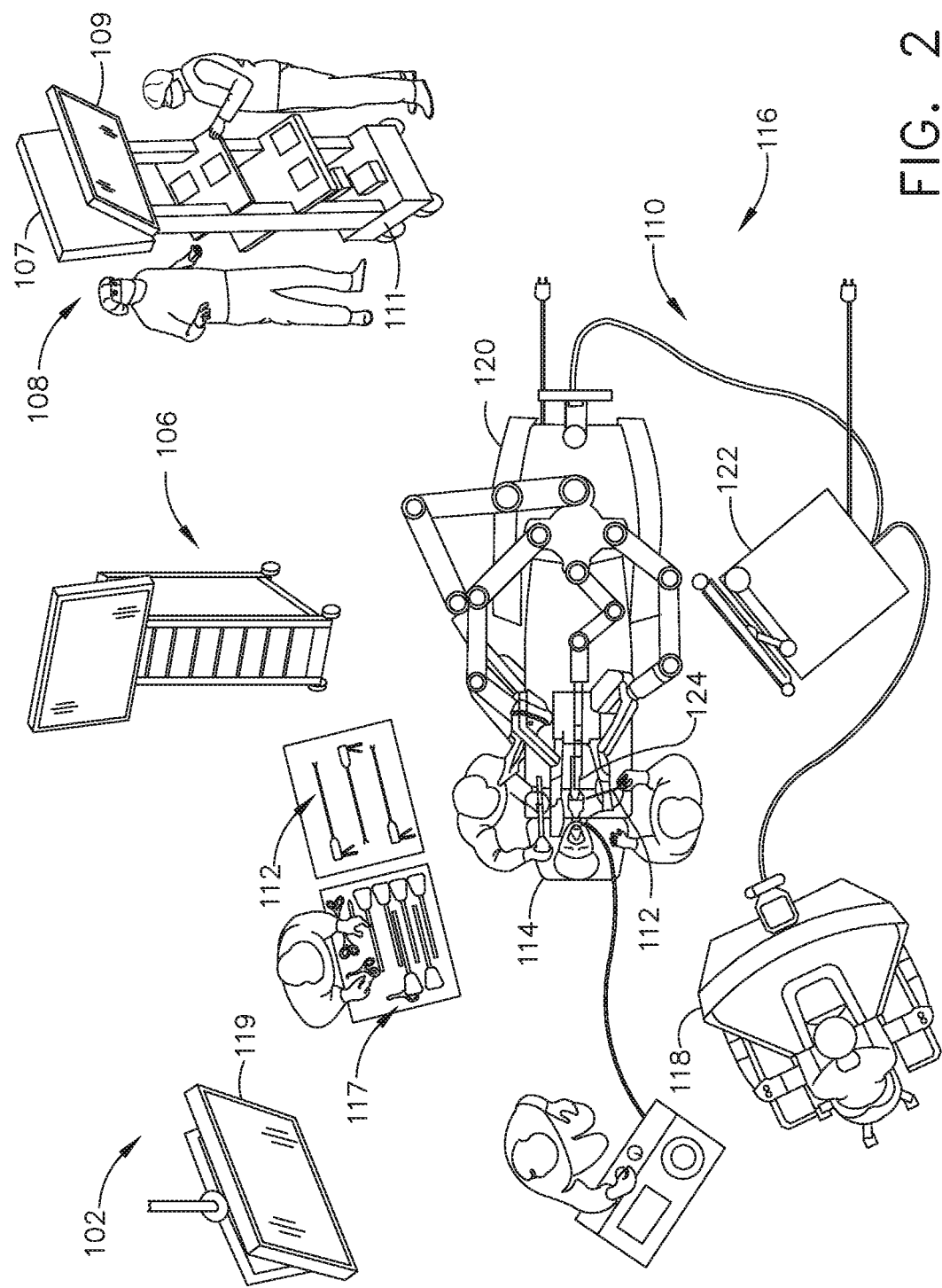
FIG. 2 is a surgical system being used to perform a surgical procedure in an operating room, in accordance with at least one aspect of the present disclosure.

In various aspects, the visualization system 108 includes one or more imaging sensors, one or more image processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snap-shot of a surgical site, as recorded by an imaging device 124, on a non-sterile display 107 or 109, while maintaining a live feed of the surgical site on the primary display 119. The snap-shot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snap-shot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
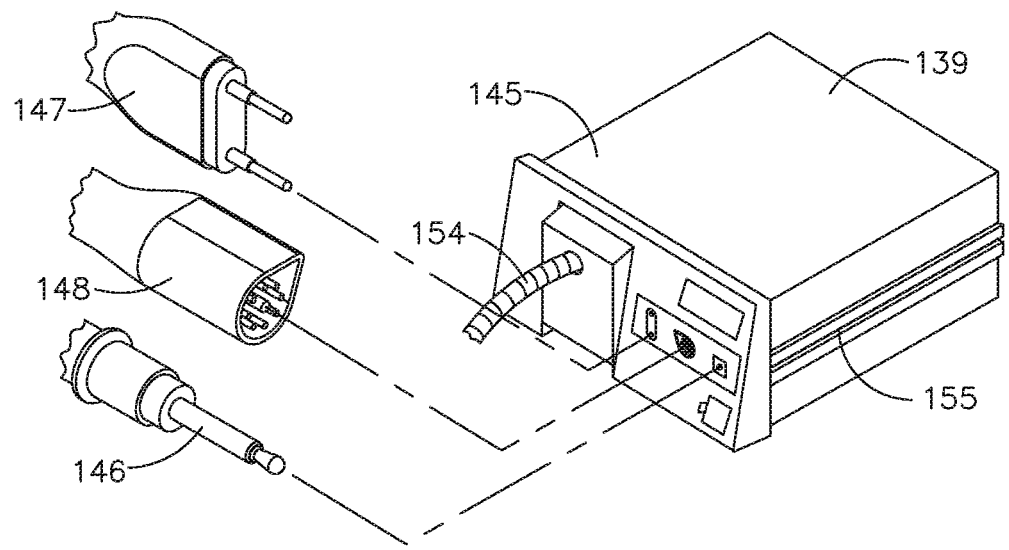
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

Figure 4:
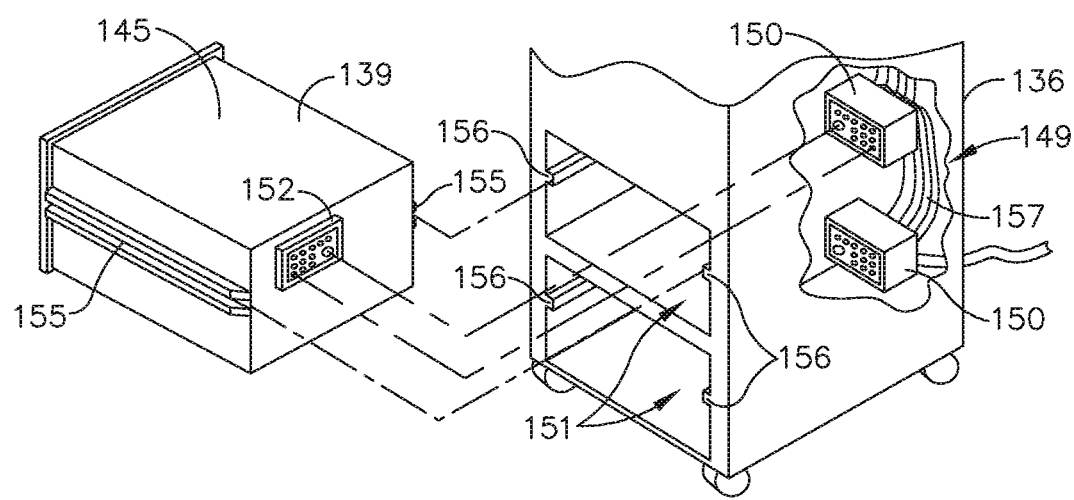
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
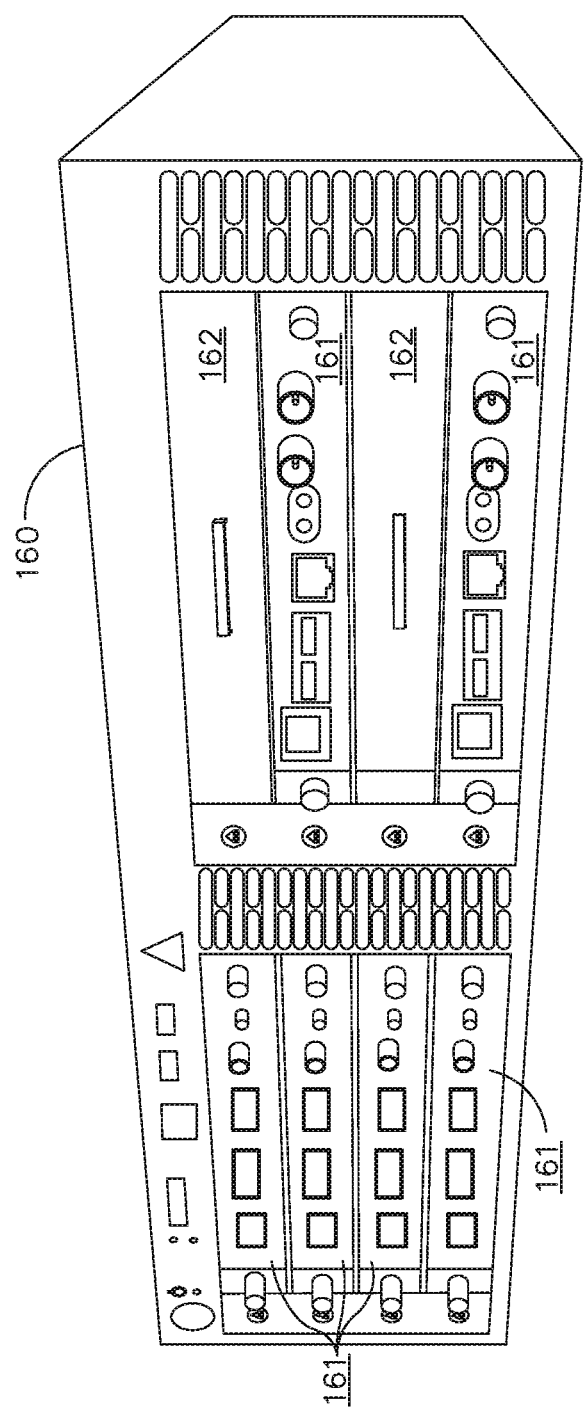
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
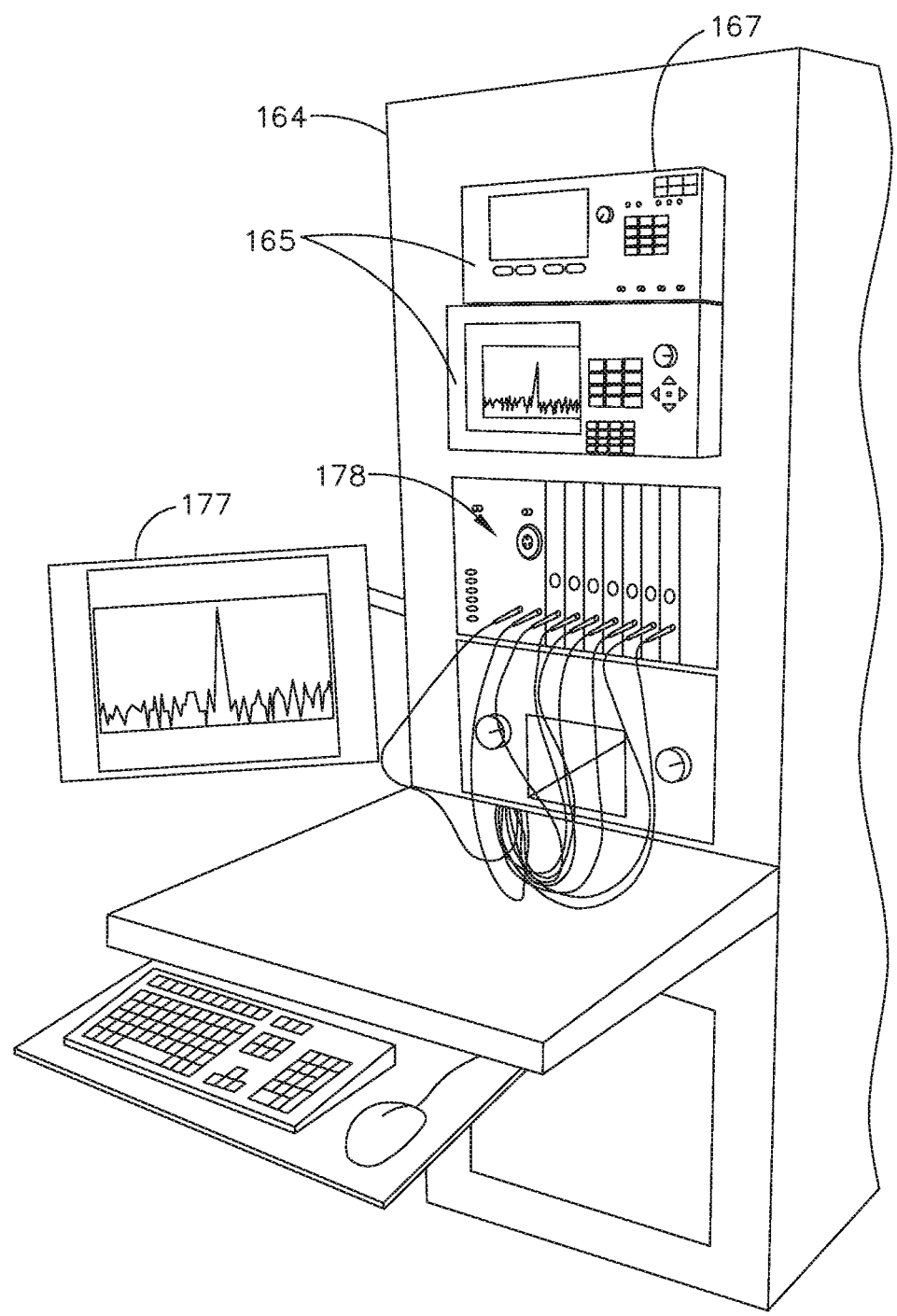
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Figure 8:
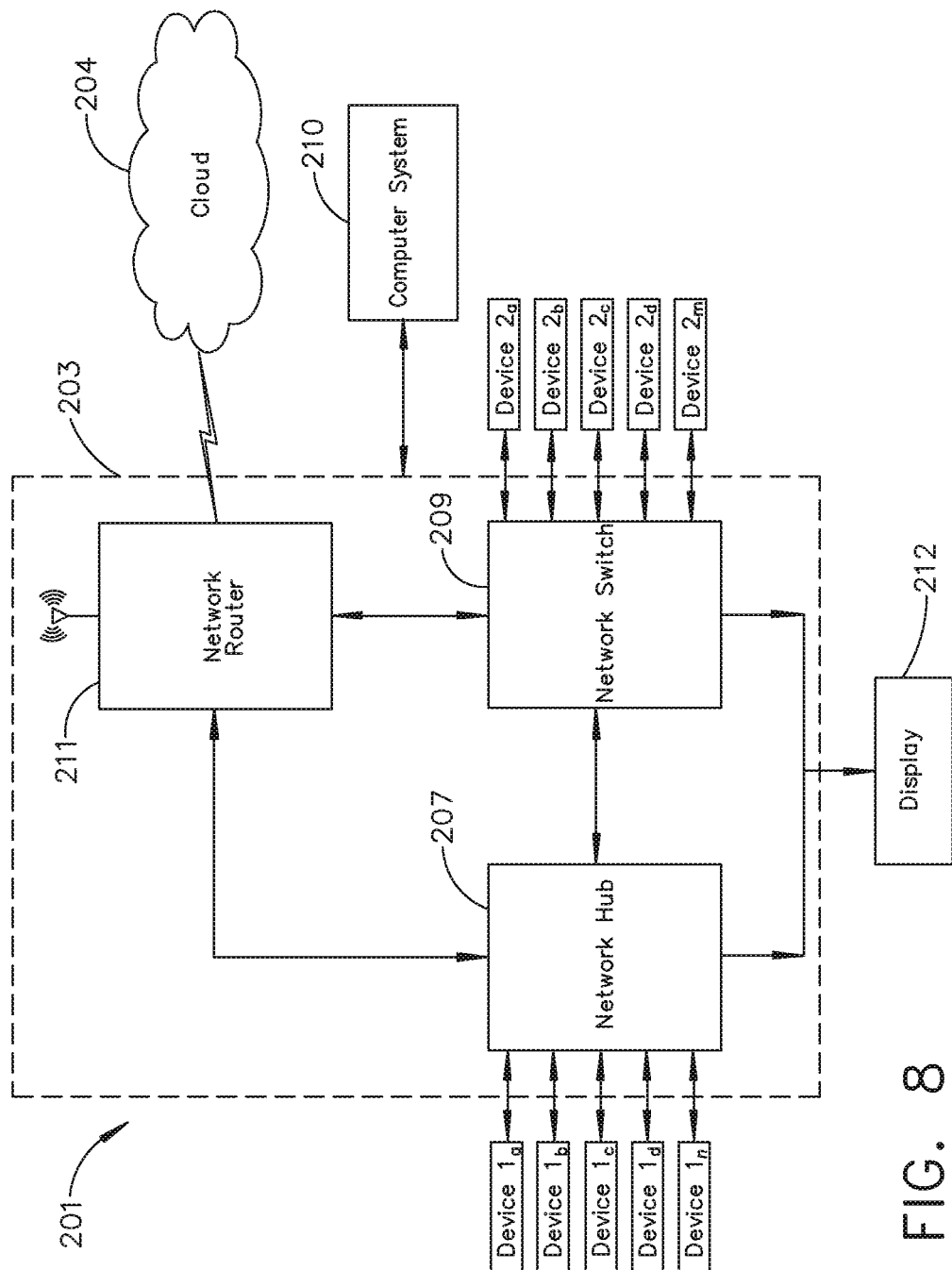
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/internet protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LIE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
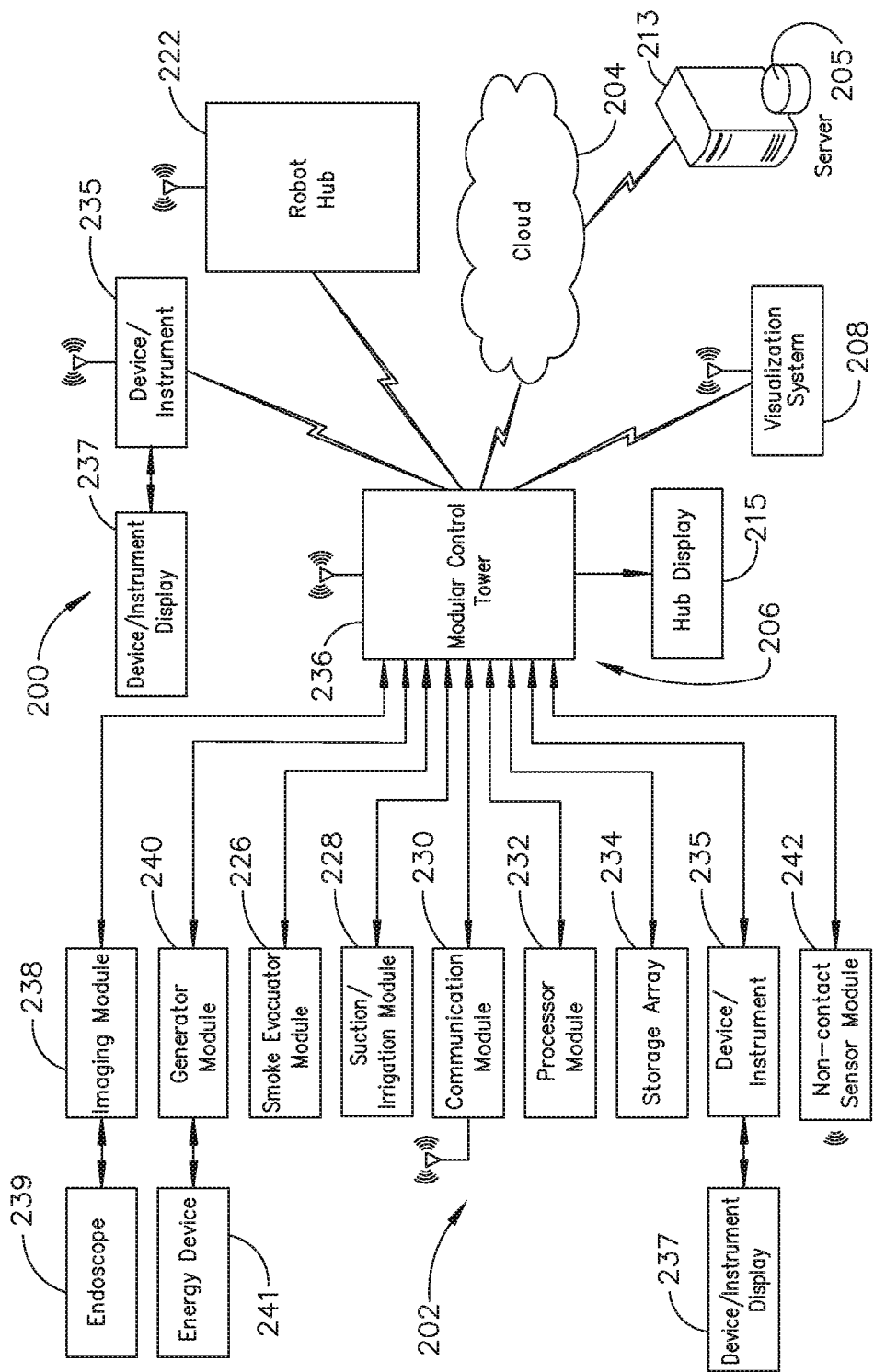
FIG. 9 illustrates a computer-implemented interactive surgical system, in accordance with at least one aspect of the present disclosure.
Figure 10:
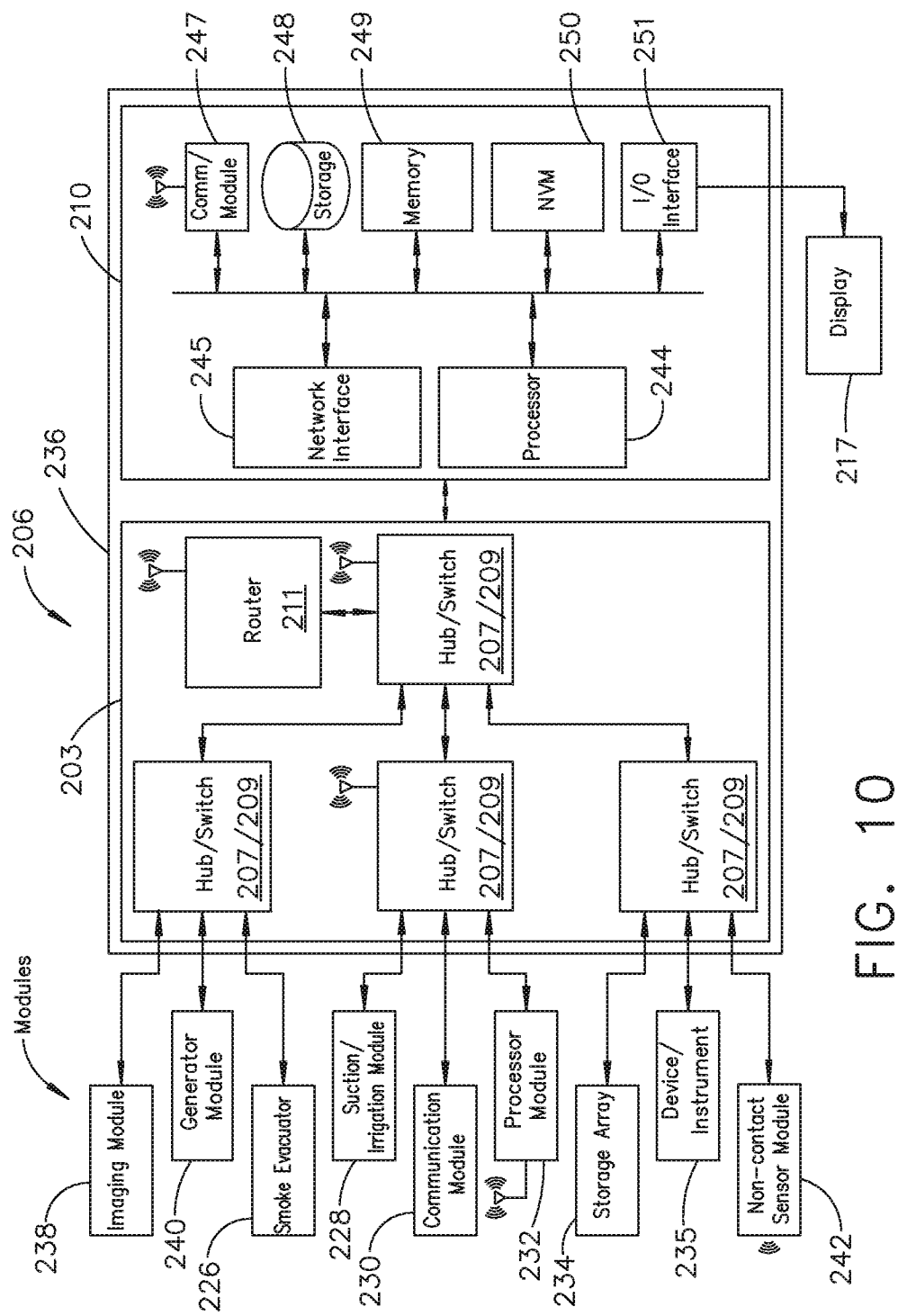
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, the disclosure of which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
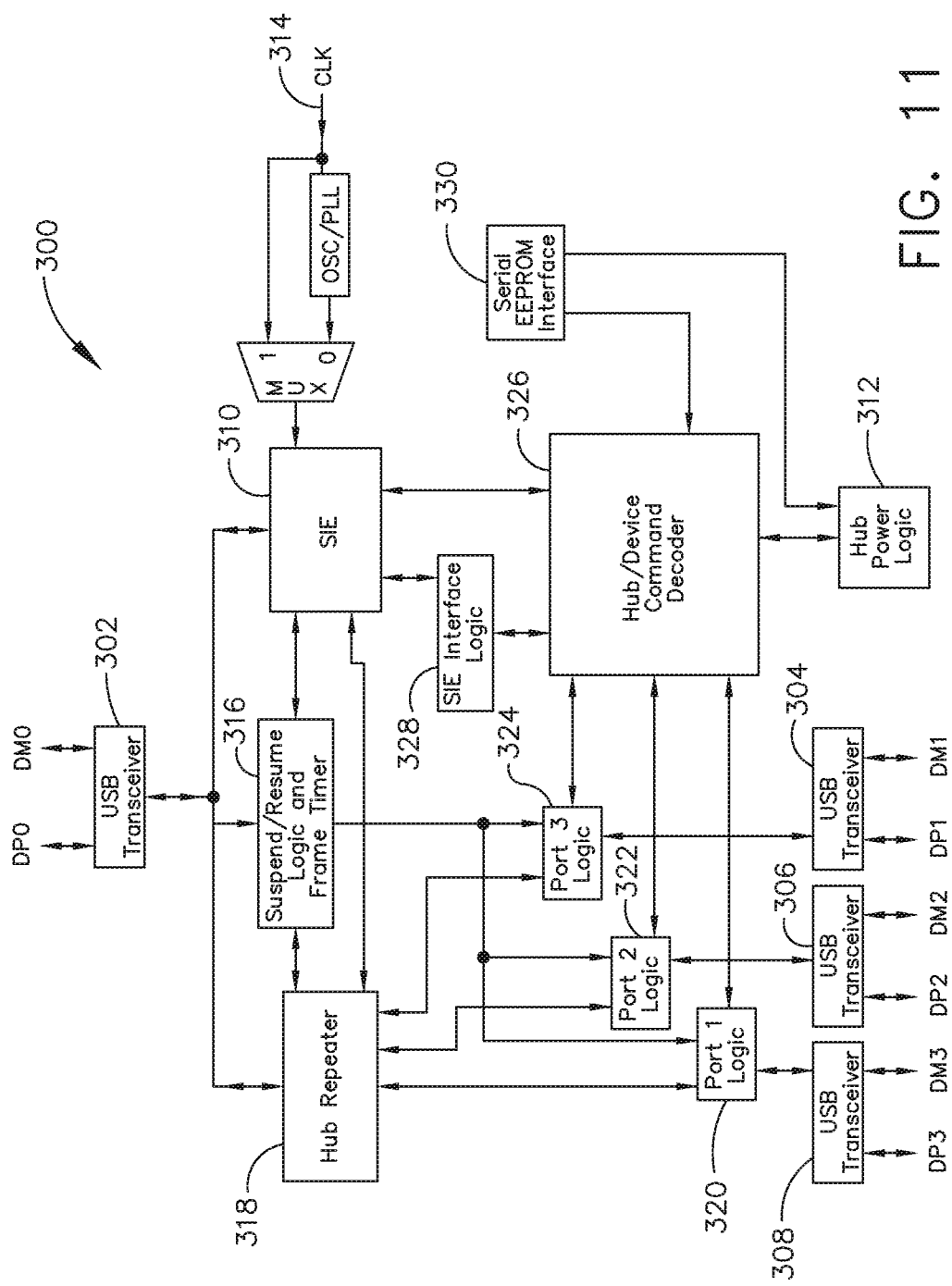
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, according to one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
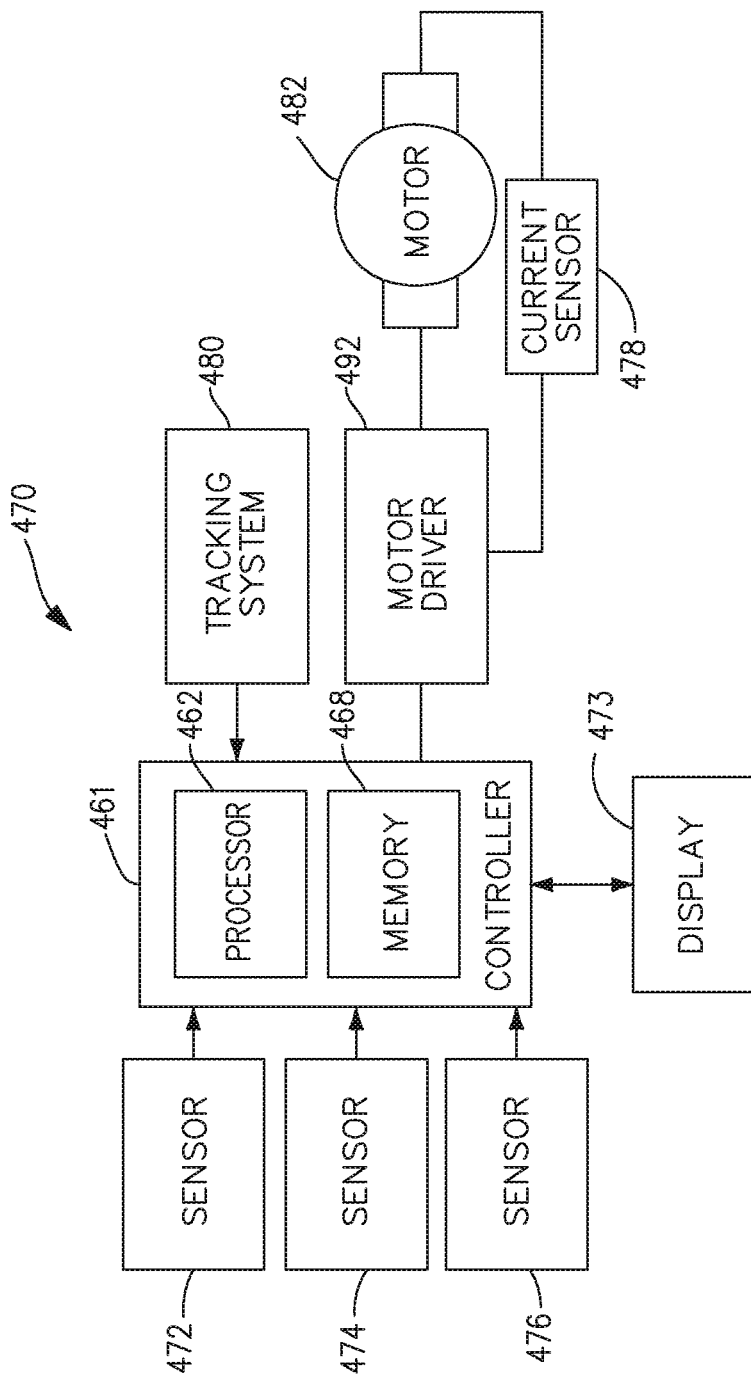
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 is configured to determine the position of the longitudinally movable displacement member. The position information is provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the I-beam, each of which can be adapted and configured to include a rack of drive teeth. Accordingly, as used herein, the term displacement member is used generically to refer to any movable member of the surgical instrument or tool such as the drive member, the firing member, the firing bar, the I-beam, or any element that can be displaced. In one aspect, the longitudinally movable drive member is coupled to the firing member, the firing bar, and the I-beam. Accordingly, the absolute positioning system can, in effect, track the linear displacement of the I-beam by tracking the linear displacement of the longitudinally movable drive member. In various other aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, I-beam, or combinations thereof.

A single revolution of the sensor element associated with the position sensor 472 is equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also includes a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
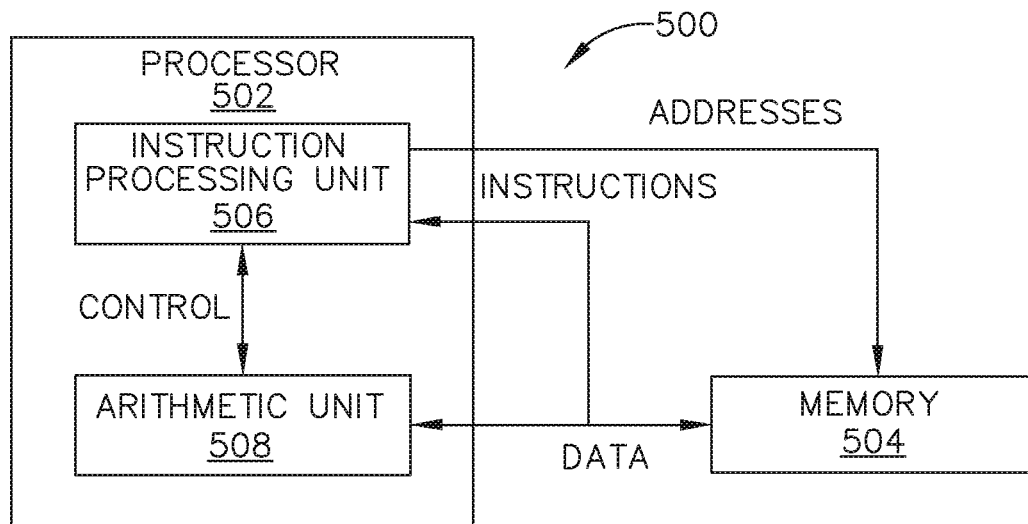
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
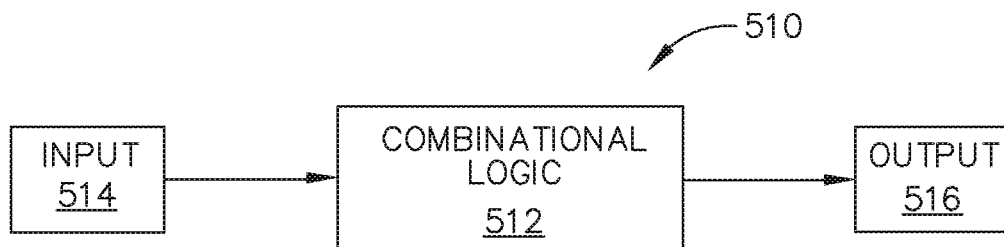
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
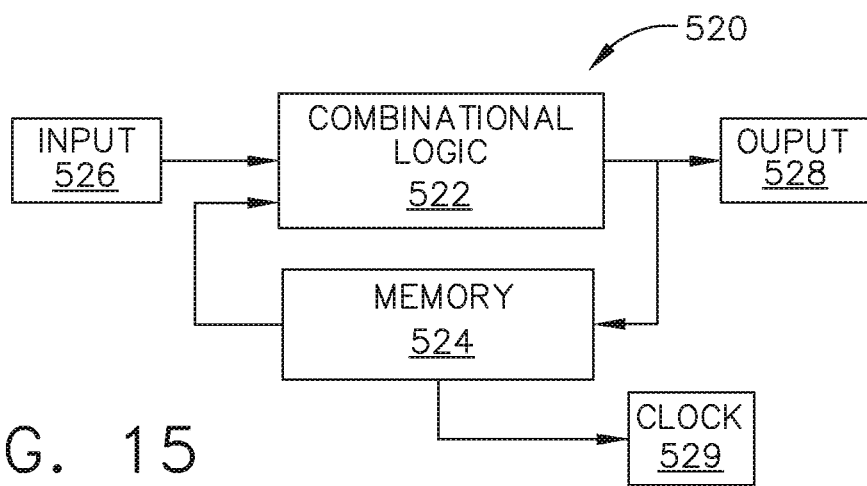
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
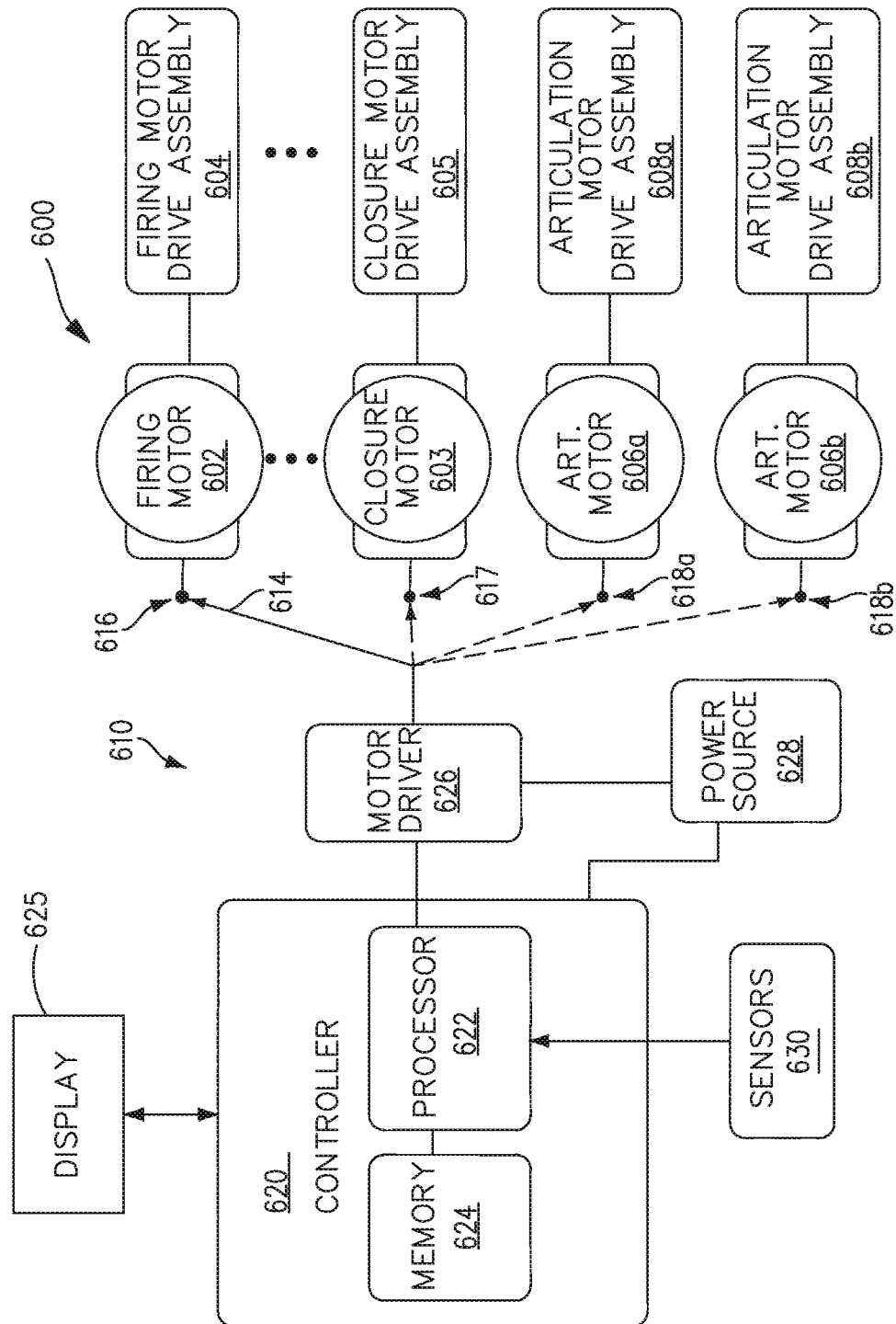
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 17:
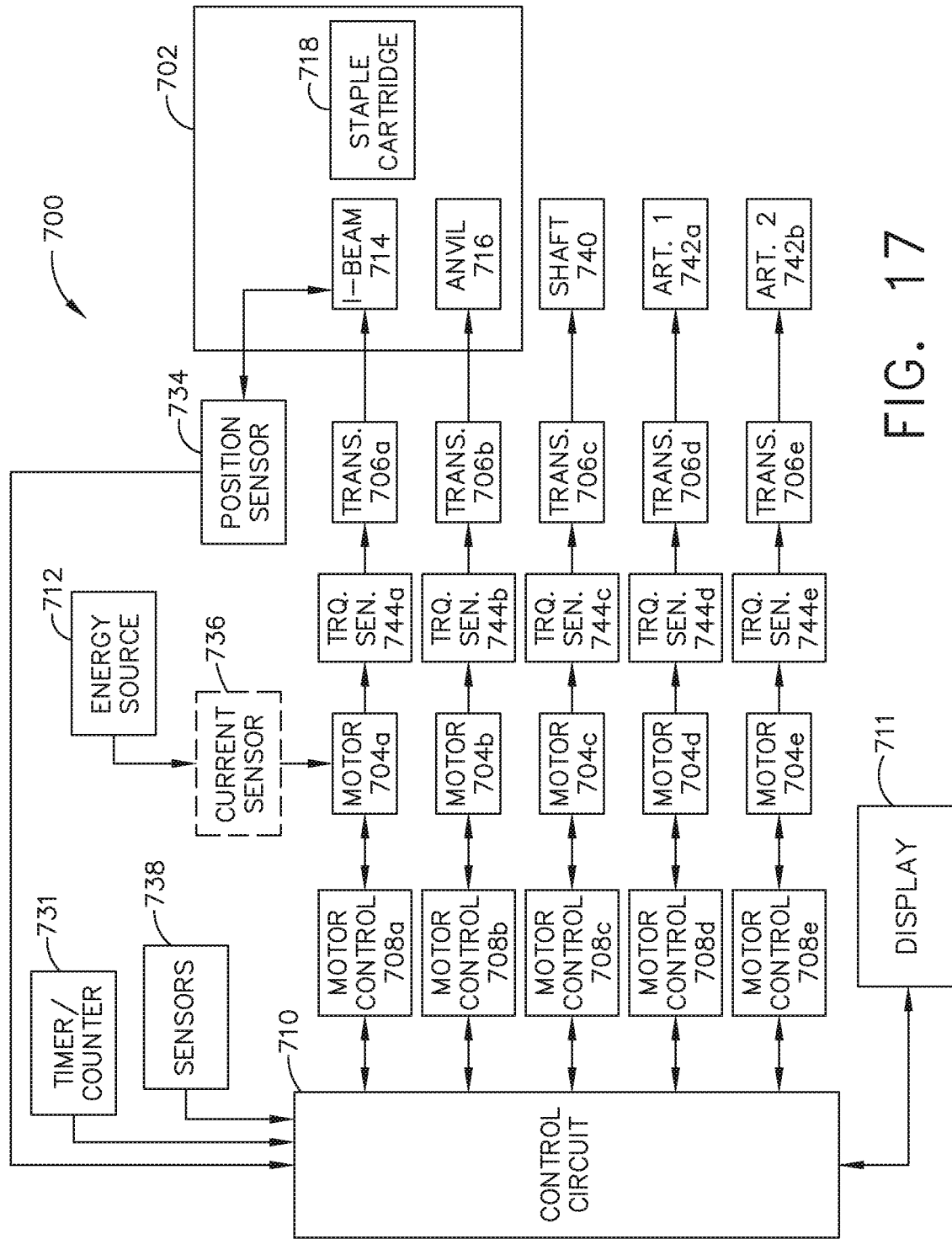
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links In one aspect, the surgical instrument 700 may be programmed or configured to individually control a firing member, a closure member, a shaft member, and/or one or more articulation members. The surgical instrument 700 comprises a control circuit 710 configured to control motor-driven firing members, closure members, shaft members, and/or one or more articulation members.

In one aspect, the robotic surgical instrument 700 comprises a control circuit 710 configured to control an anvil 716 and an I-beam 714 (including a sharp cutting edge) portion of an end effector 702, a removable staple cartridge 718, a shaft 740, and one or more articulation members 742a, 742b via a plurality of motors 704a-704e. A position sensor 734 may be configured to provide position feedback of the I-beam 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the I-beam 714 as determined by the position sensor 734 with the output of the timer/counter 731 such that the control circuit 710 can determine the position of the I-beam 714 at a specific time (t) relative to a starting position or the time (t) when the I-beam 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the I-beam 714, anvil 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the I-beam 714. The position sensor 734 may be or include any type of sensor that is capable of generating position data that indicate a position of the I-beam 714. In some examples, the position sensor 734 may include an encoder configured to provide a series of pulses to the control circuit 710 as the I-beam 714 translates distally and proximally. The control circuit 710 may track the pulses to determine the position of the I-beam 714. Other suitable position sensors may be used, including, for example, a proximity sensor. Other types of position sensors may provide other signals indicating motion of the I-beam 714. Also, in some examples, the position sensor 734 may be omitted. Where any of the motors 704a-704e is a stepper motor, the control circuit 710 may track the position of the I-beam 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the I-beam 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the I-beam 714. The transmission 706a comprises movable mechanical elements such as rotating elements and a firing member to control the movement of the I-beam 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the I-beam 714. A position sensor 734 may be configured to provide the position of the I-beam 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the firing member translates distally, an I-beam 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the anvil 716. The transmission 706b comprises movable mechanical elements such as rotating elements and a closure member to control the movement of the anvil 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708b. In response to the closure signal, the motor 704b advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702 ±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it, and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704a-704e. The force required to advance any of the movable mechanical elements such as the I-beam 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move an I-beam 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

Figure 18:
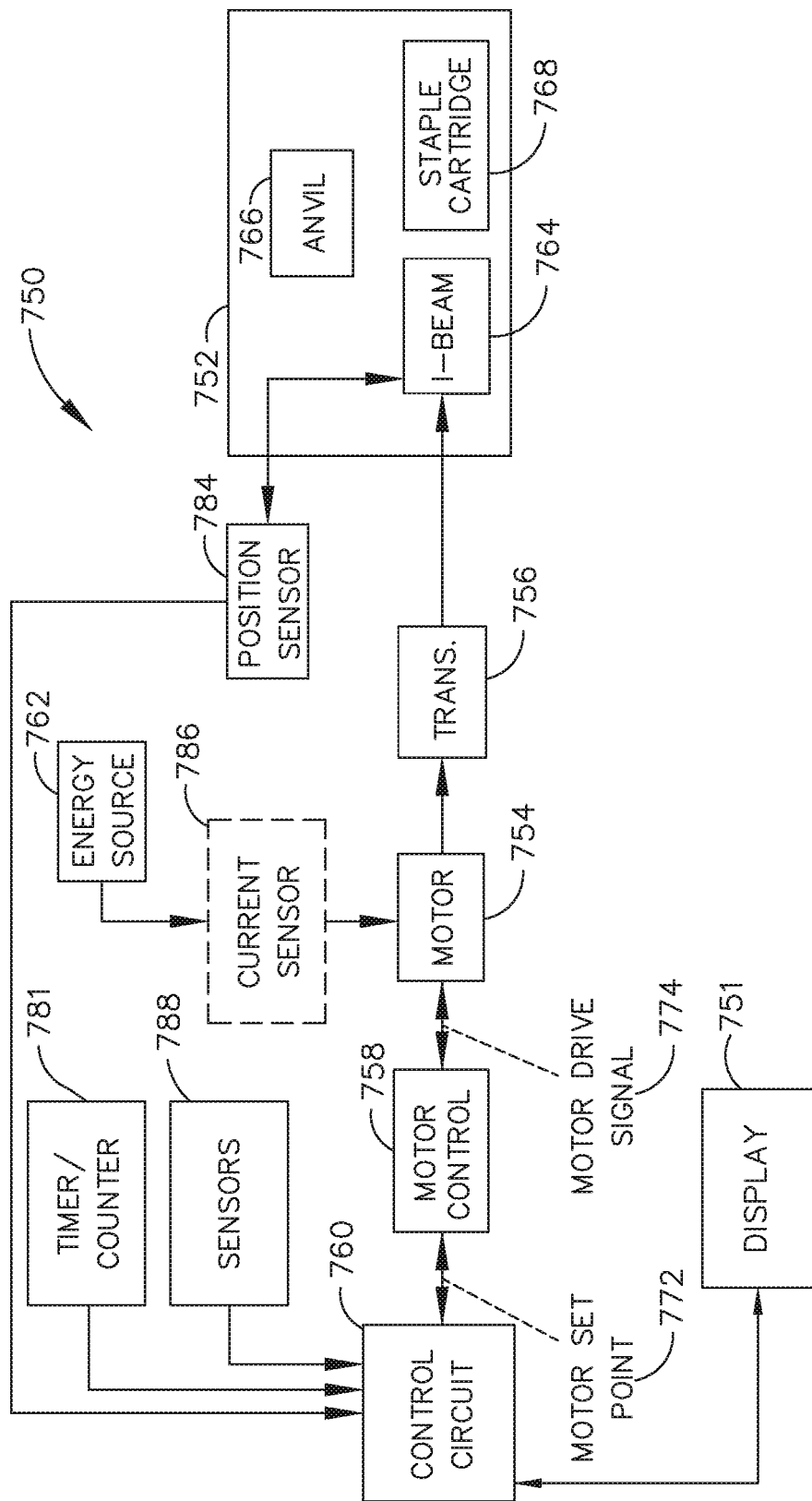
FIG. 18 illustrates a block diagram of a surgical instrument programmed to control the distal translation of a displacement member, in accordance with at least one aspect of the present disclosure.

FIG. 18 illustrates a block diagram of a surgical instrument 750 programmed to control the distal translation of a displacement member according to one aspect of this disclosure. In one aspect, the surgical instrument 750 is programmed to control the distal translation of a displacement member such as the I-beam 764. The surgical instrument 750 comprises an end effector 752 that may comprise an anvil 766, an I-beam 764 (including a sharp cutting edge), and a removable staple cartridge 768.

The position, movement, displacement, and/or translation of a linear displacement member, such as the I-beam 764, can be measured by an absolute positioning system, sensor arrangement, and position sensor 784. Because the I-beam 764 is coupled to a longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move an I-beam 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or I-beam 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, an I-beam 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the I-beam 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 19:
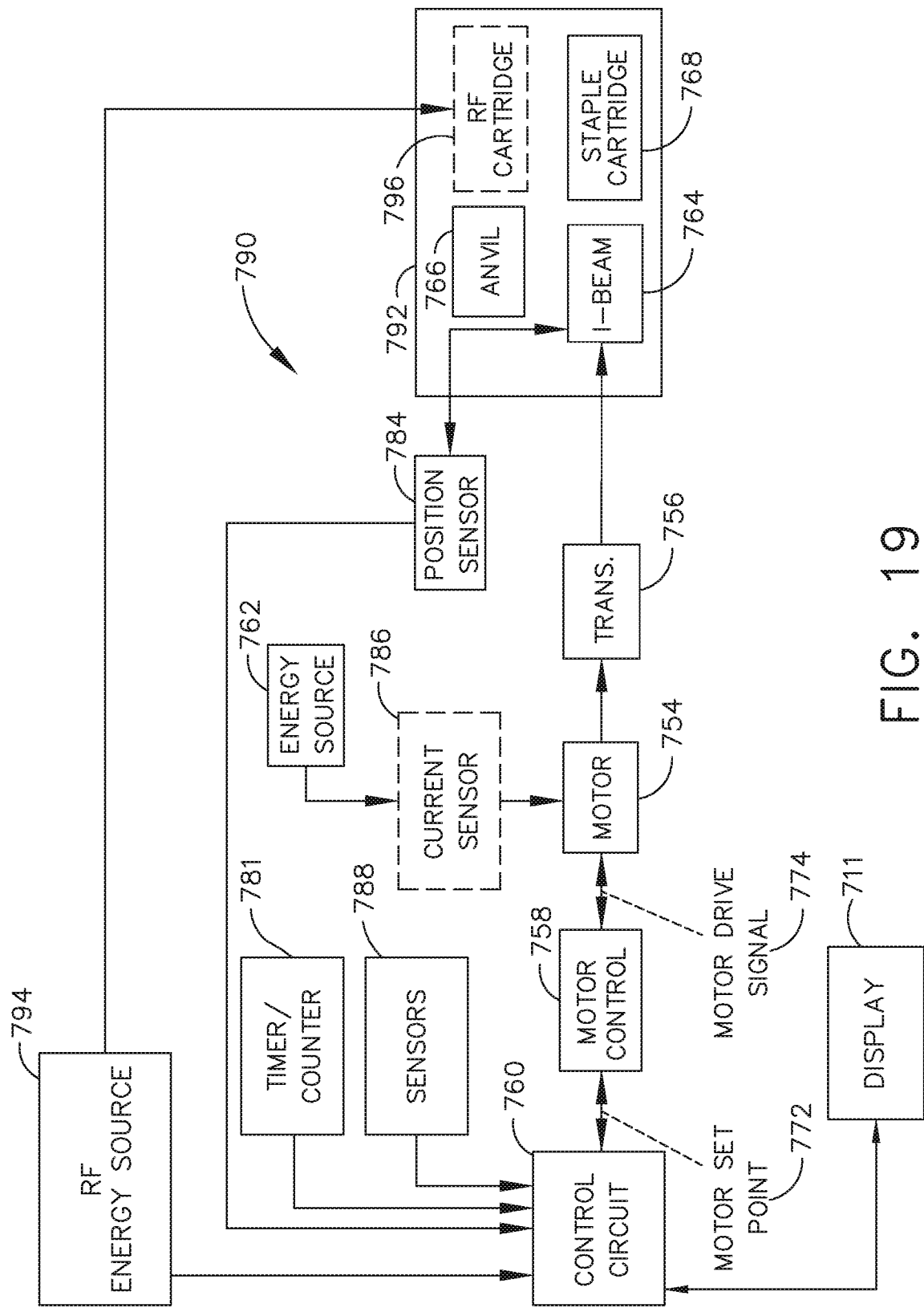
FIG. 19 is a schematic diagram of a surgical instrument configured to control various functions, in accordance with at least one aspect of the present disclosure.

FIG. 19 is a schematic diagram of a surgical instrument 790 configured to control various functions according to one aspect of this disclosure. In one aspect, the surgical instrument 790 is programmed to control distal translation of a displacement member such as the I-beam 764. The surgical instrument 790 comprises an end effector 792 that may comprise an anvil 766, an I-beam 764, and a removable staple cartridge 768 which may be interchanged with an RF cartridge 796 (shown in dashed line).

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the I-beam 764 may be implemented as a knife member comprising a knife body that operably supports a tissue cutting blade thereon and may further include anvil engagement tabs or features and channel engagement features or a foot. In one aspect, the staple cartridge 768 may be implemented as a standard (mechanical) surgical fastener cartridge. In one aspect, the RF cartridge 796 may be implemented as an RF cartridge. These and other sensors arrangements are described in commonly owned U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety.

The position, movement, displacement, and/or translation of a linear displacement member, such as the I-beam 764, can be measured by an absolute positioning system, sensor arrangement, and position sensor represented as position sensor 784. Because the I-beam 764 is coupled to the longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764, as described herein. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by the closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor portion of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

An RF energy source 794 is coupled to the end effector 792 and is applied to the RF cartridge 796 when the RF cartridge 796 is loaded in the end effector 792 in place of the staple cartridge 768. The control circuit 760 controls the delivery of the RF energy to the RF cartridge 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Generator Hardware

Figure 20:
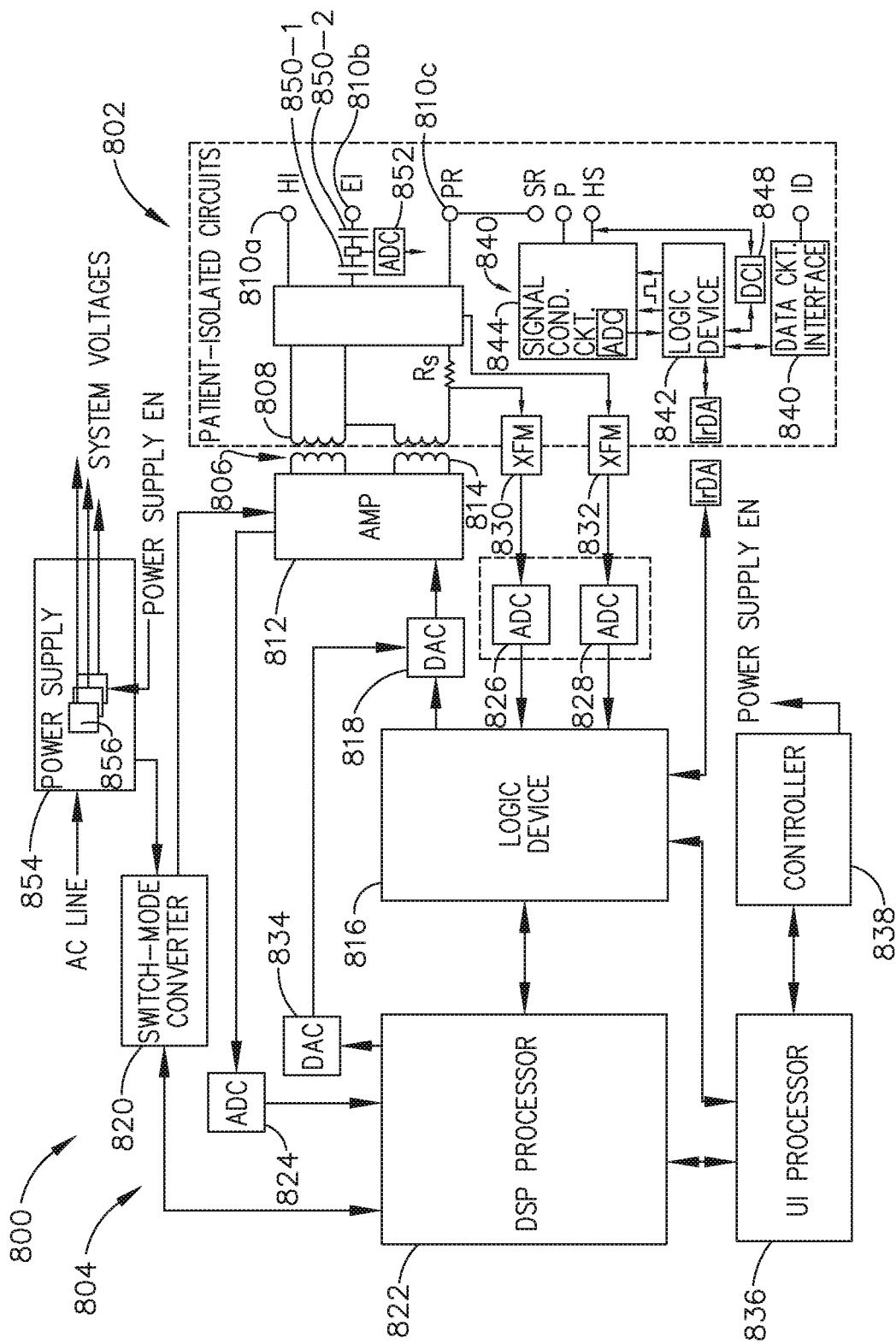
FIG. 20 is a simplified block diagram of a generator configured to provide inductorless tuning, among other benefits, in accordance with at least one aspect of the present disclosure.

FIG. 20 is a simplified block diagram of a generator 800 configured to provide inductorless tuning, among other benefits. Additional details of the generator 800 are described in U.S. Pat. No. 9,060,775, titled SURGICAL GENERATOR FOR ULTRASONIC AND ELECTROSURGICAL DEVICES, which issued on Jun. 23, 2015, which is herein incorporated by reference in its entirety. The generator 800 may comprise a patient isolated stage 802 in communication with a non-isolated stage 804 via a power transformer 806. A secondary winding 808 of the power transformer 806 is contained in the isolated stage 802 and may comprise a tapped configuration (e.g., a center-tapped or a non-center-tapped configuration) to define drive signal outputs 810a, 810b, 810c for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, drive signal outputs 810a, 810c may output an ultrasonic drive signal (e.g., a 420V root-mean-square (RMS) drive signal) to an ultrasonic surgical instrument, and drive signal outputs 810b, 810c may output an RF electrosurgical drive signal (e.g., a 100V RMS drive signal) to an RF electrosurgical instrument, with the drive signal output 810b corresponding to the center tap of the power transformer 806.

In certain forms, the ultrasonic and electrosurgical drive signals may be provided simultaneously to distinct surgical instruments and/or to a single surgical instrument, such as the multifunction surgical instrument, having the capability to deliver both ultrasonic and electrosurgical energy to tissue. It will be appreciated that the electrosurgical signal, provided either to a dedicated electrosurgical instrument and/or to a combined multifunction ultrasonic/electrosurgical instrument may be either a therapeutic or sub-therapeutic level signal where the sub-therapeutic signal can be used, for example, to monitor tissue or instrument conditions and provide feedback to the generator. For example, the ultrasonic and RF signals can be delivered separately or simultaneously from a generator with a single output port in order to provide the desired output signal to the surgical instrument, as will be discussed in more detail below. Accordingly, the generator can combine the ultrasonic and electrosurgical RF energies and deliver the combined energies to the multifunction ultrasonic/electrosurgical instrument. Bipolar electrodes can be placed on one or both jaws of the end effector. One jaw may be driven by ultrasonic energy in addition to electrosurgical RF energy, working simultaneously. The ultrasonic energy may be employed to dissect tissue, while the electrosurgical RF energy may be employed for vessel sealing.

The non-isolated stage 804 may comprise a power amplifier 812 having an output connected to a primary winding 814 of the power transformer 806. In certain forms, the power amplifier 812 may comprise a push-pull amplifier. For example, the non-isolated stage 804 may further comprise a logic device 816 for supplying a digital output to a digital-to-analog converter (DAC) circuit 818, which in turn supplies a corresponding analog signal to an input of the power amplifier 812. In certain forms, the logic device 816 may comprise a programmable gate array (PGA), a FPGA, programmable logic device (PLD), among other logic circuits, for example. The logic device 816, by virtue of controlling the input of the power amplifier 812 via the DAC circuit 818, may therefore control any of a number of parameters (e.g., frequency, waveform shape, waveform amplitude) of drive signals appearing at the drive signal outputs 810a, 810b, 810c. In certain forms and as discussed below, the logic device 816, in conjunction with a processor (e.g., a DSP discussed below), may implement a number of DSP-based and/or other control algorithms to control parameters of the drive signals output by the generator 800.

Power may be supplied to a power rail of the power amplifier 812 by a switch-mode regulator 820, e.g., a power converter. In certain forms, the switch-mode regulator 820 may comprise an adjustable buck regulator, for example. The non-isolated stage 804 may further comprise a first processor 822, which in one form may comprise a DSP processor such as an Analog Devices ADSP-21469 SHARC DSP, available from Analog Devices, Norwood, Mass., for example, although in various forms any suitable processor may be employed. In certain forms the DSP processor 822 may control the operation of the switch-mode regulator 820 responsive to voltage feedback data received from the power amplifier 812 by the DSP processor 822 via an ADC circuit 824. In one form, for example, the DSP processor 822 may receive as input, via the ADC circuit 824, the waveform envelope of a signal (e.g., an RF signal) being amplified by the power amplifier 812. The DSP processor 822 may then control the switch-mode regulator 820 (e.g., via a PWM output) such that the rail voltage supplied to the power amplifier 812 tracks the waveform envelope of the amplified signal. By dynamically modulating the rail voltage of the power amplifier 812 based on the waveform envelope, the efficiency of the power amplifier 812 may be significantly improved relative to a fixed rail voltage amplifier schemes.

In certain forms, the logic device 816, in conjunction with the DSP processor 822, may implement a digital synthesis circuit such as a direct digital synthesizer control scheme to control the waveform shape, frequency, and/or amplitude of drive signals output by the generator 800. In one form, for example, the logic device 816 may implement a DDS control algorithm by recalling waveform samples stored in a dynamically updated lookup table (LUT), such as a RAM LUT, which may be embedded in an FPGA. This control algorithm is particularly useful for ultrasonic applications in which an ultrasonic transducer, such as an ultrasonic transducer, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 800 is impacted by various sources of distortion present in the output drive circuit (e.g., the power transformer 806, the power amplifier 812), voltage and current feedback data based on the drive signal may be input into an algorithm, such as an error control algorithm implemented by the DSP processor 822, which compensates for distortion by suitably pre-distorting or modifying the waveform samples stored in the LUT on a dynamic, ongoing basis (e.g., in real time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 804 may further comprise a first ADC circuit 826 and a second ADC circuit 828 coupled to the output of the power transformer 806 via respective isolation transformers 830, 832 for respectively sampling the voltage and current of drive signals output by the generator 800. In certain forms, the ADC circuits 826, 828 may be configured to sample at high speeds (e.g., 80 mega samples per second (MSPS)) to enable oversampling of the drive signals. In one form, for example, the sampling speed of the ADC circuits 826, 828 may enable approximately 200× (depending on frequency) oversampling of the drive signals. In certain forms, the sampling operations of the ADC circuit 826, 828 may be performed by a single ADC circuit receiving input voltage and current signals via a two-way multiplexer. The use of high-speed sampling in forms of the generator 800 may enable, among other things, calculation of the complex current flowing through the motional branch (which may be used in certain forms to implement DDS-based waveform shape control described above), accurate digital filtering of the sampled signals, and calculation of real power consumption with a high degree of precision. Voltage and current feedback data output by the ADC circuits 826, 828 may be received and processed (e.g., first-in-first-out (FIFO) buffer, multiplexer) by the logic device 816 and stored in data memory for subsequent retrieval by, for example, the DSP processor 822. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 816 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the DSP processor 822, for example, with the frequency control signal being supplied as input to a DDS control algorithm implemented by the logic device 816.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a proportional-integral-derivative (PID) control algorithm, in the DSP processor 822. Variables controlled by the control algorithm to suitably control the current amplitude of the drive signal may include, for example, the scaling of the LUT waveform samples stored in the logic device 816 and/or the full-scale output voltage of the DAC circuit 818 (which supplies the input to the power amplifier 812) via a DAC circuit 834.

The non-isolated stage 804 may further comprise a second processor 836 for providing, among other things user interface (UI) functionality. In one form, the UI processor 836 may comprise an Atmel AT91SAM9263 processor having an ARM 926EJ-S core, available from Atmel Corporation, San Jose, Calif., for example. Examples of UI functionality supported by the UI processor 836 may include audible and visual user feedback, communication with peripheral devices (e.g., via a USB interface), communication with a foot switch, communication with an input device (e.g., a touch screen display) and communication with an output device (e.g., a speaker). The UI processor 836 may communicate with the DSP processor 822 and the logic device 816 (e.g., via SPI buses). Although the UI processor 836 may primarily support UI functionality, it may also coordinate with the DSP processor 822 to implement hazard mitigation in certain forms. For example, the UI processor 836 may be programmed to monitor various aspects of user input and/or other inputs (e.g., touch screen inputs, foot switch inputs, temperature sensor inputs) and may disable the drive output of the generator 800 when an erroneous condition is detected.

In certain forms, both the DSP processor 822 and the UI processor 836, for example, may determine and monitor the operating state of the generator 800. For the DSP processor 822, the operating state of the generator 800 may dictate, for example, which control and/or diagnostic processes are implemented by the DSP processor 822. For the UI processor 836, the operating state of the generator 800 may dictate, for example, which elements of a UI (e.g., display screens, sounds) are presented to a user. The respective DSP and UI processors 822, 836 may independently maintain the current operating state of the generator 800 and recognize and evaluate possible transitions out of the current operating state. The DSP processor 822 may function as the master in this relationship and determine when transitions between operating states are to occur. The UI processor 836 may be aware of valid transitions between operating states and may confirm if a particular transition is appropriate. For example, when the DSP processor 822 instructs the UI processor 836 to transition to a specific state, the UI processor 836 may verify that requested transition is valid. In the event that a requested transition between states is determined to be invalid by the UI processor 836, the UI processor 836 may cause the generator 800 to enter a failure mode.

The non-isolated stage 804 may further comprise a controller 838 for monitoring input devices (e.g., a capacitive touch sensor used for turning the generator 800 on and off, a capacitive touch screen). In certain forms, the controller 838 may comprise at least one processor and/or other controller device in communication with the UI processor 836. In one form, for example, the controller 838 may comprise a processor (e.g., a Meg168 8-bit controller available from Atmel) configured to monitor user input provided via one or more capacitive touch sensors. In one form, the controller 838 may comprise a touch screen controller (e.g., a QT5480 touch screen controller available from Atmel) to control and manage the acquisition of touch data from a capacitive touch screen.

In certain forms, when the generator 800 is in a "power off" state, the controller 838 may continue to receive operating power (e.g., via a line from a power supply of the generator 800, such as the power supply 854 discussed below). In this way, the controller 838 may continue to monitor an input device (e.g., a capacitive touch sensor located on a front panel of the generator 800) for turning the generator 800 on and off. When the generator 800 is in the power off state, the controller 838 may wake the power supply (e.g., enable operation of one or more DC/DC voltage converters 856 of the power supply 854) if activation of the "on/off" input device by a user is detected. The controller 838 may therefore initiate a sequence for transitioning the generator 800 to a "power on" state. Conversely, the controller 838 may initiate a sequence for transitioning the generator 800 to the power off state if activation of the "on/off" input device is detected when the generator 800 is in the power on state. In certain forms, for example, the controller 838 may report activation of the "on/off" input device to the UI processor 836, which in turn implements the necessary process sequence for transitioning the generator 800 to the power off state. In such forms, the controller 838 may have no independent ability for causing the removal of power from the generator 800 after its power on state has been established.

In certain forms, the controller 838 may cause the generator 800 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 802 may comprise an instrument interface circuit 840 to, for example, provide a communication interface between a control circuit of a surgical instrument (e.g., a control circuit comprising handpiece switches) and components of the non-isolated stage 804, such as, for example, the logic device 816, the DSP processor 822, and/or the UI processor 836. The instrument interface circuit 840 may exchange information with components of the non-isolated stage 804 via a communication link that maintains a suitable degree of electrical isolation between the isolated and non-isolated stages 802, 804, such as, for example, an IR-based communication link. Power may be supplied to the instrument interface circuit 840 using, for example, a low-dropout voltage regulator powered by an isolation transformer driven from the non-isolated stage 804.

In one form, the instrument interface circuit 840 may comprise a logic circuit 842 (e.g., logic circuit, programmable logic circuit, PGA, FPGA, PLD) in communication with a signal conditioning circuit 844. The signal conditioning circuit 844 may be configured to receive a periodic signal from the logic circuit 842 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical instrument control circuit (e.g., by using a conductive pair in a cable that connects the generator 800 to the surgical instrument) and monitored to determine a state or configuration of the control circuit. The control circuit may comprise a number of switches, resistors, and/or diodes to modify one or more characteristics (e.g., amplitude, rectification) of the interrogation signal such that a state or configuration of the control circuit is uniquely discernable based on the one or more characteristics. In one form, for example, the signal conditioning circuit 844 may comprise an ADC circuit for generating samples of a voltage signal appearing across inputs of the control circuit resulting from passage of interrogation signal therethrough. The logic circuit 842 (or a component of the non-isolated stage 804) may then determine the state or configuration of the control circuit based on the ADC circuit samples.

In one form, the instrument interface circuit 840 may comprise a first data circuit interface 846 to enable information exchange between the logic circuit 842 (or other element of the instrument interface circuit 840) and a first data circuit disposed in or otherwise associated with a surgical instrument. In certain forms, for example, a first data circuit may be disposed in a cable integrally attached to a surgical instrument handpiece or in an adaptor for interfacing a specific surgical instrument type or model with the generator 800. The first data circuit may be implemented in any suitable manner and may communicate with the generator according to any suitable protocol, including, for example, as described herein with respect to the first data circuit. In certain forms, the first data circuit may comprise a non-volatile storage device, such as an EEPROM device. In certain forms, the first data circuit interface 846 may be implemented separately from the logic circuit 842 and comprise suitable circuitry (e.g., discrete logic devices, a processor) to enable communication between the logic circuit 842 and the first data circuit. In other forms, the first data circuit interface 846 may be integral with the logic circuit 842.

In certain forms, the first data circuit may store information pertaining to the particular surgical instrument with which it is associated. Such information may include, for example, a model number, a serial number, a number of operations in which the surgical instrument has been used, and/or any other type of information. This information may be read by the instrument interface circuit 840 (e.g., by the logic circuit 842), transferred to a component of the non-isolated stage 804 (e.g., to logic device 816, DSP processor 822, and/or UI processor 836) for presentation to a user via an output device and/or for controlling a function or operation of the generator 800. Additionally, any type of information may be communicated to the first data circuit for storage therein via the first data circuit interface 846 (e.g., using the logic circuit 842). Such information may comprise, for example, an updated number of operations in which the surgical instrument has been used and/or dates and/or times of its usage.

As discussed previously, a surgical instrument may be detachable from a handpiece (e.g., the multifunction surgical instrument may be detachable from the handpiece) to promote instrument interchangeability and/or disposability. In such cases, conventional generators may be limited in their ability to recognize particular instrument configurations being used and to optimize control and diagnostic processes accordingly. The addition of readable data circuits to surgical instruments to address this issue is problematic from a compatibility standpoint, however. For example, designing a surgical instrument to remain backwardly compatible with generators that lack the requisite data reading functionality may be impractical due to, for example, differing signal schemes, design complexity, and cost. Forms of instruments discussed herein address these concerns by using data circuits that may be implemented in existing surgical instruments economically and with minimal design changes to preserve compatibility of the surgical instruments with current generator platforms.

Additionally, forms of the generator 800 may enable communication with instrument-based data circuits. For example, the generator 800 may be configured to communicate with a second data circuit contained in an instrument (e.g., the multifunction surgical instrument). In some forms, the second data circuit may be implemented in a many similar to that of the first data circuit described herein. The instrument interface circuit 840 may comprise a second data circuit interface 848 to enable this communication. In one form, the second data circuit interface 848 may comprise a tri-state digital interface, although other interfaces may also be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information.

In some forms, the second data circuit may store information about the electrical and/or ultrasonic properties of an associated ultrasonic transducer, end effector, or ultrasonic drive system. For example, the first data circuit may indicate a burn-in frequency slope, as described herein. Additionally or alternatively, any type of information may be communicated to second data circuit for storage therein via the second data circuit interface 848 (e.g., using the logic circuit 842). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 800 and provide an indication to a user (e.g., a light emitting diode indication or other visible indication) based on the received data.

In certain forms, the second data circuit and the second data circuit interface 848 may be configured such that communication between the logic circuit 842 and the second data circuit can be effected without the need to provide additional conductors for this purpose (e.g., dedicated conductors of a cable connecting a handpiece to the generator 800). In one form, for example, information may be communicated to and from the second data circuit using a one-wire bus communication scheme implemented on existing cabling, such as one of the conductors used transmit interrogation signals from the signal conditioning circuit 844 to a control circuit in a handpiece. In this way, design changes or modifications to the surgical instrument that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical instrument.

In certain forms, the isolated stage 802 may comprise at least one blocking capacitor 850-1 connected to the drive signal output 810b to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 850-2 may be provided in series with the blocking capacitor 850-1, with current leakage from a point between the blocking capacitors 850-1, 850-2 being monitored by, for example, an ADC circuit 852 for sampling a voltage induced by leakage current. The samples may be received by the logic circuit 842, for example. Based changes in the leakage current (as indicated by the voltage samples), the generator 800 may determine when at least one of the blocking capacitors 850-1, 850-2 has failed, thus providing a benefit over single-capacitor designs having a single point of failure.

In certain forms, the non-isolated stage 804 may comprise a power supply 854 for delivering DC power at a suitable voltage and current. The power supply may comprise, for example, a 400 W power supply for delivering a 48 VDC system voltage. The power supply 854 may further comprise one or more DC/DC voltage converters 856 for receiving the output of the power supply to generate DC outputs at the voltages and currents required by the various components of the generator 800. As discussed above in connection with the controller 838, one or more of the DC/DC voltage converters 856 may receive an input from the controller 838 when activation of the "on/off" input device by a user is detected by the controller 838 to enable operation of, or wake, the DC/DC voltage converters 856.

Figure 21:
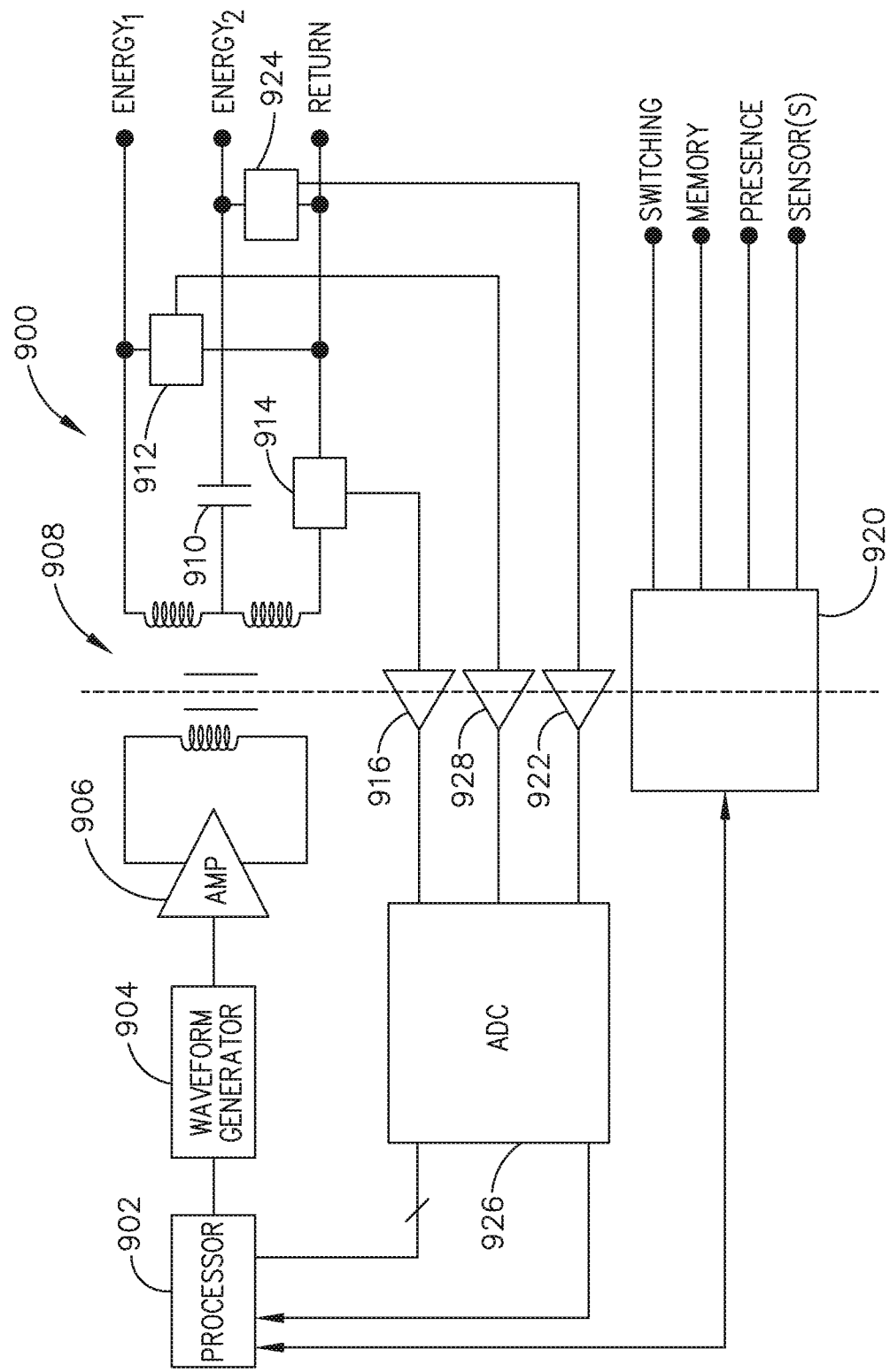
FIG. 21 illustrates an example of a generator, which is one form of the generator of FIG. 20, in accordance with at least one aspect of the present disclosure.

FIG. 21 illustrates an example of a generator 900, which is one form of the generator 800 (FIG. 20). The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue.

The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY1 and RETURN. A second signal of a second energy modality is coupled across a capacitor 910 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 912 is coupled across the terminals labeled ENERGY1 and the RETURN path to measure the output voltage therebetween. A second voltage sensing circuit 924 is coupled across the terminals labeled ENERGY2 and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY1/RETURN or the second voltage sensing circuit 924 coupled across the terminals labeled ENERGY2/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 21 shows a single return path RETURN may be provided for two or more energy modalities, in other aspects, multiple return paths RETURNn may be provided for each energy modality ENERGYn. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 21, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled ENERGY1 and RETURN as shown in FIG. 21. In one example, a connection of RF bipolar electrodes to the generator 900 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIGS. 3 and 9, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Situational Awareness

Situational awareness is the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g. a robotic arm and/or robotic surgical tool) that are connected to it and provide contextualized information or suggestions to the surgeon during the course of the surgical procedure.

Referring now to FIG. 56, a timeline 5200 depicting situational awareness of a hub, such as the surgical hub 106 or 206, for example, is depicted. The timeline 5200 is an illustrative surgical procedure and the contextual information that the surgical hub 106, 206 can derive from the data received from the data sources at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step 5202 in this illustrative procedure, the hospital staff members retrieve the patient's Electronic Medical Record (EMR) from the hospital's EMR database. Based on select patient data in the EMR, the surgical hub 106, 206 determines that the procedure to be performed is a thoracic procedure.

Second step 5204, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step 5206, the medical personnel scan the patient band via a scanner that is communicably connected to the surgical hub 106, 206. The surgical hub 106, 206 can then confirm the patient's identity based on the scanned data.

Fourth step 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step 5210, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step 5212, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step 5212, the pre-operative portion of the lung segmentectomy procedure is completed and the operative portion begins.

Seventh step 5214, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step 5216, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step 5218, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step 5220, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step 5222, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step 5224, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step 5224, the incisions are closed up and the post-operative portion of the procedure begins.

Thirteenth step 5226, the patient's anesthesia is reversed. The surgical hub 106, 206 can infer that the patient is emerging from the anesthesia based on the ventilator data (i.e., the patient's breathing rate begins increasing), for example.

Lastly, the fourteenth step 5228 is that the medical personnel remove the various patient monitoring devices from the patient. The surgical hub 106, 206 can thus infer that the patient is being transferred to a recovery room when the hub loses EKG, BP, and other data from the patient monitoring devices. As can be seen from the description of this illustrative procedure, the surgical hub 106, 206 can determine or infer when each step of a given surgical procedure is taking place according to data received from the various data sources that are communicably coupled to the surgical hub 106, 206.

Situational awareness is further described in U.S. Provisional Patent Application Ser. No. 62/611,341, titled INTERACTIVE SURGICAL PLATFORM, filed Dec. 28, 2017, the disclosure of which is incorporated by reference herein in its entirety. In certain instances, operation of a robotic surgical system, including the various robotic surgical systems disclosed herein, for example, can be controlled by the hub 106, 206 based on its situational awareness and/or feedback from the components thereof and/or based on information from the cloud 104.

Robotic Systems

Robotic surgical systems can be used in minimally invasive medical procedures. During such medical procedures, a patient can be placed on a platform adjacent to a robotic surgical system, and a surgeon can be positioned at a console that is remote from the platform and/or from the robot. For example, the surgeon can be positioned outside the sterile field that surrounds the surgical site. The surgeon provides input to a user interface via an input device at the console to manipulate a surgical tool coupled to an arm of the robotic system. The input device can be a mechanical input devices such as control handles or joysticks, for example, or contactless input devices such as optical gesture sensors, for example.

The robotic surgical system can include a robot tower supporting one or more robotic arms. At least one surgical tool (e.g. an end effector and/or endoscope) can be mounted to the robotic arm. The surgical tool(s) can be configured to articulate relative to the respective robotic arm via an articulating wrist assembly and/or to translate relative to the robotic arm via a linear slide mechanism, for example. During the surgical procedure, the surgical tool can be inserted into a small incision in a patient via a cannula or trocar, for example, or into a natural orifice of the patient to position the distal end of the surgical tool at the surgical site within the body of the patient. Additionally or alternatively, the robotic surgical system can be employed in an open surgical procedure in certain instances.

Figure 22:
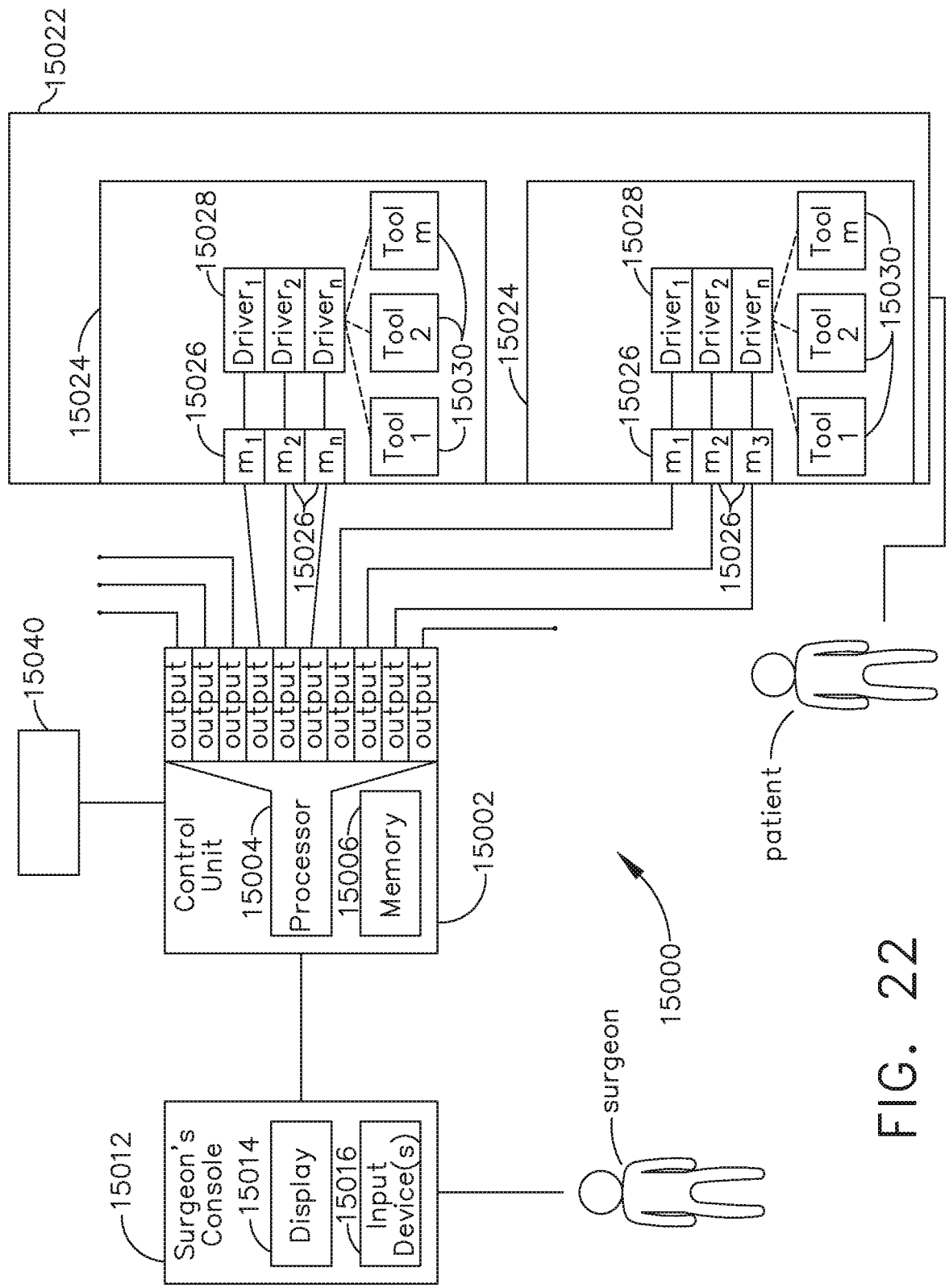
FIG. 22 is a schematic of a robotic surgical system, in accordance with one aspect of the present disclosure.

A schematic of a robotic surgical system 15000 is depicted in FIG. 22. The robotic surgical system 15000 includes a central control unit 15002, a surgeon's console 15012, a robot 15022 including one or more robotic arms 15024, and a primary display 15040 operably coupled to the control unit 15002. The surgeon's console 15012 includes a display 15014 and at least one manual input device 15016 (e.g., switches, buttons, touch screens, joysticks, gimbals, etc.) that allow the surgeon to telemanipulate the robotic arms 15024 of the robot 15022. The reader will appreciate that additional and alternative input devices can be employed.

The central control unit 15002 includes a processor 15004 operably coupled to a memory 15006. The processor 15004 includes a plurality of inputs and outputs for interfacing with the components of the robotic surgical system 15000. The processor 15004 can be configured to receive input signals and/or generate output signals to control one or more of the various components (e.g., one or more motors, sensors, and/or displays) of the robotic surgical system 15000. The output signals can include, and/or can be based upon, algorithmic instructions which may be pre-programmed and/or input by the surgeon or another clinician. The processor 15004 can be configured to accept a plurality of inputs from a user, such as the surgeon at the console 15012, and/or may interface with a remote system. The memory 15006 can be directly and/or indirectly coupled to the processor 15004 to store instructions and/or databases.

The robot 15022 includes one or more robotic arms 15024. Each robotic arm 15024 includes one or more motors 15026 and each motor 15026 is coupled to one or more motor drivers 15028. For example, the motors 15026, which can be assigned to different drivers and/or mechanisms, can be housed in a carriage assembly or housing. In certain instances, a transmission intermediate a motor 15026 and one or more drivers 15028 can permit coupling and decoupling of the motor 15026 to one or more drivers 15028. The drivers 15028 can be configured to implement one or more surgical functions. For example, one or more drivers 15028 can be tasked with moving a robotic arm 15024 by rotating the robotic arm 15024 and/or a linkage and/or joint thereof. Additionally, one or more drivers 15028 can be coupled to a surgical tool 15030 and can implement articulating, rotating, clamping, sealing, stapling, energizing, firing, cutting, and/or opening, for example. In certain instances, the surgical tools 15030 can be interchangeable and/or replaceable. Examples of robotic surgical systems and surgical tools are further described herein.

The reader will readily appreciate that the computer-implemented interactive surgical system 100 (FIG. 1) and the computer-implemented interactive surgical system 200 (FIG. 9) can incorporate the robotic surgical system 15000. Additionally or alternatively, the robotic surgical system 15000 can include various features and/or components of the computer-implemented interactive surgical systems 100 and 200.

In one exemplification, the robotic surgical system 15000 can encompass the robotic system 110 (FIG. 2), which includes the surgeon's console 118, the surgical robot 120, and the robotic hub 122. Additionally or alternatively, the robotic surgical system 15000 can communicate with another hub, such as the surgical hub 106, for example. In one instance, the robotic surgical system 15000 can be incorporated into a surgical system, such as the computer-implemented interactive surgical system 100 (FIG. 1) or the computer-implemented interactive surgical system 200 (FIG. 9), for example. In such instances, the robotic surgical system 15000 may interact with the cloud 104 or the cloud 204, respectively, and the surgical hub 106 or the surgical hub 206, respectively. In certain instances, a robotic hub or a surgical hub can include the central control unit 15002 and/or the central control unit 15002 can communicate with a cloud. In other instances, a surgical hub can embody a discrete unit that is separate from the central control unit 15002 and which can communicate with the central control unit 15002.

Figure 23:
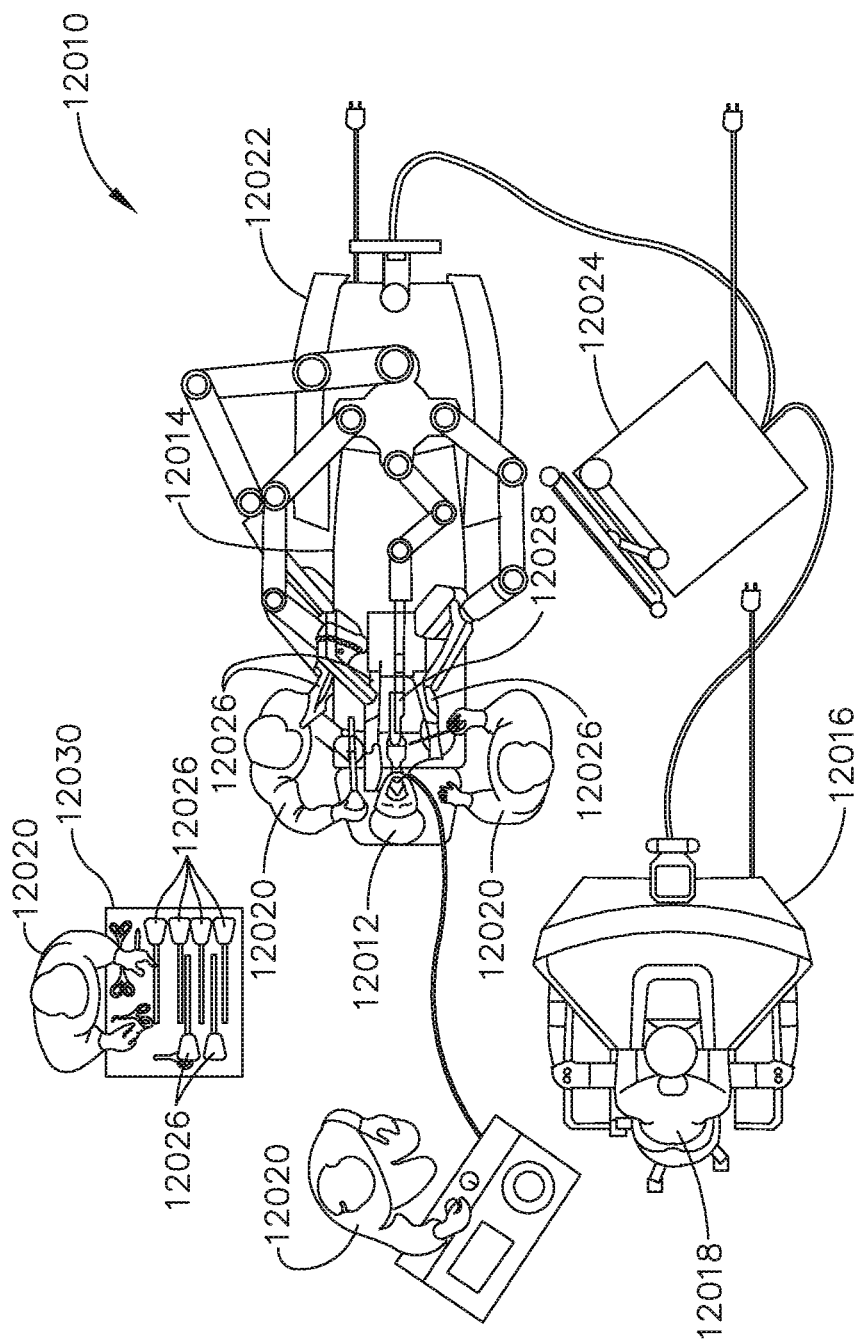
FIG. 23 is a plan view of a minimally invasive telesurgically-controlled robotic surgical system being used to perform a surgery, in accordance with one aspect of the present disclosure.

Another surgical robotic system is the da Vinci® surgical robotic system by Intuitive Surgical, Inc. of Sunnyvale, Calif. An example of a system is depicted in FIGS. 23-29. FIG. 23 depicts a minimally invasive robotic surgical (MIRS) system 12010 typically used for performing a minimally invasive diagnostic or surgical procedure on a patient 12012 who is lying down on an operating table 12014. The system 12010 includes a surgeon's console 12016 for use by a surgeon 12018 during the procedure. One or more assistants 12020 may also participate in the procedure. The MIRS system 12010 can further include a patient side cart 12022, i.e. a surgical robot, and an electronics cart 12024. The surgical robot 12022 can manipulate at least one removably coupled tool assembly 12026 (hereinafter referred to as a "tool") through a minimally invasive incision in the body of the patient 12012 while the surgeon 12018 views the surgical site through the console 12016. An image of the surgical site can be obtained by an imaging device such as a stereoscopic endoscope 12028, which can be manipulated by the surgical robot 12022 to orient the endoscope 12028. Various alternative imaging devices are further described herein.

The electronics cart 12024 can be used to process the images of the surgical site for subsequent display to the surgeon 12018 through the surgeon's console 12016. The number of robotic tools 12026 used at one time will generally depend on the diagnostic or surgical procedure and the space constraints within the operating room among other factors. If it is necessary to change one or more of the robotic tools 12026 being used during a procedure, an assistant 12020 may remove the robotic tool 12026 from the surgical robot 12022, and replace it with another tool 12026 from a tray 12030 in the operating room.

Figure 24:
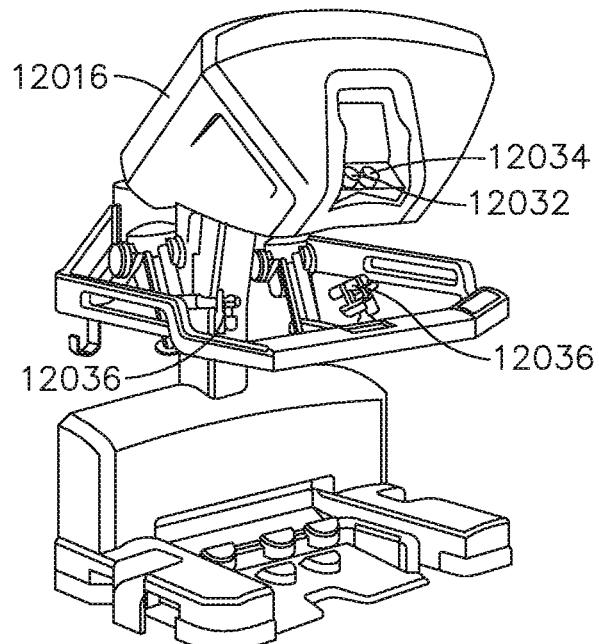
FIG. 24 is a perspective view of a surgeon's control console of the surgical system of FIG. 23, in accordance with one aspect of the present disclosure.

Referring primarily to FIG. 24, the surgeon's console 12016 includes a left eye display 12032 and a right eye display 12034 for presenting the surgeon 12018 with a coordinated stereo view of the surgical site that enables depth perception. The console 12016 further includes one or more input control devices 12036, which in turn cause the surgical robot 12022 (FIG. 23) to manipulate one or more tools 12026 (FIG. 23). The input control devices 12036 can provide the same degrees of freedom as their associated tools 12026 (FIG. 23) to provide the surgeon with telepresence, or the perception that the input control devices 12036 are integral with the robotic tools 12026 so that the surgeon has a strong sense of directly controlling the robotic tools 12026. To this end, position, force, and tactile feedback sensors may be employed to transmit position, force, and tactile sensations from the robotic tools 12026 back to the surgeon's hands through the input control devices 12036. The surgeon's console 12016 is usually located in the same room as the patient 12012 so that the surgeon 12018 may directly monitor the procedure, be physically present if necessary, and speak to an assistant 12020 directly rather than over the telephone or other communication medium. However, the surgeon 12018 can be located in a different room, a completely different building, or other remote location from the patient 12012 allowing for remote surgical procedures. A sterile field can be defined around the surgical site. In various instances, the surgeon 12018 can be positioned outside the sterile field. A sterile adapter can define a portion of the boundary of the sterile field. An example of a sterile adapter for a robotic arm is described in U.S. Patent Application Publication No. 2015/0257842, filed Mar. 17, 2015, titled BACKUP LATCH RELEASE FOR SURGICAL INSTRUMENT, which issued on Dec. 12, 2017 as U.S. Pat. No. 9,839,487, which is herein incorporated by reference in its entirety.

Figure 25:
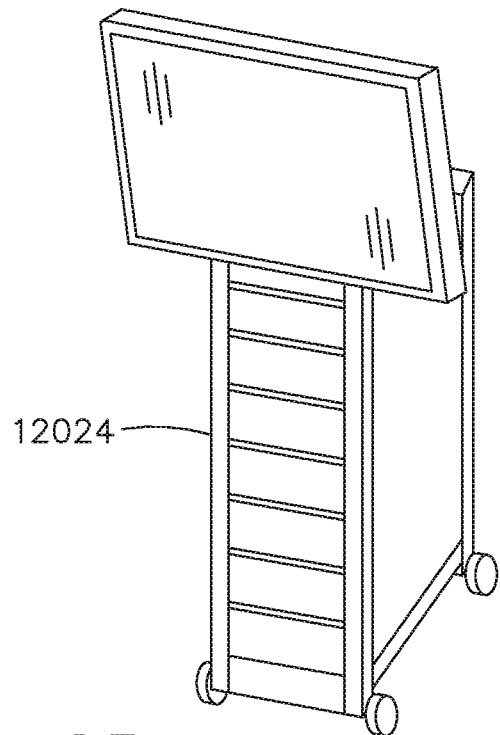
FIG. 25 is a perspective view of an electronics cart of the surgical system of FIG. 23, in accordance with one aspect of the present disclosure.

Referring primarily now to FIG. 25, the electronics cart 12024 can be coupled with the endoscope 12028 and can include a processor to process captured images for subsequent display, such as to a surgeon on the surgeon's console, or on another suitable display located locally and/or remotely. For example, where the stereoscopic endoscope 12028 is used, the electronics cart 12024 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations, for example.

Figure 26:
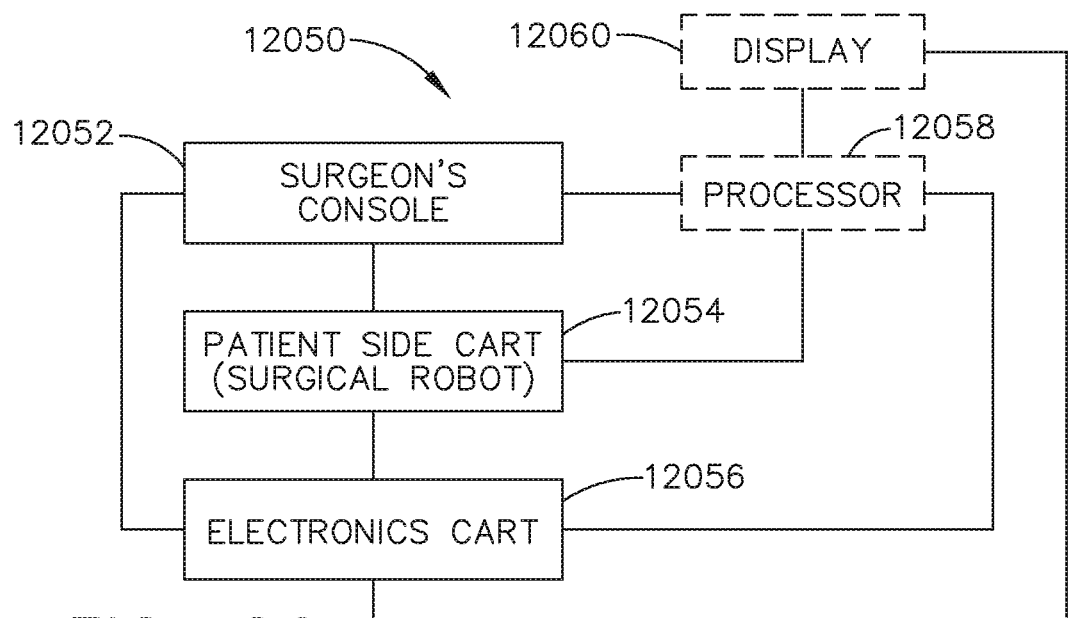
FIG. 26 is a diagram of a telesurgically-controlled surgical system, in accordance with one aspect of the present disclosure.

FIG. 26 diagrammatically illustrates a robotic surgery system 12050, such as the MIRS system 12010 of FIG. 23. As discussed herein, a surgeon's console 12052, such as the surgeon's console 12016 in FIG. 23, can be used by a surgeon to control a surgical robot 12054, such as the surgical robot 12022 in FIG. 23, during a minimally invasive procedure. The surgical robot 12054 can use an imaging device, such as a stereoscopic endoscope, to capture images of the procedure site and output the captured images to an electronics cart 12056, such as the electronics cart 12024 in FIG. 23. As discussed herein, the electronics cart 12056 can process the captured images in a variety of ways prior to any subsequent display. For example, the electronics cart 12056 can overlay the captured images with a virtual control interface prior to displaying the combined images to the surgeon via the surgeon's console 12052. The surgical robot 12054 can output the captured images for processing outside the electronics cart 12056. For example, the surgical robot 12054 can output the captured images to a processor 12058, which can be used to process the captured images. The images can also be processed by a combination of the electronics cart 12056 and the processor 12058, which can be coupled together to process the captured images jointly, sequentially, and/or combinations thereof. One or more separate displays 12060 can also be coupled with the processor 12058 and/or the electronics cart 12056 for local and/or remote display of images, such as images of the procedure site, or other related images.

Figure 27:
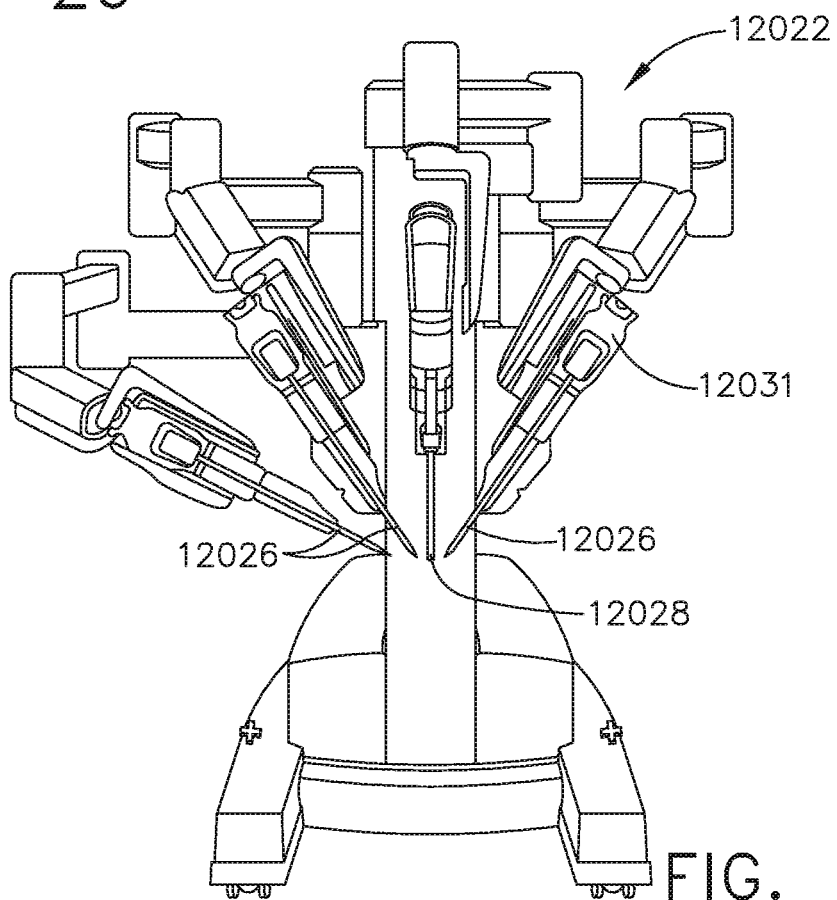
FIG. 27 is a partial view of a patient side cart of the surgical system of FIG. 23, in accordance with one aspect of the present disclosure.
Figure 28:
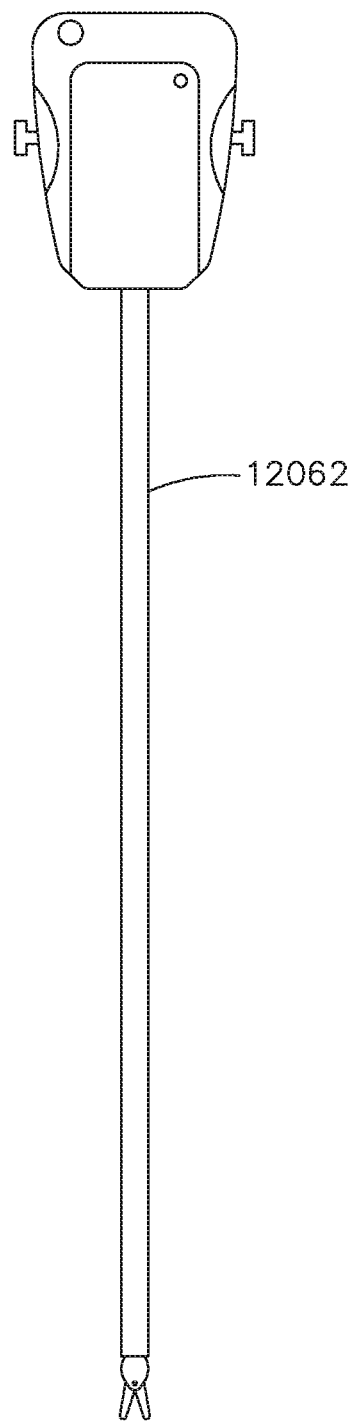
FIG. 28 is a front view of a telesurgically-operated surgery tool for the surgical system of FIG. 23, in accordance with one aspect of the present disclosure.

FIGS. 27 and 28 show the surgical robot 12022 and a robotic tool 12062, respectively. The robotic tool 12062 is an example of the robotic tools 12026 (FIG. 23). The reader will appreciate that alternative robotic tools can be employed with the surgical robot 12022 and exemplary robotic tools are described herein. The surgical robot 12022 shown provides for the manipulation of three robotic tools 12026 and the imaging device 12028, such as a stereoscopic endoscope used for the capture of images of the site of the procedure Manipulation is provided by robotic mechanisms having a number of robotic joints. The imaging device 12028 and the robotic tools 12026 can be positioned and manipulated through incisions in the patient so that a kinematic remote center or virtual pivot is maintained at the incision to minimize the size of the incision. Images of the surgical site can include images of the distal ends of the robotic tools 12026 when they are positioned within the field-of-view (FOV) of the imaging device 12028. Each tool 12026 is detachable from and carried by a respective surgical manipulator 12031, which is located at the distal end of one or more of the robotic joints. The surgical manipulator 12031 provides a moveable platform for moving the entirety of a tool 12026 with respect to the surgical robot 12022, via movement of the robotic joints. The surgical manipulator 12031 also provides power to operate the robotic tool 12026 using one or more mechanical and/or electrical interfaces.

Figure 29:
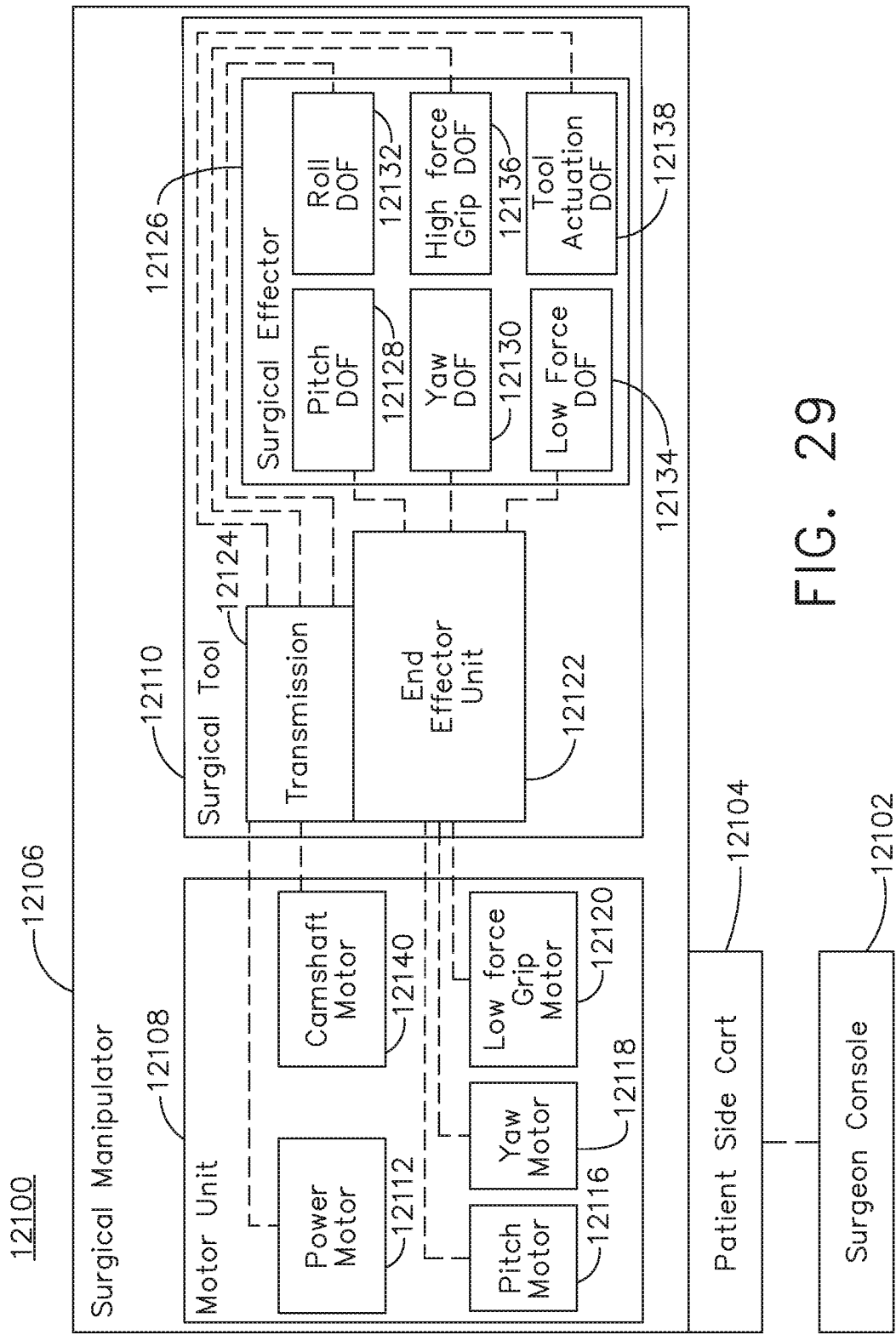
FIG. 29 is a control schematic diagram of a telesurgically-controlled surgical system, in accordance with one aspect of the present disclosure.

FIG. 29 is a schematic of a telesurgically-controlled surgical system 12100. The surgical system 12100 includes a surgeon console 12102, which for example can be the surgeon's console 12052 (FIG. 26). The surgeon console 12102 drives a surgical robot 12104, which for example can be the surgical robot 12022 (FIG. 23). The surgical robot 12104 includes a surgical manipulator 12106, which for example can be the surgical manipulator 12031 (FIG. 27). The surgical manipulator 12106 includes a motor unit 12108 and a robotic tool 12110. The motor unit 12108 is a carriage assembly that holds five motors, which can be assigned to different mechanisms. In some exemplifications only five motors are used, while in other exemplifications more or less than five motors can be used. The motor unit 12108 includes a power motor 12112, a camshaft motor 12140, a pitch motor 12116, a yaw motor 12118, and low-force grip motor 12120, although these motors can be used for different purposes depending on the attached instrument. Generally, each motor is an electric motor that mechanically and electrically couples with corresponding inputs of the robotic tool 12110. In some exemplifications, the motor unit 12108 may be located at a proximal end of the robotic tool 12110 in a shared chassis with the robotic tool, as generally depicted by the proximal housing shown in FIG. 28. A motor housing is further described in U.S. Patent Application Publication No. 2012/0150192, filed Nov. 15, 2011, titled METHOD FOR PASSIVELY DECOUPLING TORQUE APPLIED BY A REMOTE ACTUATOR INTO AN INDEPENDENTLY ROTATING MEMBER, which issued on Aug. 4, 2015 as U.S. Pat. No. 9,095,362, which is herein incorporated by reference in its entirety.

The robotic tool 12110 for example, can be the robotic tool 12026 (FIG. 23) described herein. The robotic tool 12110 includes an elongated effector unit 12122 that includes three discrete inputs that each mechanically couple with the pitch motor 12116, the yaw motor 12118, and the low-force grip motor 12120, respectively, by way of the surgical manipulator 12106. The robotic tool 12110 also includes a transmission 12124, which mechanically couples with the power motor 12112 and the camshaft motor 12140. Examples of tools are further described in International Patent Application Publication No. WO 2015/153642, filed Mar. 31, 2015, titled SURGICAL INSTRUMENT WITH SHIFTABLE TRANSMISSION, and in International Patent Application Publication No. WO 2015/153636, filed Mar. 31, 2015, titled CONTROL INPUT ACCURACY FOR TELEOPERATED SURGICAL INSTRUMENT, each of which is herein incorporated by reference in its entirety.

A surgical end effector 12126 is located at the distal end of the effector unit 12122. The surgical end effector 12126 and effector unit 12122 are connected by way of a moveable wrist. An example of such a wrist is shown at U.S. Patent Application Publication No. 2011/0118708, filed Nov. 12, 2010, titled DOUBLE UNIVERSAL JOINT, and in U.S. Pat. No. 9,216,062, filed Feb. 15, 2012, titled SEALS AND SEALING METHODS FOR A SURGICAL INSTRUMENT HAVING AN ARTICULATED END EFFECTOR ACTUATED BY A DRIVE SHAFT, each of which is herein incorporated by reference in its entirety. In simplistic terms, the surgical end effector can be characterized by a plurality of discrete but interrelated mechanisms, with each mechanism providing a degree of freedom (DOF) for the surgical end effector 12126. As used herein with respect to surgical system 12100, a DOF is one or more interrelated mechanisms for affecting a corresponding movement. The DOFs endow the surgical end effector 12126 with different modes of operation that can operate concurrently or discretely. For example, the wrist enables the surgical end effector 12126 to pitch and yaw with respect to the surgical manipulator 12106, and accordingly includes a pitch DOF 12128 and a yaw DOF 12130. The surgical end effector 12126 also includes a roll DOF 12132 rotating surgical end effector 12126 about an elongated axis. Different robotic tool can have different DOFs, as further described herein.

The surgical end effector 12126 may include a clamping and cutting mechanism, such as a surgical stapler. An example of such an instrument, including a staple cartridge therefor, is further described in U.S. Patent Application Publication No. 2013/0105552, filed Oct. 26, 2012, titled CARTRIDGE STATUS AND PRESENCE DETECTION, and U.S. Patent Application Publication No. 2013/0105545, filed Oct. 26, 2012, titled SURGICAL INSTRUMENT WITH INTEGRAL KNIFE BLADE, both of which are incorporated by reference herein in their respective entireties. A clamping mechanism can grip according to two modes, and accordingly include two DOFs. A low-force DOF 12134 (e.g., a cable actuated mechanism) operates to toggle the clamp with low force to gently manipulate tissue. The low-force DOF 12134 is useful for staging the surgical end effector for a cutting or stapling operation. A high-force DOF 12136 (e.g., a lead screw actuated mechanism) operates to further open the clamp or close the clamp onto tissue with relatively high force, for example, to tourniquet tissue in preparation for a cutting or stapling operation. Once clamped, the surgical end effector 12126 employs a tool actuation DOF 12138 to further affect the tissue, for example, to affect tissue by a stapling, cutting, and/or cauterizing device. Clamping systems for a surgical end effector are further described in U.S. Pat. No. 9,393,017, filed May 15, 2012, titled METHODS AND SYSTEMS FOR DETECTING STAPLE CARTRIDGE MISFIRE OR FAILURE, which issued on Jul. 19, 2016, U.S. Pat. No. 8,989,903, filed Jan. 13, 2012, titled METHODS AND SYSTEMS FOR INDICATING A CLAMPING PREDICTION, which issued on Mar. 2, 2015, and U.S. Pat. No. 9,662,177, filed Mar. 2, 2015, titled METHODS AND SYSTEMS FOR INDICATING A CLAMPING PREDICTION, which issued on May 30, 2017, all of which are incorporated by reference herein in their respective entireties.

As shown in FIG. 29, the pitch motor 12116, the yaw motor 12118, and the low-force grip motor 12120 drive the pitch DOF 12128, the yaw DOF 12130, and the low-force grip DOF 12134, respectively. Accordingly, each of the pitch DOF 12128, the yaw DOF 12130, and the low force grip DOF 12134 is discretely paired with a motor, and can operate independently and concurrently with respect to other DOFs. However, the high force grip DOF 12136, the roll DOF 12132, and the tool actuation DOF 12138 share a single input with the power motor 12112, via the transmission 12124. Accordingly, only one of the high-force grip DOF 12136, the roll DOF 12132, and the tool actuation DOF 12138 can operate at one time, since coupling with the power motor 12112 occurs discretely. The camshaft motor 12140 is actuated to shift output of the power motor 12112 between the high force grip DOF 12136, the roll DOF 12132, and the tool actuation DOF 12138. Accordingly, the transmission 12124 advantageously allows a greater amount of DOFs than an arrangement where each motor is dedicated to a single DOF.

Additional features and operations of a surgical robotic system, such as the robotic surgical system of FIGS. 23-29, are further described in the following references, which are herein incorporated by reference in their respective entireties:

U.S. Patent Application Publication No. 2011/0118708, filed Nov. 12, 2010, titled DOUBLE UNIVERSAL JOINT;

U.S. Pat. No. 9,095,362, filed Nov. 15, 2011, titled METHOD FOR PASSIVELY DECOUPLING TORQUE APPLIED BY A REMOTE ACTUATOR INTO AN INDEPENDENTLY ROTATING MEMBER, which issued on Aug. 4, 2015;

U.S. Pat. No. 8,989,903, filed Jan. 13, 2012, titled METHODS AND SYSTEMS FOR INDICATING A CLAMPING PREDICTION, which issued on Mar. 24, 2015;

U.S. Pat. No. 9,216,062, filed Feb. 15, 2012, titled SEALS AND SEALING METHODS FOR A SURGICAL INSTRUMENT HAVING AN ARTICULATED END EFFECTOR ACTUATED BY A DRIVE SHAFT, which issued on Dec. 22, 2015;

U.S. Pat. No. 9,393,017, filed May 15, 2012, titled METHODS AND SYSTEMS FOR DETECTING STAPLE CARTRIDGE MISFIRE OR FAILURE, which issued on Jul. 19, 2016;

U.S. Patent Application Publication No. 2013/0105552, filed Oct. 26, 2012, titled CARTRIDGE STATUS AND PRESENCE DETECTION;

U.S. Patent Application Publication No. 2013/0105545, filed Oct. 26, 2012, titled SURGICAL INSTRUMENT WITH INTEGRAL KNIFE BLADE;

International Patent Application Publication No. WO 2015/142814, filed Mar. 17, 2015, titled SURGICAL CANNULA MOUNTS AND RELATED SYSTEMS AND METHODS;

U.S. Patent Application Publication No. 2015/0257842, filed Mar. 17, 2015, titled BACKUP LATCH RELEASE FOR SURGICAL INSTRUMENT, which issued on Dec. 12, 2017 as U.S. Pat. No. 9,839,487;

U.S. Patent Application Publication No. 2015/0257841, filed Mar. 17, 2015, titled LATCH RELEASE FOR SURGICAL INSTRUMENT;

International Patent Application Publication No. WO 2015/153642, filed Mar. 31, 2015, titled SURGICAL INSTRUMENT WITH SHIFTABLE TRANSMISSION;

International Patent Application Publication No. WO 2015/153636, filed Mar. 31, 2015, titled CONTROL INPUT ACCURACY FOR TELEOPERATED SURGICAL INSTRUMENT; and U.S. Pat. No. 9,662,177, filed Mar. 2, 2015, titled METHODS AND SYSTEMS FOR INDICATING A CLAMPING PREDICTION, which issued on May 30, 2017.

The robotic surgical systems and features disclosed herein can be employed with the da Vinci® surgical robotic system referenced herein and/or the system of FIGS. 23-29. The reader will further appreciate that various systems and/or features disclosed herein can also be employed with alternative surgical systems including the computer-implemented interactive surgical system 100, the computer-implemented interactive surgical system 200, the robotic surgical system 110, the robotic hub 122, the robotic hub 222, and/or the robotic surgical system 15000, for example.

In various instances, a robotic surgical system can include a robotic control tower, which can house the control unit of the system. For example, the processor 12058 (FIG. 26) can be housed within a robotic control tower. The robotic control tower can comprise a robot hub such as the robotic hub 122 (FIG. 2) or the robotic hub 222 (FIG. 9), for example. Such a robotic hub can include a modular interface for coupling with one or more generators, such as an ultrasonic generator and/or a radio frequency generator, and/or one or more modules, such as an imaging module, a suction module, an irrigation module, a smoke evacuation module, and/or a communication module.

A robotic hub can include a situational awareness module, which can be configured to synthesize data from multiple sources to determine an appropriate response to a surgical event. For example, a situational awareness module can determine the type of surgical procedure, step in the surgical procedure, type of tissue, and/or tissue characteristics, as further described herein. Moreover, such a module can recommend a particular course of action or possible choices based on the synthesized data. In various instances, a sensor system encompassing a plurality of sensors distributed throughout the robotic system can provide data, images, and/or other information to the situational awareness module. Such a situational awareness module can be accessible to the processor 12058, for example. In various instances, the situational awareness module can obtain data and/or information from a non-robotic surgical hub and/or a cloud, such as the surgical hub 106 (FIG. 1), the surgical hub 206 (FIG. 10), the cloud 104 (FIG. 1), and/or the cloud 204 (FIG. 9), for example. Situational awareness of a surgical system is further disclosed herein and in U.S. Provisional Patent Application Ser. No. 62/611,341, titled INTERACTIVE SURGICAL PLATFORM, filed Dec. 28, 2017, and in U.S. Provisional Patent Application Ser. No. 62/611,340, titled CLOUD-BASED MEDICAL ANALYTICS, filed Dec. 28, 2017, the disclosure of each of which is herein incorporated by reference in its entirety.

Surgical systems including a robot, a visualization system (such as the visualization system 108 or the visualization system 208), and one or more hubs (such as the hub 106, the robotic hub 122, the hub 206, and/or the robotic hub 222) can benefit from robust communication systems for data collection and dissemination. For example, various parameters regarding the surgical site, the surgical instrument(s), and/or the surgical procedure can be important information to the robot, the visualization system, and the hub(s). Moreover, the robot can include one or more subassemblies, such as a control console, which may require information regarding the surgical site, the surgical instrument(s), and/or the surgical procedure, for example. It can be helpful to collect and disseminate the information to the appropriate assemblies and/or subassemblies in real-time or near real-time to inform the machine learning and/or decision-making process, for example. In certain instances, data collection and dissemination can inform the situational awareness of a surgical system that includes one or more robotic systems.

In one aspect, a robotic surgical system can include additional communication paths. For example, a robotic surgical system can include a primary wired communication path and a secondary wireless communication path. In certain instances, the two communication paths can be independent such that a secondary path is redundant and/or parallel to a primary path. In various instances, a first type and/or amount of data can be transferred along the primary path and a second type and/or amount of data can be transferred along the secondary path. The multiple communication paths can improve connectivity of the robot and/or the robotic surgical tools to one or more displays within the surgical theater, a control console, and/or control unit. The communication paths can connect a surgical robot to a central control unit (e.g. a hub) and/or a visualization system (e.g. a display), for example. In various instances, the additional communication paths can provide additional data to the robot and/or to a generator module and/or a processor in communication with the generator module.

Figure 30:
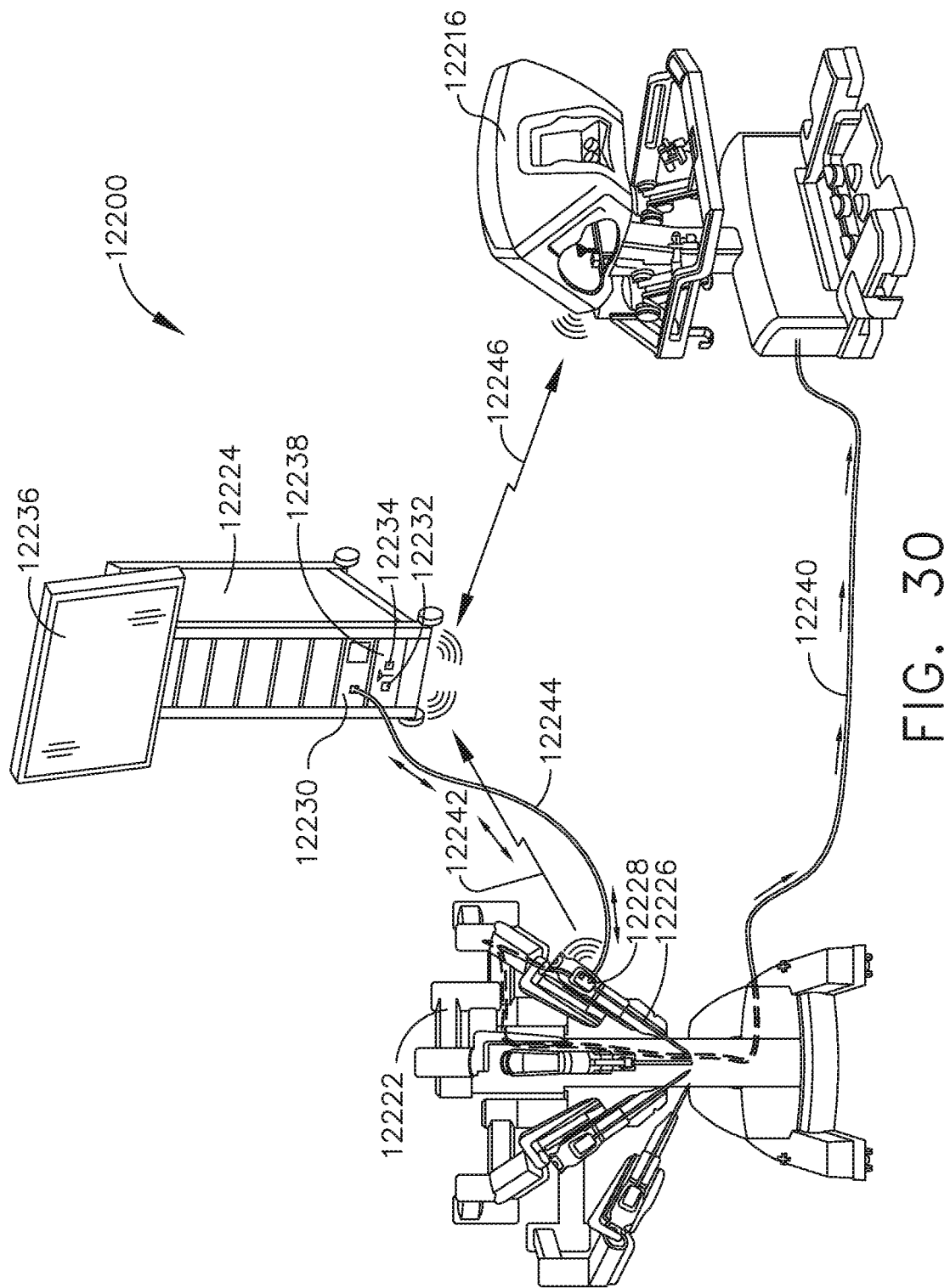
FIG. 30 is an elevation view of a robotic surgical system and various communication paths thereof, in accordance with one aspect of the present disclosure.

Referring primarily to FIG. 30, a robotic surgical system 12200 including a console 12216 and a robot 12222 is depicted. The console 12216 can be similar in many respects to the console 12016 (FIGS. 23 and 24), and the robot 12222 can be similar in many respects to the robot 12022 (FIGS. 23 and 27). A robotic tool 12226, which can be similar in many respects to the robotic tool 12026 (FIG. 23), for example, is positioned at the distal end of one of the arms of the robot 12222. The robotic tool 12226 is an energy device. For example, energy can be supplied to the robotic tool 12226 by a generator that is coupled to the robotic tool 12226.

The robotic surgical system 12200 also includes a hub 12224, which can be similar in many respects to the robotic hub 122 (FIG. 2) and/or the robotic hub 222 (FIG. 9). The hub 12224 includes a generator module 12230, which is similar in many respects to the generator module 140 (FIG. 3), and a wireless communication module 12238, which is similar in many respects to the communication module 130 (FIG. 3). The generator module 12230 is configured to supply energy to the robotic tool 12226 via a first wired connection 12244.

In one instance, the first wired connection 12244 can be a two-way communication path between the robotic tool 12226 and the surgical hub 12224. The first wired connection 12244 can convey advanced energy parameters or other electrical data between the robotic tool 12226 and the surgical hub 12224. For example, the surgical hub 12224 can provide information to the robotic tool 12226 regarding the power level (e.g. current for an RF device and amplitude and/or frequency for an ultrasonic device) supplied thereto. Additionally, the robotic tool 12226 can provide information to the robot 12222 regarding the detected conductivity and/or impedance at the tissue interface, corresponding to a property of the tissue and/or the effectiveness of the energy device.

Additionally, a second wired connection 12240 between the console 12216 and the robotic tool 12226 mounted to the robot 12222 provides a communication path for control signals from the robot console 12216 to the robotic tool 12226. In one instance, the second wired connection 12240 can be a one-way communication path from the robot 12222 to the console 12216 with respect to control parameters or other mechanical data collected by the robot 12222 and/or the robotic tool 12226. For example, the robot 12222 can provide information to the console 12216 about a surgical actuation of the robotic tool, such as a closing motion and/or a firing motion. More specifically, the robot can communicate force-to-clamp parameters (e g clamping pressure by the robotic tool 12226 on tissue) and/or force-to-fire parameters from the robotic tool 12226 to the console 12216, for example.

Referring still to FIG. 30, absent the wireless communication paths 12242 and 12246, the robotic hub 12224 may be unable to communicate with the console 12216 and vice versa. Additionally, the robotic tool 12226 may be unable to communicate with the hub 12224. In instances in which communication paths between the hub 12224 and the robot 12222 and/or the robotic tool 12226 are lacking, the mechanical control parameters (e g clamping force) from the robotic tool 12226 may not be communicated to the robotic hub 12224 and the generator module 12230 thereof. Additionally, electrical advanced energy parameters may not be communicated from the robot 12222 to the robotic hub 12224 and/or to the console 12216. In such instances, the system 12200 would comprise open-loop controls.

Different energy parameters and different clamping pressures may be better suited for certain types of tissue and/or certain applications. For example, an ultrasonic weld is generally a function of transducer amplitude and clamping pressure over time. Similarly, an RF weld is generally a function of current and clamping pressure over time. However, without the wireless communication paths 12242 and 12246 mentioned above, the generator module 12230 can be unaware of the clamping pressure. Similarly, the console 12216 can be unaware of the energy parameters.

To optimize the control of the robotic tool 12226, the robotic tool 12226 can convey one or more mechanical control parameters to the robotic hub 12224. Additionally, the hub 12224 can convey one or more advanced energy parameters to the console 12216. The data transfer can provide closed-loop controls for the system 12200. In one instance, the mechanical control parameters and advanced energy parameters can be balanced for different types of tissue and/or particular applications. For example, the clamping pressure can be decreased and the power to the robotic tool 12226 can be increased, or vice versa.

Referring still to FIG. 30, the robotic tool 12226 includes a wireless communication module 12228, as further described herein. The wireless communication module 12228 is in signal communication with the wireless communication module 12238 of the robotic hub 12224 via the wireless communication path 12242. For example, the wireless communication module 12238 can include a first receiver 12232 configured to receive wireless signals from the robotic tool 12226. The wireless communication module 12238 also includes a second receiver 12234, which can receive signals from the console 12216 via the second wireless communication path 12246. In such instances, the first and second wireless communication paths 12242 and 12246, respectively, can complete a communication circuit back to the console 12216 from the robotic tool 12226 via the surgical hub 12224, for example.

In other instances, the wireless communication module 12228 can be on the robot 12222. For example, the wireless communication module 12228 can be positioned on an arm of the robot and/or a tool mounting portion of the robot 12222.

Additionally or alternatively, a wireless communication path can be provided between the robotic tool 12226 and the console 12216.

The wireless paths described herein can provide data transfer without encumbering the mobility of the robotic tool 12226 and/or creating additional opportunities for entanglement or cords and/or wires. In other instances, one or more of the wireless communication paths described herein can be replaced with wired connection(s).

In one aspect, the robotic tool 12226 and/or the hub 12224 can share information regarding sensed tissue parameters (e.g. conductivity or inductance corresponding to a property of the tissue) and/or control algorithms for energizing the tissue (e.g. power levels), which can be based on the sensed tissue parameters. The robotic tool 12226 can provide information regarding the status, the activation state, identification information, and/or smart data to the hub 12224, for example. Data provided to the hub 12224 can be stored, analyzed, and/or further disseminated by the hub 12224 such as to a display screen 12236 thereof. In such instances, the hub 12224 is a conduit or relay post for transmitting the data to additional locations via the wired or wireless connections.

In certain instances, the hub 12224 includes a situational awareness module, as further described herein. The situational awareness module can be configured to determine and/or confirm a step in a surgical procedure and/or suggest a particular surgical action based on information received from various sources, including the robot 12222 and the console 12216. The wireless communication paths 12242 and 12246 linking the hub 12224 to the robot 12222 and the console 12216, respectively, can be configured to inform the situational awareness module. For example, mechanical control parameters regarding clamping and/or firing can be communicated to the hub 12224 and the situational awareness module thereof via the second wireless communication path 12246. Additionally or alternatively, energy parameters regarding activation of the energy tool and/or sensed tissue parameters can be communicated to the hub 12224 and the situational awareness module thereof via the first wireless communication path 12242.

In certain instances, the data wirelessly transmitted to the hub 12224 can inform the situational awareness module thereof. For example, based on sensed tissue parameters detected by the robotic tool 12226 and transmitted along the first wireless communication path 12242, the situational awareness module can determine and/or confirm the type of tissue involved in the surgical procedure and, in certain instances, can suggest a therapeutic response based on the type of tissue encountered.

Referring still to FIG. 30, the second wired connection 12240 from the robot 12222 to the console 12216 provides a first communication path. Moreover, the wired or wireless connection between the robot 12222 and the hub 12224 in combination with the wireless communication path 12246 between the hub 12224 and the console 12216 forms a second, parallel communication path from the robot 12222 to the console 12212. Because the second communication path communicates via the hub 12224 and the wireless communication module 12238 thereof, the second communication path is different than the first communication path. However, such a path provides a parallel and alternative path to the second wired connection 12240 between the robot 12222 and the console 12216. Similarly, parallel and/or redundant paths are also provided via the wireless path 12242 and the wired path 12244 between the robot 12222 and the hub 12224. The alternative parallel communication path(s) can bolster the integrity of the communications systems and enables robot communication between the various components of the surgical system.

Additionally or alternatively, information may be communicated directly to a device or system having wireless capabilities such as a visualization system or display like the visualization system 108 or the visualization system 208, for example. A surgical system 12300 depicted in FIG. 55 includes the console 12216 for a surgeon S, the robot 12222 including the robotic tool 12226 mounted thereto, and the surgical hub 12224. The surgical system 12300 also includes a monitor 12350, which is positioned within the surgical theater. Additional clinicians can be within the surgical theater including a nurse N, a medical assistant MA, and an anesthesiologist A. Certain clinicians can be positioned within the sterile field. For example, the nurse N, who is stationed at a table 12352 supporting a plurality of medical instruments and robotic tools, can be sterile. The medical assistant MA holding the handheld surgical instrument and the anesthesiologist A may be positioned outside the sterile field. The monitor 12350 is viewable by clinicians within the sterile field and outside the sterile field. An additional display 12354 can be positioned within the sterile field. The additional display 12354 can be a mobile computer with wireless, cellular and/or Bluetooth capabilities, for example. In one instance, the additional display 12354 can be a tablet, such as an iPad® tablet, that is positionable on the patient P or patient table 12358. In such instances, the display 12354 is positioned within the sterile field.

The wireless communication module 12228 (FIG. 30) on the robotic tool 12226 can be in signal communication with the monitor 12350 and/or the display 12354. In such instances, data and/or information obtained at the surgical site and/or by the robotic tool 12226 can be directly communicated to a screen within the surgical theater and immediately viewable to various clinicians with the surgical theater, including clinicians within the sterile field or outside the sterile field. In such instances, data can be provided in real time, or near real time, to inform the clinicians' decisions during the surgical procedure. Additionally, certain information can be communicated to the hub 12224 for further storage, analysis and/or dissemination, as further described herein.

Owing to wireless communication paths, the monitor 12350 and/or the display 12354 can also display information from the hub, including energy parameters, in certain instances. For example, the hub 12224 can obtain data indicative of an activation state or activation level of the generator module 12230 (FIG. 30) and/or can receive data indicative of sensed tissue parameters from the robotic tool 12226, as further described herein. In such instances, the activation information and/or tissue information can be displayed on the monitor 12350 and/or the display 12354 such that the information is readily available to operators both within the sterile filed and outside the sterile field.

In one aspect, the hub 12224 can ultimately communicate with a cloud, such as the cloud 104 or the cloud 204, for example, to further inform the machine-learning and decision-making processes related to the advanced energy parameters and/or mechanical control parameters of the robotic tool 12226. For example, a cloud can determine an appropriate surgical action and/or therapeutic response for a particular tissue parameter, surgical procedure, and/or patient demographic based on aggregated data stored therein. To protect patient confidentiality, the hub 12224 can communicate redacted and/or a confidential version of the data, for example.

As described herein with respect to FIG. 30, the robotic tool 12226 includes the wireless communication module 12228. The wireless communication module 12228 is also shown in FIG. 31. Specifically, a proximal portion of the robotic tool 12226 including the wireless communication module 12228 is depicted in FIG. 31, as well as a tool mounting portion, or attachment portion, 12250 of the robot 12222 for releasably attaching the proximal housing of the robotic tool 12226. A detailed view of a mechanical and electrical interface between the robotic tool 12226 and the tool mounting portion 12250 is depicted in FIG. 32.

The robotic tool 12226 includes a first drive interface 12252 that drivingly couples with a second drive interface 12254 on the tool mounting portion 12250. The tool mounting portion 12250 includes a carriage or motor housing that houses a plurality of motors, which can be similar in many respects to the motors 12112, 12116, 12118, 12120, and 12140 (FIG. 29), for example. The motors are driving coupled to rotary outputs 12256 at the second drive interface 12254 that engage rotary inputs 12258 on the robotic tool 12226. For example, the rotary inputs 12258 are positioned and structured to mechanically mate with the rotary outputs 12256 on the tool mounting portion 12250.

A plug 12260 for supplying power to the motors is shown in FIG. 31. The plug 12260 is also coupled to the wireless communication module 12228. In such instances, the wireless communication module 12228 can be powered via a current supplied by the plug 12260. The plug 12260 can ultimately be wired to the generator module 12230 in the hub 12224 to complete the wired connection 12244 between the robotic tool 12226 and the hub 12224 (see FIG. 30).

Referring primarily now to FIG. 31, the tool mounting portion 12250 also includes electrical contacts 12262, and the robotic tool 12226 includes electrical contacts 12264 positioned and structured to mate with the electrical contacts 12262 on the tool mounting portion 12250. Electrical signals can be communicated between the robotic tool 12226 and the robot 12222 (FIG. 30) via the mating electrical contacts 12262, 12264. In certain instances, mechanical control parameters from the robotic tool 12262 can be communicated to the robot 12222 via the electrical contacts 12262, 12264, as further described herein. Additionally or alternatively, advanced energy parameters can be communicated to the robot 12222 and/or to the robotic tool 12226 via the mating electrical contacts 12262, 12264, or vice versa, as further described herein.

As depicted in FIG. 32, when the robotic tool 12226 is mounted to the tool mounting portion 12250, a flex circuit 12270 is positioned intermediate the mating electrical contacts 12264 of the robotic tool 12226 and the electrical contacts 12262 of the tool mounting portion 12250 to facilitate data transmission. The flex circuit 12270 is positioned to intercept communication signals between the robotic tool 12262 and the tool mounting portion 12250. In such instances, the flex circuit 12270 is configured to capture signals passing between those contacts 12262, 12264. In certain instances, the flex circuit 12270 can provide intelligence features to the robotic tool 12226.

In various instances, the flex circuit 12270 can include a feedback pigtail connector. The pigtail connector can intercept the connection between the robotic tool 12226 and the tool mounting portion 12250.

In various instances, the flex circuit 12270 of FIG. 31 can also include a wireless transmitter that is configured to communicate with the hub 12224 (FIG. 30) via the wireless communication path 12242. In other instances, the flex circuit 12270 can be coupled to a wireless communication module like the module 12228 in FIGS. 30 and 31, which can include a wireless transmitter and/or a wireless receiver.

The flex circuit 12270 occupies a small footprint between the tool mounting portion 12250 and the robotic tool 12226. In one aspect, existing robotic systems can be retrofit with such flex circuits. In other words, existing robotic tools and tool mounting portion can utilize the robust communication systems described herein without modifying the current robotic tools and/or tool mounting portions.

In various instances, the flex circuit 12270, or another intermediate pigtail connector, can be configured to acquire one or more signals between an external controller (e.g., an energy generator of a generator module 140 in a hub 106 (FIG. 3)) and the robotic tool 12226. Moreover, such a circuit or connector can be used to deliver signals to the robotic tool 12226 via the intercepting connections.

In one aspect, the robotic hub includes a processor and a memory communicatively coupled to the processor, as described herein. The memory stores instructions executable by the processor to relay a wireless signal between a robot and a control console, as described herein. In certain instances, the memory stores instructions executable by the processor to adjust a control parameter of the generator (e.g. power level) based on signals intercepted by a flex circuit and/or transmitted along a wireless communication path. Additionally or alternatively, the memory stores instructions executable by the processor to adjust a control parameter of the energy tool (e g clamping pressure) based on signals indicative of a tissue property intercepted by the flex circuit and/or transmitted along the wireless communication path.

In various aspects, the present disclosure provides a control circuit to relay a wireless signal between a robot and a control console, adjust a control parameter of the generator, and/or adjust a control parameter of an energy tool, as described herein. In various aspects, the present disclosure provides a non-transitory computer readable medium storing computer readable instructions which, when executed, cause a machine to relay a wireless signal between a robot and a control console, adjust a control parameter of the generator, and/or adjust a control parameter of an energy tool, as described herein.

In one aspect, one or more features and/or effects of a robotically-controlled surgical tool and end effector thereof can be controlled by a control algorithm. For example, the intensity of an end effector effect can be controlled by a control algorithm stored in the memory of the robot and executable by a processor. In one instance, an end effector effect can be smoke evacuation, insufflation, and/or cooling. In another instance, an end effector effect can be articulation and/or retraction. As an example, a robot can implement a load control holding algorithm for articulation of a robotic tool that results in a predefined lateral load on tissue and is limited by a displacement limit, as further described herein.

In certain instances, it can be desirable to incorporate a pump into a robotically-controlled surgical tool, such as an energy tool including an RF electrode and/or an ultrasonic blade, for example. A pump can provide insufflation gases or air to a surgical site. In certain instances, a pump can provide coolant to a surgical site and/or can extract smoke and/or steam from the surgical site.

Robotically-controlled surgical tools include a drive system for releasably engaging with a robot and transferring drive motions from the robot to the robotic tool. For example, a robotically-controlled surgical tool can include an interface including rotary driver(s) configured to receive rotary inputs from motor(s) in a motor housing or tool mounting portion. Exemplary drive systems and interfaces therefor are further described herein.

The rotary drivers in the robotic tools are configured to actuate various surgical functions such as rotation of a shaft, closure of end effector jaws, and articulation of the end effector, for example. Examples of interface configurations are further described herein and in International Patent Application Publication No. WO 2015/153642, filed Mar. 31, 2015, titled SURGICAL INSTRUMENT WITH SHIFTABLE TRANSMISSION, in International Patent Application Publication No. WO 2015/153636, filed Mar. 31, 2015, titled CONTROL INPUT ACCURACY FOR TELEOPERATED SURGICAL INSTRUMENT, and in U.S. Pat. No. 9,095,362, filed Nov. 15, 2011, titled METHOD FOR PASSIVELY DECOUPLING TORQUE APPLIED BY A REMOTE ACTUATOR INTO AN INDEPENDENTLY ROTATING MEMBER, each of which is herein incorporated by reference in its entirety.

In certain instances, the number of motors, the number of rotary drivers, and/or the arrangements of motors and/or rotary drivers can be limited or constrained by the footprint of the drive system and/or coupling between the robotic tool and the tool mounting portion. In one aspect, it can be desirable for new and/or improved robotically-controlled surgical tools to be compatible with existing robotic platforms. For example, without enlarging the motor housing or tool mounting portion, it can be desirable to change the functionality and/or add functionality to robotic tools for use with an existing motor housing and tool mounting portion. In such instances, it can be challenging to incorporate certain features, like a pump for example, into a robotic tool compatible with an existing surgical robot. Moreover, it can be desirable to include controls and/or control algorithms for such a pump within the existing architecture of the surgical robot.

In one aspect, a pump for a robotic tool can be powered by a rotary drive of the robotic tool interface. The rotary drive and, thus, the pump can be driven at a variable rate, which can depend on the needs of the robotic tool and/or the surgical procedure. For example, the speed of the rotary drive coupled to the pump can be related to the volume of smoke being evacuated from the surgical site and/or the application of energy to tissue by the robotic tool. In one instance, the robotic tool can be an intelligent tool that includes a processor configured to determine the appropriate rate for the pump based on sensors on the robotic tool and/or other inputs thereto. In other instances, a processor in the control unit of the robot can be configured to determine the appropriate rate for the pump based on sensors on the robot and/or modules thereof, such as a smoke evacuation module in a robotic hub, for example.

Energy devices utilize energy to affect tissue. In an energy device, the energy is supplied by a generator. Energy devices include devices with tissue-contacting electrodes, such as an electrosurgical device having one or more radio frequency (RF) electrodes, and devices with vibrating surfaces, such as an ultrasonic device having an ultrasonic blade. For an electrosurgical device, a generator is configured to generate oscillating electric currents to energize the electrodes. For an ultrasonic device, a generator is configured to generate ultrasonic vibrations to energize the ultrasonic blade.

As provided herein, energy devices deliver mechanical or electrical energy to a target tissue in order to treat the tissue (e.g. to cut the tissue and/or cauterize blood vessels within and/or near the target tissue). The cutting and/or cauterization of tissue can result in fluids and/or particulates being released into the air. Such fluids and/or particulates emitted during a surgical procedure can constitute smoke, for example, which can include carbon and/or other particles suspended in air.

In various instances, an energy tool for use with a robotic system can include a suction port coupled to a pump that is powered by a motor on the tool driver. For example, an energy tool for the da Vinci® surgical robotic system can include a suction port coupled to a pump that is powered by a motor on the tool driver. The pump can be configured to extract smoke from a surgical site via the suction port. In such instances, the energy tool can include a smoke evacuation system. In one aspect, the robotic tool can include a pump. Alternatively, the robotic tool can be coupled to a pump.

The reader will appreciate that such an evacuation system can be referred to as a "smoke evacuation system" though such an evacuation system can be configured to evacuate more than just smoke from a surgical site. Throughout the present disclosure, the "smoke" evacuated by an evacuation system is not limited to just smoke. Rather, the evacuation systems disclosed herein can be used to evacuate a variety of fluids, including liquids, gases, vapors, smoke, steam, or combinations thereon. The fluids can be biologic in origin and/or can be introduced to the surgical site from an external source during a procedure. The fluids can include water, saline, lymph, blood, exudate, and/or pyogenic discharge, for example. Moreover, the fluids can include particulates or other matter (e.g. cellular matter or debris) that is evacuated by the evacuation system. For example, such particulates can be suspended in the fluid.

Figure 33:
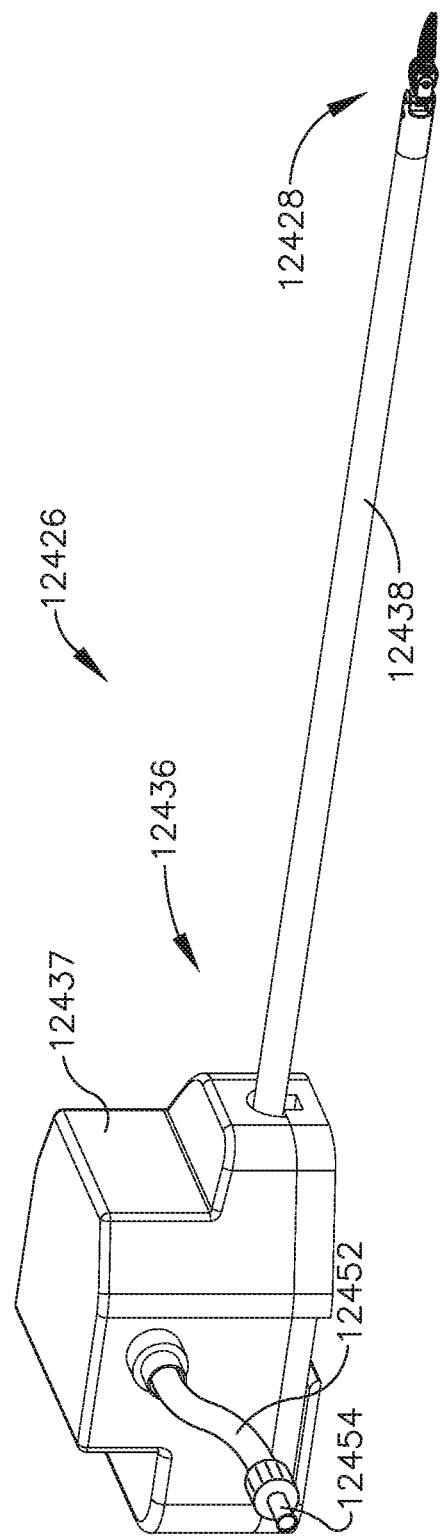
FIG. 33 is a perspective view of a bipolar radio frequency (RF) robotic tool having a smoke evacuation pump for use with a robotic surgical system, in accordance with one aspect of the present disclosure.
Figure 34:
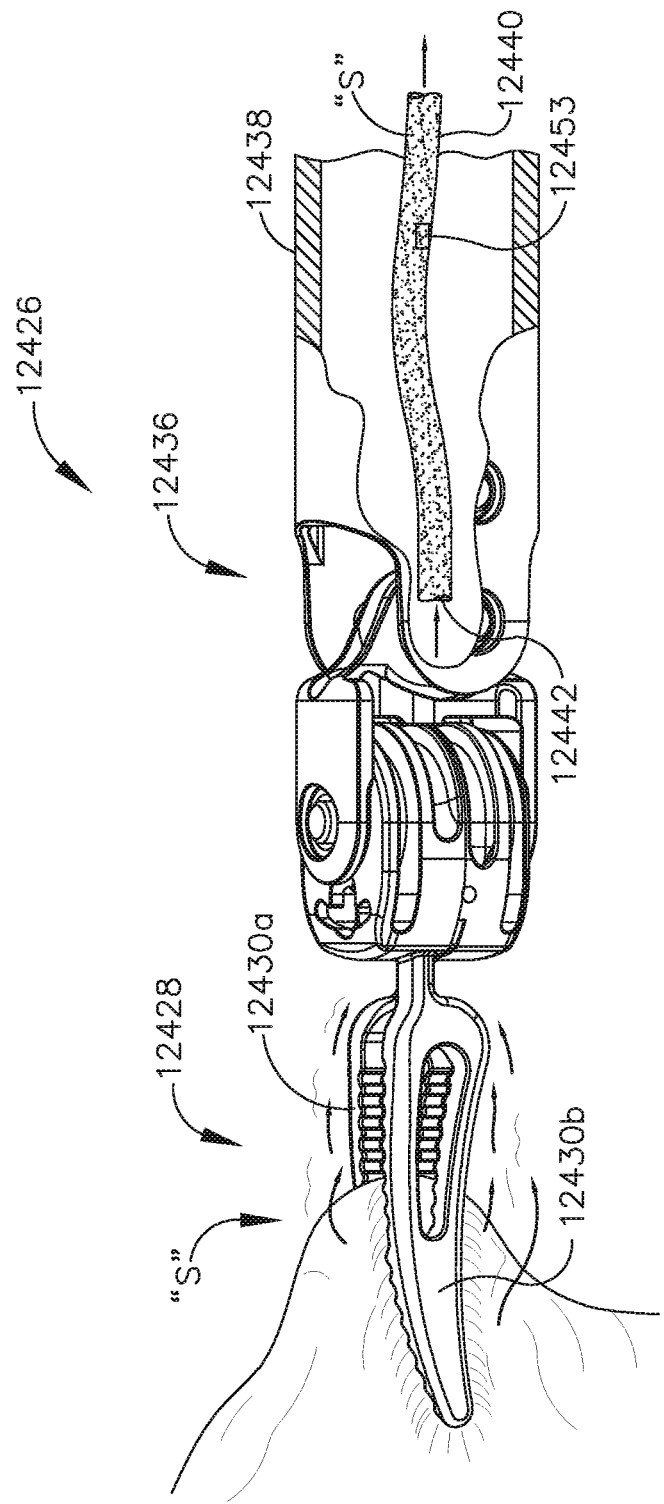
FIG. 34 is a perspective view of the end effector of the bipolar radio frequency robotic tool of FIG. 33 depicting the end effector clamping and treating tissue, in accordance with one aspect of the present disclosure.
Figure 35:
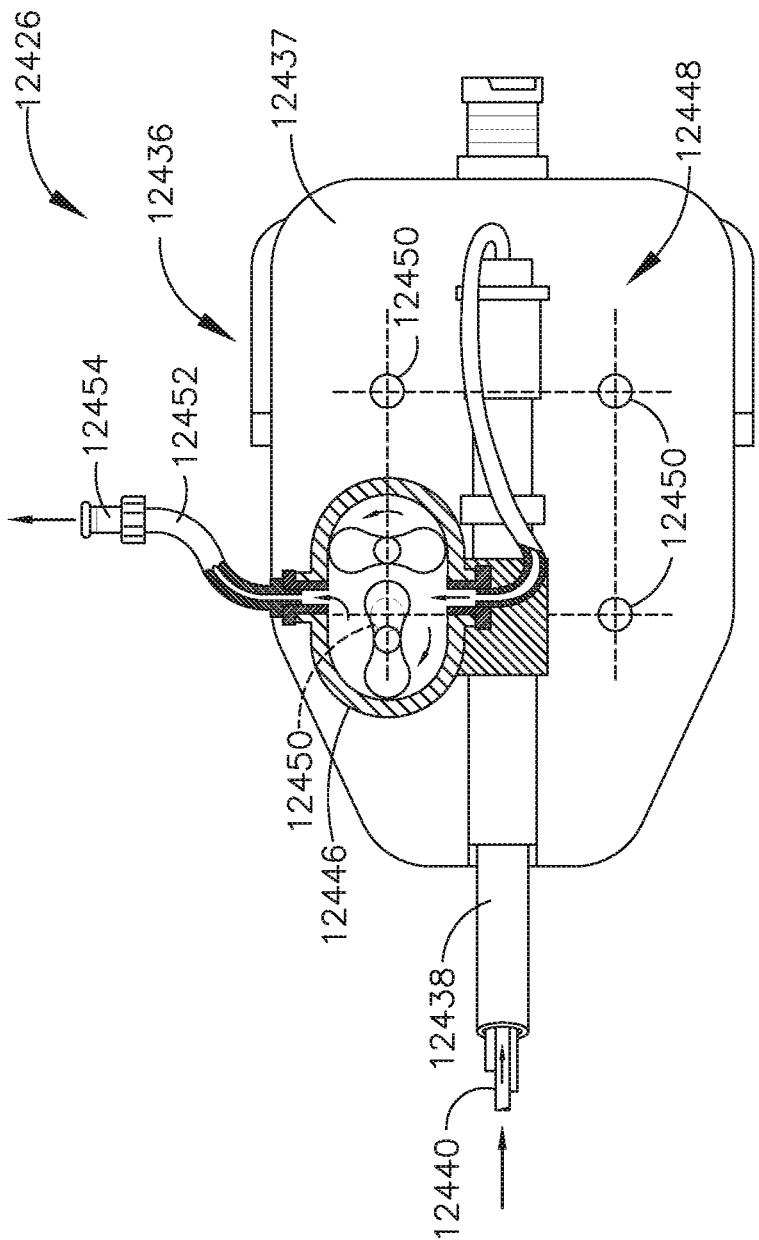
FIG. 35 is a plan view of the tool drive interface of the bipolar radio frequency robotic tool of FIG. 33 with components removed for clarity, in accordance with one aspect of the present disclosure.

Referring primarily to FIGS. 33-35, a robotic tool 12426 for use with a robotic surgical system is depicted. The robotic tool 12426 can be employed with the robotic surgical system 12010 (FIG. 23), for example. The robotic tool 12426 is a bipolar radio-frequency (RF) robotic tool. For example, the tool can be similar in many respects to the tool disclosed in U.S. Pat. No. 8,771,270, filed on Jul. 16, 2008, titled BIPOLAR CAUTERY INSTRUMENT, which is herein incorporated by reference in its entirety.

In other instances, the robotic tool 12426 can be a monopolar RF tool, an ultrasonic tool, or a combination ultrasonic-RF tool. For example, the robotic tool 12426 can be similar in many similar to the tool disclosed in U.S. Pat. No. 9,314,308, filed Mar. 13, 2013, titled ROBOTIC ULTRASONIC SURGICAL DEVICE WITH ARTICULATING END EFFECTOR, which is herein incorporated by reference in its entirety.

The robotic tool 12426 includes a proximal housing 12437, a shaft 12438 extending from the proximal housing 12437, and an end effector 12428 extending from a distal end of the shaft 12438. Referring primarily to FIG. 34, the end effector 12428 includes opposing jaws 12430a, 12430b. Each jaw 12430a, 12430b includes a tissue-contacting surface including an electrode. For example, the jaw 12430a can include a supply electrode, and the jaw 12430b can include a return electrode, or vice versa. The end effector 12428 is shown in a clamped configuration and generating an RF weld in FIG. 34. In such instances, smoke S from the RF weld may accumulate around the end effector 12428. For example, the smoke S can accumulate in the abdomen of a patient in certain instances.

The robotic tool 12426 also includes an evacuation system 12436. For example, to improve visibility and efficiency of the robotic tool 12426, the smoke S at the surgical site can be evacuated along an evacuation channel, or suction conduit, 12440 extending proximally from the end effector 12428. The evacuation channel 12440 can extend through the shaft 12438 of the robotic tool 12426 to the proximal housing 12437. The evacuation conduit 12440 terminates at a suction port 12442 adjacent to the end effector 12428. During operating of the evacuation system 12436, smoke S at the surgical site is drawn into the suction port 12442 and through the evacuation conduit 12440.

In various instances, the robotic tool 12426 can include insufflation, cooling, and/or irrigation capabilities, as well. For example, the evacuation system 12436 can be configured to selectively pump a fluid, such as saline or $CO_2$ for example, toward the end effector 12428 and into the surgical site.

Figure 39:
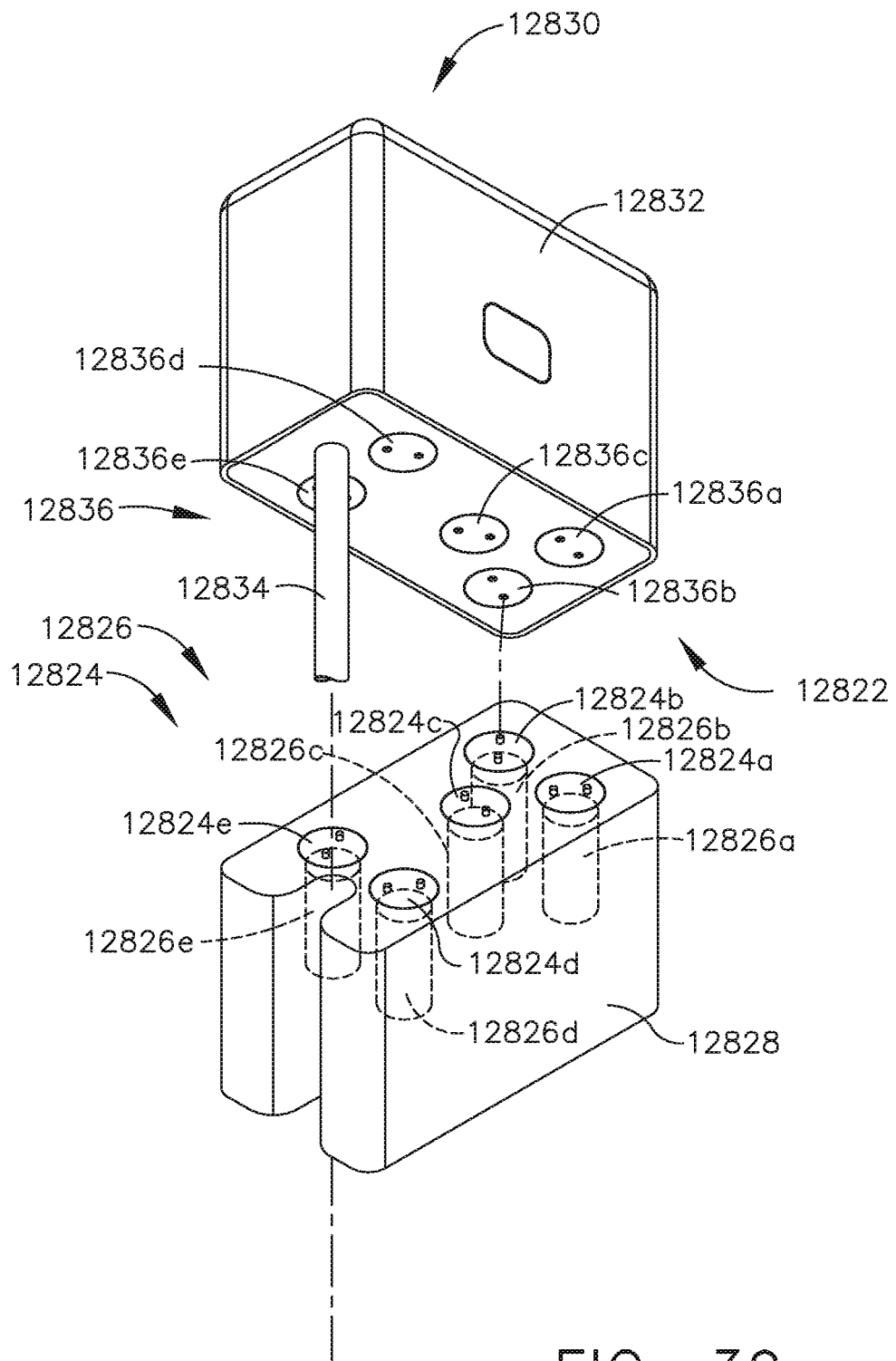
FIG. 39 is an exploded perspective view of the drive system of FIG. 38, in accordance with at least one aspect of the present disclosure.

In various instances, the evacuation channel 12440 can be coupled to a pump for drawing the smoke S along the evacuation channel 12440 within the shaft 12438 of the robotic tool 12426. Referring primarily to FIG. 35, the evacuation system 12436 includes a pump 12446. The pump 12446 is housed in the proximal housing 12437 of the robotic tool 12426. The pump 12446 is a lobe pump, which has been incorporated into a drive interface 12448 of the robotic tool 12426. The drive interface 12448 includes rotary drivers 12450, which are driven by rotary outputs from motors in the tool mounting portion of the robot, as described herein (see rotary outputs 12256 (FIG. 31) and rotary outputs 12824a-12824e (FIG. 39), for example).

Lobe pumps can be low volume and quiet or noiseless and, thus, desirable in certain instances. For example, a lobe pump can ensure the noise generated by the evacuation system 12436 is not distracting to the clinicians and/or allows communication between clinicians in the surgical theater. The reader will readily appreciate that different pumps can be utilized by the evacuation system 12436 in other instances.

A channel 12452 terminating in a fitting 12454 extends from the pump 12446 in FIGS. 33 and 35. The fitting 12454 is a luer fitting, however, the reader will readily appreciate that alternative fittings are envisioned. The luer fitting can be selectively coupled to a reservoir that is configured to receive the smoke S from the surgical site, for example. Additionally or alternatively, the luer fitting can supply discharge from the pump 12446 to a filter.

Referring still to FIG. 35, internal components of the drive interface 12448 are depicted, however, certain components are excluded for clarity. The evacuation channel 12440 extends through the shaft 12438 to the lobe pump 12446 in the proximal housing 12437. The pump 12446 is driven by a rotary driver 12450 of the interface 12448. In various instances, the interface 12448 can include four rotary drivers 12450. In one example, a first rotary driver 12450 is configured to power an articulation motion, a second rotary driver 12450 is configured to power a jaw closure motion, a third rotary driver 12450 is configured to power a shaft rotation, and a fourth rotary driver 12450 is configured to power the pump 12446. The reader will appreciate that alternative interface arrangements can include more than or less than four rotary drivers 12450. Additionally, the drive motions generated by the rotary drivers 12450 can vary depending on the desired functionality of the robotic tool 12426. Moreover, in certain instances, the drive interface 12448 can include a transmission or shifter such that the rotary drivers 12450 can shift between multiple surgical functions, as further described herein (see transmission 12124 in FIG. 29 and transmission assembly 12840 in FIGS. 40-45, for example). In one instance, the rotary driver 12450 coupled to the pump 12446 can also actuate a clamping motion of the end effector 12428, for example.

In one aspect, activation of the pump 12446 of the robotic tool 12426 can be coordinated with the application of energy by the robotic tool 12426. In various instances, a control algorithm for the rotary driver 12450 for the pump 12446 can be related to the rate at which smoke S is extracted from the surgical site. In such instances, the robot (e.g. the robot 12022 in FIGS. 23 and 27) can have direct control over the volume of evacuation and/or extraction from the surgical site.

In one instance, the on/off control for the pump 12446 is controlled based on inputs from a camera, such as the camera of the imaging device 124 (FIG. 2) like an endoscope, for example. The imaging device 124 can be configured to detect the presence of smoke S in a visual field at the surgical site. In another aspect, the on/off control for the pump 12446 is controlled based on inputs from a smoke sensor 12453 (FIG. 34) in-line with the fluid being pumped out of the patient. For example, the pump 12446 can remain on as long as a threshold amount of smoke S is detected by the smoke sensor 12453 and can be turned off or paused when the detected volume of smoke S falls below the threshold amount. In still another aspect, the pump 12446 is turned on when energy is activated and, in certain instances, can remain on for a period of time after the energy has been stopped. The duration of time for which the pump 12446 can remain on after the energy has stopped may be fixed or may be proportional to the length of time the energy was activated, for example.

Figure 37:
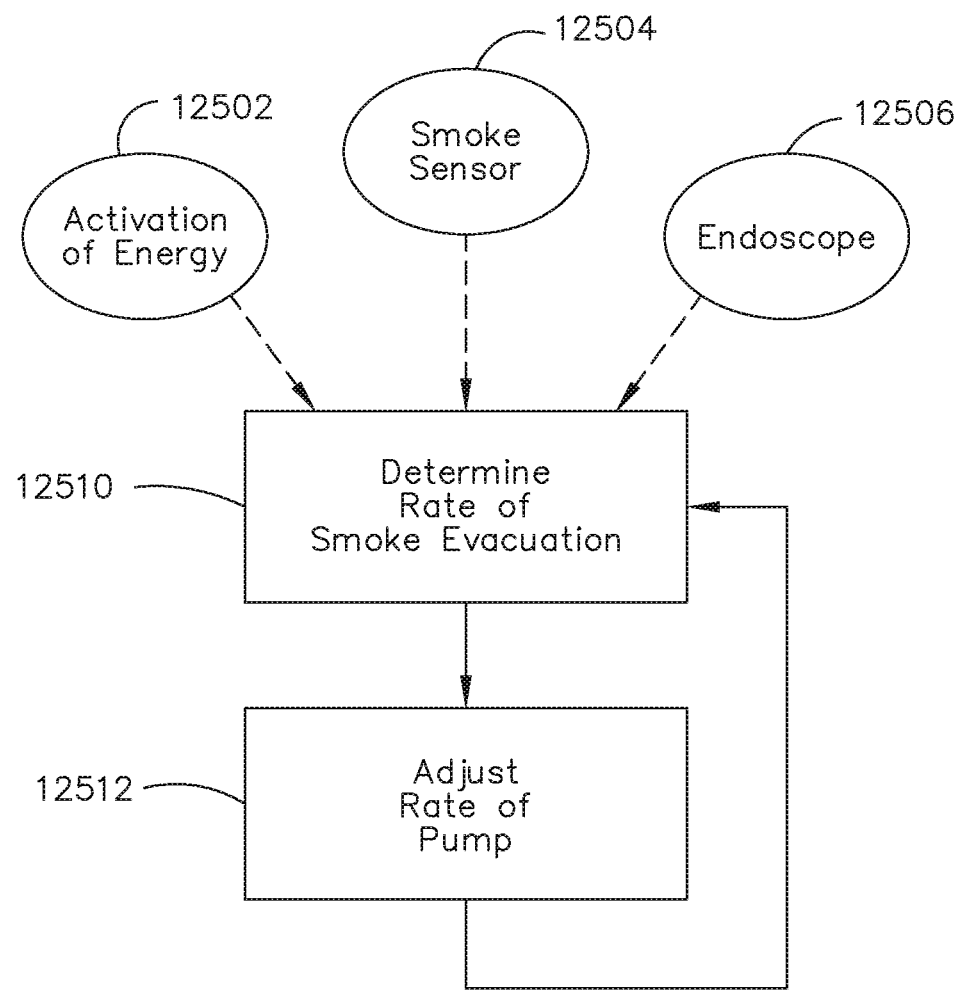
FIG. 37 is a flow chart of a control algorithm for a robotic tool for use with a robotic surgical system, in accordance with one aspect of the present disclosure.

Referring primarily to FIG. 37, a flow chart depicting logic steps for operating a pump, such as the pump 12446, is depicted. A processor for the robot (e.g. robot 12022) and/or a processor of a hub (e.g. hub 106, hub 206, robotic hub 122, and robotic hub 222) that is in signal communication with the robot can determine or estimate the rate of smoke evacuation from the surgical site. The rate of smoke evacuation can be determined at step 12510 by one or more factors or inputs including the activation of energy by the robotic tool (a first input 12502), a smoke sensor in-line with the smoke evacuation channel (a second input 12504), and/or an imaging device configured to view the surgical site (a third input 12506). The first input 12502 can correspond to the duration of energy application and/or the power level, for example. Based on the one or more factors, the pump can be adjusted at step 12512. For example, the rate at which the rotary driver drives the pump can be adjusted. In other instances, the rotary driver can stop or pause the operation of the pump while the detected rate of smoke evacuation is below a threshold volume. The flow chart of FIG. 37 can continue throughout the operation of a robotic tool. In certain instances, the steps 12510 and 12512 can be repeated at predefined intervals during a surgical procedure and/or when requested by a clinician and/or recommend by a hub.

Figure 36:
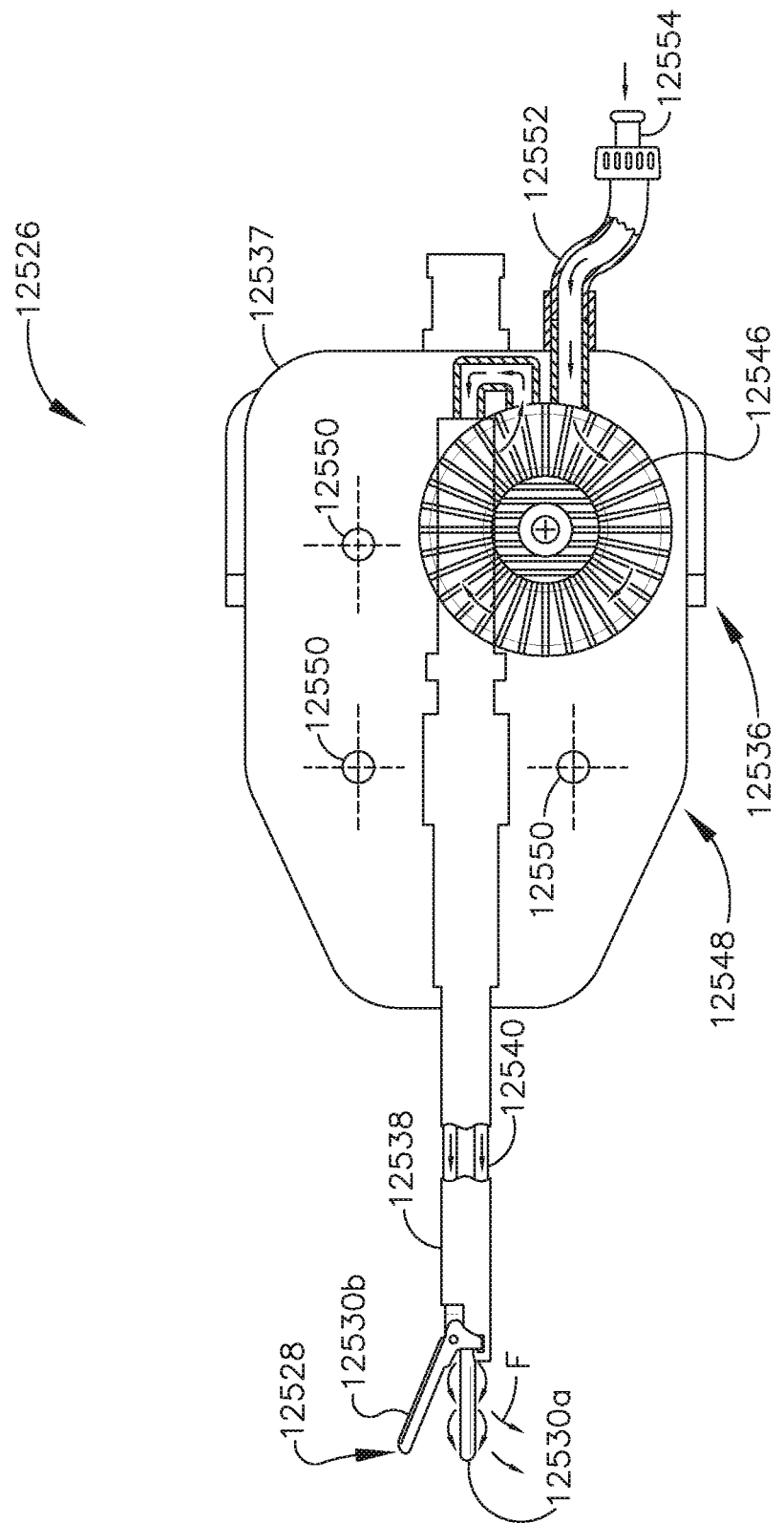
FIG. 36 is a plan view of an ultrasonic robotic tool having cooling and insufflation features for use with a robotic surgical system, in accordance with one aspect of the present disclosure.

Referring now to FIG. 36, a robotic tool 12526 for use with a robotic surgical system is depicted. The robotic tool 12526 can be employed with the robotic surgical system 12010 (FIG. 23), for example. The robotic tool 12526 is an ultrasonic robotic tool having cooling and insufflation capabilities. For example, the robotic tool 12526 can be similar in many respects to the robotic tool disclosed in U.S. Pat. No. 9,314,308, filed Mar. 13, 2013, titled ROBOTIC ULTRASONIC SURGICAL DEVICE WITH ARTICULATING END EFFECTOR, which is herein incorporated by reference in its entirety.

The robotic tool 12526 includes a proximal housing 12537, a shaft 12538 extending from the proximal housing 12537, and an end effector 12528 extending from a distal end of the shaft 12538. The end effector 12528 includes an ultrasonic blade 12530*a* and an opposing clamp arm 12530*b*. The robotic tool 12526 also includes an irrigation system 12536, which is configured to provide a coolant, such as saline or cool $CO_2$ for example, to the surgical site. Irrigation can be configured to cool the tissue and/or the ultrasonic blade 12530*a*, for example. The irrigation system 12536 includes an irrigation channel 12540, which extends through the shaft 12538 to the proximal housing 12537. The irrigation channel 12540 terminates at an irrigation port adjacent to the end effector 12528.

In various instances, the irrigation channel 12540 can be coupled to a blower configured to direct fluid along the irrigation channel 12540 within the shaft 12538 of the robotic tool 12526. The irrigation system 12536 includes a blower 12546. The blower 12546 is housed in the proximal housing 12537 of the robotic tool 12526. The blower 12546 is a regenerative blower, which has been incorporated into a drive interface 12548 of the robotic tool 12526. The drive interface 12548 includes rotary drivers 12550, which are driven by rotary outputs from motors in the tool mounting portion of the robot, as described herein (see rotary outputs 12256 (FIG. 31) and rotary outputs 12824*a*-12824*e* (FIG. 39), for example).

A channel 12552 terminating in a fitting 12554 extends from the blower 12546. The fitting 12554 is a luer fitting, however, the reader will readily appreciate that alternative fittings are envisioned. The luer fitting can be selectively coupled to a reservoir that is configured to provide the irrigation fluid to the blower 12546. In operation, coolant can enter the insufflation line through the fitting 12554 and the blower 12546 can draw the coolant toward the blower 12546 at the drive interface 12548 and then blow the coolant distally along the shaft 12538 of the robotic tool 12526 toward the end effector 12528. The coolant can be expelled at or adjacent to the end effector 12528, which can cool the ultrasonic blade and/or maintain insufflation of the surgical site, such as insufflation of an abdomen, for example.

In FIG. 36, internal components of the drive interface 12548 are depicted, however, certain components are excluded for clarity. The irrigation channel 12540 extends through the shaft 12538 to the blower 12546 in the proximal housing 12537. The blower 12546 is driven by a rotary driver 12550 of the drive interface 12548. Similar to the interface 12448 (FIG. 35), the interface 12548 includes four rotary drivers 12550. In one example, a first rotary driver 12550 is configured to power an articulation motion, a second rotary driver 12550 is configured to power a jaw closure motion, a third rotary driver 12550 is configured to power a shaft rotation, and a fourth rotary driver 12550 is configured to power the irrigation system 12536. The reader will appreciate that alternative interface arrangements can include more than or less than four rotary drivers 12550. Additionally, the drive motions generated by the rotary drivers 12550 can vary depending on the desired functionality of the robotic tool. Moreover, in certain instances, the drive interface 12548 can include a transmission or shifter such that the rotary drivers 12550 can shift between multiple surgical functions, as further described herein (see transmission 12124 in FIG. 29 and transmission assembly 12840 in FIGS. 40-45, for example). In one instance, the rotary driver 12550 coupled to the blower 12546 can also actuate a clamping motion of the end effector 12528, for example.

As described herein with respect to the pump 12446 in FIG. 35, operation of the blower 12546 in FIG. 36 can be coordinated with the application of energy by the robotic tool 12526. For example, the blower 12546 can be turned on when energy is activated and, in certain instances, the blower 12546 can remain on for a period of time after the energy has been stopped. The duration of time for which the blower 12546 can remain on after the energy has stopped may be fixed or may be proportional to the length of time the energy was activated, for example. Additionally or alternatively, the power level of the blower 12546 can be proportional or otherwise related to the activation level of the robotic tool 12526. For example, a high power level can correspond to a first rate and a lower power level can correspond to a second rate. In one example, the second rate can be less than the first rate.

In one aspect, the robotic tool 12526 can also include an insufflation pump that is upstream of the regenerative blower 12546. The insufflation pump can direct a first volume of fluid into a trocar and a second volume of fluid into the regenerative blower 12546. The fluid provided to the trocar can be configured to insufflate the surgical site, for example, the abdomen of a patient. The fluid provided by the regenerative blower 12546 can be configured to cool the ultrasonic blade, for example.

The robotic surgical tools 12426 and 12526 can be used in connection with a hub, such as the robotic hub 122 or the robotic hub 222, for example. In one aspect, the robotic hubs can include a situational awareness module, as described herein. The situational awareness module can be configured to determine and/or confirm a step in a surgical procedure and/or suggest a particular surgical action based on information received from various sources, including one or more robotic surgical tool(s) and/or a generator module. In one instance, the actuation of a pump on a robotic surgical tool can inform the situational awareness module that evacuation and/or irrigation have been employed, which can lead to a conclusion regarding a particular surgical procedure or group of surgical procedures. Similarly, data from the situational awareness module can be supplied to a processor. In certain instances, the processor can be communicatively coupled to a memory that stores instructions executable by the processor to adjust a pumping rate of the pump based on data from the situational awareness module which can indicate, for example, the type of surgical procedure and/or the step in the surgical procedure. For example, situational awareness can indicate that insufflation is necessary for at least a portion of a particular surgical procedure. In such instances, a pump, such as the blower 12546 (FIG. 36) can be activated and/or maintained at a level to maintain a sufficient insufflation.

In one aspect, the robotic surgical system includes a processor and a memory communicatively coupled to the processor, as described herein. The memory stores instructions executable by the processor to rotate a driver in a robotic tool at a variable rate to provide an adjustable power level to a pump in the robotic tool, as described herein.

In various aspects, the present disclosure provides a control circuit to rotate a rotary driver in a robotic tool at a variable rate, as described herein. In various aspects, the present disclosure provides a non-transitory computer readable medium storing computer readable instructions which, when executed, cause a machine to rotate a rotary driver in a robotic tool at a variable rate to provide an adjustable power level to a pump in the robotic tool, as described herein.

Referring now to FIGS. 51 and 52, a surgical procedure utilizing two robotic tools is depicted. In FIG. 51, the robotic tools are engaged with tissue at a surgical site. The first tool in this example is a flexible robotic retractor 12902, which is applying a retracting force to a portion of a patient's liver L. In FIG. 52, the flexible robotic retractor 12902 can be moved along a longitudinal axis of the tool shaft in a direction A and/or can be moved laterally (e.g. pivoted at a joint between two rigid linkages in the robotic retractor) in a direction B.

The second tool in this example is an articulating bipolar tool 12904, which is being clamped on tissue. For example, the articulating bipolar tool 12904 can be configured to mobilize liver attachments A to the liver utilizing bipolar RF currents. The articulating bipolar tool 12904 can be articulated laterally (e.g. pivoted at an articulation joint proximal to the bipolar jaws of the robotic tool 12904) in the direction C. The directions A, B, and C are indicated with arrows in FIG. 52.

In the depicted example, the flexible robotic retractor 12902 seeks to hold back an organ, the liver L, as the bipolar jaws of the articulating bipolar tool 12904 seek to cut and/or seal clamped tissue to mobilize the liver attachments A. In one aspect, movement of the liver L by the flexible robotic retractor 12902 can be configured to maintain a constant retraction force as the bipolar tool 12904 mobilizes the liver attachments A to the liver L. A load control algorithm can be configured to maintain the constant retraction force on the tissue. In certain instances, the load control algorithm can be an articulation control algorithm that provides a set, or predetermined, torque at the articulation joint(s) of the articulating bipolar tool 12904 and/or the flexible robotic retractor 12902. The set torque at an articulation joint can be approximated based on current supplied to the articulation motor, for example.

In certain instances, the flexible robotic retractor 12902 can risk or otherwise threaten over-retraction of the liver L. For example, if displacement of the flexible robotic retractor 12902 approaches a set displacement limit, the flexible robot retractor 12902 can risk tearing a portion of the tissue. To prevent such an over-retraction, as the displacement of the flexible robotic retractor 12902 approaches the displacement limit, the force generated by the flexible robotic retractor 12902 can be reduced by the load control algorithm. For example, the force can be reduced below a constant, or substantially constant, retraction force when a displacement limit has been met.

Referring now to a graphical display 12910 in FIG. 53, the retraction force F exerted on an organ and the displacement δ of the robotic tool, and by extension the organ, is plotted over time. The reader will appreciate that the robotic tools 12902 and 12904, as depicted in the surgical procedure of FIGS. 51 and 52, can be utilized to generate the graphical display 12910. Alternative surgical tool(s) and surgical procedures are also contemplated. In one aspect, an operator can set a retraction force threshold Y and a displacement limit X as depicted in FIG. 53. In other instances, the retraction force threshold Y and/or the displacement limit X can be determined and/or computed based on information from a surgical hub and/or cloud. In certain instances, a particular retraction force threshold Y and/or displacement limit X can be recommended to a clinician based on data stored in the memory of the robot, the surgical hub, and/or the cloud. The retraction force threshold Y and/or the displacement limit X can depend on patient information, for example.

During the surgical procedure, if the retraction force F drops below the constant retraction force threshold Y, or drops by a predefined percentage or amount relative to the constant retraction force threshold Y, as at times $t_1$, $t_2$, and $t_3$, the flexible robotic retractor 12902 can be further displaced, to displace the organ, and increase the retraction force F toward the threshold Y. Similarly, if the displacement δ approaches the displacement limit X, as at time $t_4$, the retraction force can be reduced to limit further displacement beyond the displacement limit X. For example, referring again to FIG. 51, the liver L is depicted in a second position indicated as L'. The position of the liver L' can correspond to the displacement limit X of the flexible robotic retractor 12902.

Referring now to FIG. 54, a flow chart depicting logic steps for operating a robotic tool, such as the tool 12902 (FIGS. 51 and 52) for example, is depicted. A processor for the robot (e.g. the robot 12022) and/or of a processor of a hub (e.g. the hub 106, the hub 206, the robotic hub 122, and the robotic hub 222) that is in signal communication with the robot can set a displacement limit at step 12920. Additionally, the processor can set a force limit at step 12922. The displacement limit and the force limit can be selected based on input from one or more sources including a clinician input 12930, a robot input 12932, a hub input 12934, and/or a cloud input 12936, as further described herein. In certain instances, the hub can suggest a particular limit based on data collected by a robot, provided to the hub, and/or stored in the cloud. For example, a situational awareness module can suggest a particular limit based on the surgical procedure or step thereof ascertained by the situational awareness module. Additionally or alternatively, the clinician can provide an input and/or select the limit from the hub's suggestions. In other instances, the clinician can override the hub's suggestions. The limits can correspond to a range of values, such as the limit ±one percent, ±five percent, or ±ten percent, for example.

The robotic tool can initially operate in a constant force mode. At step 12924 in the constant force mode, the force exerted by the robotic tool can be maintained at the force limit. The processor can monitor the force to ensure the force stays below the force limit Y. If the force exceeds the force limit Y, the displacement value can be increased at step 12926 until the force reaches or sufficiently approaches the force limit Y. A force can sufficiently approach the force limit when the force is within a range of values corresponding to the force limit. The processor can monitor the displacement to ensure the displacement stays below the displacement limit X.

If the displacement approaches the displacement limit X (or enters the range of values corresponding to the displacement limit), the robotic tool can switch to a displacement limit mode. In the displacement limit mode, the force value can be decreased at step 12928 to ensure the robotic tool stays within the displacement limit. A new force limit can be set at step 12922 to ensure the displacement stays within the displacement limit. In such instances, the robotic tool can switch back to the constant force mode (with the new, reduced force limit) and steps 12924, 12926, and 12928 can be repeated.

In certain instances, the stiffness of the shaft of one or more of the robotic tools can be factored into the load control algorithm in order to achieve the desired amount of lateral force on an organ, like the liver L. For example, the flexible robotic retractor 12902 can define a stiffness that affects the lateral load exerted on a tissue by the end effector thereof.

In certain instances, a drive housing for a robotic tool can include a plurality of rotary drivers, which can be operably driven by one or more motors. The motors can be positioned in a motor carriage, which can be located at the distal end of a robotic arm. In other instances, the motors can be incorporated into the robotic tool. In certain instances, a motor can operably drive multiple rotary drivers and a transmission can be configured to switch between the multiple rotary drivers. In such instances, the robotic tool cannot simultaneously actuate two or more rotary drivers that are associated with the single drive motor. For example, as described herein with respect to FIG. 29, the motor 12112 can selectively power one of the roll DOF 12132, the high force grip DOF 12136, or the tool actuation DOF 12138. The transmission 12124 can selectively couple the motor 12112 to the appropriate DOF.

In certain instances, it can be desirable to increase the torque delivered to an output of the robotic tool. For example, clamping and/or firing of a surgical stapler may benefit from additional torque in certain instances, such as when the tissue to be cut and/or stapled is particularly thick or tough. Especially for longer end effectors and/or longer firing strokes, additional torque can be required to complete the firing stroke. In certain instances, an I-beam firing structure can be utilized, especially for longer end effectors and/or longer firing strokes. The I-beam can limit deflection at the distal tip of the firing stroke for example. However, an I-beam can require increased torque.

Additionally, certain robotic tools may require additional flexibility regarding the simultaneous operation of multiple DOFs or surgical end effector functions. To increase the power, torque, and flexibility of a robotic system, additional motors and/or larger motors can be incorporated into the motor carriage. However, the addition of motors and/or utilization of larger motors can increase the size of the motor carriage and the drive housing.

In certain instances, a robotic surgical tool can include a compact drive housing. A compact drive housing can improve the access envelope of the robotic arm. Moreover, a compact drive housing can minimize the risk of arm collisions and entanglements. Though the drive housing is compact, it can still provide sufficient power, torque, and flexibility to the robotic tool.

In certain instances, shifting between end effector functions can be achieved with one of the drive shafts. Shifting and locking of the rotary drives may only occur when a robotic surgical system is in a rest mode, for example. In one aspect, it can be practical to have three rotary drives operate as many end effector functions as needed based on the cam structure of the shifting drive. In one aspect, by using three rotary drives in cooperation, a robotic surgical tool can shift between four different possible functions instead of three different functions. For example, three rotary drives can affect shaft rotation, independent head rotation, firing, closing, and a secondary closing means. In still other instances, a rotary drive can selectively power a pump, such as in the surgical tools 12426 and 12526 in FIGS. 35 and 36, respectively, for example.

Additionally or alternatively, multiple rotary drives can cooperatively drive a single output shaft in certain instances. For example, to increase the torque delivered to a surgical tool, multiple motors can be configured to deliver torque to the same output shaft at a given time. For example, in certain instances, two drive motors can drive a single output. A shifter drive can be configured to independently engage and disengage the two drive motors from the single output. In such instances, increased torque can be delivered to the output by a compact drive housing that is associated with multiple rotary drivers and end effector functions. As a result, load capabilities of the surgical tool can be increased. Moreover, the drive housing can accommodate surgical tools that require different surgical functions, including the operation of multiple DOFs or surgical functions.

Referring now to FIGS. 38-45, a drive system 12800 for a robotic surgical tool 12830 is depicted. The drive system 12800 includes a housing 12832 and a motor carriage 12828. A shaft 12834 of the surgical tool 12830 extends from the housing 12832. The motor carriage 12828 houses five motors 12826 similar to the motor carriage 12108 (FIG. 29). In other instances, the motor carriage 12828 can house less than five motors or more than five motors. In other instances, the motors 12826 can be housed in the robotic surgical tool 12830.

Each motor 12826 is coupled to a rotary output 12824 and each rotary output 12824 is coupled to a rotary input 12836 in the housing 12832 at a drive interface 12822. The rotary motions from the motors 12826 and corresponding rotary outputs 12824 are transferred to a respective rotary input 12836. The rotary inputs 12836 correspond to rotary drivers, or rotary drive shafts, in the housing 12832. In one example, a first motor 12826a can be a left/right articulation (or yaw) motor, a second motor 12826b can be an up/down articulation (or pitch) motor, a third motor 12826c can be a shifter motor, a fourth motor 12826d can be a first cooperative motor, and a fifth motor 12826e can be a second cooperative motor. Similarly, a first rotary output 12824a can be a left/right articulation (or yaw) output, a second rotary output 12824b can be an up/down articulation (or pitch) output, a third rotary output 12824c can be a shifter output, a fourth rotary output 12824d can be a first cooperative output, and a fifth rotary output 12824e can be a second cooperative output. Furthermore, a first rotary input 12836a can be a left/right articulation (or yaw) drive shaft, a second rotary input 12836b can be an up/down articulation (or pitch) drive shaft, a third rotary input 12836c can be a shifter drive shaft, a fourth rotary input 12836d can be a first cooperative drive shaft, and a fifth rotary input 12836e can be a second cooperative drive shaft. In other instances, the drive shafts 12836a-12836e can be operably positionable in different orientations to effectuate different gear trains configurations to transmit a desired rotary output.

The surgical tool 12830 is depicted in a plurality of different configurations in FIGS. 47-50. For example, the surgical tool 12830 is in an unactuated configuration in FIG. 47. The shaft 12834 has been articulated about the yaw and pitch axes (in the directions of the arrows A and B) in FIG. 48. Rotation of the first and second rotary inputs 12836a and 12836b is configured to articulate the shaft 12834 about the yaw and pitch axes, respectively. In FIG. 49, the shaft 12834 has been rotated in the direction of the arrow C about the longitudinal axis of the shaft 12834 and a jaw of the end effector 12835 has been closed with a low-force actuation in the direction of arrow D. Rotation of the fourth rotary output 12836d is configured to selectively affect the rotation of the shaft 12834, and rotation of the fifth rotary output 12836e is configured to selectively affect the low-force closure of the end effector 12835. In FIG. 50, the jaw of the end effector 12835 has been clamped with a high-force actuation in the direction of arrow E, and the firing member has been advanced in the direction of arrow F. Rotation of the fourth rotary output 12836d and the fifth rotary output 12836e is configured to selectively and cooperatively affect the high-force closure of the end effector 12835 and the firing of the firing member therein, respectively.

Referring primarily now to FIGS. 40-45, the housing 12832 includes multiple layers of gear train assemblies. Specifically, the housing 12832 includes a first gear train assembly 12838a layered under a second gear train assembly 12838b, which is layered under a third gear train assembly 12838c, which is layered under a fourth gear train assembly 12838d. The first gear train assembly 12838a corresponds to a first DOF, such as rotation of the shaft 12834, for example. The second gear train assembly 12838b corresponds to a second DOF, such as closure (i.e. fast closure) of the end effector 12835 with a low closure force, for example. The third gear train assembly 12838c corresponds to a third DOF, such as clamping (i.e. slow closure) of the end effector 12835 with a high closure force, for example. The fourth gear train assembly 12838d corresponds to a fourth DOF, such as firing of a firing element in the end effector 12835, for example. The five rotary inputs 12836a-12836e extend through the four layers of gear train assemblies 12838a-12838d.

Figure 41:
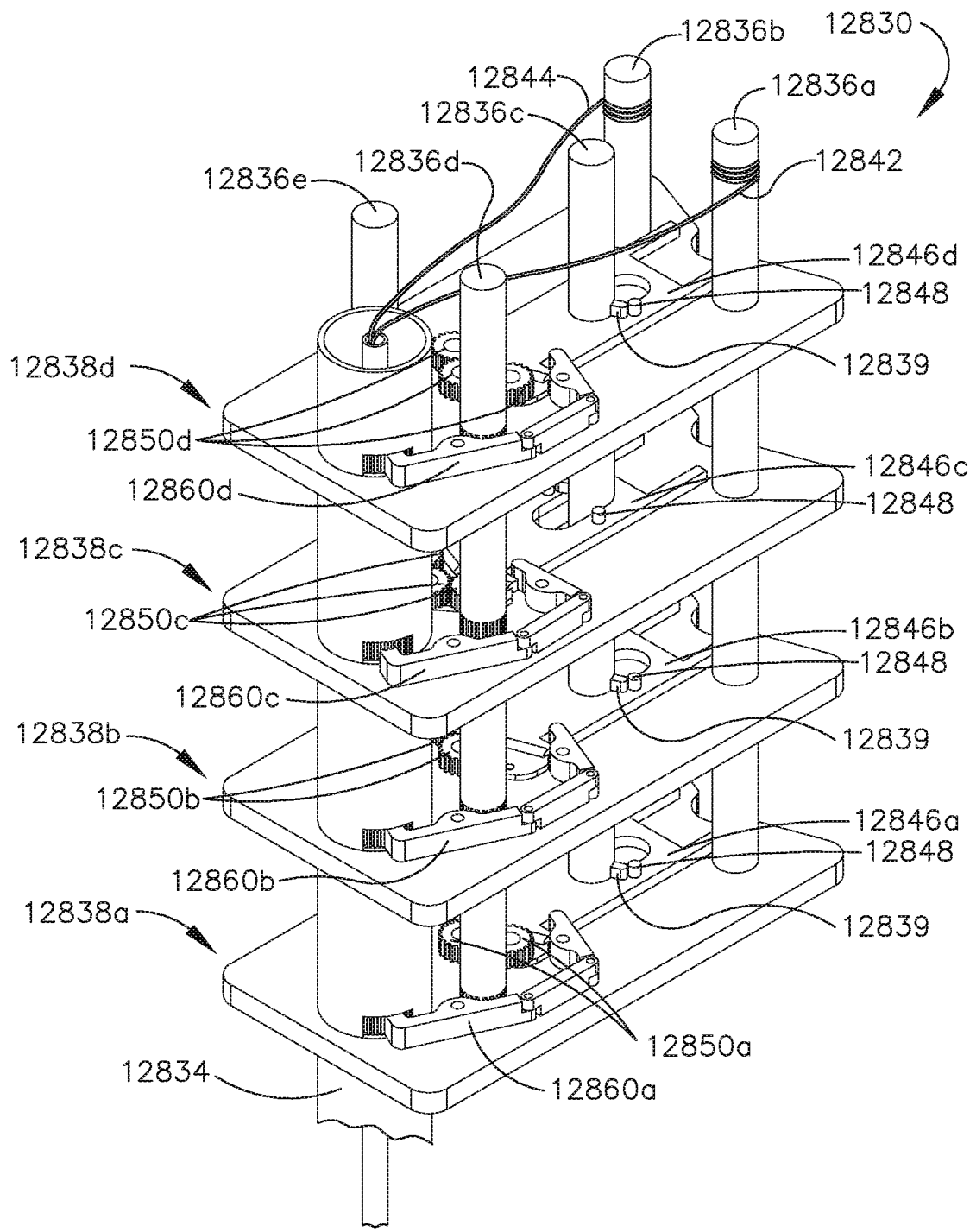
FIG. 41 is an exploded perspective view of the transmission arrangement of FIG. 40, in accordance with one aspect of the present disclosure.

The first motor 12826a is drivingly coupled to the first rotary input 12836a. In such instances, the first motor 12826a is singularly configured to drive the first rotary input 12836a, which affects the first DOF. For example, referring primarily to FIG. 41, articulation wires 12842 can extend from the first rotary input 12836a through the shaft 12834 of the robotic tool 12830 toward the end effector 12835. Rotation of the first rotary input 12836a is configured to actuate the articulation wires 12842 to affect left/right articulation of the end effector 12835. Similarly, the second motor 12826b is drivingly coupled to the second rotary input 12836b. In such instances, the second motor 12826b is singularly configured to drive the second rotary input 12836b, which affects the second DOF. Referring still to FIG. 41, articulation wires 12844 can extend from the second rotary input 12836b through the shaft 12834 of the robotic tool 12830 toward the end effector 12835. Rotation of the second rotary input 12836b is configured to actuate the articulation wires 12844 to affect up/down articulation of the end effector 12835. In other instances, at least one of the first rotary input 12836*a* and the second rotary input 12836*b* can correspond to a different DOF or different surgical function.

The housing 12832 also includes a transmission assembly 12840. For example, the third rotary input 12836*c* is a shifter drive shaft of the transmission assembly 12840. As depicted in FIGS. 40-45, the third rotary input 12836*c* can be a camshaft, including a plurality of caroming lobes. An arrangement of cam lobes 12839 can correspond with each gear train assembly 12838*a*-12838*d* layered in the housing 12832. Moreover, each gear train assembly 12838*a*-12838*d* includes a respective shuttle 12846*a*-12846*d* operably engaged by the third rotary input 12836*c*. For example, the third rotary input 12836*c* can extend through an opening in each shuttle 12846*a*-12846*d* and selectively engage at least one protrusion 12848 on the shuttle 12846*a*-12846*d* to affect shifting of the respective shuttle 12846*a*-12846*d* relative to the third rotary input 12836*c*. In other words, rotation of the third rotary input 12836*c* is configured to affect shifting of the shuttles 12846*a*-12846*d*. As the shuttles 12846*a*-12846*d* shift within each gear train assembly 12838*a*-12838*d*, respectively, the cooperative drive shafts 12836*d* and 12836*e* are selectively drivingly coupled to one or more output shafts of the robotic tool 12830, as further described herein.

In other instances, a drive system for a robotic tool can include a vertically shifting gear selector, which can be configured to shift the shuttles 12846*a*-12846*d* or otherwise engage an output drive from a motor to one or more input drives on the robotic tool 12830.

Referring still to FIGS. 38-45, the fourth and fifth output drives, or the first and second cooperative drive shafts, 12836*d* and 12836*e*, respectively, can operate independently or in a coordinated, synchronized manner. For example, in certain instances, each cooperative drive shaft 12836*d* and 12836*e* can be paired with a single output gear or output shaft. In other instances, both cooperative drives 12836*d* and 12836*e* can be paired with a single output gear or output shaft.

Referring primarily to FIG. 42, in a first configuration of the transmission arrangement 12840, the first cooperative drive shaft 12836*d* is drivingly engaged with a first output gear 12852 of the first gear train assembly 12838*a*. For example, the first gear train assembly 12838*a* includes one or more first idler gears 12850*a*. In FIG. 42, the first gear train assembly 12838*a* includes two first idler gears 12850*a*. The first idler gears 12850*a* are positioned on the first shuttle 12846*a* in the first gear train assembly 12838*a*. In the first configuration (FIG. 42), the first shuttle 12846*a* has been shifted toward the first output gear 12852 by the camshaft 12836*c* such that one of the first idler gears 12850*a* on the first shuttle 12846*a* is moved into meshing engagement with the first output gear 12852 and one of the first idler gears 12850*a* is moved into meshing engagement with the first cooperative drive shaft 12836*d*. In other words, the first cooperative drive shaft 12836*d* is drivingly engaged with the first output gear 12852.

Rotation of the first output gear 12852 corresponds to a particular DOF. For example, rotation of the first output gear 12852 is configured to rotate the shaft 12834 of the robotic tool 12830. In other words, in the first configuration of the transmission arrangement 12840 (FIG. 42), a rotation of the fourth motor 12826*d* and the fourth rotary output 12824*d* is configured to rotate the first cooperative drive shaft 12836*d*, which is coupled to the first output gear 12852 via the first idlers gears 12850*a* and rotates (or rolls) the shaft 12834.

The first gear train assembly 12838*a* also includes a first locking arm 12860*a*. The first locking arm 12860*a* extends from the first shuttle 12846*a*. Movement of the first shuttle 12846*a* is configured to move the first locking arm 12860*a*. For example, in the first configuration of FIG. 42, the first locking arm 12860*a* is disengaged from the first gear train assembly 12838*a* such that the first output gear 12852 can rotate. Movement of the first shuttle 12846*a* can move the first locking arm 12860*a* into engagement with the first output gear 12852. For example, when the first idler gears 12850*a* are moved out of engagement with the first output gear 12852, the first locking arm 12860*a* can engage the first output gear 12852 or another gear in the first gear train assembly 12838*a* to prevent the rotation of the first output gear 12852.

Referring still to FIG. 42, in the first configuration of the transmission arrangement 12840, the second cooperative drive shaft 12836*e* is drivingly engaged with a second output gear 12854 of the second gear train assembly 12838*b*. For example, the second gear train assembly 12838*b* includes one or more second idler gears 12850*b* and a planetary gear 12853 that is meshingly engaged with the second output gear 12854. In FIG. 42, the second gear train assembly 12838*b* includes two second idler gears 12850*b*. The second idler gears 12850*b* are positioned on the second shuttle 12846*b* in the second gear train assembly 12838*b*. In the first configuration, the second shuttle 12846*b* has been shifted toward the second output gear 12854 by the camshaft 12836*c* such that one of the second idler gears 12850*b* on the second shuttle 12846*b* is moved into meshing engagement with the planetary gear 12853, and one of the second idler gears 12850*b* is moved into meshing engagement with the second cooperative drive shaft 12836*e*. In other words, the second cooperative drive shaft 12836*e* is drivingly engaged with the second output gear 12854 via the second idler gears 12850*b* and the planetary gear 12853. The second output gear 12854 is configured to drive a second output shaft 12864 (FIGS. 43-45), which transfers a drive motion to the end effector 12835.

Rotation of the second output gear 12854 corresponds to a particular DOF. For example, a rotation of the second output gear 12854 is configured to close the end effector 12835 of the robotic tool 12830 with a low closure force. In other words, in the first configuration of the transmission arrangement 12840, a rotation of the fifth motor 12826*e* and the fifth rotary output 12824*e* is configured to rotate the second cooperative drive shaft 12836*e*, which is coupled to the second output gear 12854, via the second idlers gears 12850*b* and the planetary gear 12853, and closes the end effector 12835 of the robotic tool 12830 with a low closure force.

The second gear train assembly 12838*b* also includes a second locking arm 12860*b*. The second locking arm 12860*b* extends from the second shuttle 12846*b*. Movement of the second shuttle 12846*b* is configured to move the second locking arm 12860*b*. For example, in the first configuration of FIG. 42, the second locking arm 12860*b* is disengaged from the planetary gear 12853. Movement of the second shuttle 12846*b* can move the second locking arm 12860*b* into engagement with the second planetary gear 12853. For example, when the second idler gears 12850*b* are moved out of engagement with the second gear train assembly 12838*b* or planetary gear 12853 thereof, the second locking arm 12860*b* can engage a portion of the second gear train assembly 12838*b*, such as planetary gear 12853, for example, to prevent rotation of the planetary gear 12853 and the second output gear 12854.

In the first configuration, rotary drive motions can be concurrently applied to the first and second cooperative drive shafts 12836*d* and 12836*e*, respectively, to concurrently affect multiple degrees of freedom. For example, the transmission arrangement 12840 can permit the simultaneous rotation of the shaft 12834 and closing of the end effector jaws. In other instances, one of the output gears 12852, 12854 can be locked by the respective locking arm when the other output gear 12852, 12854 is drivingly coupled to the respective cooperative drive shaft 12836*d*, 12836*e*.

Referring still to FIG. 42, in the first configuration of the transmission arrangement 12840, a third output gear 12856 in the third gear train assembly 12838*c* and a fourth output gear 12858 in the fourth gear train assembly 12838*d* are locked via the locking arms 12860*c* and 12860*d*, respectively. As a result, rotation of the third output gear 12856, which corresponds to clamping or high-force closing of the end effector jaws, is prevented by the first configuration. Additionally, rotation of the fourth output gear 12858, which corresponds to firing the firing member in the end effector 12835, is also prevented. In other words, when the transmission arrangement 12840 is configured to deliver rotary motions to affect a low-force closure DOF or shaft rotation DOF, high-force clamping and firing is prevented. In such instances, the high-force clamping function and firing function can be selectively locked out by the transmission arrangement 12840.

Referring now to FIG. 43, a second configuration of the transmission arrangement 12840 is depicted. In the second configuration, the first and second cooperative drive shafts 12836*d* and 12836*e* are drivingly engaged with a third output gear 12856 of the third gear train assembly 12838*c*. The third output gear 12856 is configured to drive a third output shaft 12866 (FIGS. 43-45), which transfers a drive motion to the end effector 12835. For example, the third gear train assembly 12838*c* includes one or more third idler gears 12850*c* and a planetary gear 12855 that is meshingly engaged with the third output gear 12856. In FIG. 43, the third gear train assembly 12838*c* includes three third idler gears 12850*c*. The third idler gears 12850*c* are positioned on the third shuttle 12846*c* in the third gear train assembly 12838*c*. In the second configuration, the third shuttle 12846*c* has been shifted toward the third output gear 12856 by the camshaft 12836*c* such that one of the third idler gears 12850*c* is moved into meshing engagement with the planetary gear 12855, one of the third idler gears 12850*c* is moved into meshing engagement with the first cooperative drive shaft 12836*d*, and one of the third idler gears 12850*c* is moved into meshing engagement with the second cooperative drive shaft 12836*e*. In other words, both cooperative drive shafts 12836*d* and 12836*e* are drivingly engaged with the third output gear 12856 via the third idler gears 12850*c* and the planetary gear 12855.

Rotation of the third output gear 12856 corresponds to a particular DOF. For example, a rotation of the third output gear 12856 is configured to clamp the end effector 12835 of the robotic tool 12830 with a high closure force. In other words, in the second configuration of the transmission arrangement 12840, a rotation of the fourth motor 12826*d* and the fifth motor 12826*e* and the corresponding rotation of the fourth rotary output 12824*d* and the fifth rotary output 12824*e* are configured to rotate the cooperative drive shafts 12836*d* and 12836*e*, respectively. In such instances, a torque supplied by both cooperative drive shafts 12836*d* and 12836*e* is coupled to the third output gear 12856 via the third idlers gears 12850*c* to clamp the end effector 12835 of the robotic tool 12830 with a high closure force.

Referring still to FIG. 43, in the second configuration of the transmission arrangement 12840, the third output gear 12856 is unlocked. More specifically, the third locking arm 12860*c* is disengaged from the third gear train assembly 12838*c* such that the third output gear 12856 can rotate. Additionally, the camshaft 12836*c* has moved the first locking arm 12860*a* into engagement with the first gear train assembly 12838*a*, the second locking arm 12860*b* into engagement with the second gear train assembly 12838*b*, and the fourth locking arm 12860*d* into engagement with the fourth gear train assembly 12838*d* to prevent rotation of the first output gear 12852, the second output gear 12854, and the fourth output gear 12858, respectively. As a result, rotation of the shaft 12834, low-force closing of the end effector jaws, and firing of the end effector 12835, is prevented by the transmission arrangement 12840 in the second configuration. In such instances, the shaft rotation function, the low-force closing function, and the firing function can be selectively locked out by the transmission arrangement 12840.

Referring now to FIG. 44, a third configuration of the transmission arrangement 12840 is depicted. In the third configuration, the first and second cooperative drive shafts 12836*d* and 12836*e* are drivingly engaged with a fourth output gear 12858 of the fourth gear train assembly 12838*d*. For example, the fourth gear train assembly 12838*d* includes one or more fourth idler gears 12850*d* and a planetary gear 12857 that is meshingly engaged with the fourth output gear 12858. In FIG. 44, the fourth gear train assembly 12838*d* includes three fourth idler gears 12850*d*. The fourth idler gears 12850*d* are positioned on the fourth shuttle 12846*d* in the fourth gear train assembly 12838*d*. In the third configuration, the fourth shuttle 12846*d* has been shifted toward the fourth output gear 12858 by the camshaft 12836*c* such that one of the fourth idler gears 12850*d* is moved into meshing engagement with the planetary gear 12857, one of the fourth idler gears 12850*d* is moved into meshing engagement with the first cooperative drive shaft 12836*d*, and one of the fourth idler gears 12850*d* is moved into meshing engagement with the second cooperative drive shaft 12836*e*. In other words, both cooperative drive shafts 12836*d* and 12836*e* are drivingly engaged with the fourth output gear 12858 via the fourth idler gears 12850*d* and the planetary gear 12857. The fourth output gear 12858 is configured to drive a third output shaft 12868 (FIGS. 43-45), which transfers a drive motion to the end effector 12835.

Rotation of the fourth output gear 12858 corresponds to a particular DOF. For example, a rotation of the fourth output gear 12858 is configured to firing a firing member in the end effector 12835 of the robotic tool 12830. In other words, in the third configuration of the transmission arrangement 12840, a rotation of the fourth motor 12826*d* and the fifth motor 12826*e* and the corresponding rotation of the fourth rotary output 12824*d* and the fifth rotary output 12824*e* are configured to rotate the cooperative drive shafts 12836*d* and 12836*e*, respectively. In such instances, a torque supplied by both cooperative drive shafts 12836*d* and 12836*e* is coupled to the fourth output gear 12858 via the fourth idlers gears 12850*d* and planetary gear 12857 to fire the end effector 12835 of the robotic tool 12830.

Referring still to FIG. 44, in the third configuration of the transmission arrangement 12840, the fourth output gear 12858 is unlocked. More specifically, the fourth locking arm 12860*d* is disengaged from the fourth gear train assembly 12838*d* such that the fourth output gear 12858 can rotate.

Additionally, the camshaft 12836*c* has moved the first locking arm 12860*a* into engagement with the first gear train assembly 12838*a*, the second locking arm 12860*b* into engagement with the second gear train assembly 12838*b*, and the third locking arm 12860*c* into engagement with the third gear train assembly 12838*c* to prevent rotation of the first output gear 12852, the second output gear 12854, and the third output gear 12856, respectively. As a result, rotation of the shaft 12852, low-force closing of the end effector jaws, and high-force clamping of the end effector jaws is prevented by the transmission arrangement 12840 in the third configuration. In such instances, the shaft rotation function, the low-force closing function, and the high-force clamping function can be selectively locked out by the transmission arrangement 12840.

In one aspect, the dual drive motors 12826*d* and 12826*e* can coordinate with the shifting motor 12826*c* to provide a compact drive housing 12832 that enables multiple end effector functions. Moreover, a greater torque can be supplied for one or more end effector functions via the cooperative drive shafts 12836*d* and 12836*e*.

In one aspect, when the cooperative drive shafts 12836*d* and 12836*e* are operated together, the two drives shafts 12836*d* and 12836*e* are synchronized. For example, the drive shafts 12836*d* and 12836*e* can both drive a common output shaft such as the output shafts 12866 and/or 12868. Torque can be provided to the common output shafts 12866 and/or 12868 via both drive shafts 12836*d* and 12836*e*.

Referring now to FIG. 46, a graphical display 12890 of output torque for different surgical functions of a robotic tool, such as the robotic tool 12830 (FIGS. 38-45), for example, is depicted. The output torque for rotating the tool shaft (e.g. shaft 12834) via a first cooperative drive shaft and for low-force closing of end effector jaws via a second cooperative drive shaft are less than t1, the maximum output torque from a single shaft. The lower output torques for shaft rotation and low-force jaw closure can be within the range of loads obtainable from a cable on a spindle, for example. In certain instances, other lower load functionalities of the surgical tool can be affected with the output from a single shaft.

To affect high-force clamping, the torque approaches t2, the maximum output torque from the cooperative drive shafts (e.g. cooperative drive shafts 12836*d* and 12836*e*). For example, t2 can be twice the value of t1. The values "a" and "b" in FIG. 46 show relative forces for the robotic tool. The value "a" is the load difference between a low-force closure and high-force clamping, such as closure with a closure tube system and clamping via an I-beam, example. In certain instances, a closure tube system and an I-beam system can cooperate, or overlap temporally as shown in FIG. 46, to complete the clamping of the end effector. The value "b" can be equal to or less than the value "a". For example, the torque required to fire the end effector can be the same, or substantially the same, as the difference in torque between low-force closing and high-force clamping. The values "a" and "b" are more than the maximum output torque from a single shaft, but less than the maximum output torque from cooperative drive shafts.

In one instance, the synchronization of multiple drive shafts (e.g. cooperative drive shafts 12836*d* and 12836*e*) can be the slaving of one drive shaft to the following of the other drive shaft. For example, a different maximum torque threshold can be set on the slaved drive shaft such that it can push up to the first drive shaft's limit but not over it. In one aspect, the speed of the output shaft can be monitored for increases and/or decreases in rotational speed. For example, a sensor can be positioned to detect the rotational speed of the output shaft. Further, the cooperative drive shafts can be coordinated to balance the torque when one of the cooperative drive shafts begins to slow down or brake the output shaft instead of both cooperative drive shafts accelerating it.

The motors described herein are housed in a tool mount on a robotic arm. In other instances, one or more of the motors can be housed in the robotic tool.

In one aspect, input drivers at an interface of the robotic tool are configured to mechanically and electrically couple with output drivers in a tool mount. As described herein, motors in the tool mount can be configured to deliver rotary drive motions to the drivers in the robotic tool. In other instances, the drivers in the robotic tool can be configured to receive linear drive motions from output drivers in the tool mount. For example, one or more linear drive motions can be transferred across the interface between the tool mount and the robotic tool.

When a single motor is drivingly coupled to an output shaft, the transmission assembly is in a low-torque operating state in comparison to a high-torque operating state in which more than one motor is drivingly coupled to the output shaft. The maximum torque deliverable to the output shaft in the high-torque operating state is greater than the maximum torque deliverable to the output shaft in the low-torque operating state. In one instance, the maximum torque in the high-torque operating state can be double the maximum torque in the low-torque operating state. The maximum torques deliverable to the output shaft can be based on the size and torque capabilities of the motors.

In one aspect, the robotic surgical system includes a processor and a memory communicatively coupled to the processor, as described herein. The memory stores instructions executable by the processor to selectively operably couple a first rotary driver and a second rotary driver to output shafts of a tool housing, wherein one of the first rotary driver and the second rotary driver is configured to supply torque to an output shaft in a low-torque operating state, and wherein the first rotary driver and the second rotary driver are configured to concurrently supply torque to an output shaft in the high-torque operating state, as described herein.

In various aspects, the present disclosure provides a control circuit to selectively operably couple a first rotary driver and/or a second rotary driver to an output shaft as described herein. In various aspects, the present disclosure provides a non-transitory computer readable medium storing computer readable instructions which, when executed, cause a machine to selectively operably couple a first rotary driver and/or a second rotary driver to an output shaft, as described herein.

Another robotic surgical system is depicted in FIGS. 57 and 58. With reference to FIG. 57, the robotic surgical system 13000 includes robotic arms 13002, 13003, a control device 13004, and a console 13005 coupled to the control device 13004. As illustrated in FIG. 57, the surgical system 13000 is configured for use on a patient 13013 lying on a patient table 13012 for performance of a minimally invasive surgical operation. The console 13005 includes a display device 13006 and input devices 13007, 13008. The display device 13006 is set up to display three-dimensional images, and the manual input devices 13007, 13008 are configured to allow a clinician to telemanipulate the robotic arms 13002, 13003. Controls for a surgeon's console, such as the console 13005, are further described in International Patent Publication No. WO2017/075121, filed Oct. 27, 2016, titled HAPTIC FEEDBACK FOR A ROBOTIC SURGICAL SYSTEM INTERFACE, which is herein incorporated by reference in its entirety.

Each of the robotic arms 13002, 13003 is made up of a plurality of members connected through joints and includes a surgical assembly 13010 connected to a distal end of a corresponding robotic arm 13002, 13003. Support of multiple arms is further described in U.S. Patent Application Publication No. 2017/0071693, filed Nov. 11, 2016, titled SURGICAL ROBOTIC ARM SUPPORT SYSTEMS AND METHODS OF USE, which is herein incorporated by reference in its entirety. Various robotic arm configurations are further described in International Patent Publication No. WO2017/044406, filed Sep. 6, 2016, titled ROBOTIC SURGICAL CONTROL SCHEME FOR MANIPULATING ROBOTIC END EFFECTORS, which is herein incorporated by reference in its entirety. In an exemplification, the surgical assembly 13010 includes a surgical instrument 13020 supporting an end effector 13023. Although two robotic arms 13002, 13003, are depicted, the surgical system 13000 may include a single robotic arm or more than two robotic arms 13002, 13003. Additional robotic arms are likewise connected to the control device 13004 and are telemanipulatable via the console 13005. Accordingly, one or more additional surgical assemblies 13010 and/or surgical instruments 13020 may also be attached to the additional robotic arm(s).

The robotic arms 13002, 13003 may be driven by electric drives that are connected to the control device 13004. According to an exemplification, the control device 13004 is configured to activate drives, for example, via a computer program, such that the robotic arms 13002, 13003 and the surgical assemblies 13010 and/or surgical instruments 13020 corresponding to the robotic arms 13002, 13003, execute a desired movement received through the manual input devices 13007, 13008. The control device 13004 may also be configured to regulate movement of the robotic arms 13002, 13003 and/or of the drives.

The control device 13004 may control a plurality of motors (for example, Motor 1 . . . n) with each motor configured to drive a pushing or a pulling of one or more cables, such as cables coupled to the end effector 13023 of the surgical instrument 13020. In use, as these cables are pushed and/or pulled, the one or more cables affect operation and/or movement of the end effector 13023. The control device 13004 coordinates the activation of the various motors to coordinate a pushing or a pulling motion of one or more cables in order to coordinate an operation and/or movement of one or more end effectors 13023. For example, articulation of an end effector by a robotic assembly such as the surgical assembly 13010 is further described in U.S. Patent Application Publication No. 2016/0303743, filed Jun. 6, 2016, titled WRIST AND JAW ASSEMBLIES FOR ROBOTIC SURGICAL SYSTEMS and in International Patent Publication No. WO2016/144937, filed Mar. 8, 2016, titled MEASURING HEALTH OF A CONNECTOR MEMBER OF A ROBOTIC SURGICAL SYSTEM, each of which is herein incorporated by reference in its entirety. In an exemplification, each motor is configured to actuate a drive rod or a lever arm to affect operation and/or movement of end effectors 13023 in addition to, or instead of, one or more cables.

Driver configurations for surgical instruments, such as drive arrangements for a surgical end effector, are further described in International Patent Publication No. WO2016/183054, filed May 10, 2016, titled COUPLING INSTRUMENT DRIVE UNIT AND ROBOTIC SURGICAL INSTRUMENT, International Patent Publication No. WO2016/205266, filed Jun. 15, 2016, titled ROBOTIC SURGICAL SYSTEM TORQUE TRANSDUCTION SENSING, International Patent Publication No. WO2016/205452, filed Jun. 16, 2016, titled CONTROLLING ROBOTIC SURGICAL INSTRUMENTS WITH BIDIRECTIONAL COUPLING, and International Patent Publication No. WO2017/053507, filed Sep. 22, 2016, titled ELASTIC SURGICAL INTERFACE FOR ROBOTIC SURGICAL SYSTEMS, each of which is herein incorporated by reference in its entirety. The modular attachment of surgical instruments to a driver is further described in International Patent Publication No. WO2016/209769, filed Jun. 20, 2016, titled ROBOTIC SURGICAL ASSEMBLIES, which is herein incorporated by reference in its entirety. Housing configurations for a surgical instrument driver and interface are further described in International Patent Publication No. WO2016/144998, filed Mar. 9, 2016, titled ROBOTIC SURGICAL SYSTEMS, INSTRUMENT DRIVE UNITS, AND DRIVE ASSEMBLIES, which is herein incorporated by reference in its entirety. Various endocutter instrument configurations for use with the robotic arms 13002, 13003 are further described in International Patent Publication No. WO2017/053358, filed Sep. 21, 2016, titled SURGICAL ROBOTIC ASSEMBLIES AND INSTRUMENT ADAPTERS THEREOF and International Patent Publication No. WO2017/053363, filed Sep. 21, 2016, titled ROBOTIC SURGICAL ASSEMBLIES AND INSTRUMENT DRIVE CONNECTORS THEREOF, each of which is herein incorporated by reference in its entirety. Bipolar instrument configurations for use with the robotic arms 13002, 13003 are further described in International Patent Publication No. WO2017/053698, filed Sep. 23, 2016, titled ROBOTIC SURGICAL ASSEMBLIES AND ELECTROMECHANICAL INSTRUMENTS THEREOF, which is herein incorporated by reference in its entirety. Reposable shaft arrangements for use with the robotic arms 13002, 13003 are further described in International Patent Publication No. WO2017/116793, filed Dec. 19, 2016, titled ROBOTIC SURGICAL SYSTEMS AND INSTRUMENT DRIVE ASSEMBLIES, which is herein incorporated by reference in its entirety.

The control device 13004 includes any suitable logic control circuit adapted to perform calculations and/or operate according to a set of instructions. The control device 13004 can be configured to communicate with a remote system "RS," either via a wireless (e.g., Wi-Fi, Bluetooth, LTE, etc.) and/or wired connection. The remote system "RS" can include data, instructions and/or information related to the various components, algorithms, and/or operations of system 13000. The remote system "RS" can include any suitable electronic service, database, platform, cloud "C" (see FIG. 57), or the like. The control device 13004 may include a central processing unit operably connected to memory. The memory may include transitory type memory (e.g., RAM) and/or non-transitory type memory (e.g., flash media, disk media, etc.). In some exemplifications, the memory is part of, and/or operably coupled to, the remote system "RS."

The control device 13004 can include a plurality of inputs and outputs for interfacing with the components of the system 13000, such as through a driver circuit. The control device 13004 can be configured to receive input signals and/or generate output signals to control one or more of the various components (e.g., one or more motors) of the system 13000. The output signals can include, and/or can be based upon, algorithmic instructions which may be pre-programmed and/or input by a user. The control device 13004 can be configured to accept a plurality of user inputs from a user interface (e.g., switches, buttons, touch screen, etc. of operating the console 13005) which may be coupled to remote system "RS."

A memory 13014 can be directly and/or indirectly coupled to the control device 13004 to store instructions and/or databases including pre-operative data from living being(s) and/or anatomical atlas(es). The memory 13014 can be part of, and/or or operatively coupled to, remote system "RS."

In accordance with an exemplification, the distal end of each robotic arm 13002, 13003 is configured to releasably secure the end effector 13023 (or other surgical tool) therein and may be configured to receive any number of surgical tools or instruments, such as a trocar or retractor, for example.

A simplified functional block diagram of a system architecture 13400 of the robotic surgical system 13010 is depicted in FIG. 58. The system architecture 13400 includes a core module 13420, a surgeon master module 13430, a robotic arm module 13440, and an instrument module 13450. The core module 13420 serves as a central controller for the robotic surgical system 13000 and coordinates operations of all of the other modules 13430, 13440, 13450. For example, the core module 13420 maps control devices to the arms 13002, 13003, determines current status, performs all kinematics and frame transformations, and relays resulting movement commands In this regard, the core module 13420 receives and analyzes data from each of the other modules 13430, 13440, 13450 in order to provide instructions or commands to the other modules 13430, 13440, 13450 for execution within the robotic surgical system 13000. Although depicted as separate modules, one or more of the modules 13420, 13430, 13440, and 13450 are a single component in other exemplifications.

The core module 13420 includes models 13422, observers 13424, a collision manager 13426, controllers 13428, and a skeleton 13429. The models 13422 include units that provide abstracted representations (base classes) for controlled components, such as the motors (for example, Motor 1 . . . n) and/or the arms 13002, 13003. The observers 13424 create state estimates based on input and output signals received from the other modules 13430, 13440, 13450. The collision manager 13426 prevents collisions between components that have been registered within the system 13010. The skeleton 13429 tracks the system 13010 from a kinematic and dynamics point of view. For example, the kinematics item may be implemented either as forward or inverse kinematics, in an exemplification. The dynamics item may be implemented as algorithms used to model dynamics of the system's components.

The surgeon master module 13430 communicates with surgeon control devices at the console 13005 and relays inputs received from the console 13005 to the core module 13420. In accordance with an exemplification, the surgeon master module 13430 communicates button status and control device positions to the core module 13420 and includes a node controller 13432 that includes a state/mode manager 13434, a fail-over controller 13436, and a N-degree of freedom ("DOF") actuator 13438.

The robotic arm module 13440 coordinates operation of a robotic arm subsystem, an arm cart subsystem, a set up arm, and an instrument subsystem in order to control movement of a corresponding arm 13002, 13003. Although a single robotic arm module 13440 is included, it will be appreciated that the robotic arm module 13440 corresponds to and controls a single arm. As such, additional robotic arm modules 13440 are included in configurations in which the system 13010 includes multiple arms 13002, 13003. The robotic arm module 13440 includes a node controller 13442, a state/mode manager 13444, a fail-over controller 13446, and a N-degree of freedom ("DOF") actuator 13348.

The instrument module 13450 controls movement of an instrument and/or tool component attached to the arm 13002, 13003. The instrument module 13450 is configured to correspond to and control a single instrument. Thus, in configurations in which multiple instruments are included, additional instrument modules 13450 are likewise included. In an exemplification, the instrument module 13450 obtains and communicates data related to the position of the end effector or jaw assembly (which may include the pitch and yaw angle of the jaws), the width of or the angle between the jaws, and the position of an access port. The instrument module 13450 has a node controller 13452, a state/mode manager 13454, a fail-over controller 13456, and a N-degree of freedom ("DOF") actuator 13458.

The position data collected by the instrument module 13450 is used by the core module 13420 to determine when the instrument is within the surgical site, within a cannula, adjacent to an access port, or above an access port in free space. The core module 13420 can determine whether to provide instructions to open or close the jaws of the instrument based on the positioning thereof. For example, when the position of the instrument indicates that the instrument is within a cannula, instructions are provided to maintain a jaw assembly in a closed position. When the position of the instrument indicates that the instrument is outside of an access port, instructions are provided to open the jaw assembly.

Additional features and operations of a robotic surgical system, such as the surgical robot system depicted in FIGS. 57 and 58, are further described in the following references, each of which is herein incorporated by reference in its entirety:

U.S. Patent Application Publication No. 2016/0303743, filed Jun. 6, 2016, titled WRIST AND JAW ASSEMBLIES FOR ROBOTIC SURGICAL SYSTEMS;

U.S. Patent Application Publication No. 2017/0071693, filed Nov. 11, 2016, titled SURGICAL ROBOTIC ARM SUPPORT SYS ELMS AND METHODS OF USE;

International Patent Publication No. WO2016/144937, filed Mar. 8, 2016, titled MEASURING HEALTH OF A CONNECTOR MEMBER OF A ROBOTIC SURGICAL SYSTEM;

International Patent Publication No. WO2016/144998, filed Mar. 9, 2016, titled ROBOTIC SURGICAL SYSTEMS, INSTRUMENT DRIVE UNITS, AND DRIVE ASSEMBLIES;

International Patent Publication No. WO2016/183054, filed May 10, 2016, titled COUPLING INSTRUMENT DRIVE UNIT AND ROBOTIC SURGICAL INSTRUMENT;

International Patent Publication No. WO2016/205266, filed Jun. 15, 2016, titled ROBOTIC SURGICAL SYSTEM TORQUE TRANSDUCTION SENSING;

International Patent Publication No. WO2016/205452, filed Jun. 16, 2016, titled CONTROLLING ROBOTIC SURGICAL INSTRUMENTS WITH BIDIRECTIONAL COUPLING;

International Patent Publication No. WO2016/209769, filed Jun. 20, 2016, titled ROBOTIC SURGICAL ASSEMBLIES;

International Patent Publication No. WO2017/044406, filed Sep. 6, 2016, titled ROBOTIC SURGICAL CONTROL SCHEME FOR MANIPULATING ROBOTIC END EFFECTORS;

International Patent Publication No. WO2017/053358, filed Sep. 21, 2016, titled SURGICAL ROBOTIC ASSEMBLIES AND INSTRUMENT ADAPTERS THEREOF;

International Patent Publication No. WO2017/053363, filed Sep. 21, 2016, titled ROBOTIC SURGICAL ASSEMBLIES AND INSTRUMENT DRIVE CONNECTORS THEREOF;

International Patent Publication No. WO2017/053507, filed Sep. 22, 2016, titled ELASTIC SURGICAL INTERFACE FOR ROBOTIC SURGICAL SYSTEMS;

International Patent Publication No. WO2017/053698, filed Sep. 23, 2016, titled ROBOTIC SURGICAL ASSEMBLIES AND ELECTROMECHANICAL INSTRUMENTS THEREOF;

International Patent Publication No. WO2017/075121, filed Oct. 27, 2016, titled HAPTIC FEEDBACK CONTROLS FOR A ROBOTIC SURGICAL SYSTEM INTERFACE;

International Patent Publication No. WO2017/116793, filed Dec. 19, 2016, titled ROBOTIC SURGICAL SYSTEMS AND INSTRUMENT DRIVE ASSEMBLIES.

The robotic surgical systems and features disclosed herein can be employed with the robotic surgical system of FIGS. 57 and 58. The reader will further appreciate that various systems and/or features disclosed herein can also be employed with alternative surgical systems including the computer-implemented interactive surgical system 100, the computer-implemented interactive surgical system 200, the robotic surgical system 110, the robotic hub 122, the robotic hub 222, and/or the robotic surgical system 15000, for example.

In various instances, a robotic surgical system can include a robotic control tower, which can house the control unit of the system. For example, the control unit 13004 of the robotic surgical system 13000 (FIG. 57) can be housed within a robotic control tower. The robotic control tower can include a robotic hub such as the robotic hub 122 (FIG. 2) or the robotic hub 222 (FIG. 9), for example. Such a robotic hub can include a modular interface for coupling with one or more generators, such as an ultrasonic generator and/or a radio frequency generator, and/or one or more modules, such as an imaging module, suction module, an irrigation module, a smoke evacuation module, and/or a communication module.

A robotic hub can include a situational awareness module, which can be configured to synthesize data from multiple sources to determine an appropriate response to a surgical event. For example, a situational awareness module can determine the type of surgical procedure, step in the surgical procedure, type of tissue, and/or tissue characteristics, as further described herein. Moreover, such a module can recommend a particular course of action or possible choices to the robotic system based on the synthesized data. In various instances, a sensor system encompassing a plurality of sensors distributed throughout the robotic system can provide data, images, and/or other information to the situational awareness module. Such a situational awareness module can be incorporated into a control unit, such as the control unit 13004, for example. In various instances, the situational awareness module can obtain data and/or information from a non-robotic surgical hub and/or a cloud, such as the surgical hub 106 (FIG. 1), the surgical hub 206 (FIG. 10), the cloud 104 (FIG. 1), and/or the cloud 204 (FIG. 9), for example. Situational awareness of a surgical system is further disclosed herein and in U.S. Provisional Patent Application Ser. No. 62/611,341, titled INTERACTIVE SURGICAL PLATFORM, filed Dec. 28, 2017, and U.S. Provisional Patent Application Ser. No. 62/611,340, titled CLOUD-BASED MEDICAL ANALYTICS, filed Dec. 28, 2017, the disclosure of each of which is herein incorporated by reference in its entirety.

In certain instances, the activation of a surgical tool at certain times during a surgical procedure and/or for certain durations may cause tissue trauma and/or may prolong a surgical procedure. For example, a robotic surgical system can utilize an electrosurgical tool having an energy delivery surface that should only be energized when a threshold condition is met. In one example, the energy delivery surface should only be activated when the energy delivery surface is in contact with the appropriate, or targeted, tissue. As another example, a robotic surgical system can utilize a suction element that should only be activated when a threshold condition is met, such as when an appropriate volume of fluid is present. Due to visibility restrictions, evolving situations, and the multitude of moving parts during a robotic surgical procedure, it can be difficult for a clinician to determine and/or monitor certain conditions at the surgical site. For example, it can be difficult to determine if an energy delivery surface of an electrosurgical tool is in contact with tissue. It can also be difficult to determine if a particular suctioning pressure is sufficient for the volume of fluid in the proximity of the suctioning port.

Moreover, a plurality of surgical devices can be used in certain robotic surgical procedures. For example, a robotic surgical system can use one or more surgical tools during the surgical procedure. Additionally, one or more handheld instruments can also be used during the surgical procedure. One or more of the surgical devices can include a sensor. For example, multiple sensors can be positioned around the surgical site and/or the operating room. A sensor system including the one or more sensors can be configured to detect one or more conditions at the surgical site. For example, data from the sensor system can determine if a surgical tool mounted to the surgical robot is being used and/or if a feature of the surgical tool should be activated. More specifically, a sensor system can detect if an electrosurgical device is positioned in abutting contact with tissue, for example. As another example, a sensor system can detect if a suctioning element of a surgical tool is applying a sufficient suctioning force to fluid at the surgical site.

When in an automatic activation mode, the robotic surgical system can automatically activate one or more features of one or more surgical tools based on data, images, and/or other information received from the sensor system. For example, an energy delivery surface of an electrosurgical tool can be activated upon detecting that the electrosurgical tool is in use (e.g. positioned in abutting contact with tissue). As another example, a suctioning element on a surgical tool can be activated when the suction port is moved into contact with a fluid. In certain instances, the surgical tool can be adjusted based on the sensed conditions.

A robotic surgical system incorporating an automatic activation mode can automatically provide a scenario-specific result based on detected condition(s) at the surgical site. The scenario-specific result can be outcome-based, for example, and can streamline the decision-making process of the clinician. In certain instances, such an automatic activation mode can improve the efficiency and/or effectiveness of the clinician. For example, the robotic surgical system can aggregate data to compile a more complete view of the surgical site and/or the surgical procedure in order to determine the best possible course of action. Additionally or alternatively, in instances in which the clinician makes fewer decisions, the clinician can be better focused on other tasks and/or can process other information more effectively.

In one instance, a robotic surgical system can automatically adjust a surgical tool based on the proximity of the tool to a visually-detectable need and/or the situational awareness of the system. Referring to FIGS. 59A and 59B, an ultrasonic surgical tool for a robotic system 13050 is depicted in two different positions. In a first position, as depicted in FIG. 59A, the blade 13052 of an ultrasonic surgical tool 13050 is positioned out of contact with tissue 13060. In such a position, a sensor on the ultrasonic surgical tool 13050 can detect a high resistance. When the resistance detected is above a threshold value, the ultrasonic blade 13052 can be de-energized. Referring now to FIG. 59B, the ultrasonic blade 13052 is depicted in a second position in which the distal end of the blade 13052 is positioned in abutting contact with tissue 13060. In such instances, a sensor on the ultrasonic surgical tool 13050 can detect a low resistance. When the detected resistance is below a threshold value, the ultrasonic blade 13052 can be activated such that therapeutic energy is delivered to the tissue 13060. Alternative sensor configurations are also envisioned and various sensors are further described herein.

Referring to FIGS. 60A and 60B, another surgical tool, a monopolar cautery pencil 13055, is depicted in two different positions. In a first position, as depicted in FIG. 60A, the monopolar cautery pencil 13055 is positioned out of contact with tissue. In such a position, a sensor on the monopolar cautery pencil 13055 can detect a high resistance. When the resistance detected is above a threshold value, the monopolar cautery pencil 13055 can be de-energized. Referring now to FIG. 60B, the monopolar cautery pencil 13055 is depicted in a second position in which the distal end of the monopolar cautery pencil 13055 is positioned in abutting contact with tissue. In such instances, a sensor on the monopolar cautery pencil 13055 can detect a low resistance. When the detected resistance is below a threshold value, the monopolar cautery pencil 13055 can be activated such that therapeutic energy is delivered to the tissue. Alternative sensor configurations are also envisioned and various sensors are further described herein.

FIG. 61 shows a graphical display 13070 of continuity C and current I over time t for the ultrasonic surgical tool 13050 of FIGS. 59A and 59B. Similarly, the monopolar cautery pencil 13055 can generate a graphical display similar in many respects to the graphical display 13070, in certain instances. In the graphical display 13070, continuity C is represented by a dotted line, and current I is represented by a solid line. When the resistance is high and above a threshold value, the continuity C can also be high. The threshold value can be between 40 and 400 ohms, for example. At time A', the continuity C can decrease below the threshold value, which can indicate a degree of tissue contact. As a result, the robotic surgical system can automatically activate advanced energy treatment of the tissue. The ultrasonic transducer current depicted in FIG. 61 increases from time A' to B' when the continuity parameters indicate the degree of tissue contact. In various instances, the current I can be capped at a maximum value indicated at B', which can correspond to an open jaw transducer limit, such as in instances in which the jaw is not clamped, as shown in FIGS. 59A and 59B. In various instances, the situational awareness module of the robotic surgical system may indicate that the jaw is unclamped Referring again to the graphical display 13070 in FIG. 61, energy is applied until time C', at which time a loss of tissue contact is indicated by the increase in continuity C above the threshold value. As a result, the ultrasonic transducer current I can decrease to zero as the ultrasonic blade is de-energized.

In various instances, a sensor system can be configured to detect at least one condition at the surgical site. For example, a sensor of the sensor system can detect tissue contact by measuring continuity along the energy delivery surface of the ultrasonic blade. Additionally or alternatively, the sensor system can include one or more additional sensors positioned around the surgical site. For example, one or more surgical tools and/or instruments being used in the surgical procedure can be configured to detect a condition at the surgical site. The sensor system can be in signal communication with a processor of the robotic surgical system. For example, the robotic surgical system can include a central control tower including a control unit housing a processor and memory, as further described herein. The processor can issue commands to the surgical tool based on inputs from the sensor system. In various instances, situational awareness can also dictate and/or influence the commands issued by the processor.

Turning now to FIG. 62, an end effector 196400 includes RF data sensors 196406, 196408*a*, 196408*b* located on jaw member 196402. The end effector 196400 includes jaw member 196402 and an ultrasonic blade 196404. The jaw member 196402 is shown clamping tissue 196410 located between the jaw member 196402 and the ultrasonic blade 196404. A first sensor 196406 is located in a center portion of the jaw member 196402. Second and third sensors 196408*a*, 196408*b*, respectively, are located on lateral portions of the jaw member 196402. The sensors 196406, 196408*a*, 196408*b* are mounted or formed integrally with a flexible circuit 196412 (shown more particularly in FIG. 63) configured to be fixedly mounted to the jaw member 196402.

The end effector 196400 is an example end effector for various surgical devices described herein. The sensors 196406, 196408*a*, 196408*b* are electrically connected to a control circuit via interface circuits. The sensors 196406, 196408*a*, 196408*b* are battery powered and the signals generated by the sensors 196406, 196408*a*, 196408*b* are provided to analog and/or digital processing circuits of the control circuit.

In one aspect, the first sensor 196406 is a force sensor to measure a normal force $F_3$ applied to the tissue 196410 by the jaw member 196402. The second and third sensors 196408*a*, 196408*b* include one or more elements to apply RF energy to the tissue 196410, measure tissue impedance, down force $F_1$, transverse forces $F_2$, and temperature, among other parameters. Electrodes 196409*a*, 196409*b* are electrically coupled to an energy source such as an electrical circuit and apply RF energy to the tissue 196410. In one aspect, the first sensor 196406 and the second and third sensors 196408*a*, 196408*b* are strain gauges to measure force or force per unit area. It will be appreciated that the measurements of the down force $F_1$, the lateral forces $F_2$, and the normal force $F_3$ may be readily converted to pressure by determining the surface area upon which the force sensors 196406, 196408*a*, 196408*b* are acting upon. Additionally, as described with particularity herein, the flexible circuit 196412 may include temperature sensors embedded in one or more layers of the flexible circuit 196412. The one or more temperature sensors may be arranged symmetrically or asymmetrically and provide tissue 196410 temperature feedback to control circuits of an ultrasonic drive circuit and an RF drive circuit.

One or more sensors such as a magnetic field sensor, a strain gauge, a pressure sensor, a force sensor, an inductive sensor such as, for example, an eddy current sensor, a resistive sensor, a capacitive sensor, an optical sensor, and/or any other suitable sensor, may be adapted and configured to measure tissue compression and/or impedance.

FIG. 63 illustrates one aspect of the flexible circuit 196412 shown in FIG. 62 in which the sensors 196406, 196408*a*, 196408*b* may be mounted to or formed integrally therewith. The flexible circuit 196412 is configured to fixedly attach to the jaw member 196402. As shown particularly in FIG. 63, asymmetric temperature sensors 196414*a*, 196414*b* are mounted to the flexible circuit 196412 to enable measuring the temperature of the tissue 196410 (FIG. 62).

The reader will appreciate that alternative surgical tools can be utilized in the automatic activation mode described above with respect to FIGS. 59A-63.

FIG. 64 is a flow chart 13150 depicting an automatic activation mode 13151 of a surgical tool. In various instances, the robotic surgical system and processor thereof is configured to implement the processes indicated in FIG. 64. Initially, a sensor system is configured to detect a condition at step 13152. The detected condition is communicated to a processor, which compares the detected condition to a threshold parameter at step 13154. The threshold parameter can be a maximum value, minimum value, or range of values. If the sensed condition is an out-of-bounds condition, the processor can adjust the surgical function at step 13156 and the processor can repeat the comparison process of steps 13152 and 13154. If the sensed condition is not an out-of-bounds condition, no adjustment is necessary (13158) and the comparison process of steps 13152 and 13154 can be repeated again.

In various instances, the robotic surgical system can permit a manual override mode 13153. For example, upon activation of the manual override input 13160, such as by a clinician, the surgical system can exit the automatic activation mode 13151 at step 13162 depicted in FIG. 64. In such instances, even when a sensed condition is an out-of-bounds condition, the surgical function would not be automatically adjusted by the processor. However, in such instances, the processor can issue a warning or recommendation to the clinician recommending a particular course of action based on the sensed condition(s).

In various instances, an automatic activation mode can be utilized with a robotic surgical system including a suctioning feature. In one instance, a robotic surgical system can communicate with a suction and/or irrigation tool. For example, a suction and/or irrigation device (see module 128 in FIG. 3) can communicate with a robotic surgical system via the surgical hub 106 (FIG. 1) and/or the surgical hub 206 (FIG. 9) and a suction and/or irrigation tool can be mounted to a robotic arm. The suction/irrigation device can include a distal suction port and a sensor. In another instance, a robotic surgical tool, such as an electrosurgical tool, can include a suctioning feature and a suction port on the end effector of the tool.

Referring to FIG. 65, when a suction port on an end effector 13210 is moved into contact with a fluid, a processor of the robotic surgical system can automatically activate the suction feature. For example, a fluid detection sensor 13230 on the tool 13200 can detect fluid 13220 in the proximity of the tool 13200 and/or contacting the tool 13200. The fluid detection sensor 13230 can be a continuity sensor, for example. The fluid detection sensor 13230 can be in signal communication with the processor such that the processor is configured to receive input and/or feedback from the fluid detection sensor 13230. In certain instances, the suctioning feature can be automatically activated when the suction port is moved into proximity with a fluid 13220. For example, when the suction port moves within a predefined spatial range of a fluid 13220, the suction feature can be activated by the processor. The fluid 13220 can be saline, for example, which can be provided to the surgical site to enhance conductivity and/or irrigate the tissue.

In various instances, the tool can be a smoke evacuation tool and/or can include a smoke evacuation system, for example. A detail view of an end effector 13210 of a bipolar radio-frequency surgical tool 13200 is shown in FIG. 65. The end effector 13210 is shown in a clamped configuration. Moreover, smoke and steam 13220 from an RF weld accumulate around the end effector 13210. In various instances, to improve visibility and efficiency of the tool 13200, the smoke and steam 13220 at the surgical site can be evacuated along a smoke evacuation channel 13240 extending proximally from the end effector. The evacuation channel 13240 can extend through the shaft 13205 of the surgical tool 13200 to the interface of the surgical tool 13200 and the robot. The evacuation channel 13240 can be coupled to a pump for drawing the smoke and/or steam 13220 along the smoke evacuation channel 13240 within the shaft 13205 of the surgical tool 13200. In various instances, the surgical tool 13200 can include insufflation, cooling, and/or irrigation capabilities, as well.

In one instance, the intensity of the suction pressure can be automatically adjusted based on a measured parameter from one or more surgical devices. In such instances, the suction pressure can vary depending on the sensed parameters. Suction tubing can include a sensor for detecting the volume of fluid being extracted from the surgical site. When increased volumes of fluid are being extracted, the power to the suction feature can be increased such that the suctioning pressure is increased. Similarly, when decreased volumes of fluid are being extracted, the power to the suction feature can be decreased such that the suctioning pressure is decreased.

In various instances, the sensing system for a suction tool can include a pressure sensor. The pressure sensor can detect when an occlusion is obstructing, or partially obstructing, the fluid flow. The pressure sensor can also detect when the suction port is moved into abutting contact with tissue. In such instances, the processor can reduce and/or pause the suctioning force to release the tissue and/or clear the obstruction. In various instances, the processor can compare the detected pressure to a threshold maximum pressure. Exceeding the maximum threshold pressure may lead to unintentional tissue trauma from the suctioning tool. Thus, to avoid such trauma, the processor can reduce and/or pause the suctioning force to protect the integrity of tissue in the vicinity thereof.

A user can manually override the automatic adjustments implemented in the automatic activation mode(s) described herein. The manual override can be a one-time adjustment to the surgical tool. In other instances, the manual override can be a setting that turns off the automatic activation mode for a specific surgical action, a specific duration, and/or a global override for the entire procedure.

In one aspect, the robotic surgical system includes a processor and a memory communicatively coupled to the processor, as described herein. The processor is communicatively coupled to a sensor system, and the memory stores instructions executable by the processor to determine a use of a robotic tool based on input from the sensor system and to automatically energize an energy delivery surface of the robotic tool when the use is determined, as described herein.

In various aspects, the present disclosure provides a control circuit to automatically energize an energy delivery surface, as described herein. In various aspects, the present disclosure provides a non-transitory computer readable medium storing computer readable instructions which, when executed, cause a machine to automatically energize an energy delivery surface of a robotic tool, as described herein.

In one aspect, the robotic surgical system includes a processor and a memory communicatively coupled to the processor, as described herein. The processor is communicatively coupled to a fluid detection sensor, and the memory stores instructions executable by the processor to receive input from the fluid detection sensor and to automatically activate a suctioning mode when fluid is detected, as described herein.

In various aspects, the present disclosure provides a control circuit to automatically activate a suctioning mode, as described herein. In various aspects, the present disclosure provides a non-transitory computer readable medium storing computer readable instructions which, when executed, cause a machine to automatically activate a suctioning mode, as described herein.

Multiple surgical devices, including a robotic surgical system and various handheld instruments, can be used by a clinician during a particular surgical procedure. When manipulating one or more robotic tools of the robotic surgical system, a clinician is often positioned at a surgeon's command console or module, which is also referred to as a remote control console. In various instances, the remote control console is positioned outside of a sterile field and, thus, can be remote to the sterile field and, in some instances, remote to the patient and even to the operating room. If the clinician desires to use a handheld instrument, the clinician may be required to step away from the remote control console. At this point, the clinician may be unable to control the robotic tools. For example, the clinician may be unable to adjust the position or utilize the functionality of the robotic tools. Upon stepping away from the remote control console, the clinician may also lose sight of one or more displays on the robotic surgical system. The separation between the control points for the handheld instruments and the robotic surgical system may inhibit the effectiveness with which the clinician can utilize the surgical devices, both robotic tools and surgical instruments, together.

In various instances, an interactive secondary display is configured to be in signal communication with the robotic surgical system. The interactive secondary display includes a control module in various instances. Moreover, the interactive secondary display is configured to be wireless and movable around an operating room. In various instances, the interactive secondary display is positioned within a sterile field. In one instance, the interactive secondary display allows the clinician to manipulate and control the one or more robotic tools of the robotic surgical system without having to be physically present at the remote control console. In one instance, the ability for the clinician to operate the robotic surgical system away from the remote control console allows multiple devices to be used in a synchronized manner. As a safety measure, in certain instances, the remote control console includes an override function configured to prohibit control of the robotic tools by the interactive secondary display.

FIG. 66 depicts a surgical system 13100 for use during a surgical procedure that utilizes a surgical instrument 13140 and a robotic surgical system 13110. The surgical instrument 13140 is a powered handheld instrument. The surgical instrument 13140 can be a radio frequency (RF) instrument, an ultrasonic instrument, a surgical stapler, and/or a combination thereof, for example. The surgical instrument 13140 includes a display 13142 and a processor 13144. In certain instances, the handheld surgical instrument 13140 can be a smart or intelligent surgical instrument having a plurality of sensors and a wireless communication module.

The robotic surgical system 13110 includes a robot 13112 including at least one robotic tool 13117 configured to perform a particular surgical function. The robotic surgical system 13110 is similar in many respects to robotic surgical system 13000 discussed herein. The robotic tool 13117 is movable in a space defined by a control envelope of the robotic surgical system 13110. In various instances, the robotic tool 13117 is controlled by various clinician inputs at a remote control console 13116. In other words, when a clinician applies an input at the remote control console 13116, the clinician is away from the patient's body and outside of a sterile field 13138. Clinician input to the remote control console 13116 is communicated to a robotic control unit 13114 that includes a robot display 13113 and a processor 13115. The processor 13115 directs the robotic tool(s) 13117 to perform the desired function(s).

In various instances, the surgical system 13100 includes a surgical hub 13120, which is similar in many respects to the hub 106, the hub 206, the robotic hub 122, or the robotic hub 222, for example. The surgical hub 13120 is configured to enhance cooperative and/or coordinated usage of the robotic surgical system 13110 and the surgical instrument(s) 13140. The surgical hub 13120 is in signal communication with the control unit 13114 of the robotic surgical system 13110 and the processor 13144 of the surgical instrument(s) 13140. In various instances, a signal is transmitted through a wireless connection, although any suitable connection can be used to facilitate the communication. The control unit 13114 of the robotic surgical system 13110 is configured to send information to the surgical hub 13120 regarding the robotic tool(s) 13117. Such information includes, for example, a position of the robotic tool(s) 13117 within the surgical site, an operating status of the robotic tool(s) 13117, a detected force by the robotic tool(s), and/or the type of robotic tool(s) 13117 attached to the robotic surgical system 13110, although any relevant information and/or operating parameters can be communicated. Examples of surgical hubs are further described herein and in U.S. Provisional Patent Application Ser. No. 62/611,341, titled INTERACTIVE SURGICAL PLATFORM, filed Dec. 28, 2017, the disclosure of which is herein incorporated by reference in its entirety.

In other instances, the robotic surgical system 13110 can encompass the surgical hub 13120 and/or the control unit 13114 can be incorporated into the surgical hub 13120. For example, the robotic surgical system 13110 can include a robotic hub including a modular control tower that includes a computer system and a modular communication hub. One or more modules can be installed in the modular control tower of the robotic hub. Examples of robotic hubs are further described herein and in U.S. Provisional Patent Application Ser. No. 62/611,341, titled INTERACTIVE SURGICAL PLATFORM, filed Dec. 28, 2017, the disclosure of which is herein incorporated by reference in its entirety.

The processor 13144 of the surgical instrument(s) 13140 is configured to send information to the surgical hub 13120 regarding the surgical instrument 13140. Such information includes, for example, a position of the surgical instrument(s) 13140 within the surgical site, an operating status of the surgical instrument(s) 13140, a detected force by the surgical instrument(s) 13140, and/or identification information regarding the surgical instrument(s) 13140, although any relevant information and/or operating parameters can be sent to the surgical hub.

In various instances, a hub display 13125 is in signal communication with the surgical hub 13120 and may be incorporated into the modular control tower, for example. The hub display 13125 is configured to display information received from the robotic surgical system 13110 and the surgical instrument(s) 13140. The hub display 13125 can be similar in many respects to the visualization system 108 (FIG. 1), for example. In one aspect, the hub display 13125 can include an array of displays such as video monitors and/or heads-up displays around the operating room, for example.

In various instances, the surgical hub 13120 is configured to recognize when the surgical instrument 13140 is activated by a clinician via wireless communication signal(s). Upon activation, the surgical instrument 13140 is configured to send identification information to the surgical hub 13120. Such identification information may include, for example, a model number of the surgical instrument, an operating status of the surgical instrument, and/or a location of the surgical instrument, although other suitable device parameters can be communicated. In various instances, the surgical hub 13120 is configured to utilize the communicated information to assess the compatibility of the surgical instrument 13140 with the capabilities of the surgical hub 13120. Examples of capabilities of the surgical hub with compatible surgical instruments are further discussed herein.

In various instances, the control unit 13114 of the robotic surgical system 13110 is configured to communicate a video feed to the surgical hub 13120, and the surgical hub 13120 is configured to communicate the information, or a portion thereof, to the surgical instrument 13140, which can replicate a portion of the robot display 13113, or other information from the robotic surgical system 13110, on a display 13142 of the surgical instrument 13140. In other instances, the robotic surgical system 13110 (e.g. the control unit 13114 or surgical tool 13117) can communicate directly with the surgical instrument 13140, such as when the robotic surgical system 13110 includes a robotic hub and/or the surgical tool 13117 includes a wireless communication module, for example. The reproduction of a portion of the robot display 13113 on the surgical instrument 13140 allows the clinician to cooperatively use both surgical devices by providing, for example, alignment data to achieve integrated positioning of the surgical instrument 13140 relative to the robotic tool(s) 13117. In various instances, the clinician is able to remove any unwanted information displayed on the display 13142 of the surgical instrument 13140.

Referring still to FIG. 66, in various instances, the surgical system 13100 further includes an interactive secondary display 13130 within the sterile field 13138. The interactive secondary display 13130 is also a local control module within the sterile field 13138. The remote control console 13116, or the primary control, can be positioned outside the sterile field 13138. For example, the interactive secondary display 13130 can be a handheld mobile electronic device, such as an iPad® tablet, which can be placed on a patient or the patient's table during a surgical procedure. For example, the interactive secondary display 13130 can be placed on the abdomen or leg of the patient during the surgical procedure. In other instances, the interactive secondary display 13130 can be incorporated into the surgical instrument 13140 within the sterile field 13138. In various instances, the interactive secondary display 13130 is configured to be in signal communication with the robotic surgical system 13110 and/or the surgical instrument 13140. In such instances, the interactive secondary display 13130 is configured to display information received from the robotic tool(s) 13117 (for example, robotic tool 1, robotic tool 2, . . . robotic tool n) and the surgical instruments 13140 (for example, surgical instrument 1, surgical instrument 2, . . . surgical instrument n). The interactive secondary display 13130 depicts tool information 13133 and instrument information 13135 thereon. In various instances, the user is able to interact with the interactive secondary display 13130 to customize the size and/or location of the information displayed.

Referring still to FIG. 66, in various instances, the surgical hub 13120 is configured to transmit robot status information of the surgical robot system 13100 to the surgical instrument 13140, and the surgical instrument 13140 is configured to display the robot status information on the display 13142 of the surgical instrument 13140.

In various instances, the display 13142 of the surgical instrument 13140 is configured to communicate commands through the surgical hub 13120 to the control unit 13114 of the robotic surgical system 13110. After viewing and interpreting the robot status information displayed on the display 13142 of the surgical instrument 13140 as described herein, a clinician may want to utilize one or more functions of the robotic surgical system 13110. Using the buttons and/or a touch-sensitive display 13142 on the surgical instrument 13140, the clinician is able to input a desired utilization of and/or adjustment to the robotic surgical system 13110. The clinician input is communicated from the surgical instrument 13140 to the surgical hub 13120. The surgical hub 13120 is then configured to communicate the clinician input to the control unit 13114 of the robotic surgical system 13110 for implementation of the desired function. In other instances, the handheld surgical instrument 13140 can communicate directly with the control unit 13114 of the robotic surgical system 13110, such as when the robotic surgical system 13110 includes a robotic hub, for example.

In various instances, the surgical hub 13120 is in signal communication with both the robotic surgical system 13110 and the surgical instrument 13140, allowing the surgical system 13100 to adjust multiple surgical devices in a synchronized, coordinated, and/or cooperative manner. The information communicated between the surgical hub 13120 and the various surgical devices includes, for example, surgical instrument identification information and/or the operating status of the various surgical devices. In various instances, the surgical hub 13120 is configured to detect when the surgical instrument 13140 is activated. In one instance, the surgical instrument 13140 is an ultrasonic dissector. Upon activation of the ultrasonic dissector, the surgical hub 13120 is configured to communicate the received activation information to the control unit 13114 of the robotic surgical system 13110.

In various instances, the surgical hub 13120 automatically communicates the information to the control unit 13114 of the robotic surgical system 13110. The reader will appreciate that the information can be communicated at any suitable time, rate, interval and/or schedule. Based on the information received from the surgical hub 13120, the control unit 13114 of the robotic surgical system 13110 is configured to decide whether to activate at least one robotic tool 13117 and/or activate a particular operating mode, such as a smoke evacuation mode, for example. For example, upon activation of a surgical tool that is known to generate, or possibly generate, smoke and/or contaminants at the surgical site, such as an ultrasonic dissector, the robotic surgical system 13110 can automatically activate the smoke evacuation mode or can cue the surgeon to activate the smoke evacuation mode. In various instances, the surgical hub 13120 is configured to continuously communicate additional information to the control unit 13114 of the robotic surgical system 13110, such as various sensed tissue conditions, in order to adjust, continue, and/or suspend further movement of the robotic tool 13117 and/or the entered operating mode.

In various instances, the surgical hub 13120 may calculate parameters, such as smoke generation intensity, for example, based on the additional information communicated from the surgical instrument 13140. Upon communicating the calculated parameter to the control unit 13114 of the robotic surgical system 13110, the control unit 13114 is configured to move at least one robotic tool and/or adjust the operating mode to account for the calculated parameter. For example, when the robotic surgical system 13110 enters the smoke evacuation mode, the control unit 13114 is configured to adjust a smoke evacuation motor speed to be proportionate to the calculated smoke generation intensity.

In certain instances, an ultrasonic tool mounted to the robot 13112 can include a smoke evacuation feature that can be activated by the control unit 13114 to operate in a smoke evacuation mode. In other instances, a separate smoke evacuation device can be utilized. For example, a smoke evacuation tool can be mounted to another robotic arm and utilized during the surgical procedure. In still other instances, a smoke evacuation instrument that is separate from the robotic surgical system 13110 can be utilized. The surgical hub 13120 can coordinate communication between the robotically-controlled ultrasonic tool and the smoke evacuation instrument, for example.

In FIGS. 67-70, various surgical devices and components thereof are described with reference to a colon resection procedure. The reader will appreciate that the surgical devices, systems, and procedures described with respect to those figures are an exemplary application of the system of FIG. 66. Referring now to FIG. 67, a handle portion 13202 of a handheld surgical instrument 13300 is depicted. In certain aspects, the handheld surgical instrument 13300 corresponds to the surgical instrument 13140 of the surgical system 13100 in FIG. 66. In one instance, the handheld surgical instrument 13300 is a powered circular stapler and includes a display 13310 on the handle portion 13302 thereof.

Before pairing the handheld surgical instrument 13300 to a robotic surgical system (e.g. the robotic surgical system 13110 in FIG. 66) via the surgical hub 13320 (FIG. 68), as described herein, the display 13310 on the handle 13302 of the handheld surgical instrument 13300 can include information regarding the status of the instrument 13300, such as the clamping load 13212, the anvil status 13214, and/or the instrument or cartridge status 13216, for example. In various instances, the display 13310 of the handheld surgical instrument 13300 includes an alert 13318 to the user that communicates the status of the firing system. In various instances, the display 13310 is configured to display the information in a manner that communicates the most important information to the user. For example, in various instances, the display 13310 is configured to display warning information in a larger size, in a flashing manner, and/or in a different color. When the handheld surgical instrument 13300 is not paired with a surgical hub, the display 13310 can depict information gathered only from the handheld surgical instrument 13300 itself.

Referring now to FIG. 68, after pairing the handheld surgical instrument 13300 with the surgical hub 13320, as described herein with respect to FIG. 66, for example, the information detected and displayed by the handheld surgical instrument 13300 can be communicated to the surgical hub 13320 and displayed on a hub display (e.g. the hub display 13125 of FIG. 66). Additionally or alternatively, the information can be displayed on the display of the robotic surgical system. Additionally or alternatively, the information can be displayed on the display 13310 on the handle portion 13302 of the handheld surgical instrument 13300. In various instances, a clinician can decide what information is displayed at the one or multiple locations. As mentioned above, in various instances, the clinician is able to remove any unwanted information displayed on the display 13310 of the handheld surgical instrument 13300, the display of the robotic surgical system, and/or the display on the hub display.

Referring still to FIG. 68, after pairing the handheld surgical instrument 13300 with the robotic surgical system, the display 13310 on the handle portion 13302 of the handheld surgical instrument 13300 can be different than the display 13310 on the handheld surgical instrument 13300 before pairing with the robotic surgical system. For example, procedural information from the surgical hub 13320 and/or robotic surgical system can be displayed on the powered circular stapler. For example, as seen in FIG. 68, robot status information including alignment information 13312 from the surgical hub 13320 and one or more retraction tensions 13316, 13317 exerted by a robotic tool on particular tissue(s), is displayed on the display 13310 of the handheld surgical instrument 13300 for the convenience of the clinician. In various instances, the display 13310 of the handheld surgical instrument 13300 includes an alert 13318 to the user that communicates a parameter monitored by the surgical hub 13320 during a surgical procedure. In various instances, the display 13310 is configured to display the information in a manner that communicates the most important information to the user. For example, in various instances, the display 13310 is configured to display warning information in a larger size, in a flashing manner, and/or in a different color.

Referring still to FIG. 68, the display 13310 of the handheld surgical instrument 13300 is configured to display information regarding one or more retraction tensions 13316, 13317 exerted by one or more devices during a surgical procedure involving one or more robotic tools. For example, the handheld surgical instrument 13300, the powered circular stapler, is involved in a the colon resection procedure of FIG. 69. In this procedure, one device (e.g. a robotic tool) is configured to grasp colonic tissue and another device (e.g. the handheld circular stapler) is configured to grasp rectal tissue. As the devices move apart from one another, the force of retracting the colonic tissue $F_{RC}$ and the force of retracting the rectal tissue $F_{RR}$ are monitored. In the illustrated example, an alert notification 13318 is issued to the user as the force of retracting the colonic tissue has exceeded a predetermined threshold. Predetermined thresholds for both retracting forces $F_{RC}$, $F_{RR}$ are indicated by horizontal dotted lines on the display 13310. The user is notified when one or both thresholds are surpassed and/or reached in an effort to minimize damage and/or trauma to the surrounding tissue.

In FIG. 70, graphical displays 13330, 13340 of retracting forces $F_{RC}$, $F_{RR}$ are illustrated. In the circumstances illustrated in the graphical displays 13330, 13340, the user is notified when pre-determined thresholds are exceeded, depicted by the shaded region 13332 of the graphical display 13330, indicating that the retracting force of the colonic tissue $F_{RC}$ has exceeded a predetermined threshold of 0.5 lbs.

In certain instances, it can be difficult to align the end effector of a circular stapler with targeted tissue during a colorectal procedure because of visibility limitations. For example, referring again to FIG. 69, during a colon resection, the surgical instrument 13300, a circular stapler, can be positioned adjacent to a transected rectum 13356. Moreover, the anvil 13301 of the surgical instrument 13300 can be engaged with a transected colon 13355. A robotic tool 133175 is configured to engage the anvil 13301 and apply the retracting force $F_{RC}$. It can be difficult to confirm the relative position of the surgical instrument 13300 with the targeted tissue, for example, with the staple line through the transected colon 13355. In certain instances, information from the surgical hub 13320 and robotic surgical system can facilitate the alignment. For example, as shown in FIG. 68, the center of the surgical instrument 13300 can be shown relative to the center of the targeted tissue 13318 on the display screen 13310 of the surgical instrument 13300. In certain instances, and as shown in FIG. 69, sensors and a wireless transmitter on the surgical instrument 13300 can be configured to convey positioning information to the surgical hub 13320, for example.

A colorectal procedure, visibility limitations thereof, and an alignment tool for a surgical hub are further described herein and in U.S. Provisional Patent Application Ser. No. 62/611,341, titled INTERACTIVE SURGICAL PLATFORM, filed Dec. 28, 2017, the disclosure of which is herein incorporated by reference in its entirety.

As mentioned above, the display 13310 on the handheld instrument 13300 can also be configured to alert the clinician in certain scenarios. For example, the display 13310 in FIG. 68 includes an alert 13318 because the one or more of the forces exceed the predefined force thresholds. Referring again to FIGS. 69 and 70, during the colon resection, the robotic arm can exert a first force $F_{RC}$ on the anvil, and the handheld instrument 13300 can exert a second force $F_{RR}$ on the rectum 13356. The tension on the rectum 13356 by the circular stapler can be capped at a first limit (for example 0.5 lb in FIG. 70), and the tension on the colon 13355 from the robotic arm can be capped at a second limit (for example 0.5 lb in FIG. 70). An intervention may be suggested to the clinician when the tension on the rectum 13356 or colon 13355 exceeds a threshold value.

The tension on the colon $F_{RC}$ in FIGS. 69 and 70 can be ascertained by resistance to the robotic arm, and thus, can be determined by a control unit (e.g. the control unit 13114 of the robotic surgical system 13110). Such information can be communicated to the handheld surgical instrument 13300 and displayed on the display 13310 thereof in the sterile field such that the information is readily available to the appropriate clinician in real-time, or near real-time, or any suitable interval, rate, and/or schedule, for example.

In various instances, a surgical system, such as a surgical system 13360 of FIGS. 71 and 72, includes interactive secondary displays 13362, 13364 within the sterile field. The interactive secondary displays 13362, 13364 are also mobile control modules in certain instances and can be similar to the interactive secondary displays 13130 in FIG. 66, for example. A surgeon's command console, or remote control module, 13370, is the primary control module and can be positioned outside the sterile field. In one instance, the interactive secondary display 13362 can be a mobile device, a watch, and/or a small tablet, which can be worn on the wrist and/or forearm of the user, and the interactive secondary display 13364 can be a handheld mobile electronic device, such as an iPad® tablet, which can be placed on a patient 13361 or the patient's table during a surgical procedure. For example, the interactive secondary displays 13362, 13364 can be placed on the abdomen or leg of the patient 13361 during the surgical procedure. In other instances, the interactive secondary displays 13362, 13364 can be incorporated into a handheld surgical instrument 13366 within the sterile field.

In one instance, the surgical system 13360 is shown during a surgical procedure. For example, the surgical procedure can be the colon resection procedure described herein with respect to FIGS. 67-70. In such instances, the surgical system 13360 includes a robot 13372 and a robotic tool 13374 extending into the surgical site. The robotic tool can be an ultrasonic device comprising an ultrasonic blade and a clamp arm, for example. The surgical system 13360 also includes the remote command console 13370 that encompasses a robotic hub 13380. The control unit for the robot 13372 is housed in the robotic hub 13380. A surgeon 13371 is initially positioned at the remote command console 13370. An assistant 13367 holds the handheld surgical instrument 13366, a circular stapler that extends into the surgical site. The assistant 13367 also holds a secondary display 13364 that communicates with the robotic hub 13380. The secondary display 13364 is a mobile digital electronic device, which can be secured to the assistant's forearm, for example. The handheld surgical instrument 13366 includes a wireless communication module. A second surgical hub 13382 is also stationed in the operating room. The surgical hub 13382 includes a generator module and can include additional modules as further described herein and in U.S. Provisional Patent Application Ser. No. 62/611,341, titled INTERACTIVE SURGICAL PLATFORM, filed Dec. 28, 2017, the disclosure of which is herein incorporated by reference in its entirety.

Referring primarily to FIG. 71, hubs 13380, 13382 include wireless communication modules such that a wireless communication link is established between the two hubs 13380, 13382. Additionally, the robotic hub 13380 is in signal communication with the interactive secondary displays 13362, 13364 within the sterile field. The hub 13382 is in signal communication with the handheld surgical instrument 13366. If the surgeon 13371 moves over towards the patient 13361 and within the sterile field (as indicated by the reference character 13371'), the surgeon 13371 can use one of the wireless interactive displays 13362, 13364 to operate the robot 13372 away from the remote command console 13370. The plurality of secondary displays 13362, 13364 within the sterile field allows the surgeon 13371 to move away from the remote command console 13370 without losing sight of important information for the surgical procedure and controls for the robotic tools utilized therein.

The interactive secondary displays 13362, 13364 permit the clinician to step away from the remote command console 13370 and into the sterile field while maintaining control of the robot 13372. For example, the interactive secondary displays 13362, 13364 allow the clinician to maintain cooperative and/or coordinated control over the powered handheld surgical instrument(s) 13366 and the robotic surgical system at the same time. In various instances, information is communicated between the robotic surgical system, one or more powered handheld surgical instruments 13366, surgical hubs 13380, 13382, and the interactive secondary displays 13362, 13364. Such information may include, for example, the images on the display of the robotic surgical system and/or the powered handheld surgical instruments, a parameter of the robotic surgical system and/or the powered handheld surgical instruments, and/or a control command for the robotic surgical system and/or the powered handheld surgical instruments.

In various instances, the control unit of the robotic surgical system (e.g. the control unit 13113 of the robotic surgical system 13110) is configured to communicate at least one display element from the surgeon's command console (e.g. the console 13116) to an interactive secondary display (e.g. the display 13130). In other words, a portion of the display at the surgeon's console is replicated on the display of the interactive secondary display, integrating the robot display with the interactive secondary display. The replication of the robot display on to the display of the interactive secondary display allows the clinician to step away from the remote command console without losing the visual image that is displayed there. For example, at least one of the interactive secondary displays 13362, 13364 can display information from the robot, such as information from the robot display and/or the surgeon's command console 13370.

In various instances, the interactive secondary displays 13362, 13364 are configured to control and/or adjust at least one operating parameter of the robotic surgical system. Such control can occur automatically and/or in response to a clinician input. Interacting with a touch-sensitive screen and/or buttons on the interactive secondary display(s) 13362, 13364, the clinician is able to input a command to control movement and/or functionality of the one or more robotic tools. For example, when utilizing a handheld surgical instrument 13366, the clinician may want to move the robotic tool 13374 to a different position. To control the robotic tool 13374, the clinician applies an input to the interactive secondary display(s) 13362, 13364, and the respective interactive secondary display(s) 13362, 13364 communicates the clinician input to the control unit of the robotic surgical system in the robotic hub 13380.

In various instances, a clinician positioned at the remote command console 13370 of the robotic surgical system can manually override any robot command initiated by a clinician input on the one or more interactive secondary displays 13362, 13364. For example, when a clinician input is received from the one or more interactive secondary displays 13362, 13364, a clinician positioned at the remote command console 13370 can either allow the command to be issued and the desired function performed or the clinician can override the command by interacting with the remote command console 13370 and prohibiting the command from being issued.

In certain instances, a clinician within the sterile field can be required to request permission to control the robot 13372 and/or the robotic tool 13374 mounted thereto. The surgeon 13371 at the remote command console 13370 can grant or deny the clinician's request. For example, the surgeon can receive a pop-up or other notification indicating the permission is being requested by another clinician operating a handheld surgical instrument and/or interacting with an interactive secondary display 13362, 13364.

In various instances, the processor of a robotic surgical system, such as the robotic surgical systems 13000 (FIG. 57), 13400 (FIG. 58), 13150 (FIG. 64), 13100 (FIG. 66), and/or the surgical hub 13380, 13382, for example, is programmed with pre-approved functions of the robotic surgical system. For example, if a clinician input from the interactive secondary display 13362, 13364 corresponds to a pre-approved function, the robotic surgical system allows for the interactive secondary display 13362, 13364 to control the robotic surgical system and/or does not prohibit the interactive secondary display 13362, 13364 from controlling the robotic surgical system. If a clinician input from the interactive secondary display 13362, 13364 does not correspond to a pre-approved function, the interactive secondary display 13362, 13364 is unable to command the robotic surgical system to perform the desired function. In one instances, a situational awareness module in the robotic hub 13370 and/or the surgical hub 13382 is configured to dictate and/or influence when the interactive secondary display can issue control motions to the robot surgical system.

In various instances, an interactive secondary display 13362, 13364 has control over a portion of the robotic surgical system upon making contact with the portion of the robotic surgical system. For example, when the interactive secondary display 13362, 13364 is brought into contact with the robotic tool 13374, control of the contacted robotic tool 13374 is granted to the interactive secondary display 13362, 13364. A clinician can then utilize a touch-sensitive screen and/or buttons on the interactive secondary display 13362, 13364 to input a command to control movement and/or functionality of the contacted robotic tool 13374. This control scheme allows for a clinician to reposition a robotic arm, reload a robotic tool, and/or otherwise reconfigure the robotic surgical system. In a similar manner as discussed above, the clinician 13371 positioned at the remote command console 13370 of the robotic surgical system can manually override any robot command initiated by the interactive secondary display 13362, 13364.

In one aspect, the robotic surgical system includes a processor and a memory communicatively coupled to the processor, as described herein. The memory stores instructions executable by the processor to receive a first user input from a console and to receive a second user input from a mobile wireless control module for controlling a function of a robotic surgical tool, as described herein.

In various aspects, the present disclosure provides a control circuit to receive a first user input from a console and to receive a second user input from a mobile wireless control module for controlling a function of a robotic surgical tool, as described herein. In various aspects, the present disclosure provides a non-transitory computer readable medium storing computer readable instructions which, when executed, cause a machine to receive a first user input from a console and to receive a second user input from a mobile wireless control module for controlling a function of a robotic surgical tool, as described herein.

A robotic surgical system may include multiple robotic arms that are configured to assist the clinician during a surgical procedure. Each robotic arm may be operable independently of the others. A lack of communication may exist between each of the robotic arms as they are independently operated, which may increase the risk of tissue trauma. For example, in a scenario where one robotic arm is configured to apply a force that is stronger and in a different direction than a force configured to be applied by a second robotic arm, tissue trauma can result. For example, tissue trauma and/or tearing may occur when a first robotic arm applies a strong retracting force to the tissue while a second robotic arm is configured to rigidly hold the tissue in place.

In various instances, one or more sensors are attached to each robotic arm of a robotic surgical system. The one or more sensors are configured to sense a force applied to the surrounding tissue during the operation of the robotic arm. Such forces can include, for example, a holding force, a retracting force, and/or a dragging force. The sensor from each robotic arm is configured to communicate the magnitude and direction of the detected force to a control unit of the robotic surgical system. The control unit is configured to analyze the communicated forces and set limits for maximum loads to avoid causing trauma to the tissue in a surgical site. For example, the control unit may minimize the holding force applied by a first robotic arm if the retracting or dragging force applied by a second robotic arm increases.

FIG. 73 depicts a robotic surgical system 13800 including a control unit 13820 and a robot 13810. The robotic surgical system 13800 is similar in many respects to the robotic surgical system 13000 including the robot 13002 (FIG. 57), for example. The control unit 13820 includes a processor 13822 and a display 13824. The robot 13810 includes two robotic arms, 13830, 13840 configured to carry out various surgical functions. Each of the robotic arms 13830, 13840 are independently operable and are free to move in a space defining a control envelope of the robotic surgical system 13800. The one or more robotic arms, 13830, 13840, are configured to receive a tool, such as a stapler, a radio frequency (RF) tool, an ultrasonic blade, graspers, and/or a cutting instrument, for example. Other suitable surgical tool can be used. In various instances, the robotic arms 13830, 13840 each include a different tool configured to perform different functions. In other instances, all of the robotic arms 13830, 13840 include the same tool, although any suitable arrangement can be used.

The first robotic arm 13830 includes a first driver 13834 and a first motor 13836. When activated by the processor 13822, the first motor 13836 drives the first driver 13834 actuating the corresponding component of the first robotic arm 13830. The second robotic arm 13840 includes a second driver, 13844 and a second motor 13846. When activated by the processor 13822, the second motor 13846 drives the second driver 13844 actuating the corresponding component of the second robotic arm 13840.

Each of the robotic arms 13830, 13840, includes a sensor 13832, 13842 in signal communication with the processor 13822 of the control unit 13820. The sensors 13832, 13842 can be positioned on the drivers 13834, 13844, respectively, and/or on the motors 13836, 13846, respectively. In various instances, the sensors 13832, 13842 are configured to detect the location of each individual robotic arm 13830, 13840 within the control envelope of the robotic surgical system 13800. The sensors 13832, 13842 are configured to communicate the detected locations to the processor 13822 of the robotic surgical system 13800. In various instances, the positions of the robotic arms 13830, 13840 are displayed on the display 13824 of the control unit 13820. As described in more detail below, in various instances, the processor 13822 is configured to run an algorithm to implement position limits specific to each robotic arm 13830, 13840 in an effort to avoid tissue trauma and damage to the robotic surgical system 13800, for example. Such position limits may increase the clinician's ability to cooperatively operate numerous robotic arms 13830, 13840 of the robotic surgical system 13800 at the same time.

In various instances, the sensors 13832, 13842 are configured to detect the force exerted by each robotic arm 13830, 13840. The sensors 13832, 13842 can be torque sensors. As stated above, each robotic arm 13830, 13840 of the robotic surgical system 13800 is independently operable. During a particular surgical procedure, a clinician may want to perform different surgical functions with each robotic arm 13830, 13840. Upon detecting the exerted forces of each robotic arm 13830, 13840, each sensor 13832, 13842 is configured to communicate the detected forces to the processor 13822. The processor 13822 is then configured to analyze the communicated information and set maximum and/or minimum force limits for each robotic arm 13830, 13840 to reduce the risk of causing tissue trauma, for example. In addition, the processor 13822 is configured to continuously monitor the exerted forces by each robotic arm 13830, 13840 and, based on the direction and magnitude of the exerted forces, proportionally control each robotic arm 13830, 13840 with respect to one another. For example, the opposing force between two robotic arms 13830, 13840 can be measured and maintained below a maximum force limit. To maintain the opposing force below a maximum force limit, at least one of the forces can be reduced, which can result in displacement of the robotic arm 13830, 13840.

By way of example, FIG. 74 depicts a surgical site and a portion of the surgical system 13800, which includes three robotic arms, including a robotic arm 13850 (a third robotic arm) in addition to the robotic arms 13830 and 13840, which are also schematically depicted in FIG. 73. The first robotic arm 13830 is configured to hold a portion of stomach connective tissue. In order to hold the portion of stomach connective tissue, the first robotic arm 13830 exerts an upward force $F_{H1}$. The second robotic arm 13840 applies a dragging and/or cutting force $F_{D2}$ to the tissue. Simultaneously, the third robotic arm 13850 retracts a portion of liver tissue away from the current surgical cut location, further exposing the next surgical cut location. In order to move the portion of liver tissue out of the way of the advancing second robotic arm 13840, the third robotic arm 13850 applies a retracting force $F_{R3}$ away from the second robotic arm 13840. In various exemplifications, as the second robotic arm 13840 advances further into the surgical site, the control unit of the robotic surgical system directs the third robotic arm 13850 to increase the exerted retracting force $F_{R3}$ to continue exposing the next surgical cut location. While FIG. 74 depicts a particular surgical procedure and specific robotic arms, any suitable surgical procedure can be performed, and any suitable combination of robotic arms can utilize the control algorithms disclosed herein.

FIG. 75 depicts graphical representations 13852, 13854 of the forces exerted by the robotic arms 13830, 13840, and 13850 of FIG. 74 and the relative locations of the robotic arm 13830, 13840, and 13850, respectively, from the particular surgical procedure detailed above. The graphical display 13852 in FIG. 75 represents the exerted forces of each robotic arm 13830, 13840, and 13850 over a period of time, while the graphical display 13854 represents the relative positions of each robotic arm 13830, 13840, and 13850 over the same period of time. As discussed above, the first robotic arm 13830 is configured to exert a holding force $F_{H1}$ on a portion of stomach connective tissue. The holding force $F_{H1}$ is represented by a solid line on the graphs 13852, 13854. The second robotic arm 13840 is configured to exert a dragging and/or cutting force $F_{D2}$ on the stomach connective tissue. The dragging force $F_{D2}$ is represented by a dash-dot line on the graphs 13852, 13854. The third robotic arm 13850 is configured to exert a retracting force $F_{R3}$ on a portion of liver tissue. The retracting force $F_{R3}$ is represented by a dotted line on the graphs 13852, 13854.

In various instances, the control unit of the robotic surgical system imposes at least one force threshold, such as a maximum force threshold, as depicted in the graphical display 13852. Thus, the third robotic arm 13850 is prevented from exerting a retraction force $F_{R3}$ greater than the maximum retraction force threshold. Such maximum force limits are imposed in order to avoid tissue trauma and/or avoid damage to the various robotic arms 13830, 13840, and 13850, for example.

Additionally or alternatively, the control unit 13820 of the robotic surgical system 13800 can impose least one force threshold, such as a minimum force threshold, as depicted in the graphical display 13852. In the depicted instance, the first robotic arm 13830 is prevented from exerting a holding force $F_{H1}$ less than the minimum holding force threshold. Such minimum force limits are imposed in order to avoid maintain appropriate tissue tension and/or visibility of the surgical site, for example.

In various instances, the control unit 13820 of the robotic surgical system 13800 imposes maximum force differentials detected between various robotic arms during a load control mode. In order to set maximum force differentials, the control unit 13820 of the robotic surgical system is configured to continuously monitor the difference in magnitude and direction of opposing forces by the robotic arms. As stated above, the first robotic arm 13830 is configured to hold a portion of the stomach connective tissue by exerting a holding force $F_m$. The second robotic arm 13840 is configured to apply a dragging force $F_{D2}$, which opposes the holding force $F_{H1}$ exerted by the first robotic arm 13830. In various instances, maximum force differentials prevent inadvertent overloading and/or damaging an object caught between the robotic arms 13830, 13840, and 13850. Such objects include, for example, surrounding tissue and/or surgical components like clasps, gastric bands, and/or sphincter reinforcing devices. $F_{max\ opposing}$ represents the maximum force differential set by the control unit 13820 in this particular exemplification.

As can be seen in the graphical display 13852, the holding force $F_{H1}$ and the dragging force $F_{D2}$ both increase in magnitude at the beginning of the surgical procedure. Such an increase in magnitudes can indicate a pulling of the tissue. The holding force $F_{H1}$ and the dragging force $F_{D2}$ increase in opposite directions to a point where the difference between the opposing forces is equal to $F_{max\ opposing}$. In the graphic display 13852, the slanted lines highlight the point in time when $F_{max\ opposing}$ is reached. Upon reaching $F_{max\ opposing}$, the processor 13822 instructs the first robotic arm 13830 to reduce the holding force $F_{H1}$ and continues to allow the second robotic arm 13840 to exert the dragging force $F_{D2}$ at the same value, and may allow a clinician to increase the dragging force. In various instances, the value of $F_{max\ opposing}$ is set by the processor 13822 based on various variables, such as the type of surgery and/or relevant patient demographics. In various instances, $F_{max\ opposing}$ is a default value stored in a memory of the processor 13822.

The relative positions of the robotic arms 13830, 13840, and 13850 within the surgical site are depicted in the graph display 13854 of FIG. 75. As the first robotic arm 13830 exerts a holding force $F_{H1}$ on the stomach connective tissue and the third robotic arm 13850 exerts a retracting force $F_{R3}$ on the liver tissue, the surgical site becomes clear and allows the second robotic arm 13840 to exert a dragging and/or cutting force $F_{D2}$ on the desired tissue. The second robotic arm 13840 and the third robotic arm 13850 become farther away from the first robotic arm 13830 as the procedure progresses. When the force differential $F_{max\ opposing}$ is reached between the holding force $F_{H1}$ and the dragging force $F_{D2}$, the first robotic arm 13830 is moved closer towards the second robotic arm 13840, lessening the exerted holding force $F_{H1}$ by the first robotic arm 13830. In one aspect, the processor 13822 can transition the first robotic arm 13830 from the load control mode into a position control mode such that the position of the first robotic arm 13830 is held constant. As depicted in the graphical representations of FIG. 75, when the first robotic arm 13830 is held in a constant position, the force control for the second robotic arm 13840 can continue to displace the second robotic arm 13840.

In various instances, the control unit 13820 of the robotic surgical system directs the first robotic arm 13830 to hold a specific position until a pre-determined force threshold between the first robotic arm 13830 and a second robotic arm 13840 is reached. When the pre-determined force threshold is reached, the first robotic arm 13830 is configured to automatically move along with the second robotic arm 13840 in order to maintain the pre-determined force threshold. The first robotic arm 13830 stops moving (or may move at a different rate) when the detected force of the second robotic arm 13840 no longer maintains the pre-determined force threshold.

In various instances, the control unit 13820 of the robotic surgical system is configured to alternate between the position control mode and the load control mode in response to detected conditions by the robotic arms 13830, 13840, and 13850. For example, when the first robotic arm 13830 and the second robotic arm 13840 of the robotic surgical system 13800 are freely moving throughout a surgical site, the control unit 13820 may impose a maximum force that each arm 13830, 13840 can exert. In various instances, the first and second arms 13830, 13840 each include a sensor configured to detect resistance. In other instances, the sensors can be positioned on a surgical tool, such as an intelligent surgical stapler or jawed tool. A resistance can be encountered upon contact with tissue and/or other surgical instruments. When such resistance is detected, the control unit 13820 may activate the load control mode and lower the exerted forces by one and/or more than one of the robotic arms 13830, 13840 to, for example, reduce damage to the tissue. In various instances, the control unit 13820 may activate the position control mode and move the one and/or more than one of the robotic arms 13830, 13840 to a position where such resistance is no longer detected.

In one aspect, the processor 13822 of the control unit 13820 is configured to switch from the load control mode to the position control mode upon movement of a surgical tool mounted to one of the robotic arms 13830, 13840 outside a defined surgical space. For example, if one of the robotic arms 13830, 13840 moves out of a defined boundary around the surgical site, or into abutting contact with an organ or other tissue, or too close to another surgical device, the processor 13822 can switch to a position control mode and prevent further movement of the robotic arm 13830, 13840 and/or move the robotic arm 13830, 13840 back within the defined surgical space.

Turning now to the flow chart shown in FIG. 76, an algorithm 13500 is initiated at step 13501 when the clinician and/or the robotic surgical system activates one or more of the robotic arms at step 13505. The algorithm 13500 can be employed by the robotic surgical system 13800 in FIG. 73, for example. Each robotic arm is in signal communication with the processor 13822 of the robotic surgical system. Following activation, each robotic arm is configured to send information to the processor. In various instances, the information may include, for example, identification of the tool attachment and/or the initial position of the activated robotic arm. In various instances, such information is communicated automatically upon attachment of the tool to the robotic arm, upon activation of the robotic arm by the robotic surgical system, and/or after interrogation of the robotic arm by the processor, although the information may be sent at any suitable time. Furthermore, the information may be sent automatically and/or in response to an interrogation signal.

Based on the information gathered from each of the activated robotic arms at step 13510, the processor is configured to set a position limit for each specific robotic arm within a work envelope of the robotic surgical system at step 13515. The position limit can set three-dimensional boundaries for where each robotic arm can travel. The setting of position limits allows for efficient and cooperative usage of each activated robotic arm while, for example, preventing trauma to surrounding tissue and/or collisions between activated robotic arms. In various instances, the processor includes a memory including a set of stored data to assist in defining each position limit. The stored data can be specific to the particular surgical procedure, the robotic tool attachment, and/or relevant patient demographics, for example. In various instances, the clinician can assist in the definition of the position limit for each activated robotic arm. The processor is configured to determine if the robotic arms are still activated at step 13520. If the processor determines that the robotic arms are no longer activated, the processor is configured to end position monitoring at step 13522. Once the processor determines that the robotic arms are still activated, the processor is configured to monitor the position of each activated robotic arm at step 13525.

The processor is then configured to evaluate whether the detected position is within the predefined position limit(s) at step 13530. In instances where information is unable to be gathered from the robotic arm and clinician input is absent, a default position limit is assigned at step 13533. Such a default position limit assigns a conservative three-dimensional boundary to minimize, for example, tissue trauma and/or collisions between robotic arms. If the detected limit is within the position limit, the processor is configured to allow the robotic arm(s) to remain in position and/or freely move within the surgical site at step 13535, and the monitoring process continues as long as the robotic arm is still activated. If the detected limit is outside of the position limit, the processor is configured to move the robotic arm back into the position limit at step 13532, and the monitoring process continues as long as the robotic arm is still activated.

The processor is configured to continuously monitor the position of each robotic arm at step 13525. In various instances, the processor is configured to repeatedly send interrogation signals in pre-determined time intervals. As discussed above, if the detected position exceeds the position limit set for the specific robotic arm, in certain instances, the processor is configured to automatically move the robotic arm back within the three-dimensional boundary at step 13532. In certain instances, the processor is configured to re-adjust the position limits of the other robotic arms in response to one robotic arm exceeding its original position limit. In certain instances, prior to moving the robotic arm back within its position limit and/or adjusting the position limits of the other robotic arms, the processor is configured to alert the clinician. If the detected position is within the position limit set for the robotic arm, the processor permits the robotic arm to remain in the same position and/or freely travel until the detected position exceeds the position limit at step 13535. If the processor is unable to detect the position of the robotic arm, the processor is configured to alert the clinician and/or assign the robotic arm with the default position limit at step 13533. The processor is configured to monitor the position of each robotic arm until the surgery is completed and/or the robotic arm is deactivated.

Similar to the algorithm of FIG. 76, the flow chart of FIG. 77 depicts an algorithm 13600 that is initiated at step 13601 when a clinician and/or a robotic surgical system activates one or more of the robotic arms at step 13605. The algorithm 13600 can be employed by the robotic surgical system 13800 in FIG. 73, for example. Each robotic arm is in signal communication with the processor. Following activation, each robotic arm is configured to send information to the processor at step 13610. In various instances, the information may include, for example, identification of the tool attachment, exerted forces detected by one or more force sensors on the robotic arm, and/or the initial position of the activated robotic arm. In various instances, such information is communicated automatically upon attachment of the tool to the robotic arm, upon activation of the robotic arm by the robotic surgical system, and/or after interrogation of the robotic arm by the processor, although the information may be sent at any suitable time. Furthermore, the information may be sent automatically and/or in response to an interrogation signal.

Based on the information gathered from each of the activated robotic arms, the processor is configured to set a force limit for each specific robotic arm at step 13615. The force limit sets maximum and minimum force thresholds for forces exerted by each robotic arm. Additionally or alternatively, a force limit can be the maximum force differential between two or more arms. The setting of force limits allows for efficient and cooperative usage of all of the activated robotic arms while, for example, preventing trauma to surrounding tissue and/or damage to the robotic arms. In various instances, the processor includes a memory including a set of stored data to assist in defining each force limit. The stored data can be specific to the particular surgical procedure, the robotic tool attachment, and/or relevant patient demographics, for example. In various instances, the clinician can assist in the definition of the force limit for each activated robotic arm. In instances where information is unable to be gathered from the robotic arm and clinician input is absent, a default force limit is assigned. Such a default force limit assigns conservative maximum and minimum force thresholds to minimize, for example, tissue trauma and/or damage to the robotic arms.

The processor is configured to determine if the robotic arm is active at step at step 13620. If the processor determines that the robotic arm has been deactivated, the processor is configured to end force monitoring at step 13622. Once it has been determined that the robotic arm is still activated at step 13620, the processor is configured to continuously monitor the force exerted by each robotic arm at step 13625. In various instances, the processor is configured to repeatedly send interrogation signals in pre-determined time intervals. If the detected force exceeds the maximum force threshold set for the specific robotic arm, in certain instances, the processor is configured to automatically decrease the force exerted by the robotic arm and/or decrease an opposing force exerted by another robotic arm at step 13632. In certain instances, the processor is configured to re-adjust the force limits assigned to the other robotic arms in response to one robotic arm exceeding its original force limits. In certain instances, prior to adjusting the force exerted by the robotic arm, adjusting the opposing force exerted by another robotic arm, and/or adjusting the force limits of the other robotic arms, the processor is configured to alert the clinician. If the detected force is within the force limit set for the robotic arm, the robotic arm is permitted to maintain the exertion of the force and/or the clinician can increase or decrease the exerted force until the force is out of the set force limit at step 13635. If the processor is unable to detect the exerted force of the robotic arm, the processor is configured to alert the clinician and/or assign the robotic arm with a default force limit at step 13633. The processor is configured to monitor the exerted force of each robotic arm until the surgery is completed and/or the robotic arm is deactivated at step 13620.

Similar to the algorithms of FIGS. 76 and 77, the flow chart of FIG. 78 depicts an algorithm 13700 that is initiated 13701 when a clinician and/or a robotic surgical system activates one or more of the robotic arms 13705. The algorithm 13700 can be employed by the robotic surgical system 13800 in FIG. 73, for example. Each robotic arm is in signal communication with the processor. Following activation, each robotic arm is configured to send information to the processor at step 13710. In various instances, the information may include, for example, identification of the tool attachment, forces detected by one or more force sensors on the robotic arm, and/or the initial position of the activated robotic arm. In various instances, such information is communicated automatically upon attachment of the tool to the robotic arm, upon activation of the robotic arm by the robotic surgical system, and/or after interrogation of the robotic arm by the processor, although the information may be sent at any suitable time. In various instances, the information is sent automatically and/or in response to an interrogation signal.

Based on the information gathered from all of the activated robotic arms, the processor is configured to set both a position limit within a work envelope of the robotic surgical system and a force limit for each specific robotic arm at step 13715. The position limit sets three-dimensional boundaries for where each robotic arm can travel. The setting of position limits allows for efficient and cooperative usage of all of the activated robotic arms while, for example, preventing trauma to surrounding tissue and/or collisions between activated robotic arms. The force limit sets maximum and/or minimum force thresholds for forces exerted by each robotic arm. Additionally or alternatively, a force limit can be the maximum force differential between two or more arms. The setting of force limits allows for efficient and cooperative usage of the activated robotic arms while, for example, preventing trauma to surrounding tissue and/or damage to the robotic arms.

In various instances, the processor includes a memory including a set of stored data to assist in defining each position limit and force limit. The stored data can be specific to the particular surgical procedure, the robotic tool attachment, and/or relevant patient demographics, for example. In various instances, the clinician can assist in the definition of the position limit and force limit for each activated robotic arm. In instances where information is unable to be gathered from the robotic arm and clinician input is absent, a default position limit and/or default force limit is assigned to the robotic arm. Such a default position limit assigns a conservative three-dimensional boundary to minimize, for example, tissue trauma and/or collisions between robotic arms, while the default force limit assigns conservative maximum and/or minimum force thresholds to minimize, for example, tissue trauma and/or damage to the robotic arms. In various instances, the processor is configured to adjust the position limit of one robotic arm based on the force limit of another robotic arm, adjust the force limit of one robotic arm based on the position limit of another robotic arm, and vice versa.

The processor is configured to determine whether the robotic arm is active at step 13720. Once the processor has determined that the robotic arm is activated at step 13720, the processor is configured to continuously monitor the position of each arm 13737 and the force exerted by each robotic arm at step 13725. If the robotic arm is no longer activated, the processor is configured to end position monitoring at step 13727 and end force monitoring at step 13722. In various instances, the processor is configured to repeatedly send interrogation signals in pre-determined time intervals. If the detected position exceeds the position limit set for the specific robotic arm, in certain instances, the processor is configured to automatically move the robotic arm back within the three-dimensional boundary at step 13742. In certain instances, prior to moving the robotic arm back within its position limit, the processor is configured to alert the clinician. If the detected position is within the position limit set for the robotic arm, the robotic arm is permitted to remain in the same position and/or freely travel until the detected position exceeds the position limit at step 13745. If the processor is unable to detect the position of the robotic arm, the processor is configured to alert the clinician and/or rewrite the original position limit of the robotic arm with the default position limit at step 13743. The processor is configured to monitor the position of each robotic arm until the surgery is completed and/or the robotic arm is deactivated.

In certain instances, the robotic surgical system includes a manual override configured to control the position of each robotic arm. If the detected force exceeds the maximum force threshold set for the specific robotic arm, in certain instances, the processor is configured to automatically decrease the force exerted by the robotic arm and/or decrease an opposing force exerted by another robotic arm at step 13732. In certain instances, prior to decreasing the force exerted by the robotic arm and/or decrease the opposing force exerted by another robotic arm, the processor is configured to alert the clinician. If the detected force is within the force limit set for the robotic arm, the robotic arm is permitted to maintain the exertion of the force and/or increase or decrease the exerted force until the force is out of the set force limit at step 13735. If the processor is unable to detect the exerted force of the robotic arm, the processor is configured to alert the clinician and/or rewrite the original force limit of the robotic arm with the default force limit at step 13733. The processor is configured to monitor the exerted force of each robotic arm until the surgery is completed and/or the robotic arm is deactivated.

In various instances, the position monitoring system and the force monitoring system are interconnected. In certain instances, the force monitoring system can override the resultant decision 13742, 14743, 14745 of the position detection step 13740. In certain instances, the position monitoring system can override the resultant decision 13732, 13733, 13735 of the force detection step 13730. In other instances, the position monitoring system and the force monitoring system are independent of one another.

A clinician can manually override the automatic adjustments implemented in the automatic load and/or position control mode(s) described herein. The manual override can be a one-time adjustment to the surgical robot. In other instances, the manual override can be a setting that turns off the automatic load and/or position mode for a specific surgical action, a specific duration, and/or a global override for the entire procedure.

In one aspect, the robotic surgical system includes a processor and a memory communicatively coupled to the processor, as described herein. The processor is communicatively coupled to a first force sensor and a second force sensor, and the memory stores instructions executable by the processor to affect cooperative movement of a first robotic arm and a second robotic arm based on a first input from the first force sensor and from a second input from the second force sensor in a load control mode, as described herein.

In various aspects, the present disclosure provides a control circuit to affect cooperative movement of a first robotic arm and a second robotic arm, as described herein. In various aspects, the present disclosure provides a non-transitory computer readable medium storing computer readable instructions which, when executed, cause a machine to affect cooperative movement of a first robotic arm and a second robotic arm, as described herein.

During a particular surgical procedure, clinicians may rely on one or more powered handheld surgical instruments in addition to a robotic surgical system. In various instances, the instruments are controlled and monitored through different platforms, which may inhibit communication between the instruments and the robotic surgical system. For example, the instruments can be produced by different manufacturers and even by competitors. Such instruments may have different communication packages and/or communication and/or linking protocols. The lack of communication between a powered instrument and the robotic surgical system may hinder cooperative and/or coordinated usage and may complicate the surgical procedure for the clinician. For example, each surgical instrument may include an individual display to communicate various information and operating parameters. In such a scenario, a clinician may have to look at numerous instrument-specific displays to monitor the operating status of and analyze data gathered by each device.

In various instances, a robotic surgical system is configured to detect the presence of other powered surgical instruments that are controlled by platforms other than the robotic surgical system. The robotic surgical system can incorporate a hub, i.e., a robotic hub like the robotic hubs 122 (FIG. 2) and 222 (FIG. 9), which can detect other powered surgical instruments, for example. In other instances, a stand-alone surgical hub like the hub 106 (FIGS. 1-3) or the hub 206 (FIG. 9) in communication with the robotic surgical system can facilitate detection of the non-robotic surgical instruments and cooperative and/or coordinated usage of the detected surgical instruments with the robotic surgical system. The hub, which can be a robotic hub or a surgical hub, is configured to display the position and orientation of the powered surgical instruments with respect to the work envelope of the robotic surgical system. In certain instances, the work envelope can be an operating room, for example. A surgical hub having spatial awareness capabilities is further described herein and in U.S. Provisional Patent Application Ser. No. 62/611,341, titled INTERACTIVE SURGICAL PLATFORM, filed Dec. 28, 2017, the disclosure of which is herein incorporated by reference in its entirety. In one aspect, the hub can first ascertain the boundaries of the work envelope and then detect the presence of other powered surgical instruments within the work envelope.

FIG. 79 depicts a surgical system 13860 including a robotic surgical system 13865, a surgical instrument 13890, and a surgical hub 13870. The surgical instrument 13890 is a powered handheld instrument, and can be a motorized surgical stapler, such as the motorized linear stapler depicted in FIG. 80, for example. The surgical system 13865 can be similar in many respects to the robotic surgical system 13000 (FIG. 57), for example. As described herein, the surgical hub 13870 can be incorporated into the robotic surgical system 13865, for example. The surgical hub 13870 is configured to be in signal communication with the robotic surgical system 13865 and the surgical instrument 13890. In other instances, the surgical system 13860 can include additional handheld surgical instruments. The robotic surgical system 13865 includes a robot 13861, which can be similar to the robot 13002, for example. The robotic surgical system 13865 also includes a control unit 13862 and a surgeon's command console, or remote control module, 13864. The surgeon's command console 13864 is configured to receive a clinician input. The control unit 13862 includes a robot display 13868 and a processor 13866. The surgical instrument 13890 includes a display 13894 and a processor 13892.

In various instances, the surgical hub 13870 includes a surgical hub display 13880, which can be similar to the displays of the visualization system 108 (FIG. 1). The surgical hub display 13880 can include, for example, a heads up display. The surgical hub 13880 is configured to detect the presence of the surgical instrument 13890 within a certain distance of the surgical hub 13870. For example, the surgical hub 13870 is configured to detect the presence of all activated surgical instruments 13890 within one operating room, although any suitable distance can be monitored. In various instances, the surgical hub 13870 is configured to display the presence of all activated surgical instruments 13890 on the surgical hub display 13880.

A particular handheld surgical instrument communicates via a first communication process through a first language. A particular robotic surgical system communicates via a second communication process through a second language. In various instances, the first communication process is the same as the second communication process. When the first communication process is the same as the second communication process, the surgical instrument 13890 is configured to directly communicate information to the surgical hub 13870 and/or to the robotic surgical system 13865. Such information includes, for example, a model number and/or type of the surgical instrument, a position of the surgical instrument, an operating status of the surgical instrument, and/or any other relevant parameter of the surgical instrument.

In various instances, the first communication process is different from the second communication process. For example, a surgical system (e.g. a robot) developed by a first manufacturer may utilize a first proprietary language or communication scheme and a surgical system (e g a handheld surgical tool) developed by a second manufacturer may utilize a second, different proprietary language or communication scheme. Despite the language difference/barrier, the surgical hub 13870 and/or surgical robot 13865 is configured to sense surgical instruments 13890 that operate on different communication processes. When the surgical hub 13870 does not recognize the communication process utilized by a particular powered handheld surgical instrument, the surgical hub 13870 is configured to detect various signals, such as Wi-Fi and Bluetooth transmissions emitted by activated powered handheld surgical instruments. Based on the detected signal transmissions, the surgical hub 13870 is configured to alert the clinician of all powered handheld surgical instruments that do not use the same communication process as the robotic surgical system 13865. All data received from newly-detected powered handheld surgical instruments can be stored within the surgical hub 13870 so that the newly-detected powered handheld surgical instruments are recognized by the surgical hub 13870 in the future.

In various instances, the surgical hub 13870 is configured to detect the presence of powered handheld surgical instruments by sensing a magnetic presence of a battery, power usage, and/or electro-magnetic field emitted from activated powered handheld surgical instruments, regardless of whether the activated powered handheld surgical instruments made any attempt to communicate with another surgical instrument, such as the robotic surgical system.

The robot 13861 and the surgical instrument 13890 are exemplified in an example surgical procedure in FIG. 80. In this exemplification, the surgical instrument 13890 is an articulating linear stapler. As depicted in FIG. 80, the surgical instrument 13890 includes a motor 13895 in the handle 13892 thereof. In other instances, the surgical instrument 13890 can include a plurality of motors positioned throughout the surgical instrument. The motor 13895 is configured to emit an electromagnetic field 13896, which can be detected by the robotic surgical system 13865 or the surgical hub 13870. For example, the main robot tower or the modular control tower of the surgical hub 13870 can include a receiver for detecting the electromagnetic fields within the operating room.

In one aspect, a processor of the robotic surgical system (e.g. a processor of the control unit 13862) is configured to calculate a boundary around the surgical instrument 13890. For example, based on the electromagnetic field 13896 and corresponding type of surgical instrument, the processor can determine the dimensions of the surgical instrument 13890 and possible range of positions thereof. For example, when the surgical instrument 13890 includes one or more articulation joints 13891, the range of positions can encompass the articulated positions of the surgical instrument 13890.

In one instance, the robotic surgical system can calculate a first wider boundary $B_2$ around the surgical instrument. When a robotic surgical tool approaches the wider boundary $B_2$, the robotic surgical tool 13861 can issue a notification or warning to the surgeon that the robotic surgical tool attached to the robot 13861 is approaching another surgical instrument 13890. In certain instances, if the surgeon continues to advance the robotic surgical tool toward the surgical instrument 13890 and to a second narrower boundary $B_1$, the robotic surgical system 13865 can stop advancing the robotic surgical tool. For example, if the robotic surgical tool crosses the narrower boundary $B_1$, advancement of the robotic surgical tool can be stopped. In such instances, if the surgeon still desires to continue advancing the robotic surgical tool within the narrower boundary $B_1$, the surgeon can override the hard stop feature of the robotic surgical system 13865.

Referring again to FIG. 79, the surgical system 13860 includes multiple display monitors. Each handheld surgical instrument 13890 and the robotic surgical system 13865 is configured to communicate a video and/or image feed representative of the display on each device to the surgical hub 13870 and/or the hub display 13880. Such video and/or image feeds can include operating parameters of and/or detected conditions by each handheld surgical instrument 13890 and/or the robotic surgical system 13865. The hub 13870 is configured to control the displayed video and/or image feeds on each of the one or more display monitors throughout the system 13800. In various instances, each of the display monitors displays an individual video and/or image feed from a particular surgical device or system. In various instances, the individual video and/or image feed can be overlaid with additional information and/or video and/or image feeds from other devices or systems. Such information can include operating parameters and/or detected conditions. The surgical hub 13870 is configured to request which display monitor displays which video and/or image feed. In other words, the communication link between the surgical hub 13870 and the hub display 13880 allows the surgical hub 13870 to dictate which video and/or image feed is assigned to which display monitor, while direct control of the one or more display monitors remains with the video hub. In various instances, the hub display 13880 is configured to separate one or more of the display monitors from the surgical hub 13870 and allow a different surgical hub or surgical device to display relevant information on the separated display monitors.

In various instances, the surgical hub is configured to communicate stored data with other data systems within an institution data barrier allowing for cooperative utilization of data. Such established data systems may include, for example, an electronic medical records (EMR) database. The surgical hub is configured to utilize the communication between the surgical hub and the EMR database to link overall surgical trends for the hospital with local data sets recorded during use of the surgical hub.

In various instances, the surgical hub is located in a particular operating room at a hospital and/or surgery center. As shown in FIG. 81, the hospital and/or surgery center includes operating rooms, $OR_1$, $OR_2$, $OR_3$, and OR). Three of the operating rooms $OR_2$, $OR_3$, and $OR_4$ shown in FIG. 81 includes a surgical hub 13910, 13920, 13930, respectively, however any suitable number of surgical hubs can be used. Each surgical hub 13910, 13920, 13930 is configured to be in signal communication with one another, represented by signal arrows A. Each surgical hub 13910, 13920, 13930 is also configured to be in signal communication with a primary server 13940, represented by signal arrows B in FIG. 81.

In various exemplifications, as data is communicated between the surgical hub(s) 13910, 13920, 13930 and the various surgical instruments during a surgical procedure, the surgical hub(s) 13910, 13920, 13930 are configured to temporarily store the communicated data. At the end of the surgical procedure and/or at the end of a pre-determined time period, each surgical hub 13910, 13920, 13930 is configured to communicate the stored information to the primary server 13940. Once the stored information is communicated to the primary server 13940, the information can be deleted from the memory of the individual surgical hub 13910, 13920, 13930. The stored information is communicated to the primary server 13940 to alleviate the competition amongst the surgical hubs 13910, 13920, 13930 for bandwidth to transmit the stored data to cloud analytics "C", for example. Instead, the primary server 13940 is configured to compile and store and communicated data. The primary server 13940 is configured to be the single clearinghouse for communication of information back to the individual surgical hubs 13910, 13920, 13930 and/or for external downloading. In addition, as all of the data is stored in one location in the primary server 13940, the data is better protected from data destructive events, such as power surges and/or data intrusion, for example. In various instances, the primary server 13940 includes additional server-level equipment that allows for better data integrity. Examples of cloud systems are further described herein and in U.S. Provisional Patent Application Ser. No. 62/611,340, titled CLOUD- BASED MEDICAL ANALYTICS, filed Dec. 28, 2017, the disclosure of which is herein incorporated by reference in its entirety.

Referring to FIGS. 81 and 82, as data begins to be communicated from each control hub 13910, 13920, 13930 to the primary server 13940, a queue 13990 is created to prioritize the order in which data is communicated. In various instances, the queue 13990 prioritizes data as first in, first out, although any suitable prioritization protocol can be used. In various instances, the queue 13990 is configured to re-prioritize the order in which received data is communicated when priority events and/or abnormal data are detected. As illustrated in FIG. 82, a first surgical hub communicates a first set of data at a time t=1 at block 13960. As the first set of data is the only data in the queue for external output at block 13992, the first set of data is the first to be communicated. Thus, the queue 13990 prioritizes the first set of data for external output at block 13965. A second surgical hub communicates a second set of data at a time t=2 at block 13970. At the time t=2, the first set of data has not been externally communicated at block 13994. However, because no priority events and/or abnormal data are present in the second set of data, the second set of data is the second in line to be externally communicated at block 13975. A third surgical hub communicates a third set of data flagged as urgent at a time t=3 at block 13980. At the time t=3, the first set of data and the second set of data have not been externally communicated, however a priority event has been detected in the third set of data at block 13985. The queue is configured to re-prioritize the sets of data to allow the prioritized third set of data to be in the first position for external output at block 13996 above the first set of data and the second set of data collected at time t=1 and t=2, respectively.

In one aspect, the surgical hub includes a processor and a memory communicatively coupled to the processor, as described herein. The memory stores instructions executable by the processor to detect the presence of a powered surgical instrument and represent the powered surgical instrument on a hub display, as described herein.

In various aspects, the present disclosure provides a control circuit to detect the presence of a powered surgical instrument and represent the powered surgical instrument on a hub display, as described herein. In various aspects, the present disclosure provides a non-transitory computer readable medium storing computer readable instructions which, when executed, cause a machine to detect the presence of a powered surgical instrument and represent the powered surgical instrument on a hub display, as described herein.

Another robotic surgical system is the VERSIUS® robotic surgical system by Cambridge Medical Robots Ltd. of Cambridge, England. An example of such a system is depicted in FIG. 83. Referring to FIG. 83, the surgical robot includes an arm 14400 which extends from a base 14401. The arm 14400 includes a number of rigid limbs 14402 that are coupled together by revolute joints 14403. The most proximal limb 14402a is coupled to the base 14401 by a joint 14403a. The most proximal limb 14402a and the other limbs (e.g. limbs 14402b and 14402c) are coupled in series to further limbs at the joints 14403. A wrist 14404 can be made up of four individual revolute joints. The wrist 14404 couples one limb (e.g. limb 14402b) to the most distal limb (e.g. the limb 14402c in FIG. 83) of the arm 14400. The most distal limb 14402c carries an attachment 14405 for a surgical tool 14406. Each joint 14403 of the arm 14400 has one or more motors 14407, which can be operated to cause rotational motion at the respective joint, and one or more position and/or torque sensors 14408, which provide information regarding the current configuration and/or load at that joint 14403. The motors 14407 can be arranged proximally of the joints 14403 whose motion they drive, so as to improve weight distribution, for example. For clarity, only some of the motors and sensors are shown in FIG. 83. The arm 14400 may be generally as described in Patent Application PCT/GB2014/053523 and International Patent Application Publication No. WO 2015/025140, titled DISTRIBUTOR APPARATUS WITH A PAIR OF INTERMESHING SCREW ROTORS, filed Aug. 18, 2014, which published on Feb. 26, 2015, and which is herein incorporated by reference in its entirety. Torque sensing is further described in U.S. Patent Application Publication No. 2016/0331482, titled TORQUE SENSING IN A SURGICAL ROBOTIC WRIST, filed May 13, 2016, which published on Nov. 17, 2016, which is herein incorporated by reference in its entirety.

The arm 14400 terminates in the attachment 14405 for interfacing with the surgical tool 14406. The attachment 14405 includes a drive assembly for driving articulation of the surgical tool 14406. Movable interface elements of a drive assembly interface mechanically to engage corresponding movable interface elements of the tool interface in order to transfer drive motions from the robot arm 14400 to the surgical tool 14406. One surgical tool may be exchanged for another surgical tool one or more times during a typical operation. The surgical tool 14406 can be attachable and detachable from the robot arm 14400 during the operation. Features of the drive assembly interface and the tool interface can aid in their alignment when brought into engagement with each other, so as to reduce the accuracy with which they need to be aligned by the user. A bar for guiding engagement of a robotic arm and surgical tool is further described in U.S. Patent Application Publication No. 2017/0165012, titled GUIDING ENGAGEMENT OF A ROBOT ARM AND SURGICAL INSTRUMENT, filed Dec. 9, 2016, which published on Jun. 15, 2017, which is herein incorporated by reference in its entirety.

The surgical tool 14406 further includes an end effector for performing an operation. The end effector may take any suitable form. For example, the end effector may include smooth jaws, serrated jaws, a gripper, a pair of shears, a needle for suturing, a camera, a laser, a knife, a stapler, one or more electrodes, an ultrasonic blade, a cauterizer, and/or a suctioner. Alternative end effectors are further described herein. The surgical tool 14406 can include an articulation junction between the shaft and the end effector, which can permit the end effector to move relative to the shaft of the tool. The joints in the articulation junction can be actuated by driving elements, such as pulley cables. Pulley arrangements for articulating the surgical tool 14406 are described in U.S. Patent Application Publication No. 2017/0172553, titled PULLEY ARRANGEMENT FOR ARTICULATING A SURGICAL INSTRUMENT, filed Dec. 9, 2016, which published on Jun. 22, 2017, which is herein incorporated by reference in its entirety. The driving elements for articulating the surgical tool 14406 are secured to the interface elements of the tool interface. Thus, the robot arm 14400 can transfer drive motions to the end effector as follows: movement of a drive assembly interface element moves a tool interface element, which moves a driving element in the tool 14406, which moves a joint of the articulation junction, which moves the end effector. Control of a robotic arm and tool, such as the arm 14400 and the tool 14406, are further described in U.S. Patent Application Publication No. 2016/0331482, titled TORQUE SENSING IN A SURGICAL ROBOTIC WRIST, filed May 13, 2016 and which was published on Nov. 17, 2016, and in International Patent Application Publication No. WO 2016/116753, titled ROBOT TOOL RETRACTION, filed Jan. 21, 2016 and which was published on Jul. 28, 2016, each of which is herein incorporated by reference in its entirety.

Controllers for the motors 14407 and the sensors 14408 (e.g. torque sensors and encoders) are distributed within the robot arm 14400. The controllers are connected via a communication bus to a control unit 14409. Examples of communication paths in a robotic arm, such as the arm 14400, are further described in U.S. Patent Application Publication No. 2017/0021507, titled DRIVE MECHANISMS FOR ROBOT ARMS and in U.S. Patent Application Publication No. 2017/0021508, titled GEAR PACKAGING FOR ROBOTIC ARMS, each of which was filed Jul. 22, 2016 and published on Jan. 26, 2017, and each of which is herein incorporated by reference in its entirety. The control unit 14409 includes a processor 14410 and a memory 14411. The memory 14411 can store software in a non-transient way that is executable by the processor 14410 to control the operation of the motors 14407 to cause the arm 14400 to operate in the manner described herein. In particular, the software can control the processor 14410 to cause the motors 14407 (for example via distributed controllers) to drive in dependence on inputs from the sensors 14408 and from a surgeon command interface 14412.

The control unit 14409 is coupled to the motors 14407 for driving them in accordance with outputs generated by execution of the software. The control unit 14409 is coupled to the sensors 14408 for receiving sensed input from the sensors 14408, and to the command interface 14412 for receiving input from it. The respective couplings may, for example, each be electrical or optical cables, and/or may be provided by a wireless connection. The command interface 14412 includes one or more input devices whereby a user can request motion of the end effector in a desired way. The input devices could, for example, be manually operable mechanical input devices such as control handles or joysticks, or contactless input devices such as optical gesture sensors. The software stored in the memory 14411 is configured to respond to those inputs and cause the joints of the arm 14400 and the tool 14406 to move accordingly, in compliance with a pre-determined control strategy. The control strategy may include safety features which moderate the motion of the arm 144400 and the tool 14406 in response to command inputs. In summary, a surgeon at the command interface 14412 can control the surgical tool 14406 to move in such a way as to perform a desired surgical procedure. The control unit 14409 and/or the command interface 14412 may be remote from the arm 14400.

Additional features and operations of a surgical robot system, such as the robotic surgical system depicted in FIG. 83, are further described in the following references, each of which is herein incorporated by reference in its entirety:

International Patent Application Publication No. WO 2016/116753, titled ROBOT TOOL RETRACTION, filed Jan. 21, 2016, which published on Jul. 28, 2016;

U.S. Patent Application Publication No. 2016/0331482, titled TORQUE SENSING IN A SURGICAL ROBOTIC WRIST, filed May 13, 2016, which published on Nov. 17, 2016;

U.S. Patent Application Publication No. 2017/0021507, titled DRIVE MECHANISMS FOR ROBOT ARMS, filed Jul. 22, 2016, which published on Jan. 27, 2017;

U.S. Patent Application Publication No. 2017/0021508, titled GEAR PACKAGING FOR ROBOTIC ARMS, filed Jul. 22, 2016, which published on Jan. 27, 2017;

U.S. Patent Application Publication No. 2017/0165012, titled GUIDING ENGAGEMENT OF A ROBOT ARM AND SURGICAL INSTRUMENT, filed Dec. 9, 2016, which published on Jun. 15, 2017; and U.S. Patent Application Publication No. 2017/0172553, titled PULLEY ARRANGEMENT FOR ARTICULATING A SURGICAL INSTRUMENT, filed Dec. 9, 2016, which published on Jun. 22, 2017.

In one instance, the robotic surgical systems and features disclosed herein can be employed with the VERSIUS® robotic surgical system and/or the robotic surgical system of FIG. 83. The reader will further appreciate that various systems and/or features disclosed herein can also be employed with alternative surgical systems including the computer-implemented interactive surgical system 100, the computer-implemented interactive surgical system 200, the robotic surgical system 110, the robotic hub 122, the robotic hub 222, and/or the robotic surgical system 15000, for example.

In various instances, a robotic surgical system can include a robotic control tower, which can house the control unit of the system. For example, the control unit 14409 of the robotic surgical system depicted in FIG. 83 can be housed within a robotic control tower. The robotic control tower can include a robot hub such as the robotic hub 122 (FIG. 2) or the robotic hub 222 (FIG. 9), for example. Such a robotic hub can include a modular interface for coupling with one or more generators, such as an ultrasonic generator and/or a radio frequency generator, and/or one or more modules, such as an imaging module, a suction module, an irrigation module, a smoke evacuation module, and/or a communication module, for example.

The reader will readily appreciate that the computer-implemented interactive surgical system 100 (FIG. 1) and the computer-implemented interactive surgical system 200 (FIG. 9) disclosed herein can incorporate the robotic arm 14400. Additionally or alternatively, the robotic surgical system depicted in FIG. 83 can include various features and/or components of the computer-implemented interactive surgical systems 100 and 200.

A robotic hub can include a situational awareness module, which can be configured to synthesize data from multiple sources to determine an appropriate response to a surgical event. For example, a situational awareness module can determine the type of surgical procedure, step in the surgical procedure, type of tissue, and/or tissue characteristics, as further described herein. Moreover, such a module can recommend a particular course of action or possible choices to the robotic system based on the synthesized data. In various instances, a sensor system encompassing a plurality of sensors distributed throughout the robotic system can provide data, images, and/or other information to the situational awareness module. Such a situational awareness module can be incorporated into a control unit, such as the control unit 14409, for example. In various instances, the situational awareness module can obtain data and/or information from a non-robotic surgical hub and/or a cloud, such as the surgical hub 106, the surgical hub 206, the cloud 104, and/or the cloud 204, for example. Situational awareness of a surgical system is further disclosed herein and in U.S. Provisional Patent Application Ser. No. 62/611,341, titled INTERACTIVE SURGICAL PLATFORM, filed Dec. 28, 2017, and in U.S. Provisional Patent Application Ser. No. 62/611,340, titled CLOUD-BASED MEDICAL ANALYTICS, filed Dec. 28, 2017, the disclosure of each of which is herein incorporated by reference in its entirety.

Referring again to FIG. 83, the robotic arm 14400 does not include a linear slide mechanism for moving the attached surgical tool 14406 along a longitudinal axis of the tool 14406. Rather, the limbs 14402 of the arm 14400 are configured to rotate about the various joints 14403 of the arm 14400 to move the surgical tool 14406. In other words, even movement of the surgical tool 14406 along the longitudinal axis $A_T$ thereof requires the articulation of various limbs 14402. For example, to move the surgical tool 14406 along the longitudinal axis $A_T$, the robotic arm 14400 would move at multiple revolute joints 14403 thereof. In effect, linear displacement of the tool 14406 for extending the end effector through a trocar, retracting the end effector from the trocar, and/or for localized displacements of the surgical tool 14406 along the longitudinal axis $A_T$, such as during a suturing process, for example, would require the actuation of multiple revolute joints 14403 and the corresponding movement of multiple rigid limb portions 14402 of the arm 14400.

In instances in which a robotic surgical system lacks a linear slide mechanism, as described herein, intelligent sensing systems, additional communication paths, and/or interactive displays can enable more precise control of the robotic arm including the implementation of control motions that involve a linear displacement of the surgical tool along an axis thereof. For example, to ensure the accurate positioning of the tool 14406 and to avoid inadvertent collisions within an operating room, it may be desirable to include additional systems in the robotic system for determining the position of a surgical tool 14406 and/or portions of the robotic arm 14400, for repositioning of the robotic arm 14400 from within the sterile field, for communicating the position of the surgical tool 14406 relative to the surgical site, for visualizing the surgical tool 14406 at the surgical site, and/or for manipulating the surgical tool 14406 around the surgical site, for example.

In one aspect, a robotic surgical system can include a primary control mechanism for positioning the tool and a secondary means for directly and/or independently measuring the position of the tool. In one aspect, a redundant or secondary sensing system can be configured to determine and/or verify a position of a robotic arm and/or a surgical tool attached to the robotic arm. The secondary sensing system can be independent of a primary sensing system.

In one instance, the primary control mechanism can rely on closed-loop feedback to calculate the position of the tool. For example, a control unit of a robotic surgical system can issue control motions for the robotic arm, including the various motors and/or drivers thereof to move portions of the robotic arm in a three-dimensional space, as further described herein. Such a control unit can determine the position and/or orientation of the portions of the robotic arm based on torque sensors on the motors and/or displacement sensors on the drivers, for example. In such instances, the position of the surgical tool, the end effector, and/or components thereof can be determined by proximally-located sensors. The proximally-located sensors can be located in a proximal housing or mounting portion of the tool and/or the robotic arm. In one instance, such proximally-located sensors can be positioned outside the sterile field, for example. The position of a surgical tool mounted to a robotic arm can be determined by measuring the angle(s) of each joint of the arm, for example. The control unit and sensors in communication therewith, which determine the position of the arm based on the control motions delivered thereto, can be considered a primary or first sensing system of the robotic surgical system.

In addition to a primary sensing system, as described herein, a redundant or secondary sensing system can be employed by the robotic surgical system. The secondary sensing system can include one or more distally-located sensors. The distally-located sensors can be positioned within the sterile field and/or on the end effector, for example. The distally-located sensors are distal to the proximally-located sensors of the primary sensing system, for example. In one instance, the distally-located sensors can be "local" sensors because they are local to the sterile field and/or the surgical site, and the proximally-located sensors can be "remote" sensors because they are remote from the sterile field and/or the surgical site.

Referring now to FIG. 91, portions of a robotic surgical system 14300 are schematically depicted. The robotic surgical system 14300 is similar in many respects to the robotic surgical system of FIG. 83. For example, the robotic surgical system 14300 includes a plurality of movable components 14302. In one aspect, the movable components 14302 are rigid limbs that are mechanically coupled in series at revolute joints. Such moveable components 14302 can form a robotic arm, similar to the robotic arm 14440 (FIG. 83), for example. The distal-most component 14302 includes an attachment for releasably attaching interchangeable surgical tools, such as the surgical tool 14306, for example. Each component 14302 of the robotic arm has one or more motors 14307 and motor drivers 14314, which can be operated to affect rotational motion at the respective joint.

Each component 14302 includes one or more sensors 14308, which can be position sensors and/or torque sensors, for example. The sensors 14308 can provide information regarding the current configuration and/or load at the respective joint between the components 14402. The motors 14307 can be controlled by a control unit 14309, which is configured to receive inputs from the sensors 14308 and/or from a surgical command interface, such as surgical command interface 14412 (FIG. 83), for example.

A primary sensing system 14310 is incorporated into the control unit 14309. In one aspect, the primary sensing system 14310 can be configured to detect the position of one or more components 14302. For example, the primary sensing system 14310 can include the sensors 14308 for the motors 14307 and/or the drivers 14314. Such sensors 14308 are remote from the patient P and located outside of the sterile field. Though located outside of the sterile field, the primary sensing system 14310 can be configured to detect the position(s) of the component(s) 14302 and/or the tool 14306 within the sterile field, such as at the position of the distal end of the robotic arm and/or the attachment portion thereof. Based on the position of the robotic arm and components 14302 thereof, the control unit 14309 can extrapolate the position of the surgical tool 14306, for example.

The robotic surgical system 14300 of FIG. 91 also includes a secondary sensing system 14312 for directly tracking the position and/or orientation or various parts of the robotic surgical system 14300 and/or parts of an associated, non-robotic system such as handheld surgical instruments 14350. Referring still to FIG. 91, the secondary sensing system 14312 includes a magnetic field emitter 14320 that is configured to emit a magnetic field in the vicinity of one or more magnetic sensors to detect the positions thereof. Components 14302 of the robotic arm include magnetic sensors 14322, which can be utilized to determine and/or verify the position of the respective components 14302. The magnetic sensors 14322 are remote to the motors 14307 and the drivers 14308, for example. In any event, the torque through the motor and/or the displacement of a driver may not affect the output from the magnetic sensors. Consequently, the sensing systems are independent.

In certain instances, the magnetic sensors 14322 can be positioned within the sterile field. For example, the surgical tool 14306 can include the magnetic sensor 14324, which can be utilized to determine and/or verify the position of the surgical tool 14306 attached to the robotic arm and/or to determine and/or verify the position of a component of the surgical tool 14306, such as a firing element, for example. Additionally or alternatively, one or more patient sensors 14326 can be positioned within the patient P to measure the patient's location and/or anatomic orientation. Additionally or alternatively, one or more trocar sensors 14328 can be positioned on a trocar 14330 to measure the trocar's location and/or orientation, for example.

Referring again to the robotic arm 14400 depicted in FIG. 83, the surgical tool 14406 is attached to the attachment portion 14405 at the distal end of the robotic arm 14400. When the surgical tool 14406 is positioned within a trocar, the robotic surgical system can establish a virtual pivot which can be fixed by the robotic surgical system, such that the arm 14400 and/or the surgical tool 14406 can be manipulated thereabout to avoid and/or minimize the application of lateral forces to the trocar. In certain instances, applying force(s) to the trocar may damage the surrounding tissue, for example. Thus, to avoid inadvertent damage to tissue, the robotic arm 14400 and/or the surgical tool 14406 can be configured to move about the virtual pivot of the trocar without upsetting the position thereof and, thus, without upsetting the corresponding position of the trocar. Even when applying a linear displacement of the surgical tool 14406 to enter or exit the trocar, the virtual pivot can remain undisturbed.

In one aspect, the trocar sensor(s) 14328 in FIG. 91A can be positioned at a virtual pivot 14332 on the trocar 14330. In other instances, the trocar sensors 14328 can be adjacent to the virtual pivot 14332. Placement of the trocar sensors 14328 at and/or adjacent to the virtual pivot 14332 thereof can track the position of the trocar 14330 and virtual pivot 14332 and help to ensure that the trocar 14330 does not move during displacement of the surgical tool 14306, for example. In such instances, without physically engaging or holding the trocar 14330, the robotic surgical system 14300 can confirm and/or maintain the location of the trocar 14330. For example, the secondary sensing system 14312 can confirm the location of the virtual pivot 14332 of the trocar 14330 and the surgical tool 14306 relative thereto.

Additionally or alternatively, one or more sensors 14352 can be positioned on one or more handheld surgical instruments 14350, which can be employed during a surgical procedure in combination with the surgical tools 14306 utilized by the robotic surgical system 14300.

The secondary sensing system 14312 is configured to detect the position and/or orientation of one or more handheld surgical instruments 14350 within the surgical field, for example, within the operating room and/or sterile field. Such handheld surgical instruments 14350 can include autonomous control units, which may not be robotically controlled, for example. As depicted in FIG. 91, the handheld surgical instruments 14350 can include sensors 14352, which can be detected by the magnetic field emitter 14320, for example, such that the position and/or location of the handheld surgical instruments 14350 can be ascertained by the robotic surgical system 14300. In other instances, components of the handheld surgical instruments 14350 can provide a detectable output. For example, a motor and/or battery pack can be detectable by a sensor in the operating room.

In one aspect, the magnetic field emitter 14320 can be incorporated into a main robot tower. The sensors 14322, 14324, 14326, 14328, and/or 14352 within the sterile field can reflect the magnetic field back to the main robot tower to identity the positions thereof. In various instances, data from the magnetic field emitter 14320 can be communicated to a display 14340, such that the position of the various components of the surgical robot, surgical tool 14302, trocar 14330, patient P, and/or handheld surgical instruments 14350 can be overlaid onto a real-time view of the surgical site, such as views obtained by an endoscope at the surgical site. For example, the display 14340 can be in signal communication with the control unit of the robotic surgical system and/or with a robotic hub, such as the hub 106, robotic hub 122, the hub 206, and/or the robot hub 222 (FIG. 9), for example.

In other instances, the magnetic field emitter 14320 can be external to the robot control tower. For example, the magnetic field emitter 14320 can be incorporated into a hub.

Similar to the secondary sensing system 14312, which includes the magnetic field emitter 14320, in certain instances, time-of-flight sensors can be positioned on one or more of the robot component(s) 14302, the surgical tool(s) 14306, the patient P, the trocar(s) 14328, and/or the handheld surgical instrument(s) 14350 to provide an array of distances between the emitter and the reflector points. Such time-of-flight sensors can provide primary or secondary (e.g. redundant) sensing of the position of the robot component(s) 14302, the surgical tool(s) 14306, the patient P, the trocar(s) 14328, and/or the handheld surgical instrument(s) 14350, for example. In one instance, the time-of-flight sensor(s) can employ an infrared light pulse to provide distance mapping and/or facilitate 3D imaging within the sterile field.

In one instance, the secondary sensing system 14312 can include a redundant sensing system that is configured to confirm the position of the robotic components and/or tools. Additionally or alternatively, the secondary sensing system 14312 can be used to calibrate the primary sensing system 14310. Additionally or alternatively, the secondary sensing system 14312 can be configured to prevent inadvertent entanglement and/or collisions between robotic arms and/or components of a robotic surgical system.

Referring again to FIG. 91, in one instance, the components 14302 of the robotic surgical system 14300 can correspond to discrete robotic arms, such as the robotic arms 15024 in the robotic surgical system 15000 (FIG. 22) and/or the robotic arms depicted in FIG. 2, for example. The secondary sensing system 14312 can be configured to detect the position of the robotic arms and/or portions thereof as the multiple arms are manipulated around the surgical theater. In certain instances, as one or more arms are commanded to move towards a potential collision, the secondary sensing system 14312 can alert the surgeon via an alarm and/or an indication at the surgeon's console in order to prevent an inadvertent collision of the arms.

Referring now to FIG. 92, a flow chart for a robotic surgical system is depicted. The flow chart can be utilized by the robotic surgical system 14300 (FIG. 91), for example. In various instances, two independent sensing systems can be configured to detect the location and/or orientation of a surgical component, such as a portion of a robotic arm and/or a surgical tool. The first sensing system, or primary sensing system, can rely on the torque and/or load sensors on the motors and/or motor drivers of the robotic arm. The second sensing system, or secondary sensing system, can rely on magnetic and/or time-of-flight sensors on the robotic arm and/or surgical tool. The first and second sensing systems are configured to operate independently and in parallel. For example, at step 14502, the first sensing system determines the location and orientation of a robotic component and, at step 14504, communicates the detected location and orientation to a control unit. Concurrently, at step 14506, the second sensing system determines the location and orientation of the robotic component and, at step 14508, communicates the detected location and orientation to the control unit.

The independently-ascertained locations and orientations of the robotic component are communicated to a central control unit at step 14510, such as to the robotic control unit 14309 and/or a surgical hub. Upon comparing the locations and/or orientations, the control motions for the robotic component can be optimized at step 14512. For example, discrepancies between the independently-determined positions can be used to improve the accuracy and precision of control motions. In certain instances, the control unit can calibrate the control motions based on the feedback from the secondary sensing system. The data from the primary and secondary sensing systems can be aggregated by a hub, such as the hub 106 or the hub 206, for example, and/or data stored in a cloud, such as the cloud 104 or the cloud 204, for example, to further optimize the control motions of the robotic surgical system.

In certain instances, the robotic system 14300 can be in signal communication with a hub, such as the hub 106 of the hub 206, for example. The hubs 106, 206 can include a situational awareness module, as further described herein. In one aspect, at least one of the first sensor system 14310 and the second sensor system 14312 are data sources for the situational awareness module. For example, the sensor systems 14310 and 14312 can provide position data to the situational awareness module. Further, the hub 106, 206 can be configured to optimize and/or calibrate the control motions of the robotic arm 14300 and/or the surgical tool 14306 based on the data from the sensor systems in combination with the situational awareness, for example. In one aspect, a sensing system, such as the secondary sensing system 14312 can inform the hub 106, 206 and situational awareness module thereof when a handheld surgical instrument 14350 has entered the operating room or surgical theater and/or when an end effector has been fired, for example. Based on such information, the hub 106, 206 can determine and/or confirm the particular surgical procedure and/or step thereof.

The reader will appreciate that various independent and redundant sensing systems disclosed herein can be utilized by a robotic surgical system to improve the accuracy of the control motions, especially when moving the surgical tool along a longitudinal axis without relying on a linear slide mechanism, for example.

In one aspect, the surgical hub includes a processor and a memory communicatively coupled to the processor, as described herein. The memory stores instructions executable by the processor to detect a position of a robotically-controlled component independent of a primary sensing system, as described above.

In various aspects, the present disclosure provides a control circuit configured to detect a position of a robotically-controlled component independent of a primary sensing system, as described above. In various aspects, the present disclosure provides a non-transitory computer readable medium storing computer readable instructions which, when executed, cause a machine to detect a position of a robotically-controlled component independent of a primary sensing system, as described above.

In one aspect, a robotic surgical system can be configured to wirelessly communicate with one or more intelligent surgical tools mounted to a robotic arm thereof. The control unit of the robotic system can communicate with the one or more intelligent surgical tools via a wireless connection, for example. Additionally or alternatively, the robotic surgical system can include a robotic hub, which can wirelessly communicate with the intelligent surgical tool(s) mounted to the robotic arm(s). In still other instances, a non-robotic surgical hub can wirelessly communicate with the intelligent surgical tool(s) mounted to a robotic arm. In certain instances, information and/or commands can be provided to the intelligent surgical tool(s) from the control unit via the wireless connection. For example, certain functions of a surgical tool can be controlled via data received through a wireless communication link on the surgical tool. Similarly, in one aspect, closed-loop feedback can be provided to the robotic surgical system via data received via the wireless communication link to the surgical tool.

Referring primarily to FIGS. 88-90, a surgical tool 14206 is mounted to a robotic arm 14000 of a surgical robot. The robotic arm 14000 is similar in many respects to the robotic arm 14400 in FIG. 83. For example, the arm 14000 includes a plurality of movable components 14002. In one aspect, the movable components 14002 are rigid limbs that are mechanically coupled in series at revolute joints 14003. Such moveable components 14002 form the robotic arm 14400, similar to the arm 14400 (FIG. 83), for example. A distal-most component 14002*c* of the robotic arm 14400 includes an attachment 14005 for releasably attaching interchangeable surgical tools, such as the surgical tool 14206. Each component 14002 of the arm 14000 has one or more motors and motor drivers, which can be operated to affect rotational motion at the respective joint 14003.

Each component 14002 includes one or more sensors, which can be position sensors and/or torque sensors, for example, and can provide information regarding the current configuration and/or load at the respective joint between the components 14002. The motors can be controlled by a control unit, such as the control unit 14409 (FIG. 83), which is configured to receive inputs from the sensors 14008 and/or from a command interface, such as the surgeon's command console 14412 (FIG. 83), for example.

The surgical tool 14206 is a linear stapler including a wireless communication module 14208 (FIG. 89). The linear stapler can be an intelligent linear stapler and can include an intelligent fastener cartridge, an intelligent end effector, and/or an intelligent shaft, for example. Intelligent surgical components can be configured to determine various tissue properties, for example. In one instance, one or more advanced end effector functions may be implemented based on the detected tissue properties. A surgical end effector can include one or more sensors for determining tissue thickness, compression, and/or impedance, for example. Moreover, certain sensed parameters can indicate tissue variations, such as the location of a tumor, for example. Intelligent surgical devices for sensing various tissue properties are further disclosed the following references:

U.S. Pat. No. 9,757,128, filed Sep. 5, 2014, titled MULTIPLE SENSORS WITH ONE SENSOR AFFECTING A SECOND SENSOR'S OUTPUT OR INTERPRETATION, which issued on Sep. 12, 2017;

U.S. patent application Ser. No. 14/640,935, titled OVERLAID MULTI SENSOR RADIO FREQUENCY (RF) ELECTRODE SYSTEM TO MEASURE TISSUE COMPRESSION, filed Mar. 6, 2015, now U.S. Patent Application Publication No. 2016/0256071, which published on Sep. 8, 2016;

U.S. patent application Ser. No. 15/382,238, titled MODULAR BATTERY POWERED HANDHELD SURGICAL INSTRUMENT WITH SELECTIVE APPLICATION OF ENERGY BASED ON TISSUE CHARACTERIZATION, filed Dec. 16, 2016, now U.S. Patent Application Publication No. 2017/0202591, which published on Jul. 20, 2017; and U.S. patent application Ser. No. 15/237,753, titled CONTROL OF ADVANCEMENT RATE AND APPLICATION FORCE BASED ON MEASURED FORCES, filed Aug. 16, 2016, now U.S. Patent Application Publication No. 2018/0049822, which published on Feb. 22, 2018;

each of which is herein incorporated by reference in its entirety.

As depicted in FIG. 88, a wireless communication link 14210 is provided between the surgical tool 14206 and a hub 14212. The hub 14212 is a surgical hub, like the hub 106 or the hub 206, for example. In other instances, the hub 14212 can be a robotic hub, like the robotic hub 122 or the robotic hub 222, for example. In FIG. 88, the wireless communication module 14208 includes a wireless signal transmitter that is located near the distal end of the end effector of the surgical tool 14206. In other instances, the wireless transmitter can be positioned on a proximal portion of the end effector or on the shaft of the surgical tool 14206.

The wireless communication link 14212 between the surgical tool 14206 and the surgical hub 14212 provides real-time data transfer through a sterile barrier 14230. Additionally or alternatively, the wireless communication module 14208 can be configured to communicate with a robot control tower and/or the control unit, which issues the control motions to the robotic arm 14000 and actuations to the surgical tool 14206 based on inputs at the surgeon's command console. In certain instances, the control unit for the robotic arm 14000 can be incorporated into the surgical hub 14212 and/or a robotic hub, such as the robotic hub 122 (FIG. 2) or the robotic hub 222 (FIG. 9), for example.

In certain instances, it can be difficult to confirm the position of the surgical tool 14206 within the surgical theater, around the surgical site, and/or relative to the targeted tissue. For example, lateral displacement of the surgical tool 14206 can be constrained by a physical boundary, such as a longitudinally-extending trocar, for example. In such instances, lateral displacement of the surgical tool 14206 can be determined by a resistance force from and/or on the trocar. Conversely, linear displacement of the surgical tool 14206 can be unconstrained by physical boundaries of the surgical system. In such instances, when the control unit directs linear displacement of the surgical tool 14206 or a portion thereof, and the various movable links 14002 and joints 14003 articulate to affect the linear displacement, it can be difficult to determine and/or confirm the position of the surgical tool 14206 and respective portions thereof.

When the surgical tool 14206 is moved along the longitudinal axis of the tool $A_T$ (FIG. 89), which is collinear with the shaft of the surgical tool 14206, it can be difficult to determine and/or confirm the exact position of the surgical tool 14206. In certain instances, as provided herein, the robotic surgical system can include a secondary sensing system, which is configured to detect the position of the surgical tool 14206. For example, the wireless communication module 14208 can be in signal communication with a secondary sensing system, such as the secondary sensing system 14312 (FIG. 91) and/or a sensor thereof. Moreover, the wireless communication module 14208 can communicate the position of the surgical tool 14206, as detected by the secondary sensing system 14312, to the surgical hub 14212 via the wireless communication link 14210. Additionally or alternatively, the wireless communication module 14208 can communicate information from the various sensors and/or systems of the intelligent surgical tool 14206 to the surgical hub 14212. The surgical hub 14212 can disseminate the information to displays within the operating room or external displays, to a cloud, and/or to one or more hubs and/or control units used in connection with the surgical procedure.

Referring primarily to FIG. 89, in one instance, the surgical tool 14206 can be employed to remove a cancerous tumor 14242 from patient tissue T. To ensure complete removal of the tumor 14242 while minimizing the removal of healthy tissue, a predefined margin zone 14240 can be defined around the tumor 14242. The margin zone can be determined by the surgeon based on patient data, aggregated data from a hub and/or a cloud, and/or data sensed by one or more intelligent components of the surgical system, for example. During the operation, the surgical tool 14206 can transect the tissue T along the margin zone 14240 such that the margin zone 14240 is removed along with the tumor 14242. The primary and secondary sensing systems 14310 and 14312 (FIG. 91) can determine the position of the surgical tool 14206 relative to the margin zone, for example. Moreover, the wireless communication module 14208 can communicate the detected position(s) to the control unit.

In certain instances, the robotic system of FIGS. 89 and 90 can be configured to actuate (e.g. fire) the surgical tool 14206 when the surgical tool 14206 moves within the margin zone 14240. For example, referring primarily to FIG. 90, a graphical display 14250 of distance and force-to-close over time for the linear stapler 14206 during the surgical procedure of FIG. 88 is depicted. As the surgical tool 14206 approaches the margin zone 14240 at time $t_1$, the force-to-close (FTC) increases indicating that the surgical tool 14206 is being clamped on tissue T around the tumor 14242 between time $t_1$ and time $t_2$. More specifically, the surgical tool 14206 is clamped when moved into position a distance between distances $D_1$ and $D_2$. The distance $D_1$ can refer to the outer boundary of the margin zone 14240 around the tumor 14242, for example, and the distance $D_2$ can refer to the inner boundary of the margin zone 14240, which can be assumed boundary of the tumor 14242, for example.

In various instances, the control unit and the processor thereof can automatically affect the clamping motion when the surgical tool 14206 is positioned at the appropriate distance based on input from a primary sensing system and/or a secondary sensing system. In other instances, the control unit and the processor thereof can automatically alert the surgeon that the surgical tool 14206 is positioned at the appropriate distance. Similarly, in certain instances, the processor can automatically fire the surgical tool 14206 and/or suggest to the surgeon that the surgical tool 14206 be fired based on the detected position(s) of the surgical tool 14206. The reader will readily appreciate that other actuation motions are envisioned, such as energizing an energy tool and/or articulating and articulatable end effector, for example.

In certain instances, the hub 14212 can include a situational awareness system, as further described herein. In one aspect, the position of the tumor 14242 and/or the margin zone 14240 therearound can be determined by the situational awareness system or module of the hub 14212. In certain instances, the wireless communication module 14208 can be in signal communication with the situational awareness module of the hub 14212. For example, referring again to FIG. 56, the stapler data and/or the cartridge data provided at steps 5220 and 5222 can be provided via the wireless communication module 14208 of the stapling tool 14206, for example.

In one aspect, sensors positioned on the surgical tool 14206 can be utilized to determine and/or confirm the position of the surgical tool 14206 (i.e. a secondary sensing system). Moreover, the detected position of the linear stapler can be communicated to the surgical hub 14212 across the wireless communication link 14210, as further described herein. In such instances, the surgical hub 14212 can obtain real-time, or near real-time, information regarding the position of the surgical tool 14206 relative to the tumor 14242 and the margin zone 14240 based on the data communicated via the wireless communication link 14230. In various instances, the robotic surgical system can also determine the position of the surgical tool 14206 based on the motor control algorithms utilized to position the robotic arm 14000 around the surgical theater (i.e. a primary sensing system).

In one aspect, a robotic surgical system can integrate with an imaging system. Real-time feeds from the surgical site, which are obtained by the imaging system, can be communicated to the robotic surgical system. For example, referring again to FIGS. 2 and 3, real-time feeds from the imaging module 138 in the hub 106 can be communicated to the robotic surgical system 110. For example, the real-time feeds can be communicated to the robotic hub 122. In various instances, the real-time feed can be overlaid onto one or more active robot displays, such as the feeds at the surgeon's command console 118. Overlaid images can be provided to one or more displays within the surgical theater, such as the displays 107, 109, and 119, for example.

In certain instances, the overlay of real-time feeds onto a robot display can enable the surgical tools to be precisely controlled within an axes system that is defined by the surgical tool and/or the end effector(s) thereof as visualized by the real-time imaging system. In various instances, cooperating between the robotic surgical system 110 and the imaging system 138 can provide triangulation and instrument mapping of the surgical tools within the visualization field, which can enable precise control of the tool angles and/or advancements thereof. Moreover, shifting control from a standard multi-axes, fixed Cartesian coordinate system to the axis defined by the currently-mounted tool and/or to the end effector thereof can enable the surgeon to issue commands along clear planes and/or axes. For example, a processor of the robotic surgical system can direct a displacement of a surgical tool along the axis of the elongate shaft of the surgical tool or a rotation of the surgical tool at a specific angle from the current position based on a selected point to rotate about. In one exemplification, the overlaid feed of a surgical tool can incorporate a secondary or redundant sensing system, as further described herein, to determine the location and/or orientation of the surgical tool.

In certain instances, a robotic arm, such as the robotic arm 14400 (FIG. 83) can be significantly heavy. For example, the weight of a robotic arm can be such that manually lifting or repositioning the robotic arm is difficult for most able-bodied clinicians. Moreover, the motors and drive mechanisms of the robotic arm may only be controlled by a primary control system located at the control unit based on inputs from the surgeon's command console. Stated differently, a robotic surgical system, such as the system depicted in FIG. 83, for example, may not include a secondary control system for the robotic arm 14400 that is local to the robotic arm 14400 and within the sterile field.

A robotic arm in a robotic surgical system may be prone to inadvertent collisions with equipment and/or people within the sterile field. For example, during a surgical procedure, surgeon(s), nurse(s), and/or medical assistant(s) positioned within the sterile field may move around the sterile field and/or around the robotic arms. In certain instances, the surgeon(s), nurse(s), and/or medical assistant (s), for example, may reposition equipment within the sterile field, such as tables and/or carts, for example. When a surgeon positioned outside of the sterile field is controlling the robotic arm, another surgeon, nurse, and/or medical assistant positioned within the sterile field may also want to manually move and/or adjust the position of one of more robotic arms in order to avoid a potential collision with the arm(s), entanglement of the arm with other equipment and/or other arms, and/or to replace, reload, and/or reconfigure a surgical tool mounted to the arm. However, to reposition the robotic arm, the surgeon may need to power down the robotic surgical system to enable the clinician within the sterile field to manually reposition the robotic arm. In such instances, the clinician can be required to carry the significant weight of the unpowered, or powered down, robotic arm.

In one instance, a robotic surgical system can include an interactive display that is local to the sterile field and/or local to the robotic arm(s). Such a local display can facilitate manipulation and/or positioning of the arm(s) by a clinician within the sterile field. Stated differently, an operator other than the surgeon at the command console can control the position of the robotic arm(s).

Referring now to FIG. 84, a clinician is applying a force to the robotic arm 14000 to manually adjust the position of the robotic arm 14000. In certain instances, the robotic surgical system employing the robotic arm 14000 can employ a passive power assist mode, in which the robotic arm 14400 can easily be repositioned by a clinician within the sterile field. For example, though the robotic arm 14000 is powered and is controlled by a remote control unit, the clinician can manually adjust the position of the robotic arm 14000 without requiring the clinician to carry the entire weight of the robotic arm 14000. The clinician can pull and/or push the robotic arm 14000 to adjust the position thereof. In the passive power assist mode, the power to the robotic arm 14000 can be constrained and/or limited to permit the passive repositioning by the clinician.

Referring now to FIG. 85, a graphical display 14050 of force over time of the robotic arm 14000 (FIG. 84) in a passive power assist mode is depicted. In the passive power assist mode, a clinician can apply a manual force to the robotic arm 14000 to initiate the repositioning of the robotic arm 14000. The clinician can be within the sterile field. In certain instances, the passive power assist mode can be activated when the robotic arm 14000 senses a manual manipulation.

As depicted in FIG. 85, the manual force exerted by a clinician can increase to exceed a predefined threshold, such as the 15-lb limit indicated in FIG. 85, for example, to affect repositioning of the robotic arm 14000. In certain instances, the predefined threshold can correspond to the maximum force an able-bodied assist can easily exert on the robotic arm 14000 without undue stress or strain. In other instances, the predefined threshold can correspond to a minimum threshold force on the robotic arm 14000 in order to avoid providing a powered assist to unintentional or inadvertent contacts with the robotic arm 14000.

When the user exerts a force on the robotic arm 14000 above the predefined threshold, one or more motors (e.g. motors 14407 in FIG. 83) of the robotic surgical system can apply an assisting force to the robotic arm 14000 to help reposition the robotic arm 14000 in the direction indicated by the operator's force on the robotic arm 14000. In such instances, the operator can easily manipulate the position of the arm to avoid inadvertent collisions and/or entanglements and, when the operator's force exceeds a comfortable threshold force, the motors can assist or cooperate in the repositioning of the arm. The passive power assist provided by the motors of the robotic surgical system can compensate for the weight of the robotic arm 14000. In other instances, the assisting force can be less than the weight of the robotic arm 14000. In certain instances, the assisting force can be capped at a maximum force, such as the 5-lb limit indicated in FIG. 85, for example. Capping the assisting force may ensure that the robotic arm 14000 does not forcefully collide with a person, surgical equipment, and/or another robotic arm in the surgical theater.

In one aspect, the passive power assist mode can be deactivated or locked out during portions of a surgical procedure. For example, when a surgical tool is positioned at the surgical site or within a predefined radius of the surgical site and/or the target tissue, the passive power assist mode can be locked out. Additionally or alternatively, during certain steps of a surgical procedure the passive power assist mode can be locked out. Situational awareness can be configured to determine whether the passive power assist mode should be locked out. For example, based on information that a hub knows regarding the step of the surgical procedure (see, e.g. FIG. 56), a passive power assist mode may be ill-advised by the situational awareness module. Similarly, the passive power assist mode can be activated during certain portions of the surgical timeline shown in FIG. 56.

In one aspect, the control unit for operating a robotic arm includes a processor and a memory communicatively coupled to the processor, as described herein. The memory stores instructions executable by the processor to operate in a passive power assist mode in which the processor is configured to process a manual force applied to the robotic arm and, if the manual force exceeds a predefined threshold, to direct one or more motors of the robotic arm to provide an assisting force to reposition the robotic arm in the direction indicated by the manual force.

In various aspects, the present disclosure provides a control circuit configured to operate a passive power assist mode, as described above. In various aspects, the present disclosure provides a non-transitory computer readable medium storing computer readable instructions which, when executed, cause a machine to operate a passive power assist mode, as described above.

Referring now to FIGS. 86 and 87, a clinician within the sterile field is utilizing a local control module 14160 within a sterile field to affect repositioning of a robotic arm 14100. The robotic arm 14100 is similar in many respects to the robotic arm 14400 in FIG. 83. For example, the robotic arm 14100 includes a plurality of movable components 14102. The movable components 14102 are rigid limbs that are mechanically coupled in series at revolute joints 14103. The moveable components 14102 form the robotic arm 14100, similar to the robotic arm 14400 (FIG. 83), for example. A distal-most component 14102c includes an attachment 14105 for releasably attaching interchangeable surgical tools, such as the surgical tool 14106, for example. Each component 14102 of the robotic arm 14100 has one or more motors and motor drivers, which can be operated to affect rotational motion at the respective joint 14103.

Each component 14102 includes one or more sensors, which can be position sensors and/or torque sensors, for example, and can provide information regarding the current configuration and/or load at the respective joint between the components 14102. The motors can be controlled by a control unit, such as the control unit 14409 (FIG. 83), which is configured to receive inputs from the sensors and/or from a surgical command interface, such as the surgical command interface 14412 (FIG. 83), for example.

The local control module 14160 includes an interactive display 14164 and a touch screen 14166 that is configured to accept inputs, such as inputs from a finger and/or a stylus 14168, for example. The local control module 14160 is a handheld, mobile digital electronic device. For example, the local control module 14160 can be an iPad® tablet or other mobile tablet or smart phone, for example. In use, the clinician provides repositioning instructions to the robotic arm 14100 via the display 14164 and/or the touch screen 14166 of the local control module 14160. The local control module 14160 is a wireless communication module 14162 such that the inputs from the clinician can be communicated to the robotic arm 14140 to affect arm control motions. The local control module 14140 can wirelessly communicate with the robotic arm 14140 and/or a control unit (e.g. the control unit 14409 in FIG. 83) of the robotic system via a Wi-Fi connection, for example.

The robotic arm 14100 includes six degrees of freedom indicated by the six arrows in FIG. 86. The proximal degrees of freedom can be controlled by the local control module 14160 and the distal degrees of freedom can be controlled by the remote control module. In one instance, the three most-proximal degrees of freedom (articulation about the two most-proximal joints 14103 and rotation of the intermediate limb 14102 about the axis thereof) can be controlled by the local control module and the three most-distal degrees of freedom (articulation about the most-distal joint 14103, rotation of the most-distal limb 14102c about the axis thereof, and displacement of the surgical tool 14106 along the axis thereof) can be controlled by the remote control module. In such instances, the clinician within the sterile field can affect gross robotic arm control motions, such as control motions of the proximal arms and/or joints. For example, the clinician within the sterile field can quickly and easily move a robotic arm to a general position, such as a pre-operative position, tool exchanging position, and/or reloading position via the local control module 14160. In such instances, the local control module 14160 is a secondary control system for the robotic arm 14100. The surgeon outside the sterile field can affect more localized or finessed robotic arm control motions via inputs at the surgeon's command interface 14412 (FIG. 83). In such instances, the surgeon's command interface 14412 outside the sterile field is the primary control system.

The reader will readily appreciate that fewer or greater than six degrees of freedom are contemplated. Alternative degrees of freedom are also contemplated. Moreover, different degrees of freedom can be assigned to the local control module 14160 and/or the remote control module. In certain instances, one or more degrees of freedom can be assigned to both the local control module 14106 and the remote control module.

Referring primarily now to FIG. 87, a graphical display 14150 of force over time of the robotic arm 14100 is depicted. From time 0 to time $t_1$, locally-actuated, in-field forces are applied to the robotic arm 14100 by a clinician within the sterile field to adjust the general position of the robotic arm 14100. In certain instances, the force attributable to inputs from the local control module 14160 can be capped at a first maximum force (for example the 50-lb limit indicated in FIG. 87). By utilizing the local control module 14160, the clinician within the sterile field can quickly reposition the robotic arm 14100 to exchange and/or reload the surgical tool 14160, for example. Time 0 to time $t_1$ can correspond to a local actuation mode. Active setup or reloading time in a surgical procedure can occur during the local actuation mode. For example, during the local actuation mode, the robotic arm 14100 can be out of contact with patient tissue and/or outside a predefined boundary around the surgical site, for example.

Thereafter, the surgeon at the surgeon's command console can further actuate the robotic arm 14100. For example, from time $t_2$ to time $t_3$, the remotely-actuated forces are attributable to inputs from the surgeon's command console. The remotely-actuated forces can be capped at a second maximum force (for example the 5-lb limit indicated in FIG. 87), which is less than the first maximum force. By limiting the second maximum force, a surgeon is less likely to cause a high-force or high-speed collision within the sterile field while the larger first maximum force allows the robotic arm 14100 to be quickly repositioned in certain instances. Time $t_2$ to time $t_3$ can correspond to a remote actuation mode during a surgical procedure, which can include when the robotic tool 14106 is actively manipulating tissue (grasping, pulling, holding, transecting, sealing, etc.) and/or when the robotic arm 14100 and/or surgical tool 14106 thereof is within the predefined boundary around the surgical site.

In one aspect, the local actuation mode and/or the remote actuation mode can be deactivated or locked out during portions of a surgical procedure. For example, the local actuation mode can be locked out when the surgical tool is engaged with tissue or otherwise positioned at the surgical site. Situational awareness can be configured to determine whether the local actuation mode should be locked out. For example, based on information that a hub knows regarding the step of the surgical procedure (see, e.g. FIG. 56), a local actuation mode may be ill-advised by the situational awareness module. Similarly, the remote actuation mode may be ill-advised during other portions of the surgical procedure.

In one aspect, the control unit for operating a robotic arm includes a processor and a memory communicatively coupled to the processor, as described herein. The memory stores instructions executable by the processor to provide control motions to the robotic arm based on input from a local control module during portion(s) of a surgical procedure and to provide control motions to the robotic arm based on input from a remote control module during portion(s) of the surgical procedure. A first maximum force can limit the control motions from the local control module and a second maximum force can limit the control motions from the remote control module.

In various aspects, the present disclosure provides a control circuit configured to operate a robotic arm via a local control module and a remote control module, as described above. In various aspects, the present disclosure provides a non-transitory computer readable medium storing computer readable instructions which, when executed, cause a machine to operate a robotic arm via a local control module and a remote control module, as described above.

Examples of Surgical Devices, Systems and Methods

The foregoing surgical devices, systems, and methods can incorporate one or more of the following surgical devices, systems, and methods.

An example of a non-limiting surgical tool 121200 that is well-adapted for use with a robotic system that has a tool drive assembly 121010 (FIG. 94) that is operatively coupled to a master controller that is operable by inputs from an operator (i.e., a surgeon) is depicted in FIG. 93. As can be seen in that Figure, the surgical tool 121200 includes a surgical end effector 122012 that comprises an endocutter. In at least one form, the surgical tool 121200 generally includes an elongated shaft assembly 122008 that has a proximal closure tube 122040 and a distal closure tube 122042 that are coupled together by an articulation joint 122011. The surgical tool 121200 is operably coupled to the manipulator by a tool mounting portion, generally designated as 121300. The surgical tool 121200 further includes an interface 121230 which mechanically and electrically couples the tool mounting portion 121300 to the manipulator. One form of interface 121230 is illustrated in FIGS. 94 and 95. In various exemplifications, the tool mounting portion 121300 includes a tool mounting plate 121302 that operably supports a plurality of (four are shown in FIG. 95) rotatable body portions, driven discs or elements 121304, that each include a pair of pins 121306 that extend from a surface of the driven element 121304. One pin 121306 is closer to an axis of rotation of each driven elements 121304 than the other pin 121306 on the same driven element 121304, which helps to ensure positive angular alignment of the driven element 121304. Interface 121230 includes an adaptor portion 121240 that is configured to mounting engage the mounting plate 121302 as will be further discussed below. The adaptor portion 121240 may include an array of electrical connecting pins 121242 (FIG. 95) which may be coupled to a memory structure by a circuit board within the tool mounting portion 121300. While interface 121230 is described herein with reference to mechanical, electrical, and magnetic coupling elements, it should be understood that a wide variety of telemetry modalities might be used, including infrared, inductive coupling, or the like.

As can be seen in FIG. 94, the adapter portion 121240 generally includes a tool side 121244 and a holder side 121246. In various forms, a plurality of rotatable bodies 121250 are mounted to a floating plate 121248 which has a limited range of movement relative to the surrounding adaptor structure normal to the major surfaces of the adaptor 121240. Axial movement of the floating plate 121248 helps decouple the rotatable bodies 121250 from the tool mounting portion 121300 when levers 121303 along the sides of tool mounting portion housing 121301 are actuated (See FIG. 93). Other mechanisms/arrangements may be employed for releasably coupling the tool mounting portion 121300 to the adaptor 121240. In at least one form, rotatable bodies 121250 are resiliently mounted to floating plate 121248 by resilient radial members which extend into a circumferential indentation about the rotatable bodies 121250. The rotatable bodies 121250 can move axially relative to plate 121248 by deflection of these resilient structures. When disposed in a first axial position (toward tool side 121244) the rotatable bodies 121250 are free to rotate without angular limitation. However, as the rotatable bodies 121250 move axially toward tool side 121244, tabs 121252 (extending radially from the rotatable bodies 121250) laterally engage detents on the floating plates so as to limit angular rotation of the rotatable bodies 121250 about their axes. This limited rotation can be used to help drivingly engage the rotatable bodies 121250 with drive pins 121272 of a corresponding tool holder portion 121270 of the robotic system, as the drive pins 121272 will push the rotatable bodies 121250 into the limited rotation position until the pins 121272 are aligned with (and slide into) openings 121256'. Openings 121256 on the tool side 121244 and openings 121256' on the holder side 121246 of rotatable bodies 121250 are configured to accurately align the driven elements 121304 (FIG. 95) of the tool mounting portion 121300 with drive elements 121271 of the tool holder 121270. As described above regarding inner and outer pins 121306 of driven elements 121304, the openings 121256, 121256' are at differing distances from the axis of rotation on their respective rotatable bodies 121250 so as to ensure that the alignment is not 180 degrees from its intended position. Additionally, each of the openings 121256 is slightly radially elongated so as to fittingly receive the pins 121306 in the circumferential orientation. This allows the pins 121306 to slide radially within the openings 121256, 121256' and accommodate some axial misalignment between the surgical tool 121200 and tool holder 121270, while minimizing any angular misalignment and backlash between the drive and driven elements. Openings 121256 on the tool side 121244 are offset by about 90 degrees from the openings 121256' on the holder side 121246.

Various exemplifications may further include an array of electrical connector pins 121242 located on holder side 121246 of adaptor 121240, and the tool side 121244 of the adaptor 121240 may include slots for receiving a pin array from the tool mounting portion 121300. In addition to transmitting electrical signals between the surgical tool 121200 and the tool holder 121270, at least some of these electrical connections may be coupled to an adaptor memory device by a circuit board of the adaptor 121240.

A detachable latch arrangement may be employed to releasably affix the adaptor 121240 to the tool holder 121270. As used herein, the term "tool drive assembly" when used in the context of the robotic system, at least encompasses various exemplifications of the adapter 121240 and tool holder 121270 and which has been generally designated as 121010 in FIG. 94. For example, as can be seen in FIG. 94, the tool holder 121270 may include a first latch pin arrangement 121274 that is sized to be received in corresponding clevis slots 121241 provided in the adaptor 121240. In addition, the tool holder 121270 may further have second latch pins 121276 that are sized to be retained in corresponding latch devises 121243 in the adaptor 121240. In at least one form, a latch assembly 121245 is movably supported on the adapter 121240 and is biasable between a first latched position wherein the latch pins 121276 are retained within their respective latch clevis 121243 and an unlatched position wherein the second latch pins 121276 may be into or removed from the latch devises 121243. A spring or springs are employed to bias the latch assembly into the latched position. A lip on the tool side 121244 of adaptor 121240 may slidably receive laterally extending tabs of tool mounting housing 121301.

Turning next to FIGS. 95-100, in at least one exemplification, the surgical tool 121200 includes a surgical end effector 122012 that comprises in this example, among other things, at least one component 122024 that is selectively movable between first and second positions relative to at least one other component 122022 in response to various control motions applied thereto as will be discussed in further detail below. In various exemplifications, component 122022 comprises an elongated channel 122022 configured to operably support a surgical staple cartridge 122034 therein and component 122024 comprises a pivotally translatable clamping member, such as an anvil 122024. Various exemplifications of the surgical end effector 122012 are configured to maintain the anvil 122024 and elongated channel 122022 at a spacing that assures effective stapling and severing of tissue clamped in the surgical end effector 122012. The surgical end effector 122012 further includes a cutting instrument and a sled. The cutting instrument may be, for example, a knife. The surgical staple cartridge 122034 operably houses a plurality of surgical staples therein that are supported on movable staple drivers. As the cutting instrument is driven distally through a centrally-disposed slot in the surgical staple cartridge 122034, it forces the sled distally as well. As the sled is driven distally, its "wedge-shaped" configuration contacts the movable staple drivers and drives them vertically toward the closed anvil 122024. The surgical staples are formed as they are driven into the forming surface located on the underside of the anvil 122024. The sled may be part of the surgical staple cartridge 122034, such that when the cutting instrument is retracted following the cutting operation, the sled does not retract. The anvil 122024 may be pivotably opened and closed at a pivot point 122025 located at the proximal end of the elongated channel 122022. The anvil 122024 may also include a tab 122027 at its proximal end that interacts with a component of the mechanical closure system (described further below) to facilitate the opening of the anvil 122024. The elongated channel 122022 and the anvil 122024 may be made of an electrically conductive material (such as metal) so that they may serve as part of an antenna that communicates with sensor(s) in the end effector, as described above. The surgical staple cartridge 122034 could be made of a nonconductive material (such as plastic) and the sensor may be connected to or disposed in the surgical staple cartridge 122034, as was also described above.

As can be seen in FIGS. 95-100, the surgical end effector 122012 is attached to the tool mounting portion 121300 by an elongated shaft assembly 122008 according to various exemplifications. As shown in the illustrated exemplification, the shaft assembly 122008 includes an articulation joint generally indicated as 122011 that enables the surgical end effector 122012 to be selectively articulated about an articulation axis AA-AA that is substantially transverse to a longitudinal tool axis LT-LT. See FIG. 96. In other exemplifications, the articulation joint is omitted. In various exemplifications, the shaft assembly 122008 may include a closure tube assembly 122009 that comprises proximal closure tube 122040 and distal closure tube 122042 that are pivotably linked by pivot links 122044 and operably supported on a spine assembly generally depicted as 122049. In the illustrated exemplification, the spine assembly 122049 comprises a distal spine portion 122050 that is attached to the elongated channel 122022 and is pivotally coupled to the proximal spine portion 122052. The closure tube assembly 122009 is configured to axially slide on the spine assembly 122049 in response to actuation motions applied thereto. The distal closure tube 122042 includes an opening 122045 into which the tab 122027 on the anvil 122024 is inserted in order to facilitate opening of the anvil 122024 as the distal closure tube 122042 is moved axially in the proximal direction "PD". The closure tubes 122040, 122042 may be made of electrically conductive material (such as metal) so that they may serve as part of the antenna, as described above.

In use, it may be desirable to rotate the surgical end effector 122012 about the longitudinal tool axis LT-LT. In at least one exemplification, the tool mounting portion 121300 includes a rotational transmission assembly 122069 that is configured to receive a corresponding rotary output motion from the tool drive assembly 121010 of the robotic system and convert that rotary output motion to a rotary control motion for rotating the elongated shaft assembly 122008 (and surgical end effector 122012) about the longitudinal tool axis LT-LT. In various exemplifications, for example, a proximal end 122060 of the proximal closure tube 122040 is rotatably supported on the tool mounting plate 121302 of the tool mounting portion 121300 by a forward support cradle 121309 and a closure sled 2100 that is also movably supported on the tool mounting plate 1302. In at least one form, the rotational transmission assembly 122069 includes a tube gear segment 122062 that is formed on (or attached to) the proximal end 122060 of the proximal closure tube 122040 for operable engagement by a rotational gear assembly 122070 that is operably supported on the tool mounting plate 121302. As can be seen in FIG. 98, the rotational gear assembly 122070, in at least one exemplification, comprises a rotation drive gear 122072 that is coupled to a corresponding first one of the driven discs or elements 121304 on the adapter side 121307 of the tool mounting plate 121302 when the tool mounting portion 121300 is coupled to the tool drive assembly 121010. See FIG. 95. The rotational gear assembly 122070 further comprises a rotary driven gear 122074 that is rotatably supported on the tool mounting plate 121302 in meshing engagement with the tube gear segment 122062 and the rotation drive gear 122072. Application of a first rotary output motion from the tool drive assembly 121010 of the robotic system to the corresponding driven element 121304 will thereby cause rotation of the rotation drive gear 122072. Rotation of the rotation drive gear 2072 ultimately results in the rotation of the elongated shaft assembly 122008 (and the surgical end effector 122012) about the longitudinal tool axis LT-LT (represented by arrow "R" in FIG. 98). It will be appreciated that the application of a rotary output motion from the tool drive assembly 121010 in one direction will result in the rotation of the elongated shaft assembly 122008 and surgical end effector 122012 about the longitudinal tool axis LT-LT in a first direction and an application of the rotary output motion in an opposite direction will result in the rotation of the elongated shaft assembly 122008 and surgical end effector 122012 in a second direction that is opposite to the first direction.

In at least one exemplification, the closure of the anvil 122024 relative to the staple cartridge 122034 is accomplished by axially moving the closure tube assembly 122009 in the distal direction "DD" on the spine assembly 122049. As indicated above, in various exemplifications, the proximal end 122060 of the proximal closure tube 122040 is supported by the closure sled 122100 which comprises a portion of a closure transmission, generally depicted as 122099. In at least one form, the closure sled 122100 is configured to support the closure tube 122009 on the tool mounting plate 121320 such that the proximal closure tube 122040 can rotate relative to the closure sled 122100, yet travel axially with the closure sled 122100. In particular, the closure sled 122100 has an upstanding tab that extends into a radial groove 122063 in the proximal end portion of the proximal closure tube 122040. In addition, as can be seen in FIG. 100, the closure sled 122100 has a tab portion 122102 that extends through a slot 121305 in the tool mounting plate 121302. The tab portion 122102 is configured to retain the closure sled 122100 in sliding engagement with the tool mounting plate 121302. In various exemplifications, the closure sled 122100 has an upstanding portion 122104 that has a closure rack gear 122106 formed thereon. The closure rack gear 122106 is configured for driving engagement with a closure gear assembly 122110. See FIGS. 99 and 100.

In various forms, the closure gear assembly 122110 includes a closure spur gear 122112 that is coupled to a corresponding second one of the driven discs or elements 121304 on the adapter side 121307 of the tool mounting plate 121302. See FIG. 95. Thus, application of a second rotary output motion from the tool drive assembly 121010 of the robotic system to the corresponding second driven element 121304 will cause rotation of the closure spur gear 122112 when the tool mounting portion 121300 is coupled to the tool drive assembly 121010. The closure gear assembly 122110 further includes a closure reduction gear set 122114 that is supported in meshing engagement with the closure spur gear 122112. As can be seen in FIGS. 99 and 100, the closure reduction gear set 122114 includes a driven gear 122116 that is rotatably supported in meshing engagement with the closure spur gear 122112. The closure reduction gear set 122114 further includes a first closure drive gear 122118 that is in meshing engagement with a second closure drive gear 122120 that is rotatably supported on the tool mounting plate 121302 in meshing engagement with the closure rack gear 122106. Thus, application of a second rotary output motion from the tool drive assembly 121010 of the robotic system to the corresponding second driven element 121304 will cause rotation of the closure spur gear 122112 and the closure transmission 122110 and ultimately drive the closure sled 122100 and closure tube assembly 122009 axially. The axial direction in which the closure tube assembly 122009 moves ultimately depends upon the direction in which the second driven element 121304 is rotated. For example, in response to one rotary output motion received from the tool drive assembly 121010 of the robotic system 121000, the closure sled 122100 will be driven in the distal direction "DD" and ultimately drive the closure tube assembly 122009 in the distal direction. As the distal closure tube 122042 is driven distally, the end of the closure tube segment 122042 will engage a portion of the anvil 122024 and cause the anvil 122024 to pivot to a closed position. Upon application of an "opening" out put motion from the tool drive assembly 121010 of the robotic system, the closure sled 122100 and shaft assembly 122008 will be driven in the proximal direction "PD". As the distal closure tube 122042 is driven in the proximal direction, the opening 122045 therein interacts with the tab 122027 on the anvil 122024 to facilitate the opening thereof. In various exemplifications, a spring may be employed to bias the anvil to the open position when the distal closure tube 122042 has been moved to its starting position. In various exemplifications, the various gears of the closure gear assembly 122110 are sized to generate the necessary closure forces needed to satisfactorily close the anvil 122024 onto the tissue to be cut and stapled by the surgical end effector 122012. For example, the gears of the closure transmission 122110 may be sized to generate approximately 70-120 pounds.

In various exemplifications, the cutting instrument is driven through the surgical end effector 122012 by a knife bar. In at least one form, the knife bar may be fabricated from, for example, stainless steel or other similar material and has a substantially rectangular cross-sectional shape. Such knife bar configuration is sufficiently rigid to push the cutting instrument through tissue clamped in the surgical end effector 122012, while still being flexible enough to enable the surgical end effector 122012 to articulate relative to the proximal closure tube 122040 and the proximal spine portion 122052 about the articulation axis AA-AA as will be discussed in further detail below. As can be seen in FIG. 96, the proximal spine portion 122052 has a rectangular-shaped passage 122054 extending therethrough to provide support to the knife bar as it is axially pushed therethrough. The proximal spine portion 122052 has a proximal end that is rotatably mounted to the tool mounting plate 121032. Such arrangement permits the proximal spine portion 122052 to rotate, but not move axially, within the proximal closure tube 122040.

The distal end of the knife bar is attached to the cutting instrument. The proximal end of the knife bar is rotatably affixed to a knife rack gear 122206 such that the knife bar is free to rotate relative to the knife rack gear 122206. As can be seen in FIGS. 97-100, a knife rack gear 122206 is slidably supported within a rack housing 122210 that is attached to the tool mounting plate 121302 such that the knife rack gear 122206 is retained in meshing engagement with a knife gear assembly 122220. More specifically and with reference to FIG. 100, in at least one exemplification, the knife gear assembly 122220 includes a knife spur gear 122222 that is coupled to a corresponding third one of the driven discs or elements 121304 on the adapter side 121307 of the tool mounting plate 121302. See FIG. 95. Thus, application of another rotary output motion from the robotic system through the tool drive assembly 121010 to the corresponding third driven element 121304 will cause rotation of the knife spur gear 122222. The knife gear assembly 22220 further includes a knife gear reduction set 122224 that includes a first knife driven gear 122226 and a second knife drive gear 122228. The knife gear reduction set 122224 is rotatably mounted to the tool mounting plate 121302 such that the first knife driven gear 122226 is in meshing engagement with the knife spur gear 122222. Likewise, the second knife drive gear 122228 is in meshing engagement with a third knife drive gear 122230 that is rotatably supported on the tool mounting plate 121302 in meshing engagement with the knife rack gear 122206. In various exemplifications, the gears of the knife gear assembly 122220 are sized to generate the forces needed to drive the cutting element through the tissue clamped in the surgical end effector 122012 and actuate the staples therein. For example, the gears of the knife drive assembly 122230 may be sized to generate approximately 40 to 100 pounds. It will be appreciated that the application of a rotary output motion from the tool drive assembly 121010 in one direction will result in the axial movement of the cutting instrument in a distal direction and application of the rotary output motion in an opposite direction will result in the axial travel of the cutting instrument in a proximal direction.

In various exemplifications, the surgical tool 121200 employs an articulation system that includes an articulation joint 122011 that enables the surgical end effector 122012 to be articulated about an articulation axis AA-AA that is substantially transverse to the longitudinal tool axis LT-LT. In at least one exemplification, the surgical tool 121200 includes first and second articulation bars 122250*a*, 122250*b* that are slidably supported within corresponding passages 122053 provided through the proximal spine portion 122052. See FIG. 96. In at least one form, the first and second articulation bars 122250*a*, 122250*b* are actuated by an articulation transmission generally designated as 122249 that is operably supported on the tool mounting plate 121302. Each of the articulation bars 122250*a*, 122250*b* has a proximal end that has a guide rod protruding therefrom which extend laterally through a corresponding slot in the proximal end portion of the proximal spine portion 2052 and into a corresponding arcuate slot in an articulation nut 2260 which comprises a portion of the articulation transmission. It will be understood that articulation bar 122250*b* is similarly constructed. The articulation bar 122250*a* has a guide rod which extends laterally through a corresponding slot in the proximal end portion 122056 of the distal spine portion 122050 and into a corresponding arcuate slot in the articulation nut 122260. In addition, the articulation bar 122250*a* has a distal end 122251*a* that is pivotally coupled to the distal spine portion 122050 by, for example, by a pin 122253*a*, and articulation bar 122250*b* has a distal end 122251*b* that is pivotally coupled to the distal spine portion 122050 by, for example, a pin 122253*b*. In particular, the articulation bar 122250*a* is laterally offset in a first lateral direction from the longitudinal tool axis LT-LT and the articulation bar 122250*b* is laterally offset in a second lateral direction from the longitudinal tool axis LT-LT. Thus, axial movement of the articulation bars 122250*a* and 122250*b* in opposing directions will result in the articulation of the distal spine portion 122050 as well as the surgical end effector 122012 attached thereto about the articulation axis AA-AA as will be discussed in further detail below.

Articulation of the surgical end effector 122012 is controlled by rotating an articulation nut 122260 about the longitudinal tool axis LT-LT. The articulation nut 122260 is rotatably journaled on the proximal end portion 122056 of the distal spine portion 122050 and is rotatably driven thereon by an articulation gear assembly 122270. More specifically and with reference to FIG. 98, in at least one exemplification, the articulation gear assembly 122270 includes an articulation spur gear 122272 that is coupled to a corresponding fourth one of the driven discs or elements 121304 on the adapter side 121307 of the tool mounting plate 121302. See FIG. 95. Thus, application of another rotary input motion from the robotic system through the tool drive assembly 121010 to the corresponding fourth driven element 121304 will cause rotation of the articulation spur gear 122272 when the interface 121230 is coupled to the tool holder 121270. An articulation drive gear 122274 is rotatably supported on the tool mounting plate 121302 in meshing engagement with the articulation spur gear 122272 and a gear portion 122264 of the articulation nut 122260. As can be seen in FIG. 97, the articulation nut 122260 has a shoulder formed thereon that defines an annular groove 122267 for receiving retaining posts 122268 therein. Retaining posts 122268 are attached to the tool mounting plate 121302 and serve to prevent the articulation nut 122260 from moving axially on the proximal spine portion 122052 while maintaining the ability to be rotated relative thereto. Thus, rotation of the articulation nut 122260 in a first direction, will result in the axial movement of the articulation bar 122250*a* in a distal direction "DD" and the axial movement of the articulation bar 122250*b* in a proximal direction "PD" because of the interaction of the guide rods with the spiral slots in the articulation gear 122260. Similarly, rotation of the articulation nut 122260 in a second direction that is opposite to the first direction will result in the axial movement of the articulation bar 122250*a* in the proximal direction "PD" as well as cause articulation bar 122250*b* to axially move in the distal direction "DD". Thus, the surgical end effector 122012 may be selectively articulated about articulation axis "AA-AA" in a first direction "FD" by simultaneously moving the articulation bar 122250*a* in the distal direction "DD" and the articulation bar 122250*b* in the proximal direction "PD". Likewise, the surgical end effector 122012 may be selectively articulated about the articulation axis "AA-AA" in a second direction "SD" by simultaneously moving the articulation bar 122250*a* in the proximal direction "PD" and the articulation bar 122250*b* in the distal direction "DD." See FIG. 96.

The tool exemplification described above employs an interface arrangement that is particularly well-suited for mounting the robotically controllable medical tool onto at least one form of robotic arm arrangement that generates at least four different rotary control motions. Those of ordinary skill in the art will appreciate that such rotary output motions may be selectively controlled through the programmable control systems employed by the robotic system/controller. For example, the tool arrangement described above may be well-suited for use with those robotic systems manufactured by Intuitive Surgical, Inc. of Sunnyvale, Calif., U.S.A., many of which may be described in detail in various patents and publications incorporated herein by reference. The unique and novel aspects of various exemplifications of the present disclosure serve to utilize the rotary output motions supplied by the robotic system to generate specific control motions having sufficient magnitudes that enable end effectors to cut and staple tissue. Thus, the unique arrangements and principles of various exemplifications of the present disclosure may enable a variety of different forms of the tool systems disclosed and claimed herein to be effectively employed in connection with other types and forms of robotic systems that supply programmed rotary or other output motions. In addition, as will become further apparent as the present Detailed Description proceeds, various end effector exemplifications of the present disclosure that require other forms of actuation motions may also be effectively actuated utilizing one or more of the control motions generated by the robotic system.

FIGS. 101-105 illustrate yet another surgical tool 2300 that may be effectively employed in connection with the robotic system that has a tool drive assembly that is operably coupled to a controller of the robotic system that is operable by inputs from an operator and which is configured to provide at least one rotary output motion to at least one rotatable body portion supported on the tool drive assembly. In various forms, the surgical tool 122300 includes a surgical end effector 122312 that includes an elongated channel 122322 and a pivotally translatable clamping member, such as an anvil 122324, which are maintained at a spacing that assures effective stapling and severing of tissue clamped in the surgical end effector 122312. As shown in the illustrated exemplification, the surgical end effector 122312 may include, in addition to the previously-mentioned elongated channel 122322 and anvil 122324, a cutting instrument 122332 that has a sled portion 122333 formed thereon, a surgical staple cartridge 122334 that is seated in the elongated channel 122322, and a rotary end effector drive shaft 122336 that has a helical screw thread formed thereon. The cutting instrument 122332 may be, for example, a knife. As will be discussed in further detail below, rotation of the end effector drive shaft 122336 will cause the cutting instrument 122332 and sled portion 122333 to axially travel through the surgical staple cartridge 122334 to move between a starting position and an ending position. The direction of axial travel of the cutting instrument 122332 depends upon the direction in which the end effector drive shaft 122336 is rotated. The anvil 122324 may be pivotably opened and closed at a pivot point 122325 connected to the proximate end of the elongated channel 122322. The anvil 122324 may also include a tab 122327 at its proximate end that operably interfaces with a component of the mechanical closure system (described further below) to open and close the anvil 122324. When the end effector drive shaft 122336 is rotated, the cutting instrument 122332 and sled 122333 will travel longitudinally through the surgical staple cartridge 122334 from the starting position to the ending position, thereby cutting tissue clamped within the surgical end effector 122312. The movement of the sled 122333 through the surgical staple cartridge 122334 causes the staples therein to be driven through the severed tissue and against the closed anvil 122324, which turns the staples to fasten the severed tissue. In one form, the elongated channel 122322 and the anvil 122324 may be made of an electrically conductive material (such as metal) so that they may serve as part of the antenna that communicates with sensor(s) in the end effector, as described above. The surgical staple cartridge 122334 could be made of a nonconductive material (such as plastic) and the sensor may be connected to or disposed in the surgical staple cartridge 122334, as described above.

It should be noted that although the exemplifications of the surgical tool 2300 described herein employ a surgical end effector 122312 that staples the severed tissue, in other exemplifications different techniques for fastening or sealing the severed tissue may be used. For example, end effectors that use RF energy or adhesives to fasten the severed tissue may also be used. Accordingly, although the description herein refers to cutting/stapling operations and the like, it should be recognized that this is an exemplary exemplification and is not meant to be limiting. Other tissue-fastening techniques may also be used.

In the illustrated exemplification, the surgical end effector 122312 is coupled to an elongated shaft assembly 122308 that is coupled to a tool mounting portion 122460 and defines a longitudinal tool axis LT-LT. In this exemplification, the elongated shaft assembly 122308 does not include an articulation joint. Those of ordinary skill in the art will understand that other exemplifications may have an articulation joint therein. In at least one exemplification, the elongated shaft assembly 122308 comprises a hollow outer tube 122340 that is rotatably supported on a tool mounting plate 122462 of the tool mounting portion 122460 as will be discussed in further detail below. In various exemplifications, the elongated shaft assembly 122308 further includes a distal spine shaft 122350. Distal spine shaft 122350 has a distal end portion 122354 that is coupled to, or otherwise integrally formed with, a distal stationary base portion 122360 that is non-movably coupled to the channel 122322. See FIGS. 102-104.

As shown in FIG. 102, the distal spine shaft 122350 has a proximal end portion 122351 that is slidably received within a slot 122355 in a proximal spine shaft 122353 that is non-movably supported within the hollow outer tube 122340 by at least one support collar 122357. As can be further seen in FIGS. 102 and 103, the surgical tool 122300 includes a closure tube 122370 that is constrained to only move axially relative to the distal stationary base portion 122360. The closure tube 122370 has a proximal end 122372 that has an internal thread 122374 formed therein that is in threaded engagement with a transmission arrangement, generally depicted as 122375 that is operably supported on the tool mounting plate 122462. In various forms, the transmission arrangement 122375 includes a rotary drive shaft assembly, generally designated as 122485. When rotated, the rotary drive shaft assembly 122485 will cause the closure tube 122370 to move axially as will be describe in further detail below. In at least one form, the rotary drive shaft assembly 122485 includes a closure drive nut 122382 of a closure clutch assembly generally designated as 122380. More specifically, the closure drive nut 122382 has a proximal end portion 122384 that is rotatably supported relative to the outer tube 122340 and is in threaded engagement with the closure tube 122370. For assembly purposes, the proximal end portion 122384 may be threadably attached to a retention ring 122386. Retention ring 122386, in cooperation with an end 122387 of the closure drive nut 122382, defines an annular slot 122388 into which a shoulder 122392 of a locking collar 122390 extends. The locking collar 122390 is non-movably attached (e.g., welded, glued, etc.) to the end of the outer tube 122340. Such arrangement serves to affix the closure drive nut 122382 to the outer tube 122340 while enabling the closure drive nut 122382 to rotate relative to the outer tube 122340. The closure drive nut 122382 further has a distal end 122383 that has a threaded portion 122385 that threadably engages the internal thread 122374 of the closure tube 122370. Thus, rotation of the closure drive nut 122382 will cause the closure tube 122370 to move axially as represented by arrow "D" in FIG. 103.

Closure of the anvil 122324 and actuation of the cutting instrument 122332 are accomplished by control motions that are transmitted by a hollow drive sleeve 122400. As can be seen in FIGS. 102 and 103, the hollow drive sleeve 122400 is rotatably and slidably received on the distal spine shaft 122350. The drive sleeve 122400 has a proximal end portion 122401 that is rotatably mounted to the proximal spine shaft 122353 that protrudes from the tool mounting portion 122460 such that the drive sleeve 122400 may rotate relative thereto. See FIG. 102. As can also be seen in FIGS. 102-104, the drive sleeve 122400 is rotated about the longitudinal tool axis "LT-LT" by a drive shaft 122440. The drive shaft 122440 has a drive gear 122444 that is attached to its distal end 122442 and is in meshing engagement with a driven gear 122450 that is attached to the drive sleeve 122400.

The drive sleeve 122400 further has a distal end portion 122402 that is coupled to a closure clutch 122410 portion of the closure clutch assembly 122380 that has a proximal face 122412 and a distal face 122414. The proximal face 122412 has a series of proximal teeth 122416 formed thereon that are adapted for selective engagement with corresponding proximal teeth cavities 122418 formed in the proximal end portion 122384 of the closure drive nut 2382. Thus, when the proximal teeth 122416 are in meshing engagement with the proximal teeth cavities 122418 in the closure drive nut 122382, rotation of the drive sleeve 122400 will result in rotation of the closure drive nut 122382 and ultimately cause the closure tube 122370 to move axially as will be discussed in further detail below.

As can be most particularly seen in FIGS. 102 and 103, the distal face 122414 of the drive clutch portion 122410 has a series of distal teeth 122415 formed thereon that are adapted for selective engagement with corresponding distal teeth cavities 122426 formed in a face plate portion 122424 of a knife drive shaft assembly 122420. In various exemplifications, the knife drive shaft assembly 122420 comprises a hollow knife shaft segment 122430 that is rotatably received on a corresponding portion of the distal spine shaft 122350 that is attached to or protrudes from the stationary base 122360. When the distal teeth 122415 of the closure clutch portion 122410 are in meshing engagement with the distal teeth cavities 122426 in the face plate portion 122424, rotation of the drive sleeve 122400 will result in rotation of the drive shaft segment 122430 about the stationary shaft 122350. As can be seen in FIGS. 102-104, a knife drive gear 122432 is attached to the drive shaft segment 122430 and is meshing engagement with a drive knife gear 122434 that is attached to the end effector drive shaft 122336. Thus, rotation of the drive shaft segment 122430 will result in the rotation of the end effector drive shaft 122336 to drive the cutting instrument 122332 and sled 122333 distally through the surgical staple cartridge 122334 to cut and staple tissue clamped within the surgical end effector 122312. The sled 122333 may be made of, for example, plastic, and may have a sloped distal surface. As the sled 122333 traverses the elongated channel 122322, the sloped forward surface of the sled 122333 pushes up or "drive" the staples in the surgical staple cartridge 122334 through the clamped tissue and against the anvil 122324. The anvil 122324 turns or "forms" the staples, thereby stapling the severed tissue. As used herein, the term "fire" refers to the initiation of actions required to drive the cutting instrument and sled portion in a distal direction through the surgical staple cartridge to cut the tissue clamped in the surgical end effector and drive the staples through the severed tissue.

In use, it may be desirable to rotate the surgical end effector 122312 about the longitudinal tool axis LT-LT. In at least one exemplification, the transmission arrangement 122375 includes a rotational transmission assembly 122465 that is configured to receive a corresponding rotary output motion from the tool drive assembly 121010 of the robotic system and convert that rotary output motion to a rotary control motion for rotating the elongated shaft assembly 122308 (and surgical end effector 122312) about the longitudinal tool axis LT-LT. As can be seen in FIG. 105, a proximal end 122341 of the outer tube 122340 is rotatably supported within a cradle arrangement 122343 attached to the tool mounting plate 122462 of the tool mounting portion 122460. A rotation gear 122345 is formed on or attached to the proximal end 122341 of the outer tube 122340 of the elongated shaft assembly 122308 for meshing engagement with a rotation gear assembly 122470 operably supported on the tool mounting plate 122462. In at least one exemplification, a rotation drive gear 122472 is coupled to a corresponding first one of the driven discs or elements 121304 on the adapter side of the tool mounting plate 122462 when the tool mounting portion 122460 is coupled to the tool drive assembly 121010. See FIGS. 95 and 105. The rotation drive assembly 122470 further comprises a rotary driven gear 122474 that is rotatably supported on the tool mounting plate 122462 in meshing engagement with the rotation gear 122345 and the rotation drive gear 122472. Application of a first rotary output motion from the robotic system through the tool drive assembly 121010 to the corresponding driven element 121304 will thereby cause rotation of the rotation drive gear 122472 by virtue of being operably coupled thereto. Rotation of the rotation drive gear 122472 ultimately results in the rotation of the elongated shaft assembly 122308 (and the end effector 122312) about the longitudinal tool axis LT-LT (primary rotary motion).

Closure of the anvil 122324 relative to the staple cartridge 122034 is accomplished by axially moving the closure tube 122370 in the distal direction "DD". Axial movement of the closure tube 122370 in the distal direction "DD" is accomplished by applying a rotary control motion to the closure drive nut 122382. To apply the rotary control motion to the closure drive nut 2382, the closure clutch 122410 must first be brought into meshing engagement with the proximal end portion 122384 of the closure drive nut 122382. In various exemplifications, the transmission arrangement 122375 further includes a shifter drive assembly 122480 that is operably supported on the tool mounting plate 122462. More specifically and with reference to FIG. 105, it can be seen that a proximal end portion 122359 of the proximal spine portion 122353 extends through the rotation gear 122345 and is rotatably coupled to a shifter gear rack 122481 that is slidably affixed to the tool mounting plate 122462 through slots 122482. The shifter drive assembly 122480 further comprises a shifter drive gear 122483 that is coupled to a corresponding second one of the driven discs or elements 121304 on the adapter side of the tool mounting plate 122462 when the tool mounting portion 122460 is coupled to the tool holder 121270. See FIGS. 95 and 105. The shifter drive assembly 122480 further comprises a shifter driven gear 122484 that is rotatably supported on the tool mounting plate 122462 in meshing engagement with the shifter drive gear 122483 and the shifter rack gear 122482. Application of a second rotary output motion from the robotic system through the tool drive assembly 121010 to the corresponding driven element 121304 will thereby cause rotation of the shifter drive gear 122483 by virtue of being operably coupled thereto. Rotation of the shifter drive gear 122483 ultimately results in the axial movement of the shifter gear rack 122482 and the proximal spine portion 122353 as well as the drive sleeve 122400 and the closure clutch 122410 attached thereto. The direction of axial travel of the closure clutch 122410 depends upon the direction in which the shifter drive gear 122483 is rotated by the robotic system. Thus, rotation of the shifter drive gear 122483 in a first rotary direction will result in the axial movement of the closure clutch 122410 in the proximal direction "PD" to bring the proximal teeth 122416 into meshing engagement with the proximal teeth cavities 122418 in the closure drive nut 122382. Conversely, rotation of the shifter drive gear 122483 in a second rotary direction (opposite to the first rotary direction) will result in the axial movement of the closure clutch 122410 in the distal direction "DD" to bring the distal teeth 122415 into meshing engagement with corresponding distal teeth cavities 122426 formed in the face plate portion 122424 of the knife drive shaft assembly 122420.

Once the closure clutch 122410 has been brought into meshing engagement with the closure drive nut 122382, the closure drive nut 122382 is rotated by rotating the closure clutch 122410. Rotation of the closure clutch 122410 is controlled by applying rotary output motions to a rotary drive transmission portion 122490 of transmission arrangement 122375 that is operably supported on the tool mounting plate 122462 as shown in FIG. 105. In at least one exemplification, the rotary drive transmission 122490 includes a rotary drive assembly 122490' that includes a gear 122491 that is coupled to a corresponding third one of the driven discs or elements 121304 on the adapter side of the tool mounting plate 122462 when the tool mounting portion 122460 is coupled to the tool holder 121270. See FIGS. 95 and 105. The rotary drive transmission 122490 further comprises a first rotary driven gear 122492 that is rotatably supported on the tool mounting plate 122462 in meshing engagement with a second rotary driven gear 122493 and the rotary drive gear 122491. The second rotary driven gear 122493 is coupled to a proximal end portion 122443 of the drive shaft 122440.

Rotation of the rotary drive gear 122491 in a first rotary direction will result in the rotation of the drive shaft 122440 in a first direction. Conversely, rotation of the rotary drive gear 122491 in a second rotary direction (opposite to the first rotary direction) will cause the drive shaft 122440 to rotate in a second direction. As indicated above, the drive shaft 122440 has a drive gear 122444 that is attached to its distal end 122442 and is in meshing engagement with a driven gear 122450 that is attached to the drive sleeve 122400. Thus, rotation of the drive shaft 122440 results in rotation of the drive sleeve 122400.

A method of operating the surgical tool 122300 will now be described. Once the tool mounting portion 122462 has been operably coupled to the tool holder 121270 of the robotic system and oriented into position adjacent the target tissue to be cut and stapled, if the anvil 122324 is not already in the open position (FIG. 102), the robotic system may apply the first rotary output motion to the shifter drive gear 122483 which results in the axial movement of the closure clutch 122410 into meshing engagement with the closure drive nut 122382 (if it is not already in meshing engagement therewith). See FIG. 103. Once the controller of the robotic system has confirmed that the closure clutch 122410 is meshing engagement with the closure drive nut 122382 (e.g., by means of sensor(s)) in the surgical end effector 122312 that are in communication with the robotic control system), the robotic controller may then apply a second rotary output motion to the rotary drive gear 122492 which, as was described above, ultimately results in the rotation of the rotary drive nut 122382 in the first direction which results in the axial travel of the closure tube 122370 in the distal direction "DD". As the closure tube 122370 moves in the distal direction, it contacts a portion of the anvil 122324 and causes the anvil 122324 to pivot to the closed position to clamp the target tissue between the anvil 122324 and the surgical staple cartridge 122334.

Once the robotic controller determines that the anvil 122334 has been pivoted to the closed position by corresponding sensor(s) in the surgical end effector 122312 in communication therewith, the robotic system discontinues the application of the second rotary output motion to the rotary drive gear 122491. The robotic controller may also provide the surgeon with an indication that the anvil 122324 has been fully closed. The surgeon may then initiate the firing procedure. In alternative exemplifications, the firing procedure may be automatically initiated by the robotic controller. The robotic controller then applies the rotary control motion to the shifter drive gear 122483 which results in the axial movement of the closure clutch 122410 into meshing engagement with the face plate portion 122424 of the knife drive shaft assembly 122420. See FIG. 104.

Once the controller of the robotic system has confirmed that the closure clutch 122410 is meshing engagement with the face plate portion 122424 (by means of sensor(s)) in the end effector 122312 that are in communication with the robotic controller), the robotic controller may then apply the second rotary output motion to the rotary drive gear 122492 which, as was described above, ultimately results in the axial movement of the cutting instrument 122332 and sled portion 122333 in the distal direction "DD" through the surgical staple cartridge 122334. As the cutting instrument 122332 moves distally through the surgical staple cartridge 122334, the tissue clamped therein is severed. As the sled portion 122333 is driven distally, it causes the staples within the surgical staple cartridge to be driven through the severed tissue into forming contact with the anvil 122324.

Once the robotic controller has determined that the cutting instrument 122332 has reached the end position within the surgical staple cartridge 122334 (by means of sensor(s)) in the end effector 122312 that are in communication with the robotic controller), the robotic controller discontinues the application of the second rotary output motion to the rotary drive gear 122491. Thereafter, the robotic controller applies the secondary rotary output motion to the rotary drive gear 122491 which ultimately results in the axial travel of the cutting instrument 122332 and sled portion 122333 in the proximal direction "PD" to the starting position. Once the robotic controller has determined that the cutting instrument 122332 has reached the starting position by means of sensor(s) in the surgical end effector 122312 that are in communication with the robotic controller, the robotic controller discontinues the application of the secondary rotary output motion to the rotary drive gear 122491. Thereafter, the robotic controller applies the rotary output motion to the shifter drive gear 122483 to cause the closure clutch 122410 to move into engagement with the rotary drive nut 122382.

Once the closure clutch 122410 has been moved into meshing engagement with the rotary drive nut 122382, the robotic controller then applies the secondary output motion to the rotary drive gear 122491 which ultimately results in the rotation of the rotary drive nut 122382 in the second direction to cause the closure tube 122370 to move in the proximal direction "PD". As can be seen in FIGS. 102-104, the closure tube 122370 has an opening 122345 therein that engages the tab 122327 on the anvil 122324 to cause the anvil 122324 to pivot to the open position. In alternative exemplifications, a spring may also be employed to pivot the anvil 122324 to the open position when the closure tube 122370 has been returned to the starting position (FIG. 102).

FIGS. 106-109 depict another non-limiting exemplification of a surgical tool 126000 of the present disclosure that is well-adapted for use with a robotic system that has a tool drive assembly 121010 (FIG. 94) that is operatively coupled to a master controller that is operable by inputs from an operator (i.e., a surgeon). As can be seen in FIG. 106, the surgical tool 126000 includes a surgical end effector 126012 that comprises an endocutter. In at least one form, the surgical tool 126000 generally includes an elongated shaft assembly 126008 that has a proximal closure tube 126040 and a distal closure tube 126042 that are coupled together by an articulation joint 126100. The surgical tool 126000 is operably coupled to the manipulator by a tool mounting portion, generally designated as 126200. The surgical tool 126000 further includes an interface 126030 which may mechanically and electrically couple the tool mounting portion 126200 to the manipulator in the various manners described in detail above.

In at least one exemplification, the surgical tool 126000 includes surgical end effector 126012 that comprises, among other things, at least one component 126024 that is selectively movable between first and second positions relative to at least one other component 126022 in response to various control motions applied to component 126024 as will be discussed in further detail below to perform a surgical procedure. In various exemplifications, component 126022 comprises an elongated channel 126022 configured to operably support a surgical staple cartridge 126034 therein and component 126024 comprises a pivotally translatable clamping member, such as an anvil 126024. Various exemplifications of the surgical end effector 126012 are configured to maintain the anvil 126024 and elongated channel 126022 at a spacing that assures effective stapling and severing of tissue clamped in the surgical end effector 126012. Unless otherwise stated, the end effector 126012 is similar to the surgical end effector 122012 described above and includes a cutting instrument and a sled. The anvil 126024 may include a tab 126027 at its proximal end that interacts with a component of the mechanical closure system (described further below) to facilitate the opening of the anvil 126024. The elongated channel 126022 and the anvil 126024 may be made of an electrically conductive material (such as metal) so that they may serve as part of an antenna that communicates with sensor(s) in the end effector, as described above. The surgical staple cartridge 126034 could be made of a nonconductive material (such as plastic) and the sensor may be connected to or disposed in the surgical staple cartridge 126034, as was also described above.

As can be seen in FIG. 106, the surgical end effector 126012 is attached to the tool mounting portion 126200 by the elongated shaft assembly 126008 according to various exemplifications. As shown in the illustrated exemplification, the elongated shaft assembly 126008 includes an articulation joint generally designated as 126100 that enables the surgical end effector 126012 to be selectively articulated about a first tool articulation axis TA1-TA1 that is substantially transverse to a longitudinal tool axis LT-LT and a second tool articulation axis TA2-TA2 that is substantially transverse to the longitudinal tool axis LT-LT as well as the first articulation axis TA1-TA1. See FIG. 107. In various exemplifications, the elongated shaft assembly 126008 includes a closure tube assembly 126009 that comprises proximal closure tube 126040 and distal closure tube 126042 that are pivotably linked by pivot links 126044 and 126046. The closure tube assembly 126009 is movably supported on a spine assembly generally designated as 126102.

As can be seen in FIG. 108, the proximal closure tube 126040 is pivotally linked to an intermediate closure tube joint 126043 by an upper pivot link 126044U and a lower pivot link 126044L such that the intermediate closure tube joint 126043 is pivotable relative to the proximal closure tube 126040 about a first closure axis CA1-CA1 and a second closure axis CA2-CA2. In various exemplifications, the first closure axis CA1-CA1 is substantially parallel to the second closure axis CA2-CA2 and both closure axes CA1-CA1, CA2-CA2 are substantially transverse to the longitudinal tool axis LT-LT. As can be further seen in FIG. 108, the intermediate closure tube joint 126043 is pivotally linked to the distal closure tube 126042 by a left pivot link 126046L and a right pivot link 126046R such that the intermediate closure tube joint 126043 is pivotable relative to the distal closure tube 126042 about a third closure axis CA3-CA3 and a fourth closure axis CA4-CA4. In various exemplifications, the third closure axis CA3-CA3 is substantially parallel to the fourth closure axis CA4-CA4 and both closure axes CA3-CA3, CA4-CA4 are substantially transverse to the first and second closure axes CA1-CA1, CA2-CA2 as well as to longitudinal tool axis LT-LT.

The closure tube assembly 126009 is configured to axially slide on the spine assembly 126102 in response to actuation motions applied thereto. The distal closure tube 126042 includes an opening 126045 which interfaces with the tab 126027 on the anvil 126024 to facilitate opening of the anvil 126024 as the distal closure tube 126042 is moved axially in the proximal direction "PD". The closure tubes 126040, 6042 may be made of electrically conductive material (such as metal) so that they may serve as part of the antenna, as described above. Components of the spine assembly 126102 may be made of a nonconductive material (such as plastic).

As indicated above, the surgical tool 126000 includes a tool mounting portion 126200 that is configured for operable attachment to the tool mounting assembly 121010 of the robotic system in the various manners described in detail above. As can be seen in FIG. 106, the tool mounting portion 126200 comprises a tool mounting plate 126202 that operably supports a transmission arrangement thereon. In various exemplifications, the transmission arrangement includes an articulation transmission that comprises a portion of an articulation system for articulating the surgical end effector 126012 about a first tool articulation axis TA1-TA1 and a second tool articulation axis TA2-TA2. The first tool articulation axis TA1-TA1 is substantially transverse to the second tool articulation axis TA2-TA2 and both of the first and second tool articulation axes are substantially transverse to the longitudinal tool axis LT-LT. See FIG. 107.

To facilitate selective articulation of the surgical end effector 126012 about the first and second tool articulation axes TA1-TA1, TA2-TA2, the spine assembly 126102 comprises a proximal spine portion 126110 that is pivotally coupled to a distal spine portion 126120 by pivot pins 126122 for selective pivotal travel about TA1-TA1. Similarly, the distal spine portion 126120 is pivotally attached to the elongated channel 126022 of the surgical end effector 126012 by pivot pins 126124 to enable the surgical end effector 126012 to selectively pivot about the second tool axis TA2-TA2 relative to the distal spine portion 126120.

In various exemplifications, the articulation system further includes a plurality of articulation elements that operably interface with the surgical end effector 126012 and an articulation control arrangement that is operably supported in the tool mounting member 126200 as will described in further detail below. In at least one exemplification, the articulation elements comprise a first pair of first articulation cables 126144 and 126146. The first articulation cables are located on a first or right side of the longitudinal tool axis. Thus, the first articulation cables are referred to herein as a right upper cable 126144 and a right lower cable 126146. The right upper cable 126144 and the right lower cable 126146 extend through corresponding passages respectively along the right side of the proximal spine portion 126110. See FIG. 107. The articulation system further includes a second pair of second articulation cables 126150 and 126152. The second articulation cables are located on a second or left side of the longitudinal tool axis. Thus, the second articulation cables are referred to herein as a left upper articulation cable 126150 and a left articulation cable 126152. The left upper articulation cable 126150 and the left lower articulation cable 126152 extend through passages respectively in the proximal spine portion 126110.

As can be seen in FIG. 107, the right upper cable 126144 extends around an upper pivot joint 126123 and is attached to a left upper side of the elongated channel 126022 at a left pivot joint 126125. The right lower cable 126146 extends around a lower pivot joint 126126 and is attached to a left lower side of the elongated channel 126022 at left pivot joint 126125. The left upper cable 126150 extends around the upper pivot joint 126123 and is attached to a right upper side of the elongated channel 126022 at a right pivot joint 126127. The left lower cable 126152 extends around the lower pivot joint 126126 and is attached to a right lower side of the elongated channel 126022 at right pivot joint 126127. Thus, to pivot the surgical end effector 126012 about the first tool articulation axis TA1-TA1 to the left (arrow "L"), the right upper cable 126144 and the right lower cable 126146 must be pulled in the proximal direction "PD". To articulate the surgical end effector 126012 to the right (arrow "R") about the first tool articulation axis TA1-TA1, the left upper cable 126150 and the left lower cable 126152 must be pulled in the proximal direction "PD". To articulate the surgical end effector 126012 about the second tool articulation axis TA2-TA2, in an upward direction (arrow "U"), the right upper cable 126144 and the left upper cable 126150 must be pulled in the proximal direction "PD". To articulate the surgical end effector 126012 in the downward direction (arrow "DW") about the second tool articulation axis TA2-TA2, the right lower cable 126146 and the left lower cable 126152 must be pulled in the proximal direction "PD". The proximal ends of the articulation cables 126144, 126146, 126150, 126152 are coupled to the articulation control arrangement which comprises a ball joint assembly that is a part of the articulation transmission, as further described in issued U.S. Pat. No. 9,072,535, filed May 27, 2011, entitled SURGICAL STAPLING INSTRUMENTS WITH ROTATABLE STAPLE DEPLOYMENT ARRANGEMENTS, which issued Jul. 7, 2015, the entire disclosure of which is incorporated by reference herein.

As can be appreciated from the foregoing description, the surgical tool 126000 represents a vast improvement over prior robotic tool arrangements. The unique and novel shifter arrangements of various exemplifications of the present disclosure described above enable two different articulation actions to be powered from a single rotatable body portion of the robotic system.

The various exemplifications of the present disclosure have been described above in connection with cutting-type surgical instruments. It should be noted, however, that in other exemplifications, the inventive surgical instrument disclosed herein need not be a cutting-type surgical instrument, but rather could be used in any type of surgical instrument including remote sensor transponders. For example, it could be a non-cutting endoscopic instrument, a grasper, a stapler, a clip applier, an access device, a drug/gene therapy delivery device, an energy device using ultrasound, RF, laser, etc. In addition, the present disclosure may be in laparoscopic instruments, for example. The present disclosure also has application in conventional endoscopic and open surgical instrumentation as well as robotic-assisted surgery.

FIGS. 185-109 and additional exemplifications are further described in U.S. Pat. No. 9,072,535, filed May 27, 2011, entitled SURGICAL STAPLING INSTRUMENTS WITH ROTATABLE STAPLE DEPLOYMENT ARRANGEMENTS, which issued Jul. 7, 2015, the entire disclosure of which is incorporated by reference herein.

A surgical tool 130100 that is well-adapted for use with a robotic system is depicted in FIG. 109. As can be seen in that Figure, the surgical tool 130100 includes a surgical end effector 131000 that comprises an endocutter. The surgical tool 130100 generally includes an elongate shaft assembly 130200 that is operably coupled to a manipulator of a robotic system by a tool mounting portion, generally designated as 130300. The surgical tool 130100 further includes an interface, similar to interface 121230 above, which mechanically and electrically couples the tool mounting portion 130300 to the manipulator of a robotic system. In the exemplification depicted in FIG. 109, the tool mounting portion 130300 includes a tool mounting plate 130304, which is substantially similar to tool mounting plate 121302, that operably supports a plurality of rotatable body portions, driven discs or elements, that are substantially similar to driven disks 121304 illustrated in FIG. 94.

Referring now to FIG. 110, the tool mounting portion 130300 operably supports a plurality of drive systems for generating various forms of control motions necessary to operate a particular type of end effector that is coupled to the distal end of the elongate shaft assembly 130200. As shown in FIG. 110, the tool mounting portion 130300 includes a first drive system generally designated as 130350 that is configured to receive a corresponding "first" rotary output motion from the tool drive assembly of the robotic system and convert that first rotary output motion to a first rotary control motion to be applied to the surgical end effector. In the illustrated exemplification, the first rotary control motion is employed to rotate the elongate shaft assembly 130200 (and surgical end effector 131000) about a longitudinal tool axis LT-LT.

In the exemplification of FIG. 110 the first drive system 130350 includes a tube gear segment 130354 that is formed on (or attached to) the proximal end of the elongate shaft assembly 130200. The proximal end 208 of the elongate shaft assembly 130200 is rotatably supported on the tool mounting plate 130304 of the tool mounting portion 130300 by a forward support cradle 130352 that is mounted on the tool mounting plate 130304. See FIG. 110. The tube gear segment 130354 is supported in meshing engagement with a first rotational gear assembly 130360 that is operably supported on the tool mounting plate 130304. The rotational gear assembly 130360 comprises a first rotation drive gear 130362 that is coupled to a corresponding first one of the driven discs or elements on the holder side of the tool mounting plate 130304 when the tool mounting portion 130300 is coupled to the tool drive assembly. The rotational gear assembly 130360 further comprises a first rotary driven gear 130364 that is rotatably supported on the tool mounting plate 130304. The first rotary driven gear 130364 is in meshing engagement with a second rotary driven gear 130366 which, in turn, is in meshing engagement with the tube gear segment 130354. Application of a first rotary output motion from the tool drive assembly of the robotic system to the corresponding driven element will thereby cause rotation of the rotation drive gear 130362. Rotation of the rotation drive gear 130362 ultimately results in the rotation of the elongate shaft assembly 130200 (and the surgical end effector 131000) about the longitudinal tool axis LT-LT (represented by arrow "R" in FIG. 110). It will be appreciated that the application of a rotary output motion from the tool drive assembly in one direction will result in the rotation of the elongate shaft assembly 130200 and surgical end effector 131000 about the longitudinal tool axis LT-LT in a first rotary direction and an application of the rotary output motion in an opposite direction will result in the rotation of the elongate shaft assembly 130200 and surgical end effector 131000 in a second rotary direction that is opposite to the first rotary direction.

In the exemplification of FIG. 110, the tool mounting portion 130300 further includes a second drive system generally designated as 130370 that is configured to receive a corresponding "second" rotary output motion from the tool drive assembly of the robotic system and convert that second rotary output motion to a second rotary control motion for application to the surgical end effector. The second drive system 130370 includes a second rotation drive gear 130372 that is coupled to a corresponding second one of the driven discs or elements on the holder side of the tool mounting plate 130304 when the tool mounting portion 130300 is coupled to the tool drive assembly of the robotic system. The second drive system 130370 further comprises a first rotary driven gear 130374 that is rotatably supported on the tool mounting plate 130304. The first rotary driven gear 130374 is in meshing engagement with a shaft gear 130376 that is movably and non-rotatably mounted onto a proximal drive shaft segment. Rotation of the proximal drive shaft segment results in the transmission of a second rotary control motion to the surgical end effector 131000.

The exemplification depicted in FIG. 110, includes a surgical end effector 131000 that is attached to the tool mounting portion 130300 by the elongate shaft assembly 130200. In that illustrated exemplification, the elongate shaft assembly includes a coupling arrangement in the form of a quick disconnect arrangement or joint 130210 that facilitates quick attachment of a distal portion 130230 of the shaft assembly 130200 to a proximal shaft portion 130201 of the shaft assembly 130200. The quick disconnect joint 130210 serves to facilitate the quick attachment and detachment of a plurality of drive train components used to provide control motions from a source of drive motions to an end effector that is operably coupled thereto. In the exemplification illustrated in FIG. 110, for example, the quick disconnect joint 130210 is employed to couple a distal shaft portion 130230 of end effector 131000 to a proximal shaft portion 130201.

The end effector exemplification 131000 illustrated in FIG. 111 includes a drive arrangement generally designated as 130748 that facilitates the selective application of rotary control motions to the end effector 131000. The end effector 131000 includes a firing member 131200 that is threadably journaled on an implement drive shaft 131300. As can be seen in FIG. 112, the implement drive shaft 131300 has a bearing segment 131304 formed thereon that is rotatably supported in a bearing sleeve 131011. The implement drive shaft 131300 has an implement drive gear 131302 that operably meshes with a rotary transmission generally designated as 130750 that operably interfaces with elongate channel 131020 and is operably supported by a portion of the elongate shaft assembly 130200. In one instance, the rotary transmission 130750 includes a differential interlock assembly 130760. As can be seen in FIGS. 115 and 116, the differential interlock assembly 130760 includes a differential housing 130762 that is configured to selectively rotate relative to end effector drive housing 131010 and to rotate with the end effector drive housing 131010.

A distal drive shaft segment is attached to a sun gear shaft 130752 that has a sun gear 130754 attached thereto. Thus, sun gear 130754 will rotate when the distal drive shaft segment is rotated. Sun gear 130754 will also move axially with the distal drive shaft segment. The differential interlock assembly 130760 further includes a plurality of planet gears 130764 that are rotatably attached to the differential housing 130762. In at least one exemplification, for example, three planet gears 130764 are employed. Each planet gear 130764 is in meshing engagement with a first end effector ring gear 131016 formed within the end effector drive housing 131010. In the illustrated example shown in FIG. 111, the end effector drive housing 131010 is non-rotatably attached to the elongate channel 131020 by a pair of opposing attachment lugs 131018 (only one attachment lug 131018 can be seen in FIG. 111) into corresponding attachment slots 131024 (only one attachment slot 131024 can be seen in FIG. 111) formed in the proximal end 131021 of the elongate channel 131020. Other methods of non-movably attaching the end effector drive housing 131010 to the elongate channel 131020 may be employed or the end effector drive housing 131010 may be integrally formed with the elongate channel 131020. Thus, rotation of the end effector drive housing 131010 will result in the rotation of the elongate channel 131020 of the end effector 131000.

In the exemplification depicted in FIGS. 112-116, the differential interlock assembly 130760 further includes a second ring gear 130766 that is formed within the differential housing 130762 for meshing engagement with the sun gear 130754. The differential interlock assembly 130760 also includes a third ring gear 130768 formed in the differential housing 130762 that is in meshing engagement with the implement drive gear 131302. Rotation of the differential housing 130762 within the end effector drive housing 131010 will ultimately result in the rotation of the implement drive gear 131302 and the implement drive shaft 131300 attached thereto.

When the clinician desires to rotate the end effector 131000 about the longitudinal tool axis LT-LT distal to articulation joint 130700 to position the end effector in a desired orientation relative to the target tissue, the robotic controller may activate a shifter solenoid to axially move a proximal drive shaft segment such that the sun gear 130754 is moved to a "first axial" position shown in FIGS. 116, 118-121. The distal drive shaft segment is operably coupled to the proximal drive shaft segment. Thus, axial movement of the proximal drive shaft segment may result in the axial movement of the distal drive shaft segment and the sun gear shaft 130752 and sun gear 130754. A shifting system controls the axial movement of the proximal drive shaft segment. When in a first axial position, the sun gear 130754 is in meshing engagement with the planetary gears 130764 and the second ring gear 130766 to thereby cause the planetary gears 130764 and the differential housing 130762 to rotate as a unit as the sun gear 130754 is rotated.

Rotation of the proximal drive shaft segment is controlled by the second drive system 130370. Rotation of the proximal drive shaft segment results in rotation of the distal drive shaft segment, the sun gear shaft 130752, and sun gear 130754. Such rotation of the differential housing 130762 and planetary gears 130764 as a unit applies a rotary motion to the end effector drive housing 131010 of sufficient magnitude to overcome a first amount of friction F1 between the end effector drive housing 131010 and the distal socket portion 130730 of the intermediate articulation tube 130712 to thereby cause the end effector drive housing 131010 and end effector 131000 attached thereto to rotate about the longitudinal tool axis "LT-LT" relative to the distal socket tube 130730. Thus, when in such position, the end effector drive housing 131010, the differential housing 130762 and the planetary gears 130764 all rotate together as a unit. Because the implement shaft 131300 is supported by the bearing sleeve 131011 in the end effector drive housing, the implement shaft 131300 also rotates with the end effector drive housing 131010. See FIG. 112. Thus, rotation of the end effector drive housing 131010 and the end effector 131000 does not result in relative rotation of the implement drive shaft 131300 which would result in displacement of the firing member 131200. In the illustrated example, such rotation of the end effector 131000 distal of the articulation joint 130700 does not result in rotation of the entire elongate shaft assembly 130200.

When it is desired to apply a rotary drive motion to the implement drive shaft 131300 for driving the firing member 131200 within the end effector 131000, the sun gear 130754 is axially positioned in a "second axial" position to disengage the second ring gear 130766 while meshingly engaging the planetary gears 130764 as shown in FIGS. 112, 113, 115 and 117. Thus, when it is desired to rotate the implement drive shaft 131300, the robotic controller activates the shifter solenoid to axially position the sun gear 130754 into meshing engagement with the planetary gears 130764. When in that second axial or "firing position", the sun gear 130754 only meshingly engages the planetary gears 130764.

Rotation of the proximal drive shaft segment may be controlled by the second drive system 130370. Rotation of the proximal drive shaft segment results in rotation of the distal drive shaft segment, the sun gear shaft 130752 and sun gear 130754. As the sun gear 130754 is rotated in a first firing direction, the planetary gears 130764 are also rotated. As the planetary gears 130764 rotate, they also cause the differential housing 130762 to rotate. Rotation of the differential housing 130762 causes the implement shaft 131300 to rotate due to the meshing engagement of the implement drive gear 131302 with the third ring gear 130768. Because of the amount of friction F1 existing between the end effector drive housing 131010 and the distal socket portion 130730 of the intermediate articulation tube 130712, rotation of the planetary gears 130764 does not result in the rotation of the end effector housing 131010 relative to the intermediate articulation tube 130712. Thus, rotation of the drive shaft assembly results in rotation of the implement drive shaft 131300 without rotating the entire end effector 131000.

Such unique and novel rotary transmission 130750 comprises a single drive system that can selectively rotate the end effector 131000 or fire the firing member 131200 depending upon the axial position of the rotary drive shaft. One advantage that may be afforded by such arrangement is that it simplifies the drives that must transverse the articulation joint 130700. It also translates the central drive to the base of the elongate channel 131020 so that the implement drive shaft 131300 can exist under staple cartridge 131040 to the drive the firing member 131200. The ability for an end effector to be rotatable distal to the articulation joint may vastly improve the ability to position the end effector relative to the target tissue.

As indicated above, when the drive shaft assembly is positioned in a first axial position, rotation of the drive shaft assembly may result in rotation of the entire end effector 131000 distal of the articulation joint 130700. When the drive shaft assembly is positioned in a second axial position (in one example-proximal to the first axial position), rotation of the drive shaft assembly may result in the rotation of the implement drive shaft 131300.

The rotary transmission exemplification depicted in FIGS. 115 and 116 includes a differential locking system 130780 which is configured to retain the drive shaft assembly in the first and second axial positions. As can be seen in FIGS. 115 and 116, the differential locking system 130780 comprises a first retention formation 130756 in the sun gear shaft 130752 that corresponds to the first axial position of the drive shaft assembly and a second retention formation 130758 in the sun gear shaft 130752 that correspond to the second axial position of the drive shaft assembly. In the illustrated example, the first retention formation comprises a first radial locking groove 130757 in the sun gear shaft 130752 and the second retention formation 130758 comprises a second radial locking groove 130759 formed in the sun gear shaft 130752. The first and second locking grooves 130757, 130759 cooperate with at least one spring-biased locking member 130784 that is adapted to retainingly engage the locking grooves 130757, 130759 when the drive shaft assembly is in the first and second axial positions, respectively.

The locking members 130784 have a tapered tip 130786 and are movably supported within the differential housing 130762. A radial wave spring 130782 may be employed to apply a biasing force to the locking members 130784 as shown in FIG. 114. When the drive shaft assembly is axially moved into the first position, the locking members 130784 snap into engagement with the first radial locking groove 130757. See FIG. 116. When the drive shaft assembly is axially moved into the second axial position, the locking members 130784 snap into engagement with the second radial locking groove 130759. See FIG. 115. In alternative exemplifications, the first and second retention formations may comprise, for example, dimples that correspond to each of the locking members 130784. Also in alternative exemplifications wherein the drive shaft assembly is axially positionable in more than two axial positions, addition retention formations may be employed which correspond to each of those axial positions.

FIGS. 121 and 122 illustrate an alternative differential locking system 130790 that is configured to ensure that the drive shaft assembly is locked into one of a plurality of predetermined axial positions. The differential locking system 130790 is configured to ensure that the drive shaft assembly is positionable in one of the first and second axial positions and is not inadvertently positioned in another axial position wherein the drive system is not properly operable. In the exemplification depicted in FIGS. 121 and 122, the differential locking system 130790 includes a plurality of locking springs 130792 that are attached to the drive shaft assembly. Each locking spring 130792 is formed with first and second locking valleys 130794, 130796 that are separated by a pointed peak portion 130798. The locking springs 130792 are located to cooperate with a pointed locking members 130763 formed on the differential housing 130762. Thus, when the pointed locking members 130763 are seated in the first locking valley 130794, the drive shaft assembly is retained in the first axial position and when the pointed locking members 130763 are seated in the second locking valleys 130796, the drive shaft assembly is retained in the second axial position. The pointed peak portion 130798 between the first and second locking valleys 130794, 130796 ensure that the drive shaft assembly is in one of the first and second axial positions and does not get stopped in an axial position between those two axial positions. If additional axial positions are desired, the locking springs may be provided with additional locking valleys that correspond to the desired axial positions.

Referring to FIGS. 111, 123 and 124, a thrust bearing 131030 is supported within a cradle 131026 in the elongate channel 131020. The distal end portion 131306 of the implement drive shaft 131300 is rotatably received within the thrust bearing 131030 and protrudes therethrough. A retaining collar 131032 is pinned or otherwise affixed to the distal end portion 131306 as shown in FIG. 124 to complete the installation Use of the thrust bearing 131030 in this manner may enable the firing member 131200 to be "pulled" as it is fired from a starting position to an ending position within the elongate channel 131020. Such arrangement may minimize the risk of buckling of the implement drive shaft 131300 under high load conditions. The unique and novel mounting arrangement and location of the thrust bearing 131030 may result in a seating load that increases with the anvil load which further increases the end effector stability. Such mounting arrangement may essentially serve to place the implement drive shaft 131300 in tension during the high load firing cycle. This may avoid the need for the drive system gears to both rotate the implement drive shaft 131300 and resist the buckling of the shaft 131300. Use of the retaining collar 131032 may also make the arrangement easy to manufacture and assemble. The firing member 131200 is configured to engage the anvil and retain the anvil at a desired distance from the cartridge deck as the firing member 131200 is driven from the starting to ending position. In this arrangement for example, as the firing member 131200 assembly moves distally down the elongate channel 131020, the length of the portion of the anvil that resembles a cantilever beam becomes shorter and stiffer thereby increasing the magnitude of downward loading occurring at the distal end of the elongate channel 131020 further increasing the bearing seating load.

One of the advantages of utilizing rotary drive members for firing, closing, rotating, etc. may include the ability to use the high mechanical advantage of the drive shaft to accommodate the high loads needed to accomplish those instrument tasks. However, when employing such rotary drive systems, it may be desirable to track the number of rotations that the drive shaft is driven to avoid catastrophic failure or damage to the drive screw and other instrument components in the event that the drive shaft or movable end effector component is driven too far in the distal direction.

Thus, some systems that include rotary drive shafts have, in the past, employed encoders to track the motor rotations or sensors to monitor the axial position of the movable component. The use of encoders and/or sensors require the need for additional wiring, electronics and processing power to accommodate such a system which can lead to increased instrument costs. Also, the system's reliability may be somewhat difficult to predict and its reliability depends upon software and processors.

FIGS. 110-124 and additional exemplifications are further described in U.S. Pat. No. 9,072,536, filed Jun. 28, 2012, entitled DIFFERENTIAL LOCKING ARRANGEMENTS FOR ROTARY POWERED SURGICAL INSTRUMENTS, which issued Jul. 7, 2015, the entire disclosure of which is incorporated by reference herein.

A surgical tool 140100 that is well-adapted for use with a robotic system is depicted in FIG. 125. FIG. 125 illustrates an additional exemplification of the surgical tool 140100 and electrosurgical end effector 143000. As can be seen in FIG. 125, the surgical tool 140100 includes an electrosurgical end effector 143000. The electrosurgical end effector 143000 may utilize electrical energy to treat and/or destroy tissue. The electrosurgical end effector 143000 generally comprises first and second jaw members 143008A, 143008B which may be straight or curved. One or both of the jaw members 143008A, 143008B generally comprise various electrodes for providing electrosurgical energy to tissue. The surgical tool 140100 generally includes an elongate shaft assembly 140200 that is operably coupled to the manipulator by a tool mounting portion, generally designated as 140300. Electrosurgical tools (e.g., surgical tools that include an electrosurgical end effector, such at the tool 140100 and end effector 143000) may be used in any suitable type of surgical environment including, for example, open, laparoscopic, endoscopic, etc.

Generally, electrosurgical tools comprise one or more electrodes for providing electric current. The electrodes may be positioned against and/or positioned relative to tissue such that electrical current can flow through the tissue. The electrical current may generate heat in the tissue that, in turn, causes one or more hemostatic seals to form within the tissue and/or between tissues. For example, tissue heating caused by the electrical current may at least partially denature proteins within the tissue. Such proteins, such as collagen, for example, may be denatured into a proteinaceous amalgam that intermixes and fuses, or "welds", together as the proteins renature. As the treated region heals over time, this biological "weld" may be reabsorbed by the body's wound healing process.

Electrical energy provided by electrosurgical tools may be of any suitable form including, for example, direct or alternating current. For example, the electrical energy may include high frequency alternating current such as radio frequency or "RF" energy. RF energy may include energy in the range of 300 kilohertz (kHz) to 1 megahertz (MHz). When applied to tissue, RF energy may cause ionic agitation or friction, increasing the temperature of the tissue. Also, RF energy may provide a sharp boundary between affected tissue and other tissue surrounding it, allowing surgeons to operate with a high level of precision and control. The low operating temperatures of RF energy enables surgeons to remove, shrink or sculpt soft tissue while simultaneously sealing blood vessels. RF energy works particularly well on connective tissue, which is primarily comprised of collagen and shrinks when contacted by heat.

In certain arrangements, some bi-polar (e.g., two-electrode) electrosurgical tools can comprise opposing first and second jaw members, where the face of each jaw can comprise a current path and/or electrode. In use, the tissue can be captured between the jaw faces such that electrical current can flow between the electrodes in the opposing jaw members and through the tissue positioned therebetween. Such tools may have to coagulate, seal or "weld" many types of tissues, such as anatomic structures having walls with irregular or thick fibrous content, bundles of disparate anatomic structures, substantially thick anatomic structures, and/or tissues with thick fascia layers such as large diameter blood vessels, for example. Some exemplifications may include a knife or cutting edge to transect the tissue, for example, during or after the application of electrosurgical energy. With particular regard to cutting and sealing large diameter blood vessels, for example, such applications may require a high strength tissue weld immediately post-treatment.

Referring now to FIGS. 125-127, the tool mounting portion 140300 operably supports a plurality of drive systems for generating various forms of control motions necessary to operate a particular type of end effector that is coupled to the distal end of the elongate shaft assembly 140200. As shown in FIGS. 125-127, the tool mounting portion 140300 includes a first drive system generally designated as 140350 that is configured to receive a corresponding "first" rotary output motion from the tool drive assembly of the robotic system and convert that first rotary output motion to a first rotary control motion to be applied to the surgical end effector. In the illustrated exemplification, the first rotary control motion is employed to rotate the elongate shaft assembly 140200 (and surgical end effector 143000) about a longitudinal tool axis LT-LT.

In the exemplification of FIGS. 125-127, the first drive system 140350 includes a tube gear segment 140354 that is formed on (or attached to) the proximal end 140208 of a proximal tube segment 140202 of the elongate shaft assembly 140200. The proximal end 140208 of the proximal tube segment 140202 is rotatably supported on tool mounting plate 140304 of the tool mounting portion 140300 by a forward support cradle 140352 that is mounted on the tool mounting plate 140304. See FIG. 126. The tube gear segment 140354 is supported in meshing engagement with a first rotational gear assembly 140360 that is operably supported on the tool mounting plate 140304. As can be seen in FIG. 126, the rotational gear assembly 140360 comprises a first rotation drive gear 140362 that is coupled to a corresponding first one of the driven discs or elements on the holder side of the tool mounting plate 140304 when the tool mounting portion 140300 is coupled to the tool drive assembly. The rotational gear assembly 140360 further comprises a first rotary driven gear 140364 that is rotatably supported on the tool mounting plate 140304. The first rotary driven gear 140364 is in meshing engagement with a second rotary driven gear 140366 which, in turn, is in meshing engagement with the tube gear segment 140354. Application of a first rotary output motion from the tool drive assembly of the robotic system to the corresponding driven element will thereby cause rotation of the rotation drive gear 140362. Rotation of the rotation drive gear 140362 ultimately results in the rotation of the elongate shaft assembly 140200 (and the surgical end effector 143000) about the longitudinal tool axis LT-LT (represented by arrow "R" in FIG. 125). It will be appreciated that the application of a rotary output motion from the tool drive assembly in one direction will result in the rotation of the elongate shaft assembly 140200 and surgical end effector 143000 about the longitudinal tool axis LT-LT in a first rotary direction and an application of the rotary output motion in an opposite direction will result in the rotation of the elongate shaft assembly 140200 and surgical end effector 143000 in a second rotary direction that is opposite to the first rotary direction.

In the exemplification of FIGS. 125-127, the tool mounting portion 140300 further includes a second drive system generally designated as 140370 that is configured to receive a corresponding "second" rotary output motion from the tool drive assembly of the robotic system and convert that second rotary output motion to a second rotary control motion for application to the surgical end effector. The second drive system 140370 includes a second rotation drive gear 140372 that is coupled to a corresponding second one of the driven discs or elements on the holder side of the tool mounting plate 140304 when the tool mounting portion 140300 is coupled to the tool drive assembly of the robotic system. The second drive system 140370 further comprises a first rotary driven gear 140374 that is rotatably supported on the tool mounting plate 140304. The first rotary driven gear 140374 is in meshing engagement with a shaft gear 140376 that is movably and non-rotatably mounted onto a proximal drive shaft segment 140380. In this illustrated exemplification, the shaft gear 140376 is non-rotatably mounted onto the proximal drive shaft segment 140380 by a series of axial keyways 140384 that enable the shaft gear 140376 to axially move on the proximal drive shaft segment 140380 while being non-rotatably affixed thereto. Rotation of the proximal drive shaft segment 140380 results in the transmission of a second rotary control motion to the surgical end effector 143000.

The second drive system 140370 in the exemplification of FIGS. 125-127 includes a shifting system 140390 for selectively axially shifting the proximal drive shaft segment 140380 which moves the shaft gear 140376 into and out of meshing engagement with the first rotary driven gear 140374. For example, as can be seen in FIGS. 126-127, the proximal drive shaft segment 140380 is supported within a second support cradle 140382 that is attached to the tool mounting plate 140304 such that the proximal drive shaft segment 140380 may move axially and rotate relative to the second support cradle 140382. In at least one form, the shifting system 140390 further includes a shifter yoke 140392 that is slidably supported on the tool mounting plate 140304. The proximal drive shaft segment 140380 is supported in the shifter yoke 140392 and has a pair of collars 140386 thereon such that shifting of the shifter yoke 140392 on the tool mounting plate 140304 results in the axial movement of the proximal drive shaft segment 140380. In at least one form, the shifting system 140390 further includes a shifter solenoid 140394 that operably interfaces with the shifter yoke 140392. The shifter solenoid 140394 receives control power from the robotic controller such that when the shifter solenoid 140394 is activated, the shifter yoke 140392 is moved in the distal direction "DD".

In this illustrated exemplification, a shaft spring 140396 is journaled on the proximal drive shaft segment 140380 between the shaft gear 140376 and the second support cradle 140382 to bias the shaft gear 140376 in the proximal direction "PD" and into meshing engagement with the first rotary driven gear 140374. See FIGS. 126-127. Rotation of the second rotation drive gear 140372 in response to rotary output motions generated by the robotic system ultimately results in the rotation of the proximal drive shaft segment 140380 and other drive shaft components coupled thereto (drive shaft assembly 140388) about the longitudinal tool axis LT-LT. It will be appreciated that the application of a rotary output motion from the tool drive assembly in one direction will result in the rotation of the proximal drive shaft segment 140380 and ultimately of the other drive shaft components attached thereto in a first direction and an application of the rotary output motion in an opposite direction will result in the rotation of the proximal drive shaft segment 140380 in a second direction that is opposite to the first direction. When it is desirable to shift the proximal drive shaft segment 140380 in the distal direction "DD" as will be discussed in further detail below, the robotic controller activates the shifter solenoid 140390 to shift the shifter yoke 140392 in the distal direction "DD". In some exemplifications, the shifter solenoid 140390 may be capable of shifting the proximal drive shaft segment 140380 between more than two longitudinal positions. For example, some exemplifications, such as those described herein with respect to FIGS. 140-153, may utilize the rotary drive shaft (e.g., coupled to the proximal drive shaft segment 140380) in more than two longitudinal positions.

The exemplification illustrated in FIGS. 125-127 includes a manually-actuatable reversing system, generally designated as 140410, for manually applying a reverse rotary motion to the proximal drive shaft segment 140380 in the event that the motor fails or power to the robotic system is lost or interrupted. Such manually-actuatable reversing system 140410 may also be particularly useful, for example, when the drive shaft assembly 140388 becomes jammed or otherwise bound in such a way that would prevent reverse rotation of the drive shaft components under the motor power alone. In the illustrated exemplification, the mechanically-actuatable reversing system 140410 includes a drive gear assembly 140412 that is selectively engageable with the second rotary driven gear 140376 and is manually actuatable to apply a reversing rotary motion to the proximal drive shaft segment 140380. The drive gear assembly 140412 includes a reversing gear 140414 that is movably mounted to the tool mounting plate 140304. The reversing gear 140414 is rotatably journaled on a pivot shaft 140416 that is movably mounted to the tool mounting plate 140304 through a slot 140418. See FIG. 127. In the exemplification of FIGS. 125-127, the manually-actuatable reversing system 140410 further includes a manually actuatable drive gear 140420 that includes a body portion 140422 that has an arcuate gear segment 140424 formed thereon. The body portion 140422 is pivotally coupled to the tool mounting plate 140304 for selective pivotal travel about an actuator axis A-A (FIG. 126) that is substantially normal to the tool mounting plate 140304.

FIGS. 126-127 depict the manually-actuatable reversing system 140410 in a first unactuated position. In one example form, an actuator handle portion 140426 is formed on or otherwise attached to the body portion 140422. The actuator handle portion 140426 is sized relative to the tool mounting plate 140304 such that a small amount of interference is established between the handle portion 140426 and the tool mounting plate 140304 to retain the handle portion 140426 in the first unactuated position. However, when the clinician desires to manually actuate the drive gear assembly 140412, the clinician can easily overcome the interference fit by applying a pivoting motion to the handle portion 140426. As can also be seen in FIGS. 126-127, when the drive gear assembly 140412 is in the first unactuated position, the arcuate gear segment 140424 is out of meshing engagement with the reversing gear 140414. When the clinician desires to apply a reverse rotary drive motion to the proximal drive shaft segment 140380, the clinician begins to apply a pivotal ratcheting motion to drive gear 140420. As the drive gear 140420 begins to pivot about the actuation axis A-A, a portion of the body 140422 contacts a portion of the reversing gear 140414 and axially moves the reversing gear 140414 in the distal direction DD taking the drive shaft gear 140376 out of meshing engagement with the first rotary driven gear 140374 of the second drive system 140370. As the drive gear 140420 is pivoted, the arcuate gear segment 140424 is brought into meshing engagement with the reversing gear 140414. Continued ratcheting of the drive gear 140420 results in the application of a reverse rotary drive motion to the drive shaft gear 140376 and ultimately to the proximal drive shaft segment 140380. The clinician may continue to ratchet the drive gear assembly 140412 for as many times as are necessary to fully release or reverse the associated end effector component(s). Once a desired amount of reverse rotary motion has been applied to the proximal drive shaft segment 140380, the clinician returns the drive gear 140420 to the starting or unactuated position wherein the arcuate gear segment 140424 is out of meshing engagement with the drive shaft gear 140376. When in that position, the shaft spring 140396 once again biases the shaft gear 140376 into meshing engagement with first rotary driven gear 140374 of the second drive system 140370.

In use, the clinician may input control commands to the controller or control unit of the robotic system which "robotically-generates" output motions that are ultimately transferred to the various components of the second drive system 140370. As used herein, the terms "robotically-generates" or "robotically-generated" refer to motions that are created by powering and controlling the robotic system motors and other powered drive components. These terms are distinguishable from the terms "manually-actuatable" or "manually generated" which refer to actions taken by the clinician which result in control motions that are generated independent from those motions that are generated by powering the robotic system motors. Application of robotically-generated control motions to the second drive system in a first direction results in the application of a first rotary drive motion to the drive shaft assembly 140388. When the drive shaft assembly 140388 is rotated in a first rotary direction, an axially movable member is driven in the distal direction "DD" from its starting position toward its ending position in the end effector 143000, for example, as described herein with respect to FIGS. 129-153. Application of robotically-generated control motions to the second drive system in a second direction results in the application of a second rotary drive motion to the drive shaft assembly 140388. When the drive shaft assembly 140388 is rotated in a second rotary direction, the axially movable member is driven in the proximal direction "PD" from its ending position toward its starting position in the end effector 143000. When the clinician desires to manually-apply rotary control motion to the drive shaft assembly 140388, the drive shaft assembly 140388 is rotated in the second rotary direction which causes a firing member (e.g., the axially movable member) to move in the proximal direction "PD" in the end effector. Other exemplifications containing the same components are configured such that the manual-application of a rotary control motion to the drive shaft assembly could cause the drive shaft assembly to rotate in the first rotary direction which could be used to assist the robotically-generated control motions to drive the axially movable member in the distal direction.

The drive shaft assembly that is used to fire, close and rotate the end effector can be actuated and shifted manually allowing the end effector to release and be extracted from the surgical site as well as the abdomen even in the event that the motor(s) fail, the robotic system loses power or other electronic failure occurs. Actuation of the handle portion 140426 results in the manual generation of actuation or control forces that are applied to the drive shaft assembly 140388 by the various components of the manually-actuatable reversing system 140410. If the handle portion 140426 is in its unactuated state, it is biased out of actuatable engagement with the reversing gear. The beginning of the actuation of the handle portion 140426 shifts the bias. The handle 140426 is configured for repeated actuation for as many times as are necessary to fully release the axially movable member and the end effector 143000.

As illustrated in FIGS. 125-127, the tool mounting portion 140300 includes a third drive system 140430 that is configured to receive a corresponding "third" rotary output motion from the tool drive assembly of the robotic system and convert that third rotary output motion to a third rotary control motion. The third drive system 140430 includes a third drive pulley 140432 that is coupled to a corresponding third one of the driven discs or elements on the holder side of the tool mounting plate 140304 when the tool mounting portion 140300 is coupled to the tool drive assembly of the robotic system. The third drive pulley 140432 is configured to apply a third rotary control motion (in response to corresponding rotary output motions applied thereto by the robotic system) to a corresponding third drive cable 140434 that may be used to apply various control or manipulation motions to the end effector that is operably coupled to the shaft assembly 140200. As can be most particularly seen in FIGS. 126-127, the third drive cable 140434 extends around a third drive spindle assembly 140436. The third drive spindle assembly 140436 is pivotally mounted to the tool mounting plate 140304 and a third tension spring 140438 is attached between the third drive spindle assembly 140436 and the tool mounting plate 140304 to maintain a desired amount of tension in the third drive cable 140434. As can be seen in the Figures, cable end portion 140434A of the third drive cable 140434 extends around an upper portion of a pulley block 140440 that is attached to the tool mounting plate 140304 and cable end portion 140434B extends around a sheave pulley or standoff on the pulley block 140440. It will be appreciated that the application of a third rotary output motion from the tool drive assembly in one direction will result in the rotation of the third drive pulley 140432 in a first direction and cause the cable end portions 140434A and 140434B to move in opposite directions to apply control motions to the end effector 143000 or elongate shaft assembly 140200 as will be discussed in further detail below. That is, when the third drive pulley 140432 is rotated in a first rotary direction, the cable end portion 140434A moves in a distal direction "DD" and cable end portion 140434B moves in a proximal direction "PD". Rotation of the third drive pulley 140432 in an opposite rotary direction result in the cable end portion 140434A moving in a proximal direction "PD" and cable end portion 140434B moving in a distal direction "DD".

The tool mounting portion 140300 illustrated in FIGS. 125-127 includes a fourth drive system 140450 that is configured to receive a corresponding "fourth" rotary output motion from the tool drive assembly of the robotic system and convert that fourth rotary output motion to a fourth rotary control motion. The fourth drive system 140450 includes a fourth drive pulley 140452 that is coupled to a corresponding fourth one of the driven discs or elements on the holder side of the tool mounting plate 140304 when the tool mounting portion 140300 is coupled to the tool drive assembly of the robotic system. The fourth drive pulley 140452 is configured to apply a fourth rotary control motion (in response to corresponding rotary output motions applied thereto by the robotic system) to a corresponding fourth drive cable 140454 that may be used to apply various control or manipulation motions to the end effector that is operably coupled to the shaft assembly 140200. As can be most particularly seen in FIGS. 126-127, the fourth drive cable 140454 extends around a fourth drive spindle assembly 140456. The fourth drive spindle assembly 140456 is pivotally mounted to the tool mounting plate 140304 and a fourth tension spring 140458 is attached between the fourth drive spindle assembly 140456 and the tool mounting plate 140304 to maintain a desired amount of tension in the fourth drive cable 140454. Cable end portion 140454A of the fourth drive cable 140454 extends around a bottom portion of the pulley block 140440 that is attached to the tool mounting plate 140304 and cable end portion 140454B extends around a sheave pulley or fourth standoff on the pulley block 140440. It will be appreciated that the application of a rotary output motion from the tool drive assembly in one direction will result in the rotation of the fourth drive pulley 140452 in a first direction and cause the cable end portions 140454A and 140454B to move in opposite directions to apply control motions to the end effector or elongate shaft assembly 140200 as will be discussed in further detail below. That is, when the fourth drive pulley 140434 is rotated in a first rotary direction, the cable end portion 140454A moves in a distal direction "DD" and cable end portion 140454B moves in a proximal direction "PD". Rotation of the fourth drive pulley 140452 in an opposite rotary direction result in the cable end portion 140454A moving in a proximal direction "PD" and cable end portion 140454B to move in a distal direction "DD".

The surgical tool 140100 as depicted in FIG. 125 includes an articulation joint 143500. In such exemplification, the third drive system 140430 may also be referred to as a "first articulation drive system" and the fourth drive system 140450 may be referred to herein as a "second articulation drive system". Likewise, the third drive cable 140434 may be referred to as a "first proximal articulation cable" and the fourth drive cable 140454 may be referred to herein as a "second proximal articulation cable".

The tool mounting portion 140300 of the exemplification illustrated in FIGS. 125-127 includes a fifth drive system generally designated as 140470 that is configured to axially displace a drive rod assembly 140490. The drive rod assembly 140490 includes a proximal drive rod segment 140492 that extends through the proximal drive shaft segment 140380 and the drive shaft assembly 140388. The fifth drive system 140470 includes a movable drive yoke 140472 that is slidably supported on the tool mounting plate 140304. The proximal drive rod segment 140492 is supported in the drive yoke 140472 and has a pair of retainer balls 140494 thereon such that shifting of the drive yoke 140472 on the tool mounting plate 140304 results in the axial movement of the proximal drive rod segment 140492. In at least one example form, the fifth drive system 140470 further includes a drive solenoid 140474 that operably interfaces with the drive yoke 140472. The drive solenoid 140474 receives control power from the robotic controller. Actuation of the drive solenoid 140474 in a first direction will cause the drive rod assembly 140490 to move in the distal direction "DD" and actuation of the drive solenoid 140474 in a second direction will cause the drive rod assembly 140490 to move in the proximal direction "PD". As can be seen in FIG. 125, the end effector 143000 includes a jaw members that are movable between open and closed positions upon application of axial closure motions to a closure system. In the illustrated exemplification of FIGS. 125-127, the fifth drive system 140470 is employed to generate such closure motions. Thus, the fifth drive system 140470 may also be referred to as a "closure drive".

The surgical tool 140100 depicted in FIGS. 125-127 includes an articulation joint 143500 that cooperates with the third and fourth drive systems 140430, 140450, respectively for articulating the end effector 143000 about the longitudinal tool axis "LT". The articulation joint 143500 includes a proximal socket tube 143502 that is attached to the distal end 140233 of the distal outer tube portion 140231 and defines a proximal ball socket 143504 therein. See FIG. 128. A proximal ball member 143506 is movably seated within the proximal ball socket 143504. As can be seen in FIG. 128, the proximal ball member 143506 has a central drive passage 143508 that enables a distal drive shaft segment 143740 to extend therethrough. In addition, the proximal ball member 143506 has four articulation passages 143510 therein which facilitate the passage of distal cable segments 140444, 140445, 140446, 140447 therethrough (only distal cable segments 140444 and 140445 are shown in FIG. 128). In various exemplifications, distal cable segments 140444, 140445, 140446, 140447 may be directly or indirectly coupled to proximal cable end portions 140434A, 140434B, 140454A, 140454B, respectively, for example. As can be further seen in FIG. 128, the articulation joint 143500 further includes an intermediate articulation tube segment 143512 that has an intermediate ball socket 143514 formed therein. The intermediate ball socket 143514 is configured to movably support therein an end effector ball 143522 formed on an end effector connector tube 143520. The distal cable segments 140444, 140445, 140446, 140447 extend through cable passages 143524 formed in the end effector ball 143522 and are attached thereto by lugs 143526 received within corresponding passages 143528 in the end effector ball 143522. Other attachment arrangements may be employed for attaching distal cable segments 140444, 140445, 140446, 140447 to the end effector ball 143522.

The articulation joint 143500 facilitates articulation of the end effector 143000 about the longitudinal tool axis LT. For example, when it is desirable to articulate the end effector 143000 in a first direction "FD" as shown in FIG. 125, the robotic system may power the third drive system 140430 such that the third drive spindle assembly 140436 (FIGS. 126-127) is rotated in a first direction thereby drawing the proximal cable end portion 140434A and ultimately distal cable segment 140444 in the proximal direction "PD" and releasing the proximal cable end portion 140434B and distal cable segment 140445 to thereby cause the end effector ball 143522 to rotate within the socket 143514. Likewise, to articulate the end effector 143000 in a second direction "SD" opposite to the first direction FD, the robotic system may power the third drive system 140430 such that the third drive spindle assembly 140436 is rotated in a second direction thereby drawing the proximal cable end portion 140434B and ultimately distal cable segment 140445 in the proximal direction "PD" and releasing the proximal cable end portion 140434A and distal cable segment 140444 to thereby cause the end effector ball 143522 to rotate within the socket 143514. When it is desirable to articulate the end effector 143000 in a third direction "TD" as shown in FIG. 125, the robotic system may power the fourth drive system 140450 such that the fourth drive spindle assembly 140456 is rotated in a third direction thereby drawing the proximal cable end portion 140454A and ultimately distal cable segment 140446 in the proximal direction "PD" and releasing the proximal cable end portion 140454B and distal cable segment 140447 to thereby cause the end effector ball 143522 to rotate within the socket 143514. Likewise, to articulate the end effector 143000 in a fourth direction "FTHD" opposite to the third direction TD, the robotic system may power the fourth drive system 140450 such that the fourth drive spindle assembly 140456 is rotated in a fourth direction thereby drawing the proximal cable end portion 140454B and ultimately distal cable segment 140447 in the proximal direction "PD" and releasing the proximal cable end portion 140454A and distal cable segment 140446 to thereby cause the end effector ball 3522 to rotate within the socket 143514.

Referring to FIGS. 129-137, a multi-axis articulating and rotating surgical tool 140600 comprises an end effector 140550 comprising a first jaw member 140602A and a second jaw member 140602B. The first jaw member 140602A is movable relative to the second jaw member 140602B between an open position (FIGS. 129, 131-134, and 136) and a closed position (FIGS. 135 and 137) to clamp tissue between the first jaw member 140602A and the second jaw member 140602B. The surgical tool 140600 is configured to independently articulate about an articulation joint 140640 in a vertical direction (labeled direction V in FIGS. 129 and 131-137) and a horizontal direction (labeled direction H in FIGS. 129 and 130-133). Actuation of the articulation joint 140640 may be brought about in a manner similar to that described above with respect to FIGS. 126-128. The surgical tool 140600 is configured to independently rotate about a head rotation joint 140645 in a longitudinal direction (labeled direction H in FIGS. 129 and 131-137). The end effector 140550 comprises an I-beam member 140620 and a jaw assembly 140555 comprising the first jaw member 140602A, the second jaw member 140602B, a proximal portion 140603 of the second jaw member 140602B, and a rotary drive nut 140606 seated in the proximal portion 140603. The I-beam member 140620 and jaw assembly 140555 may operate in a manner described herein and similar to that described above with respect to the axially movable member and jaw members 143008A, 143008B described herein above.

The end effector 140550 is coupled to a shaft assembly 140560 comprising an end effector drive housing 140608, an end effector connector tube 140610, an intermediate articulation tube segment 140616, and a distal outer tube portion 140642. The end effector 140550 and the shaft assembly 140560 together comprise the surgical tool 140600. The end effector 140550 may be removably coupled to the end effector drive housing 140608 using a mechanism. The end effector connector tube 140610 comprises a cylindrical portion 140612 and a ball member 140614. The end effector drive housing 140608 is coupled to the cylindrical portion 140612 of the end effector connector tube 140610 through the head rotation joint 140645. The end effector 140550 and the end effector drive housing 140608 together comprise a head portion 140556 of the surgical tool 140600. The head portion 140556 of the surgical tool 140600 is independently rotatable about the head rotation joint 140645, as described in greater detail below.

The intermediate articulation tube segment 140616 comprises a ball member 140618 and a ball socket 140619. The end effector connector tube 140610 is coupled to the intermediate articulation tube segment 140616 through a ball-and-socket joint formed by the mutual engagement of the ball member 140614 of the end effector connector tube 140610 and the ball socket 140619 of the intermediate articulation tube segment 140616. The intermediate articulation tube segment 140616 is coupled to the distal outer tube portion 140642 through a ball-and-socket joint formed by the mutual engagement of the ball member 140618 of the intermediate articulation tube segment 140616 and a ball socket of the distal outer tube portion 140642. The articulation joint 140640 comprises the end effector connector tube 140610, the intermediate articulation tube segment 140616, and the distal outer tube portion 140642. The independent vertical articulation and/or horizontal articulation of the surgical tool 140600 about the articulation joint 140640 may be actuated, for example, using independently actuatable cable segments, such as 140444, 140445, 140446, 140447 described herein above, connected to the ball member 140614 of the end effector connector tube 140610. This independent articulation functionality is described, for example, in connection with FIG. 126-128. Robotic and hand-held apparatuses for allowing a clinician to initiate articulation functionality are described, for example, in connection with FIGS. 125-128.

The movement of the first jaw member 140602A relative to the second jaw member 140602B between an open position (FIGS. 129, 131-134, and 136) and a closed position (FIGS. 135 and 137) may be actuated with a suitable closure actuation mechanism. Referring to FIGS. 138 and 139, closure of the jaw assembly 140555 may be actuated by translation of the I-beam member 140620. The I-beam member 140620 comprises a first I-beam flange 140622A and a second I-beam flange 140622B. The first I-beam flange 140622A and the second I-beam flange 140622B are connected with an intermediate portion 140624. The intermediate portion 140624 of the I-beam member 140620 comprises a cutting member 140625, which is configured to transect tissue clamped between the first jaw member 140602A and the second jaw member 140602B when the jaw assembly 140555 is in a closed position.

The I-beam member 140620 is configured to translate within a first channel 140601A in the first jaw member 140602A and within a second channel 140601B in the second jaw member 140602B. The first channel 140601A comprises a first channel flange 140605A, and the second channel 140601B comprises a second channel flange 140605B. The first I-beam flange 140622A can define a first cam surface 140626A, and the second I-beam flange 140622B can define a second cam surface 140626B. The first and second cam surfaces 140626A and 140626B can slidably engage outwardly-facing opposed surfaces of the first and second channel flanges 140605A and 140605B, respectively. More particularly, the first cam surface 140626A can comprise a suitable profile configured to slidably engage the opposed surface of the first channel flange 140605A of the first jaw member 140602A and, similarly, the second cam surface 140626B can comprise a suitable profile configured to slidably engage the opposed surface of the second channel flange 140605B of the second jaw member 140602B, such that, as the I-beam member 140620 is advanced distally, the cam surfaces 140626A and 140626B can co-operate to cam first jaw member 140602A toward second jaw member 140602B and move the jaw assembly 140555 from an open position to a closed position as indicated by arrow 140629 in FIG. 139.

FIG. 138 shows the I-beam member 140620 in a fully proximal position and the jaw assembly 140555 in an open position. In the position shown in FIG. 138, the first cam surface 140626A is engaging a proximal portion of an arcuate-shaped anvil surface 140628, which mechanically holds the first jaw member 140602A open relative to the second jaw member 140602B (FIGS. 134 and 136). Translation of the I-beam member 140620 distally in a longitudinal direction (labeled direction L in FIGS. 129 and 131-139) results in sliding engagement of the first cam surface 140626A with the length of the arcuate-shaped anvil surface 140628, which cams first jaw member 140602A toward second jaw member 140602B until the first cam surface 140626A is engaging a distal portion of the arcuate-shaped anvil surface 140628. After the distal translation of the I-beam member 140620 for a predetermined distance, the first cam surface 140626A engages a distal portion of the arcuate-shaped anvil surface 140628 and the jaw assembly is in the closed position (FIG. 139). Thereafter, the I-beam member 140620 can be further translated distally in order to transect tissue clamped between the first jaw member 140602A and the second jaw member 140602B when in the closed position.

During distal translation of the I-beam member 140620 after closure of the jaw assembly, the first and second cam surfaces 140626A and 140626B of the first and second I-beam flanges 140622A and 140622B slidably engage the opposed surfaces of the first and second channel flanges 140605A and 140605B, respectively. In this manner, the I-beam member is advanced distally through the first and second channels 140601A and 140601B of the first and second jaw members 140602A and 140602B.

The distal, or leading, end of the I-beam member 140620 comprises the cutting member 140625, which may be a sharp edge or blade configured to cut through clamped tissue during a distal translation stroke of the I-beam member, thereby transecting the tissue. FIGS. 137 and 135 show the I-beam member 140620 in a fully distal position after a distal translation stroke. After a distal translation stroke, the I-beam member 140620 may be proximally retracted back to the longitudinal position shown in FIG. 139 in which the jaw assembly remains closed, clamping any transected tissue between the first jaw member 140602A and the second jaw member 140602B. Further retraction of the I-beam member to the fully proximal position (FIGS. 134, 136, and 138) will result in engagement of the first cam surface 140626A and the proximal portion of the anvil surface 140628, which cams the first jaw member 140602A away from the second jaw member 140602B, opening the jaw assembly 140555.

Before, during, and/or after the I-beam member 140620 is advanced through tissue clamped between the first jaw member 140602A and the second jaw member 140602B, electrical current can be supplied to electrodes located in the first and/or second jaw members 140602A and 140602B in order to weld/fuse the tissue, as described in greater detail in this specification. For example, electrodes may be configured to deliver RF energy to tissue clamped between the first jaw member 140602A and the second jaw member 140602B when in a closed position to weld/fuse the tissue.

Distal and proximal translation of the I-beam member 140620 between a proximally retracted position (FIGS. 129, 131-134, 136, and 138), an intermediate position (FIG. 139), and a distally advanced position (FIGS. 135 and 137) may be accomplished with a suitable translation actuation mechanism Referring to FIGS. 130-137, the I-beam member 140620 is connected to a threaded rotary drive member 140604. The threaded rotary drive nut 140606 is threaded onto the threaded rotary drive member 140604. As described above, the threaded rotary drive nut 140606 is seated in the proximal portion 140603 of the second jaw member 140602B. The threaded rotary drive nut 140606 is mechanically constrained from translation in any direction, but the threaded rotary drive nut 140606 is rotatable within the proximal portion 140603 of the second jaw member 140602B. Therefore, given the threaded engagement of the rotary drive nut 140606 and the threaded rotary drive member 140604, rotational motion of the rotary drive nut 140606 is transformed into translational motion of the threaded rotary drive member 140604 in the longitudinal direction and, in turn, into translational motion of the I-beam member 140620 in the longitudinal direction.

The threaded rotary drive member 140604 is threaded through the rotary drive nut 140606 and is located inside a lumen of a rotary drive shaft 140630. The threaded rotary drive member 140604 is not attached or connected to the rotary drive shaft 140630. The threaded rotary drive member 140604 is freely movable within the lumen of the rotary drive shaft 140630 and will translate within the lumen of the rotary drive shaft 140630 when driven by rotation of the rotary drive nut 140606. The rotary drive shaft 140630 comprising the threaded rotary drive member 140604 located within the lumen of the rotary drive shaft 140630 forms a concentric rotary drive shaft/screw assembly that is located in the lumen of the shaft assembly 140560.

As shown in FIG. 130, the end effector drive housing 140608, the end effector connector tube 140610, and the intermediate articulation tube segment 140616, which together comprise the shaft assembly 140560, have open lumens and, therefore, the shaft assembly has a lumen, as shown in FIGS. 131-133. Referring again to FIGS. 131-133, the concentric rotary drive shaft/threaded rotary drive member assembly is located within the lumen of the shaft assembly 140560 and passes through the end effector drive housing 140608, the end effector connector tube 140610, and the intermediate articulation tube segment 140616. Although not shown in FIGS. 131-133, at least the rotary drive shaft 140630 passes through a lumen of the distal outer tube portion 140642 and is operably coupled to a driving mechanism that provides rotational and axial translational motion to the rotary drive shaft 140630. For example, in some exemplifications, the surgical tool 140600 may be operably coupled through the shaft assembly 140560 to a robotic surgical system that provides rotational motion and axial translational motion to the rotary drive shaft 140630, such as, for example, the robotic surgical systems described in connection with FIGS. 125-127. For example, the rotary drive shaft 140630 may be operably coupled, through the shaft assembly 140560, to the proximal drive shaft segment 140380 described herein above. Also, in some exemplifications, the surgical tool 140600 may be utilized in conjunction with a hand-held surgical device.

The rotary drive shaft 140630 comprises a rotary drive head 140632. The rotary drive head 140632 comprises a female hex coupling portion 140634 on the distal side of the rotary drive head 140632, and the rotary drive head 140632 comprises a male hex coupling portion 140636 on the proximal side of the rotary drive head 140632. The distal female hex coupling portion 140634 of the rotary drive head 140632 is configured to mechanically engage with a male hex coupling portion 140607 of the rotary drive nut 140606 located on the proximal side of the rotary drive nut 140606. The proximal male hex coupling portion 140636 of the rotary drive head 140632 is configured to mechanically engage with a female hex shaft coupling portion 140609 of the end effector drive housing 140608.

Referring to FIGS. 131, 132, 134, and 135, the rotary drive shaft 140630 is shown in a fully distal axial position in which the female hex coupling portion 140634 of the rotary drive head 140632 is mechanically engaged with the male hex coupling portion 140607 of the rotary drive nut 140606. In this configuration, rotation of the rotary drive shaft 140630 actuates rotation of the rotary drive nut 140606, which actuates translation of the threaded rotary drive member 140604, which actuates translation of the I-beam member 140620. The orientation of the threading of the threaded rotary drive member 140604 and the rotary drive nut 140606 may be established so that either clockwise or counterclockwise rotation of the rotary drive shaft 140630 will actuate distal or proximal translation of the threaded rotary drive member 140604 and I-beam member 140620. In this manner, the direction, speed, and duration of rotation of the rotary drive shaft 140630 can be controlled in order to control the direction, speed, and magnitude of the longitudinal translation of the I-beam member 140620 and, therefore, the closing and opening of the jaw assembly and the transection stroke of the I-beam member along the first and second channels 140601A and 140601B, as described above.

Referring to FIG. 134, for example, rotation of the rotary drive shaft 140630 in a clockwise direction (as viewed from a proximal-to-distal vantage point) actuates clockwise rotation of the rotary drive nut 140606, which actuates distal translation of the threaded rotary drive member 140604, which actuates distal translation of the I-beam member 140620, which actuates closure of the jaw assembly and a distal transection stroke of the I-beam member 140620/cutting member 140625. Referring to FIG. 135, for example, rotation of the rotary drive shaft 140630 in a counterclockwise direction (as viewed from a proximal-to-distal vantage point) actuates counterclockwise rotation of the rotary drive nut 140606, which actuates proximal translation of the threaded rotary drive member 140604, which actuates proximal translation of the I-beam member 140620, which actuates a proximal return stroke of the I-beam member 140620/cutting member 140625 and opening of the jaw assembly. In this manner, the rotary drive shaft 140630 may be used to independently actuate the opening and closing of the jaw assembly and the proximal-distal transection stroke of the I-beam 140620/cutting member 140625.

Referring to FIGS. 133, 136, and 137, the rotary drive shaft 140630 is shown in a fully proximal axial position in which the male hex coupling portion 140636 of the rotary drive head 140632 is mechanically engaged with the female hex shaft coupling portion 140609 of the end effector drive housing 140608. In this configuration, rotation of the rotary drive shaft 140630 actuates rotation of the head portion 140556 of the surgical tool 140600 about rotation joint 140645, including rotation of the end effector 140550 and the end effector drive housing 140608. In this configuration, the portion of the surgical tool 140600 that is distal to the head rotation joint 140645 (i.e., the head portion 140556 of the surgical tool 140600, comprising the end effector 140550 and the end effector drive housing 140608) rotates with rotation of the rotary drive shaft 140630, and the portion of the surgical tool that is proximal to the head rotation joint 140645 (e.g., the end effector connector tube 140610, the intermediate articulation tube segment 140616, and the distal outer tube portion 140642) does not rotate with rotation of the rotary drive shaft 140630. It will be appreciated that a desired rotation speed of the rotary drive shaft 140630 to drive the rotary drive nut 140606 may be greater than a desired rotational speed for rotating the head portion 140556. For example, the rotary drive shaft 140630 may be driven by a motor that is operable at different rotary speeds.

Referring to FIG. 136, for example, rotation of the rotary drive shaft 140630 in a clockwise direction (as viewed from a proximal-to-distal vantage point) actuates clockwise rotation of the end effector 140550 and the end effector drive housing 140608 (i.e., the head portion 140556 of the surgical tool 140600) with the jaw assembly 140555 in an open position. Rotation of the rotary drive shaft 140630 in a counterclockwise direction (as viewed from a proximal-to-distal vantage point) actuates counterclockwise rotation of the end effector 140550 and the end effector drive housing 140608 with the jaw assembly 140555 in an open position. Referring to FIG. 137, for example, rotation of the rotary drive shaft 140630 in a clockwise direction (as viewed from a proximal-to-distal vantage point) actuates clockwise rotation of the end effector 140550 and the end effector drive housing 140608 with the jaw assembly 140555 in a closed position. Rotation of the rotary drive shaft 140630 in a counterclockwise direction (as viewed from a proximal-to-distal vantage point) actuates counterclockwise rotation of the end effector 140550 and the end effector drive housing 140608 with the jaw assembly 140555 in a closed position. Although not shown, it is understood that the I-beam member 140620 may be located in an intermediate position where the jaw assembly is closed but the I-beam is not fully distally advanced (see, e.g., FIG. 139) when the rotary drive shaft 140630 is in a fully proximal axial position and the male hex coupling portion 140636 of the rotary drive head 140632 is mechanically engaged with the female hex shaft coupling portion 140609 of the end effector drive housing 140608 to actuate rotation of the head portion of the surgical tool.

Thus, the rotary drive shaft 140630 may be used to independently actuate the opening and closing of the jaw assembly, the proximal-distal transection stroke of the I-beam 140620/cutting member 140625, and the rotation of the head portion 140556 of the surgical tool 140600.

Referring to FIGS. 140-148, a multi-axis articulating and rotating surgical tool 141200 comprises an end effector 141202 including a jaw assembly 141211 comprising a first jaw member 141204 and a second jaw member 141206. The first jaw member 141204 is movable relative to the second jaw member 141206 between an open position and a closed position to clamp tissue between the first jaw member 141204 and the second jaw member 141206. The surgical tool 141200 is configured to independently articulate about an articulation joint 141208. As described above, the surgical tool 141200 is also configured to independently rotate about a head rotation joint 141210. Referring primarily to FIG. 140, the end effector 141202 further comprises a proximal shaft portion 141212.

The end effector 141202 is coupled to a shaft assembly 141214 comprising an end effector drive housing 141216, an end effector connector tube 141218, an intermediate articulation tube segment 141220, and a distal outer tube portion. The end effector 141202 and the shaft assembly 141214 together can comprise the surgical tool 141200. The end effector 141202 may be removably coupled to the end effector drive housing 141216 using a mechanism. The end effector connector tube 141218 comprises a cylindrical portion 141222 and a ball portion 141224. The end effector drive housing 141216 is coupled to the cylindrical portion 141222 of the end effector connector tube 141218 through the head rotation joint 141210. The end effector 141202 and the end effector drive housing 141216 together comprise a head portion of the surgical tool 141200. The head portion of the surgical tool 141200 is independently rotatable about the head rotation joint 141210.

Referring primarily to FIGS. 140-144, the surgical tool 141200 may include a closure mechanism 141226 for moving the first jaw member 141204 relative to the second jaw member 141206 between an open position (FIG. 143) and a closed position (FIG. 144).

As illustrated, in FIG. 140, the first jaw member 141204 may include first mounting holes 141228, and the second jaw member 141206 may include second mounting holes. The first jaw member 141204 can be arranged relative to the second jaw member 141206 such that a pivot or trunnion pin extends through the first mounting holes 141228 of the first jaw member 141204 and the second mounting holes of the second jaw member 141206 to pivotally couple the first jaw member 141204 to the second jaw member 141206. Other suitable means for coupling the first jaw member 141204 and the second jaw member 141206 are within the scope of this disclosure.

Referring to FIGS. 140-148, the closure mechanism 141226 may comprise a linkage arrangement which may comprise a first link 141230 and a second link. The closure mechanism 141226 may also comprise a closure driver in the form of a closure nut 141232 for example. The closure nut 141232 (FIG. 140) may be at least partially positioned within the end effector drive housing 141216. In use, the closure nut 141232 may translate axially between a first position (FIG. 143) and a second position (FIG. 144) relative to the end effector drive housing 141216 and may include a first arm 141234 and a second arm 141236. Referring primarily to FIG. 141, the first arm 141234 and the second arm 141236 may extend distally from a distal portion 141238 of the closure nut 141232, wherein the first arm 141234 may comprise a first opening 141240 and the first arm 141234 may be pivotally connected to the first link 141230 by a first pin through the first opening 141240. Similarly, the second arm 141236 may comprise a second opening 141244, wherein the second arm 141236 may be pivotally connected to the second link by a second pin through the second opening 141244. The first link 141230 and the second link are also pivotally connected to the first jaw member 141204 such that when the closure nut 141232 is advanced distally from the first position (FIG. 143) to the second position (FIG. 144), the first jaw member 141204 is pivoted relative to the second jaw member 141206 towards a closed position. Correspondingly, when the closure nut 141232 is refracted proximally from the second position (FIG. 146) to the first position (FIG. 148), the first jaw member 141204 is pivoted relative to the second jaw member 141206 towards the open position. FIG. 142 illustrates the closure nut 141232 in a first position and the jaw assembly 141211 in an open position. FIG. 144 shows the closure nut 141232 in a second position and the jaw assembly 141211 in a closed position. The closure nut 141232, however, may be constrained from rotation relative to the end effector drive housing 141216 by an indexing feature, for example, abutting against the end effector drive housing 141216.

Referring to FIGS. 140-148, the surgical tool 141200 may include a firing mechanism 141246 having a suitable firing driver. The firing mechanism 141246 may include an I-beam member 141247, a threaded drive member 141248, and a threaded rotary drive nut 141250. The I-beam member 141247 may comprise a first I-beam flange 141252 and a second I-beam flange 141254. The I-beam member 141247 may operate in a manner similar to that described above with respect to the axially movable member described herein above. For example, the first I-beam flange 141252 and the second I-beam flange 141254 are connected with an intermediate portion 141256. The intermediate portion 141256 of the I-beam member 141247 may comprise a cutting member 141258 on a distal or a leading end thereof. The I-beam member 141247 is configured to translate within a first channel 141260 in the first jaw member 141204 and within a second channel 141262 in the second jaw member 141206. FIG. 140 shows the I-beam member 141247 in a fully proximal position and the jaw assembly 141211 in an open position. The I-beam member 141247 may be translated distally in order for the cutting member 141258 to transect tissue clamped between the first jaw member 141204 and the second jaw member 141206 when in the closed position. The cutting member 141258, which may comprise a sharp edge or blade for example, is configured to cut through clamped tissue during a distal translation (firing) stroke of the I-beam member 141247, thereby transecting the tissue. FIG. 145 shows the I-beam member 141247 in a fully distal position after a firing stroke.

Before, during, and/or after the I-beam member 141247 is advanced through tissue clamped between the first jaw member 141204 and the second jaw member 141206, electrical current can be supplied to electrodes located in the first jaw member 141204 and/or second jaw member 141206 in order to weld/fuse the tissue, as described in greater detail in this specification. For example, electrodes may be configured to deliver RF energy to tissue clamped between the first jaw member 141204 and the second jaw member 141206 when in a closed position to weld/fuse the tissue.

Distal and proximal translation of the I-beam member 141247 between a proximally retracted position and a distally advanced position may be accomplished with a suitable firing mechanism 141246. Referring to FIGS. 140-148, the I-beam member 141247 is connected to the threaded drive member 141248, wherein the threaded rotary drive nut 141250 is in a threaded engagement with the threaded drive member 141248. Referring primarily to FIG. 140, the threaded rotary drive nut 141250 is positioned within in the end effector drive housing 141216 proximal to the closure nut 141232 between a proximal annular flange 141264 and a distal annular flange 141266. The threaded rotary drive nut 141250 is mechanically constrained from translation in any direction, but is rotatable within the end effector drive housing 141216 around a central axis A. Therefore, given the threaded engagement of the rotary drive nut 141250 and the threaded drive member 141248, rotational motion of the rotary drive nut 141250 is transformed into translational motion of the threaded drive member 141248 along the central axis A and, in turn, into translational motion of the I-beam member 141247 along the central axis A.

The threaded drive member 141248 is threaded through the rotary drive nut 141250 and is located at least partially inside a lumen 141268 of a rotary drive shaft 141270. The threaded drive member 141248 is not attached or connected to the rotary drive shaft 141270. In use, the threaded drive member 141248 is freely movable within the lumen of the rotary drive shaft 141270 and will translate within the lumen of the rotary drive shaft 141270 when driven by rotation of the rotary drive nut 141250. The rotary drive shaft 141270 and the threaded drive member 141248 form a concentric rotary drive shaft/screw assembly that is located in the shaft assembly 141214. In addition, the threaded drive member 141248 extends distally through a lumen 141272 of the closure nut 141232. Similar to the above, the threaded drive member 141248 is freely movable within the lumen 141272 of the closure nut 141232, and, as a result, the threaded drive member 141248 will translate within the lumen 141272 of the closure nut 141232 when driven by rotation of the rotary drive nut 141250.

Referring to FIGS. 140-148, the rotary drive nut 141250 may comprise a threaded distal portion 141274. The closure nut 141232 may comprise a threaded proximal portion 141276. The threaded distal portion 141274 of the rotary drive nut 141250 and the threaded proximal portion 141276 of the closure nut 141232 are in a threaded engagement. As described above, the threaded rotary drive nut 141250 is mechanically constrained from translation in any direction, but is rotatable within the end effector drive housing 141216 around a central axis A. Therefore, given the threaded engagement of the rotary drive nut 141250 and the closure nut 141232, the rotational motion of the rotary drive nut 141250 is transformed into translational motion of the closure nut 141232 along the central axis A and, in turn, into pivotal motion in the jaw assembly 141211.

As shown in FIG. 140, the end effector drive housing 141216, the end effector connector tube 141218, and the intermediate articulation tube segment 141220, which together comprise the shaft assembly 141214, have open lumens and, therefore, the shaft assembly 141214 comprises a lumen extending longitudinally therethrough, as shown in FIGS. 140 and 142-148. Referring again to FIGS. 140 and 142-148, the concentric rotary drive shaft/threaded drive member assembly is located within the lumen of the shaft assembly 141214 and passes through the end effector drive housing 141216, the end effector connector tube 141218, and the intermediate articulation tube segment 141220. Although not shown in FIGS. 140-148, at least the rotary drive shaft 141270 passes through a lumen of the shaft assembly 141214 and is operably coupled to a driving mechanism that provides rotational motion and axial translational motion to the rotary drive shaft 141270. For example, in some exemplifications, the surgical tool 141200 may be operably coupled through the shaft assembly 141214 to a robotic surgical system that provides rotational motion and axial translational motion to the rotary drive shaft 141270, such as, for example, the robotic surgical systems described in connection with FIGS. 125-127. For example, the rotary drive shaft 141270 may be coupled, through the shaft assembly, to the proximal drive shaft segment 140380 described herein above. In some exemplifications, for example, the surgical tool 141200 may be operably coupled through the shaft assembly 141214 to a hand-held surgical device.

In some exemplifications, the threaded drive member 141248 has a length that is less than the length of the rotary drive shaft 141270 and, therefore, lies within only a distal portion of the rotary drive shaft 141270, for example. The threaded drive member 141248 and the rotary drive shaft 141270 may be flexible so that the threaded drive member 141248 and the rotary drive shaft 141270 can bend without damage or loss of operability during articulation of the surgical tool 141200 about the articulation joint 141208.

Described in greater detail elsewhere in the specification, the rotary drive shaft 141270 may comprise a rotary drive head 141278. The rotary drive head 141278 comprises a female hex coupling portion 141280 on the distal side of the rotary drive head 141278 and the rotary drive head 141278 comprises a male hex coupling portion 141282 on the proximal side of the rotary drive head 141278. The distal female hex coupling portion 141280 of the rotary drive head 141278 is configured to mechanically engage with a male hex coupling portion 141284 of the rotary drive nut 141250 located on the proximal side of the rotary drive nut 141250. As described elsewhere, the proximal male hex coupling portion 141282 of the rotary drive head 141278 is configured to mechanically engage with a female hex coupling portion 141286 of the end effector drive housing 141216 in order to rotate the end effector 141202 around the central axis A.

Referring to FIG. 142, the rotary drive shaft 141270 is shown in a fully proximal axial position in which the hex coupling portion 141282 of the rotary drive head 141278 is mechanically engaged with the female hex coupling portion 141286 of the end effector drive housing 141216. In this configuration, rotation of the rotary drive shaft 141270 causes rotation of the head portion of the surgical tool 141200 about the head rotation joint 141210, including rotation of the end effector 141202 and the end effector drive housing 141216. In this configuration, the portion of the surgical tool 141200 that is distal to the head rotation joint 141210 (e.g., a head portion) rotates with rotation of the rotary drive shaft 141270, and the portion of the surgical tool 141200 that is proximal to the head rotation joint 141210 does not rotate with rotation of the rotary drive shaft 1270. An example of a head rotation joint 1210 is described in connection with FIGS. 140-148 and 149-153. Other suitable techniques and rotation means for rotating the end effector 141202 relative to the shaft assembly 141214 are within the scope of the current disclosure. It will be appreciated that a desired rotation speed of the rotary drive shaft 141270 to drive the rotary drive nut 141250 may be greater than a desired rotational speed for rotating the head portion. For example, the rotary drive shaft 141270 may be driven by a motor that is operable at different rotary speeds.

The orientation of the threading of the threaded drive member 141248 and the rotary drive nut 141250 may be established so that either clockwise or counterclockwise rotation of the rotary drive shaft 141270 will cause distal or proximal translation of the threaded drive member 141248 and I-beam member 141247. Stated another way, the rotary drive shaft 141270, and the rotary drive nut 141250 can be rotated in a first direction to advance the threaded drive member 141248 distally and correspondingly, rotated in a second opposite direction to retract the threaded drive member 141248 proximally. The pitch and/or number of starts of the threading of the threaded drive member 141248 and the threading of the rotary drive nut 141250 may be selected to control the speed and/or duration of the rotation of the rotary drive nut 141250 and, in turn, the translation of the threaded drive member 141248. In this manner, the direction, speed, and/or duration of rotation of the rotary drive shaft 141270 can be controlled in order to control the direction, speed, and magnitude of the longitudinal translation of the I-beam member 141247 along the first channel 141260 and second channel 141262, as described above.

Similar to the above, the orientation of the threading of the threaded distal portion 141274 of the rotary drive nut 141250 and the threading of the threaded proximal portion 141276 of the closure nut 141232 may be established so that either clockwise or counterclockwise rotation of the rotary drive shaft 141270 will cause distal or proximal translation of the closure nut 141232 and in turn closure or opening of the jaw assembly 141211. Stated another way, threaded distal portion 141274 can be rotated in a first direction to advance the threaded proximal portion 141276 distally and correspondingly, rotated in a second opposite direction to retract the threaded proximal portion 141276 proximally. The pitch and/or number of starts of the threading of the threaded distal portion 141274 of the threaded drive member 141248 and the threading of threaded proximal portion 141276 of the closure nut 141232 may be selected to control speed and/or duration of the rotation of the rotary drive nut 141250 and translation of the closure nut 141232. In this manner, the direction, speed, and/or duration of rotation of the rotary drive shaft 141270 can be controlled in order to control the direction, speed, and magnitude of the pivoting of the of the jaw assembly 141211.

Referring to FIGS. 143-145, the rotary drive shaft 141270 is shown in a fully extended distal axial position in which the female hex coupling portion 141280 of the rotary drive head 141278 is mechanically engaged with the male hex coupling portion 141284 of the rotary drive nut 141250. In this configuration, rotation of the rotary drive shaft 141270 in a first direction (for example a clockwise direction) around the central axis A begins a firing stroke by causing rotation of the rotary drive nut 141250 in the first direction. The rotation of the rotary drive nut advances the threaded drive member 141248, which, in turn, advances the I-beam member 141247 distally. Simultaneously, the rotation of the rotary drive nut 141250 advances the closure nut 141232 distally, which closes the jaw assembly 141211. The closure nut 141232 and the threaded drive member 141248 are advanced distally until the closure nut 141232 is disengaged from threaded engagement with the rotary drive nut 141250 as illustrated in FIG. 145. Stated another way, the closure nut 141232 can be advanced distally until the threads of the threaded distal portion 141274 of the rotary drive nut 141250 are no longer threadedly engaged with the threads of the threaded proximal portion 141276 of the closure nut 141232. Thus, as a result, further rotation of the rotary drive nut 141250 in the first direction will not advance the closure nut 141232 distally. The closure nut 141232 will sit idle during the remainder of a firing stroke. Additional rotation of the rotary drive nut 141250, in the same direction, continues the distal advancement of the threaded drive member 141248, which continues the distal advancement of the I-beam member 141247 for the remainder of the firing stroke.

The surgical tool 141200 may comprise a biasing member 141288, a helical spring, and/or a washer spring for example, situated at least partially around the threaded distal portion 141274 of the rotary drive nut 141250. As illustrated in FIG. 143, the biasing member 141288 may include a proximal end abutted against the distal annular flange 141266 of the end effector drive housing 141216, and a distal end abutted against a proximal end 141290 of the closure nut 141232. Once the closure nut 141232 is released from threaded engagement with the rotary drive nut 141250, the biasing member 141288 can keep the closure nut 141232 from reengaging the rotary drive nut 141250 by pushing the closure nut 141232 axially in a distal direction along the central axis A until the distal portion 141238 of the closure nut 141232 abuts against a terminal wall 141294 of the proximal shaft portion 141212 of the end effector 141202. The biasing member 141288 also ensures that the jaw assembly 141211 remains under positive closure pressure by biasing the closure nut 141232 abutted against the terminal wall 141294 of the proximal shaft portion 141212 of the end effector 141202 as the I-beam member 141247 is being advanced distally through the closed jaw assembly 141211.

Referring primarily to FIG. 141, the closure nut 141232 may comprise a cam member 141296 extending distally from the closure nut 141232. Referring primarily to FIG. 144, the cam member 141296 may extend through an opening 141298 of the terminal wall 141294 of the proximal shaft portion 141212 of the end effector 141202 when the distal portion 141238 of the closure nut 141232 is abutted against the terminal wall 141294 of the proximal shaft portion 141212 of the end effector 141202 under positive pressure from the biasing member 141288.

Referring to FIG. 145, the rotary drive shaft 141270 is shown in a fully extended distal axial position in which the female hex coupling portion 141280 of the rotary drive head 141278 is mechanically engaged with the male hex coupling portion 141284 of the rotary drive nut 141250. In this configuration, rotation of the rotary drive shaft 141270 in a second direction opposite the first direction (for example a counter clockwise direction) begins a reverse stroke by causing an opposite rotation of the rotary drive nut 141250, which retracts the threaded drive member 141248, which in turn retracts the I-beam member 141247. At least during the initial phase of the reverse stroke, the closure nut 141232 remains disengaged from the rotary drive nut 141250. However, when the I-beam member 141247 is being retracted, the I-beam member 141247 can engage the cam member 141296 of the closure nut 141232. Any further retraction of the I-beam member 141247 can simultaneously open the jaw assembly 141211 by pushing the closure nut 141232 axially in a proximal direction along the central axis A toward the rotary drive nut 141250. In order for the I-beam member 141247 to push the closure nut 141232 proximally, the I-beam member 141247 must compress the biasing member 141288. As the I-beam member 141247 is refracted, the I-beam member 141247 can push the closure nut 141232 proximally until the closure nut is returned into threaded engagement with the rotary drive nut 141250. At such point, the rotary drive nut 141250 can pull the closure nut 141232 proximally owing to the threaded engagement therebetween. As the closure nut 141232 is retracted proximally, the first link 141230, and the second link will cause the jaw assembly 141211 to open. The retraction of the I-beam member 141247 and the opening of the jaw assembly 141211 continue simultaneously during the remainder of the reverse stroke.

The sequence of events causing the closure of the jaw assembly 141211, the full extension of the I-beam member 141247, the full refraction of the I-beam member 141247, and the reopening of the jaw assembly 141211 is illustrated in FIGS. 142-148 in a chronological order. FIG. 142 shows the jaw assembly 141211 in a fully open position, the I-beam member 141247 in a fully retracted position, and the rotary drive shaft 141270 in a fully retracted axial position, wherein the female hex coupling portion 141280 of the rotary drive head 141278 is mechanically disengaged from the male hex coupling portion 141284 of the rotary drive nut 141250. In a first phase of operation, returning to FIG. 143, the rotary drive shaft 141270 is advanced axially to mechanically engage the female hex coupling portion 141280 of the rotary drive head 141278 with the male hex coupling portion 141284 of the rotary drive nut 141250. Referring again to FIG. 143, the rotation of the rotary drive shaft 141270 in a first direction (for example a clockwise direction) around the central axis A causes the rotation of the rotary drive nut 141250 in the first direction. The closure nut 141232 and the threaded drive member 141248 are simultaneously advanced distally by rotation of the rotary drive nut 141250 in the first direction. In turn, the closure of the jaw assembly 141211 and the initial advancement of the I-beam member 141247 occur simultaneously during the first phase of operation. In a second phase of operation, referring now to FIG. 144, the closure nut 141232 is disengaged from threaded engagement with the rotary drive nut 141250. During the remainder of the second phase of operation, the rotary drive nut 141250 continues to advance the threaded drive member 141248 independently of the closure nut 141232. As a result, referring primarily to FIG. 145, the jaw assembly 141211 remains closed and the I-beam member 141247 continues to advance until the end of the second phase of operation.

In a third phase of operation, as illustrated in FIG. 146, the rotary drive shaft 141270 is rotated in a second direction opposite the first direction, which causes the rotation of the rotary drive nut 141250 in the second direction. In the third phase of operation, the closure nut 141232 remains disengaged from rotary drive nut 141250. The rotation of the rotary drive nut 141250 retracts the threaded drive member 141248 independent of the closure nut 141232. In result, the jaw assembly 141211 remains closed, and the I-beam member 141247 is retracted in response to the rotation of the rotary drive. In a fourth phase of operation, referring primarily to FIG. 147, the rotary drive nut 141250 continues its rotation in the second direction thereby retracting the threaded drive member 141248 which retracts I-beam member 141247 until the I-beam member 141247 engages the cam member 141296 of closure nut 141232. Any further retraction of the I-beam member 141247 simultaneously opens the jaw assembly 141211 by pushing the closure nut 141232 axially in a proximal direction along the central axis A towards the rotary drive nut 141250 compressing the biasing member 141288. Referring primarily to FIG. 148, the I-beam member 141247 can continue to push the closure nut 141232 proximally until it is returned into threaded engagement with the rotary drive nut 141250. The retraction of the I-beam member 141247 and the opening of the jaw assembly 141211 continue simultaneously during the remainder of the fourth phase of operation.

Referring to FIGS. 149-153, a multi-axis articulating and rotating surgical tool 141300 comprises an end effector 141302 including a jaw assembly 141311 comprising a first jaw member 141304 and a second jaw member 141306. The first jaw member 141304 is movable relative to the second jaw member 141306 between an open position and a closed position to clamp tissue between the first jaw member 141304 and the second jaw member 141306. The surgical tool 141300 is configured to independently articulate about an articulation joint 141308. As described above, the surgical tool 141300 is also configured to independently rotate about a head rotation joint 141310.

The end effector 141302 is coupled to a shaft assembly 141314 comprising an end effector drive housing 141316, an end effector connector tube 141318, an intermediate articulation tube segment 141320, and a distal outer tube portion. The end effector 141302 and the shaft assembly 141314 together can comprise the surgical tool 141300. The end effector 141302 may be removably coupled to the end effector drive housing 141316 using a mechanism. The end effector connector tube 141318 comprises a cylindrical portion 141322 and a ball portion 141324. The end effector drive housing 141316 is coupled to the cylindrical portion 141322 of the end effector connector tube 141318 through the head rotation joint 141310. The end effector 141302 and the end effector drive housing 141316 together comprise a head portion of the surgical tool 141300. The head portion of the surgical tool 141300 is independently rotatable about the head rotation joint 141310.

Referring primarily to FIG. 149, the surgical tool 141300 may include a closure mechanism 141326 for moving the first jaw member 141304 relative to the second jaw member 141306 between an open position (FIG. 150) and a closed position (FIG. 151). As illustrated, in FIG. 149, the first jaw member 141304 may include first mounting holes 141328, and the second jaw member 141306 may include second mounting holes. The first jaw member 141304 can be arranged relative to the second jaw member 141306 such that a pivot or trunnion pin extends through the first mounting holes 141328 of the first jaw member 141304 and the second mounting holes of the second jaw member 141306 to pivotally couple the first jaw member 141304 to the second jaw member 141306. Other suitable means for coupling the first jaw member 141304 and the second jaw member 141306 are within the scope of this disclosure.

Referring to FIGS. 149-153, the closure mechanism may comprise a closure link 141330 which translates axially relative to the end effector drive housing 141316 between a first position and a second position. The closure link 141330 may comprise a distal end 141332 and a proximal end 141334. The distal end 141332 may be pivotally connected to a proximal portion 141336 of the first jaw member 141304 such that when the closure link 141330 is translated between the first position and the second position, the first jaw member 141304 is moved relative to the second jaw member 141306 between an open and a closed position.

Referring to FIGS. 149-153, the closure mechanism 141326 may also comprise a closure driver in the form of a barrel cam 141338 for example. The barrel cam 141338 may be positioned within the end effector drive housing 141316. The barrel cam 141338 may comprise a generally cylindrical shape having a lumen 141340 therethrough. The barrel cam 141338 may include a first arcuate groove 141346, and a second arcuate groove 141348 defined in a peripheral surface thereof. The first arcuate groove 141346 may receive a first pin 141352 extending from the end effector drive housing 141316. The second arcuate groove 141348 may receive a second pin extending from the end effector drive housing 141316. The first pin 141352 and the second pin may extend from circumferentially opposite sides of an inner wall of the end effector drive housing 141316. The barrel cam 141338 may rotate around central axis A, wherein, as the barrel cam 141338 is rotated around central axis A, the first pin 141352 travels along the first arcuate groove 141346, and the second pin travels along the second arcuate groove 141348 thereby translating the barrel cam 141338 axially along central axis A. The result is a conversion of the rotational motion of the barrel cam 141338 into an axial motion of the closure link 141330. Stated another way, the rotation of the barrel cam 141338 in a first direction (for example a clockwise direction) around the central axis A may result in advancing the barrel cam 141338 axially in a distal direction. Correspondingly, the rotation of the barrel cam 141338 in a second direction (for example a counter clockwise direction) opposite the first direction may result in retracting the barrel cam 141338 axially in a proximal direction along the central axis A.

Referring to FIGS. 149-153, the proximal end 141334 of the closure link 141330 may be operatively engaged with the barrel cam 141338 such that the axially advancement of the barrel cam 141338 may cause the closure link 141330 to be advanced axially, and, in turn close the jaw assembly 141311. Similarly, the proximal retraction of the barrel cam 141338 may retract the closure link 141330, which may open the jaw assembly 141311. As illustrated in FIGS. 149-153, the barrel cam 141338 may include a circumferential recess 141354 on the external wall of the barrel cam 141338 at a distal portion thereof. The proximal end of the closure link 141330 may comprise a connector member 141356. The connector member 141356 may be operably engaged with the barrel cam 141338 along the recess 141354. As a result, the barrel cam 141338 may translate axial motions to the closure link 141330 through the connector member 141356.

Referring primarily to FIG. 149, the surgical tool 141300 may include a firing mechanism 141358. The firing mechanism 141358 may include an I-beam member 141360, a threaded drive member 141362, and a threaded rotary drive nut 141364. The I-beam member 141360 may operate in a manner similar to that of the axially movable member described herein above and may comprise a first I-beam flange 141367 and a second I-beam flange 141368. The first I-beam flange 141367 and the second I-beam flange 141368 are connected with an intermediate portion 141370. The intermediate portion 141370 of the I-beam member 141360 may comprise a cutting member 141372, which may comprise a sharp edge or blade for example, to transect tissue clamped between the first jaw member 141304 and the second jaw member 141306 when the jaw assembly 141311 is closed. The I-beam member 141360 may translate distally within a first channel defined in the first jaw member 141304 and within a second channel 141376 defined in the second jaw member 141306 to cut through clamped tissue during a distal translation (firing) stroke. FIG. 153 illustrates the I-beam member 141360 after a firing stroke.

Before, during, and/or after the I-beam member 141360 is advanced through tissue clamped between the first jaw member 141304 and the second jaw member 141306, electrical current can be supplied to electrodes 141378 located in the first jaw member 141304 and/or second jaw member 141306 in order to weld/fuse the tissue, as described in greater detail in this specification. For example, electrodes 141378 may be configured to deliver RF energy to tissue clamped between the first jaw member 141304 and the second jaw member 141306 when in a closed position to weld/fuse the tissue.

Distal and proximal translation of the I-beam member 141360 between a proximally retracted position and a distally advanced position may be accomplished with a suitable firing mechanism 141358. Referring to FIGS. 149-153, the I-beam member 141360 is connected to the threaded drive member 141362, wherein the threaded drive member 141362 is threadedly engaged with the rotary drive nut 141364. The threaded rotary drive nut 141364 is positioned within the end effector drive housing 141316 distal to the barrel cam 141338 between a proximal annular flange 141339A and a distal annular flange 141339B. The threaded rotary drive nut 141364 is mechanically constrained from translation in any direction, but is rotatable within the end effector drive housing 141316. Therefore, given the threaded engagement of the rotary drive nut 141364 and the threaded drive member 141362, rotational motion of the rotary drive nut 141364 is transformed into translational motion of the threaded drive member 141362 along the central axis A and, in turn, into translational motion of the I-beam member 141360 along the central axis A.

The threaded drive member 141362 is threaded through the rotary drive nut 141364 and is located at least partially inside a lumen 141381 of a rotary drive shaft 141382. The threaded drive member 141362 is not attached or connected to the rotary drive shaft 141382. The threaded drive member 141362 is freely movable within the lumen 141381 of the rotary drive shaft 141382 and will translate within the lumen 141381 of the rotary drive shaft 141382 when driven by rotation of the rotary drive nut 141364. The rotary drive shaft 141382 and the threaded drive member 141362 form a concentric rotary drive shaft/threaded drive member assembly that is located in the shaft assembly 141314. In addition, the threaded drive member 141362 extends distally through a lumen 141384 of the barrel cam 141338 wherein the threaded drive member 141362 is freely movable within the lumen 141384 of the barrel cam 141338 and will translate within the lumen 141384 of the barrel cam 141338 when the threaded drive member is driven by rotation of the rotary drive nut 141364.

As shown in FIG. 149, the end effector drive housing 141316, the end effector connector tube 141318, and the intermediate articulation tube segment 141320, which together comprise the shaft assembly 141314, have lumens extending therethrough. As a result, the shaft assembly 141314 can comprise a lumen extending therethrough, as illustrated in FIGS. 149-153. Referring again to FIGS. 149-153, the concentric rotary drive shaft/threaded drive member assembly is located within the lumen of the shaft assembly 141314 and passes through the end effector drive housing 141316, the end effector connector tube 141318, and the intermediate articulation tube segment 141320. Although not shown in FIGS. 149-153, at least the rotary drive shaft 141382 passes through a lumen of the shaft assembly 141314 and is operably coupled to a driving mechanism that provides rotational and/or axial translational motion to the rotary drive shaft 141382. For example, in some exemplifications, the surgical tool 141300 may be operably coupled through the shaft assembly 141314 to a robotic surgical system that provides rotational motion and/or axial translational motion to the rotary drive shaft 141382, such as, for example, the robotic surgical systems described in connection with FIGS. 125-127. For example, the rotary drive shaft 141382 may be operably coupled, though the shaft assembly 141314, to the proximal drive shaft segment 140380 described herein above. Also, in some exemplifications, the surgical tool 141300 may be utilized in conjunction with a hand-held surgical device.

In some exemplifications, the threaded drive member 141362 has a length that is less than the length of the rotary drive shaft 141382 and, therefore, lies within only a distal portion of the rotary drive shaft 141382, for example. The threaded drive member 141362 and the rotary drive shaft 141382 may be flexible so that the threaded drive member 141362 and the rotary drive shaft 141382 can bend without damage or loss of operability during articulation of the surgical tool 141300 about the articulation joint 141308.

The rotary drive shaft 141382 may comprise a rotary drive head 141386. The rotary drive head 141386 may comprise spline members 141388 disposed circumferentially around an external surface of the rotary drive head 141386 and oriented co-axially with the shaft assembly 141314. The end effector drive housing 141316 may comprise a spline coupling portion 141390 comprising spline members 141392 disposed circumferentially around an internal wall of the end effector drive housing 141316 and oriented co-axially with the shaft assembly 141314. The barrel cam 141338 may comprise a spline coupling portion 141394 comprising spline members 141396 disposed circumferentially around an internal wall of barrel cam 141338 and oriented co-axially with the shaft assembly 141314. The rotary drive nut 141364 may also comprise a spline coupling portion 141397 comprising spline members 141398 disposed circumferentially around an internal wall of rotary drive nut 141364 and oriented co-axially with the shaft assembly 141314. As illustrated in FIG. 150, the rotary drive shaft 141382 may be selectively retracted proximally to bring the rotary drive head 141386 into operable engagement with the spline coupling portion 141390 of the end effector drive housing 141316. In this configuration, rotation of the rotary drive shaft 141382 causes rotation of the head portion of the surgical tool 141300 about the head rotation joint 141310, including rotation of the end effector 141302 and the end effector drive housing 141316. In this configuration, the portion of the surgical tool 141300 that is distal to the head rotation joint 141310 rotates with rotation of the rotary drive shaft 141382, and the portion of the surgical tool 141300 that is proximal to the head rotation joint 141310 does not rotate with rotation of the rotary drive shaft 141382.

An example of a head rotation joint 141310 is described in connection with FIGS. 140-148 and 149-153. Other suitable techniques and rotation means for rotating the end effector 141302 relative to the shaft assembly 141314 are within the scope of the current disclosure. It will be appreciated that a desired rotation speed of the rotary drive shaft 141382 to drive the rotary drive nut 141364 may be greater than a desired rotational speed for rotating the head portion. For example, the rotary drive shaft 141270 may be driven by a motor that is operable at different rotary speeds.

As illustrated in FIG. 151, the rotary drive shaft 141382 may be selectively advanced distally to bring the rotary drive head 141386 into operable engagement with the spline coupling portion 141394 of the barrel cam 141338. In this configuration, rotation of the rotary drive shaft 141382 causes rotation of the barrel cam 141338. As described above, the rotation of the barrel cam 141338 causes axial motions in the closure link 141330. In result, the rotation of the rotary drive shaft 141382 in a first direction (for example a clockwise direction) around the central axis A may cause the closure link 141330 to be advanced distally along the central axis A, which may close the jaw assembly 141311. Alternatively, the rotation of the rotary drive shaft 141382 in a second direction (for example a clockwise direction) opposite the first direction may cause the closure link 141330 to be retracted proximally along the central axis A, which in turn may open the jaw assembly 141311.

As illustrated ire FIG. 152, the rotary drive shaft 1382 may be selectively advanced distally to pass the rotary drive head 141386 through the lumen of the barrel cam 141338 into a space 141399 in the end effector drive housing 141316 between the barrel cam 141338 and the rotary drive nut 141364 wherein the rotary drive head 141386 is not in operable engagement with any of the spline coupling portions. The rotary drive shaft 141382 may then be further advanced distally to bring rotary drive head 141386 into operable engagement with the spline coupling portion 141397 of the rotary drive nut 141364 as illustrated in FIG. 153. In this configuration, rotation of the rotary drive shaft 141382 causes rotation of the rotary drive nut 141364. As described above, the rotation of the rotary drive nut 141364 causes axial motions in the threaded drive member 141362. In result, rotation of the rotary drive shaft 141382 in a first direction (for example a clockwise direction) around the central axis A, may cause the threaded drive member 141362 to be advanced distally, which in turn may advance the I-beam member 141360 distally. Alternatively, rotation of the rotary drive shaft 141382 in a second direction (for example a clockwise direction) opposite the first direction may cause the threaded drive member 141362 to be retracted proximally, which may retract the I-beam member 141360 proximally.

The sequence of events causing the closure of the jaw assembly 141311, the full extension of the I-beam member 141360, the full refraction of the I-beam member 141360, and the reopening of the jaw assembly 141311 is illustrated in FIGS. 150-153 in a chronological order. FIG. 150 shows the jaw assembly 141311 in a fully open position, the I-beam member 141360 in a fully retracted position, and the rotary drive shaft 141382 in a retracted axial position, wherein the rotary drive head 141386 is operably engaged with the spline coupling portion 141390 of the end effector drive housing 141316. In a first phase of operation, the rotary drive shaft 141382 is rotated to rotate the end effector 141302 into an appropriate orientation, for example relative to a blood vessel. In a second phase of operation, the rotary drive shaft 141382 is advanced axially to bring the rotary drive head 141386 into operable engagement with the spline coupling portion 141394 of the barrel cam 141338. In this configuration, the rotary drive shaft 141382 may be rotated in a first direction (for example a clockwise direction) around the central axis A to close the jaw assembly 1311 around the blood vessel. The electrodes 1378 in the first jaw member 141304 and the second jaw member 141306 may be activated to seal the blood vessel. In a third phase of operation, the rotary drive shaft 141382 may then be advanced axially to bring the rotary drive head 141386 into operable engagement with the spline coupling portion 141397 of the rotary drive nut 141364. In this configuration, the rotary drive shaft 141382 may be rotated in a first direction around the central axis A (for example a clockwise direction) to advance the I-beam member 141360 thereby transecting the sealed blood vessel. In a fourth phase of operation, the rotary drive shaft 141382 may be rotated in a second direction (for example a counter clockwise direction) opposite the first direction to retract the I-beam member 141360.

In a fifth phase of operation, the rotary drive shaft 141382 is retracted axially to bring the rotary drive head 141386 into operable engagement with the spline coupling portion 141394 of the barrel cam 141338. In this configuration, the rotary drive shaft 141382 may be rotated in a second direction (for example a counter clockwise direction) opposite the first direction to reopen the jaw assembly 141311 thereby releasing the sealed cut blood vessel.

As illustrated in FIG. 154, surgical end effector 141001 may be interchanged with other surgical end effectors suitable for use with shaft assembly 141003. For example, surgical end effector 141001 may be detached from shaft assembly 141003 and a second surgical end effector 141024 may be attached to shaft assembly 141003. In another example, the second surgical end effector 141024 may be replaced with a third surgical end effector 141026. Surgical end effectors 141001, 141024, and 141026 may include common drive train components that are operably engageable with their counter parts in the shaft assembly 141003. Yet, surgical end effectors 141001, 141024, and 141026 may each include unique operational features suitable for certain surgical tasks.

The surgical end effector 141001 may include an actuation mechanism. The actuation mechanism may comprise a closure mechanism for moving a first jaw member 141002 relative to the second jaw member 141004. The actuation mechanism may comprise a firing mechanism for transecting tissue grasped between the first jaw member 141002 and the second jaw member 141004. The closure and firing may be accomplished by separate mechanisms, which may be driven separately or contemporaneously. Alternatively, the closure and firing may be accomplished via a single mechanism. Suitable closure mechanisms and suitable firing mechanisms are described, for example, in connection with FIGS. 140-148 and 149-153.

FIGS. 125-154 and additional exemplifications are further described in U.S. Pat. No. 9,204,879, filed Jun. 28, 2012, entitled FLEXIBLE DRIVE MEMBER, which issued on Dec. 8, 2015, the entire disclosure of which is incorporated by reference herein.

During various surgical procedures, a surgeon, or other clinician, may apply a clip to a patient's tissue in order to achieve various effects and/or therapeutic results. Referring to FIG. 155, a surgical instrument, such as a clip applier 150100, for example, can be configured to apply one or more clips to tissue located within a surgical site in the patient. Generally, referring now to 167, the clip applier 150100 can be structured and arranged to position a clip 150140 relative to the tissue in order to compress the tissue within the clip 150140. The clip applier 150100 can be configured to deform the clip 150140 as illustrated in FIGS. 157 and 158, for example, and as described in greater detail further below. Each clip 150140 can comprise a base 150142 and opposing legs 150144 extending from the base 150142. The base 150142 and the legs 150144 can comprise any suitable shape and can define a substantially U-shaped configuration and/or a substantially V-shaped configuration, for example. The base 150142 can comprise angled portions 150141 which are connected together by a joint 150143. In use, the legs 150144 of the clip 150140 can be positioned on opposite sides of the tissue wherein the legs 150144 can be pushed toward one another to compress the tissue positioned between the legs 150144. The joint 150143 can be configured to permit the angled portions 150141 of the base 150142, and the legs 150144 extending therefrom, to deform inwardly. In various circumstances, the clip 150140 can be configured to yield, or deform plastically, when the clip 150140 is sufficiently compressed, although some amount of elastic deformation, or spring-back, may occur within the deformed clip 150140.

Referring now to FIGS. 155 and 156, the clip applier 150100 can include a shaft 150110, an end effector 150120, and a replaceable clip cartridge, or magazine, 150130. Referring to FIGS. 168-170, the clip cartridge 150130 can comprise a housing 150132 and a plurality of clips 150140 positioned within the housing 150132. The housing 150132 can define a storage chamber 150134 in which the clips 150140 can be stacked. The storage chamber 150134 can comprise sidewalls which extend around, or at least substantially around, the perimeter of the clips 150140. Referring again to 167, each clip 150140 can comprise opposing faces, such as a top face 150145 and a bottom face 150146 on opposite sides of the clip 150140 wherein, when the clips 150140 are stacked in the housing 150132, the top face 150145 of a clip 150140 can be positioned against the bottom face 150146 of an adjacent clip 150140 and wherein the bottom face 150146 of the clip 150140 can be positioned against the top face 150145 of another adjacent clip 150140. In various circumstances, the bottom faces 150146 of the clips 150140 can face downwardly toward one or more support shelves, or platforms, 150135 defined in the housing 150132 while the top faces 150145 of the clips 150140 can face upwardly away from the support shelves 150135. The top faces 150145 and the bottom faces 150146 of the clips 150140 may be identical, or at least substantially identical, in some cases, while, in other cases, the top faces 150145 and the bottom faces 150146 may be different. The stack of clips 150140 depicted in FIGS. 168-170 comprises five clips 150140, for example; however, other exemplifications are envisioned in which the stack of clips 150140 can include more than five clips 150140 or less than five clips 150140. In any event, the clip cartridge 150130 can further comprise at least one biasing member, such as biasing member 150136, for example, positioned intermediate the housing 150132 and the top clip 150140 in the stack of clips 150140. As described in greater detail below, the biasing member 150136 can be configured to bias the bottom clip 150140 in the stack of clips 150140 or, more particularly, the bottom face 150146 of the bottom clip 150140, against the support shelves 150135 defined in the housing 150132. The biasing member 150136 can comprise a spring, and/or any suitable compressed elastic element, for example, which can be configured to apply a biasing force to the clips 150140, or at least apply a biasing force to the top clip 150140 which is transmitted downwardly through the stack of clips 150140.

When a clip 150140 is positioned against the support shelves 150135 as described above, the clip 150140 can be supported in a firing position in which the clip 150140 can be advanced and ejected from the cartridge 150130. In various circumstances, the support shelves 150135 can define at least a portion of a firing chamber 150149 in which the clips 150140 can be sequentially positioned in the firing position. In some cases, the firing chamber 150149 can be entirely defined within the cartridge 150130 or, in other cases, the firing chamber 150149 can be defined within and/or between the shaft 150110 and the cartridge 150130. In any event, as described in greater detail further below, the clip applier 150100 can comprise a firing drive which can advance a firing member into the cartridge 150130 and push the clip 150140 from its firing position positioned against the support shelves 150135 to a fired position in which it is received within the end effector 150120 of the clip applier 150100. Referring primarily to FIGS. 168-170, the housing 150132 of the cartridge 150130 can comprise a proximal opening, or window, 150133 which can be aligned, or at least substantially aligned, with the support shelves 150135 such that the firing member can enter into the cartridge 150130 through the proximal opening 150133 and advance a clip 150140 distally out of the cartridge 150130. In at least one such exemplification, the housing 150132 can further comprise a distal, or discharge, opening, or window, 150137 which is also aligned with the support shelves 150135 such that the clip 150140 can be advanced, or fired, distally along a firing axis 150139 extending through the proximal opening 150133, the firing chamber 150149, and the distal opening 150137, for example.

In order to advance a clip 150140 out of the cartridge 150130, further to the above, the firing member of the firing drive can be advanced into to the cartridge housing 150132 and, in various circumstances, into the firing chamber 150149. As disclosed in greater detail further below, the firing member can pass entirely through the cartridge 150130 in order to advance the clip 150140 into its fired position within the end effector 150120. After the clip 150140 positioned in the firing chamber 150149 has been advanced distally by the firing member, as outlined above, the firing member can be retracted sufficiently such that the biasing member 150136 can position another clip 150140 against the support shelves 150135. In various circumstances, the biasing member 150136 can bias a clip 150140 against the firing member while the firing member is positioned within the housing 150132. Such a clip 150140 can be referred to as a queued clip. After the firing member has been sufficiently retracted and slid out from underneath the queued clip 150140, the biasing member 150136 can then bias the clip 150140 against the support shelves 150135 where it is staged for the next stroke of the reciprocating firing member. Referring primarily to FIGS. 156 and 168-170, the cartridge 150130 can be configured to supply the clips 150140 to the firing chamber 150149 along a predetermined path, such as supply axis 150138, for example. The supply axis 150138 can be transverse to the firing axis 150139 such that the clips 150140 are fed into the firing chamber 150149 in a direction which is different than the direction in which the firing member passes through the firing chamber 150149. In at least one such exemplification, the supply axis 150138 can be perpendicular, or at least substantially perpendicular, to the firing axis 150139, for example.

Referring again to 156, the shaft 150110 can comprise a cartridge, or magazine, aperture 150131 which can be sized and configured to receive a clip cartridge 150130, for example, therein. The cartridge aperture 150131 can be sized and configured such that the housing 150132 of the cartridge 150130 is closely received within the cartridge aperture 150131. The sidewalls which define the cartridge aperture 150131 can limit, or at least substantially limit, the lateral movement of the cartridge 150130 relative to the shaft 150110. The shaft 150110 and/or the cartridge 150130 can further comprise one or more locks which can be configured to releasably hold the cartridge 150130 in the cartridge aperture 150131. As illustrated in 156, the cartridge 150130 can be loaded into the cartridge aperture 150131 along an axis which is, in at least one exemplification, parallel to or collinear with the supply axis 150138. As also illustrated in 156, the shaft 150110 can further comprise a pad or seat 150118 extending from the frame 150111 of the shaft 150110 wherein the pad 150118 can be configured to be received within and/or engaged with the housing 150132 of the cartridge 150130. The pad 150118 can be sized and configured to be closely received within a recess 150148 defined in the cartridge housing such that the pad 150118 can limit, or at least substantially limit, the lateral movement of the cartridge 150130 relative to the shaft 150110. The pad 150118 can be sized and configured to align the cartridge 150130 within the shaft 150110 and/or support the cartridge housing 150132.

Once the clip cartridge 150130 has been positioned and seated within the shaft aperture 150131, referring now to FIGS. 159 and 160, a firing drive 150160 of the clip applier 150100 can be actuated to advance the clips 150140 from the clip cartridge 150130 as described above. The firing drive 150160 can comprise a rotary drive input such as a drive screw 150161, for example, and a displaceable firing nut 150163 operably engaged with the drive screw 150161. The drive screw 150161 can comprise at least one drive thread 150162 which can be threadably engaged with a threaded aperture extending through the firing nut 150163. In various exemplifications, the clip applier 150100 can further include an electric motor, for example, operably coupled with the drive screw 150161. In various instances, the drive screw 150161 can be operably coupled with the motor of a surgical instrument system comprising a hand-held instrument or a robotic arm, for example. In any event, the movement of the firing nut 150163 within the shaft 150110 can be constrained such that the firing nut 150163 moves along a longitudinal axis 150164 when the drive screw 150161 is rotated about the longitudinal axis 150164 by the motor. For instance, when the drive screw 150161 is rotated in a first direction by the motor, the drive screw 150161 can advance the firing nut 150163 distally toward the end effector 150120, as illustrated in 160. When the drive screw 150161 is rotated in a direction opposite the first direction by the motor, the drive screw 150161 can retract the firing nut 150163 proximally away from the end effector 150120. The shaft 150110 can comprise one or more bearings which can be configured to rotatably support the drive screw 150161. For instance, a bearing 150159 can be configured to rotatably support the distal end of the drive screw 150161, for example, as illustrated in FIGS. 159 and 160.

The firing drive 150160 can further comprise a firing member 150165 extending from the firing nut 150163 which can be advanced distally and retracted proximally with the firing nut 150163, as described in greater detail further below. Upon comparing FIGS. 159 and 160, the reader will note that the firing nut 150163 and the firing member 150165 have been advanced from a proximal, unfired position, illustrated in 159, to a distal, fired position, illustrated in 160, in which the firing member 150165 has advanced a clip 150140 from the clip cartridge 150130 into the end effector 150120. Referring primarily to 159, the clip cartridge 150130 is illustrated as comprising a plurality of clips 150140 stored therein wherein one of the clips 150140 is positioned in a firing position, as described above. As illustrated in FIGS. 159 and 160, the firing member 150165 can include a distal portion 150166 which can be advanced into the staple cartridge 150130 along a firing axis 150167 and engage the clip 150140 positioned in the firing position when the firing member 150165 and the firing nut 150163 are advanced distally. In some cases, the firing member 150165 can comprise a linear member while, in other cases, the distal end 150166 of the firing member 150165 can extend upwardly from the firing member 150165, for example. Further to the above, the firing member 150165 can advance the clip 150140 distally out of the clip cartridge 150130 along the firing axis 150167 and into a receiving cavity 150122 defined in the end effector 150120.

In various cases, the firing member 150165 can be attached to and extend distally from the firing nut 150163 while, in other cases, the firing member 150165 and the firing nut 150163 can be operably connected to one another by a firing actuator 150168. The firing actuator 150168 can be pivotably mounted to the firing member 150165 at a pivot 150169 and can include a distal arm 150170a and a proximal arm 150170b which can be engaged with a longitudinal slot 150113 defined in the housing 150112 of the shaft 150110. In at least one such exemplification, each of the arms 150170a, 150170b can include a projection, such as projections 150171a and 150171b, respectively, extending therefrom which can be configured to slide within the longitudinal slot 150113. Further to the above, the firing nut 150163 can further include a firing pin 150172 extending therefrom which can be configured to engage the distal arm 150170a in order to advance the actuator 150168 and the firing member 150165 distally, as described above. In use, referring again to the progression illustrated in FIGS. 159 and 160, the firing nut 150163 can be advanced distally by the drive screw 150161 wherein the firing pin 150172, which is positioned intermediate the distal arm 150170a and the proximal arm 150170b, can contact the distal arm 150170a and drive the actuator 150168 and the firing member 150165 distally. As the actuator 150168 is advanced distally, the actuator 150168 may be prevented from rotating about the pivot pin 150169 as one or both of the projections 150171a and 150171b sliding in the shaft slot 150113 can be prevented from being moved laterally relative to the longitudinal shaft slot 150113 until the actuator 150168 reaches the position illustrated in 160.

When the actuator 150168 has reached the position illustrated in 160, the distal projection 150171a can enter into a distal end 150114 of the longitudinal slot 150113 which can be configured to pivot the actuator 150168 downwardly, or permit the actuator 150168 to be pivoted downwardly, as illustrated in 163. In at least one such exemplification, the distal projection 150171a can come into contact with the sidewall of the distal end 150114 which can guide the distal projection 150171a downwardly and pivot the actuator 150168 about the pivot 150169 as the actuator 150168 is advanced forward by the firing nut 150163. In such a pivoted position, the firing pin 150172 extending from the firing nut 150163 may no longer be engaged with the distal arm 150170a of the actuator 150168 wherein, subsequently, the firing nut 150163 may move distally independently of the actuator 150168 thereby leaving behind the actuator 150168 and the firing member 150165. Stated another way, the distal end 150114 of the longitudinal shaft slot 150113 may deactivate the firing member 150165 wherein, at such point, the position of the firing member 150165 may represent the fully-fired or distal-most position of the firing member 150165. In such a position, the clip 150140 has been fully advanced into the receiving cavity, or receiver, 150122. Furthermore, in such a position, the next clip 150140 to be advanced into the receiving cavity 150122 may be biased against the top surface of the firing member 150165, further to the above.

Once a clip 150140 has been positioned within the receiving cavity 150122, further to the above, the clip 150140 can be deformed by a crimping drive 150180, for example. Referring now to FIGS. 157 and 158, the end effector 150120 of the clip applier 150100 can further comprise a first jaw 150123a and a second jaw 150123b wherein the first jaw 150123a and the second jaw 150123b can at least partially define the receiving chamber 150122. As illustrated in FIGS. 157 and 158, the first jaw 150123a can comprise a first channel 150124a and the second jaw 150123b can comprise a second channel 150124b which can each be configured to receive and support at least a portion of a clip 150140 therein. The first jaw 150123a can be pivotably coupled to the frame 150111 of the shaft 150110 by a pin 150125a and the second jaw 150123b can be pivotably coupled to the frame 150111 by a pin 150125b. In use, the crimping drive 150180 can be configured to rotate the first jaw 150123a toward the second jaw 150123b and/or rotate the second jaw 150123b toward the first jaw 150123a in order to compress the clip 150140 positioned therebetween. In at least one such exemplification, the crimping drive 150180 can comprise a cam actuator 150181 which can be configured to engage a first cam surface 150126a defined on the first jaw 150123a and a second cam surface 150126b on the second jaw 150123b in order to pivot the first jaw 150123a and the second jaw 150123b toward one another. The cam actuator 150181 can comprise a collar which at least partially surrounds the first jaw 150123a and the second jaw 150123b. In at least one such exemplification, the collar can comprise an inner cam surface 150182 which can be contoured to contact the cam surfaces 150126a, 150126b of the jaws 150123a, 150123b and drive them inwardly toward one another. In various circumstances, the clip 150140 positioned within the receiving chamber 150122 defined in the end effector 150120 can be positioned relative to tissue before the crimping drive 150180 is actuated. In some circumstances, the crimping drive 150180 can be at least partially actuated prior to positioning the clip 150140 relative to the tissue in order to at least partially compress the clip 150140. In certain instances, the clip 150140 and the receiving chamber 150122 can be sized and configured such that the clip 150140 can be biased or flexed inwardly when the end effector 150120 is in its unactuated state, as illustrated in FIG. 157. In various instances, the first jaw 150123a and the second jaw 150123b can be actuated to elastically crimp and/or permanently crimp the clip 150140 positioned therebetween.

Further to the above, the firing nut 150163 can be configured to actuate the crimping drive 150180. More particularly, referring now to 161, the crimping drive 150180 can comprise a crimping actuator 150188 operably coupled with the cam actuator 150181 wherein the crimping actuator 150188 can be selectively engaged by the firing nut 150163 as the firing nut 150163 is advanced distally as described above. In at least one such exemplification, the firing nut 150163 can further comprise a second firing pin, such as firing pin 150184, for example, extending therefrom which can be configured to engage the crimping actuator 150188 as the firing nut 150163 is advancing the firing actuator 150168. Referring again to 161, the crimping actuator 150188 is positioned in an unactuated position and, when the firing nut 150163 is advanced sufficiently to engage a distal arm 150190*a* of the crimping actuator 150188, the firing nut 150163 can rotate the crimping actuator 150188 upwardly into an actuated position as illustrated in 162. As also illustrated in 162, the distal arm 150190*a* and a proximal arm 150190*b* can each comprise a projection, such as projections 150191*a* and 150191*b*, respectively, extending therefrom which can be positioned within a second longitudinal slot defined in shaft 150110, such as slot 150115, for example. As the crimping actuator 150188 is rotated upwardly from its unactuated position about a pivot 150189, the projections 150191*a* and 150191*b* can move from a proximal curved end 150116 of the longitudinal slot 150115 into a portion of the longitudinal slot 150115 which is substantially linear Similar to the above, the sidewalls of the longitudinal slot 150115 can be configured to confine the movement of the crimping actuator 150188 along a longitudinal path and can be configured to limit or prevent the rotation of the crimping actuator 150188 once the crimping actuator 150188 has been rotated upwardly into an at least partially actuated position, as discussed above. As the reader will understand, the firing pin 150172 of the firing drive 150160 and the firing pin 150184 of the crimping drive 150180 both extend from the firing nut 150163. For the sake of expediency and demonstration, the firing pins 150172 and 150184 are illustrated as extending from the same side of the firing nut 150163; however, it is envisioned that the firing pin 150172 can extend from a first lateral side of the firing nut 150163 while the firing pin 150184 can extend from the other lateral side of the firing nut 150163. In such circumstances, the firing actuator 150168 can be positioned alongside the first lateral side of the drive screw 150161 and the crimping actuator 150188 can be positioned alongside the opposite lateral side of the drive screw 150161. Correspondingly, the longitudinal slot 150113 can be defined in a first lateral side of the shaft housing 150112 while the longitudinal slot 150115 can be defined in the opposite lateral side of the shaft housing 150112.

Further to the above, the cam actuator 150181 can be operably coupled with crimping actuator 150188 such that, when the crimping actuator 150188 is advanced distally by the firing nut 150163, the cam actuator 150181 can be advanced distally, as illustrated in FIGS. 162 and 165, until the distal projection 150191*a* extending from the distal arm 150190*a* reaches the distal end 150117 of the longitudinal slot 150115. In such a distal position, the cam actuator 150181 may be in a fully advanced position and the clip 150140 positioned within the receiving chamber 150122 can be in a fully deformed or crimped configuration. Thereafter, the cam actuator 150181 can be retracted and the end effector 150120 can be reopened. More particularly, the drive screw 150161 can be rotated in an opposite direction in order to move the firing nut 150163 proximally and retract the cam actuator 150181 wherein, in certain instances, the end effector 150120 can further include a biasing member which can be configured to bias the first jaw 150123 and the second jaw 150123*b* from the closed, or fired, position illustrated in 158 into the open, or unfired, position illustrated in FIG. 157. As the firing nut 150163 is retracted from its position illustrated in 165, the firing pin 150184 extending from the firing nut 150163 can engage the proximal arm 150190*b* of the crimping actuator 150188 and move the crimping actuator 150188, and the cam actuator 150181 extending therefrom, proximally as illustrated in 166. Similar to the above, the proximal projection 150191*b* extending from the proximal arm 150190*b* of the crimping actuator 150188 can be configured to contact the sidewall of the curved proximal end 150116 wherein the sidewall can guide the crimping actuator 150188 downwardly and rotate the crimping actuator 150188 about the pivot 150189. At such point, the firing pin 150184 may no longer be engaged with the crimping actuator 150188, the cam actuator 150181 may be fully retracted, and the firing nut 150163 may continue to be retracted proximally relative to the crimping actuator 150188.

Further to the above, referring now to 166, the firing nut 150163 can be configured to re-engage the firing actuator 150168 as the firing nut 150163 is being retracted proximally. As discussed above, the firing actuator 150168 is rotated downwardly when the firing actuator 150168 reaches the distal end 150114 of the longitudinal slot 150113 and, as a result, the firing actuator 150168 may still be in its downwardly rotated position when the firing nut 150163 is retracted proximally to re-engage the firing actuator 150168. As illustrated in 166, the firing pin 150172 extending from the firing nut 150163 can engage the proximal arm 150170*b* of the firing actuator 150168 and, as the firing nut 150163 is further retracted, the firing nut 150163 can rotate the firing actuator 150168 upwardly such that the projections 150171*a* and 150171*b* extending from the arms 150170*a* and 150170*b*, respectively, can re-enter the longitudinal portion of the longitudinal slot 150113. Thereafter, the firing nut 150163 and can be retracted until the firing actuator 150168 and the firing member 150165 extending therefrom have been returned to their starting, or unfired, positions illustrated in FIG. 159. In such circumstances, the firing member 150165 can be withdrawn from the clip cartridge 150130 as the firing member 150165 is retracted proximally by the firing nut 150163 such that a new clip 150140 can be biased into the firing chamber of the clip cartridge 150130 by the biasing member 150136. Once the firing member 150165 and the firing actuator 150168 have been retracted to their starting positions and the next clip 150140 has been positioned within the firing chamber, the firing drive 150160 can be actuated once again in order to move the firing nut 150163 and the firing member 150165 distally to advance the next clip 150140 into the end effector 150120. Likewise, the firing nut 150163 can re-actuate the crimping drive 150180 as the firing nut 150163 is moved distally once again in order to deform the next clip 150140. Thereafter, the firing nut 150163 can be retracted in order to re-set the crimping drive 150180 and the firing drive 150160 once again. This process can be repeated until a sufficient number of clips 150140 have been applied to the targeted tissue and/or until the clips 150140 contained within the clip cartridge 150130 have been depleted. In the event that additional clips 150140 are needed, the expended clip cartridge 150130 can be removed from the shaft 150110 and a replacement clip cartridge 150130 containing additional clips 150140 can be inserted into the shaft 150110. In some circumstances, an at least partially depleted clip cartridge 150130 can be replaced with an identical, or at least nearly identical, replacement clip cartridge 150130 while, in other circumstances, the clip cartridge 150130 can be replaced with a clip cartridge having more than or less than five clips 150140 contained therein and/or a clip cartridge having clips other than clips 150140 contained therein, for example.

Referring again to FIGS. 160-163, the firing nut 150163 of the illustrated exemplification can be configured to become disengaged from the firing actuator 150168 at the same time that the firing nut 150163 becomes engaged with the crimping actuator 150188. Stated another way, the firing drive 150160 can be deactivated at the same time that the crimping drive 150180 is activated. In various circumstances, such timing can be achieved when the distal end 150114 of the longitudinal slot 150113 is aligned, or at least substantially aligned, with the proximal end 150116 of the second longitudinal slot 150115, for example. In the illustrated exemplification and/or any other suitable exemplification, a lag can exist between the deactivation of the firing drive 150160 and the activation of the crimping drive 150180. Such a lag between the end of the firing stroke of the firing member 150165 and the beginning of the firing stroke of the cam actuator 150181 can be created, in some circumstances, to assure that the clip 150140 has been positioned in its fully-seated position within the receiving chamber 150122 before the clip 150140 is deformed by the cam actuator 150181. In various circumstances, such a lag can be created when the distal end 150114 of the longitudinal slot 150113 is positioned proximally with respect to the proximal end 150116 of the second longitudinal slot 150115, for example. In the illustrated exemplification and/or any other suitable exemplification, the deactivation of the firing drive 150160 may occur after the activation of the crimping drive 150180. Such an overlap between the end of the firing stroke of the firing member 150165 and the beginning of the firing stroke of the cam actuator 150181 can be created, in some circumstances, to apply at least some inward pressure on the clip 150140 as it is moved into its fully-seated position within the receiving chamber 150122 so as to reduce or eliminate relative movement between the clip 150140 and the sidewalls of the receiving chamber 150122, for example. In various circumstances, such an overlap can be created when the distal end 150114 of the longitudinal slot 150113 is positioned distally with respect to the proximal end 150116 of the second longitudinal slot 150115, for example.

As discussed above, the firing drive of the clip applier 150100 can be operated by a surgical instrument system comprising an electric motor. A robotic surgical instrument system is can comprise a plurality of movable arms as describe further above. Each arm can comprise an actuator module comprising an electric motor configured to supply the rotary motion to the shaft 150110 of a clip applier 150100, and/or any other suitable surgical instrument. Referring now to FIG. 171, an end effector 150620 may be selectively engageable with and disengageable from an actuator shaft 150610 of a clip applier wherein the end effector 150620 can comprise a proximal end 150621 which can be coupled to a distal end 150611 of the shaft 150610. The proximal end 150621 of the end effector 150620 can comprise an outer housing 150629, a frame extending through the outer housing 150629, an outer drive shaft extending through the frame, and an inner drive shaft extending through the outer drive shaft. Similarly, the distal end 150611 of the shaft 150610 can comprise an outer housing 150619, a frame 150663 extending through the outer housing 150619, an outer drive shaft 150662 extending through the frame 150663, and an inner drive shaft 150661 extending through the outer drive shaft 150662. With regard to the distal end 150611 of the shaft 150610, the frame 150663, the outer drive shaft 150662, and the inner drive shaft 150661 can each comprise a portion of a tongue connector 150613 extending therefrom and a portion of a connector groove 150612 defined therein, wherein the tongue connector 150613 can be configured to be received within a tongue groove 150623 defined in the proximal end 150621 of the end effector 150620, and wherein the tongue groove 150612 can be configured to receive a tongue connector 150622 extending from the proximal end 150621 of the end effector 150620. Similar to the tongue connector 150613 which extends across the frame 150663, the outer drive shaft 150662, and the inner drive shaft 150661 of the distal shaft end 150611, the tongue connector 150622 can extend across the frame, the outer drive shaft, and the inner drive shaft of the proximal end 150621 of the end effector 150620. Also, similar to the tongue groove 150612 which extends across the frame 150663, the outer drive shaft 150662, and the inner drive shaft 150661 of the distal shaft end 150611, the tongue groove 150623 can extend across the frame, the outer drive shaft, and the inner drive shaft of the proximal end 150621 of the end effector 150620. In the configuration depicted in FIG. 171, the tongue connector 150622 of the end effector 150620 can be slid laterally into the tongue groove 150612 of the shaft 150610 at the same time that the tongue connector 150613 of the shaft 150610 is slid laterally into the tongue groove 150623 of the end effector 150620. Owing to such assembly, the frame of the end effector 150620 can be securely coupled to the frame 150663 of the shaft 150610, the outer drive shaft of the end effector 150620 can be operably coupled to the outer drive shaft 150662 of the shaft 150110, and the inner drive shaft of the end effector 150620 can be operable coupled to the inner drive shaft 150661 of the shaft 150110. The reader will note that the portions of the tongue connector 150612 are aligned with one another, the portions of the tongue groove 150613 are aligned with one another, the portions of the tongue groove 150622 are aligned with one another, and the portions of the tongue connector 150623 are aligned with one another when the end effector 150620 is assembled to the shaft 150610. Once assembled, the outer drive shaft 150662 of the shaft 150110 can rotate the outer drive shaft of the end effector 150620, and the inner drive shaft 150661 of the shaft 150610 can rotate the inner drive shaft of the end effector 150620. When the outer drive shaft 150662 and/or the inner drive shaft 150661 are rotated, the portions of the tongue connector 150612, the portions of the tongue groove 150613, the portions of the tongue groove 150622, and the portions of the tongue connector 150623 may no longer be aligned. In order to remove the end effector 150620 from the shaft 150610, the inner drive shaft 150661 and/or the outer drive shaft 150662 can be rotated into one or more positions in which the tongue connectors 150612 and 150623 and the tongue grooves 150613 and 150622 are sufficiently aligned.

Referring again to FIG. 171, the outer housing 150619 of the shaft 150610 can further comprise a stop 150614 which can be configured to limit the lateral movement of the end effector 150620 as the end effector 150620 is being slid transversely onto the distal end 150611 of the shaft 150610. The stop 150614 can provide a datum from which the inner drive shaft of the end effector 150620 and the inner drive shaft 150661 of the shaft 150610 are aligned along longitudinal axis 150615, the outer drive shaft of the end effector 150620 and the other drive shaft 150662 of the shaft 150610 are aligned along longitudinal axis 150615, and/or the frame of the end effector 150620 and the frame 150663 of the shaft 150610 are aligned along the longitudinal axis 150615. Further to the above, the inner drive shaft 150661 can extend into an actuator module 150632 which can comprise an electric motor and/or gear train 150664 operably coupled with the inner drive shaft 150661 configured to rotate the inner drive shaft 150661. Furthermore, the actuator module 150632 can comprise a second electric motor and gear train operably engaged with the second drive shaft 150662 configured to drive the second drive shaft 150662. As described in greater detail below, a second electric motor can be utilized to articulate the end effector 150620. Also, further to the above, the outer housing 150619 and/or the frame 150663 of the shaft 150610 can further comprise a gear 150617 mounted thereto which is operably engaged with an electric motor and gear train 150618 which can be configured to rotate the shaft 150610 and the end effector 150620 about the longitudinal axis 150615. For instance, if the electric motor and gear train 150618 are operated in a first direction, the shaft 150610 and the end effector 150620 can be rotated about the axis 150615 in a clockwise direction while, if the electric motor and gear train 150618 are operated in a second direction, the shaft 150610 and the end effector 150620 can be rotated about the axis 150615 in a counter-clockwise direction in order to position and orient the end effector 150620.

Further to the above, the end effector 150120 and the shaft 150110 of the clip applier 150100 can be aligned along a longitudinal axis of the clip applier 150100. Turning now to FIG. 172, the end effector 150120 and/or the shaft 150110 can further comprise an articulation joint 150101 which can be configured to permit the end effector 150120 to be articulated relative to the longitudinal axis of the clip applier 150100. The shaft 150110 can comprise an outer housing, or frame portion, 150119 which can comprise a proximal end 150102 and can comprise a distal portion of the articulation joint 150101. The proximal end 150102 can comprise a spherical, or an at least substantially spherical, end 150102', for example, which can be received within a spherical, or an at least substantially spherical, cavity 150104 defined in an articulation joint member 150103. The articulation joint member 150103 can also comprise a spherical, or at least substantially spherical, end 150105, for example, which can be received within a spherical, or an at least substantially spherical, cavity 150107 defined in a shaft frame portion 150106. The proximal end 150102 of the shaft 150110 can be at least partially captured within the cavity 150104 such that the proximal end 150102 cannot be readily removed from the cavity 150104. That said, the proximal end 150102 and the cavity 150104 can be sized and configured to permit the proximal end 150102 to be rotated in any suitable direction within the cavity 150104. As also illustrated in FIG. 172, the clip applier 150100 can further comprise articulation controls 150108a and 150108b, for example, which can extend through the articulation joint 150101 and can comprise distal ends mounted within mounting apertures 150109a and 150109b, respectively, defined within the proximal end 150102 of the shaft housing 150119. In use, the articulation controls 150108a and 150108b can be pushed and/or pulled in order to move the proximal end 150102 within the cavity 150104. Further to the above, the end 150105 of the articulation joint member 150103 can be at least partially captured within the cavity 150107 defined in the shaft frame portion 150106 such that the end 150105 cannot be readily removed from the cavity 150107. That said, the end 150105 and the cavity 150107 can be sized and configured to permit the end 150105 to be rotated in any suitable direction within the cavity 150107 when the shaft end 150102 is pushed and/or pulled by the articulation controls 150108a and 150108b as described above.

Further to the above, referring again to FIG. 172, the drive screw 150161 can be rotated by an input shaft, such as input shaft 150152, for example. The input shaft 150152 can extend through an aperture 150156 defined within the shaft frame portion 150106, the articulation joint member 150103, and the proximal end 150102 of the shaft housing 150119. The input shaft 150152 can comprise an input gear 150151 mounted to the distal end thereof which can be operably coupled with an output gear 150155 mounted to the proximal end of the drive screw 150161. In use, the input shaft 150152 can be rotated by the electric motor, described above, wherein the input shaft 150152 can rotate the drive screw 150161. As outlined above, the articulation joint 150101 can be configured to permit the end effector 150120 and at least a portion of the shaft 150110 to be articulated relative to a longitudinal axis defined by the clip applier 150100. In order to accommodate such movement, at least the portion of the input shaft 150152 extending through the articulation joint 150101 can be sufficiently flexible.

FIGS. 155-172 and additional exemplifications are further described in U.S. Pat. No. 9,561,038, filed Jun. 28, 2012, entitled INTERCHANGEABLE CLIP APPLIER, which issued on Feb. 7, 2017, the entire disclosure of which is incorporated by reference herein.

FIG. 173 is a logic diagram illustrating one exemplification of a process 163220 for determining one or more tissue properties based on a plurality of sensors. In one exemplification, a plurality of sensors generate 163222a-163222d a plurality of signals indicative of one or more parameters of an end effector. The plurality of generated signals is converted 163224a-163224d to digital signals and provided to a processor. For example, in one exemplification comprising a plurality of strain gauges, a plurality of electronic .mu.S-train (micro-strain) conversion circuits convert 163224a-163224d the strain gauge signals to digital signals. The digital signals are provided to a processor. The processor determines 163226 one or more tissue characteristics based on the plurality of signals. The processor may determine the one or more tissue characteristics by applying an algorithm and/or a look-up table. The one or more tissue characteristics are displayed 163026 to an operator, for example, by a display embedded in the surgical instrument.

FIG. 174 illustrates one exemplification of a staple cartridge 163270 comprising a plurality of sensors 163272a-163272h formed integrally therein. The staple cartridge 163270 comprises a plurality of rows containing a plurality of holes for storing staples therein. One or more of the holes in the outer row 163278 are replaced with one of the plurality of sensors 163272a-163272h. A cut-away section 163274 is shown to illustrate the sensor 163272f coupled to a sensor wire 163276b. Sensor wires 163276a, 163276b may comprise a plurality of wires for coupling the plurality of sensors 163272a-163272h to one or more circuits of a surgical instrument. In some exemplifications, one or more of the plurality of sensors 163272a-163272h comprise dual purpose sensor and tissue stabilizing elements having electrodes and/or sensing geometries configured to provide tissue stabilization In some exemplifications, the plurality of sensors 163272a-163272h may be replaced with and/or co-populated with a plurality of tissue stabilizing elements. Tissue stabilization may be provided by, for example, controlling tissue flow and/or staple formation during a clamping and/or stapling process. The plurality of sensors 163272a-163272h provide signals to one or more circuits of the surgical instrument to enhance feedback of stapling performance and/or tissue thickness sensing.

FIG. 175 is a logic diagram illustrating one exemplification of a process 163280 for determining one or more parameters of a tissue section clamped within an end effector. In one exemplification, a first sensor 163258 is configured to detect one or more parameters of the end effector and/or a tissue section located between an anvil and a staple cartridge. A first signal is generated 163282 by the first sensors 163258. The first signal is indicative of the one or more parameters detected by the first sensor 163258. One or more secondary sensors 163260 are configured to detect one or more parameters of the end effector and/or the tissue section. The secondary sensors 163260 may be configured to detect the same parameters, additional parameters, or different parameters as the first sensor 163258. Secondary signals 163284 are generated by the secondary sensors 163260. The secondary signals 163284 are indicative of the one or more parameters detected by the secondary sensors 163260. The first signal and the secondary signals are provided to a processor. The processor adjusts 163286 the first signal generated by the first sensor 163258 based on input generated by the secondary sensors 163260. The adjusted signal may be indicative of, for example, the true thickness of a tissue section and the fullness of the bite. The adjusted signal is displayed 163026 to an operator by, for example, a display embedded in the surgical instrument.

FIG. 176 is a flow chart illustrating one exemplification of a process 3550 for determining uneven tissue loading in an end effector. In one exemplification, the process 163550 comprises utilizing one or more first sensors 163552, such as, for example, a plurality of pressure sensors, to detect 163554 the presence of tissue within an end effector. During a clamping operation of the end effector, the input from the pressure sensors, P, is analyzed to determine the value of P. If P is less 163556 than a predetermined threshold, the end effector continues 163558 the clamping operation. If P is greater than or equal to 163560 the predetermined threshold, clamping is stopped. The delta (difference) between the plurality of sensors 163552 is compared 163562. If the delta is greater than a predetermined delta, the surgical instrument displays 163564 a warning to the user. The warning may comprise, for example, a message indicating that there is uneven clamping in the end effector. If the delta is less than or equal to the predetermined delta, the input of the one or more sensors 163552 is compared to an input from an additional sensor 163566.

In some exemplifications, a second sensor 163566 is configured to detect one or more parameters of the surgical instrument. For example, in one some exemplifications, a magnetic sensor, such as, for example, a Hall effect sensor, is located in a shaft of the surgical instrument. The second sensor 163566 generates a signal indicative of the one or more parameters of the surgical instrument. A preset calibration curve is applied 163568 to the input from the second sensor 163566. The preset calibration curve may adjust 163568 a signal generated by the second sensor 163566, such as, for example, a Hall voltage generated by a Hall effect sensor. For example, in one exemplification, the Hall effect voltage is adjusted such that the generated Hall effect voltage is set at a predetermined value when the gap between the anvil and the body of the end effector, $X_1$, is equal to zero. The adjusted sensor 163566 input is used to calculate 163570 a distance, $X_3$, between the anvil and the body of the end effector when the pressure threshold P is met. The clamping process is continued 163572 to deploy a plurality of staples into the tissue section clamped in the end effector. The input from the second sensor 163566 changes dynamically during the clamping procedure and is used to calculate the distance, $X_2$, between the anvil and the body in real-time. A real-time percent compression is calculated 163574 and displayed to an operator. In one exemplification, the percent compression is calculated as: $[((X_3-X_2)/X_3)*100]$.

In some exemplifications, one or more of the sensors described herein are used to indicate: whether the anvil is attached to the body of the surgical device; the compressed tissue gap; and/or whether the anvil is in a proper position for removing the device, or any combination of these indicators.

In some exemplifications, one or more of the sensors described herein are used to affect device performance. One or more control parameters of a surgical device may be adjusted by at least one sensor output. For example, in some exemplifications, the speed control of a firing operation may be adjusted by the output of one or more sensors, such as, for example, a Hall effect sensor. In some exemplifications, one or more the sensors may adjust a closure and/or clamping operation based on load and/or tissue type. In some exemplifications, multiple stage compression sensors allow the surgical instrument to stop closure at a predetermined load and/or a predetermined displacement. A control circuit may apply one or more predetermined algorithms to apply varying compression to a tissue section to determine a tissue type, for example, based on a tissue response. The algorithms may be varied based on closure rate and/or predetermined tissue parameters. In some exemplifications, one or more sensors are configured to detect a tissue property and one or more sensors are configured to detect a device property and/or configuration parameter. For example, in one exemplification, capacitive blocks may be formed integrally with a staple cartridge to measure skew.

FIGS. 177-178 illustrate one exemplification of an end effector 163800 comprising a pressure sensor. The end effector 163800 comprises a first jaw member, or anvil, 163802 pivotally coupled to a second jaw member 163804. The second jaw member 163804 is configured to receive a staple cartridge 163806 therein. The staple cartridge 163806 comprises a plurality of staples. A first sensor 163808 is coupled to the anvil 163802 at a distal tip. The first sensor 163808 is configured to detect one or more parameters of the end effector, such as, for example, the distance, or gap 163814, between the anvil 163802 and the staple cartridge 163806. The first sensor 163808 may comprise any suitable sensor, such as, for example, a magnetic sensor. A magnet 163810 may be coupled to the second jaw member 163804 and/or the staple cartridge 163806 to provide a magnetic signal to the magnetic sensor.

In some exemplifications, the end effector 163800 comprises a second sensor 163812. The second sensor 163812 is configured to detect one or more parameters of the end effector 163800 and/or a tissue section located therebetween. The second sensor 163812 may comprise any suitable sensor, such as, for example, one or more pressure sensors. The second sensor 163812 may be coupled to the anvil 163802, the second jaw member 163804, and/or the staple cartridge 163806. A signal from the second sensor 163812 may be used to adjust the measurement of the first sensor 163808 to adjust the reading of the first sensor to accurately represent proximal and/or distal positioned partial bites true compressed tissue thickness. In some exemplifications, the second sensor 163812 may be surrogate with respect to the first sensor 163808.

In some exemplifications, the second sensor 163812 may comprise, for example, a single continuous pressure sensing film and/or an array of pressure sensing films. The second sensor 163812 is coupled to the deck of the staple cartridge 163806 along the central axis covering, for example, a slot 163816 configured to receive a cutting and/or staple deployment member. The second sensor 163812 provides signals indicative of the amplitude of pressure applied by the tissue during a clamping procedure. During firing of the cutting and/or deployment member, the signal from the second sensor 163812 may be severed, for example, by cutting electrical connections between the second sensor 163812 and one or more circuits. In some exemplifications, a severed circuit of the second sensor 163812 may be indicative of a spent staple cartridge 163806. In other exemplifications, the second sensor 163812 may be positioned such that deployment of a cutting and/or deployment member does not sever the connection to the second sensor 163812.

FIG. 179 illustrates one exemplification of an end effector 163850 comprising a second sensor 163862 located between a staple cartridge 163856 and a second jaw member 163854. The end effector 163850 comprises a first jaw member, or anvil, 163852 pivotally coupled to the second jaw member 163854. The second jaw member 163854 is configured to receive the staple cartridge 163856 therein. A first sensor 163858 is coupled to the anvil 163852 at a distal tip. The first sensor 163858 is configured to detect one or more parameters of the end effector 163850, such as, for example, the distance, or gap 163864, between the anvil 163852 and the staple cartridge 163856. The first sensor 163858 may comprise any suitable sensor, such as, for example, a magnetic sensor. A magnet 163860 may be coupled to the second jaw member 163854 and/or the staple cartridge 163856 to provide a magnetic signal to the magnetic sensor. In some exemplifications, the end effector 163850 comprises second sensor 163862 similar in all respect to the second sensor 163812 of FIGS. 177-178, except that it is located between the staple cartridge 163856 and the second jaw member 163854.

FIG. 180 is a logic diagram illustrating one exemplification of a process 163870 for determining and displaying the thickness of a tissue section clamped in an end effector 163800 or 163850, according to FIGS. 177-178 or FIG. 179. The process comprises obtaining a Hall effect voltage 163872, for example, through a Hall effect sensor located at the distal tip of the anvil 163802. The Hall effect voltage 163872 is provided to an analog to digital converter 163874 and converted into a digital signal. The digital signal is provided to a processor. The processor calibrates 163876 the curve input of the Hall effect voltage 163872 signal. Pressure sensors, such as for example second sensor 163812, is configured to measure 163880 one or more parameters of, for example, the end effector 163800, such as for example the amount of pressure being exerted by the anvil 163802 on the tissue clamped in the end effector 163800. In some exemplifications the pressure sensors may comprise a single continuous pressure sensing film and/or array of pressure sensing films. The pressure sensors may thus be operable to determine variations in the measured pressure at different locations between the proximal and distal ends of the end effector 163800. The measured pressure is provided to the processor. The processor uses one or more algorithms and/or lookup tables to adjust 163882 the Hall effect voltage 163872 in response to the pressure measured by the pressure sensors 163880 to more accurately reflect the thickness of the tissue clamped between, for example, the anvil 163802 and the staple cartridge 163806. The adjusted thickness is displayed 163878 to an operator by, for example, a display embedded in the surgical instrument.

FIG. 181 illustrates one exemplification of an end effector 166000 comprising a magnet 166008 and a Hall effect sensor 166010 wherein the detected magnetic field 166016 can be used to identify a staple cartridge 166006. The end effector 166000 is similar to the end effectors described above. The end effector 166000 comprises a first jaw member or anvil 166002, pivotally coupled to a second jaw member or elongated channel 166004. The elongated channel 166004 is configured to operably support the staple cartridge 166006 therein. The staple cartridge 166006 is similar to the staple cartridges described above. The anvil 166002 further comprises magnet 166008. The staple cartridge 166006 further comprises Hall effect sensor 166010 and a processor 166012. The Hall effect sensor 166010 is operable to communicate with the processor 166012 through a conductive coupling 166014. The Hall effect sensor 166010 is positioned within the staple cartridge 166006 to operatively couple with the magnet 166008 when the anvil 166002 is in a closed position. The Hall effect sensor 166010 can be operable to detect the magnetic field 166016 produced by the magnet 166008. The polarity of the magnetic field 166016 can be one of north or south depending on the orientation of the magnet 166008 within the anvil 166002. In the illustrated exemplification of FIG. 181, the magnet 166008 is oriented such that its south pole is directed towards the staple cartridge 166006. The Hall effect sensor 166010 can be operable to detect the magnetic field 166016 produced by a south pole. If the Hall effect sensor 166010 detects a magnetic south pole, then the staple cartridge 166006 can be identified as of a first type.

FIG. 182 illustrates on exemplification of an end effector 166050 comprising a magnet 166058 and a Hall effect sensor 166060 wherein the detected magnetic field 166066 can be used to identify a staple cartridge 166056. The end effector 166050 comprises a first jaw member or anvil 166052, pivotally coupled to a second jaw member or elongated channel 166054. The elongated channel 166054 is configured to operably support staple cartridge 166056 therein. The anvil 166052 further comprises magnet 166058. The staple cartridge 166056 further comprises Hall effect sensor 166060 in communication with a processor 166062 over a conductive coupling 166064. The Hall effect sensor 166060 is positioned such that it will operatively couple with the magnet 166058 when the anvil 166052 is in a closed position. The Hall effect sensor 166060 can be operable to detect the magnetic field 166066 produced by the magnet 166058. In the illustrated exemplification, the magnet 166058 is oriented such that its north magnetic pole is directed towards the staple cartridge 166056. The Hall effect sensor 166060 can be operable to detect the magnetic field 166066 produced by a north pole. If the Hall effect sensor 166060 detects a north magnetic pole, then the staple cartridge 166056 can be identified as a second type.

It can be recognized that the second type staple cartridge 166056 of FIG. 182 can be substituted for the first type staple cartridge 166006 of FIG. 181, and vice versa. In FIG. 181, the second type staple cartridge 166056 would be operable to detect a magnetic north pole, but will detect a magnetic south pole instead. In this case, end effector 166000 will identify the staple cartridge 166056 as being of the second type. If the end effector 166000 did not expect a staple cartridge 166056 of the second type, the operator of the instrument can be alerted, and/or a function of the instrument can be disabled. The type of the staple cartridge 166056 can additionally or alternatively be used to identify some parameter of the staple cartridge 166056, such as for instance the length of the cartridge and/or the height and length of the staples.

Similarly, as shown in FIG. 182, the first type staple cartridge 66006 can be substituted for the second staple cartridge 166056. The first type staple cartridge 166006 would be operable to detect a south magnetic pole, but will instead detect a north magnetic pole. In this case, the end effector 166050 will identify the staple cartridge 166006 as being of the first type.

FIG. 183 illustrates a graph 166020 of voltage 166022 detected by a Hall effect sensor located in the distal tip of a staple cartridge, such as is illustrated in FIGS. 181 and 182, in response to a distance or gap 166024 between a magnet located in the anvil and the Hall effect sensor in the staple cartridge, such as illustrated in FIGS. 181 and 182. As illustrated FIG. 183, when the magnet in the anvil is oriented such that its north pole is towards the staple cartridge, the voltage will tend towards a first value as the magnet comes in proximity to the Hall effect sensor; when the magnet is oriented with its south pole towards the staple cartridge, the voltage will tend towards a second, different value. The measured voltage can be used by the instrument to identify the staple cartridge.

FIGS. 184 and 185 illustrate one exemplification of an end effector 166200 comprising a sensor 166208 for identifying staple cartridges 166206 of different types. The end effector 166200 comprises a first jaw member or anvil 166202, pivotally coupled to a second jaw member or elongated channel 166204. The elongated channel 166204 is configured to operably support staple cartridge 166206 therein. The end effector 166200 further comprises sensor 166208 located in the proximal area. The sensor 166208 can be any of an optical sensor, a magnetic sensor, an electrical sensor, or any other suitable sensor.

The sensor 166208 can be operable to detect a property of the staple cartridge 166206 and thereby identify the staple cartridge 166206 type. FIG. 185 illustrates an example where the sensor 166208 is an optical emitter and detector 166210. The body of the staple cartridge 166206 can be different colors, such that the color identifies the staple cartridge 166206 type. An optical emitter and detector 166210 can be operable to interrogate the color of the staple cartridge 166206 body. In the illustrated example, the optical emitter and detector 166210 can detect white 166212 by receiving reflected light in the red, green, and blue spectrums in equal intensity. The optical emitter and detector 166210 can detect red 166214 by receiving very little reflected light in the green and blue spectrums while receiving light in the red spectrum in greater intensity.

Alternately or additionally, the optical emitter and detector 166210, or another suitable sensor 166208, can interrogate and identify some other symbol or marking on the staple cartridge 166206. The symbol or marking can be any one of a barcode, a shape or character, a color-coded emblem, or any other suitable marking. The information read by the sensor 166208 can be communicated to a microcontroller in the surgical device. The microcontroller can be configured to communicate information about the staple cartridge 166206 to the operator of the instrument. For instance, the identified staple cartridge 166206 may not be appropriate for a given application; in such case, the operator of the instrument can be informed, and/or a function of the instrument may be inappropriate. In such instance, microcontroller can optionally be configured to disable a function of the surgical instrument. Alternatively or additionally, microcontroller can be configured to inform the operator of the surgical instrument of the parameters of the identified staple cartridge 166206 type, such as for instance the length of the staple cartridge 166206, or information about the staples, such as the height and length.

FIG. 186 illustrates one exemplification of the operable dimensions that relate to the operation of a Hall effect sensor 170010. A first dimension 170020 is between the bottom of the center of a magnet 170008 and the top of staple cartridge 170006. The first dimension 170020 can vary with the size and shape of the staple cartridge 170006, such as for instance between 0.0466 inches, 0.0325 inches, 0.0154 inches, or 0.0154 inches, or any reasonable value. A second dimension 170022 is between the bottom of the center of the magnet 170008 and the top of the Hall effect sensor 170010. The second dimension can also vary with the size and shape of the staple cartridge 170006, such as for instance 0.0666 inches, 0.0525 inches, 0.0354 inches, 0.0347 inches, or any reasonable value. A third dimension 170024 is between the top of a processor 170012 and a lead-in surface 170028 of the staple cartridge 170006. The Hall effect sensor 170010 is operable to communicate with the processor 170012 through a conductive coupling 170014. The third dimension can also vary with the size and the shape of the staple cartridge, such as for instance 0.0444 inches, 0.0440 inches, 0.0398 inches, 0.0356 inches, or any reasonable value. An angle 170026 is the angle between anvil 170002 and the top of the staple cartridge 170006. The angle 170026 also can vary with the size and shape of the staple cartridge 170006, such as for instance 0.91 degrees, 0.68 degrees, 0.62 degrees, 0.15 degrees, or any reasonable value.

FIGS. 187-191 illustrate one exemplification of an end effector 170100 that comprises, by way of example, a magnet 170058a. FIG. 187 illustrates a front-end cross-sectional view of the end effector 170100. The end effector 170100 is similar to the end effectors described above. The end effector 170100 comprises a first jaw member or anvil 170102, a second jaw member or elongated channel 170104, and a staple cartridge 170106 operatively coupled to the elongated channel 170104. The anvil 170102 further comprises the magnet 170058a. The staple cartridge 170106 further comprises a Hall effect sensor 170110. The anvil 170102 is here illustrated in a closed position. FIG. 188 illustrates a front-end cutaway view of the anvil 170102 and the magnet 170058a in an optional location. FIG. 189 illustrates a perspective cutaway view of the anvil 170102 and the magnet 170058a in an optional location. FIG. 190 illustrates a side cutaway view of the anvil 170102 and the magnet 170058a in an optional location. FIG. 191 illustrates a top cutaway view of the anvil 170102 and the magnet 170058a in an optional location.

FIGS. 192-196 illustrate one exemplification of an end effector 170150 that comprises, by way of example, a magnet 170058d. FIG. 192 illustrates a front-end cross-sectional view of the end effector 170150. The end effector 170150 comprises an anvil 170152, an elongated channel 170154, and a staple cartridge 170156. The anvil 170152 further comprises magnet 170058d. The staple cartridge 170156 further comprises a Hall effect sensor 170160. FIG. 193 illustrates a front-end cutaway view of the anvil 170152 and the magnet 170058d in an optional location. FIG. 194 illustrates a perspective cutaway view of the anvil 170152 and the magnet 170058d in an optional location. FIG. 195 illustrates a side cutaway view of the anvil 170152 and the magnet 170058d in an optional location. FIG. 196 illustrates a top cutaway view of the anvil 170152 and magnet 170058d in an optional location.

FIGS. 197 and 198 illustrate one exemplification of a staple cartridge 170706 that comprises a flex cable 170730, a Hall effect sensor 170710, and a processor 170712. FIG. 197 is an exploded view of the staple cartridge 170706. The staple cartridge 170706 comprises a cartridge body 170720, a wedge sled 170718, a cartridge tray 170722, and flex cable 170730. The flex cable 170730 further comprises electrical contacts 170732 placed to make an electrical connection when the staple cartridge 170706 is operatively coupled with an end effector. The electrical contacts 170732 are integrated with cable traces 170734. The cable traces connect 170736 near the distal end of the staple cartridge 170706, and this connection 170736 joins with a conductive coupling 170714. The Hall effect sensor 170710 and the processor 170712 are operatively connected to the conductive coupling 170714 such that they are able to communicate.

FIG. 198 illustrates the assembly of the staple cartridge 170706 and the flex cable 170730 in greater detail. As illustrated, the cartridge tray 170722 encloses the underside of the cartridge body 170720, thereby enclosing the wedge sled 170718. The flex cable 170730 can be located on the exterior of the cartridge tray 170722 with the conductive coupling 170714 positioned within the distal end of the cartridge body 170720. The flex cable 170730 can be placed on the exterior of the cartridge tray 170722 by any appropriate means, such as for instance bonding or laser etching.

FIGS. 199-204 illustrate one exemplification of an end effector 170800 with a flex cable 170830 operable to provide power to a staple cartridge 170806 that comprises a distal sensor plug 170816. The end effector 170800 is similar to the end effectors described above. The end effector 170800 comprises a first jaw member or anvil 170802, a second jaw member or elongated channel 170804, and staple cartridge 170806 operatively coupled to the elongated channel 170804. The end effector 170800 is operatively coupled to a shaft assembly 170900. The shaft assembly 170900 is similar to the shaft assemblies described above. The shaft assembly 170900 further comprises a closure tube 170902 that encloses the exterior of the shaft assembly 170900. In some exemplifications the shaft assembly 170900 further comprises an articulation joint 170904, which includes a double pivot closure sleeve assembly 170906. The double pivot closure sleeve assembly 170906 includes an end effector closure sleeve assembly 170908 that is operable to couple with the end effector 170800.

FIG. 199 illustrates a perspective view of the end effector 170800 coupled to the shaft assembly 170900. In various exemplifications, the shaft assembly 170900 further comprises flex cable 170830 that is configured to not interfere with the function of the articulation joint 170904, as described in further detail below. FIG. 200 illustrates a perspective view of the underside of the end effector 170800 and shaft assembly 170900. In some exemplifications, the closure tube 170902 of the shaft assembly 170900 further comprises a first aperture 170911, through which the flex cable 170830 can extend. The closure sleeve assembly 170908 further comprises a second aperture 170910, through which the flex cable 170830 can also pass.

FIG. 201 illustrates the end effector 170800 with the flex cable 170830 and without the shaft assembly 170900. As illustrated, in some exemplifications the flex cable 170830 can include a single coil 170832 operable to wrap around the articulation joint 170904, and thereby be operable to flex with the motion of the articulation joint 170904.

FIGS. 202 and 203 illustrate the elongated channel 170804 portion of the end effector 170800 without the anvil 170802 or the staple cartridge 170806, to illustrate how the flex cable 170830 can be seated within the elongated channel 170804. In some exemplifications, the elongated channel 170804 further comprises a third aperture 170824 for receiving the flex cable 170830. Within the body of the elongated channel 170804 the flex cable 170830 splits 170834 to form extensions 170836 on either side of the elongated channel 170804. FIG. 203 further illustrates that connectors 170838 can be operatively coupled to the flex cable extensions 170836.

FIG. 204 illustrates the flex cable 170830 alone. As illustrated, the flex cable 170830 comprises the single coil 170832 operative to wrap around the articulation joint 170904, and the split 170834 that attaches to extensions 170836. The extensions can be coupled to connectors 170838 that have on their distal facing surfaces prongs 170840 for coupling to the staple cartridge 170806, as described below.

FIG. 205 illustrates a close up view of the elongated channel 170804 with staple cartridge 170806 coupled thereto. The staple cartridge 170806 comprises a cartridge body 170822 and a cartridge tray 170820. In some exemplifications the staple cartridge 170806 further comprises electrical traces 170828 that are coupled to proximal contacts 170856 at the proximal end of the staple cartridge 170806. The proximal contacts 170856 can be positioned to form a conductive connection with the prongs 170840 of the connectors 170838 that are coupled to the flex cable extensions 170836. Thus, when the staple cartridge 170806 is operatively coupled with the elongated channel 170804, the flex cable 170830, through the connectors 170838 and the connector prongs 170840, can provide power to the staple cartridge 170806.

FIGS. 206-209 further illustrate one exemplification of staple cartridge 170806 operative with the present exemplification of an end effector 170800. FIG. 206 illustrates a close up view of the proximal end of the staple cartridge 170806. As discussed above, the staple cartridge 170806 comprises electrical traces 170828 that, at the proximal end of the staple cartridge 170806, form proximal contacts 170856 that are operable to couple with the flex cable 170830 as described above. FIG. 207 illustrates a close-up view of the distal end of the staple cartridge 170806, with a space for distal sensor plug 170816, described below. As illustrated, the electrical traces 170828 can extend along the length of the staple cartridge body 170822 and, at the distal end, form distal contacts 170858. FIG. 208 further illustrates the distal sensor plug 170816, which in some exemplifications is shaped to be received by the space formed for it in the distal end of the staple cartridge 170806. FIG. 209 illustrates the proximal-facing side of the distal sensor plug 170816. As illustrated, the distal sensor plug 170816 has sensor plug contacts 170854, positioned to couple with the distal contacts 170858 of the staple cartridge 170806. Thus, in some exemplifications the electrical traces 170828 can be operative to provide power to the distal sensor plug 170816.

FIGS. 210 and 211 illustrate one exemplification of distal sensor plug 170816. FIG. 210 illustrates a cutaway view of the distal sensor plug 170816. As illustrated, the distal sensor plug 170816 comprises a Hall effect sensor 170810 and a processor 110812. The distal sensor plug 170816 further comprises a flex board 170814. As further illustrated in FIG. 211, the Hall effect sensor 170810 and the processor 170812 are operatively coupled to the flex board 170814 such that they are capable of communicating.

FIGS. 173-211 and additional exemplifications are further described in U.S. Pat. No. 9,757,128, filed Sep. 5, 2014, entitled MULTIPLE SENSORS WITH ONE SENSOR AFFECTING A SECOND SENSOR'S OUTPUT OR INTERPRETATION, which issued on Sep. 12, 2017, the entire disclosure of which is incorporated by reference herein.

Referring now to FIG. 212, in one aspect, RF electrodes 186084-186116 may be positioned on staple cartridge 186082 inserted into the channel frame 186080 (or other component of an end-effector) based on various points for which compression information is desired. Referring now to FIG. 213, in one aspect, RF electrodes 186122-186140 may be positioned on staple cartridge 186120 at discrete points for which compression information is desired. Referring now to FIG. 214, RF electrodes 186152-186172 may be positioned at different points in multiple zones of a staple cartridge based on how accurate or precise the compression measurements should be. For example, RF electrodes 186152-186156 may be positioned in zone 186158 of staple cartridge 186150 depending on how accurate or precise the compression measurements in zone 186158 should be. Further, RF electrodes 186160-186164 may be positioned in zone 186166 of staple cartridge 186150 depending on how accurate or precise the compression measurements in zone 186166 should be. Additionally, RF electrodes 186168-186172 may be positioned in zone 186174 of staple cartridge 186150 depending on how accurate or precise the compression measurements in zone 186174 should be.

The RF electrodes discussed herein may be wired through a staple cartridge inserted in the channel frame. Referring now to FIG. 215, in one aspect, an RF electrode may have a stamped "mushroom head" 186180 of about 1.0 mm in diameter. While the RF electrode may have the stamped "mushroom head" of about 1.0 mm in diameter, this is intended to be a non-limiting example and the RF electrode may be differently shaped and sized depending on each particular application or design. The RF electrode may be connected to, fastened to, or may form, a conductive wire 186182. The conductive wire 186182 may be about 0.5 mm in diameter, or may have a larger or smaller diameter based on a particular application or design. Further, the conductive wire may have an insulative coating 186184. In one example, the RF electrode may protrude through a staple cartridge, channel frame, knife, or other component of an end-effector.

Referring now to FIG. 216, one or more aspects of the present disclosure are described in circuit diagram 186250. In an implementation, a power source at a handle 186252 of an endocutter may provide power to a frequency generator 186254. The frequency generator 186254 may generate one or more RF signals. The one or more RF signals may be multiplexed or overlaid at a multiplexer 186256, which may be in a shaft 186258 of the endocutter. In this way, two or more RF signals may be overlaid (or, e.g., nested or modulated together) and transmitted to the end-effector. The one or more RF signals may energize one or more RF electrodes 186260 at an end-effector 186262 (e.g., positioned in a staple cartridge) of the endocutter. A tissue may be compressed and/or communicatively coupled between the one or more of RF electrodes 186260 and one or more electrical contacts. For example, the tissue may be compressed and/or communicatively coupled between the one or more RF electrodes 186260 and the electrical contact 186264 positioned in a channel frame of the end-effector 186262 or the electrical contact 186266 positioned in an anvil of the end-effector 186262. A filter 186268 may be communicatively coupled to the electrical contact 186264 and a filter 186270 may be communicatively coupled to the electrical contact 186266.

A voltage V and a current I associated with the one or more RF signals may be used to calculate an impedance Z associated with a tissue that may be compressed between the staple cartridge (and communicatively coupled to one or more RF electrodes 166260) and the channel frame or anvil (and communicatively coupled to one or more of electrical contacts 166264 or 166266).

In one aspect, various components of the tissue compression sensor system described herein may be located in shaft 166258 of the endocutter. For example, as shown in circuit diagram 186250 (and in addition to the frequency generator 186254), an impedance calculator 186272, a controller 186274, a non-volatile memory 186276, and a communication channel 186278 may be located in the shaft 186258. In one example, the frequency generator 186254, impedance calculator 186272, controller 186274, non-volatile memory 186276, and communication channel 186278 may be positioned on a circuit board in the shaft 186258.

The two or more RF signals may be returned on a common path via the electrical contacts. Further, the two or more RF signals may be filtered prior to the joining of the RF signals on the common path to differentiate separate tissue impedances represented by the two or more RF signals. Current I1 and current I2 may be measured on a return path corresponding to electrical contacts 186264 and 186266. Using a voltage V applied between the supply and return paths, impedances Z1 and Z2 may be calculated. Z1 may correspond to an impedance of a tissue compressed and/or communicatively coupled between one or more of RF electrodes 186260 and electrical contact 186264. Further, Z2 may correspond to an impedance of the tissue compressed and/or communicatively coupled between one or more of RF electrodes 186260 and electrical contact 186266. Applying the formulas $Z1=V/I1$ and $Z2=V/I2$, impedances Z1 and Z2 corresponding to different compressions of a tissue compressed by an end-effector 186262 may be calculated. In example, the impedances Z1 and Z2 may be calculated by the impedance calculator 186272. The impedances Z1 and Z2 may be used to calculate various compression levels of the tissue.

FIGS. 217 and 218 show examples of sensed parameters as well as parameters derived therefrom. FIG. 217 is an illustrative graph showing gap distance over time, where the gap is the space between the jaws being occupied by clamped tissue. The vertical (y) axis is distance and the horizontal (x) axis is time. In one exemplification the gap distance is the distance between an anvil and the staple cartridge of an end effector. In the open jaw position, at time zero, the gap between the anvil and the staple cartridge is at its maximum distance. The width of the gap decreases as the anvil closes, such as during tissue clamping. The gap distance rate of change can vary because tissue has non-uniform resiliency. For example, certain tissue types may initially show rapid compression, resulting in a faster rate of change. However, as tissue is continually compressed, the viscoelastic properties of the tissue can cause the rate of change to decrease until the tissue cannot be compressed further, at which point the gap distance will remain substantially constant. The gap decreases over time as the tissue is squeezed between the anvil and the staple cartridge of the end effector. One or more sensors such as, for example, a magnetic field sensor, a strain gauge, a pressure sensor, a force sensor, an inductive sensor such as, for example, an eddy current sensor, a resistive sensor, a capacitive sensor, an optical sensor, and/or any other suitable sensor, may be adapted and configured to measure the gap distance "d" between the anvil and the staple cartridge over time "t" as represented graphically in FIG. 217. The rate of change of the gap distance "d" over time "t" is the Slope of the curve shown in FIG. 217, where Slope=$\Delta i/\Delta t$.

FIG. 218 is an illustrative graph showing firing current of the end effector jaws. The vertical (y) axis is current and the horizontal (x) axis is time. A surgical instrument and/or the microcontroller thereof can include a current sensor that detects the current utilized during various operations, such as clamping, cutting, and/or stapling tissue. For example, when tissue resistance increases, the instrument's electric motor can require more current to clamp, cut, and/or staple the tissue. Similarly, if resistance is lower, the electric motor can require less current to clamp, cut, and/or staple the tissue. As a result, firing current can be used as an approximation of tissue resistance. The sensed current can be used alone or more preferably in conjunction with other measurements to provide feedback about the target tissue. Referring still to FIG. 218, during some operations, such as stapling, firing current initially is high at time zero but decreases over time. During other device operations, current may increase over time if the motor draws more current to overcome increasing mechanical load. In addition, the rate of change of firing current is can be used as an indicator that the tissue is transitioning from one state to another state. Accordingly, firing current and, in particular, the rate of change of firing current can be used to monitor device operation. The firing current decreases over time as the knife cuts through the tissue. The rate of change of firing current can vary if the tissue being cut provides more or less resistance due to tissue properties or sharpness of the knife. As the cutting conditions vary, the work being done by the motor varies and hence will vary the firing current over time. A current sensor may be may be employed to measure the firing current over time while the knife is firing as represented graphically in FIG. 218. For example, the motor current may be monitored employing a current sensor in series with a battery. The current sensors may be adapted and configured to measure the motor firing current "i" over time "t" as represented graphically in FIG. 218. The rate of change of the firing current "i" over time "t" is the Slope of the curve shown in FIG. 218, where Slope=$\Delta i/\Delta t$.

FIG. 219 is an illustrative graph of impedance over time. The vertical (y) axis is impedance and the horizontal (x) axis is time. At time zero, impedance is low but increases over time as tissue pressure increases under manipulation (e.g., clamping and stapling). The rate of change varies over time because the tissue between the anvil and the staple cartridge of the end effector is severed by the knife or is sealed using RF energy between electrodes located between the anvil and the staple cartridge of the end effector. For example, as the tissue is cut the electrical impedance increases and reaches infinity when the tissue is completely severed by the knife. Also, if the end effector includes electrodes coupled to an RF energy source, the electrical impedance of the tissue increases as energy is delivered through the tissue between the anvil and the staple cartridge of the end effector. The electrical impedance increase as the energy through the tissue dries out the tissue by vaporizing moistures in the tissue. Eventually, when a suitable amount of energy is delivered to the tissue, the impedance increases to a very high value or infinity when the tissue is severed. In addition, as illustrated in FIG. 219, different tissues can have unique compression properties, such as rate of compression, that distinguish tissues. The tissue impedance can be measured by driving a sub-therapeutic RF current through the tissue grasped between the first and second jaw members. One or more electrodes can be positioned on either or both the anvil and the staple cartridge. The tissue compression/impedance of the tissue between the anvil and the staple cartridge can be measured over time as represented graphically in FIG. 219. One or more sensors such as, for example, a magnetic field sensor, a strain gauge, a pressure sensor, a force sensor, an inductive sensor such as, for example, an eddy current sensor, a resistive sensor, a capacitive sensor, an optical sensor, and/or any other suitable sensor, may be adapted and configured to measure tissue compression/impedance. The sensors may be adapted and configured to measure tissue impedance "Z" over time "t" as represented graphically in FIG. 219. The rate of change of the tissue impedance "Z" over time "t" is the Slope of the curve shown in FIG. 219, where Slope=$\Delta Z/\Delta t$.

FIGS. 212-219 and additional exemplifications are further described in U.S. patent application Ser. No. 14/640,935, entitled OVERLAID MULTI SENSOR RADIO FREQUENCY (RF) ELECTRODE SYSTEM TO MEASURE TISSUE COMPRESSION, filed Mar. 6, 2015, now U.S. Pat. No. 10,548,504, the entire disclosure of which is incorporated by reference herein.

FIG. 220 illustrates a modular battery powered handheld electrosurgical instrument 191100 with distal articulation, according to one aspect of the present disclosure. The surgical instrument 191100 comprises a handle assembly 191102, a knife drive assembly 191104, a battery assembly 191106, a shaft assembly 191110, and an end effector 191112. The end effector 191112 comprises a pair of jaw members 191114a, 191114b in opposing relationship affixed to a distal end thereof. The end effector 191112 is configured to articulate and rotate. FIG. 221 is an exploded view of the surgical instrument 191100 shown in FIG. 220, according to one aspect of the present disclosure. The end effector 191112 for use with the surgical instrument 191100 for sealing and cutting tissue includes jaw members 191114a, 191114b that are in opposing relationship and movable relative to each other to grasp tissue therebetween. A jaw member 191114a, 191114b includes a jaw housing and an electrically conductive surface 191116a, 191116b, e.g., electrodes, adapted to connect to a source of electrosurgical energy (RF source) such that the electrically conductive surfaces are capable of conducting electrosurgical energy through tissue held therebetween to effect a tissue seal. One of the electrically conductive surfaces 191116b includes a channel defined therein and extending along a length thereof that communicates with a drive rod 191145 connected to a motor disposed in the knife drive assembly 191104. The knife is configured to translate and reciprocate along the channel to cut tissue grasped between the jaw members 191114a, 191114b.

FIG. 222 is a perspective view of the surgical instrument 191100 shown in FIGS. 220 and 221 with a display located on the handle assembly 191102, according to one aspect of the present disclosure. The handle assembly 191102 of the surgical instrument shown in FIGS. 220-222 comprises a motor assembly 191160 and a display assembly. The display assembly comprises a display 191176, such as an LCD display, for example, which is removably connectable to a housing 191148 portion of the handle assembly 191102. The display 191176 provides a visual display of surgical procedure parameters such as tissue thickness, status of seal, status of cut, tissue thickness, tissue impedance, algorithm being executed, battery capacity, among other parameters.

FIG. 223 is a perspective view of the instrument shown in FIGS. 220 and 221 without a display located on the handle assembly 191102, according to one aspect of the present disclosure. The handle assembly 191102 of surgical instrument 191150 shown in FIG. 223 includes a different display assembly 191154 on a separate housing 191156. With reference now to FIGS. 220-223, the surgical instrument 191100, 191150 is configured to use high-frequency (RF) current and a knife to carry out surgical coagulation/cutting treatments on living tissue, and uses high-frequency current to carry out a surgical coagulation treatment on living tissue. The high-frequency (RF) current can be applied independently or in combination with algorithms or user input control. The display assembly, battery assembly 191106, and shaft assembly 191110 are modular components that are removably connectable to the handle assembly 191102. A motor 191140 is located within the handle assembly 191102. RF generator circuits and motor drive circuits are located within the housing 191148.

The shaft assembly 191110 comprises an outer tube 191144, knife drive rod 191145, and an inner tube. The shaft assembly 191110 comprises an articulation section 191130 and a distal rotation section 191134. The end effector 191112 comprises jaw members 191114a, 191114b in opposing relationship and a motor driven knife. The jaw members 191114a, 191114b comprise electrically conductive surfaces 191116a, 191116b coupled to the RF generator circuit for delivering high-frequency current to tissue grasped between the opposed jaw members 191114a, 191114b. The jaw members 191114a, 191114b are pivotally rotatable about a pivot pin 191136 to grasp tissue between the jaw members 191114a, 191114b. The jaw members 191114a, 191114b are operably coupled to a trigger 191108 such that when the trigger 191108 is squeezed the jaw members 191114a, 191114b close to grasp tissue and when the trigger 191108 is released the jaw members 191114a, 191114b open to release tissue.

In a one-stage trigger configuration, the trigger 191108 is squeezed to close the jaw members 191114a, 191114b and, once the jaw members 191114a, 191114b are closed, a first switch 191121a of a switch section 191120 is activated to energize the RF generator to seal the tissue. After the tissue is sealed, a second switch 191121b of the switch section 191120 is activated to advance a knife to cut the tissue. In various aspects, the trigger 191108 may be a two-stage, or a multi-stage, trigger. In a two-stage trigger configuration, during the first stage, the trigger 191108 is squeezed part of the way to close the jaw members 191114a, 191114b and, during the second stage, the trigger 191108 is squeezed the rest of the way to energize the RF generator circuit to seal the tissue. After the tissue is sealed, one of the first and second switches 191121a, 191121b can be activated to advance the knife to cut the tissue. After the tissue is cut, the jaw members 191114a, 191114b are opened by releasing the trigger 191108 to release the tissue. In another aspect, force sensors such as strain gages or pressure sensors may be coupled to the trigger 191108 to measure the force applied to the trigger 191108 by the user. In another aspect, force sensors such as strain gages or pressure sensors may be coupled to the switch section 191120 first and second switch 191121a, 191121b buttons such that displacement intensity corresponds to the force applied by the user to the switch section 191120 first and second switch 191121a, 191121b buttons.

The battery assembly 191106 is electrically connected to the handle assembly 191102 by an electrical connector 191132. The handle assembly 191102 is provided with switch section 191120. The first switch 191121a and the second switch 191121b are provided in the switch section 191120. The RF generator is energized by actuating the first switch 191121a and the knife is activated by energizing the motor 191140 by actuating the second switch 191121b. Accordingly, the first switch 191121a energizes the RF circuit to drive the high-frequency current through the tissue to form a seal and the second switch 191121b energizes the motor to drive the knife to cut the tissue. For conciseness and clarity of disclosure, the structural and functional aspects of the battery assembly 191106 are further described in U.S. Pat. No. 11,229,471, entitled MODULAR BATTERY POWERED HANDHELD SURGICAL INSTRUMENT WITH SELECTIVE APPLICATION OF ENERGY BASED TISSUE CHARACTERIZATION, filed Dec. 16, 2016, the entire disclosure of which is incorporated by reference herein.

A rotation knob 191118 is operably coupled to the shaft assembly 191110. Rotation of the rotation knob 191118±360° in the direction indicated by arrows 191126 causes the outer tube 191144 to rotate ±360° in the respective direction of arrows 191119. In one aspect, another rotation knob 191122 may be configured to rotate the end effector 191112±360° in the direction indicated by arrows 191128 independently of the rotation of the outer tube 191144. The end effector 191112 may be articulated by way of first and second control switches 191124a, 191124b such that actuation of the first control switch 191124a articulates the end effector 191112 about a pivot 191138 in the direction indicated by arrow 191132a and actuation of the second control switch 191124b articulates the end effector 191112 about the pivot 191138 in the direction indicated by arrow 191132b. Further, the outer tube 191144 may have a diameter $D_3$ ranging from 5 mm to 10 mm, for example.

FIG. 224 is a graphical representation 193700 of determining wait time based on tissue thickness. A first graph 193702 represents tissue impedance Z versus time (t) where the horizontal axis represents time (t) and the vertical axis represents tissue impedance Z. A second graph 193704 represents change in gap distance Δgap versus time (t) where the horizontal axis represents time (t) and the vertical axis represents change in gap distance Δgap.

A third graph 193706 represents force F versus time (t) where the horizontal axis represents time (t) and the vertical axis represents force F. A constant force F applied to tissue and impedance Z interrogation define a wait period, energy modality (e.g., RF and ultrasonic) and motor control parameters. Displacement at a time provides velocity. With reference to the three graphs 193702, 193704, 193706, impedance sensing energy is applied during a first period to determine the tissue type such as thin mesentery tissue (solid line), intermediate thickness vessel tissue (dashed line), or thick uterus/bowel tissue (dash-dot line).

Using the thin mesentery tissue (solid line) as an example, as shown in the third graph 193706, the clamp arm initially applies a force which ramps up from zero until it reaches a constant force 193724 at or about a first time t1. As shown in the first and second graphs 193702, 193704, from the time the clamp force is applied to the mesentery tissue until the first time t1, the gap distance Δgap curve 193712 decreases and the tissue impedance 193718 also decreases until the first time t1 is reached. From the first time t1, a short wait period 193728 is applied before treatment energy, e.g., RF, is applied to the mesentery tissue at tE1. Treatment energy is applied for a second period 193710, after which the tissue may be ready for a cut operation.

As shown in the first and second graphs 193702, 193704, for intermediate thickness vessel tissue (dashed line), similar operations are performed. However, a medium wait period 193730 is applied before treatment energy is applied to the tissue at tE2.

As shown in the first and second graphs 193702, 193704, for thick uterus/bowel tissue (dash-dot line), similar operations are performed. However, a long wait period 193726 is applied before treatment energy is applied to the tissue at tE3.

Therefore, different wait periods may be applied based on the thickness of the tissue. The thickness of the tissue may be determined based on different gap distance behavior or impedance behavior before the time the constant force is reached. For example, as shown in the second graph 193704, depending on the minimum gap distance reached when the constant force is reached, i.e., small gap, medium gap, or large gap, the tissue is determined as a thin tissue, an intermediate thickness tissue, or a thick tissue, respectively. As shown in the first graph 193702, depending on the minimum impedance reached when the constant force is reached, e.g., small impedance, medium impedance, or large impedance, the tissue is determined as a thick tissue, an intermediate thickness tissue, or a thin tissue, respectively.

Alternatively, as shown in the second graph 193704, the thin tissue has a relatively steep gap distance slope, the intermediate thickness tissue has a medium gap distance slope, and the thick tissue has a relatively flat gap distance slope. As shown in the first graph 193702, the thin tissue has a relatively flat impedance slope, and the intermediate thickness and thick tissues have relatively steep impedance slopes. Tissue thickness may be determined accordingly.

FIG. 225 is a graphical depiction of impedance bath tub (e.g., the tissue impedance versus time initially decreases, stabilizes, and finally increases and the curve resembles a bath tub shape). A graph 194000 comprises three graphs 194002, 194004, 194006, where the first graph 194002 represents RF power (P), RF voltage (V), and RF current ($I_{RF}$) versus tissue impedance (Z), the second graph 194004 and third graph 194006 represent tissue impedance (Z) versus time (t). The first graph 194002 illustrates the application of power (P) for thick tissue impedance range 194010 and thin tissue impedance range 194012. As the tissue impedance Z increases, the current $I_{RF}$ decreases and the voltage $V_{RF}$ increases. The power P increases until it reaches a maximum power output 194008. When the RF power P is not high enough, for example as shown in the impedance range 194010, RF energy may not be enough to treat tissues, therefore ultrasonic energy is applied instead.

The second graph 194004 represents the measured tissue impedance Z versus time (t). The tissue impedance threshold limit 194020 is the cross over limit for switching between the RF and ultrasonic energy modalities. For example, as shown in the third graph 194006, RF energy is applied while the tissue impedance is above the tissue impedance threshold limit 194020 and ultrasonic energy 194024 is applied while the tissue impedance is below the tissue impedance threshold limit 194020. Accordingly, with reference back to the second graph 194004, the tissue impedance of the thin tissue curve 194016 remains above the tissue impedance threshold limit 194020, thus only RF energy modality is applied to the tissue. On the other hand, for the thick tissue curve 194018, RF energy modality is applied to the tissue while the impedance is above the tissue impedance threshold limit 194020 and ultrasonic energy is applied to the tissue when the impedance is below the tissue impedance threshold limit 194020.

Accordingly, the energy modality switches from RF to ultrasonic when the tissue impedance falls below the tissue impedance threshold limit 194020 and thus RF power P is low, and the energy modality switches from ultrasonic to RF when the tissue impedance rises above the tissue impedance threshold limit 194020 and thus RF power P is high enough. As shown in the third graph 194006, the switching from ultrasonic to RF may be set to occur when the impedance reaches a certain amount or certain percentage above the threshold limit 194020.

Turning now to FIG. 226 end effector 196400 comprises RF data sensors 196406, 196408*a*, 196408*b* located on jaw member 196402. The end effector 196400 comprises jaw member 196402 and an ultrasonic blade 196404. The jaw member 196402 is shown clamping tissue 196410 located between the jaw member 196402 and the ultrasonic blade 196404. A first sensor 196406 is located in a center portion of the jaw member 196402. Second and third sensors 196408*a*, 196408*b* are located on lateral portions of the jaw member 196402. The sensors 196406, 196408*a*, 196408*b* are mounted or formed integrally with a flexible circuit 196412 (shown more particularly in FIG. 227) configured to be fixedly mounted to the jaw member 196402.

The end effector 196400 is an example end effector for various surgical devices described herein. The sensors 196406, 196408*a*, 196408*b* are electrically connected to a control circuit via interface circuits. The sensors 196406, 196408*a*, 196408*b* are battery powered and the signals generated by the sensors 196406, 196408*a*, 196408*b* are provided to analog and/or digital processing circuits of the control circuit.

In one aspect, the first sensor 196406 is a force sensor to measure a normal force $F_3$ applied to the tissue 196410 by the jaw member 196402. The second and third sensors 196408*a*, 196408*b* include one or more elements to apply RF energy to the tissue 196410, measure tissue impedance, down force $F_1$, transverse forces $F_2$, and temperature, among other parameters. Electrodes 196409*a*, 196409*b* are electrically coupled to an energy source such as an electrical circuit and apply RF energy to the tissue 196410. In one aspect, the first sensor 196406 and the second and third sensors 196408*a*, 196408*b* are strain gauges to measure force or force per unit area. It will be appreciated that the measurements of the down force $F_1$, the lateral forces $F_2$, and the normal force $F_3$ may be readily converted to pressure by determining the surface area upon which the force sensors 196406, 196408*a*, 196408*b* are acting upon. Additionally, as described with particularity herein, the flexible circuit 196412 may comprise temperature sensors embedded in one or more layers of the flexible circuit 196412. The one or more temperature sensors may be arranged symmetrically or asymmetrically and provide tissue 196410 temperature feedback to control circuits of an ultrasonic drive circuit and an RF drive circuit.

FIG. 227 illustrates one aspect of the flexible circuit 196412 shown in FIG. 226 in which the sensors 196406, 196408*a*, 196408*b* may be mounted to or formed integrally therewith. The flexible circuit 196412 is configured to fixedly attach to the jaw member 196402. As shown particularly in FIG. 227, asymmetric temperature sensors 196414*a*, 196414*b* are mounted to the flexible circuit 196412 to enable measuring the temperature of the tissue 196410 (FIG. 226).

FIG. 228 illustrates one aspect of an end effector 196470 comprising segmented flexible circuit 196468. The end effector 196470 comprises a jaw member 196472 and an ultrasonic blade 196474. The segmented flexible circuit 196468 is mounted to the jaw member 196472. Each of the sensors disposed within the segments 1-5 are configured to detect the presence of tissue positioned between the jaw member 196472 and the ultrasonic blade 196474 and represent tissue zones 1-5. In the configuration shown in FIG. 228, the end effector 196470 is shown in an open position ready to receive or grasp tissue between the jaw member 196472 and the ultrasonic blade 196474.

FIG. 229 illustrates the end effector 196470 shown in FIG. 228 with the jaw member 196472 clamping tissue 196476 between the jaw member 196472 and the ultrasonic blade 196474. As shown in FIG. 229, the tissue 196476 is positioned between segments 1-3 and represents tissue zones 1-3. Accordingly, tissue 196476 is detected by the sensors in segments 1-3 and the absence of tissue (empty) is detected in section 196478 by segments 4-5. The information regarding the presence and absence of tissue 196476 positioned within certain segments 1-3 and 4-5, respectively, is communicated to a control circuit via interface circuits, for example. The control circuit is configured to energize only the segments 1-3 where tissue 196476 is detected and does not energize the segments 4-5 where tissue is not detected. It will be appreciated that the segments 1-5 may contain any suitable temperature, force/pressure, and/or Hall effect magnetic sensors to measure tissue parameters of tissue located within certain segments 1-5 and electrodes to deliver RF energy to tissue located in certain segments 1-5.

FIG. 230 illustrates graphs 196480 of energy applied by the right and left side of an end effector based on locally sensed tissue parameters. As discussed herein, the jaw member of an end effector may comprise temperature sensors, force/pressure sensors, Hall effector sensors, among others, along the right and left sides of the jaw member. Thus, RF energy can be selectively applied to tissue positioned between the clam jaw and the ultrasonic blade. The top graph 196482 depicts power $P_R$ applied to a right side segment of the jaw member versus time (t) based on locally sensed tissue parameters. Thus, a control circuit via interface circuits, for example, is configured to measure the sensed tissue parameters and to apply power $P_R$ to a right side segment of the jaw member. An RF drive circuit delivers an initial power level $P_1$ to the tissue via the right side segment and then decreases the power level to $P_2$ based on local sensing of tissue parameters (e.g., temperature, force/pressure, thickness) in one or more segments. The bottom graph 196484 depicts power $P_L$ applied to a left side segment of the jaw member versus time (t) based on locally sensed tissue parameters. An RF drive circuit delivers an initial power level of $P_1$ to the tissue via the left side segment and then increases the power level to $P_3$ based local sensing of tissue parameters (e.g., temperature, force/pressure, thickness). As depicted in the bottom graph 196484, the RF drive circuit is configured to re-adjust the energy delivered $P_3$ based on sensing of tissue parameters (e.g., temperature, force/pressure, thickness).

FIG. 231 is a cross-sectional view of one aspect of an end effector 196530 configured to sense force or pressure applied to tissue located between a jaw member and an ultrasonic blade. The end effector 196530 comprises a clamp jaw 196532 and a flexible circuit 196534 fixedly mounted to the jaw member 196532. The jaw member 196532 applies forces $F_1$ and $F_2$ to the tissue 196536 of variable density and thickness, which can be measure by first and second force/pressure sensors 196538, 196540 located in different layers of the flexible circuit 196534. A compressive layer 196542 is sandwiched between the first and second force/pressure sensors 196538, 196540. An electrode 196544 is located on outer portion of the flexible circuit 196534 which contacts the tissue. As described herein, other layers of the flexible circuit 196534 may comprise additional sensors such temperature sensors, thickness sensors, and the like.

FIGS. 232-233 illustrate various schematic diagrams of flexible circuits of the signal layer, sensor wiring, and an RF energy drive circuit. FIG. 232 is a schematic diagram of one aspect of a signal layer of a flexible circuit 196550. The flexible circuit 196550 comprises multiple layers (~4 to ~6, for example). One layer will supply the integrated circuits with power and another layer with ground. Two additional layers will carry the RF power RF1 and RF2 separately. An analog multiplexer switch 196552 has eight bidirectional translating switches that can be controlled through the I²C bus to interface to the control circuit via the SCL-C/SDA-C interface channel. The SCL/SDA upstream pair fans out to eight downstream pairs, or channels. Any individual SCn/SDn channel or combination of channels can be selected, determined by the contents of a programmable control register. There are six down stream sensors, three on each side of the jaw member. A first side 196554a comprises a first thermocouple 196556a, a first pressure sensor 196558a, and a first Hall effect sensor 196560a. A second side 196554b comprises a second thermocouple 196556b, a second pressure sensor 196558b, and a second Hall effect sensor 196560b. FIG. 233 is a schematic diagram 196570 of sensor wiring for the flexible circuit 196550 shown in FIG. 232 to the switch 196552.

FIGS. 220-233 and additional exemplifications are further described in U.S. patent application Ser. No. 15/382,238, entitled MODULAR BATTERY POWERED HANDHELD SURGICAL INSTRUMENT WITH SELECTIVE APPLICATION OF ENERGY BASED ON TISSUE CHARACTERIZATION, filed Dec. 16, 2016, now U.S. Pat. No. 11,229,471, the entire disclosure of which is incorporated by reference herein.

FIG. 234 illustrates another exemplification of a robotic arm 195120 and a tool assembly 195130 releasably coupled to the robotic arm 195120. The robotic UM 195120 can support and move the associated tool assembly 195130 along one or more mechanical degrees of freedom (e.g., all six Cartesian degrees of freedom, five or fewer Cartesian degrees of freedom, etc.).

The robotic arm 195120 can include a tool driver 195140 at a distal end of the robotic arm 195120, which can assist with controlling features associated with the tool assembly 195130. The robotic arm 195120 can also include a movable tool guide 195132 that can retract and extend relative to the tool (Inver 195140. A shaft of the tool assembly 195130 can extend parallel to a threaded shaft of the movable tool guide 195132 and can extend through a distal end feature 195133 (e.g., a ring) of the movable tool guide 195130 and into a patient.

In order to provide a sterile operation area while using the surgical system, a barrier can be placed between the actuating portion of the surgical system. (e.g., the robotic arm 195120) and the surgical instruments (e.g., the tool assembly 195130) in the sterile surgical field. A sterile component, such as an instrument sterile adapter (ISA), can also be placed at the connecting interface between the tool assembly 1951130 and the robotic arm 195120. The placement of an ISA between the tool assembly 195130 and the robotic arm 195120 can ensure a sterile coupling point for the tool assembly 195130 and the robotic atm 195120. This permits removal of tool assemblies 195130 from the robotic arm 195120 to exchange with other tool assemblies 195130 during the course of a surgery without compromising the sterile surgical field.

The tool assembly 195130 can be loaded from a top side of the tool driver 195140 with the shaft of the tool assembly 195130 being positioned in a shaft-receiving channel 195144 formed along the side of the tool driver 195140. The shaft-receiving channel 195144 allows the shaft, which extends along a central axis of the tool assembly 195130, to extend along a central axis of the tool driver 195140 when the tool assembly 195130 is coupled to the tool driver 195140. In other exemplifications, the shaft can extend through on opening in the tool driver 195140, or the two components can mate in various other configurations.

As discussed above, the robotic surgical system can include one or more robotic arms with each robotic arm having a tool assembly coupled thereto. Each tool assembly can include an end effector that has one or more of a variety of features, such as one or more tools for assisting with performing a surgical procedure. For example, the end effector can include a cutting or boring tool that can be used to perforate or cut through tissue (e.g., create an incision).

Furthermore, some end effectors include one or more sensors that can sense a variety of characteristics associated with either the end effector or the tissue. Each robotic arm and end effector can be controlled by a control system to assist with creating a desired cut or bore and prevent against undesired cutting of tissue. As an alternative to (or in addition to) controlling the robotic arm, it is understood that the control system can control either the tool itself or the tool assembly.

One or more aspects associated with the movement of the robotic arm can be controlled by the control system, such as either a direction or a velocity of movement. For example, when boring through tissue, the robotic arm can be controlled to perform jackhammer-like movements with the cutting tool. Such jackhammer movements can include the robotic arm moving up and down along an axis (e.g., an axis that is approximately perpendicular to the tissue being perforated) in a rapid motion while also advancing the cutting tool in a downward direction towards the tissue to eventually perforate the tissue with the cutting tool (e.g. an ultrasonic blade). While performing such movements in a robotic surgical procedure, not only can it be difficult to see the tissue being perforated to thereby determine a relative position of the cutting tool, but it can also be difficult to determine when the cutting tool has completed perforating the tissue. Such position of the cutting tool relative to the tissue can include the cutting tool approaching or not yet in contact with the tissue, the cutting tool drilling down or cutting into the tissue, and the cutting tool extending through or having perforated the tissue. These positions can be difficult for either a user controlling the robotic arm or the robotic surgical system to determine which can result in potential harm to the patient due to over or under-penetrating the tissue, as well as result in longer procedure times. As such, in order to reduce procedure time and surgical errors, the robotic surgical system includes a control system that communicates with at least one sensor assembly configured to sense a force applied at a distal end of the end effector or cutting tool. The control system can thereby determine and control, based on such sensed forces, one or more appropriate aspects associated with the movement of the robotic arm, such as when boring or cutting into tissue, as will be described in greater detail below.

Although a cutting tool for perforating tissue is described in detail herein, the sensor assembly of the present disclosure that is in communication with the control system can be implemented in any number of robotic surgical systems for detecting any number of a variety of tools and/or end effectors used for performing any number of a variety of procedures without departing from the scope of this disclosure. Furthermore, any number of movements can be performed by the robotic arm to perforate or cut tissue using the robotic surgical system including the sensor assembly and control system described herein and is not limited to the jackhammering or boring of tissue.

FIG. 235 illustrates an exemplification of a sensor assembly 196000 that is configured to sense a force applied along a part of the end effector of a tool assembly, such as the tool assembly shown in FIG. 234. The sensor assembly 196000 can be either positioned within or adjacent the end effector to sense such applied forces. The forces applied to the end effector can be along one or more of a variety of parts of the end effector, such as at a distal end, including a distal end of a tool (e.g., cutting tool) of the end effector. Such forces applied to the end effector can be sensed by the sensor assembly 196000, which can be collected and monitored by a control system of the robotic surgical system, such as those described above. The control system can use such sensed forces to determine and control movements associated with the robotic arm, such as to assist with cutting or boring through tissue.

The sensor assembly 196000 includes at least one blade 196010 that can be made out of a metallic material, such as titanium. The blade 196010 can be flat such that its width is significantly greater than its thickness. The sensor assembly 196000 can further include at least one plate 196012 that is made out of lead zirconate titanate (PZT). For example, a plate 196012 can be coupled to each side of the blade 196010, as shown in FIG. 235. As illustrated, the sensor assembly 196000 also includes a contact ring 196014 that encircles a part of either the blade 196010 or plate 196012. A first connecting wire 196016 extends between the plate 196012 and the contact ring 196014 and a ground 196018 extends from the blade 196010. In use, a voltage is applied to the contact ring 196014 and a strain gauge 196019 is coupled to the contact ring 196014, which can assist with measuring the applied force on the end effector. The sensor assembly 196000 can include one or more of a strain gauge and a piezo stack that sense a resistance load, which the control system can monitor for determining and controlling an appropriate velocity and/or direction of movement of the robotic arm.

In some exemplifications, the strain gauge 196019 may be either adhered directly to the blade 196010 or end effector (e.g., one or both jaws) such that if the blade 196010 or end effector deflects or bends, the strain gauge 196019 will also bend. Applying loads to the end effector can result in biasing the blade 196010 and/or end effector perpendicular to the axis of the shaft. This movement can result in a load applied to the strain gauge 196019 mounted on the spring member. Alternatively or in addition, the strain gauge 196019 can be adhered to a spring member that is coupled to the shaft of the tool assembly. Deflection of the spring member as a result of deflection of the shaft can deflect the gauge 196019.

The tool assembly can include any number of configurations of sensors and circuits for measuring tissue parameters (e.g., temperature, tension, etc.) and/or tool assembly parameters (e.g., velocity, rotational speed, etc.). Such parameters can be used to determine appropriate tissue treatment and execution of the tool assembly. For example, any of the sensors described and/or contemplated herein, including the strain gauge 196019, can be a part of a flexible circuit. Such flexible circuits are further described in U.S. patent application Ser. No. 15/177,430, entitled SURGICAL INSTRUMENT WITH USER ADAPTABLE TECHNIQUES, filed Jun. 9, 2016, now U.S. Pat. No. 11,141,213, the entire disclosure of which is incorporated by reference herein.

The flexible circuit can be coupled to and/or integrated into any part of the tool assembly, including the end effector, and can be in communication with the control system, such as those described above. For example, the control system can collect data from the flexible circuit (e.g., sensed data by the sensor of the flexible circuit) to determine appropriate treatment and execution of the tool assembly.

In the example, the sensor assembly 196000, which can include or be a part of a flexible circuit, is coupled to a part of the shaft adjacent the end effector to allow the sensor assembly 196000 to detect forces applied to the end effector, such as a distal end or cutting end of a cutting tool. As such, when a load that is perpendicular to the axis of the shaft is placed on the blade 196010 or end effector, the blade 196010 or end effector can deflect thereby causing the strain gauge 196019 to deflect. When deflected, the internal resistance of the strain gauge 196019 changes, thereby producing a strain reading that can be sent to the control system for analysis (e.g., measuring of strain, determining and control appropriate velocities and/or directions of movement of the robotic arm, etc.).

As shown in FIG. 235, the sensor assembly 196000 includes a waveguide 196020 that is configured to deliver energy to the tissue for assisting with cutting or boring through the tissue. For example, such energy can include ultrasonic energy or radio frequency energy. The waveguide 196020 can be in communication with the sensor assembly 196000 such that the sensor assembly 196000 can sense a pressure or force applied to the waveguide 196020, such as a distal end of the waveguide 196020 as the distal end cuts or advances through tissue. Such sensed pressures or forces are monitored by the control system and used to determine and control appropriate velocities and/or directions of movement of the robotic arm, which can include either the tool assembly or end effector.

The control system can determine one or more aspects of movement (e.g., direction, velocity, etc.) of the robotic arm based on either a force sensed by the sensor assembly 196000 or a velocity sensed by a sensor. In some exemplifications, the velocity of the robotic arm can be determined based on an angular velocity of the motor controlling the velocity or movement of the robotic arm. For example, the motor angular velocity can be determined by motor encoder pulses over time. The control system can control the velocity of movement (e.g., jackhammering) of the robotic arm based on either a sensed force or a sensed velocity. In addition, the control system can control the advancement of the robotic arm in a direction (e.g., toward tissue to be or being cut) based on either the sensed force or the sensed velocity. For example, as the robotic arm is advanced and thereby causing the cutting tool to advance and cut through tissue, the amount of force sensed by the sensor assembly 196000 is used by the control system to determine an appropriate velocity to advance the cutting tool, including when to stop advancement of the cutting tool. Once the cutting tool has cut through the tissue, for example, the force applied to the distal end of the cutting tool is less than when the cutting tool was cutting through tissue, which is sensed by the sensor assembly 196000 and detected by the control system. The control system uses this information, for example, to reduce the velocity of the robotic arm and prevent the cutting tool from undesired cutting of adjacent tissue.

FIG. 236 illustrates the sensor assembly 196000 coupled adjacent to an exemplification of an end effector 196050 that includes a cutting tool 196060 (e.g., tissue boring tool). As shown in FIG. 236, the sensor assembly 196000 is coupled to a part of a shaft 196040 with the end effector 196050 at a distal end of the shaft 196040. Forces applied to a distal end of the cutting tool 196060 are sensed in the shaft 196040 by the sensor assembly 196000. The shaft 196040 and end effector 196050 can be part of a tool assembly coupled to a robotic arm of a robotic surgical system, with the sensor assembly 196000 in communication with the control system. As such, the control system can control the movement of the robotic arm and thus the cutting tool 196060 to perform a cutting or boring of tissue using the cutting tool 196060. As shown in FIG. 236, the cutting tool 196060 (which can be an ultrasonic wave guide) has an elongated cylindrical body that is configured to bore into tissue, such as by jackhammering a distal end of the elongated cylindrical body against and through tissue to puncture or cut through the tissue. Although the cutting tool 196060 is shown in FIG. 236 as having an elongated cylindrical body, the cutting tool 196060 can have any number of various shapes and features for cutting, puncturing, or making an incision in tissue without departing from the scope of this disclosure.

FIGS. 237-239 illustrate an example of the cutting tool 196060 boring through tissue 196100. As shown in FIG. 237, the distal end of the cutting tool 196060 is not in contact with the tissue 196100 and therefore a force is not applied against the distal end of the cutting tool 196060 by the tissue 196100. The control system can detect the absence of the applied force to commence or increase the advancement of the robotic arm in the direction of the tissue 196100 to assist with cutting into the tissue 196100. As shown in FIG. 238, the distal end of the cutting tool 196060 is in contact with the tissue 196100 and a force is applied against the distal end of the cutting tool 196060 by the tissue 196100. A variety of forces can be applied to the distal end of the cutting tool 196060 as the cutting tool 196060 advances through the tissue, which can be monitored by the control system for determining appropriate velocities of movement of the robotic arm (e.g., jackhammering velocity, velocity of advancement of cutting tool, etc.). Control of the robotic arm by the control system can be based on such determined appropriate velocities to assist with effectively cutting the tissue 196100. As shown in FIG. 239, the distal end of the cutting tool 196060 is extending through the tissue 196100 and is no longer in contact with the tissue 196100. As such, a force is not applied against the distal end of the cutting tool 196060 by the tissue 196100. The control system can detect the absence of the applied force to decrease, including stop, the advancement or movement of the robotic arm, which can prevent unwanted cutting or boring of adjacent tissue. As such, the control system can determine appropriate velocities and directions of movement based on current and past sensed forces and velocities.

In some exemplifications of the robotic surgical system, the tool assembly includes a force sensor that detects a force applied by the tissue against a part of the end effector, such as a blade or a first jaw. This applied force sensed by the force sensor can be used by the control system to determine a tension in the tissue. From such determination of tissue tension, the control system can control either how fast to advance the robotic arm (e.g., to cut the tissue), to what extent, if at all, to angle the end effector in order to achieve a desired tension in the tissue, as will be described in greater detail below. Other factors associated with the cutting of tissue can be determined and controlled by the control system based off of the applied force sensed by the force sensor, such as degree of jaw closure thereby effecting tissue compression therebetween and/or energy density (e.g., ultrasonic, radio frequency, etc.) applied to the cutting tool (e.g., blade), as will also be discussed in greater detail below.

When the tissue being cut has a tension that is within a desired or optimal tension range, the quality of the cut or incision is improved and surgical times can be shorter. For example, if the tissue does not have enough tension, the tissue can be hard or impossible to cut, thereby prolonging the surgical procedure and possibly harming the patient. However, if the tissue has too much tension, the tissue can be damaged (e.g., tearing of the tissue, etc.). As such, it is desirable that tissue being cut has a tension that is within a desired tension range in order to efficiently and effectively cut the tissue. The degree to which tissue is compressed between a pair of jaws of an end effector can also contribute to how efficiently and effectively tissue is cut.

FIG. 240 illustrates another exemplification of end effector 197000 positioned at a distal end of a shaft 197010 of a tool assembly that is coupled to a robotic arm (such as the tool assembly and robotic arm shown in FIG. 9). The end effector 197000 includes a first jaw 197020 and a second jaw 197030 that are movable between an open position and a closed position, as well as any number of positions therebetween. The first and second jaws 197020, 197030 are configured to releasably capture tissue therebetween, such as when in the closed or at least partially closed position. When captured between the first and second jaws 197020, 197030, the tissue can experience a variety of compressive forces as a result of the first and second jaws 197020, 197030 varying their relative positioning (e.g., more or less closed). In some implementations, compressive forces can be determined by characterizing the system. For example, the output torque of a motor can be determined by correlating voltage, current, and position (encoder determined) to an output velocity, torque, and position. The actual output force, position and velocity of the end effector with respect to velocity, torque, and position can be determined using a correlating equation and/or lookup table. The control system can use such algorithm and data to convert measurable variables, such as position, torque, and/or velocity, to compressive force, jaw position, and/or velocity.

The end effector 197000 further includes a knife blade 197035 that is slidably disposed along a part of the first jaw 197020. For example, the knife blade 197035 can be advanced in a distal direction from a first position to a second position when the tissue is captured between the first and second jaws 197020, 197030 to thereby cut the tissue. Furthermore, one or more types of energy can be delivered to and from the knife blade 197035, such as radio frequency, for assisting with cutting the tissue. The control system (such as those described above) can detect and monitor such compressive forces to determine and control an appropriate degree of closure of the first and second jaws 197020, 197030 for achieving an appropriate compression (e.g., within a desired compression range) of the tissue captured between the first and second jaws 197020, 197030 thereby assisting with efficiently and effectively cutting the tissue with the knife blade 197035.

FIG. 241 illustrates another exemplification of an end effector 198000 positioned at a distal end of the shaft 197010. The end effector 198000 includes an ultrasonic blade 197040 and a moveable upper jaw or clamp 197075 (see, for example, in FIG. 243) that assists with positioning tissue along the ultrasonic blade 197040. The ultrasonic blade 197040 can deliver ultrasonic energy to the tissue for assisting with cutting the tissue. As shown in FIG. 241, a section of tissue 197045 is positioned along a distal part of the ultrasonic blade 197040 and applying a force against the distal part of the ultrasonic blade 197040. A proximal end of the ultrasonic blade 197040 is shown coupled to a blade extension or waveguide 197050 that extends along a part of the shaft 197010. The blade extension 197050 can be manipulated at a proximal end for assisting with manipulating the ultrasonic blade 197040, such as angling the ultrasonic blade 197040 relative to the tissue being cut. As shown in FIG. 241, at least one sensor 197060 is positioned along the ultrasonic blade 197040 or blade extension 197050. The sensors 197060 can be configured to measure the forces applied on the ultrasonic blade 197040 by the tissue 197045, such as shown in FIG. 241. The control system (such as the control systems described above) can detect and monitor such sensed applied forces to determine and control an appropriate velocity of movement of the robotic arm that is coupled to the tool assembly having the end effector 198000. Such appropriate velocity of movement includes the velocity of movement of the end effector 198000 in a direction that cuts the tissue. The control system controls the robotic arm (and thus the end effector) to move at the determined appropriate velocity to assist with performing a desired cut of the tissue.

FIG. 242 illustrates a cross sectional view of the shaft of FIG. 241 showing at least one sensor 197060 positioned adjacent the ultrasonic blade 197040 or blade extension 197050. As shown in FIG. 242, more than one sensor 197060 is positioned radially about the perimeter of the blade extension 197050. Such an arrangement allows for detecting of bending in the ultrasonic blade 197040 or blade extension 197050 due to the tissue applying a force along the ultrasonic blade 197040, as shown in FIG. 241. The control system can collect and analyze sensed data from any of the one or more sensors 197060 for determining a tension in the tissue. The sensors 197060 can include any one of a variety of sensors for detecting tension in the tissue 197045, including a strain gauge.

As discussed above, the control system can determine, based on the collected sensed force data from the sensors 197060, an appropriate velocity at which to move the robotic arm to cut the tissue. Furthermore, the control system can use such collected sensed data to determine and control an angle of the end effector (including either end effector 197000 or 198000), to cause the tension in the tissue to increase or decrease. For example, it can be desirable to lift or angle the ultrasonic blade 197040 of end effector 198000 relative to a surface plane of the tissue to assist with cutting of the tissue. Such lifting or angling can assist with creating a desired or optimal tension in the tissue. Alternatively (or in addition), the control system can use the collected sensed data to determine and control a degree of closure between the first jaw 197020 and the second jaw 197030 of end effector 197000 to cause an increase or decrease in compressive forces experienced by the tissue captured between the first and second jaws 197020, 197030. For example, the first and second jaws 197020, 197030 can be moved to a more open position to decrease the compressive forces or moved to a more closed position to increase the compressive forces.

FIG. 243 illustrates the end effector of FIG. 241 being lifted or angled to cause the force applied by the tissue to increase against the ultrasonic blade 197040 thereby assisting with cutting the tissue 197045 as the end effector 198000 is advanced in a direction that cuts the tissue 197045. Such lifting or angling can be caused by the control system collecting data from the sensors 197060 and determining that the tissue 197045 does not have a tension that is within the desired or optimal tension range. As such, the control system can either adjust the velocity of movement of the robotic arm (including stop movement) in the advancing direction (e.g., to cut tissue) or adjust the orientation of the end effector 198000 relative to the tissue (e.g., angle, lift, and/or lower the end effector 198000). For example, if the control system determines that the tension is too low, the control system can either reduce the velocity of movement of the robotic arm in the advancing direction or move the end effector 198000 such that it is either lifted or angled to create more tension in the tissue 197045. Based on the determined tissue tension, the control system can determine and control an appropriate energy density that is delivered to or received from the ultrasonic blade 197040. For example, if tissue tension is determined to be below a threshold, the velocity of advancement of the robotic arm may be increased. In contrast, stopping or slowing advancement of the robotic arm may further reduce tension. As such, if the tissue tension is above the threshold, the velocity of the robotic arm can be reduced to prevent damage to the tissue. Furthermore, compression applied to the tissue (e.g., via jaw closure) can be increased when the tissue tension is above a threshold and/or additional power can be applied to the tissue to speed up cutting and thereby assist with decreasing tissue tension.

FIG. 244 illustrates a first set of graphs 197090 showing examples of relationships between the advancement speeds of the robotic arm or end effector 198000 compared to the orientation or angle of the end effector 198000 relative to the tissue (thereby affecting either the tissue tension or tissue compression) and energy density in the ultrasonic blade 197040. As shown in FIG. 244, the advancement speed or velocity can be decreased by the control system when the tissue tension is too low and thus requires the end effector to be angled to increase the tissue tension. In addition, during such periods of tissue tension being too low, the energy density can be increased to compensate.

In some implementations of the robotic surgical system, more than one robotic arm can be used to cut or perforate tissue. For example, one surgical arm can be used to detect tension in the tissue to be or being cut. Based on such detected tissue tension, the robotic surgical system can control one or more parameters of a second surgical arm to perform the cutting or perforating of the tissue, as will be discussed in greater detail below.

FIG. 245 illustrates an exemplification of a first end effector 198010 of a first tool assembly 198020 coupled to a first robotic arm and a second end effector 198030 of a second tool assembly 198040 coupled to a second robotic arm. The first end effector 198010 is coupled to a distal end of a first shaft 198015 of the first tool assembly 198020 and includes a pair of jaws 198017 that are movable between and open and closed configurations. In the closed or partially closed configuration, the pair of jaws 198017 secure a part of tissue 198050 therebetween, as shown in FIG. 245. The pair of jaws 198017 is in communication with a first sensor 198060 that is configured to measure a tension in the tissue 198050 that is partially captured between the pair of jaws 198017. The first sensor 198060 is in communication with a control system of the robotic surgical system (such as the control systems described above) and the control system can detect and monitor the measurements collected by the first sensor 198060. Based on such measurements, the control system can determine and control one or more of a variety of movement parameters associated with either the first or second robotic arm to effectively and efficiently cut the tissue 198050. The first sensor can include one or more of a variety of sensors, including a strain gauge, and can be positioned in any number of locations along the first end effector 198010 or first tool assembly 198020 for measuring tension in the tissue 198050. For example, any of the tissue tension measuring features and mechanisms discussed above (such as with respects to FIGS. 241 and 242) can be implemented in this exemplification for measuring tension in the tissue 198050.

As shown in FIG. 245, the second end effector 198030 is positioned at a distal end of a second shaft 198032 of second tool assembly 198040. The second end effector 198030 includes a cutting tool or blade 198035 that can be advanced into the tissue 198050 for cutting the tissue. The cutting tool 198035 can include any number of features for assisting with cutting tissue, including any of the features discussed above for cutting tissue, such as the blade 197040 shown in FIG. 241. The cutting tool 198035 is in communication with a second sensor 198070 that is configured to measure an amount of force applied on the cutting tool 198035. The second sensor 198070 is in communication with the control system, which can detect and monitor the applied forces measured by the second sensor 198070. Based on such measured forces, the control system can determine one or more of a variety of movement parameters associated with either the first or second robotic arm to effectively and efficiently cut the tissue 198050. The second sensor 198070 can include one or more of a variety of sensors, including a strain gauge, and can be positioned in any number of locations along the second end effector 198030 or second tool assembly 198040 for measuring the applied forces along the cutting tool 198035. For example, any of the force measuring features and mechanisms discussed above (such as with respects to FIGS. 235 and 241) can be implemented in this exemplification for measuring a force applied against the cutting tool 198035.

The control system uses the measurements collected from either the first sensor 198060 or the second sensor 198070 to determine and control one or more aspects related to either the first or second robotic arm (including either the first or second end effectors 198010, 198030) to assist with effectively and efficiently cutting the tissue 198050 with the cutting tool 198035. For example, the control system can detect and monitor tissue tension measurements taken from the first sensor 198060 to determine whether the tissue tension is within a desired tension range for cutting. If the tissue tension is not within the desired range, the control system can control the first robotic arm to move such that the first end effector 198010 pulls the tissue in a direction that creates more tension in the tissue. The control system can continue monitoring the tissue tension to determine where to position the first end effector 198010 such that the tissue has a tension that is within the desired range. The control system can also determine, based on the tissue tension, an appropriate speed or velocity at which to advance the cutting tool 198035 to create a cut or incision along the tissue 198050. For example, if the tissue tension is not within the desired tension range, the control system can stop or reduce the velocity of movement of the cutting tool 198035. This can prevent potential damage to the cutting tool 198035 due to the tissue not having sufficient tension to allow the cutting tool 198035 to cut the tissue 198050, as well as prevent damage to the tissue due to cutting tissue having undesired conditions.

FIGS. 234-245 and additional exemplifications are further described in U.S. patent application Ser. No. 15/237,753, entitled CONTROL OF ADVANCEMENT RATE AND APPLICATION FORCE BASED ON MEASURED FORCES, filed Aug. 16, 2016, the entire disclosure of which is incorporated by reference herein.

The entire disclosures of:
U.S. Pat. No. 9,072,535, filed May 27, 2011, entitled SURGICAL STAPLING INSTRUMENTS WITH ROTATABLE STAPLE DEPLOYMENT ARRANGEMENTS, which issued Jul. 7, 2015;

U.S. Pat. No. 9,072,536, filed Jun. 28, 2012, entitled DIFFERENTIAL LOCKING ARRANGEMENTS FOR ROTARY POWERED SURGICAL INSTRUMENTS, which issued Jul. 7, 2015;

U.S. Pat. No. 9,204,879, filed Jun. 28, 2012, entitled FLEXIBLE DRIVE MEMBER, which issued on Dec. 8, 2015;

U.S. Pat. No. 9,561,038, filed Jun. 28, 2012, entitled INTERCHANGEABLE CLIP APPLIER, which issued on Feb. 7, 2017;

U.S. Pat. No. 9,757,128, filed Sep. 5, 2014, entitled MULTIPLE SENSORS WITH ONE SENSOR AFFECTING A SECOND SENSOR'S OUTPUT OR INTERPRETATION, which issued on Sep. 12, 2017;

U.S. patent application Ser. No. 14/640,935, entitled OVERLAID MULTI SENSOR RADIO FREQUENCY (RF) ELECTRODE SYSTEM TO MEASURE TISSUE COMPRESSION, filed Mar. 6, 2015, now U.S. Patent Application Publication No. 2016/0256071;

U.S. patent application Ser. No. 15/382,238, entitled MODULAR BATTERY POWERED HANDHELD SURGICAL INSTRUMENT WITH SELECTIVE APPLICATION OF ENERGY BASED ON TISSUE CHARACTERIZATION, filed Dec. 16, 2016, now U.S. Patent Application Publication No. 2017/0202591; and U.S. patent application Ser. No. 15/237,753, entitled CONTROL OF ADVANCEMENT RAIL AND APPLICATION FORCE BASED ON MEASURED FORCES, filed Aug. 16, 2016 are hereby incorporated by reference herein in their respective entireties.

The surgical devices, systems, and methods disclosed herein can be implemented with a variety of different robotic surgical systems and surgical devices. Surgical devices include robotic surgical tools and handheld surgical instruments. The reader will readily appreciate that certain devices, systems, and methods disclosed herein are not limited to applications within a robotic surgical system. For example, certain systems, devices, and methods for communicating, detecting, and/or control a surgical device can be implemented without a robotic surgical system.

EXAMPLES

Various aspects of the subject matter described herein are set out in the following numbered examples.

Example 1

A robotic surgical system, comprising: a first motor; a second motor; and a robotic surgical tool, comprising: a first rotary driver configured to receive a first rotary motion from said first motor; a second rotary driver configured to receive a second rotary motion from said second motor; an output drive; and a shifter configured to selectively couple said first rotary driver and said second rotary driver to said output drive, wherein said first rotary driver and said second rotary driver are configured to concurrently supply torque to said output drive in a high-torque operating state.

Example 2

The robotic surgical system of Example 1, wherein one of said first rotary driver and said second rotary driver is configured to supply torque to a second output drive in a low-torque operating state, and wherein a maximum torque is greater in the high-torque operating state than in the low-torque operating state.

Example 3

The robotic surgical system of any one of Examples 1 and 2, wherein said robotic surgical tool further comprises: a second shifter configured to selectively couple said first rotary driver to said second output drive; a third output drive; and a third shifter configured to selectively couple said second rotary driver and said third output.

Example 4

The robotic surgical system of Example 3, further comprising a fourth output drive and a fourth shifter configured to selectively couple said first rotary driver and said second rotary driver to said fourth output drive.

Example 5

The robotic surgical system of Example 4, wherein said surgical robotic tool comprises: a housing comprising said first rotary driver and said second rotary driver; an end effector comprising a firing member; and a shaft extending intermediate said housing and said end effector, wherein said output drive is configured to clamp said end effector, wherein said second output drive is configured to rotate said shaft, wherein said third output drive is configured to close said end effector, and wherein said fourth output drive is configured to fire said firing member.

Example 6

The robotic surgical system of any one of Examples 4 and 5, further comprising a third rotary driver configured to operably engage said shifter, said second shifter, said third shifter, and said fourth shifter.

Example 7

The robotic surgical system of Example 6, wherein said third rotary driver comprises a camshaft.

Example 8

The robotic surgical system of any one of Examples 1-7, further comprising: a fourth rotary driver configured to articulate said end effector relative to said shaft about a first axis; and a fifth rotary driver configured to articulate said end effector relative to said shaft about a second axis.

Example 9

The robotic surgical system of any one of Examples 4-8, further comprising: a first lock arm extending from said shifter and configured to selectively lock said output drive; a second lock arm extending from said second shifter and configured to selectively lock said second output drive; a third lock arm extending from said third shifter and configured to selectively lock said third output drive; and a fourth lock arm extending from said fourth shifter and configured to selectively lock said fourth output drive.

Example 10

A robotic surgical tool, comprising: a transmission, comprising: a first layer comprising a first output drive and a plurality of first idler gears; a second layer comprising a second output drive and a plurality of second idler gears; a first shaft extending through said first layer and said second layer; a second shaft extending through said first layer and said second layer; and a shifting assembly, wherein said shifting assembly is configured to couple said first shaft and said second shaft to said first output drive via said plurality of first idler gears in a high torque state, and wherein said shifting assembly is configured to couple said first shaft to said second output drive via said plurality of second idler gears in a low torque state.

Example 11

The robotic surgical tool of Example 10, further comprising: a first motor drivingly coupled to said first shaft; and a second motor drivingly coupled to said second shaft.

Example 12

The robotic surgical tool of any one of Examples 10 and 11, wherein said shifting assembly further comprises: a camshaft; a first shifting plate positioned intermediate said camshaft and said plurality of first idler gears in said first layer; and a second shifting plate positioned intermediate said camshaft and said plurality of second idler gears in said second layer.

Example 13

The robotic surgical tool of any one of Example 12, wherein said shifting assembly further comprises: a first lock operably engaged with said first shifting plate and said first output drive; and a second lock operably engaged with said second shifting plate and said second output drive.

Example 14

The robotic surgical tool of any one of Examples 10-13, wherein said first output drive is configured to affect a first surgical function, and wherein said second output drive is configured to affect a second surgical function.

Example 15

A system for driving a robotic surgical tool, the system comprising: a first layer comprising a first output gear; a second layer comprising a second output gear; a first drive shaft extending through said first layer and said second layer; a second drive shaft extending through said first layer and said second layer; and a shifting assembly configured to selectively couple said first drive shaft and said second drive shaft to said first output gear in a high-torque operating state to concurrently supply torque to said first output gear.

Example 16

The system of Example 15, further comprising: a first motor drivingly coupled to said first drive shaft; and a second motor drivingly coupled to said second drive shaft.

Example 17

The system of any one of Examples 15 and 16, wherein said shifting assembly is configured to couple said first drive shaft to said second output gear in a low torque state, and wherein a maximum torque is greater in the high-torque operating state than in the low-torque operating state.

Example 18

The system of Example 17, wherein the low-torque operating state is employed for a low-force closure motion, and wherein the high-force operating state is employed for a high-force clamping motion.

Example 19

The system of any one of Examples 15-18, wherein said shifting assembly further comprises: a camshaft; a plurality of first idler gears and a first shifting plate positioned intermediate said camshaft and said plurality of first idler gears; a plurality of second idler gears and a second shifting plate positioned intermediate said camshaft and said plurality of second idler gears; a first lock operably engaged with said first shifting plate and said first output gear; and a second lock operably engaged with said second shifting plate and said second output gear.

Example 20

The system of any one of Examples 15-19, wherein said first output gear is configured to affect a first surgical function, and wherein said second output gear is configured to affect a second surgical function.

Various additional aspects of the subject matter described herein are set out in the following numbered examples.

Example 1

A surgical system comprising: a hub comprising a generator; a robot comprising a tool mount; an energy tool releasably mounted to said tool mount and operably coupled to said generator; a control console, wherein a wired communication path extends between said energy tool and said control console; and a wireless communication path extending between said energy tool and said control console, wherein said wireless communication path is configured to transmit data indicative of a detected tissue parameter to said control console.

Example 2

The surgical system of Example 1, wherein said hub further comprises a situational awareness module configured to determine a step in a surgical procedure based on one or more signals from said surgical console and one or more signals from said energy tool.

Example 3

The surgical system of any one of Examples 1 and 2, wherein said hub further comprises a wireless communication module, and wherein said wireless communication path further comprises said wireless communication module.

Example 4

The surgical system of any one of Examples 1-3, wherein said wireless communication path is configured to communicate mechanical control parameters to said hub.

Example 5

The surgical system of any one of Examples 1-4, wherein said robot further comprises a flex circuit positioned to intercept a communication path between said tool mount and said energy tool.

Example 6

A surgical system comprising: a wireless communication module; a robot comprising a tool mount and an energy tool releasably mounted to said tool mount; and a flex circuit positioned intermediate said tool mount and said energy tool, wherein said flex circuit is positioned to intercept a communication path between said tool mount and said energy tool, and wherein said flex circuit is coupled to a wireless transmitter configured to communicate with said wireless communication module.

Example 7

The surgical system of Example 6, wherein said flex circuit comprises a feedback pigtail connector.

Example 8

The surgical system of any one of Examples 6 and 7, wherein said flex circuit is configured to intercept a signal between an external controller and said energy tool.

Example 9

The surgical system of Example 8, wherein said signal is indicative of a clamping force exerted by said energy tool.

Example 10

The surgical system of any one of Examples 6-9, wherein said energy tool further comprises a first electrical contact, wherein said tool mount further comprises a second electrical contact that interfaces with said first electrical contact, wherein said flex circuit is configured to intercept signals passing between said first electrical contact and said second electrical contact.

Example 11

The surgical system of any one of Examples 6-10, further comprising a situational awareness module configured to receive signals from said energy tool via said wireless transmitter.

Example 12

The surgical system of any one of Examples 6-11, further comprising a processor and a memory communicatively coupled to said processor, wherein said memory stores instructions executable by said processor to adjust a power level of said generator based on signals intercepted by said flex circuit.

Example 13

The surgical system of any one of Examples 6-12, further comprising a processor and a memory communicatively coupled to said processor, wherein said memory stores instructions executable by said processor to adjust a clamping force of said energy tool based on signals indicative of a tissue property transmitted to said wireless communication module from said energy tool.

Example 14

A surgical system comprising: a hub comprising a wireless communication module; a robot comprising a tool mount configured to interface with a releasable surgical tool; a control console, wherein a primary communication path extends between said robot and said control console via a wired connection; a first wireless communication path extending between said robot and said wireless communication module; and a second wireless communication path extending between said control console and said wireless communication module, wherein said first wireless communication path and said second wireless communication path form at least a portion of an additional communication path between said robot and said control console that is different than said primary communication path.

Example 15

The surgical system of Example 14, wherein said first wireless communication path is configured to transmit data indicative of a clamping force to said hub.

Example 16

The surgical system of any one of Examples 14 and 15, wherein said wired connection is configured to transmit data indicative of energy parameters from said robot to said control console.

Example 17

The surgical system of any one of Examples 14-16, further comprising a flex circuit positioned to intercept a communication path between said tool mount and the releasable surgical tool.

Example 18

The surgical system of any one of Examples 14-17, further comprising said releasable surgical tool, wherein said releasable surgical tool comprises an energy tool.

Example 19

The surgical system of any one of Examples 14-18, wherein said hub further comprises a processor and a memory communicatively coupled to said processor, and wherein said memory stores instructions executable by said processor to adjust a control parameter of said energy tool based on a signal transmitted along said first wireless communication path.

Example 20

The surgical system of any one of Examples 14-19, wherein said hub further comprises a situational awareness module configured to determine a step in a surgical procedure based on one or more signals transmitted along said first wireless communication path.

Example 21

A system comprising: a wireless communication module configured to transmit a signal. The system further comprises a robotic surgical tool comprising a tool interface, wherein said tool interface comprises: a mechanical connection configured to receive a drive motion from a robotic tool driver and an electrical connection configured to transmit the signal. The system further comprises a flex circuit configured to intercept the signal when said flex circuit is engaged with said tool interface.

Various additional aspects of the subject matter described herein are set out in the following numbered examples.

Example 1

A robotic surgical tool, comprising: an end effector comprising an energy delivery surface; a channel extending to said end effector; and a proximal interface for releasable engagement with a robotic tool driver, wherein said proximal interface comprises: a plurality of rotary drivers comprising a first rotary driver; and a pump fluidically coupled to said channel and driven by said first rotary driver, wherein said first rotary driver is configured to rotate at a variable rate to provide an adjustable power level for said pump.

Example 2

The robotic surgical tool of Example 1, wherein the variable rate depends on a rate of smoke evacuation along said channel.

Example 3

The robotic surgical tool of any one of Examples 1 and 2, further comprising a sensor configured to detect a rate of smoke evacuation through said channel.

Example 4

The robotic surgical tool of any one of Examples 1-3, wherein the variable rate depends on an activation of said energy delivery surface.

Example 5

The robotic surgical tool of any one of Examples 1-4, wherein said end effector further comprises an ultrasonic blade.

Example 6

The robotic surgical tool of any one of Examples 1-5, further comprising a shaft extending intermediate said end effector and said proximal interface, wherein said shaft comprises said channel therethrough.

Example 7

The robotic surgical tool of any one of Examples 1-6, wherein said pump comprises a lobe pump.

Example 8

The robotic surgical tool of any one of Examples 1-7, further comprising: a processor and a memory communicatively coupled to said processor, wherein said memory stores instructions executable by said processor to control the rotation of said first rotary driver based on a rate of smoke evacuation along said channel.

Example 9

The robotic surgical tool of any one of Examples 1-8, further comprising a control circuit configured to control the rotation of said first rotary driver based on a rate of smoke evacuation along said channel.

Example 10

The robotic surgical tool of any one of Examples 1-9, wherein said surgical tool is configured to receive control signals from a processor to control the variable rate of said first rotary driver.

Example 11

The robotic surgical tool of any one of Examples 1-10, wherein said pump is further configured to move insufflation gases.

Example 12

A robotic surgical system comprising: an energy tool comprising: a sensor; a channel; a rotary driver; and a pump fluidically coupled to said channel and driven by said rotary driver; a processor in signal communication with said sensor; and a memory communicatively coupled to said processor, wherein said memory stores instructions executable by said processor to control the rotation of said rotary driver based on input from said sensor.

Example 13

The robotic surgical system of Example 12, wherein said sensor is configured to supply signals to said processor indicative of a volume of smoke detected by said sensor.

Example 14

The robotic surgical system of any one of Examples 12 and 13, wherein said energy tool comprises a tissue-contacting electrode, and wherein said memory stores instructions executable by said processor to control the rotation of said rotary driver based on an activation of said tissue-contacting electrode.

Example 15

The robotic surgical system of any one of Examples 12-14, wherein said sensor comprises an imaging device.

Example 16

The robotic surgical system of any one of Examples 12-15, further comprising a motor drivingly engaged with said rotary driver, and wherein said processor is in signal communication with said motor.

Example 17

The robotic surgical system of any one of Examples 12-16, wherein said energy tool comprises said processor.

Example 18

The robotic surgical system of any one of Examples 12-17, further comprising a surgical hub comprising a situational awareness module, wherein said memory stores instructions executable by said processor to control the rotation of said rotary driver based on input from said situational awareness module.

Example 19

A robotic surgical system, comprising: an energy tool, comprising: a sensor; a channel; a rotary driver; and a pump fluidically coupled to said channel and driven by said rotary driver; and a control circuit configured to control the rotation of said rotary driver based on input from said sensor.

Example 20

A non-transitory computer readable medium storing computer readable instructions which, when executed, cause a machine to: receive a signal from a sensor on a robotic surgical tool; and adjust a rotation of a rotary driver on the robotic surgical tool based on the signal, wherein the rotary driver is operably coupled to a pump on the robotic surgical tool that is fluidically coupled to an evacuation channel on the robotic surgical tool.

Various additional aspects of the subject matter described herein are set out in the following numbered examples.

Example 1

A robotic surgical system comprising: a control unit comprising a processor and a memory communicatively coupled to said processor; a robot comprising a tool mount; a tool comprising an energy delivery surface, wherein said tool is releasably mounted to said tool mount; and a sensor system configured to detect at least one condition at a surgical site, wherein said sensor system is in signal communication with said processor; wherein said memory stores instructions executable by the processor to: determine a use of said tool based on input from said sensor system and automatically energize said energy delivery surface when the use is determined.

Example 2

The robotic surgical system of Example 1, wherein said tool comprises a monopolar cautery pencil.

Example 3

The robotic surgical system of any one of Examples 1 and 2, wherein said tool comprises an ultrasonic blade.

Example 4

The robotic surgical system of any one of Examples 1-3, wherein said sensor system is configured to detect an impedance of tissue at the surgical site, and wherein said memory stores instructions executable by said processor to determine the use of said tool when the impedance is within a predefined range.

Example 5

The robotic surgical system of any one of Examples 1-4, wherein said memory stores instructions executable by the processor to determine an activation mode of said tool based on input from said sensor system.

Example 6

The robotic surgical system of any one of Examples 1-5, wherein said processor comprises a situational awareness module configured to recommend a surgical function based on input from said sensor system.

Example 7

The robotic surgical system of any one of Examples 1-6, further comprising a manual override mode in which automatic energizing of said energy delivery surface by said processor is prevented.

Example 8

A robotic surgical system comprising: a control unit; a robot comprising a tool mount; a tool comprising an energy delivery surface, wherein said tool is releasably mounted to said tool mount; and a sensor system configured to detect at least one condition at a surgical site, wherein said sensor system is in signal communication with said control unit; wherein said control unit is configured to: determine a use of said tool based on input from said sensor system and automatically energize said energy delivery surface when the use is determined.

Example 9

The robotic surgical system of Example 8, wherein said sensor system is configured to detect an impedance of tissue at the surgical site, and wherein said control unit is configured to determine the use of said tool when the impedance is within a predefined range.

Example 10

The robotic surgical system of any one of Examples 8 and 9, wherein said control unit is configured to determine an activation mode of said tool based on input from said sensor system.

Example 11

The robotic surgical system of any one of Examples 8-10, wherein said control unit comprises a situational awareness module configured to recommend a surgical function based on input from said sensor system.

Example 12

The robotic surgical system of any one of Examples 8-11, further comprising a manual override mode in which automatic energizing of said energy delivery surface by said control unit is prevented.

Example 13

A non-transitory computer readable medium storing computer readable instructions which, when executed, cause a machine to: determine a use of a surgical tool based on an input from a sensor system; and automatically energize an energy delivery surface of said surgical tool when the use is determined.

Example 14

The non-transitory computer readable medium of Example 13, wherein said surgical tool comprises a monopolar cautery pencil.

Example 15

The non-transitory computer readable medium of any one of Examples 13 and 14, wherein said surgical tool comprises an ultrasonic blade.

Example 16

The non-transitory computer readable medium of any one of Examples 13-15, wherein said sensor system is configured to detect an impedance of tissue at a surgical site, and wherein computer readable instructions cause a machine to determine the use of said surgical tool when the impedance is within a predefined range.

Example 17

The non-transitory computer readable medium of any one of Examples 13-16, wherein said computer readable instructions cause a machine to determine an activation mode based on input from said sensor system.

Example 18

The non-transitory computer readable medium of any one of Examples 13-17, wherein said non-transitory computer readable medium comprises a situational awareness module configured to recommend a surgical function based on input from said sensor system.

Example 19

The non-transitory computer readable medium of any one of Examples 13-18, further comprising a manual override mode in which automatic energizing of said energy delivery surface by said machine is prevented.

Various additional aspects of the subject matter described herein are set out in the following numbered examples.

Example 1

A robotic surgical system comprises a robotic tool, a control system, and a secondary control module. The control system comprises a control console configured to receive a first user input and a control unit in signal communication with the control console and the robotic tool. The secondary control module is configured to receive a second user input, wherein the secondary control module is in signal communication with the control system.

Example 2

The robotic surgical system of Example 1, wherein the secondary control module comprises a wireless mobile device.

Example 3

The robotic surgical system of any one of Examples 1 and 2, wherein the robotic tool is configured to receive control inputs from the control system and the secondary control module.

Example 4

The robotic surgical system of any one of Examples 1-3, wherein the control unit comprises a situational awareness module configured to recommend a surgical function based on the second user input.

Example 5

The robotic surgical system of any one of Examples 1-4, wherein the control system further comprises a manual override mode in which control of the robotic tool by the secondary control module is prevented.

Example 6

The robotic surgical system of any one of Examples 1-5, wherein the secondary control module is positioned within a sterile field, and wherein the control console is positioned outside of the sterile field.

Example 7

The robotic surgical system of any one of Examples 1-6, wherein the secondary control module can gain control of the robotic tool by coming into physical contact with the robotic tool.

Example 8

The robotic surgical system of any one of Examples 1-7, wherein the first user input at the control console allows the secondary control module to control the robotic tool.

Example 9

A robotic surgical system comprises a robotic tool, a control system, and a secondary control module. The control system comprises a control console configured to receive a first user input; and a control unit, wherein the control unit is configured to be in signal communication with the control console and the robotic tool. The secondary control module is configured to receive a second user input, wherein the secondary control module is configured to be in signal communication with the control unit, and wherein the secondary control module is configured to issue commands to the control system.

Example 10

The robotic surgical system of Example 9, wherein the secondary control module comprises a wireless mobile device.

Example 11

The robotic surgical system of any one of Examples 9 and 10, wherein the control unit is configured to prioritize the control inputs received from the control system over the control inputs received from the secondary control module.

Example 12

The robotic surgical system of any one of Examples 9-11, wherein the control unit comprises a situational awareness module configured to recommend a surgical function based on communication with the secondary control module.

Example 13

The robotic surgical system of any one of Examples 9-12, wherein the control system further comprises a manual override mode in which control of the robotic tool by the secondary control module is prevented.

Example 14

The robotic surgical system of any one of Examples 9-13, wherein the secondary control module is positioned within a sterile field, and wherein the control console is positioned outside of the sterile field.

Example 15

The robotic surgical system of any one of Examples 9-14, wherein the secondary control module can gain control of the robotic tool by coming into physical contact with the robotic tool.

Example 16

A system comprises an end effector configured to perform at least one surgical function, a control system, a processor, and a memory communicatively coupled to the processor. The control system comprises a remote controller configured to receive a first user input for controlling the at least one surgical function and a local controller comprising a wireless transmitter, wherein the local controller is configured to receive a second user input for controlling the at least one surgical function. The memory stores instructions executable by the processor to receive the first user input and receive the second user input.

Example 17

The system of Example 16, wherein the control system is configured to prioritize the first user input over the second user input.

Example 18

The system of any one of Examples 16 and 17, further comprising a situational awareness module configured to recommend a surgical function based on communication with the local controller.

Example 19

The system of any one of Examples 16-18, wherein the remote controller is positioned outside of a sterile field, and wherein the local controller is positioned within the sterile field.

Example 20

The system of any one of Examples 16-19, wherein the local controller comprises a mobile wireless control module.

Various additional aspects of the subject matter described herein are set out in the following numbered examples.

Example 1

A robotic surgical system comprises a first robotic arm comprising a first force sensor, a second robotic arm comprising a second force sensor, and a control unit comprising a processor and a memory communicatively coupled to the processor. The memory stores instructions executable by the processor to receive a first input from the first force sensor, receive a second input from the second force sensor, and effect cooperative movement of the first robotic arm and the second robotic arm based on the first input from the first force sensor and the second input from the second force sensor in a load control mode.

Example 2

The robotic surgical system of Example 1, wherein the first robotic arm comprises a first position sensor, wherein the second robotic arm comprises a second position sensor, and wherein the processor is configured to be in signal communication with the first position sensor and the second position sensor.

Example 3

The robotic surgical system of Example 2, wherein the memory is configured to store instructions operable by the processor to receive a first position input from the first position sensor, and receive a second position input from the second position sensor.

Example 4

The robotic surgical system of Example 3, wherein the memory stores instructions executable by the processor to effect cooperative movement of the first robotic arm and the second robotic arm based on the first position input from the first position sensor and the second position input from the second position sensor in a position control mode.

Example 5

The robotic surgical system of any one of Examples 1-4, wherein the memory stores instructions executable by the processor to switch from the load control mode to a position control mode upon movement of a surgical tool mounted to one of the robotic arms outside a defined boundary.

Example 6

The robotic surgical system of any one of Examples 1-5, wherein the processor is communicatively coupled to a situational awareness module configured to recommend a surgical function based on the first input received from the first force sensor and the second input received from the second force sensor.

Example 7

The robotic surgical system of any one of Examples 1-6, wherein the memory stores instructions executable by the processor to determine if the first robotic arm and the second robotic arm are inactive and stop communicating with the first force sensor and the second force sensor when the first robotic arm and the second robotic arm are inactive.

Example 8

A robotic surgical system comprises a first robotic arm comprising a first sensor, a second robotic arm comprising a second sensor, and a control unit comprising a processor and a memory communicatively coupled to the processor. The memory stores instructions executable by the processor to receive a first input from the first sensor, receive a second input from the second sensor, and effect cooperative movement of the first robotic arm and the second robotic arm based on the first input from the first sensor and the second input from the second sensor.

Example 9

The robotic surgical system of Example 8, wherein the first sensor and the second sensor are force sensors.

Example 10

The robotic surgical system of any one of Examples 8 and 9, wherein the memory stores instructions executable by the processor to enter into a load control mode upon receiving the first input from the first sensor and the second input from the second sensor.

Example 11

The robotic surgical system of Example 8, wherein the first sensor and the second sensor are position sensors.

Example 12

The robotic surgical system of Example 11, wherein the memory is configured to store stores instructions executable by the processor to enter into a position control mode upon receiving the first input from the first sensor and the second input from the second sensor.

Example 13

The robotic surgical system of Examples 8-12, wherein the processor is communicatively coupled to a situational awareness module configured to recommend a surgical function based on the first input received from the first sensor and the second input received from the second sensor.

Example 14

A non-transitory computer readable medium storing computer readable instructions which, when executed, cause a machine to receive a first input from a first force sensor, receive a second input from a second force sensor, and effect cooperative movement of a first robotic arm and a second robotic arm based on the first input from the first force sensor and the second input from the second force sensor in a load control mode.

Example 15

The non-transitory computer readable medium of Example 14, wherein the first robotic arm comprises a first position sensor, and wherein the second robotic arm comprises a second position sensor.

Example 16

The non-transitory computer readable medium of Example 15, wherein the first position sensor is configured to communicate a first position input to the machine, and wherein the second position sensor is configured to communicate a second position input to the machine.

Example 17

The non-transitory computer readable medium of Example 16, wherein the computer readable instructions, when executed, cause a machine to effect cooperative movement of the first robotic arm and the second robotic arm based on the first position input from the first position sensor and the second position input from the second position sensor in a position control mode.

Example 18

The non-transitory computer readable medium of Examples 14-17, wherein the machine is operably configured to switch from the load control mode to a position control mode upon movement of a surgical tool mounted to one of the robotic arms outside a defined boundary.

Example 19

The non-transitory computer readable medium of any one of Examples 14-18, further comprising a situational awareness module configured to recommend a surgical function based on the first input received from the first force sensor and the second input received from the second force sensor.

Example 20

The non-transitory computer readable medium of any one of Examples 14-19, wherein the computer readable instructions, when executed, cause a machine to: determine if the first robotic arm and the second robotic arm are activated; and stop communicating with the first force sensor and the second force sensor when the first robotic arm and the second robotic arm are inactive.

Example 21

A robotic surgical system comprises a first robotic arm comprising a first sensor; a second robotic arm comprising a second sensor; and a control circuit. The control circuit is configured to receive a first input from the first sensor, receive a second input from the second sensor, and effect cooperative movement of the first robotic arm and the second robotic arm based on the first input from the first sensor and the second input from the second sensor.

Example 22

The robotic surgical system of Example 21, wherein the first sensor and the second sensor are force sensors.

Example 23

The robotic surgical system of any one of Examples 21 and 22, wherein the control circuit is configured to enter into a load control mode upon receiving the first input from the first sensor and the second input from the second sensor.

Example 24

The robotic surgical system of Example 21, wherein the first sensor and the second sensor are position sensors.

Example 25

The robotic surgical system of Example 24, wherein the control circuit is configured to enter into a position control mode upon receiving the first input from the first sensor and the second input from the second sensor.

Example 26

The robotic surgical system of any one of Examples 21-25, wherein the control circuit is communicatively coupled to a situational awareness module configured to recommend a surgical function based on the first input received from the first sensor and the second input received from the second sensor.

Various additional aspects of the subject matter described herein are set out in the following numbered examples.

Example 1

A surgical system comprises a robotic tool, a robot control system, a surgical instrument, and a surgical hub comprising a display. The robot control system comprises a control console and a control unit in signal communication with the control console and the robotic tool. The surgical hub is in signal communication with the robot control system, and wherein the surgical hub is configured to detect the surgical instrument and represent the surgical instrument on the display.

Example 2

The surgical system of Example 1, wherein the surgical instrument comprises a motorized, autonomous surgical instrument.

Example 3

The surgical system of any one of Examples 1 and 2, wherein the surgical instrument is independent of the robot control system.

Example 4

The surgical system of any one of Examples 1-3, wherein the surgical hub is configured to display a location of the surgical instrument on the display.

Example 5

The surgical system of any one of Examples 1-4, wherein the surgical hub is configured to display an operating status of the surgical instrument on the display.

Example 6

The surgical system of any one of Examples 1-5, wherein the display comprises a heads up display.

Example 7

The surgical system of any one of Examples 1-6, wherein the surgical hub further comprises a situational awareness module configured to recommend a surgical function based on the detection of the surgical instrument relative to a position of the robotic tool.

Example 8

A surgical system comprises a robotic tool, a robot control system, a surgical instrument operable in a plurality of operating states, and a surgical hub comprising a display. The robot control system comprises a control console and a control unit in signal communication with the control console and the robotic tool. The surgical hub is in signal communication with the robot control system, and the surgical hub is configured to detect an activated operating state of the surgical instrument and represent the active operating state on the display.

Example 9

The surgical system of Example 8, wherein the surgical instrument comprises a motorized surgical device.

Example 10

The surgical system of any one of Examples 8 and 9, wherein the surgical instrument is an autonomous surgical instrument.

Example 11

The surgical system of any one of Examples 8-10, wherein the surgical hub is configured to display an orientation of the surgical instrument on the display.

Example 12

The surgical system of any one of Examples 8-11, wherein the surgical hub is configured to display an operating status of the surgical instrument on the display.

Example 13

The surgical system of any one of Examples 8-12, further comprising a situational awareness module configured to recommend a surgical function based on the detection of the surgical instrument relative to a position of the robotic tool.

Example 14

A surgical system comprises a robotic tool, a robot control system, a surgical instrument, a surgical hub, and a display in signal communication with the surgical hub. The robot control system comprises a control console and a control unit in signal communication with the control console and the robotic tool. The surgical hub is in signal communication with the robot control system, and the surgical hub is configured to detect the surgical instrument. The surgical hub is configured to represent the surgical instrument on the display.

Example 15

The surgical system of Example 14, wherein the surgical instrument comprises a motorized surgical instrument.

Example 16

The surgical system of any one of Examples 14 and 15, wherein the surgical instrument is independent of the robot control system.

Example 17

The surgical system of any one of Examples 14-16, wherein the surgical hub is configured to display a position of the surgical instrument on the display.

Example 18

The surgical system of any one of Examples 14-17, wherein the surgical hub is configured to display an operating status of the surgical instrument on the display.

Example 19

The surgical system of any one of Examples 14-18, wherein the display comprises a heads up display.

Example 20

The surgical system of any one of Examples 14-19, further comprising a situational awareness module configured to recommend a surgical function based on the detection of the surgical instrument relative to a position of the robotic tool.

Various additional aspects of the subject matter described herein are set out in the following numbered examples.

Example 1

A surgical system, comprising: a robotic system, comprising: a control unit; a robotic arm comprising an attachment portion; and a first sensor system in signal communication with said control unit, wherein said first sensor system is configured to detect a position of said attachment portion. The surgical system further comprises a surgical tool removably attached to said attachment portion. The surgical system further comprises a second sensor system configured to detect a position of said surgical tool, wherein said secondary sensor system is independent of said first sensor system.

Example 2

The surgical system of Example 1, wherein said second sensor system comprises: a magnetic field emitter and a magnetic field sensor incorporated into said surgical tool.

Example 3

The surgical system of any one of Examples 1 and 2, further comprising a handheld, battery-powered surgical instrument comprising an instrument sensor, wherein said second sensor system is configured to detect a position of said instrument sensor.

Example 4

The surgical system of Example 3, further comprising a real-time display configured to display the position of said surgical tool and the position of said instrument sensor based on data from said second sensor system.

Example 5

The surgical system of any one of Examples 3 and 4, wherein said handheld, battery-powered surgical instrument comprises an autonomous control unit.

Example 6

The surgical system of any one of Examples 1-5, further comprising a trocar comprising a trocar sensor, wherein said second sensor system is configured to detect a position of said trocar sensor.

Example 7

The surgical system of Example 6, further comprising a real-time display configured to display the position of said surgical tool and the position of said trocar based on data from said second sensor system.

Example 8

The surgical system of any one of Examples 1-7, further comprising a plurality of patient sensors applied to a patient, wherein said second sensor system is configured to detect the position of said patient sensors.

Example 9

The surgical system of Example 8, further comprising a real-time display configured to display the position of said surgical tool and the position of said patient sensors based on data from said second sensor system.

Example 10

A surgical system, comprising: a robotic system, comprising: a control unit; a robotic arm comprising a first portion, a second portion, and a joint intermediate said first portion and said second portion; a first sensor system configured to detect a position of said first portion and said second portion of said robotic arm; and a redundant sensor system configured to detect a position of said first portion and said second portion of said robotic arm.

Example 11

The surgical system of Example 10, wherein said robotic arm comprises a motor, and wherein said first sensor system comprises a torque sensor on said motor.

Example 12

The surgical system of Examples 10 and 11, wherein said redundant sensor system comprises a magnetic field emitter and a plurality of magnetic sensors positioned on said robotic arm.

Example 13

The surgical system of any one of Examples 10-12, wherein said control unit comprises a processor and a memory communicatively coupled to the processor, wherein said memory stores instructions executable by said processor to compare the position detected by said first sensor system to the position detected by said redundant sensor system to optimize control motions of said robotic arm.

Example 14

The surgical system of any one of Examples 10-13, further comprising a control circuit configured to compare the position detected by said first sensor system to the position detected by said redundant sensor system to optimize control motions of said robotic arm.

Example 15

A surgical system, comprising: a surgical robot, comprising: a control unit; and a robotic arm comprising a motor. The surgical system further comprises a surgical tool removably attached to said robotic arm. The surgical system further comprises a first sensor system in signal communication with said control unit, wherein said first sensor system comprises a torque sensor on said motor, and wherein said first sensor system is configured to detect a position of said surgical tool. The surgical system further comprises a second sensor system configured to independently detect a position of said surgical tool.

Example 16

The surgical system of Example 15, wherein said second sensor system comprises: a magnetic field emitter and a magnetic field sensor incorporated into said surgical tool.

Example 17

The surgical system of any one of Examples 15 and 16, further comprising a handheld, battery-powered surgical instrument comprising an instrument sensor, wherein said second sensor system is configured to detect a position of said instrument sensor.

Example 18

The surgical system of any one of Examples 15-17, further comprising a trocar comprising a trocar sensor, wherein said second sensor system is configured to detect a position of said trocar sensor.

Example 19

The surgical system of any one of Examples 15-18, further comprising a plurality of patient sensors applied to patient tissue, wherein said second sensor system is configured to detect the position of said patient sensors.

Example 20

The surgical system of any one of Examples 15-19, further comprising a real-time display configured to display one or more positions of said surgical tool based on data from said first sensor system and said second sensor system.

Example 21

The surgical system of any one of Examples 15-20, further comprising a hub comprising a situational awareness system, wherein said first sensor system and said second sensor system comprise data sources for said situational awareness system.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e g, carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A method, comprising:
collecting a first set of data by a first robotic hub;
storing the first set of data in a first memory of the first robotic hub;
wirelessly communicating the first set of data to a primary server at a first time;
collecting a second set of data by a second robotic hub;
storing the second set of data in a second memory of the second robotic hub;
wirelessly communicating the second set of data to the primary server at a second time;
prioritizing the first set of data and the second set of data within a queue in the primary server, wherein the queue is configured to order sequential analysis of the first set of data and the second set of data based on a prioritization protocol, wherein the prioritization protocol prioritizes a set of data based on a time the set of data is communicated to the primary server;
analyzing the first set of data and the second set of data for a priority event; and
reprioritizing the second set of data over the first set of data when a priority event is detected within the second set of data even if the first set of data was communicated to the primary server before the second set of data.

2. The method of claim 1, further comprising storing the first set of data and the second set of data within the primary server for output to an external server.

3. The method of claim 2, further comprising exporting the first set of data and the second set of data to the external server based on the prioritization protocol.

4. The method of claim 1, further comprising deleting the first set of data from the first memory upon communication of the first set of data to the primary server.

5. The method of claim 1, further comprising securing, by server-level equipment at the primary server, the first set of data and the second set of data.

6. The method of claim 1, further comprising inputting the first set of data and the second set of data into an electronic medical records database of the primary server.

7. The method of claim 1, further comprising identifying trends in a surgical procedure, by the primary server, based on data comprising the first set of data and the second set of data.

8. The method of claim 1, further comprising analyzing, by the primary server, institutional data for a surgical procedure based on data originating within an institutional data barrier.

9. A method, comprising:
collecting a first set of data by a first surgical hub;
storing the first set of data temporarily in a first memory of the first surgical hub;
communicating the first set of data to a primary server;
collecting a second set of data by a second surgical hub;
storing the second set of data temporarily in a second memory of the second surgical hub;
communicating the second set of data to the primary server;
prioritizing the first set of data and the second set of data within a queue in the primary server, wherein the queue is configured to order sequential analysis of the first set of data and the second set of data based on a prioritization protocol, wherein the prioritization protocol prioritizes a set of data based on a time the set of data is communicated to the primary server;
analyzing the first set of data and the second set of data for abnormal data; and
reprioritizing the second set of data over the first set of data when the second set of data comprises abnormal data even if the second set of data was received after the first set of data.

10. The method of claim 9, further comprising storing the first set of data and the second set of data within the primary server for output to an external server.

11. The method of claim 10, further comprising exporting the first set of data and the second set of data to the external server based on the prioritization protocol.

12. The method of claim 9, further comprising deleting the first set of data from the first memory of the first surgical hub upon communication of the first set of data to the primary server.

13. A method, comprising:
collecting a first set of data by a first robotic hub during a first surgical procedure;
storing the first set of data in a first memory of the first robotic hub;
communicating the first set of data to a primary server;
collecting a second set of data by a second robotic hub during a second surgical procedure;
storing the second set of data in a second memory of the second robotic hub;
communicating the second set of data to the primary server;
prioritizing the first set of data and the second set of data within a data export queue in the primary server based on a prioritization protocol;
sequentially exporting the first set of data and the second set of data from the data export queue to an external server based on the prioritization protocol, wherein the prioritization protocol prioritizes the export of a set of data based on a time the set of data is communicated to the primary server;
exporting the first set of data before exporting the second set of data based on the prioritization protocol when the first set of data is communicated to the primary server before the second set of data is communicated to the primary server;
detecting abnormal data within the first set of data and the second set of data; and
reprioritizing the second set of data over the first set of data when abnormal data is detected within the second set of data even if the second set of data was communicated to the primary server after the first set of data.

14. The method of claim 13, further comprising deleting the first set of data from the first memory upon communication of the first set of data to the primary server.

* * * * *